(12) United States Patent
Hewezi et al.

(10) Patent No.: US 12,018,270 B2
(45) Date of Patent: Jun. 25, 2024

(54) KINASE-DEAD MUTATION: A NEW APPROACH TO ENHANCE SOYBEAN RESISTANCE TO SOYBEAN CYST NEMATODE

(71) Applicant: UNIVERSITY OF TENNESSEE RESEARCH FOUNDATION, Knoxville, TN (US)

(72) Inventors: Tarek Abdelfattah Hewezi, Knoxville, TN (US); Sarbottam Piya, Knoxville, TN (US)

(73) Assignee: UNIVERSITY OF TENNESSEE RESEARCH FOUNDATION, Knoxville, TN (US)

(*) Notice: Subject to any disclaimer, the term of this patent is extended or adjusted under 35 U.S.C. 154(b) by 205 days.

(21) Appl. No.: 17/227,472

(22) Filed: Apr. 12, 2021

(65) Prior Publication Data

US 2021/0317471 A1 Oct. 14, 2021

Related U.S. Application Data

(60) Provisional application No. 63/009,120, filed on Apr. 13, 2020.

(51) Int. Cl.
 *C12N 15/82* (2006.01)
 *C12Q 1/6895* (2018.01)

(52) U.S. Cl.
 CPC ....... *C12N 15/8285* (2013.01); *C12Q 1/6895* (2013.01); *C12Q 2600/13* (2013.01); *C12Q 2600/156* (2013.01)

(58) Field of Classification Search
 None
 See application file for complete search history.

(56) References Cited

PUBLICATIONS

Hannink M, and Donoghue DJ. 1985. Proc. Natl. Acad. Sci. 82:7894-7898.*

Miyahara A, Hirani TA, Oakes M, Kereszt, Kobe B, Djordjevic MA and Gresshoff PM. 2008. The Journal of Biological Chemistry, 283(37):25381-25391.*

Block, A. et al. "Phytopathogen type III effector weaponry and their plant targets" *Curr Opin Plant Biol*, Aug. 2008, pp. 1-12, vol. 11, No. 4.

Colcombet, J. et al. "*Arabidopsis* MAPKs: a complex signalling network involved in multiple biological processes" *Biochem. J.*, 2008, pp. 217-226, vol. 413.

Dou, D. et al. "Phytopathogen Effectors Subverting Host Immunity: Different Foes, Similar Battleground" *Cell Host & Microbe*, Oct. 18, 2012, pp. 484-495, vol. 12.

Hanada, K. et al. "Importance of Lineage-Specific Expansion of Plant Tandem Duplicates in the Adaptive Response to Environmental Stimuli" *Plant Physiology*, Oct. 2008, pp. 993-1003, vol. 148.

Hewezi, T. "Cellular Signaling Pathways and Posttranslational Modifications Mediated by Nematode Effector Proteins" *Plant Physiology*, Oct. 2015, pp. 1018-1026, vol. 169.

Hewezi, T. et al. "Manipulation of Plant Cells by Cyst and Root-Knot Nematode Effectors" *Molecular Plant-Microbe Interactions*, 2013, pp. 9-16, vol. 26, No. 1.

Hewezi, T. et al. "The Cyst Nematode Effector Protein 10A07 Targets and Recruits Host Posttranslational Machinery to Mediate Its Nuclear Trafficking and to Promote Parasitism in Arabidopsis" *The Plant Cell*, Mar. 2015, pp. 891-907, vol. 27.

Hogenhout, S. A. et al. "Emerging Concepts in Effector Biology of Plant-Associated Organisms" *Molecular Plant-Microbe Interactions*, 2009, pp. 115-122, vol. 22, No. 2.

Kandoth, P. K. et al. "The Soybean Rhg1 Locus for Resistance to the Soybean Cyst Nematode *Heterodera glycines* Regulates the Expression of a Large Number of Stress- and Defense-Related Genes in Degenerating Feeding Cells" *Plant Physiology*, Apr. 2011, pp. 1960-1975, vol. 155.

Klink, V. P. et al. "A gene expression analysis of syncytia laser microdissected from the roots of the *Glycine max* (soybean) genotype PI 548402 (Peking) undergoing a resistant reaction after infection by *Heterodera glycines* (soybean cyst nematode)" *Plant Mol Biol*, Sep. 29, 2009, pp. 525-567, vol. 71.

Klink, V. P. et al. "Laser capture microdissection (LCM) and comparative microarray expression analysis of syncytial cells isolated from incompatible and compatible soybean (*Glycine max*) roots infected by the soybean cyst nematode (*Heterodera glycines*)" *Planta*, Aug. 1, 2007, pp. 1389-1409, vol. 226.

Klink, V. P. et al. "Syncytium gene expression in *Glycine max*$_{[PI\ 88788]}$ roots undergoing a resistant reaction to the parasitic nematode *Heterodera glycines*" *Plant Physiology and Biochemistry*, 2010, pp. 1-18.

Liu, J. et al. "Soybean kinome: functional classification and gene expression patterns" *Journal of Experimental Botany*, 2015, pp. 1919-1934, vol. 66, No. 7.

Mendy, B. et al. "*Arabidopsis* leucine-rich repeat receptor-like kinase NILR1 is required for induction of innate immunity to parasitic nematodes" *PLoS Pathogens*, Apr. 13, 2017, pp. 1-22, vol. 13, No. 4.

(Continued)

*Primary Examiner* — Anne Kubelik
(74) *Attorney, Agent, or Firm* — SALIWANCHIK, LLOYD & EISENSCHENK

(57) ABSTRACT

The invention relates to genes which may be utilized to induce resistance to soybean cyst nematode (SCN) and/or other abiotic or biotic stresses. More specifically the present disclosure provides genes that, when inactivated and/or overexpressed (for example, overexpression of genes encoding kinase-dead mutants) in a plant, particularly, a soybean plant, can confer upon the plant resistance to SCN and/or other abiotic or biotic stresses. Methods of using these genes to obtain plants, particularly soybean plants, that are resistant to SCN and/or other abiotic or biotic stresses are also provided.

7 Claims, 7 Drawing Sheets
Specification includes a Sequence Listing.

(56) References Cited

PUBLICATIONS

Palumbo, M. C. et al. "Integrated Network Analysis Identifies Fight-Club Nodes as a Class of Hubs Encompassing Key Putative Switch Genes That Induce Major Transcriptome Reprogramming during Grapevine Development" *The Plant Cell*, Dec. 2014, pp. 4617-4635, vol. 26.

Tena, G. et al. "Protein kinase signaling networks in plant innate immunity" *Current Opinion Plant Biology*, Oct. 2011, pp. 1-17, vol. 14, No. 5.

Vij, S. et al. "The Receptor-Like Cytoplasmic Kinase (OsRLCK) Gene Family in Rice: Organization, Phylogenetic Relationship, and Expression during Development and Stress" *Molecular Plant*, Sep. 2008, pp. 732-750, vol. 1, No. 5.

\* cited by examiner

FIG. 4

|  |  | ATP binding pocket |  |  |
|---|---|---|---|---|
| query | 307 | LIGTNRKGTVKAVL-DGGTLMVF...VAAEMGTLGTVK-----VENLVPLLSFCMT-----KRE | 369 | soybean |
| 4AGU_A | 10 | KIGEGSYGVVFKCRnRDTGQIVAIK...FLESEDDPVIKN-----IALNEIRMLKQLK-----RPNLVRLLEVFRN-----KRR | 76 | human |
| P21868 | 44 | RLGRGKYSEVFEAinITNNEKVVVK...IKPVKKKNIK:-----EIKILENLRg-----CPHITLADIVRD-----PVS | 106 | chicken |
| Q00532 | 10 | KIGEGSYGVVFKCRnrDEGQIVAIK...FLESEDDPVIKK-----IALNEIRMLKQLK-----APNLVMLLEVFRD-----KRR | 76 | human |
| Q03957 | 108 | QVGEGTYGKVYKAKRhNTEKIVALK...IRLQGEREGFpi-----tSIRNEIKLLQSFD-----RPNVSTTRAMVEs-----QKT | 255 | Saccharomyces |
| P20793 | 9 | QLGDGTYGSVLMGKSnESQELVAIK...KKRKFYSWDEcmq-----LEVKGLKKLN-----SANVIKLREVIRE-----NDH | 74 | Norway rat |
| P18265 | 124 | VIGRGSFGVVYQARLETPELVAIK...VLQDKRFKNR-----BLQIMRKLD-----RCNIVELRYFFYSsqekKDE | 189 | Norway rat |
| P22216 | 203 | VVVQGAPATVKKALEtTVKTFAVK...ISKRRVIGNMq-----qvPRELEVLQRLN-----SPRIVRLKQFYED-----TES | 268 | Saccharomyces |
| P18653 | 412 | WLGVGSYGCVCKRCvhARMMEYAVK...IDKSKRDPSE-----ELELLLRYGq-----APNITLADVDD-----GKH | 473 | house mouse |

|  |  | Substrate binding pocket |  |  |
|---|---|---|---|---|
| query | 370 | PL---LVYKNMPKGN-----LADQLHpa-----dyYSELDWTRIKIAIGAAKGLAWLRRScepPLIRKMIS | KTLLLa | 436 | soybean |
| 4AGU_A | 77 | LA---LVTEYCDHTV-----LHELDRYq-----lqVP--EHLVK-EHLVKS-STTWQTLQAVNFCHKN-----NCIHRD | VKPENILLI | 137 | human |
| P21868 | 107 | RtpaLVFEHVNNTD-----FKQLYQt-----LT---DVDIK-FDIKPFMYEILKALDYCHSM-----GIMHRD | VKPBNVMH | 166 | chicken |
| Q00532 | 77 | LA---LVFEHCDHTV-----LHELDRVq-----tqVP--EHLVK-SITWQTLQAVNFCHKH-----NCIHRD | VKPENLLI | 137 | human |
| Q03957 | 256 | VT---MIPEYADNDLSqIlNKEVQ-----IS---RSQCK-RLFKQLLLGMEYLHDN-----KILRND | VKGSNILI | 316 | Saccharomyces |
| P20793 | 75 | LX---FIPKYMK----BNLYQlmqd-----EELFF--ESVLR-NRKQLLQGLAFIRHH-----GFFARD | KPENLLC | 135 | Norway rat |
| P18265 | 169 | LVINLVTEYVF-----EHVZRvashftkaklifp-----IIYVR-VZWYQLFRSLAYIRSQ-----GVCHRD | IKPQHLLV | 254 | Norway rat |
| P22216 | 269 | YI---AVMEFVSGGD-----LMDFVAah-----gaVG--EDAGR-EISKQLLTAFKYLHSM-----GISHRD | KPDNILI | 328 | Saccharomyces |
| P18653 | 474 | VY---LNFKLMRGGS-----LLDKILrg-----KHFS--ERKEAS-FVLHTLSKLVEYLRSQ-----GVVHRD | KPSNILY | 534 | house mouse |

ATP binding pocket

Substrate binding pocket

SEQUENCE LISTING

```
<160> NUMBER OF SEQ ID NOS: 133

<210> SEQ ID NO 1
<211> LENGTH: 413
<212> TYPE: PRT
<213> ORGANISM: Glycine max

<400> SEQUENCE: 1

Met Gly Ala Cys Trp Ser Ser Arg Ile Lys Ala Val Ser Pro Ser Asn
1               5                   10                  15

Thr Gly Phe Thr Ser Arg Ser Val Ser Arg Asp Gly His Asp Ile Gln
            20                  25                  30

Ser Ser Ser Arg Asn Ser Ser Ala Ser Ile Pro Met Thr Pro Arg Ser
        35                  40                  45

Glu Gly Glu Ile Leu Gln Phe Ser Asn Leu Lys Ser Tyr Ser Tyr Asn
    50                  55                  60

Glu Leu Lys Met Ala Thr Lys Asn Phe Cys Pro Asp Ser Val Leu Gly
65                  70                  75                  80

Glu Gly Gly Phe Gly Ser Val Phe Lys Gly Trp Ile Asp Glu His Ser
                85                  90                  95

Leu Ala Val Thr Arg Pro Gly Thr Gly Met Val Ile Ala Val Lys Lys
            100                 105                 110

Leu Asn Gln Asp Ser Phe Gln Gly His Lys Glu Trp Leu Ala Glu Ile
        115                 120                 125

Asn Tyr Leu Gly Gln Leu Gln Asn Pro Asn Leu Val Lys Leu Ile Gly
    130                 135                 140

Tyr Cys Leu Glu Asp Gln His Arg Leu Leu Val Tyr Glu Tyr Met Pro
145                 150                 155                 160

Lys Gly Ser Val Glu Asn His Leu Phe Arg Arg Gly Ser His Phe Gln
                165                 170                 175

Gln Leu Ser Trp Thr Leu Arg Leu Lys Ile Ser Leu Gly Ala Ala Arg
            180                 185                 190

Gly Leu Ala Phe Leu His Ser Thr Glu Thr Lys Val Ile Tyr Arg Asp
```

-continued

```
            195                 200                 205
Phe Lys Thr Ser Asn Ile Leu Leu Asp Thr Asn Tyr Asn Ala Lys Leu
210                 215                 220

Ser Asp Phe Gly Leu Ala Arg Asp Gly Pro Thr Gly Asp Lys Ser His
225                 230                 235                 240

Val Ser Thr Arg Val Met Gly Thr His Gly Tyr Ala Ala Pro Glu Tyr
                    245                 250                 255

Leu Ala Thr Gly His Leu Thr Ala Lys Ser Asp Val Tyr Ser Phe Gly
                260                 265                 270

Val Val Leu Leu Glu Met Leu Ser Gly Arg Arg Ala Ile Asp Lys Asn
                275                 280                 285

Arg Pro Ser Gly Glu Gln Cys Leu Val Glu Trp Ala Lys Pro Tyr Leu
290                 295                 300

Ser Asn Lys Arg Arg Val Phe Arg Val Met Asp Ser Arg Leu Glu Gly
305                 310                 315                 320

Gln Tyr Ser Leu Thr Gln Ala Gln Arg Ala Ala Thr Leu Ala Phe Gln
                325                 330                 335

Cys Leu Ser Val Glu Pro Lys Tyr Arg Pro Asn Met Asp Glu Val Val
                340                 345                 350

Lys Ala Leu Glu Gln Leu Arg Glu Ser Asn Asp Lys Val Lys Asn Gly
                355                 360                 365

Asp His Lys Lys Cys Arg Val Ser Gly Ser Gly Leu Gly His Pro Asn
370                 375                 380

Gly Leu Pro Ala Ser Thr Ser Lys Gly Ser Ile Asp Ala Ala Lys Lys
385                 390                 395                 400

Phe Asn Tyr Pro Arg Pro Ser Ala Ser Leu Leu Tyr Ser
                    405                 410

<210> SEQ ID NO 2
<211> LENGTH: 371
<212> TYPE: PRT
<213> ORGANISM: Glycine max

<400> SEQUENCE: 2

Met Ser Tyr Arg Glu Arg Asn Lys Gly Lys Gly Glu Glu Lys Glu Tyr
1               5                   10                  15

Glu Asn Ser Thr Thr Arg Gly Leu Asp Ser Lys Ser Val Ser His Asn
                20                  25                  30

Asn Gly Ser Ile Glu Glu Glu Leu Leu Thr Ile Asp Glu Asn Leu Leu
            35                  40                  45

Ile Asp Pro Lys Leu Leu Phe Ile Gly Ser Lys Ile Gly Glu Gly Ala
50                  55                  60

His Gly Arg Val Tyr Glu Gly Arg Tyr Arg Asp Gln Ile Val Ala Ile
65                  70                  75                  80

Lys Val Leu His Arg Gly Gly Thr Leu Glu Glu Arg Val Ala Leu Glu
                85                  90                  95

Asn Arg Phe Ala Arg Glu Val Asn Met Met Ser Arg Val His His Glu
                100                 105                 110

Asn Leu Val Lys Phe Ile Gly Ala Cys Lys Asp Pro Leu Met Val Ile
            115                 120                 125

Val Thr Glu Met Leu Pro Gly Leu Ser Leu Arg Lys Tyr Leu Thr Thr
        130                 135                 140

Ile Arg Pro Lys Gln Leu Asp Pro Tyr Val Ala Ile Lys Phe Ala Leu
145                 150                 155                 160
```

Asp Ile Ala Arg Ala Met Asp Trp Leu His Ala Asn Gly Ile Ile His
            165                 170                 175

Arg Asp Leu Lys Pro Asp Asn Leu Leu Leu Thr Glu Asn Gln Lys Ser
        180                 185                 190

Val Lys Leu Ala Asp Phe Gly Leu Ala Arg Glu Glu Ser Val Thr Glu
    195                 200                 205

Met Met Thr Ala Glu Thr Gly Thr Tyr Arg Trp Met Ala Pro Glu Leu
210                 215                 220

Tyr Ser Thr Val Thr Leu Cys Gln Gly Glu Lys Lys His Tyr Asn Asn
225                 230                 235                 240

Lys Val Asp Val Tyr Ser Phe Gly Ile Val Leu Trp Glu Leu Leu Thr
                245                 250                 255

Asn Arg Met Pro Phe Glu Gly Met Ser Asn Leu Gln Ala Ala Tyr Ala
            260                 265                 270

Ala Ala Phe Lys Gln Glu Arg Pro Asn Leu Pro Asp Asp Ile Ser Pro
        275                 280                 285

Asp Leu Ala Phe Ile Ile Gln Ser Cys Trp Val Glu Asp Pro Asn Met
    290                 295                 300

Arg Pro Ser Phe Ser Gln Ile Ile Arg Leu Leu Asn Glu Phe His Phe
305                 310                 315                 320

Thr Leu Gln Gln Pro Ser Pro Ser Met Pro Leu Glu Pro Glu Asn Glu
                325                 330                 335

Pro Glu Ala Ile Thr Ser Asn Gly Thr Ile Thr Asp Phe Ser Thr Arg
            340                 345                 350

Asn Lys Val Lys Phe Ser Phe Ile Arg His Leu Phe Ser Ser Lys Arg
        355                 360                 365

Thr Lys Ser
    370

<210> SEQ ID NO 3
<211> LENGTH: 694
<212> TYPE: PRT
<213> ORGANISM: Glycine max

<400> SEQUENCE: 3

Met Phe Pro Leu Gln Cys Ser Asn His Pro Met Cys Ala Phe Ser Ala
1               5                   10                  15

Ala Val Thr Thr Ile Leu Leu Leu Phe Pro Ala Ala Thr Ser Gln Ala
            20                  25                  30

Gln Ile Leu Lys Lys Glu Thr Tyr Phe Phe Gly Pro Phe Asn Gln Ser
        35                  40                  45

Tyr Phe Thr Thr Phe Ala Val Leu Pro Ser Ala Ala Ile Asn Leu Gly
    50                  55                  60

Ala Leu Gln Val Thr Pro Asp Ser Thr Gly Asn Val Ser Leu Ala Asn
65                  70                  75                  80

Gln Ser Gly Arg Ile Phe Phe Ser Thr Pro Phe Thr Leu Trp Asp Asp
                85                  90                  95

Glu Asn Leu Asn Gly Lys Leu Val Ser Phe Asn Thr Ser Phe Leu Ile
            100                 105                 110

Asn Val Phe Arg Pro Gln Asn Pro Pro Gly Glu Gly Ile Ala Phe
        115                 120                 125

Leu Ile Ala Pro Ser Ser Ser Thr Val Pro Asn Asn Ser His Gly Gln
    130                 135                 140

Phe Leu Gly Leu Thr Asn Ala Ala Thr Asp Gly Asn Ala Thr Asn Lys
145                 150                 155                 160

```
Phe Ile Ala Val Glu Leu Asp Thr Val Lys Gln Asp Phe Asp Pro Asp
                165                 170                 175

Asp Asn His Ile Gly Leu Asp Ile Asn Ser Val Arg Ser Asn Val Ser
            180                 185                 190

Val Ser Leu Thr Pro Leu Gly Phe Glu Ile Ala Pro Asn Val Thr Arg
        195                 200                 205

Phe His Val Leu Trp Val Asp Tyr Asp Gly Asp Arg Lys Glu Ile Asp
    210                 215                 220

Val Tyr Ile Ala Glu Gln Pro Asp Lys Asp Val Pro Ile Val Ala Lys
225                 230                 235                 240

Pro Ala Lys Pro Val Leu Ser Ser Pro Leu Asp Leu Lys Gln Val Leu
                245                 250                 255

Asn Lys Val Ser Tyr Phe Gly Phe Ser Ala Ser Thr Gly Asp Asn Val
            260                 265                 270

Glu Leu Asn Cys Val Leu Arg Trp Asn Ile Thr Ile Glu Val Phe Pro
        275                 280                 285

Lys Lys Asn Gly Asn Gly Lys Ala Tyr Lys Ile Gly Leu Ser Val Gly
    290                 295                 300

Leu Thr Leu Leu Val Leu Ile Val Ala Gly Val Val Gly Phe Arg Val
305                 310                 315                 320

Tyr Trp Ile Arg Lys Lys Lys Arg Glu Asn Glu Ser Gln Ile Leu Gly
                325                 330                 335

Thr Leu Lys Ser Leu Pro Gly Thr Pro Arg Glu Phe Arg Tyr Gln Glu
            340                 345                 350

Leu Lys Lys Ala Thr Asn Asn Phe Asp Asp Lys His Lys Leu Gly Gln
        355                 360                 365

Gly Gly Tyr Gly Val Val Tyr Arg Gly Thr Leu Leu Pro Lys Glu Asn
    370                 375                 380

Leu Gln Val Ala Val Lys Met Phe Ser Arg Asp Lys Met Lys Ser Thr
385                 390                 395                 400

Asp Asp Phe Leu Ala Glu Leu Thr Ile Ile Asn Arg Leu Arg His Lys
                405                 410                 415

Asn Leu Val Arg Leu Leu Gly Trp Cys His Arg Asn Gly Val Leu Leu
            420                 425                 430

Leu Val Tyr Asp Tyr Met Pro Asn Gly Ser Leu Asp Asn His Ile Phe
        435                 440                 445

Cys Glu Glu Gly Ser Ser Thr Thr Pro Leu Ser Trp Pro Leu Arg Tyr
    450                 455                 460

Lys Ile Ile Thr Gly Val Ala Ser Ala Leu Asn Tyr Leu His Asn Glu
465                 470                 475                 480

Tyr Asp Gln Lys Val Val His Arg Asp Leu Lys Ala Ser Asn Ile Met
                485                 490                 495

Leu Asp Ser Asn Phe Asn Ala Arg Leu Gly Asp Phe Gly Leu Ala Arg
            500                 505                 510

Ala Leu Glu Asn Asp Lys Thr Ser Tyr Ala Glu Met Glu Gly Val His
        515                 520                 525

Gly Thr Met Gly Tyr Ile Ala Pro Glu Cys Phe His Thr Gly Arg Ala
    530                 535                 540

Thr Arg Glu Ser Asp Val Tyr Gly Phe Gly Ala Val Leu Leu Glu Val
545                 550                 555                 560

Val Cys Gly Gln Arg Pro Trp Thr Lys Asn Glu Gly Tyr Glu Cys Leu
                565                 570                 575
```

```
Val Asp Trp Val Trp His Leu His Arg Glu Gln Arg Ile Leu Asp Ala
                580                 585                 590

Val Asn Pro Arg Leu Gly Asn Asp Cys Val Val Glu Glu Ala Glu Arg
            595                 600                 605

Val Leu Lys Leu Gly Leu Ala Cys Ser His Pro Ile Ala Ser Glu Arg
        610                 615                 620

Pro Lys Met Gln Thr Ile Val Gln Ile Leu Ser Gly Ser Val His Val
625                 630                 635                 640

Pro His Leu Pro Pro Phe Lys Pro Ala Phe Val Trp Pro Ala Met Asp
                645                 650                 655

Leu Ser Ser Leu Ala Ser Asp Leu Thr Thr Gln Thr Thr Thr Thr Glu
            660                 665                 670

Tyr Thr Pro Met Ser Ser Asp Thr His Ser Met His Val Gln Phe Ser
        675                 680                 685

Asp Ser Ser Ser Leu Val
    690

<210> SEQ ID NO 4
<211> LENGTH: 624
<212> TYPE: PRT
<213> ORGANISM: Glycine max

<400> SEQUENCE: 4

Met Glu His Ser Ser Ser Leu Val Phe Trp Leu Leu Gly Leu Leu Leu
1               5                   10                  15

Leu Leu Leu Met Glu Ile Ser Ser Ala Ala Leu Ser Pro Ser Gly Ile
            20                  25                  30

Asn Tyr Glu Val Val Ala Leu Met Ala Ile Lys Asn Asp Leu Ile Asp
        35                  40                  45

Pro His Asn Val Leu Glu Asn Trp Asp Ile Asn Ser Val Asp Pro Cys
    50                  55                  60

Ser Trp Arg Met Ile Thr Cys Ser Pro Asp Gly Ser Val Ser Ala Leu
65                  70                  75                  80

Gly Leu Pro Ser Gln Asn Leu Ser Gly Thr Leu Ser Pro Gly Ile Gly
                85                  90                  95

Asn Leu Thr Asn Leu Gln Ser Val Leu Leu Gln Asn Asn Ala Ile Ser
            100                 105                 110

Gly Arg Ile Pro Ala Ala Ile Gly Ser Leu Glu Lys Leu Gln Thr Leu
        115                 120                 125

Asp Leu Ser Asn Asn Thr Phe Ser Gly Glu Ile Pro Ser Ser Leu Gly
    130                 135                 140

Gly Leu Lys Asn Leu Asn Tyr Leu Arg Leu Asn Asn Asn Ser Leu Thr
145                 150                 155                 160

Gly Ser Cys Pro Gln Ser Leu Ser Asn Ile Glu Gly Leu Thr Leu Val
                165                 170                 175

Asp Leu Ser Tyr Asn Asn Leu Ser Gly Ser Leu Pro Arg Ile Ser Ala
            180                 185                 190

Arg Thr Leu Lys Ile Val Gly Asn Ser Leu Ile Cys Gly Pro Lys Ala
        195                 200                 205

Asn Asn Cys Ser Thr Ile Leu Pro Glu Pro Leu Ser Phe Pro Pro Asp
    210                 215                 220

Ala Leu Arg Gly Gln Ser Asp Ser Gly Lys Lys Ser His Val Ala
225                 230                 235                 240

Leu Ala Phe Gly Ala Ser Phe Gly Ala Ala Phe Val Leu Val Ile Ile
                245                 250                 255
```

Val Gly Phe Leu Val Trp Trp Arg Tyr Arg Asn Gln Gln Ile Phe
            260                 265                 270

Phe Asp Val Asn Glu His Tyr Asp Pro Glu Val Arg Leu Gly His Leu
        275                 280                 285

Lys Arg Phe Ser Phe Lys Glu Leu Arg Ala Ala Thr Asp His Phe Asn
290                 295                 300

Ser Lys Asn Ile Leu Gly Arg Gly Phe Gly Ile Val Tyr Lys Ala
305                 310                 315                 320

Cys Leu Asn Asp Gly Ser Val Ala Val Lys Arg Leu Lys Asp Tyr
                325                 330                 335

Asn Ala Ala Gly Gly Glu Ile Gln Phe Gln Thr Glu Val Glu Thr Ile
            340                 345                 350

Ser Leu Ala Val His Arg Asn Leu Leu Arg Leu Ser Gly Phe Cys Ser
        355                 360                 365

Thr Gln His Glu Arg Leu Leu Val Tyr Pro Tyr Met Ser Asn Gly Ser
    370                 375                 380

Val Ala Ser Arg Leu Lys Asp His Ile His Gly Arg Pro Ala Leu Asp
385                 390                 395                 400

Trp Thr Arg Arg Lys Arg Ile Ala Leu Gly Thr Ala Arg Gly Leu Val
                405                 410                 415

Tyr Leu His Glu Gln Cys Asp Pro Lys Ile Ile His Arg Asp Val Lys
            420                 425                 430

Ala Ala Asn Ile Leu Leu Asp Glu Asp Phe Glu Ala Val Val Gly Asp
        435                 440                 445

Phe Gly Leu Ala Lys Leu Leu Asp His Arg Asp Ser His Val Thr Thr
450                 455                 460

Ala Val Arg Gly Thr Val Gly His Ile Ala Pro Glu Tyr Leu Ser Thr
465                 470                 475                 480

Gly Gln Ser Ser Glu Lys Thr Asp Val Phe Gly Phe Gly Ile Leu Leu
            485                 490                 495

Leu Glu Leu Ile Thr Gly His Lys Ala Leu Asp Phe Gly Arg Ala Ala
        500                 505                 510

Asn Gln Lys Gly Val Met Leu Asp Trp Val Lys Lys Leu His Gln Asp
    515                 520                 525

Gly Arg Leu Ser Gln Met Val Asp Lys Asp Leu Lys Gly Asn Phe Asp
530                 535                 540

Leu Ile Glu Leu Glu Glu Met Val Gln Val Ala Leu Leu Cys Thr Gln
545                 550                 555                 560

Phe Asn Pro Ser His Arg Pro Lys Met Ser Glu Val Leu Lys Met Leu
            565                 570                 575

Glu Gly Asp Gly Leu Ala Glu Arg Trp Glu Ala Ser Gln Arg Ile Glu
        580                 585                 590

Thr Pro Arg Phe Arg Ser Cys Glu Pro Gln Arg Tyr Ser Asp Leu Ile
    595                 600                 605

Glu Glu Ser Ser Leu Val Val Glu Ala Met Glu Leu Ser Gly Pro Arg
610                 615                 620

<210> SEQ ID NO 5
<211> LENGTH: 581
<212> TYPE: PRT
<213> ORGANISM: Glycine max

<400> SEQUENCE: 5

Met Ala Thr Ile Gly Ile Gly Val Gly Val Thr Lys Leu Gln Gln Pro

```
1               5                   10                  15
His Arg Pro Lys Ser Lys Ser Leu Phe Leu Gly Gln Arg Leu Arg Ile
                20                  25                  30
Ser Pro Phe Trp Gly Glu Pro Gln Cys Ser Glu Arg Arg Leu Phe Gly
                35                  40                  45
Val Ser Asn Pro Pro Arg Val Val Gln Val Phe Ala Leu Gly Gly Gly
                50                  55                  60
Glu Trp Leu Asp Thr Val His Asn Leu Phe Val Gly Val Gly Val Gly
65                  70                  75                  80
Leu Pro Cys Ser Val Met Gln Cys Gly Asp Val Ile Tyr Arg Ser Thr
                85                  90                  95
Leu Pro Lys Ser Asn Gly Leu Thr Leu Thr Val Pro Gly Val Ile Leu
                100                 105                 110
Ala Leu Gly Thr Leu Ser Tyr Leu Trp Ala Thr Pro Gly Val Ala Pro
                115                 120                 125
Gly Phe Phe Asp Met Phe Val Leu Ala Phe Val Glu Arg Leu Phe Arg
                130                 135                 140
Pro Thr Tyr Lys Lys Asp Asp Phe Val Leu Gly Lys Lys Leu Gly Glu
145                 150                 155                 160
Gly Ser Phe Gly Val Val Tyr Arg Val Ser Leu Ala Asn Lys Pro Ser
                165                 170                 175
Ser Lys Glu Gly Asp Leu Val Leu Lys Lys Ala Thr Glu Tyr Gly Ala
                180                 185                 190
Val Glu Ile Trp Met Asn Glu Arg Val Arg Arg Ala Cys Ala Ser Ser
                195                 200                 205
Cys Ala Asp Phe Val Tyr Gly Phe Leu Glu Ser Ser Ser Lys Lys Ala
                210                 215                 220
Ala Glu Tyr Trp Leu Ile Trp Arg Phe Glu Gly Asp Ala Thr Leu Ala
225                 230                 235                 240
Asp Leu Met Gln Ser Arg Asp Phe Pro Tyr Asn Val Glu Thr Leu Ile
                245                 250                 255
Leu Gly Glu Val Gln Asp Leu Pro Lys Gly Leu Glu Arg Glu Asn Arg
                260                 265                 270
Ile Ile Gln Thr Ile Met Arg Gln Ile Leu Phe Ala Leu Asp Gly Leu
                275                 280                 285
His Ser Thr Gly Ile Val His Arg Asp Ile Lys Pro Gln Asn Val Ile
                290                 295                 300
Phe Ser Glu Glu Ser Arg Thr Phe Lys Ile Ile Asp Leu Gly Ala Ala
305                 310                 315                 320
Thr Asp Leu Arg Val Gly Ile Asn Tyr Ile Pro Lys Glu Phe Leu Leu
                325                 330                 335
Asp Pro Arg Tyr Ala Ala Pro Glu Gln Tyr Ile Met Ser Thr Gln Thr
                340                 345                 350
Pro Ser Ala Pro Ser Val Pro Val Ala Thr Ala Leu Ser Pro Val Leu
                355                 360                 365
Trp Gln Leu Asn Leu Pro Asp Arg Phe Asp Ile Tyr Ser Ala Gly Leu
                370                 375                 380
Ile Phe Leu Gln Met Ala Phe Pro Ser Leu Arg Ser Asp Asn Ser Leu
385                 390                 395                 400
Ile Gln Phe Asn Arg Gln Leu Lys Arg Cys Asp Tyr Asp Leu Val Ala
                405                 410                 415
Trp Arg Lys Thr Ala Glu Ala Arg Ser Glu Leu Arg Lys Gly Phe Glu
                420                 425                 430
```

```
Leu Leu Asp Leu Asp Gly Gly Ile Gly Trp Glu Leu Leu Lys Ser Met
            435                 440                 445

Val Arg Tyr Lys Ala Arg Gln Arg Leu Ser Ala Lys Ala Ala Leu Ala
    450                 455                 460

His Pro Tyr Phe Val Arg Glu Gly Leu Leu Ala Leu Ser Phe Met Gln
465                 470                 475                 480

Thr Leu Arg Leu Gln Leu Leu Arg Ala Thr Gln Gln Asp Tyr Ser Glu
                485                 490                 495

Ala Ala Arg Trp Ile Ile Gln Leu Met Ala Lys Ser Gly Thr Gln Lys
                500                 505                 510

Asp Gly Gly Phe Thr Glu Ala Gln Leu Gln Glu Leu Arg Glu Ile Glu
            515                 520                 525

Pro Lys Lys Lys Ala Ser Ala Pro Arg Asn Ala Leu Ala Ser Ala Leu
            530                 535                 540

Lys Leu Gln Arg Lys Ile Ile Arg Thr Ile Arg Thr Leu Asn Glu Ser
545                 550                 555                 560

Met Asp Glu Leu Thr Arg Arg Lys Ser Phe Trp Trp Ser Arg Trp
                565                 570                 575

Ile Pro Arg Glu Glu
            580

<210> SEQ ID NO 6
<211> LENGTH: 621
<212> TYPE: PRT
<213> ORGANISM: Glycine max

<400> SEQUENCE: 6

Met Glu Arg Ser Gly Asp Val Ala Leu Phe Cys Leu Ala Leu Phe Phe
1               5                   10                  15

Leu Trp Thr Ser Val Ala Ala Leu Leu Ser Pro Lys Gly Val Asn Tyr
                20                  25                  30

Glu Val Gln Ala Leu Met Ser Ile Lys Asn Ser Leu Val Asp Pro His
            35                  40                  45

Ser Val Leu Asn Asn Trp Asp Thr Asp Ala Val Asp Pro Cys Asn Trp
    50                  55                  60

Ala Met Val Thr Cys Ser Ser Asp His Phe Val Ile Ala Leu Gly Ile
65              70                  75                  80

Pro Ser Gln Ser Ile Ser Gly Thr Leu Ser Pro Ser Ile Gly Asn Leu
                85                  90                  95

Thr Asn Leu Gln Thr Val Leu Leu Gln Asp Asn Asn Ile Thr Gly Pro
            100                 105                 110

Ile Pro Phe Glu Ile Gly Arg Leu Gln Lys Leu Gln Thr Leu Asp Leu
        115                 120                 125

Ser Asp Asn Phe Phe Thr Gly Gln Leu Pro Asp Thr Leu Ser Tyr Met
    130                 135                 140

Lys Gly Leu His Tyr Leu Arg Leu Asn Asn Ser Leu Thr Gly Pro
145                 150                 155                 160

Ile Pro Ser Ser Leu Ala Asn Met Thr Gln Leu Ala Phe Leu Asp Ile
                165                 170                 175

Ser Tyr Asn Asn Leu Ser Glu Pro Val Pro Arg Ile Asn Ala Lys Thr
            180                 185                 190

Phe Asn Ile Ile Gly Asn Pro Gln Ile Cys Ala Thr Gly Val Glu Lys
        195                 200                 205

Asn Cys Phe Arg Thr Thr Ser Ile Pro Ser Ala Pro Asn Asn Ser Gln
```

```
              210                 215                 220
Asp Ser Gln Ser Thr Lys Arg Pro Lys Ser His Lys Phe Ala Leu Ala
225                 230                 235                 240

Phe Ala Ser Ser Leu Ser Cys Ile Cys Leu Leu Ile Leu Gly Leu Gly
                245                 250                 255

Phe Leu Ile Trp Trp Arg Gln Arg Tyr Asn Lys Gln Ile Phe Phe Asp
                    260                 265                 270

Val Asn Glu Gln His Arg Glu Glu Val Cys Leu Gly Asn Leu Lys Lys
                275                 280                 285

Phe His Phe Arg Glu Leu Gln Leu Ala Thr Asn Asn Phe Ser Ser Lys
                290                 295                 300

Asn Leu Ile Gly Lys Gly Gly Phe Gly Asn Val Tyr Lys Gly Tyr Val
305                 310                 315                 320

Gln Asp Gly Thr Val Ile Ala Val Lys Arg Leu Lys Asp Gly Asn Ala
                    325                 330                 335

Ile Gly Gly Glu Ile Gln Phe Gln Thr Glu Val Glu Met Ile Ser Leu
                340                 345                 350

Ala Val His Arg Asn Leu Leu Arg Leu Tyr Gly Phe Cys Met Thr Ala
                355                 360                 365

Thr Glu Arg Leu Leu Val Tyr Pro Tyr Met Ser Asn Gly Ser Val Ala
370                 375                 380

Ser Arg Leu Lys Ala Lys Pro Ala Leu Asp Trp Ala Thr Arg Lys Arg
385                 390                 395                 400

Ile Ala Leu Gly Ala Gly Arg Gly Leu Leu Tyr Leu His Glu Gln Cys
                    405                 410                 415

Asp Pro Lys Ile Ile His Arg Asp Val Lys Ala Ala Asn Ile Leu Leu
                420                 425                 430

Asp Asp Tyr Cys Glu Ala Val Val Gly Asp Phe Gly Leu Ala Lys Leu
                435                 440                 445

Leu Asp His Arg Asp Ser His Val Thr Thr Ala Val Arg Gly Thr Val
                450                 455                 460

Gly His Ile Ala Pro Glu Tyr Leu Ser Thr Gly Gln Ser Ser Glu Lys
465                 470                 475                 480

Thr Asp Val Phe Gly Phe Gly Ile Leu Leu Leu Glu Leu Ile Ser Gly
                    485                 490                 495

Gln Arg Ala Leu Glu Phe Gly Lys Ala Ala Asn Gln Lys Gly Ala Met
                500                 505                 510

Leu Asp Trp Val Lys Lys Ile His Gln Glu Lys Lys Ile Asp Leu Leu
                515                 520                 525

Val Asp Lys Asp Leu Lys Asn Asn Tyr Asp Arg Ile Glu Leu Asp Glu
                530                 535                 540

Ile Val Gln Val Ala Leu Leu Cys Thr Gln Tyr Leu Pro Ser His Arg
545                 550                 555                 560

Pro Lys Met Ser Glu Val Val Arg Met Leu Glu Gly Asp Gly Leu Ala
                    565                 570                 575

Glu Lys Trp Glu Ala Ser Gln Ser Ala Glu Ser Thr Arg Ser Arg Gly
                580                 585                 590

Asn Glu Leu Ser Ser Ser Glu Arg Tyr Ser Asp Leu Thr Asp Asp Ser
                595                 600                 605

Ser Leu Leu Ala Gln Ala Met Glu Leu Ser Gly Pro Arg
                610                 615                 620

<210> SEQ ID NO 7
```

<211> LENGTH: 598
<212> TYPE: PRT
<213> ORGANISM: Glycine max

<400> SEQUENCE: 7

Met Gly Val Cys Thr Ser Lys Pro Gln Lys Pro Asn Pro Tyr Ala Leu
1               5                   10                  15

Arg Glu Ala Glu Ala Glu Ala Asp Pro Ser Gln Asn Pro Lys Thr Thr
            20                  25                  30

Leu Ser Pro Ala Gly Ala Asp Thr Pro Arg Arg Lys Asp Val Ser
        35                  40                  45

Thr Gly Lys Arg Ser Pro Phe Phe Pro Phe Tyr Ser Pro Ser Pro Ala
50                  55                  60

Arg Phe Leu Lys Lys Ser Pro Ala Pro Ala Gly Gly Ser Arg Ser Ala
65                  70                  75                  80

Ser Ser Thr Pro Arg Arg Phe Phe Arg Arg Pro Phe Pro Pro Pro Ser
                85                  90                  95

Pro Ala Lys His Ile Arg Ala Val Leu Ala Arg Gln Gly Lys Lys
            100                 105                 110

Ala Ser Ala Thr Ala Ala Ile Pro Glu Glu Gly Glu Glu Gly Ala Ala
        115                 120                 125

Asp Leu Asp Lys Arg Phe Gly Phe Ser Lys Glu Phe Thr Ser Arg Leu
130                 135                 140

Glu Val Gly Glu Glu Val Gly Arg Gly His Phe Gly Tyr Thr Cys Ser
145                 150                 155                 160

Ala Arg Phe Lys Lys Gly Glu Leu Lys Gly Gln Gln Val Ala Val Lys
                165                 170                 175

Val Ile Pro Lys Ala Lys Met Thr Thr Ala Ile Ala Ile Glu Asp Val
            180                 185                 190

Arg Arg Glu Val Lys Ile Leu Arg Ala Leu Asn Gly His Asn Asn Leu
        195                 200                 205

Ile Gln Phe Tyr Asp Ala Phe Glu Asp Gln Asp Asn Val Tyr Ile Val
    210                 215                 220

Met Glu Leu Cys Glu Gly Gly Glu Leu Leu Asp Met Ile Leu Ser Arg
225                 230                 235                 240

Gly Gly Lys Tyr Ser Glu Asp Asp Ala Lys Ala Val Met Val Gln Ile
                245                 250                 255

Leu Asn Val Val Ala Phe Cys His Leu Gln Gly Val Val His Arg Asp
            260                 265                 270

Leu Lys Pro Glu Asn Phe Leu Tyr Ala Lys Lys Asp Glu Ser Ser Glu
        275                 280                 285

Leu Lys Ala Ile Asp Phe Gly Leu Ser Asp Phe Val Arg Pro Asp Glu
    290                 295                 300

Arg Leu Asn Asp Ile Val Gly Ser Ala Tyr Tyr Val Ala Pro Glu Val
305                 310                 315                 320

Leu His Arg Ser Tyr Gly Thr Glu Ala Asp Val Trp Ser Ile Gly Val
                325                 330                 335

Ile Ala Tyr Ile Leu Leu Cys Gly Ser Arg Pro Phe Trp Ala Arg Thr
            340                 345                 350

Glu Ser Gly Ile Phe Arg Ala Val Leu Lys Ala Asp Pro Ser Phe Asp
        355                 360                 365

Glu Thr Pro Trp Pro Ser Leu Ser Leu Glu Ala Lys Asp Phe Val Lys
    370                 375                 380

Arg Ile Leu Asn Lys Asp Pro Arg Lys Arg Ile Ser Ala Ala Gln Ala

```
            385                 390                 395                 400
Leu Ser His Pro Trp Ile Arg Asn Cys Asn Asn Val Lys Val Pro Leu
                    405                 410                 415

Asp Ile Leu Ile Phe Lys Leu Met Lys Thr Tyr Met Arg Ser Ser Ser
                    420                 425                 430

Leu Arg Lys Ala Ala Leu Arg Ala Leu Ser Lys Thr Leu Thr Ala Asp
                435                 440                 445

Glu Leu Tyr Tyr Leu Arg Gly Gln Phe Ala Leu Leu Glu Pro Ser Lys
            450                 455                 460

Asn Gly Ser Ile Ser Leu Glu Asn Val Asn Lys Ala Leu Met Lys Tyr
465                 470                 475                 480

Ala Thr Asp Ala Met Lys Glu Ser Arg Ile Pro Asp Phe Leu Ser Ser
                    485                 490                 495

Leu Asn Ser Leu Gln Tyr Arg Arg Met Asp Phe Glu Glu Phe Cys Ala
                500                 505                 510

Ala Ala Leu Ser Val His Gln Leu Glu Ala Leu Asp Arg Trp Glu Gln
            515                 520                 525

His Ala Arg Cys Ala Tyr Glu Leu Phe Asp Lys Asp Gly Asn Arg Ala
        530                 535                 540

Ile Val Ile Glu Glu Leu Ala Ser Glu Leu Gly Leu Gly Pro Ser Ile
545                 550                 555                 560

Pro Val His Val Val Leu His Asp Trp Ile Arg His Thr Asp Gly Lys
                    565                 570                 575

Leu Ser Phe Leu Gly Phe Val Lys Leu Leu His Gly Val Ser Ser Arg
                580                 585                 590

Ser Leu Ala Lys Val Gln
            595
```

<210> SEQ ID NO 8
<211> LENGTH: 430
<212> TYPE: PRT
<213> ORGANISM: Glycine max

<400> SEQUENCE: 8

```
Met Ser Glu Lys Glu Lys Gly Asn Asn Ser Glu Gly Gln Ser Thr Leu
1               5                   10                  15

Leu His Gly Lys Tyr Glu Leu Gly Arg Val Leu Gly His Gly Thr Phe
                20                  25                  30

Ala Lys Val Tyr His Ala Arg Asn Leu Asn Thr Gly Gln His Val Ala
            35                  40                  45

Met Lys Val Val Gly Lys Glu Lys Val Ile Lys Val Gly Met Met Glu
        50                  55                  60

Gln Val Lys Arg Glu Ile Ser Val Met Lys Met Val Lys His Gln Asn
65                  70                  75                  80

Ile Val Glu Leu His Glu Val Met Ala Ser Lys Ser Lys Ile Tyr Ile
                85                  90                  95

Ala Met Glu Leu Val Arg Gly Gly Glu Leu Phe Asn Lys Val Ser Lys
                100                 105                 110

Gly Arg Leu Lys Glu Asp Val Ala Arg Leu Tyr Phe Gln Gln Leu Ile
            115                 120                 125

Ser Ala Val Asp Phe Cys His Ser Arg Gly Val Tyr His Arg Asp Leu
        130                 135                 140

Lys Pro Glu Asn Leu Leu Leu Asp Glu His Gly Asn Leu Lys Val Ser
145                 150                 155                 160
```

-continued

```
Asp Phe Gly Leu Thr Ala Phe Ser Glu His Leu Lys Glu Asp Gly Leu
                165                 170                 175

Leu His Thr Thr Cys Gly Thr Pro Ala Tyr Val Ser Pro Glu Val Ile
            180                 185                 190

Ala Lys Lys Gly Tyr Asp Gly Ala Lys Ala Asp Ile Trp Ser Cys Gly
        195                 200                 205

Val Ile Leu Tyr Val Leu Leu Ala Gly Phe Leu Pro Phe Gln Asp Asp
    210                 215                 220

Asn Leu Val Ala Met Tyr Lys Lys Ile Tyr Arg Gly Asp Phe Lys Cys
225                 230                 235                 240

Pro Pro Trp Phe Ser Leu Asp Ala Arg Lys Leu Val Thr Lys Leu Leu
                245                 250                 255

Asp Pro Asn Pro Asn Thr Arg Ile Ser Ile Ser Lys Val Met Glu Ser
            260                 265                 270

Ser Trp Phe Lys Lys Pro Val Pro Arg Lys Leu Ala Ala Glu Lys Val
        275                 280                 285

Asp Leu Glu Glu Glu Lys Ile Glu Ser Gln Leu Glu Thr Ile Asn Ala
    290                 295                 300

Phe His Ile Ile Ser Leu Ser Glu Gly Phe Asn Leu Ser Pro Leu Phe
305                 310                 315                 320

Glu Asp Lys Arg Arg Glu Glu Met Arg Phe Ala Thr Ala Gly Thr Pro
                325                 330                 335

Ser Thr Val Ile Ser Arg Leu Glu Glu Val Ala Lys Ala Gly Lys Phe
            340                 345                 350

Asp Val Arg Ser Ser Glu Thr Lys Val Arg Leu Gln Gly Gln Glu Arg
        355                 360                 365

Gly Arg Lys Gly Lys Leu Ala Ile Ala Ala Asp Ile Tyr Ala Val Thr
    370                 375                 380

Pro Ser Phe Met Val Val Glu Val Lys Lys Asp Asn Gly Asp Thr Leu
385                 390                 395                 400

Glu Tyr Asn Gln Phe Cys Ser Lys Gln Leu Arg Pro Ala Leu Lys Asp
                405                 410                 415

Ile Phe Trp Asn Ser Ser Gln Asn Ser Ala Pro Ala Ser Ala
            420                 425                 430

<210> SEQ ID NO 9
<211> LENGTH: 338
<212> TYPE: PRT
<213> ORGANISM: Glycine max

<400> SEQUENCE: 9

Met Glu Arg Tyr Glu Ile Leu Lys Asp Ile Gly Ser Gly Asn Phe Ala
1               5                   10                  15

Val Ala Lys Leu Val Arg Asp Asn Tyr Thr Asn Glu Leu Phe Ala Val
            20                  25                  30

Lys Phe Ile Glu Arg Gly Gln Lys Ile Asp Glu His Val Gln Arg Glu
        35                  40                  45

Ile Met Asn His Arg Ser Leu Lys His Pro Asn Ile Ile Arg Phe Lys
    50                  55                  60

Glu Val Leu Leu Thr Pro Thr His Leu Ala Ile Val Met Glu Tyr Ala
65                  70                  75                  80

Ser Gly Gly Glu Leu Phe Glu Arg Ile Cys Asn Ala Gly Arg Phe Ser
                85                  90                  95

Glu Asp Glu Ala Arg Phe Phe Gln Gln Leu Ile Ser Gly Val Ser
            100                 105                 110
```

Tyr Cys His Ser Met Gln Ile Cys His Arg Asp Leu Lys Leu Glu Asn
            115                 120                 125

Thr Leu Leu Asp Gly Ser Thr Ala Pro Arg Val Lys Ile Cys Asp Phe
130                 135                 140

Gly Tyr Ser Lys Ser Ser Val Leu His Ser Gln Pro Lys Ser Thr Val
145                 150                 155                 160

Gly Thr Pro Ala Tyr Ile Ala Pro Glu Val Leu Thr Arg Lys Glu Tyr
                165                 170                 175

Asp Gly Lys Ile Ala Asp Val Trp Ser Cys Gly Val Thr Leu Tyr Val
            180                 185                 190

Met Leu Val Gly Ala Tyr Pro Phe Glu Asp Pro Ala Asp Pro Arg Asn
            195                 200                 205

Phe Lys Lys Thr Ile Gly Lys Ile Leu Ser Val Gln Tyr Ser Val Pro
210                 215                 220

Asp Tyr Val Arg Val Ser Met Glu Cys Arg His Leu Leu Ser Gln Ile
225                 230                 235                 240

Phe Val Ala Ser Pro Glu Lys Arg Ile Thr Ile Pro Glu Ile Lys Asn
                245                 250                 255

His Pro Trp Phe Leu Arg Asn Leu Pro Met Glu Leu Thr Glu Gly Gly
            260                 265                 270

Ser Trp Gln Met Asn Asp Val Asn Asn Pro Ser Gln Asn Val Glu Glu
            275                 280                 285

Val Leu Ser Ile Ile Gln Glu Ala Arg Lys Ser Leu Asn Val Pro Lys
            290                 295                 300

Val Gly Gly Leu Leu Thr Gly Gly Ser Met Asp Leu Asp Phe Asp
305                 310                 315                 320

Ala Asp Glu Asp Leu Glu Asp Leu Glu Thr Ser Gly Glu Phe Val Cys
                325                 330                 335

Pro Ile

<210> SEQ ID NO 10
<211> LENGTH: 514
<212> TYPE: PRT
<213> ORGANISM: Glycine max

<400> SEQUENCE: 10

Met Met Ser Leu Cys Ser Ser Lys Gly Thr Cys Ser Gly Asp Thr Asn
1               5                   10                  15

Ala His Val Ser Ser Ser Thr Val Gly Asn Tyr Ser Ser Asp Lys Lys
            20                  25                  30

Arg His Asn Asn Lys Phe Ile Thr Phe Leu Arg Lys Thr Met Trp Glu
            35                  40                  45

Tyr Ala Leu Ala Cys Val Gly Val Val Pro Cys Gly Gly Asn Asn Asp
    50                  55                  60

Leu Asn Gly Gln Arg Lys Thr Thr Leu Glu His Asn Lys Ala Trp Leu
65              70                  75                  80

Leu Ala Asp Ser Gly Ala Glu Leu Ala Ser Ala Asp Pro Arg Ser Val
                85                  90                  95

His Ser Ser Phe Arg Phe Ser Phe Cys Ser Gly Val Glu Val Glu Ser
            100                 105                 110

Phe Asn Met Ser Tyr Ser Ala Ser Ala Ala Ala Thr Phe Leu
            115                 120                 125

Met Val Asn Leu Asp Tyr Glu Ser Gln Val Arg Glu Leu Lys Trp Arg
130                 135                 140

Arg Ile Gln Ser Leu Glu Lys Ser Leu Ser Pro Val Ala Asn Thr Leu
145                 150                 155                 160

Ile Arg Phe Ser Tyr Asp Glu Ile Leu Ser Ala Thr Arg Asn Phe Ser
            165                 170                 175

Lys Glu Arg Val Leu Gly Arg Gly Ala Leu Ser Cys Val Phe Arg Gly
        180                 185                 190

Arg Val Gly Ile Trp Arg Thr Ala Val Ala Ile Lys Arg Leu Asp Lys
    195                 200                 205

Glu Asp Lys Glu Cys Ala Lys Ala Phe Cys Arg Glu Leu Met Ile Ala
210                 215                 220

Ser Ser Leu Asn Asp Thr Asn Val Val Pro Leu Val Gly Phe Cys Ile
225                 230                 235                 240

Asp Ser Glu Glu Gly Leu Phe Leu Val Tyr Lys Tyr Val Ser Gly Gly
                245                 250                 255

Ser Leu Glu His His Leu His Gly Arg Lys Gly Val Lys Gly Ser
                260                 265                 270

Ser Pro Leu Pro Trp Ser Val Arg Tyr Glu Val Ala Ile Gly Ile Ala
        275                 280                 285

Glu Ala Val Ala Tyr Leu His Asn Gly Thr Glu Arg Cys Val Val His
290                 295                 300

Arg Asp Ile Lys Pro Ser Asn Ile Leu Leu Ser Ser Lys Lys Ile Pro
305                 310                 315                 320

Lys Leu Cys Asp Phe Gly Leu Ala Ser Trp Thr Ser Ala Pro Ser Val
                325                 330                 335

Pro Phe Leu Cys Lys Thr Val Lys Gly Thr Phe Gly Tyr Leu Ala Pro
                340                 345                 350

Glu Tyr Phe Glu His Gly Lys Val Ser Asp Lys Thr Asp Val Tyr Ala
                355                 360                 365

Leu Gly Val Val Leu Leu Glu Leu Leu Thr Gly Arg Asn Pro Ile Glu
    370                 375                 380

Ala Lys Arg Pro Pro Gly Glu Glu Asn Leu Val Val Trp Ala Lys Pro
385                 390                 395                 400

Leu Leu Arg Lys Gly Lys Gly Ala Ile Glu Glu Leu Leu Asp Pro Gln
                405                 410                 415

Val Lys Tyr Asn Ser Ser Tyr Thr Asp Gln Met Val Arg Met Ile Asp
                420                 425                 430

Ala Ala Ser Val Cys Val Thr Ser Glu Glu Ser Arg Arg Pro Ser Ile
                435                 440                 445

Gly Glu Ile Val Ala Ile Leu Lys Gly Val Glu His Val Leu Ser
        450                 455                 460

Arg Arg Arg Lys Ser Gly Tyr Phe Gly Asn Gly Tyr Met Ile Asp Asn
465                 470                 475                 480

Tyr Pro Lys Leu Gln Glu Thr Asn Asn Glu Met Lys Ser His Leu Ala
                485                 490                 495

Leu Ala Met Leu Gly Val Pro Glu Cys Glu Asp Asp Phe Val Tyr
                500                 505                 510

Cys Arg

<210> SEQ ID NO 11
<211> LENGTH: 517
<212> TYPE: PRT
<213> ORGANISM: Glycine max

<400> SEQUENCE: 11

```
Met Ile Leu Ile Asp Leu Leu Gln Pro Ile Met Ser Ser Asn Ser Ser
1               5                   10                  15

Leu Asn Met Glu Leu Ser Lys Lys Thr Ser Phe Leu Gly Leu Lys Arg
            20                  25                  30

Trp Val Leu Ile Gly Ile Gly Val Gly Ala Phe Ile Val Leu Ile Leu
                35                  40                  45

Cys Ile Leu Ser Ile Trp Ala Met Phe Arg Arg Lys Cys Arg Arg Ser
50                  55                  60

Leu Asp Lys Tyr Ser Val Ser Gln Ile Pro Asn Val Ser Lys Asp Ile
65                  70                  75                  80

Asp Val Asp Lys Val Gly Val Gln Ser Ser His Val Gln Pro Glu Asn
                85                  90                  95

Val Val Ile Pro Val His Asp Lys Ala Ser Asp Lys Asn Ser Asp Asn
                100                 105                 110

Val Ser Val His Leu Gly Lys Ser Lys Ser Gly Asp Pro Asp Asn Ile
            115                 120                 125

Ser Gln Cys Ser Ser Ile Tyr His His Glu Arg Gly Phe Ser Ser Met
        130                 135                 140

Ser Ala Glu Glu Gly Ser Ser Gly Asn Val Lys Lys Gln Ser Thr Leu
145                 150                 155                 160

Ser His Gly Gly Leu Ala Thr Ala Ser Pro Leu Val Gly Leu Pro Glu
                165                 170                 175

Phe Ser His Leu Gly Trp Gly His Trp Phe Thr Leu Arg Asp Leu Glu
                180                 185                 190

Met Ala Thr Asn Arg Phe Ser Ser Glu Asn Ile Ile Gly Glu Gly Gly
                195                 200                 205

Tyr Gly Ile Val Tyr Arg Gly Arg Leu Ile Asn Gly Thr Glu Val Ala
            210                 215                 220

Val Lys Lys Leu Leu Asn Asn Leu Gly Gln Ala Glu Lys Glu Phe Arg
225                 230                 235                 240

Val Glu Val Glu Ala Ile Gly His Val Arg His Lys His Leu Val Arg
                245                 250                 255

Leu Leu Gly Tyr Cys Val Glu Gly Val His Arg Leu Leu Val Tyr Glu
                260                 265                 270

Tyr Val Asn Asn Gly Asn Leu Glu Gln Trp Leu His Gly Asn Met His
            275                 280                 285

Gln Tyr Gly Thr Leu Thr Trp Glu Ala Arg Met Lys Val Ile Leu Gly
        290                 295                 300

Thr Ala Lys Ala Leu Ala Tyr Leu His Glu Ala Ile Glu Pro Lys Val
305                 310                 315                 320

Ile His Arg Asp Ile Lys Ser Ser Asn Ile Leu Ile Asp Asp Glu Phe
                325                 330                 335

Asn Ala Lys Val Ser Asp Phe Gly Leu Ala Lys Leu Leu Asp Ser Gly
                340                 345                 350

Glu Ser His Ile Thr Thr Arg Val Met Gly Thr Phe Gly Tyr Val Ala
            355                 360                 365

Pro Glu Tyr Ala Asn Ser Gly Leu Leu Asn Glu Lys Ser Asp Ile Tyr
        370                 375                 380

Ser Phe Gly Val Leu Leu Leu Glu Ala Val Thr Gly Arg Asp Pro Val
385                 390                 395                 400

Asp Tyr Ala Arg Pro Ala Asn Glu Val Asn Leu Val Glu Trp Leu Lys
                405                 410                 415
```

```
Thr Met Val Gly Thr Arg Arg Ala Glu Val Val Asp Ser Ser Leu
            420                 425                 430

Glu Val Lys Pro Pro Leu Arg Ala Leu Lys Arg Thr Leu Leu Val Ala
        435                 440                 445

Leu Arg Cys Ile Asp Pro Asp Ala Asp Lys Arg Pro Lys Met Ser Gln
    450                 455                 460

Val Val Arg Met Leu Glu Ala Asp Glu Tyr Pro Phe Arg Glu Asp Arg
465                 470                 475                 480

Arg Lys Arg Lys Ser Gly Thr Ala Ser Met Glu Ile Glu Thr Val Lys
                485                 490                 495

Asp Ile Ser Gly Pro Ser Asp Ala Glu Lys Met Val Ile Ser Glu Ser
            500                 505                 510

His Val Glu Glu Gly
        515

<210> SEQ ID NO 12
<211> LENGTH: 526
<212> TYPE: PRT
<213> ORGANISM: Glycine max

<400> SEQUENCE: 12

Met Pro Ser Arg Pro Pro Leu Ser Pro Ala Thr Ala Ala Ala
1               5                   10                  15

Ser His Arg Arg Glu Ile Ile Leu Cys Gly Ala Ile Gly Gly Ala Leu
                20                  25                  30

Phe Leu Thr Ala Leu Ile Ile Ser Val Met Ile Phe Ile Tyr Arg Lys
            35                  40                  45

Leu Ser Tyr Ser Arg Thr Ala Pro Phe Glu His Asn Gln Arg Arg Phe
    50                  55                  60

Ser Tyr Thr Val Leu Arg Arg Ala Thr Asn Ser Phe Ser Pro Ser Thr
65                  70                  75                  80

Lys Leu Gly His Gly Gly Phe Gly Ser Val His Lys Ala Thr Leu Pro
                85                  90                  95

Ser Gly Gln Thr Val Ala Leu Lys Val Met Asp Ser Pro Gly Ser Leu
            100                 105                 110

Gln Gly Glu Arg Glu Phe His Asn Glu Leu Thr Leu Cys Ser Asn Leu
        115                 120                 125

Lys Ser Pro Phe Val Ile Ser Leu Leu Gly Phe Ser Ser Asp Arg Arg
    130                 135                 140

Gly Lys Lys Leu Val Leu Val Tyr Glu Leu Met Pro Asn Arg Ser Leu
145                 150                 155                 160

Gln Asp Ala Leu Leu Asp Arg Arg Cys Pro Glu Leu Met Ser Trp Gly
                165                 170                 175

Lys Arg Phe Asp Val Ala Val Ser Ala Arg Gly Leu Glu Tyr Leu
            180                 185                 190

His His Val Cys Asp Pro Pro Val Ile His Gly Asp Ile Lys Pro Ser
        195                 200                 205

Asn Val Leu Leu Asp Arg Asp Phe Arg Ala Lys Ile Gly Asp Phe Gly
    210                 215                 220

Leu Ala Arg Val Lys Asn Val Glu Asp Leu Gly Met Val Asp Glu Asn
225                 230                 235                 240

Glu Lys Lys Lys Asp Glu Glu Phe Ser Val Leu Glu Gly Glu Ser Val
                245                 250                 255

Val Asp Val Asp Arg Ser Pro Glu Ser Cys Pro Val Arg Ala Ala Glu
            260                 265                 270
```

```
Tyr Ser Asp Ala Ser Pro Val Gly Gly Asp Lys Leu Ser Val Ser
        275                 280                 285

Asp Gly Gly Cys Phe Glu Ser Val Asp Ser Gly Ser Val Ser Val
    290                 295                 300

Asn Lys Lys Cys Gly Gly Gly Gly Gly Gly Ser Gly Arg
305                 310                 315                 320

Asp Trp Trp Arg Gln Glu Ser Gly Gly Gly Glu Ser Gly Arg
                325                 330                 335

Glu Gly Val Glu Gln Lys Lys Arg Lys Ser Lys Gly Ser Arg Gly
                340                 345                 350

Ser Ile Asp Trp Trp Leu Asp Gly Leu Ser Ala Lys Ile Gly Gly Phe
                355                 360                 365

Ser Gly Asp Val Pro Lys Ser Gly Gly Ile Ser Ser Thr Pro Ser Met
        370                 375                 380

Arg Gly Thr Val Cys Tyr Ile Ala Pro Glu Tyr Gly Gly Gly Gln
385                 390                 395                 400

Leu Ser Glu Lys Cys Asp Val Tyr Ser Phe Gly Val Leu Leu Leu Val
                405                 410                 415

Leu Val Ala Gly Arg Arg Pro Leu Gln Val Thr Ala Ser Pro Ile Ser
            420                 425                 430

Glu Phe Glu Arg Ala Asn Leu Ile Ser Trp Ala Arg Gln Leu Ala His
        435                 440                 445

Asn Gly Arg Leu Leu Asp Leu Val Asp Thr Ser Ile His Ser Leu Asp
    450                 455                 460

Lys Glu Gln Ala Leu Leu Cys Ile Thr Ile Ala Leu Leu Cys Leu Gln
465                 470                 475                 480

Arg Ser Pro Gly Lys Arg Pro Ser Ile Lys Glu Val Val Gly Met Leu
                485                 490                 495

Ser Gly Glu Ala Glu Pro Pro His Leu Pro Phe Glu Phe Ser Pro Ser
            500                 505                 510

Pro Pro Ser Asn Phe Pro Phe Lys Thr Arg Lys Lys Ala Arg
        515                 520                 525

<210> SEQ ID NO 13
<211> LENGTH: 436
<212> TYPE: PRT
<213> ORGANISM: Glycine max

<400> SEQUENCE: 13

Met Ser Asp Ser Asp Thr Arg Gln Asn Asp Ile Thr Lys Pro Leu Asp
1               5                   10                  15

Leu Glu Asn Leu Arg Val Val Ser Ala Val Gly Arg Gly Ala Lys Gly
            20                  25                  30

Val Val Phe Leu Ala Arg Thr Gly Asp Arg Ser Ser Glu Glu Cys Val
        35                  40                  45

Ala Leu Lys Val Ile Pro Lys Ala Leu Ile Leu Gln Lys Ala Lys Leu
    50                  55                  60

Ile Asn Asp Val Glu Tyr Thr Arg Val Ser Phe Glu Glu Gln Val Leu
65                  70                  75                  80

Arg Arg Phe Asp His Leu Leu Pro Arg Leu Arg Gly Val Phe Glu
                85                  90                  95

Thr Glu Lys Val Val Gly Phe Gly Ile Asp Tyr Cys His Gly Gly Thr
                100                 105                 110

Leu His Ser Leu Arg Lys Lys Gln Thr Glu Lys Met Phe Ser Asp Asp
```

```
                115                 120                 125
Thr Ile Arg Phe Tyr Ala Val Glu Leu Val Leu Ala Leu Glu Tyr Leu
            130                 135                 140

His Asn Leu Gly Ile Val Tyr Arg Asp Leu Lys Pro Glu Asn Val Met
145                 150                 155                 160

Ile Gln Asp Asn Gly His Ile Met Leu Val Asp Phe Asp Leu Ser Lys
                165                 170                 175

Lys Leu Asn Pro Lys Ser Pro His Ser Leu Ser Gln Asn Ser Ser Pro
            180                 185                 190

Ser Pro Asn Ser Lys Thr Lys Gln Thr Arg Lys Gln Arg Leu Met Arg
        195                 200                 205

Phe Tyr Ser Phe Cys Asn Ser Gly Ile Leu Pro Cys Asp Ser Asp Ser
        210                 215                 220

Glu Pro Pro Leu Ser Ser Val Asn Ser Val Arg His Thr Glu Ser Asp
225                 230                 235                 240

Leu Val Glu Lys Ser Asn Ser Phe Val Gly Thr Glu Glu Tyr Val Ala
                245                 250                 255

Pro Glu Ile Val Ser Gly Lys Gly His Gly Phe Ser Val Asp Trp Trp
            260                 265                 270

Ser Tyr Gly Val Val Leu Tyr Glu Met Leu Tyr Gly Thr Thr Pro Phe
        275                 280                 285

Lys Gly Ser Asn Arg Lys Glu Thr Phe Tyr Arg Ile Leu Met Lys Glu
        290                 295                 300

Pro Glu Leu Thr Gly Glu Lys Thr Ala Leu Arg Asp Leu Ile Gly Lys
305                 310                 315                 320

Leu Leu Glu Lys Asn Pro Asp Arg Arg Ile Gln Val Asn Glu Ile Lys
                325                 330                 335

Gly His Asn Phe Phe Lys Gly Val Lys Trp Asp Thr Val Leu His Ile
            340                 345                 350

Ala Arg Pro Pro Tyr Ile Pro Glu Asn Glu Val Glu Asn Lys Val Gly
        355                 360                 365

Phe Ser Lys Ser Asp Val Glu Val Phe Val Asp Asn Val Phe Phe Pro
        370                 375                 380

Thr Gly Asp Asp Gly Gly Glu Lys Thr Lys Thr Leu Leu Asp Asn Asn
385                 390                 395                 400

Asn Asn Asn Asn Asn Asn Asn Asn Asn Asn Asn Asn Asn Lys Val
                405                 410                 415

Trp Ile Asp Glu Leu Ser His Val Pro Ile Gly Lys Lys Asn Asp Asp
            420                 425                 430

Phe Leu Ile Phe
        435

<210> SEQ ID NO 14
<211> LENGTH: 603
<212> TYPE: PRT
<213> ORGANISM: Glycine max

<400> SEQUENCE: 14

Met Glu Gln Tyr Glu Ile Leu Glu Gln Ile Gly Lys Gly Ala Phe Gly
1               5                   10                  15

Ser Ala Leu Leu Val Arg His Lys His Glu Lys Lys Tyr Val Leu
            20                  25                  30

Lys Lys Ile Arg Leu Ala Arg Gln Thr Asp Arg Thr Arg Arg Ser Ala
        35                  40                  45
```

```
His Gln Glu Met Glu Leu Ile Ser Lys Val Arg Asn Pro Phe Ile Val
    50              55                  60
Glu Tyr Lys Asp Ser Trp Val Glu Lys Gly Cys Phe Val Cys Ile Ile
 65              70                  75                      80
Ile Gly Tyr Cys Glu Gly Gly Asp Met Ala Glu Ala Ile Lys Lys Ala
                 85                  90                  95
Asn Gly Ile Asn Phe Pro Glu Glu Lys Leu Cys Lys Trp Leu Val Gln
            100                 105                 110
Leu Leu Met Ala Leu Asp Tyr Leu His Gly Asn His Ile Leu His Arg
            115                 120                 125
Asp Val Lys Cys Ser Asn Ile Phe Leu Thr Lys Asp Gln Asp Ile Arg
130                 135                 140
Leu Gly Asp Phe Gly Leu Ala Lys Met Leu Ser Ser Asp Asp Leu Ala
145                 150                 155                 160
Ser Ser Val Val Gly Thr Pro Ser Tyr Met Cys Pro Glu Leu Leu Ala
                165                 170                 175
Asp Ile Pro Tyr Gly Ser Lys Ser Asp Ile Trp Ser Leu Gly Cys Cys
            180                 185                 190
Ile Tyr Glu Met Ala Ala Tyr Lys Pro Ala Phe Lys Ala Phe Asp Ile
            195                 200                 205
Gln Ser Leu Leu Ile Lys Ile Asn Lys Cys Ile Val Ser Pro Met Pro
210                 215                 220
Thr Met Tyr Ser Ala Ala Phe Arg Gly Leu Val Lys Ser Met Leu Arg
225                 230                 235                 240
Lys Asn Pro Glu Leu Arg Pro Thr Ala Ala Glu Leu Leu Asn His Pro
                245                 250                 255
His Leu Gln Pro Tyr Ile His Lys Ile Gln Leu Lys Leu Asn Ser Pro
            260                 265                 270
Arg Arg Ser Thr Phe Pro Phe Gln Trp Pro Glu Ser Asn Tyr Val Arg
            275                 280                 285
Arg Thr Arg Phe Val Asp Pro Glu Ser Val Tyr Thr Leu Ser Asp Leu
            290                 295                 300
Asp Lys Cys Leu Ser Phe Ser Asn Asp Met Ala Leu Asn Pro Ser Val
305                 310                 315                 320
Ser Gly Thr Glu Gln Val Ser Gln Cys Ser Thr Gln Arg Ala His Gly
                325                 330                 335
Leu Ser Thr Cys Ser Lys Glu Lys Ile Tyr Glu Leu Ser Val Gly Cys
            340                 345                 350
Val Arg Glu Lys Tyr Lys Thr Asp Lys Ser Lys Ala Ser Lys Phe Ser
            355                 360                 365
Thr Val Glu Arg Thr Pro Arg Ser Arg Ala Val Thr Val Ser Ala Thr
            370                 375                 380
Thr Lys Arg His Thr Ile Ala Thr Ser Lys Thr Thr His Ser Gly Pro
385                 390                 395                 400
Lys Arg Asp Ser Leu Pro Ala Ser His Ala Pro Ser Lys Arg Phe Ser
                405                 410                 415
Thr Pro Pro Arg Thr Arg Ala Arg Ala Thr Pro Asn Leu Tyr Thr Asn
            420                 425                 430
Val Leu Gly Ser Leu Asp Ser Leu Asp Val Ser Ile Asn Ala Pro Arg
            435                 440                 445
Ile Asp Lys Ile Val Glu Phe Pro Met Ala Phe Cys Glu Asp Pro Phe
450                 455                 460
Ser Pro Ile Arg Gly Pro Ser Ser Thr Ser Ala Arg Cys Ser Ser Ser
```

```
            465                 470                 475                 480
Ser Ala Gly Ser Thr Ala Asp Cys Ser Ile Thr Lys Asp Lys Cys Thr
                    485                 490                 495

Ile Gln Glu Asp Lys Val Thr Leu Pro Thr Ser Ile Thr Asp Ala Cys
                500                 505                 510

Pro Ala Pro Lys Glu Thr Lys Cys Ser Tyr Glu His Val Lys Asp Cys
                515                 520                 525

Val Ser Ser His Ser Ser Thr Asp Leu Asp Gln Arg Arg Phe Asp Thr
            530                 535                 540

Ser Ser Tyr Gln Gln Arg Ala Glu Ala Leu Glu Gly Leu Leu Glu Phe
545                 550                 555                 560

Ser Ala Arg Leu Leu Gln Gln Gln Arg Phe Asp Glu Leu Gly Val Leu
                565                 570                 575

Leu Lys Pro Phe Gly Leu Glu Lys Val Ser Pro Arg Glu Thr Ala Ile
                580                 585                 590

Trp Leu Thr Lys Ser Phe Lys Gln Thr Ala Val
                595                 600
```

<210> SEQ ID NO 15
<211> LENGTH: 674
<212> TYPE: PRT
<213> ORGANISM: Glycine max

<400> SEQUENCE: 15

```
Met Lys Lys Val Cys His Cys Pro Ile Phe Leu Ala Leu Ala Leu Cys
1               5                   10                  15

Leu Cys Ile Leu Cys Val Ala Ala Glu Ala Ala Gly Gln Asn Asp Thr
                20                  25                  30

Leu Ala Leu Thr Glu Phe Arg Leu Gln Thr Asp Thr His Gly Asn Leu
            35                  40                  45

Leu Thr Asn Trp Thr Gly Ala Asp Ala Cys Ser Ala Ala Trp Arg Gly
        50                  55                  60

Val Glu Cys Ser Pro Asn Gly Arg Val Val Gly Leu Thr Leu Pro Ser
65                  70                  75                  80

Leu Asn Leu Arg Gly Pro Ile Asp Thr Leu Ser Thr Leu Thr Tyr Leu
                85                  90                  95

Arg Phe Leu Asp Leu His Glu Asn Arg Leu Asn Gly Thr Ile Ser Pro
                100                 105                 110

Leu Leu Asn Cys Thr Ser Leu Glu Leu Leu Tyr Leu Ser Arg Asn Asp
            115                 120                 125

Phe Ser Gly Glu Ile Pro Ala Glu Ile Ser Ser Leu Arg Leu Leu Leu
        130                 135                 140

Arg Leu Asp Ile Ser Asp Asn Asn Ile Arg Gly Pro Ile Pro Thr Gln
145                 150                 155                 160

Leu Ala Lys Leu Thr His Leu Leu Thr Leu Arg Leu Gln Asn Asn Ala
                165                 170                 175

Leu Ser Gly His Val Pro Asp Leu Ser Ala Leu Leu Asn Leu Thr
                180                 185                 190

Val Leu Asn Val Thr Asn Asn Glu Leu Arg Gly His Val Pro Asp Ser
            195                 200                 205

Met Leu Thr Lys Phe Gly Asn Val Ser Phe Ser Gly Asn His Ala Leu
        210                 215                 220

Cys Gly Ser Thr Pro Leu Pro Lys Cys Ser Glu Thr Glu Pro Asp Thr
225                 230                 235                 240
```

```
Glu Thr Thr Thr Ile Thr Val Pro Ala Lys Pro Ser Ser Phe Pro Gln
                    245                 250                 255

Thr Ser Ser Val Thr Val Pro Asp Thr Pro Arg Lys Lys Gly Leu Ser
            260                 265                 270

Ala Gly Val Ile Val Ala Ile Val Val Ala Val Cys Val Ala Val Leu
            275                 280                 285

Val Ala Thr Ser Phe Ala Val Ala His Cys Cys Ala Arg Gly Ser Thr
        290                 295                 300

Ser Gly Ser Val Val Gly Ser Glu Thr Ala Lys Arg Lys Ser Gly Ser
305                 310                 315                 320

Ser Ser Gly Ser Glu Lys Lys Val Tyr Gly Asn Gly Gly Asn Leu Asp
                325                 330                 335

Arg Asp Ser Asp Gly Thr Asn Thr Glu Thr Glu Arg Ser Lys Leu Val
            340                 345                 350

Phe Phe Asp Arg Arg Asn Gln Phe Glu Leu Glu Asp Leu Leu Arg Ala
        355                 360                 365

Ser Ala Glu Met Leu Gly Lys Gly Ser Leu Gly Thr Val Tyr Arg Ala
        370                 375                 380

Val Leu Asp Asp Gly Cys Thr Val Ala Val Lys Arg Leu Lys Asp Ala
385                 390                 395                 400

Asn Pro Cys Glu Arg Asn Glu Phe Glu Gln Tyr Met Asp Val Val Gly
                405                 410                 415

Lys Leu Lys His Pro Asn Ile Val Arg Leu Arg Ala Tyr Tyr Tyr Ala
            420                 425                 430

Lys Glu Glu Lys Leu Leu Val Tyr Asp Tyr Leu Pro Asn Gly Ser Leu
            435                 440                 445

His Ala Leu Leu His Gly Asn Arg Gly Pro Gly Arg Ile Pro Leu Asp
        450                 455                 460

Trp Thr Thr Arg Ile Ser Leu Met Leu Gly Ala Ala Arg Gly Leu Ala
465                 470                 475                 480

Arg Ile His Ala Glu Tyr Asn Ala Ser Lys Ile Pro His Gly Asn Val
                485                 490                 495

Lys Ser Ser Asn Val Leu Leu Asp Lys Asn Gly Val Ala Leu Ile Ser
            500                 505                 510

Asp Phe Gly Leu Ser Leu Leu Asn Pro Val His Ala Ile Ala Arg
        515                 520                 525

Leu Gly Gly Tyr Arg Ala Pro Glu Gln Val Glu Val Lys Arg Leu Ser
        530                 535                 540

Gln Glu Ala Asp Val Tyr Gly Phe Gly Val Leu Leu Leu Glu Val Leu
545                 550                 555                 560

Thr Gly Arg Ala Pro Ser Lys Glu Tyr Thr Ser Pro Ala Arg Glu Ala
            565                 570                 575

Glu Val Asp Leu Pro Lys Trp Val Lys Ser Val Val Lys Glu Glu Trp
            580                 585                 590

Thr Ser Glu Val Phe Asp Gln Glu Leu Leu Arg Tyr Lys Asn Ile Glu
        595                 600                 605

Asp Glu Leu Val Ala Met Leu His Val Gly Leu Ala Cys Val Ala Ala
        610                 615                 620

Gln Ala Glu Lys Arg Pro Cys Met Leu Glu Val Lys Met Ile Glu
625                 630                 635                 640

Glu Ile Arg Val Glu Glu Ser Pro Leu Gly Asp Asp Tyr Asp Glu Ala
                645                 650                 655

Arg Ser Arg Thr Ser Leu Ser Pro Ser Leu Ala Thr Thr Glu Asp Asn
```

-continued

```
                660                 665                 670

Leu Ala

<210> SEQ ID NO 16
<211> LENGTH: 982
<212> TYPE: PRT
<213> ORGANISM: Glycine max

<400> SEQUENCE: 16

Met Ala Lys Gly Ser Tyr Ser Ile Ser Ser Lys Ala Arg Ser Met Lys
1               5                   10                  15

Phe Ile Phe Leu Phe Met Phe Met Leu Asn Phe Ile Leu Ser Asp Gly
            20                  25                  30

Asp Gln His Glu Val Gln Leu Leu Ser Phe Lys Ala Ser Leu His
        35                  40                  45

Asp Pro Leu His Phe Leu Ser Asn Trp Val Ser Phe Thr Ser Ser Ala
    50                  55                  60

Thr Ile Cys Lys Trp His Gly Ile Asn Cys Asp Asn Asn Ala Asn Ser
65                  70                  75                  80

Ser His Val Asn Ala Val Val Leu Ser Gly Lys Asn Ile Thr Gly Glu
                85                  90                  95

Val Ser Ser Ser Ile Phe Gln Leu Pro Tyr Leu Thr Asn Leu Asp Leu
            100                 105                 110

Ser Asn Asn Gln Leu Val Gly Glu Ile Thr Phe Thr His Ser His Asn
        115                 120                 125

Ser Leu Ser Gln Ile Arg Tyr Leu Asn Leu Ser Asn Asn Asn Leu Thr
    130                 135                 140

Gly Ser Leu Pro Gln Pro Leu Phe Ser Val Leu Phe Ser Asn Leu Glu
145                 150                 155                 160

Thr Leu Asp Leu Ser Asn Asn Met Phe Ser Gly Asn Ile Pro Asp Gln
                165                 170                 175

Ile Gly Leu Leu Ser Ser Leu Arg Tyr Leu Asp Leu Gly Gly Asn Val
            180                 185                 190

Leu Val Gly Lys Ile Pro Asn Ser Ile Thr Asn Met Thr Ala Leu Glu
        195                 200                 205

Tyr Leu Thr Leu Ala Ser Asn Gln Leu Val Asp Lys Ile Pro Glu Glu
    210                 215                 220

Ile Gly Ala Met Lys Ser Leu Lys Trp Ile Tyr Leu Gly Tyr Asn Asn
225                 230                 235                 240

Leu Ser Gly Glu Ile Pro Ser Ser Ile Gly Glu Leu Leu Ser Leu Asn
                245                 250                 255

His Leu Asp Leu Val Tyr Asn Asn Leu Thr Gly Leu Ile Pro His Ser
            260                 265                 270

Leu Gly His Leu Thr Glu Leu Gln Tyr Leu Phe Leu Tyr Gln Asn Lys
        275                 280                 285

Leu Ser Gly Pro Ile Pro Gly Ser Ile Phe Glu Leu Lys Lys Met Ile
    290                 295                 300

Ser Leu Asp Leu Ser Asp Asn Ser Leu Ser Gly Glu Ile Ser Glu Arg
305                 310                 315                 320

Val Val Lys Leu Gln Ser Leu Glu Ile Leu His Leu Phe Ser Asn Lys
                325                 330                 335

Phe Thr Gly Lys Ile Pro Lys Gly Val Ala Ser Leu Pro Arg Leu Gln
            340                 345                 350

Val Leu Gln Leu Trp Ser Asn Gly Leu Thr Gly Glu Ile Pro Glu Glu
```

```
            355                 360                 365
Leu Gly Lys His Ser Asn Leu Thr Val Leu Asp Leu Ser Thr Asn Asn
370                 375                 380
Leu Ser Gly Lys Ile Pro Asp Ser Ile Cys Tyr Ser Gly Ser Leu Phe
385                 390                 395                 400
Lys Leu Ile Leu Phe Ser Asn Ser Phe Glu Gly Ile Pro Lys Ser
                    405                 410                 415
Leu Thr Ser Cys Arg Ser Leu Arg Arg Val Arg Leu Gln Thr Asn Lys
                420                 425                 430
Phe Ser Gly Asn Leu Pro Ser Glu Leu Ser Thr Leu Pro Arg Val Tyr
            435                 440                 445
Phe Leu Asp Ile Ser Gly Asn Gln Leu Ser Gly Arg Ile Asp Asp Arg
        450                 455                 460
Lys Trp Asp Met Pro Ser Leu Gln Met Leu Ser Leu Ala Asn Asn Asn
465                 470                 475                 480
Phe Ser Gly Glu Ile Pro Asn Ser Phe Gly Thr Gln Asn Leu Glu Asp
                    485                 490                 495
Leu Asp Leu Ser Tyr Asn His Phe Ser Gly Ser Ile Pro Leu Gly Phe
                500                 505                 510
Arg Ser Leu Pro Glu Leu Val Glu Leu Met Leu Ser Asn Asn Lys Leu
            515                 520                 525
Phe Gly Asn Ile Pro Glu Glu Ile Cys Ser Cys Lys Lys Leu Val Ser
        530                 535                 540
Leu Asp Leu Ser Gln Asn Gln Leu Ser Gly Glu Ile Pro Val Lys Leu
545                 550                 555                 560
Ser Glu Met Pro Val Leu Gly Leu Leu Asp Leu Ser Gln Asn Gln Phe
                    565                 570                 575
Ser Gly Gln Ile Pro Gln Asn Leu Gly Ser Val Glu Ser Leu Val Gln
                580                 585                 590
Val Asn Ile Ser His Asn His Phe His Gly Ser Leu Pro Ser Thr Gly
            595                 600                 605
Ala Phe Leu Ala Ile Asn Ala Ser Ala Val Ile Gly Asn Asn Leu Cys
        610                 615                 620
Asp Arg Asp Gly Asp Ala Ser Ser Gly Leu Pro Pro Cys Lys Asn Asn
625                 630                 635                 640
Asn Gln Asn Pro Thr Trp Leu Phe Ile Met Leu Cys Phe Leu Leu Ala
                    645                 650                 655
Leu Val Ala Phe Ala Ala Ala Ser Phe Leu Val Leu Tyr Val Arg Lys
                660                 665                 670
Arg Lys Asn Phe Ser Glu Val Arg Arg Val Glu Asn Glu Asp Gly Thr
            675                 680                 685
Trp Glu Val Lys Phe Phe Tyr Ser Lys Ala Ala Arg Leu Ile Asn Val
        690                 695                 700
Asp Asp Val Leu Lys Thr Val Lys Glu Gly Lys Val Val Ser Lys Gly
705                 710                 715                 720
Thr Asn Trp Val Trp Tyr Glu Gly Lys Cys Met Glu Asn Asp Met Gln
                    725                 730                 735
Phe Val Val Lys Glu Ile Ser Asp Leu Asn Ser Leu Pro Leu Ser Met
                740                 745                 750
Trp Glu Glu Thr Val Lys Ile Arg Lys Val Arg His Pro Asn Ile Ile
            755                 760                 765
Asn Leu Ile Ala Thr Cys Arg Cys Gly Lys Arg Gly Tyr Leu Val Tyr
        770                 775                 780
```

Glu His Glu Glu Gly Glu Lys Leu Ser Glu Ile Val Asn Ser Leu Ser
785                 790                 795                 800

Trp Gln Arg Arg Cys Lys Ile Ala Val Gly Val Ala Lys Ala Leu Lys
                805                 810                 815

Phe Leu His Ser Gln Ala Ser Ser Met Leu Leu Val Gly Val Ser
        820                 825                 830

Pro Glu Ile Val Trp Val Asp Ala Lys Gly Val Pro Arg Leu Lys Val
        835                 840                 845

Thr Pro Pro Leu Met Pro Cys Leu Asp Val Lys Gly Phe Val Ser Ser
850                 855                 860

Pro Tyr Val Ala Gln Glu Val Ile Glu Arg Lys Asn Val Thr Glu Lys
865                 870                 875                 880

Ser Glu Ile Tyr Gly Phe Gly Val Met Leu Val Glu Leu Leu Thr Gly
                885                 890                 895

Arg Ser Ala Met Asp Ile Glu Ala Gly Asn Gly Met His Lys Thr Ile
                900                 905                 910

Val Glu Trp Ala Arg Tyr Cys Tyr Ser Asp Cys His Leu Asp Thr Trp
                915                 920                 925

Ile Asp Pro Val Met Lys Gly Gly Asp Ala Leu Arg Tyr Gln Asn Asp
        930                 935                 940

Ile Val Glu Met Met Asn Leu Ala Leu His Cys Thr Ala Thr Asp Pro
945                 950                 955                 960

Thr Ala Arg Pro Cys Ala Arg Asp Val Leu Lys Ala Leu Glu Thr Val
                965                 970                 975

His Arg Thr Thr Phe Cys
                980

<210> SEQ ID NO 17
<211> LENGTH: 978
<212> TYPE: PRT
<213> ORGANISM: Glycine max

<400> SEQUENCE: 17

Met Gln Ala Leu Phe Ser Ser Met Arg Val Phe Leu Arg Leu Val Trp
1               5                   10                  15

Leu Leu Glu Leu Leu Cys Val Ala Val Thr Ala Val Asn Pro Ser Leu
                20                  25                  30

Asn Asp Asp Val Leu Gly Leu Ile Val Phe Lys Ala Asp Ile Arg Asp
            35                  40                  45

Pro Lys Gly Lys Leu Ala Ser Trp Asn Glu Asp Glu Ser Ala Cys
        50                  55                  60

Gly Gly Ser Trp Val Gly Val Lys Cys Asn Pro Arg Ser Asn Arg Val
65                  70                  75                  80

Val Glu Val Asn Leu Asp Gly Phe Ser Leu Ser Gly Arg Ile Gly Arg
                85                  90                  95

Gly Leu Gln Arg Leu Gln Phe Leu Arg Lys Leu Ser Leu Ala Asn Asn
                100                 105                 110

Asn Leu Thr Gly Gly Ile Asn Pro Asn Ile Ala Arg Ile Asp Asn Leu
            115                 120                 125

Arg Val Ile Asp Leu Ser Gly Asn Ser Leu Ser Gly Glu Val Ser Glu
    130                 135                 140

Asp Val Phe Arg Gln Cys Gly Ser Leu Arg Thr Val Ser Leu Ala Arg
145                 150                 155                 160

Asn Arg Phe Ser Gly Ser Ile Pro Ser Thr Leu Gly Ala Cys Ser Ala

```
                165                 170                 175
Leu Ala Ala Ile Asp Leu Ser Asn Asn Gln Phe Ser Gly Ser Val Pro
            180                 185                 190

Ser Arg Val Trp Ser Leu Ser Ala Leu Arg Ser Leu Asp Leu Ser Asp
        195                 200                 205

Asn Leu Leu Glu Gly Glu Ile Pro Lys Gly Ile Glu Ala Met Lys Asn
    210                 215                 220

Leu Arg Ser Val Ser Val Ala Arg Asn Arg Leu Thr Gly Asn Val Pro
225                 230                 235                 240

Tyr Gly Phe Gly Ser Cys Leu Leu Arg Ser Ile Asp Leu Gly Asp
            245                 250                 255

Asn Ser Phe Ser Gly Ser Ile Pro Gly Asp Phe Lys Glu Leu Thr Leu
            260                 265                 270

Cys Gly Tyr Ile Ser Leu Arg Gly Asn Ala Phe Ser Gly Val Pro
            275                 280                 285

Gln Trp Ile Gly Glu Met Arg Gly Leu Glu Thr Leu Asp Leu Ser Asn
        290                 295                 300

Asn Gly Phe Thr Gly Gln Val Pro Ser Ser Ile Gly Asn Leu Gln Ser
305                 310                 315                 320

Leu Lys Met Leu Asn Phe Ser Gly Asn Gly Leu Thr Gly Ser Leu Pro
            325                 330                 335

Glu Ser Met Ala Asn Cys Thr Lys Leu Leu Val Leu Asp Val Ser Arg
        340                 345                 350

Asn Ser Met Ser Gly Trp Leu Pro Leu Trp Val Phe Lys Ser Asp Leu
        355                 360                 365

Asp Lys Val Leu Val Ser Glu Asn Val Gln Ser Gly Ser Lys Lys Ser
    370                 375                 380

Pro Leu Phe Ala Met Ala Glu Leu Ala Val Gln Ser Leu Gln Val Leu
385                 390                 395                 400

Asp Leu Ser His Asn Ala Phe Ser Gly Glu Ile Thr Ser Ala Val Gly
            405                 410                 415

Gly Leu Ser Ser Leu Gln Val Leu Asn Leu Ala Asn Asn Ser Leu Gly
            420                 425                 430

Gly Pro Ile Pro Pro Ala Val Gly Glu Leu Lys Thr Cys Ser Ser Leu
        435                 440                 445

Asp Leu Ser Tyr Asn Lys Leu Asn Gly Ser Ile Pro Trp Glu Ile Gly
        450                 455                 460

Gly Ala Val Ser Leu Lys Glu Leu Val Leu Glu Lys Asn Phe Leu Asn
465                 470                 475                 480

Gly Lys Ile Pro Thr Ser Ile Glu Asn Cys Ser Leu Leu Thr Thr Leu
            485                 490                 495

Ile Leu Ser Gln Asn Lys Leu Ser Gly Pro Ile Pro Ala Ala Val Ala
            500                 505                 510

Lys Leu Thr Asn Leu Gln Thr Val Asp Val Ser Phe Asn Asn Leu Thr
        515                 520                 525

Gly Ala Leu Pro Lys Gln Leu Ala Asn Leu Ala Asn Leu Leu Thr Phe
        530                 535                 540

Asn Leu Ser His Asn Leu Gln Gly Glu Leu Pro Ala Gly Gly Phe
545                 550                 555                 560

Phe Asn Thr Ile Thr Pro Ser Ser Val Ser Gly Asn Pro Ser Leu Cys
            565                 570                 575

Gly Ala Ala Val Asn Lys Ser Cys Pro Ala Val Leu Pro Lys Pro Ile
            580                 585                 590
```

Val Leu Asn Pro Asn Thr Ser Thr Asp Thr Gly Pro Ser Ser Leu Pro
                595                 600                 605

Pro Asn Leu Gly His Lys Arg Ile Ile Leu Ser Ile Ser Ala Leu Ile
            610                 615                 620

Ala Ile Gly Ala Ala Val Ile Val Ile Gly Val Ile Ser Ile Thr
625                 630                 635                 640

Val Leu Asn Leu Arg Val Arg Ser Ser Thr Ser Arg Asp Ala Ala Ala
                645                 650                 655

Leu Thr Phe Ser Ala Gly Asp Glu Phe Ser His Ser Pro Thr Thr Asp
                660                 665                 670

Ala Asn Ser Gly Lys Leu Val Met Phe Ser Gly Glu Pro Asp Phe Ser
            675                 680                 685

Ser Gly Ala His Ala Leu Leu Asn Lys Asp Cys Glu Leu Gly Arg Gly
            690                 695                 700

Gly Phe Gly Ala Val Tyr Gln Thr Val Leu Arg Asp Gly His Ser Val
705                 710                 715                 720

Ala Ile Lys Lys Leu Thr Val Ser Ser Leu Val Lys Ser Gln Glu Asp
                725                 730                 735

Phe Glu Arg Glu Val Lys Lys Leu Gly Lys Ile Arg His Gln Asn Leu
            740                 745                 750

Val Glu Leu Glu Gly Tyr Tyr Trp Thr Pro Ser Leu Gln Leu Leu Ile
            755                 760                 765

Tyr Glu Tyr Leu Ser Gly Gly Ser Leu Tyr Lys His Leu His Glu Gly
            770                 775                 780

Ser Gly Gly Asn Phe Leu Ser Trp Asn Glu Arg Phe Asn Val Ile Leu
785                 790                 795                 800

Gly Thr Ala Lys Ala Leu Ala His Leu His His Ser Asn Ile Ile His
                805                 810                 815

Tyr Asn Ile Lys Ser Thr Asn Val Leu Leu Asp Ser Tyr Gly Glu Pro
            820                 825                 830

Lys Val Gly Asp Phe Gly Leu Ala Arg Leu Leu Pro Met Leu Asp Arg
            835                 840                 845

Tyr Val Leu Ser Ser Lys Ile Gln Ser Ala Leu Gly Tyr Met Ala Pro
            850                 855                 860

Glu Phe Ala Cys Lys Thr Val Lys Ile Thr Glu Lys Cys Asp Val Tyr
865                 870                 875                 880

Gly Phe Gly Val Leu Val Leu Glu Ile Val Thr Gly Lys Arg Pro Val
                885                 890                 895

Glu Tyr Met Glu Asp Asp Val Val Leu Cys Asp Met Val Arg Gly
            900                 905                 910

Ala Leu Glu Glu Gly Arg Val Glu Glu Cys Ile Asp Glu Arg Leu Gln
            915                 920                 925

Gly Lys Phe Pro Ala Glu Glu Ala Ile Pro Val Met Lys Leu Gly Leu
            930                 935                 940

Ile Cys Thr Ser Gln Val Pro Ser Asn Arg Pro Asp Met Gly Glu Val
945                 950                 955                 960

Val Asn Ile Leu Glu Leu Ile Arg Cys Pro Ser Glu Gly Gln Glu Glu
                965                 970                 975

Leu Ala

<210> SEQ ID NO 18
<211> LENGTH: 676
<212> TYPE: PRT

<213> ORGANISM: Glycine max

<400> SEQUENCE: 18

```
Met Glu His Val Leu Glu Lys Arg Phe Pro Leu Asn Ala Glu Asp Tyr
1               5                   10                  15
Thr Leu Tyr Glu Glu Val Gly Glu Gly Val Ser Ala Ser Val Tyr Arg
            20                  25                  30
Ala Leu Cys Val Pro Leu Asn Glu Ile Val Ala Ile Lys Val Leu Asp
        35                  40                  45
Leu Glu Lys Cys Asn Asn Asp Leu Asp Gly Ile Arg Arg Glu Val Gln
    50                  55                  60
Thr Met Asn Leu Ile Asp Tyr Pro Asn Val Leu Arg Ala His Cys Ser
65                  70                  75                  80
Phe Thr Ala Gly His Asn Leu Trp Val Met Pro Tyr Met Ala Gly
                85                  90                  95
Gly Ser Cys Leu His Ile Met Lys Ser Asn Tyr Pro Glu Gly Phe Glu
            100                 105                 110
Glu Pro Val Ile Ala Thr Leu His Glu Val Leu Lys Ala Leu Val
        115                 120                 125
Tyr Leu His Ala His Gly His Ile His Arg Asp Val Lys Ala Gly Asn
    130                 135                 140
Ile Leu Leu Asp Ser Asn Gly Ala Val Lys Leu Ala Asp Phe Gly Val
145                 150                 155                 160
Ser Ala Cys Met Phe Asp Thr Gly Asp Arg Gln Arg Ser Arg Asn Thr
                165                 170                 175
Phe Val Gly Thr Pro Cys Trp Met Ala Pro Glu Val Met Gln Gln Leu
            180                 185                 190
His Gly Tyr Asp Phe Lys Ala Asp Ile Trp Ser Phe Gly Ile Thr Ala
        195                 200                 205
Leu Glu Leu Ala His Gly His Ala Pro Phe Ser Lys Tyr Pro Pro Met
    210                 215                 220
Lys Val Leu Leu Met Thr Leu Gln Asn Ala Pro Pro Gly Leu Asp Tyr
225                 230                 235                 240
Glu Arg Asp Lys Lys Phe Ser Lys Ala Phe Lys Glu Leu Val Ala Thr
                245                 250                 255
Cys Leu Val Lys Asp Pro Lys Lys Arg Pro Ser Ser Glu Lys Leu Leu
            260                 265                 270
Lys His His Phe Phe Lys Gln Ala Arg Ala Ser Lys Tyr Leu Ala Arg
        275                 280                 285
Thr Ile Leu Glu Gly Leu Ala Pro Leu Gly Asp Arg Phe Arg Met Leu
    290                 295                 300
Lys Ala Lys Glu Ala Asp Leu Leu Val Gln Asn Lys Ala Leu Tyr Glu
305                 310                 315                 320
Asp Lys Asp Gln Leu Ser Gln Lys Glu Tyr Ile Arg Gly Ile Ser Ala
                325                 330                 335
Trp Asn Phe Asn Leu Glu Asp Leu Lys Ser Gln Ala Ala Leu Ile Gln
            340                 345                 350
Asp Asp Asp Ile Pro Asn Ala Glu Glu Pro Gln Arg Asp Lys Lys Gln
        355                 360                 365
Lys Asp Arg Leu Asp Asn Phe Lys Val Ser Ala Glu Arg Leu Ser Ala
    370                 375                 380
Gly Ala Ala Asn His Ser Asp Asp Ala Pro Thr Gln Asp Lys Glu Asp
385                 390                 395                 400
```

-continued

Leu His Leu Leu Phe Gln Asp Gly Phe Asn Asn Leu Gln Asp Leu Glu
            405                 410                 415

Gly Ser Leu Val Ser Phe Pro Thr Lys Pro Leu Gln Ala Leu Lys Gly
        420                 425                 430

Cys Phe Asp Met Cys Glu Asp Ile Asn Asn Ser Ser Pro Arg Asp
        435                 440                 445

Leu Asp His Asp Gly Arg Ile Asp Asn Glu Ser Ser Arg Pro Ser Thr
    450                 455                 460

Ser Leu Gln Gln Asn Thr Thr Ser Gln Gln Lys Lys Phe Pro Ser Gly
465                 470                 475                 480

Ser Leu Leu Pro Asp Asn Phe Leu Phe Pro Lys Met Val Val Thr Asp
            485                 490                 495

Gly Asp Arg Asp Tyr Leu Gln Thr Lys Tyr Ser Ser Glu Arg Asn His
        500                 505                 510

Ser Gly Pro Leu Gln Tyr Arg Gln Lys Arg Asp Thr Asn Asn Leu Pro
    515                 520                 525

Leu Val Asp Asp Thr Ser Asp Gly Ala Phe Phe Arg Arg Arg Gly Arg
    530                 535                 540

Phe Thr Leu Thr Asp Leu Ser Pro Met Gly Pro Ser Asn Ser Thr Ser
545                 550                 555                 560

Gly Pro Val Val Ser Pro Thr Ser Pro Pro Asn Gln Asn Phe Met Ser
            565                 570                 575

Thr Ala Ile Leu Pro Ser Leu Gln Cys Ile Leu Gln His Asn Gly Leu
        580                 585                 590

Gln Arg Glu Glu Ile Ile Lys Leu Ile Lys Tyr Ala Glu Gln Ser Ser
    595                 600                 605

Gly Lys Asn Thr Glu Ser Val Glu Ala Gly Thr Gly Asp Met Leu Gln
610                 615                 620

Ala Pro Pro Ala Thr Thr Arg Glu Arg Glu Leu His Phe Gln Val Ile
625                 630                 635                 640

Gln Leu Gln Gln Ser Ile Gly Ser Leu Val Glu Glu Leu Gln Arg Gln
            645                 650                 655

Lys Met Lys Asn Val Gln Leu Glu Lys Gln Leu Asn Ser Met Ala Asn
        660                 665                 670

Arg Val Glu Lys
        675

<210> SEQ ID NO 19
<211> LENGTH: 518
<212> TYPE: PRT
<213> ORGANISM: Glycine max

<400> SEQUENCE: 19

Met Gly Asn Cys Ser Ser Gly Ala Gly Ala Pro Thr Thr Tyr Ser Asp
1               5                   10                  15

Asp His Pro His His Asn Gly Ile Thr Val Leu Pro Pro Asn Ser Asn
            20                  25                  30

Pro Ser Pro Gln Leu Pro Lys Pro Pro Thr Ser Ser Ser Ser Ser
        35                  40                  45

Ser Leu Gly Arg Val Leu Gly Arg Pro Met Glu Asp Val Arg Ser Ile
    50                  55                  60

Tyr Ile Phe Gly Arg Glu Leu Gly Arg Gly Gln Phe Gly Val Thr Tyr
65                  70                  75                  80

Leu Val Thr His Lys Ala Thr Lys Glu Gln Phe Ala Cys Lys Ser Ile
            85                  90                  95

```
Ala Thr Arg Lys Leu Val Asn Arg Asp Asp Ile Asp Ile Arg Arg
            100                 105                 110

Glu Val Gln Ile Met His His Leu Thr Gly His Arg Asn Ile Val Glu
            115                 120                 125

Leu Lys Gly Ala Tyr Glu Asp Arg His Ser Val Asn Leu Val Met Glu
            130                 135                 140

Leu Cys Ala Gly Gly Glu Leu Phe Asp Arg Ile Ile Thr Lys Gly His
145                 150                 155                 160

Tyr Ser Glu Arg Ala Ala Ala Asn Ser Cys Arg Gln Ile Val Thr Val
                165                 170                 175

Val His Asn Cys His Ser Met Gly Val Met His Arg Asp Leu Lys Pro
            180                 185                 190

Glu Asn Phe Leu Leu Leu Asn Lys Asn Asp Asp Ser Pro Leu Lys Ala
            195                 200                 205

Thr Asp Phe Gly Leu Ser Val Phe Lys Pro Gly Asp Val Phe Arg
            210                 215                 220

Asp Leu Val Gly Ser Ala Tyr Tyr Val Ala Pro Glu Val Leu Arg Arg
225                 230                 235                 240

Ser Tyr Gly Pro Glu Ala Asp Ile Trp Ser Ala Gly Val Ile Leu Tyr
                245                 250                 255

Ile Leu Leu Ser Gly Val Pro Pro Phe Trp Ala Glu Asn Glu Gln Gly
            260                 265                 270

Ile Phe Asp Ala Ile Leu Arg Gly His Ile Asp Phe Ala Ser Asp Pro
            275                 280                 285

Trp Pro Ser Ile Ser Ser Ser Ala Lys Asp Leu Val Lys Lys Met Leu
            290                 295                 300

Arg Ala Asp Pro Lys Glu Arg Leu Ser Ala Val Glu Val Leu Asn His
305                 310                 315                 320

Pro Trp Met Arg Val Asp Gly Asp Ala Pro Asp Lys Pro Leu Asp Ile
                325                 330                 335

Ala Val Leu Thr Arg Met Lys Gln Phe Arg Ala Met Asn Lys Leu Lys
            340                 345                 350

Lys Val Ala Leu Lys Val Ile Ala Glu Asn Leu Ser Glu Glu Ile
            355                 360                 365

Ile Gly Leu Lys Glu Met Phe Lys Ser Met Asp Thr Asp Asn Ser Gly
            370                 375                 380

Thr Ile Thr Phe Glu Glu Leu Lys Ala Gly Leu Pro Lys Leu Gly Thr
385                 390                 395                 400

Lys Leu Ser Glu Ser Glu Val Arg Gln Leu Met Glu Ala Ala Asp Val
                405                 410                 415

Asp Gly Asn Gly Thr Ile Asp Tyr Ile Glu Phe Ile Thr Ala Thr Met
            420                 425                 430

His Met Asn Arg Met Glu Arg Glu Asp His Leu Tyr Lys Ala Phe Glu
            435                 440                 445

Tyr Phe Asp Asn Asp Lys Ser Gly Tyr Ile Thr Met Glu Glu Leu Glu
            450                 455                 460

Ser Ala Leu Lys Lys Tyr Asn Met Gly Asp Glu Lys Thr Ile Lys Glu
465                 470                 475                 480

Ile Ile Ala Glu Val Asp Thr Asp Asn Asp Gly Arg Ile Asn Tyr Asp
                485                 490                 495

Glu Phe Val Ala Met Met Arg Lys Gly Asn Pro Asp Ile Thr His Ile
            500                 505                 510
```

Thr Gln Arg Arg Arg Lys
           515

<210> SEQ ID NO 20
<211> LENGTH: 379
<212> TYPE: PRT
<213> ORGANISM: Glycine max

<400> SEQUENCE: 20

Met Gly Ile Cys Phe Ser Ile Glu Asp Gln Asn His Leu Ser Ile Ser
1               5                   10                  15

Asp Ser Asn Ala Lys Pro Lys Pro Ala Val Gly His Glu Ser Gly Ala
            20                  25                  30

Pro Leu Ala Ser Met Asn Ile Lys Asp Leu Arg Glu Gly Ala Gly Tyr
        35                  40                  45

Ser Asn Val Asp Ile Phe Thr Tyr Glu Glu Leu Arg Leu Ala Thr Lys
    50                  55                  60

His Phe Arg Pro Asp Phe Ile Leu Gly Glu Gly Gly Phe Gly Val Val
65                  70                  75                  80

Tyr Lys Gly Val Ile Asp His Ser Val Arg Ser Gly Tyr Lys Ser Thr
                85                  90                  95

Glu Val Ala Ile Lys Glu Leu Asn Arg Glu Gly Phe Gln Gly Asp Arg
            100                 105                 110

Glu Trp Leu Ala Glu Val Asn Tyr Leu Gly Gln Phe Ser His Pro Asn
        115                 120                 125

Leu Val Lys Leu Ile Gly Tyr Cys Cys Glu Asp Asp His Arg Leu Leu
    130                 135                 140

Val Tyr Glu Tyr Met Ala Ser Gly Ser Leu Glu Lys His Leu Phe Arg
145                 150                 155                 160

Arg Val Gly Ser Thr Leu Thr Trp Ser Lys Arg Met Lys Ile Ala Leu
                165                 170                 175

His Ala Ala Arg Gly Leu Ala Phe Leu His Gly Ala Glu Arg Pro Ile
            180                 185                 190

Ile Tyr Arg Asp Phe Lys Thr Ser Asn Ile Leu Leu Asp Ala Asp Phe
        195                 200                 205

Asn Ala Lys Leu Ser Asp Phe Gly Leu Ala Lys Asp Gly Pro Met Gly
    210                 215                 220

Asp Gln Thr His Val Ser Thr Arg Val Met Gly Thr Tyr Gly Tyr Ala
225                 230                 235                 240

Ala Pro Glu Tyr Val Met Thr Gly His Leu Thr Ala Arg Ser Asp Val
                245                 250                 255

Tyr Gly Phe Gly Val Val Leu Leu Glu Met Leu Ile Gly Arg Arg Ala
            260                 265                 270

Leu Asp Lys Ser Arg Pro Ser Arg Glu His Asn Leu Val Glu Trp Ala
        275                 280                 285

Arg Pro Leu Leu Asn His Asn Lys Lys Leu Leu Lys Ile Leu Asp Pro
    290                 295                 300

Lys Leu Glu Gly Gln Tyr Ser Ser Lys Thr Ala Leu Lys Val Ala His
305                 310                 315                 320

Leu Ala Tyr Gln Cys Leu Ser Gln Asn Pro Lys Gly Arg Pro Leu Met
                325                 330                 335

Ser Gln Val Val Glu Ile Leu Glu Asn Phe Gln Ser Lys Gly Glu Asn
            340                 345                 350

Glu Glu Asp Gln Met Leu Gln Thr Gly Asp Thr Ser Ile Thr Leu Tyr
        355                 360                 365

Glu Val Pro Lys Gly Ser Asn Gly Thr Pro Thr
    370             375

<210> SEQ ID NO 21
<211> LENGTH: 411
<212> TYPE: PRT
<213> ORGANISM: Glycine max

<400> SEQUENCE: 21

Met Glu Met Asp Pro Pro Lys Ser Trp Ser Ile His Thr Arg Ser
1               5                   10                  15

Glu Ile Ile Ala Lys Tyr Glu Val Met Glu Arg Val Gly Ser Gly Ala
                20                  25                  30

Tyr Ala Asp Val Tyr Arg Gly Arg Arg Leu Ser Asp Gly Leu Thr Val
            35                  40                  45

Ala Leu Lys Glu Ile His Asp Tyr Gln Ser Ala Phe Arg Glu Ile Asp
        50                  55                  60

Ala Leu Gln Leu Leu Gly Ser Pro Asn Val Val Leu His Glu
65                  70                  75                  80

Tyr Phe Trp Arg Glu Asp Glu Asp Ala Val Leu Val Leu Glu Phe Leu
                85                  90                  95

Arg Thr Asp Leu Ala Thr Val Ile Ala Asp Thr Ala Lys Ala Asn Gln
            100                 105                 110

Pro Leu Pro Ala Gly Glu Leu Lys Cys Trp Met Ile Gln Ile Leu Ser
        115                 120                 125

Gly Leu Asp Ala Cys His Arg His Met Val Leu His Arg Asp Leu Lys
130                 135                 140

Pro Ser Asn Leu Leu Ile Ser Glu His Gly Leu Leu Lys Ile Ala Asp
145                 150                 155                 160

Phe Gly Gln Ala Arg Ile Leu Met Glu Pro Gly Ile Asp Ala Ser Asn
                165                 170                 175

Asn His Glu Glu Tyr Ser Arg Val Leu Asp Asp Ile Asp Asn Lys Asp
            180                 185                 190

Thr Ile Thr Ser Thr His Asp Gly Asn Ala Thr Cys Asn Thr Ser Asp
        195                 200                 205

Val Asp Arg Glu Glu Glu Glu Leu Gly Cys Phe Thr Ser Cys Val Gly
210                 215                 220

Thr Arg Trp Phe Arg Ala Pro Glu Leu Leu Tyr Gly Ser Arg Asn Tyr
225                 230                 235                 240

Gly Leu Glu Val Asp Leu Trp Ser Leu Gly Cys Ile Phe Ala Glu Leu
                245                 250                 255

Leu Thr Leu Gln Pro Leu Phe Pro Gly Thr Ala Asp Ile Asp Gln Leu
            260                 265                 270

Ser Arg Ile Ile Gly Val Leu Gly Asn Leu Asp Glu Asn Ala Trp Ala
        275                 280                 285

Ala Cys Ser Lys Leu Pro Asp Tyr Gly Ile Ile Ser Phe Ser Lys Val
        290                 295                 300

Glu Asn Pro Ala Gly Leu Glu Ala Cys Leu Pro Asn Arg Ser Pro Asp
305                 310                 315                 320

Glu Val Ala Leu Val Lys Lys Leu Val Cys Tyr Asp Pro Ala Lys Arg
                325                 330                 335

Ala Thr Ala Met Glu Leu Leu His Asp Lys Tyr Phe Ser Asp Glu Pro
            340                 345                 350

Leu Pro Val Leu Val Ser Glu Leu Arg Val Pro Leu Thr Arg Lys Glu

```
                355                 360                 365
Gln Asp Gly Asp Ser Pro Gly Gly Trp Gly Asp Ile Asn Asp Met Asp
    370                 375                 380

Ser Asp Ser Asp Ser Gln Phe Asp Glu Phe Gly Pro Leu Asn Ile Thr
385                 390                 395                 400

Arg Thr Gly Thr Gly Phe Ser Ile Gln Phe Pro
                405                 410

<210> SEQ ID NO 22
<211> LENGTH: 344
<212> TYPE: PRT
<213> ORGANISM: Glycine max

<400> SEQUENCE: 22

Met Ser Cys Phe Ser Cys Phe Val Ser Arg Gly Lys Asp Val Arg Arg
1               5                   10                  15

Val Glu Ile Asp Asn Gly Ser Arg Ser Ala Thr Ser Ser Ser Glu Gly
            20                  25                  30

Lys Gly Lys Lys Ser Val Ser Asn Lys Gly Thr Ser Thr Ala Ala Ala
        35                  40                  45

Ser Phe Gly Phe Arg Glu Leu Ala Glu Ala Thr Arg Gly Phe Lys Glu
    50                  55                  60

Val Asn Leu Leu Gly Glu Gly Gly Phe Gly Arg Val Tyr Lys Gly Arg
65                  70                  75                  80

Leu Ser Thr Gly Glu Tyr Val Ala Val Lys Gln Leu Ile His Asp Gly
                85                  90                  95

Arg Gln Gly Phe His Glu Phe Val Thr Glu Val Leu Met Leu Ser Leu
            100                 105                 110

Leu His Asp Ser Asn Leu Val Lys Leu Ile Gly Tyr Cys Thr Asp Gly
        115                 120                 125

Asp Gln Arg Leu Leu Val Tyr Glu Tyr Met Pro Met Gly Ser Leu Glu
    130                 135                 140

Asp His Leu Phe Asp Pro His Pro Asp Lys Glu Pro Leu Ser Trp Ser
145                 150                 155                 160

Thr Arg Met Lys Ile Ala Val Gly Ala Ala Arg Gly Leu Glu Tyr Leu
                165                 170                 175

His Cys Lys Ala Asp Pro Pro Val Ile Tyr Arg Asp Leu Lys Ser Ala
            180                 185                 190

Asn Ile Leu Leu Asp Asn Glu Phe Asn Pro Lys Leu Ser Asp Phe Gly
        195                 200                 205

Leu Ala Lys Leu Gly Pro Val Gly Asp Asn Thr His Val Ser Thr Arg
    210                 215                 220

Val Met Gly Thr Tyr Gly Tyr Cys Ala Pro Glu Tyr Ala Met Ser Gly
225                 230                 235                 240

Lys Leu Thr Leu Lys Ser Asp Ile Tyr Ser Phe Gly Val Leu Leu Leu
                245                 250                 255

Glu Leu Ile Thr Gly Arg Arg Ala Ile Asp Thr Asn Arg Arg Pro Gly
            260                 265                 270

Glu Gln Asn Leu Val Ser Trp Ser Arg Gln Phe Phe Ser Asp Arg Lys
        275                 280                 285

Lys Phe Val Gln Met Ile Asp Pro Leu Leu Gln Glu Asn Phe Pro Leu
    290                 295                 300

Arg Cys Leu Asn Gln Ala Met Ala Ile Thr Ala Met Cys Ile Gln Glu
305                 310                 315                 320
```

-continued

```
Gln Pro Lys Phe Arg Pro Leu Ile Gly Asp Ile Val Ala Leu Glu
                325                 330                 335

Tyr Leu Ala Ser His Ser Asn Pro
            340

<210> SEQ ID NO 23
<211> LENGTH: 570
<212> TYPE: PRT
<213> ORGANISM: Glycine max

<400> SEQUENCE: 23

Met Ser Ala Pro Ala Glu Ala Pro Ser Phe Thr Ala Ser Pro Ser
1               5                   10                  15

Glu Thr Thr Pro Ser Pro Asn Ser Thr Ala Leu Ser Pro Pro Pro
                20                  25                  30

Ser Thr Ile Asn Ala Thr Val Ser Pro Pro Pro Glu Ala Ala Ser
                35                  40                  45

Pro Pro Thr Ser Thr Val Asn Ser Gly Leu Ser Thr Gly Thr Val Ser
            50                  55                  60

Gly Ile Val Ile Gly Ala Val Leu Gly Ser Val Gly Met Leu Ile Ile
65                  70                  75                  80

Gly Gly Ile Phe Phe Cys Phe Tyr Arg Asn Trp Lys Arg Lys Lys Asn
                85                  90                  95

His Ser Gln Pro Pro Gln Pro Lys Ala Asp Ile Ala Gly Gly Thr Leu
                100                 105                 110

Gln Asn Trp Gln Asp Ser Val Pro Pro Thr Thr Asp Gly Lys Val Gly
                115                 120                 125

Phe Ser Pro Lys Pro Pro Gly Gly Leu Val Asn Gln Gln Gln Ser
            130                 135                 140

Ser Ala Ala Leu Leu Thr Leu Val Val Asn Ser Ser Asn Thr Ser Ser
145                 150                 155                 160

Ser Leu Gly Ser Glu Lys Ala Lys Ser Tyr Ile Ser Pro Ser Pro Gly
                165                 170                 175

Thr Ser Leu Ala Leu Ser Gln Ser Thr Phe Thr Tyr Asp Glu Leu Ser
            180                 185                 190

Met Ala Thr Asp Gly Phe Ser Arg Ser Asn Leu Leu Gly Gln Gly Gly
        195                 200                 205

Phe Gly Tyr Val His Lys Gly Val Leu Pro Asn Gly Lys Ile Val Ala
    210                 215                 220

Val Lys Gln Leu Lys Ser Glu Ser Arg Gln Gly Glu Arg Glu Phe His
225                 230                 235                 240

Ala Glu Val Asp Val Ile Ser Arg Val His His Arg His Leu Val Ser
                245                 250                 255

Leu Val Gly Tyr Cys Val Ser Asp Ser Gln Lys Met Leu Val Tyr Glu
                260                 265                 270

Tyr Val Glu Asn Asp Thr Leu Glu Phe His Leu His Gly Lys Asp Arg
                275                 280                 285

Leu Pro Met Asp Trp Ser Thr Arg Met Lys Ile Ala Ile Gly Ser Ala
            290                 295                 300

Lys Gly Leu Ala Tyr Leu His Glu Asp Cys Asn Pro Lys Ile Ile His
305                 310                 315                 320

Arg Asp Ile Lys Ala Ser Asn Ile Leu Leu Asp Glu Ser Phe Glu Ala
                325                 330                 335

Lys Val Ala Asp Phe Gly Leu Ala Lys Phe Ser Ser Asp Thr Asp Thr
                340                 345                 350
```

```
His Val Ser Thr Arg Val Met Gly Thr Phe Gly Tyr Met Ala Pro Glu
        355                 360                 365

Tyr Ala Ala Ser Gly Lys Leu Thr Glu Lys Ser Asp Val Phe Ser Phe
370                 375                 380

Gly Val Val Leu Leu Glu Leu Ile Thr Gly Arg Lys Pro Val Asp Lys
385                 390                 395                 400

Thr Gln Thr Phe Ile Asp Asp Ser Met Val Glu Trp Ala Arg Pro Leu
                405                 410                 415

Leu Ser Gln Ala Leu Glu Asn Gly Asn Leu Asn Gly Leu Val Asp Pro
                420                 425                 430

Arg Leu Gln Thr Asn Tyr Asn Leu Asp Glu Met Ile Arg Met Thr Thr
            435                 440                 445

Cys Ala Ala Thr Cys Val Arg Tyr Ser Ala Arg Leu Arg Pro Arg Met
        450                 455                 460

Ser Gln Val Val Arg Ala Leu Glu Gly Asn Ile Ser Leu Glu Asp Leu
465                 470                 475                 480

Asn Asp Gly Ile Ala Pro Gly His Ser Arg Val Phe Gly Ser Phe Glu
                485                 490                 495

Ser Ser Ser Tyr Asp Ser Val Gln Tyr Arg Glu Asp Leu Lys Asn Phe
                500                 505                 510

Lys Lys Leu Ala Leu Glu Ser Gln Glu Gln Gly Ile Ser Glu Tyr Ser
            515                 520                 525

Gly Pro Ser Ser Glu Tyr Gly Arg His Pro Ser Val Ser Thr Ser Ser
        530                 535                 540

Asp Gln Gln Asn Thr Gln Met Glu Met Gly Asn Lys Lys Gly Ser
545                 550                 555                 560

Asn His Asp Ser Gly Ile Gln Val Leu Asp
                565                 570

<210> SEQ ID NO 24
<211> LENGTH: 750
<212> TYPE: PRT
<213> ORGANISM: Glycine max

<400> SEQUENCE: 24

Met Ser Arg Glu Gln Gln Lys Arg Gly Lys Gln Glu Lys Gly Ser Asp
1               5                   10                  15

Gly Ala Glu Lys Val Ile Val Ala Val Lys Ala Ser Lys Glu Ile Pro
                20                  25                  30

Lys Thr Ala Leu Val Trp Ser Leu Ser His Val Gln Pro Gly Asp
            35                  40                  45

Cys Ile Thr Leu Leu Val Val Pro Ser Gln Ser Ser Gly Arg Arg
        50                  55                  60

Leu Trp Gly Phe Pro Arg Phe Ala Gly Asp Cys Ala Ser Gly Ile Lys
65                  70                  75                  80

Lys Tyr Pro Pro Gly Thr Ile Ser Glu Gln Lys Ser Asp Leu Thr Asp
                85                  90                  95

Ser Cys Ser Gln Met Ile Leu Gln Leu His Asn Val Tyr Asp Pro Asn
                100                 105                 110

Lys Ile Asn Val Arg Ile Lys Ile Val Ser Gly Ser Pro Cys Gly Ala
            115                 120                 125

Val Ala Ala Glu Ala Lys Lys Thr Gln Ala Asn Trp Val Val Leu Asp
        130                 135                 140

Lys Gln Leu Lys His Glu Glu Lys Arg Cys Met Glu Glu Leu Gln Cys
```

```
            145                 150                 155                 160
        Asn Ile Val Val Met Lys Arg Ser Gln Pro Lys Val Leu Arg Leu Asn
                        165                 170                 175
        Leu Ile Gly Pro Gln Lys Lys Asp Val Glu Glu Ala Gly Pro Ser Pro
                        180                 185                 190
        Ser Glu Gln Asp Asp Met Pro Glu Asn Arg Thr Lys Ile Lys Leu Asp
                        195                 200                 205
        Ser Leu Asn Ser Ile Lys Gly Pro Thr Val Thr Pro Thr Ser Ser Pro
        210                 215                 220
        Glu Leu Gly Thr Pro Phe Thr Ala Thr Glu Ala Gly Thr Ser Ser Val
        225                 230                 235                 240
        Ser Ser Ser Asp Pro Gly Thr Ser Pro Phe Ile Ser Glu Met Asn
                        245                 250                 255
        Gly Glu Phe Lys Lys Glu Glu Thr Ile Lys Glu Ser Gln Glu Leu Val
                        260                 265                 270
        Asp Thr Asn Ser Asp Thr Glu Ser Glu Ser Leu Ser Thr Ser Ser Ala
                        275                 280                 285
        Ser Met Arg Tyr Gln Pro Trp Ile Thr Glu Leu Leu Leu His Gln Gln
                        290                 295                 300
        Ser Ser Gln Arg Asn Glu Glu Arg Ser Asp Ile Ser His Gly Ile Pro
        305                 310                 315                 320
        Gln Ala Ser Thr Thr Arg Ala Phe Leu Glu Lys Tyr Ser Arg Leu Asp
                        325                 330                 335
        Arg Gly Ala Gly Phe Glu Ile Ser Thr Tyr Arg Asn Asp Met Asp Phe
                        340                 345                 350
        Ser Gly Asn Leu Arg Glu Ala Ile Ala Leu Ser Gly Asn Ala Pro Pro
                        355                 360                 365
        Gly Pro Pro Leu Cys Ser Ile Cys Gln His Lys Ala Pro Val Phe
                        370                 375                 380
        Gly Lys Pro Pro Arg Trp Phe Thr Tyr Ser Glu Leu Glu Leu Ala Thr
        385                 390                 395                 400
        Gly Gly Phe Ser Gln Ala Asn Phe Leu Ala Glu Gly Phe Gly Ser
                        405                 410                 415
        Val His Arg Gly Val Leu Pro Glu Gly Gln Val Ile Ala Val Lys Gln
                        420                 425                 430
        His Lys Leu Ala Ser Ser Gln Gly Asp Leu Glu Phe Cys Ser Glu Val
                        435                 440                 445
        Glu Val Leu Ser Cys Ala Gln His Arg Asn Val Met Leu Ile Gly
                        450                 455                 460
        Phe Cys Ile Glu Asp Lys Arg Arg Leu Leu Val Tyr Glu Tyr Ile Cys
        465                 470                 475                 480
        Asn Gly Ser Leu Asp Ser His Leu Tyr Gly Arg Gln Arg Asp Thr Leu
                        485                 490                 495
        Glu Trp Ser Ala Arg Gln Lys Ile Ala Val Gly Ala Ala Arg Gly Leu
                        500                 505                 510
        Arg Tyr Leu His Glu Glu Cys Arg Val Gly Cys Ile Ile His Arg Asp
                        515                 520                 525
        Met Arg Pro Asn Asn Ile Leu Ile Thr His Asp Phe Glu Pro Leu Val
                        530                 535                 540
        Gly Asp Phe Gly Leu Ala Arg Trp Gln Pro Asp Gly Asp Thr Gly Val
        545                 550                 555                 560
        Glu Thr Arg Val Ile Gly Thr Phe Gly Tyr Leu Ala Pro Glu Tyr Ala
                        565                 570                 575
```

-continued

```
Gln Ser Gly Gln Ile Thr Glu Lys Ala Asp Val Tyr Ser Phe Gly Val
            580                 585                 590

Val Leu Val Glu Leu Val Thr Gly Arg Lys Ala Val Asp Leu Thr Arg
            595                 600                 605

Pro Lys Gly Gln Gln Cys Leu Thr Glu Trp Ala Arg Pro Leu Leu Glu
            610                 615                 620

Glu Tyr Ala Ile Glu Glu Leu Ile Asp Pro Arg Leu Gly Lys His Tyr
625                 630                 635                 640

Ser Glu His Glu Val Tyr Cys Met Leu His Ala Ala Ser Leu Cys Ile
                645                 650                 655

Gln Arg Asp Pro Gln Cys Arg Pro Arg Met Ser Gln Val Leu Arg Ile
            660                 665                 670

Leu Glu Gly Asp Met Val Met Asp Ser Asn Tyr Ile Ser Thr Pro Gly
            675                 680                 685

Tyr Asp Ala Gly Asn Arg Ser Gly Arg Leu Trp Ser Glu Pro Leu Gln
            690                 695                 700

Arg Gln Gln His Tyr Ser Gly Pro Leu Leu Glu Glu Ser Leu Glu Ser
705                 710                 715                 720

Phe Ser Gly Lys Leu Ser Leu Asp Lys Tyr Lys Pro Ser Tyr Trp Gly
                725                 730                 735

Asp Arg Asp Lys Ala Arg Arg Ala Ser Cys Glu Asp Asp Ile
            740                 745                 750

<210> SEQ ID NO 25
<211> LENGTH: 441
<212> TYPE: PRT
<213> ORGANISM: Glycine max

<400> SEQUENCE: 25

Met Asp Pro Gln Asn Gln His Pro Asn Pro Arg Ser Ile Ile Phe
1               5                   10                  15

Asn Lys Tyr Glu Met Gly Arg Val Leu Gly Gln Gly Asn Phe Ala Lys
            20                  25                  30

Val Tyr His Ala Arg Asn Leu Asn Thr Asn Glu Ser Val Ala Ile Lys
        35                  40                  45

Val Ile Lys Lys Glu Lys Leu Lys Lys Glu Arg Leu Val Lys Gln Ile
    50                  55                  60

Lys Arg Glu Val Ser Val Met Arg Leu Val Arg His Pro His Ile Val
65                  70                  75                  80

Glu Leu Lys Glu Val Met Ala Thr Lys Gly Lys Ile Phe Leu Val Met
                85                  90                  95

Glu Tyr Val Lys Gly Gly Glu Leu Phe Ala Lys Val Asn Lys Gly Lys
            100                 105                 110

Leu Thr Glu Asp Leu Ala Arg Lys Tyr Phe Gln Gln Leu Ile Ser Ala
        115                 120                 125

Val Asp Phe Cys His Ser Arg Gly Val Thr His Arg Asp Leu Lys Pro
    130                 135                 140

Glu Asn Leu Leu Leu Asp Gln Asn Glu Asp Leu Lys Val Ser Asp Phe
145                 150                 155                 160

Gly Leu Ser Thr Leu Pro Glu Gln Arg Arg Ala Asp Gly Met Leu Val
                165                 170                 175

Thr Pro Cys Gly Thr Pro Ala Tyr Val Ala Pro Glu Val Leu Lys Lys
            180                 185                 190

Lys Gly Tyr Asp Gly Ser Lys Ala Asp Leu Trp Ser Cys Gly Val Ile
```

```
                195                 200                 205
Leu Phe Ala Leu Leu Cys Gly Tyr Leu Pro Phe Gln Gly Glu Asn Val
210                 215                 220

Met Arg Ile Tyr Arg Lys Ala Phe Arg Ala Glu Tyr Glu Phe Pro Glu
225                 230                 235                 240

Trp Ile Ser Pro Gln Ala Lys Asn Leu Ile Ser Asn Leu Leu Val Ala
                245                 250                 255

Asp Pro Gly Lys Arg Tyr Ser Ile Pro Asp Ile Met Arg Asp Pro Trp
                260                 265                 270

Phe Gln Val Gly Phe Met Arg Pro Ile Ala Phe Ser Ile Lys Glu Ser
                275                 280                 285

Tyr Val Glu Asp Asn Ile Asp Phe Asp Val Glu Asn Asn Gln Glu
290                 295                 300

Glu Glu Val Thr Met Arg Lys Pro Ala Arg Pro Phe Tyr Asn Ala Phe
305                 310                 315                 320

Glu Ile Ile Ser Ser Leu Ser His Gly Phe Asp Leu Arg Ser Leu Phe
                325                 330                 335

Glu Thr Arg Lys Arg Ser Pro Ser Met Phe Ile Cys Lys Phe Ser Ala
                340                 345                 350

Ser Ala Val Leu Ala Lys Val Glu Ala Val Ala Lys Lys Leu Asn Phe
                355                 360                 365

Arg Val Thr Gly Lys Lys Glu Phe Val Val Arg Met Gln Gly Thr Glu
370                 375                 380

Glu Gly Arg Lys Gly Lys Leu Ala Met Thr Val Glu Val Phe Glu Val
385                 390                 395                 400

Ala Pro Glu Val Ala Val Ala Glu Phe Thr Lys Ser Ala Gly Asp Thr
                405                 410                 415

Leu Glu Tyr Val Lys Phe Cys Glu Glu Gln Val Arg Pro Ser Leu Lys
                420                 425                 430

Asp Ile Val Trp Ser Trp Gln Gly Asp
                435                 440

<210> SEQ ID NO 26
<211> LENGTH: 529
<212> TYPE: PRT
<213> ORGANISM: Glycine max

<400> SEQUENCE: 26

Met Gly Cys His Gly Ser Lys Glu Lys Lys Ser Asn Thr Ser Tyr Gly
1               5                   10                  15

Ser Ala Ala Thr Gly Ser Gly Ser Gly Ser Gly Gly Tyr
                20                  25                  30

Asn Thr Val Gln Pro Ser Pro Thr Thr Asp Gln Val Gln Ala Ser
                35                  40                  45

Ala Gln Thr Pro Glu Asn Arg Lys Ala Ser Pro Thr Val Gln Lys Lys
50                  55                  60

Ala Asp Thr Ser Ile Val Gly Lys Pro Phe Asp Ile Lys Lys Tyr
65                  70                  75                  80

Tyr Ser Ile Gly Lys Glu Leu Gly Arg Gly Gln Phe Gly Ile Thr Tyr
                85                  90                  95

Leu Cys Thr Glu Asn Ser Ser Gly Gly Thr Tyr Ala Cys Lys Ser Ile
                100                 105                 110

Leu Lys Arg Lys Leu Val Ser Lys Ala Asp Arg Glu Asp Met Lys Arg
                115                 120                 125
```

```
Glu Ile Gln Ile Met Gln His Leu Ser Gly Gln Pro Asn Ile Val Glu
130                 135                 140

Phe Lys Gly Ala Phe Glu Asp Arg Phe Ser Val His Leu Val Met Glu
145                 150                 155                 160

Leu Cys Ser Gly Gly Glu Leu Phe Asp Arg Ile Ile Ala Gln Gly His
                165                 170                 175

Tyr Ser Glu Arg Ala Ala Ala Ser Leu Cys Arg Ser Ile Val Asn Val
            180                 185                 190

Val His Ile Cys His Phe Met Gly Val Met His Arg Asp Leu Lys Pro
        195                 200                 205

Glu Asn Phe Leu Leu Ser Thr Lys Asp Asp His Ala Thr Leu Lys Ala
210                 215                 220

Thr Asp Phe Gly Leu Ser Val Phe Ile Glu Gln Gly Lys Val Tyr His
225                 230                 235                 240

Asp Met Val Gly Ser Ala Tyr Tyr Val Ala Pro Glu Val Leu Arg Arg
                245                 250                 255

Ser Tyr Gly Lys Glu Ile Asp Ile Trp Ser Ala Gly Ile Ile Leu Tyr
            260                 265                 270

Ile Leu Leu Ser Gly Val Pro Pro Phe Trp Ala Glu Thr Glu Lys Gly
        275                 280                 285

Ile Phe Asn Ala Ile Leu Glu Gly Glu Ile Asp Phe Val Ser Glu Pro
290                 295                 300

Trp Pro Ser Ile Ser Asp Ser Ala Lys Asp Leu Val Arg Lys Met Leu
305                 310                 315                 320

Thr Gln Asp Pro Lys Lys Arg Ile Thr Ser Ala Gln Val Leu Glu His
                325                 330                 335

Pro Trp Met Arg Glu Gly Gly Asp Ala Ser Asp Lys Pro Ile Asp Ser
            340                 345                 350

Ala Val Leu Ser Arg Met Lys Gln Phe Arg Ala Met Asn Lys Leu Lys
        355                 360                 365

Lys Leu Ala Leu Lys Val Ile Ala Glu Asn Leu Ser Glu Glu Glu Ile
370                 375                 380

Lys Gly Leu Lys Ala Met Phe Ala Asn Met Asp Thr Asp Ser Ser Gly
385                 390                 395                 400

Thr Ile Thr Tyr Glu Glu Leu Lys Thr Gly Leu Ala Arg Ile Gly Ser
                405                 410                 415

Arg Leu Ser Glu Ala Glu Val Lys Gln Leu Met Asp Ala Ala Asp Val
            420                 425                 430

Asp Gly Asn Gly Ser Ile Asp Tyr Leu Glu Phe Ile Ser Ala Thr Met
        435                 440                 445

His Arg His Arg Leu Glu Arg Asp Glu His Leu Tyr Lys Ala Phe Gln
450                 455                 460

Tyr Phe Asp Lys Asp Asn Ser Gly Tyr Ile Thr Arg Asp Glu Leu Glu
465                 470                 475                 480

Thr Ala Met Thr Gln His Gly Met Gly Asp Glu Ala Thr Ile Lys Glu
                485                 490                 495

Ile Ile Ser Glu Val Asp Thr Asp Asn Asp Gly Arg Ile Asn Tyr Glu
            500                 505                 510

Glu Phe Cys Ala Met Met Arg Ser Gly Met Pro His Gln Gly Gln Leu
        515                 520                 525

Leu

<210> SEQ ID NO 27
```

<211> LENGTH: 461
<212> TYPE: PRT
<213> ORGANISM: Glycine max

<400> SEQUENCE: 27

```
Met Gly Asp Gly Ser Gly Asn Arg Trp Ser Arg Ala Glu Trp Val Gln
1               5                   10                  15

Gln Tyr Asp Leu Leu Gly Lys Ile Gly Glu Gly Thr Tyr Gly Leu Val
            20                  25                  30

Phe Leu Ala Arg Thr Lys Gly Thr Pro Ser Lys Ser Ile Ala Ile Lys
        35                  40                  45

Lys Phe Lys Gln Ser Lys Asp Gly Asp Gly Val Ser Pro Thr Ala Ile
50                  55                  60

Arg Glu Ile Met Leu Leu Arg Glu Ile Thr His Glu Asn Val Val Lys
65                  70                  75                  80

Leu Val Asn Val His Ile Asn His Ala Asp Met Ser Leu Tyr Leu Ala
                85                  90                  95

Phe Asp Tyr Ala Glu His Asp Leu Tyr Glu Ile Ile Arg His His Arg
            100                 105                 110

Asp Lys Leu Asn His Ser Ile Asn Gln Tyr Thr Val Lys Ser Leu Leu
        115                 120                 125

Trp Gln Leu Leu Asn Gly Leu Ser Tyr Leu His Ser Asn Trp Met Ile
130                 135                 140

His Arg Asp Leu Lys Pro Ser Asn Ile Leu Val Met Gly Glu Gly Glu
145                 150                 155                 160

Glu His Gly Val Val Lys Ile Ala Asp Phe Gly Leu Ala Arg Ile Tyr
                165                 170                 175

Gln Ala Pro Leu Lys Pro Leu Ser Asp Asn Gly Val Val Val Thr Ile
            180                 185                 190

Trp Tyr Arg Ala Pro Glu Leu Leu Gly Ala Lys His Tyr Thr Ser
        195                 200                 205

Ala Val Asp Met Trp Ala Val Gly Cys Ile Phe Ala Glu Leu Leu Thr
210                 215                 220

Leu Lys Pro Leu Phe Gln Gly Ala Glu Val Lys Ala Thr Ser Asn Pro
225                 230                 235                 240

Phe Gln Leu Asp Gln Leu Asp Lys Ile Phe Lys Val Leu Gly His Pro
                245                 250                 255

Thr Leu Glu Lys Trp Pro Ser Leu Ala Ser Leu Pro His Trp Gln Gln
            260                 265                 270

Asp Val Gln His Ile Gln Gly His Lys Tyr Asp Asn Ala Gly Leu Tyr
        275                 280                 285

Asn Val Val His Leu Ser Pro Lys Ser Pro Ala Tyr Asp Leu Leu Ser
290                 295                 300

Lys Met Leu Glu Tyr Asp Pro Arg Lys Arg Leu Thr Ala Ala Gln Ala
305                 310                 315                 320

Leu Glu His Glu Tyr Phe Lys Ile Glu Pro Leu Pro Gly Arg Asn Ala
                325                 330                 335

Leu Val Pro Cys Gln Leu Gly Glu Lys Ile Val Asn Tyr Pro Thr Arg
            340                 345                 350

Pro Val Asp Thr Thr Asp Leu Glu Gly Thr Thr Asn Leu Pro Pro
        355                 360                 365

Ser Gln Thr Val Asn Ala Val Ser Gly Ser Met Pro Gly Pro His Gly
370                 375                 380

Ser Asn Arg Ser Val Pro Arg Pro Val Asn Val Val Gly Met Gln Arg
```

```
385                 390                 395                 400
Met Pro Pro Gln Ala Met Ala Ala Tyr Asn Leu Ser Ser Gln Ala Ala
                405                 410                 415

Met Gly Asp Gly Met Asn Pro Gly Gly Ile Ser Lys Gln Arg Gly Val
                420                 425                 430

Pro Gln Ala His Gln Pro Gln Leu Arg Arg Lys Glu Gln Met Gly
                435                 440                 445

Met Pro Gly Tyr Pro Ala Gln Gln Lys Ser Arg Arg Ile
    450                 455                 460

<210> SEQ ID NO 28
<211> LENGTH: 381
<212> TYPE: PRT
<213> ORGANISM: Glycine max

<400> SEQUENCE: 28

Met Gly Asn Cys Trp Cys Arg Trp Glu Ser Ser Glu Tyr Arg Val Ser
1               5                   10                  15

Ser Asn Val Lys Ser Glu Gln Asn Gly Thr Lys Gln Arg His Asp
                20                  25                  30

Asp Ser Lys Leu Pro Ser Asn Pro Glu Val Glu Asp Leu Arg Arg
        35                  40                  45

Asp Ser Ala Ala Asn Pro Leu Ile Ala Phe Thr Tyr Asp Glu Leu Lys
    50                  55                  60

Ile Ile Thr Ala Asn Phe Arg Gln Asp Arg Val Leu Gly Gly Gly Gly
65                  70                  75                  80

Phe Gly Arg Val Tyr Lys Gly Phe Ile Ser Glu Glu Leu Arg Glu Gly
                85                  90                  95

Leu Pro Thr Leu Ala Val Ala Val Lys Val His Asp Gly Asp Asn Ser
            100                 105                 110

His Gln Gly His Arg Glu Trp Leu Ala Glu Val Ile Phe Leu Gly Gln
        115                 120                 125

Leu Ser His Pro Asn Leu Val Lys Leu Ile Gly Tyr Cys Cys Glu Asp
    130                 135                 140

Glu His Arg Val Leu Ile Tyr Glu Tyr Met Ser Arg Gly Ser Val Glu
145                 150                 155                 160

His Asn Leu Phe Ser Lys Ile Leu Leu Pro Leu Pro Trp Ser Ile Arg
                165                 170                 175

Met Lys Ile Ala Phe Gly Ala Ala Lys Gly Leu Ala Phe Leu His Glu
            180                 185                 190

Ala Glu Lys Pro Val Ile Tyr Arg Asp Phe Lys Thr Ser Asn Ile Leu
        195                 200                 205

Leu Asp Gln Glu Tyr Asn Ser Lys Leu Ser Asp Phe Gly Leu Ala Lys
    210                 215                 220

Asp Gly Pro Val Gly Asp Lys Ser His Val Ser Thr Arg Val Met Gly
225                 230                 235                 240

Thr Tyr Gly Tyr Ala Ala Pro Glu Tyr Ile Met Thr Gly His Leu Thr
                245                 250                 255

Pro Arg Ser Asp Val Tyr Ser Phe Gly Val Val Leu Leu Glu Leu Leu
            260                 265                 270

Thr Gly Arg Lys Ser Leu Asp Lys Leu Arg Pro Ala Arg Glu Gln Asn
        275                 280                 285

Leu Ala Glu Trp Ala Leu Pro Leu Leu Lys Glu Lys Lys Phe Leu
    290                 295                 300
```

Asn Ile Ile Asp Pro Arg Leu Asp Gly Asp Tyr Pro Ile Lys Ala Val
305                 310                 315                 320

His Lys Ala Ala Met Leu Ala Tyr His Cys Leu Asn Arg Asn Pro Lys
                325                 330                 335

Ala Arg Pro Leu Met Arg Asp Ile Val Asp Ser Leu Glu Pro Leu Gln
            340                 345                 350

Ala His Thr Glu Val Pro Ile Gly Lys Thr Leu Thr Ile Ile Ser Glu
        355                 360                 365

Val Pro Glu Ser Gly Leu Lys Met Lys Asp Asp Ala Ile
    370                 375                 380

<210> SEQ ID NO 29
<211> LENGTH: 816
<212> TYPE: PRT
<213> ORGANISM: Glycine max

<400> SEQUENCE: 29

Met Ala Ser Thr Leu Leu Pro Phe Leu Phe Leu Ser Met Val Leu Leu
1               5                   10                  15

Pro Phe Gln Thr Ile Ala Gln Thr Lys Ser Asn Ile Ala Ile Gly Glu
            20                  25                  30

Ser His Thr Ala Gly Ala Ser Thr Ser Pro Trp Leu Val Ser Ser Pro
        35                  40                  45

Ser Gly Asp Phe Ala Phe Gly Phe Leu Pro Leu Glu Asp Thr Pro Asp
    50                  55                  60

His Phe Met Leu Cys Ile Trp Tyr Ala Lys Ile Gln Asp Lys Thr Ile
65                  70                  75                  80

Val Trp Phe Ala Asn Arg Asp Gln Pro Ala Pro Lys Gly Ser Lys Val
                85                  90                  95

Val Leu Thr Ala Asp Asp Gly Leu Val Leu Ile Thr Ala Pro Asn Gly
            100                 105                 110

His Met Leu Trp Lys Thr Gly Gly Leu Thr Leu Arg Val Ser Ser Gly
        115                 120                 125

Val Leu Asn Asp Thr Gly Asn Phe Val Leu Gln Asp Gly His Ser Lys
    130                 135                 140

Thr Val Trp Glu Ser Phe Lys Asp Tyr Arg Asp Thr Leu Leu Pro Tyr
145                 150                 155                 160

Gln Thr Met Glu Lys Gly His Lys Leu Ser Ser Lys Leu Gly Arg Asn
                165                 170                 175

Tyr Phe Asn Lys Gly Arg Phe Val Leu Phe Gln Asn Asp Gly Ser
            180                 185                 190

Leu Val Met His Ser Ile Asn Met Pro Ser Gly Tyr Ala Asn Glu Asn
        195                 200                 205

Tyr Tyr Gln Ser Gly Thr Ile Glu Ser Asn Thr Asn Thr Ser Thr Ser
    210                 215                 220

Ala Gly Thr Gln Leu Val Phe Asp Gly Thr Gly Asp Met Tyr Val Leu
225                 230                 235                 240

Arg Lys Asn Asn Glu Lys Tyr Asn Leu Ser Lys Gly Ser Arg Ala
                245                 250                 255

Ser Ser Thr Thr Gln Phe Tyr Tyr Leu Arg Ala Thr Leu Asp Phe Asp
            260                 265                 270

Gly Val Phe Thr Leu Tyr Gln His Pro Lys Gly Ser Ser Gly Ser Gly
        275                 280                 285

Gly Trp Ser Gln Val Trp Ser His Pro Asp Asn Ile Cys Lys Asp Tyr
    290                 295                 300

```
Val Ala Ser Ala Gly Ser Gly Val Cys Gly Tyr Asn Ser Ile Cys Ser
305                 310                 315                 320

Leu Arg Asp Asp Lys Arg Pro Asn Cys Arg Cys Pro Lys Trp Tyr Ser
                325                 330                 335

Leu Val Asp Pro Asn Asp Pro Asn Gly Ser Cys Lys Pro Asp Phe Val
            340                 345                 350

Gln Ala Cys Ala Val Asp Lys Leu Ser Asn Arg Gln Asp Leu Tyr Asp
        355                 360                 365

Phe Glu Val Leu Ile Asp Thr Asp Trp Pro Gln Ser Asp Tyr Val Leu
370                 375                 380

Gln Arg Pro Phe Asn Glu Glu Gln Cys Arg Gln Ser Cys Met Glu Asp
385                 390                 395                 400

Cys Met Cys Ser Val Ala Ile Phe Arg Leu Gly Asp Ser Cys Trp Lys
                405                 410                 415

Lys Lys Leu Pro Leu Ser Asn Gly Arg Val Asp Ala Thr Leu Asn Gly
            420                 425                 430

Ala Lys Ala Phe Met Lys Val Arg Lys Asp Asn Ser Ser Leu Ile Val
        435                 440                 445

Pro Pro Ile Ile Val Asn Lys Asn Asn Lys Asn Thr Ser Ile Leu Val
450                 455                 460

Gly Ser Val Leu Leu Gly Ser Ser Ala Phe Leu Asn Leu Ile Leu Val
465                 470                 475                 480

Gly Ala Ile Cys Leu Ser Thr Ser Tyr Val Phe Arg Tyr Lys Lys Lys
                485                 490                 495

Leu Arg Ser Ile Gly Arg Ser Asp Thr Ile Val Glu Thr Asn Leu Arg
            500                 505                 510

Arg Phe Thr Tyr Glu Glu Leu Lys Lys Ala Thr Asn Asp Phe Asp Lys
        515                 520                 525

Val Leu Gly Lys Gly Ala Phe Gly Ile Val Tyr Glu Gly Val Ile Asn
        530                 535                 540

Met Cys Ser Asp Thr Arg Val Ala Val Lys Arg Leu Asn Thr Phe Leu
545                 550                 555                 560

Met Glu Asp Val His Lys Glu Phe Lys Asn Glu Leu Asn Ala Ile Gly
                565                 570                 575

Leu Thr His His Lys Asn Leu Val Arg Leu Leu Gly Phe Cys Glu Thr
            580                 585                 590

Glu Glu Lys Arg Leu Leu Val Tyr Glu Tyr Met Ser Asn Gly Thr Leu
        595                 600                 605

Ala Ser Leu Leu Phe Asn Ile Val Glu Lys Pro Ser Trp Lys Leu Arg
        610                 615                 620

Leu Gln Ile Ala Ile Gly Ile Ala Arg Gly Leu Leu Tyr Leu His Glu
625                 630                 635                 640

Glu Cys Ser Thr Gln Ile Ile His Cys Asp Ile Lys Pro Gln Asn Ile
                645                 650                 655

Leu Leu Asp Asp Tyr Tyr Asn Ala Arg Ile Ser Asp Phe Gly Leu Ala
            660                 665                 670

Lys Leu Leu Asn Met Asn Gln Ser Arg Thr Asn Thr Ala Ile Arg Gly
        675                 680                 685

Thr Lys Gly Tyr Val Ala Leu Glu Trp Phe Lys Asn Met Pro Ile Thr
        690                 695                 700

Ala Lys Val Asp Val Tyr Ser Tyr Gly Val Leu Leu Leu Glu Ile Val
705                 710                 715                 720
```

```
Ser Cys Arg Lys Ser Val Glu Phe Glu Ala Glu Asp Glu Glu Lys Ala
                725                 730                 735

Ile Leu Ala Glu Trp Ala Tyr Asp Cys Tyr Ile Glu Gly Thr Leu His
            740                 745                 750

Ala Leu Val Glu Gly Asp Lys Glu Ala Leu Asp Asp Met Lys Thr Phe
        755                 760                 765

Glu Lys Leu Val Met Ile Ala Leu Trp Cys Val Gln Glu Asp Pro Ser
770                 775                 780

Leu Arg Pro Thr Met Arg Asn Val Thr Gln Met Leu Glu Gly Val Val
785                 790                 795                 800

Glu Val Lys Met Pro Pro Cys Pro Ser Gln Phe Ser Val Gln Tyr Ser
            805                 810                 815

<210> SEQ ID NO 30
<211> LENGTH: 711
<212> TYPE: PRT
<213> ORGANISM: Glycine max

<400> SEQUENCE: 30

Met Pro Val Leu Arg Ser Gly Ala Arg Lys Gly Arg Ala Ala Pro Lys
1               5                   10                  15

Gln Gln Gln Gln Lys Gln Gln Ser Pro Val Val Glu Gly Glu Ala
            20                  25                  30

Ile Ala Thr Arg Thr Arg Arg Arg Ala Ala Ala Ala Ala Ala
        35                  40                  45

Ala Val Pro Glu Ser Asn Asn Asn Asn Asn Thr Asn Asn Gln Gln
    50                  55                  60

Gln Gln Val Glu Gln Val Ala Val Asn Glu Asn Val Ala Val Ala
65                  70                  75                  80

Ala Arg Glu Glu Asp Asn Arg Val Ala Glu Glu Gly Val Val Arg
                85                  90                  95

Gly Gly Gly Ala Glu Arg Glu Val Ala Glu Lys Lys Met Gly Gly
            100                 105                 110

Cys Asp Ser Gly Gly Arg Ser Asn Gly Lys Ala Asn Ala Ala Gly Glu
        115                 120                 125

Asp Asp Ala Asn Thr Pro Gln Val Pro Gln Lys Ile Gln Val Gly Asn
    130                 135                 140

Ser Pro Ser Tyr Lys Val Glu Lys Lys Leu Gly Lys Gly Gly Phe Gly
145                 150                 155                 160

Gln Val Tyr Val Gly Arg Arg Thr Gly Gly Asn Leu Asn Glu Arg Thr
                165                 170                 175

Gly Pro Gly Ala Val Glu Val Ala Leu Lys Leu Glu His Arg Thr Ser
            180                 185                 190

Lys Gly Cys Thr Tyr Gly Pro Pro Tyr Glu Trp Gln Val Tyr Asn Thr
        195                 200                 205

Leu Gly Gly Ser His Gly Val Pro Gln Val His Tyr Lys Gly Arg Gln
    210                 215                 220

Gly Asp Tyr Tyr Val Met Val Met Asp Met Leu Gly Pro Ser Leu Trp
225                 230                 235                 240

Asp Val Trp Asn Asn Ser Asn His His Met Thr Thr Glu Met Val Ala
                245                 250                 255

Cys Ile Ala Ile Glu Ala Ile Ser Ile Leu Glu Lys Met His Ser Arg
            260                 265                 270

Gly Tyr Val His Gly Asp Val Lys Pro Glu Asn Phe Leu Leu Gly Ala
        275                 280                 285
```

```
Pro Gly Thr Pro Asp Glu Lys Lys Leu Phe Leu Val Asp Leu Gly Leu
    290                 295                 300

Ala Thr Lys Trp Arg Asp Ser Thr Thr Gly Ser His Val Glu Tyr Asp
305                 310                 315                 320

Gln Arg Pro Asp Val Phe Arg Gly Thr Val Arg Tyr Ala Ser Val His
            325                 330                 335

Ala His Leu Gly Arg Thr Ala Ser Arg Arg Asp Asp Leu Glu Ser Leu
            340                 345                 350

Ala Tyr Thr Leu Ile Phe Leu Leu Arg Gly Arg Leu Pro Trp Gln Gly
            355                 360                 365

Phe Gln Gly Glu Asn Lys Gly Phe Leu Val Cys Lys Lys Lys Met Gly
    370                 375                 380

Thr Ser Pro Glu Thr Leu Cys Cys Phe Ser Pro Leu Pro Phe Lys Gln
385                 390                 395                 400

Phe Val Glu His Val Val Asn Leu Lys Phe Asp Glu Glu Pro Asn Tyr
            405                 410                 415

Ala Lys Tyr Ile Ser Leu Phe Asp Gly Val Val Gly Pro Asn Pro Asp
            420                 425                 430

Ile Arg Pro Ile Asn Thr Glu Gly Ala Gln Lys Leu Ile Gly His Lys
    435                 440                 445

Arg Gly Arg Leu Val Met Glu Glu Asp Asp Glu Gln Pro Lys Lys
450                 455                 460

Lys Ile Arg Ile Gly Leu Pro Ala Ser Gln Trp Ile Ser Val Tyr Asn
465                 470                 475                 480

Ala Arg Arg Pro Met Lys Gln Arg Tyr His Tyr Asn Val Ser Asp Thr
            485                 490                 495

Arg Leu Ser Gln His Ile Glu Lys Gly Asn Glu Asp Gly Leu Tyr Ile
            500                 505                 510

Ser Ser Val Ala Ser Cys Gln Asn Leu Trp Ala Leu Ile Met Asp Ala
            515                 520                 525

Gly Thr Gly Phe Thr Ala Gln Val Tyr Glu Leu Ser Pro Phe Phe Leu
    530                 535                 540

His Lys Glu Trp Ile Met Glu His Trp Glu Lys Asn Tyr Tyr Ile Ser
545                 550                 555                 560

Ala Ile Ala Gly Ala Val Asn Gly Ser Ser Leu Val Val Met Ser Lys
            565                 570                 575

Gly Thr Gln Tyr Leu Gln Gln Ser Tyr Lys Val Ser Asp Ser Phe Pro
    580                 585                 590

Phe Lys Trp Ile Asn Lys Lys Trp Arg Glu Gly Phe Tyr Val Thr Ala
            595                 600                 605

Met Ala Thr Ser Gly Ser Arg Trp Gly Val Val Met Ser Arg Gly Ala
610                 615                 620

Gly Phe Ser Asp Gln Val Val Glu Leu Asp Phe Leu Tyr Pro Ser Glu
625                 630                 635                 640

Gly Ile His Lys Arg Trp Asp Cys Gly Tyr Arg Ile Thr Ala Thr Ala
            645                 650                 655

Ala Thr Trp Asp Gln Ala Ala Phe Val Leu Ser Val Pro Arg Arg Lys
            660                 665                 670

Pro Leu Asp Glu Thr Gln Glu Thr Leu Arg Thr Ser Ala Phe Pro Ser
            675                 680                 685

Thr His Val Lys Glu Lys Trp Ala Lys Asn Leu Tyr Ile Ala Ser Ile
    690                 695                 700
```

```
Cys Tyr Gly Arg Thr Val Ser
705                 710

<210> SEQ ID NO 31
<211> LENGTH: 355
<212> TYPE: PRT
<213> ORGANISM: Glycine max

<400> SEQUENCE: 31

Met Leu Ile Leu Val Leu Gly Leu Ala Ser Ala Thr Phe Leu Val Phe
1               5                   10                  15

Val Ala Val Tyr Leu Phe Tyr Ser Lys Arg Val Ser Lys Tyr Asn
            20                  25                  30

Glu Ser Lys Asp Ile Glu Ser Glu His Lys Glu Asp Glu Glu Met
        35                  40                  45

Ala Gln Lys Glu Asp Leu Met Ile Phe Gln Gly Gly Glu Asp Leu Thr
    50                  55                  60

Ile Cys Asp Ile Leu Asp Ala Pro Gly Glu Val Ile Gly Lys Ser Asn
65                  70                  75                  80

Tyr Gly Thr Leu Tyr Lys Ala Leu Leu Gln Arg Ser Asn Lys Val Ser
                85                  90                  95

Leu Leu Arg Phe Leu Arg Pro Val Cys Thr Ala Arg Gly Glu Leu
            100                 105                 110

Asp Glu Met Ile His Phe Leu Gly Arg Ile Arg His Pro Asn Leu Val
            115                 120                 125

Pro Leu Leu Gly Phe Tyr Thr Gly Pro Arg Gly Glu Lys Leu Leu Val
    130                 135                 140

His Pro Phe Tyr Arg His Gly Ser Leu Thr Gln Phe Ile Arg Asp Gly
145                 150                 155                 160

Asn Gly Glu Cys Tyr Lys Trp Ser Asn Ile Cys Arg Ile Ser Ile Gly
                165                 170                 175

Ile Ala Lys Gly Leu Glu His Leu His Thr Ser Gln Glu Lys Pro Ile
            180                 185                 190

Ile His Gly Asn Leu Lys Ser Lys Asn Ile Leu Leu Asp Arg Ser Tyr
        195                 200                 205

Gln Pro Tyr Ile Ser Asp Ser Gly Leu His Leu Leu Leu Asn Pro Thr
    210                 215                 220

Ala Gly Gln Glu Met Leu Glu Ser Ser Ala Gln Gly Tyr Lys Ala
225                 230                 235                 240

Pro Glu Leu Ile Lys Met Lys Asp Ala Ser Glu Glu Ser Asp Ile Tyr
                245                 250                 255

Ser Leu Gly Val Ile Leu Leu Glu Leu Leu Ser Gly Lys Glu Pro Ile
            260                 265                 270

Asn Glu His Pro Thr Pro Asp Glu Asp Phe Tyr Leu Pro Asn Phe Met
        275                 280                 285

Arg Asn Ala Val Leu Gly His Arg Ile Ala Asp Leu Tyr His Pro Ala
    290                 295                 300

Ile Leu Leu Arg Asn Ser Arg Asp Asp Ser Ile Pro Val Thr Glu Glu
305                 310                 315                 320

Cys Ile Leu Lys Val Phe Gln Leu Ala Met Ala Cys Cys Ser Pro Ser
                325                 330                 335

Pro Ser Val Arg Pro Asn Ile Lys Gln Val Leu Lys Lys Leu Glu Glu
            340                 345                 350

Ile Met Phe
        355
```

<210> SEQ ID NO 32
<211> LENGTH: 1034
<212> TYPE: PRT
<213> ORGANISM: Glycine max

<400> SEQUENCE: 32

```
Met Ala Arg Cys Ile Leu Ser His Val Leu Ala Phe Ala Leu Val Ala
1               5                   10                  15

Gly Leu Cys Val Phe Ser Cys Leu Val Asn Val Ala Gln Ala Gln Ser
            20                  25                  30

Ala Asn Ala Thr Thr Asp Pro Ser Glu Ala Arg Ala Leu Asn Ser Ile
        35                  40                  45

Phe Ser Lys Trp Asp Ile Leu Ala Asn Pro Thr Gln Trp Asn Ile Ser
    50                  55                  60

Ser Glu Leu Cys Ser Gly Arg Ala Ile Asp Ala Thr Thr Ile Asp
65                  70                  75                  80

Asp Thr Thr Phe Asn Pro Phe Ile Lys Cys Asp Cys Ser Tyr Asp Ser
                85                  90                  95

Arg Thr Thr Cys Arg Ile Thr Ala Leu Lys Val Tyr Ala Met Ser Ile
            100                 105                 110

Val Gly Thr Ile Pro Glu Glu Leu Trp Thr Leu Thr Tyr Leu Thr Asn
        115                 120                 125

Leu Asn Leu Gly Gln Asn Tyr Leu Thr Gly Ser Leu Pro Pro Asn Ile
    130                 135                 140

Gly Asn Leu Thr Arg Met Gln Tyr Leu Ser Ile Gly Ile Asn Asn Phe
145                 150                 155                 160

Ser Gly Glu Leu Pro Lys Glu Leu Gly Asn Leu Thr Glu Leu Arg Ser
                165                 170                 175

Leu Ala Phe Gly Ser Asn Lys Phe Arg Gly Ser Leu Pro Ser Glu Leu
            180                 185                 190

Gly Lys Leu Thr Asn Leu Glu Gln Ile Tyr Phe Asp Ser Ser Gly Ile
        195                 200                 205

Ser Gly Pro Ile Pro Ser Thr Phe Ala Asn Leu Lys Asn Leu Leu His
    210                 215                 220

Val Gly Ala Ser Asp Thr Glu Leu Thr Gly Lys Ile Pro Asp Phe Ile
225                 230                 235                 240

Gly Asn Trp Ser Lys Leu Gln Thr Leu Arg Phe Gln Gly Asn Ser Phe
                245                 250                 255

Asn Gly Ser Ile Pro Ser Ser Phe Ser Asn Leu Ser Ser Leu Thr Glu
            260                 265                 270

Leu Arg Ile Ser Gly Leu Ser Asn Gly Ser Ser Ser Leu Glu Phe Leu
        275                 280                 285

Arg Asn Met Lys Ser Leu Thr Ile Leu Glu Leu Arg Asn Asn Asn Ile
    290                 295                 300

Ser Gly Ser Ile Ser Ser Thr Ile Gly Glu Leu His Asn Leu Asn Gln
305                 310                 315                 320

Leu Asp Leu Ser Phe Asn Asn Ile Thr Gly Gln Asn Leu Gly Ser Ile
                325                 330                 335

Phe Asn Leu Ser Ser Leu Thr Tyr Leu Phe Leu Gly Asn Asn Lys Phe
            340                 345                 350

Asn Gly Thr Leu Pro Met Gln Lys Ser Ser Ser Leu Val Asn Ile Asp
        355                 360                 365

Leu Ser Tyr Asn Asp Leu Ser Gly Ser Leu Pro Ser Trp Val Asn Glu
```

```
                370                 375                 380
Pro Asn Leu Gln Leu Asn Leu Val Ala Asn Asn Leu Asp Val Ser Asn
385                 390                 395                 400

Ala Ser Gly Leu Pro Ile Gly Leu Asn Cys Leu Gln Lys Asn Phe Pro
                405                 410                 415

Cys Asn Gln Gly Ile Gly Arg Tyr Ser Asp Phe Ala Ile Lys Cys Gly
                420                 425                 430

Gly Asn Gln Ile Arg Ser Ala Asp Gly Ile Val Tyr Glu Met Asp Asn
                435                 440                 445

Gln Thr Leu Gly Pro Ala Thr Tyr Phe Val Thr Asp Ala Asn Arg Trp
450                 455                 460

Ala Ile Ser Asn Val Gly Leu Phe Thr Gly Ser Ser Asn Pro Val Tyr
465                 470                 475                 480

Lys Ser Phe Val Ser Asn Gln Phe Thr Gly Thr Val Asn Ser Glu Leu
                485                 490                 495

Phe Gln Thr Ala Arg Leu Ser Ala Ser Ser Leu Arg Tyr Tyr Gly Leu
                500                 505                 510

Gly Leu Glu Asn Gly Phe Tyr Asn Ile Thr Leu Gln Phe Ala Glu Thr
                515                 520                 525

Ala Ile Leu Asp Ser Thr Arg Ser Trp Glu Ser Leu Gly Arg Arg Val
530                 535                 540

Phe Asp Ile Tyr Ile Gln Gly Thr Arg Val Leu Lys Asp Phe Asp Ile
545                 550                 555                 560

Gln Lys Glu Ala Gly Gly Ile Ser Tyr Lys Ala Ile Gln Arg Gln Phe
                565                 570                 575

Arg Phe Glu Val Thr Glu Asn Tyr Leu Glu Ile His Leu Phe Trp Ala
                580                 585                 590

Gly Lys Gly Thr Cys Cys Ile Pro Thr Gln Gly Thr Tyr Gly Pro Leu
                595                 600                 605

Ile Gln Ala Ile His Ala Ile Pro Asp Phe Ile Pro Thr Val Ser Asn
                610                 615                 620

Lys Pro Pro Ser Ser Asn Asn Asn Ile Gly Leu Ile Leu Gly Ile
625                 630                 635                 640

Val Leu Gly Val Gly Val Ser Val Leu Ser Ile Phe Ala Ile Phe
                645                 650                 655

Cys Ile Ile Arg Arg Arg Arg Arg Asp Asp Glu Lys Glu Leu Leu
                660                 665                 670

Gly Ile Asp Thr Lys Pro Tyr Thr Phe Ser Tyr Ser Glu Leu Lys Asn
                675                 680                 685

Ala Thr Asn Asp Phe Asn Leu Glu Asn Lys Leu Gly Glu Gly Gly Phe
690                 695                 700

Gly Pro Val Tyr Lys Gly Thr Leu Asn Asp Gly Arg Val Ile Ala Val
705                 710                 715                 720

Lys Gln Leu Ser Val Gly Ser His Gln Gly Lys Ser Gln Phe Ile Thr
                725                 730                 735

Glu Ile Ala Thr Ile Ser Ala Val Gln His Arg Asn Leu Val Lys Leu
                740                 745                 750

Tyr Gly Cys Cys Ile Glu Gly Ser Lys Arg Leu Leu Val Tyr Glu Tyr
                755                 760                 765

Leu Glu Asn Lys Ser Leu Asp Gln Ala Leu Phe Gly Lys Cys Leu Thr
                770                 775                 780

Leu Asn Trp Ser Thr Arg Tyr Asp Ile Cys Leu Gly Val Ala Arg Gly
785                 790                 795                 800
```

```
Leu Thr Tyr Leu His Glu Ser Arg Leu Arg Ile Val His Arg Asp
                805                 810                 815

Val Lys Ala Ser Asn Ile Leu Leu Asp Tyr Glu Leu Ile Pro Lys Ile
            820                 825                 830

Ser Asp Phe Gly Leu Ala Lys Leu Tyr Asp Asp Lys Lys Thr His Ile
            835                 840                 845

Ser Thr Gly Val Ala Gly Thr Ile Gly Tyr Leu Ala Pro Glu Tyr Ala
    850                 855                 860

Met Arg Gly His Leu Thr Glu Lys Ala Asp Val Phe Ser Phe Gly Val
865                 870                 875                 880

Val Ala Leu Glu Leu Val Ser Gly Arg Pro Asn Ser Asp Ser Ser Leu
                885                 890                 895

Glu Gly Glu Lys Val Tyr Leu Leu Glu Trp Ala Trp Gln Leu His Glu
            900                 905                 910

Lys Asn Cys Ile Ile Asp Leu Val Asp Arg Leu Ser Glu Phe Asn
            915                 920                 925

Glu Glu Glu Val Lys Arg Val Val Gly Ile Ala Leu Leu Cys Thr Gln
930                 935                 940

Thr Ser Pro Thr Leu Arg Pro Ser Met Ser Arg Val Val Ala Met Leu
945                 950                 955                 960

Ser Gly Asp Ile Glu Val Ser Thr Val Thr Ser Lys Pro Gly Tyr Leu
                965                 970                 975

Ser Asp Trp Lys Phe Glu Asp Val Ser Ser Phe Met Thr Gly Ile Glu
            980                 985                 990

Ile Lys Gly Ser Asp Thr Asn Tyr Gln Asn Ser Ser Gly Ser Thr Ser
            995                 1000                1005

Met Met Gly Gly Val Asp Tyr Tyr Ser Pro Arg Asp Val Ser Lys
    1010                1015                1020

Pro Ile Leu Lys Glu Thr Leu Trp Glu Gly Arg
    1025                1030

<210> SEQ ID NO 33
<211> LENGTH: 294
<212> TYPE: PRT
<213> ORGANISM: Glycine max

<400> SEQUENCE: 33

Met Asp Gln Tyr Glu Lys Val Glu Lys Ile Gly Glu Gly Thr Tyr Gly
1               5                   10                  15

Val Val Tyr Lys Ala Arg Asp Arg Ala Thr Asn Glu Thr Ile Ala Leu
            20                  25                  30

Lys Lys Ile Arg Leu Glu Gln Glu Asp Glu Gly Val Pro Ser Thr Ala
        35                  40                  45

Ile Arg Glu Ile Ser Leu Leu Lys Glu Met Gln His Arg Asn Ile Val
    50                  55                  60

Arg Leu Gln Asp Val Val His Ser Glu Lys Arg Leu Tyr Leu Val Phe
65                  70                  75                  80

Glu Tyr Leu Asp Leu Asp Leu Lys Lys His Met Asp Ser Ser Pro Glu
                85                  90                  95

Phe Val Lys Asp Pro Arg Gln Val Lys Met Phe Leu Tyr Gln Ile Leu
            100                 105                 110

Cys Gly Ile Ala Tyr Cys His Ser His Arg Val Leu His Arg Asp Leu
        115                 120                 125

Lys Pro Gln Asn Leu Leu Ile Asp Arg Arg Thr Asn Ser Leu Lys Leu
```

```
            130                 135                 140
Ala Asp Phe Gly Leu Ala Arg Ala Phe Gly Ile Pro Val Arg Thr Phe
145                 150                 155                 160

Thr His Glu Val Val Thr Leu Trp Tyr Arg Ala Pro Glu Ile Leu Leu
                    165                 170                 175

Gly Ser Arg His Tyr Ser Thr Pro Val Asp Val Trp Ser Val Gly Cys
                180                 185                 190

Ile Phe Ala Glu Met Val Asn Arg Arg Pro Leu Phe Pro Gly Asp Ser
            195                 200                 205

Glu Ile Asp Glu Leu Phe Lys Ile Phe Arg Ile Leu Gly Thr Pro Asn
210                 215                 220

Glu Asp Thr Trp Pro Gly Val Thr Ser Leu Pro Asp Phe Lys Ser Thr
225                 230                 235                 240

Phe Pro Lys Trp Pro Ser Lys Asp Leu Ala Asn Val Val Pro Asn Leu
                245                 250                 255

Asp Ala Ala Gly Leu Asn Leu Leu Ser Ser Met Leu Cys Leu Asp Pro
                260                 265                 270

Ser Lys Arg Ile Thr Ala Arg Ser Ala Val Glu His Glu Tyr Phe Lys
                275                 280                 285

Asp Ile Lys Phe Val Pro
            290

<210> SEQ ID NO 34
<211> LENGTH: 1281
<212> TYPE: PRT
<213> ORGANISM: Glycine max

<400> SEQUENCE: 34

Met Gly Val Val Leu Ala Leu Ile Leu Gln Leu Val Lys Leu Cys Ile
1               5                   10                  15

Ile Gly Phe Val Val Glu Phe Gln Gly Ser Glu Gly Ser Val Ile Ser
                20                  25                  30

Pro Ser Pro Ala Phe Leu Pro Val Ile His Pro Ser Gly Glu Ala Pro
            35                  40                  45

Ala Pro Ile His His Gly Leu Ser Trp Glu Ser Ser Pro Pro Lys Ser
        50                  55                  60

Pro Ser Asp Pro Asn Glu Phe Gly Ile Ser Pro Ser Asn Glu Ile Ile
65                  70                  75                  80

Pro Val Asp Pro Ser Pro Ser Glu Pro Pro Gly Thr Leu His Pro Arg
                85                  90                  95

Glu Pro Trp Arg Thr Ile Ala Pro Ile Pro Pro Glu Val Pro Asn Gly
            100                 105                 110

Ser Phe Leu Pro Pro Pro Val Thr Thr Leu Pro Pro Pro Thr Ser Ala
        115                 120                 125

Pro Thr Pro Gln Lys Val Lys Gly Phe Glu Pro Ser Ile Ser Pro Ser
130                 135                 140

Pro Ser Thr Ser Thr Ile Ala Ser Ser Pro Pro Ala Pro Tyr Asn Ala
145                 150                 155                 160

Ala His Ala Pro Ser Thr Ser Glu Gly Ser Val Pro Pro Ser Ile Gln
                165                 170                 175

Pro Ser Pro Pro Gln Ser Lys Thr Thr Pro Ala Ile Arg Pro Pro Val
                180                 185                 190

Ser Thr Pro Ile Ala Pro Ala Pro Ile Ala Ile Thr Ser Gly Asn Leu
            195                 200                 205
```

```
Pro Lys Thr Ser Pro Val Ser Gln Pro Ile Glu His Gly Ser Leu Pro
    210                 215                 220

Pro Lys Ile Asp Glu Arg Asn Lys Ser His Lys Pro Glu Pro Ala Leu
225                 230                 235                 240

Pro Ala Leu Val Pro Ile Pro Ser Thr Ile Leu Pro Lys Ile Ser Pro
                245                 250                 255

Val Ser Gln Pro Thr Glu Asn Gly Ser Leu Pro His Arg Glu Gly Ala
            260                 265                 270

Asn Asn Gly His Ile Ser Glu Pro Ile Ser Pro Ala Pro Thr Val Phe
            275                 280                 285

Ser Phe Pro Glu His Ser Pro Glu Ser Gln Pro Thr Glu His Gly Ser
    290                 295                 300

Leu Pro Pro Thr Val Pro Arg Arg Asn Ile Asn Thr Gly Arg Thr Leu
305                 310                 315                 320

Glu Pro Val Ser Gln Ala Pro Val Ala Thr Ala Pro Ala Ile Leu Pro
                325                 330                 335

Lys Asn Ser Ser Val Ser Gln Pro Thr His His Gly Asn Ser Pro Pro
            340                 345                 350

Asp Val Gln Asn Arg Thr Ala Asn Asn Gly His Ser His Thr Pro Ala
            355                 360                 365

Pro Glu Met Pro Pro Ser Val Thr Pro Pro Arg Pro Phe Pro Val Asp
    370                 375                 380

Pro Pro Leu Val His Pro Val Ile Pro Ala Ala Pro Pro Pro Lys Ser
385                 390                 395                 400

Pro Ala Pro Gly Gly Glu Pro Val Ser Ala Pro Val Tyr Lys Thr Pro
                405                 410                 415

Lys Pro Pro Ser Ala Ile Val His Phe His Ala Gln Ala Pro Val Val
            420                 425                 430

Ser Pro Val Ser Thr Pro Ser Arg Ser Phe Asn Trp Thr Lys Gly Gly
            435                 440                 445

Glu Pro Val Ser Ala Pro Pro Tyr Lys Thr Pro Lys Pro Leu Pro Val
    450                 455                 460

Ile Val His Ser Pro Ala Gln Ala Pro Ser Ser Ala His Lys Ala Arg
465                 470                 475                 480

Gln Phe His His Ala Pro Glu Pro Pro Ile Ser Ser Pro Glu Ser Pro
                485                 490                 495

Phe Asn Lys Asp His Pro Ala Ser Ser Pro Ser Thr Thr Phe Tyr
            500                 505                 510

Lys His His His Thr Arg Asn Thr Val Thr Ser Pro Ala Pro Ala Ser
    515                 520                 525

Ser His Ser Ile Ser Pro Ser Thr Ser Lys His Gln Asp Gly Ser Asn
    530                 535                 540

Pro Pro Leu Pro Leu Pro Thr Ser Arg Gln Arg His His Ala Pro Pro
545                 550                 555                 560

Pro Met Asn Thr Gly Ser Ser Val Ser Pro Ser Gly Leu Pro Ile Gln
                565                 570                 575

Ser Pro Val Ser Gln Val Ser Pro Ala Pro Ser Pro Leu Phe Lys Ile
            580                 585                 590

Ser Pro His Ser Thr Lys Ile Pro Leu Pro Pro Lys Val Ser Pro
            595                 600                 605

Ser Arg Pro Ser Ser Lys Thr Pro Lys Lys Pro Val Arg Pro Arg Phe
    610                 615                 620

Gln Ala Leu Pro Pro Pro Pro Asn Glu Asp Cys Ile Ser Leu Val
```

```
                625                 630                 635                 640
          Cys Ser Asp Pro Tyr Thr Ser Thr Pro Pro Gly Ala Pro Cys Lys Cys
                            645                 650                 655
          Val Trp Pro Met Lys Val Gly Leu Arg Leu Ser Val Ser Leu Tyr Thr
                            660                 665                 670
          Phe Phe Pro Leu Val Ser Glu Phe Ala Ser Glu Ile Ala Thr Gly Val
                            675                 680                 685
          Phe Met Lys Gln Ser Gln Val Arg Ile Met Gly Ala Asp Ala Ala Asn
                            690                 695                 700
          Gln Gln Pro Asp Lys Thr Ile Val Phe Val Asp Leu Val Pro Leu Gly
          705                 710                 715                 720
          Glu Glu Phe Asp Asn Thr Thr Ala Phe Leu Thr Ser Glu Arg Phe Trp
                            725                 730                 735
          His Lys Gln Val Val Ile Lys Thr Ser Tyr Phe Gly Asp Tyr Asp Val
                            740                 745                 750
          Leu Tyr Val Thr Tyr Pro Gly Leu Pro Pro Ser Pro Pro Leu Pro Pro
                            755                 760                 765
          Ser Ser Ile Ser Ile Ile Asp Gly Gly Pro Tyr Ser Gly Gly Gly Asn
              770                 775                 780
          Asn Gly Arg Thr Ile Lys Pro Leu Gly Val Asp Ile Ser Lys Arg Gln
          785                 790                 795                 800
          His Lys Gly Gly Leu Ser Lys Gly Ile Ile Ala Ile Ala Leu Ser
                            805                 810                 815
          Val Phe Leu Val Val Leu Cys Phe Ala Ala Ala Leu Ala Leu Phe
              820                 825                 830
          Lys Tyr Arg Asp His Val Ser Gln Pro Pro Ser Thr Pro Arg Val Leu
              835                 840                 845
          Pro Pro Leu Thr Lys Ala Pro Gly Ala Ala Gly Ser Val Val Gly Gly
              850                 855                 860
          Gly Leu Ala Ser Ala Ser Thr Ser Phe Arg Ser Asn Ile Ala Ala Tyr
          865                 870                 875                 880
          Thr Gly Ser Ala Lys Thr Phe Ser Met Asn Asp Ile Glu Lys Ala Thr
                            885                 890                 895
          Asp Asn Phe His Ala Ser Arg Val Leu Gly Glu Gly Gly Phe Gly Leu
                            900                 905                 910
          Val Tyr Ser Gly Thr Leu Glu Asp Gly Thr Lys Val Ala Val Lys Val
                            915                 920                 925
          Leu Lys Arg Glu Asp His His Gly Asp Arg Glu Phe Leu Ser Glu Val
              930                 935                 940
          Glu Met Leu Ser Arg Leu His Arg Asn Leu Val Lys Leu Ile Gly
          945                 950                 955                 960
          Ile Cys Ala Glu Val Ser Phe Arg Cys Leu Val Tyr Glu Leu Ile Pro
                            965                 970                 975
          Asn Gly Ser Val Glu Ser His Leu His Gly Val Asp Lys Glu Asn Ser
                            980                 985                 990
          Pro Leu Asp Trp Ser Ala Arg Leu  Lys Ile Ala Leu Gly  Ser Ala Arg
                            995                 1000                1005
          Gly Leu  Ala Tyr Leu His Glu  Asp Ser Ser Pro His  Val Ile His
              1010                1015                1020
          Arg Asp  Phe Lys Ser Ser Asn  Ile Leu Leu Glu Asn  Asp Phe Thr
              1025                1030                1035
          Pro Lys  Val Ser Asp Phe Gly  Leu Ala Arg Thr Ala  Ala Asp Glu
              1040                1045                1050
```

Gly Asn Arg His Ile Ser Thr Arg Val Met Gly Thr Phe Gly Tyr
        1055                1060                1065

Val Ala Pro Glu Tyr Ala Met Thr Gly His Leu Leu Val Lys Ser
        1070                1075                1080

Asp Val Tyr Ser Tyr Gly Val Val Leu Glu Leu Leu Thr Gly
        1085                1090                1095

Arg Lys Pro Val Asp Met Ser Arg Pro Pro Gly Gln Glu Asn Leu
        1100                1105                1110

Val Ala Trp Ala Arg Pro Leu Leu Ser Ser Glu Glu Gly Leu Glu
        1115                1120                1125

Ala Met Ile Asp Pro Ser Leu Gly His Asp Val Pro Ser Asp Ser
        1130                1135                1140

Val Ala Lys Val Ala Ala Ile Ala Ser Met Cys Val Gln Pro Glu
        1145                1150                1155

Val Ser Asp Arg Pro Phe Met Gly Glu Val Val Gln Ala Leu Lys
        1160                1165                1170

Leu Val Cys Asn Glu Cys Asp Glu Ala Arg Glu Ala Gly Ser Ser
        1175                1180                1185

Ser Ser Ser Val Asp Leu Ser His Ser Arg Gln Pro Ser Asp Asn
        1190                1195                1200

Leu Gln Gly Gln Phe Ser Ala Thr Asn Tyr Asp Ser Gly Ile Asp
        1205                1210                1215

Ile Glu Asn Gly Leu Leu Ala Ser Glu Leu Phe Ser Ser Ser Ala
        1220                1225                1230

Arg Tyr Gly Arg Arg Val Ser Gly Ser Phe Arg Arg His Ser Tyr
        1235                1240                1245

Ser Gly Pro Leu Asn Thr Gly Arg Ser Lys Arg Leu Trp Gln Ile
        1250                1255                1260

Ile Arg Lys Leu Ser Gly Gly Ser Ile Ser Glu His Gly Thr Met
        1265                1270                1275

Phe Lys Leu
        1280

<210> SEQ ID NO 35
<211> LENGTH: 462
<212> TYPE: PRT
<213> ORGANISM: Glycine max

<400> SEQUENCE: 35

Met Thr Ser Arg Ser Gly Gln Gly Ser Ser Gly Gly Ser Ser Arg
1               5                   10                  15

Thr Arg Val Gly Lys Tyr Glu Leu Gly Arg Thr Leu Gly Glu Gly Asn
            20                  25                  30

Phe Ala Lys Val Lys Phe Ala Arg His Val Glu Thr Arg Glu Asn Val
        35                  40                  45

Ala Ile Lys Ile Leu Asp Lys Glu Lys Leu Leu Lys His Lys Met Ile
    50                  55                  60

Ala Gln Ile Lys Arg Glu Ile Ser Thr Met Lys Leu Ile Arg His Pro
65                  70                  75                  80

Asn Val Ile Arg Met Tyr Glu Val Met Ala Ser Lys Thr Lys Ile Tyr
                85                  90                  95

Ile Val Leu Glu Phe Val Thr Gly Gly Glu Leu Phe Asp Lys Ile Ala
            100                 105                 110

Arg Ser Gly Arg Leu Lys Glu Asp Glu Ala Arg Lys Tyr Phe Gln Gln

```
                        115                 120                 125
Leu Ile Cys Ala Val Asp Tyr Cys His Ser Arg Gly Val Phe His Arg
            130                 135                 140

Asp Leu Lys Pro Glu Asn Leu Leu Asp Ala Asn Gly Val Leu Lys
145                 150                 155                 160

Val Ser Asp Phe Gly Leu Ser Ala Leu Pro Gln Gln Val Arg Glu Asp
                        165                 170                 175

Gly Leu Leu His Thr Thr Cys Gly Thr Pro Asn Tyr Val Ala Pro Glu
            180                 185                 190

Val Ile Asn Asn Lys Gly Tyr Asp Gly Ala Lys Ala Asp Leu Trp Ser
            195                 200                 205

Cys Gly Val Ile Leu Phe Val Leu Met Ala Gly Tyr Leu Pro Phe Glu
            210                 215                 220

Glu Thr Asn Leu Ser Ala Leu Tyr Lys Lys Ile Phe Lys Ala Glu Phe
225                 230                 235                 240

Thr Cys Pro Pro Trp Phe Ser Ser Ala Lys Lys Leu Ile Asn Lys
                        245                 250                 255

Ile Leu Asp Pro Asn Pro Ala Thr Arg Ile Thr Phe Ala Glu Val Ile
            260                 265                 270

Glu Asn Asp Trp Phe Lys Lys Gly Tyr Lys Pro Pro Val Phe Glu Gln
            275                 280                 285

Ala Asn Val Ser Leu Asp Asp Leu Asp Ser Ile Phe Ser Asp Ser Thr
            290                 295                 300

Asp Ser Gln Asn Leu Val Val Glu Arg Arg Glu Gly Pro Met Ala
305                 310                 315                 320

Pro Val Ala Pro Val Thr Met Asn Ala Phe Glu Leu Ile Ser Lys Ser
                        325                 330                 335

Gln Gly Leu Asn Leu Ser Ser Leu Phe Glu Lys Gln Met Gly Leu Val
            340                 345                 350

Lys Arg Glu Thr Arg Phe Thr Ser Lys Cys Ser Ala Asp Glu Ile Ile
            355                 360                 365

Ser Lys Ile Glu Lys Ala Ala Gly Pro Leu Gly Phe Asp Val Lys Lys
            370                 375                 380

Asn Asn Cys Lys Leu Lys Ile Gln Gly Glu Lys Thr Gly Arg Lys Gly
385                 390                 395                 400

His Leu Ser Val Ala Thr Glu Ile Leu Glu Val Ala Pro Ser Leu Tyr
                        405                 410                 415

Met Val Glu Leu Arg Lys Ser Glu Gly Asp Thr Leu Glu Phe His Lys
            420                 425                 430

Phe Tyr Lys Asn Leu Ala Thr Gly Leu Lys Asp Ile Val Trp Lys Ala
            435                 440                 445

Glu Pro Ile Asp Glu Glu Lys Asp Gly Ala Asn Pro Ser Lys
            450                 455                 460

<210> SEQ ID NO 36
<211> LENGTH: 440
<212> TYPE: PRT
<213> ORGANISM: Glycine max

<400> SEQUENCE: 36

Met Met Gly Glu Lys Ser Asn Ser Asn Ser Gly Asp Ala Ile Asn Ser
1               5                   10                  15

Thr Leu Leu His Gly Lys Tyr Glu Leu Gly Arg Leu Leu Gly His Gly
            20                  25                  30
```

-continued

```
Ser Phe Ala Lys Val Tyr His Ala Arg His Leu Asn Thr Gly Lys Ser
         35                  40                  45

Val Ala Met Lys Val Val Gly Lys Glu Lys Val Lys Val Gly Met
 50                  55                  60

Met Glu Gln Ile Lys Arg Glu Ile Ser Ala Met Asn Met Val Lys His
 65                  70                  75                  80

Pro Asn Ile Val Gln Leu His Glu Val Met Ala Ser Lys Ser Lys Ile
                 85                  90                  95

Tyr Ile Ala Met Glu Leu Val Arg Gly Gly Glu Leu Phe Asn Lys Ile
                100                 105                 110

Ala Arg Gly Arg Leu Arg Glu Glu Thr Ala Arg Leu Tyr Phe Gln Gln
             115                 120                 125

Leu Ile Ser Ala Val Asp Phe Cys His Ser Arg Gly Val Phe His Arg
 130                 135                 140

Asp Leu Lys Pro Glu Asn Leu Leu Leu Asp Asp Gly Asn Leu Lys
 145                 150                 155                 160

Val Thr Asp Phe Gly Leu Ser Thr Phe Ser Glu His Leu Arg His Asp
                 165                 170                 175

Gly Leu Leu His Thr Thr Cys Gly Thr Pro Ala Tyr Val Ala Pro Glu
             180                 185                 190

Val Ile Gly Lys Arg Gly Tyr Asp Gly Ala Lys Ala Asp Ile Trp Ser
             195                 200                 205

Cys Gly Val Ile Leu Tyr Val Leu Leu Ala Gly Phe Leu Pro Phe Gln
 210                 215                 220

Asp Glu Asn Leu Val Ala Leu Tyr Lys Lys Ile Tyr Arg Gly Asp Phe
 225                 230                 235                 240

Lys Cys Pro Pro Trp Phe Ser Ser Glu Ala Arg Arg Leu Ile Thr Lys
                 245                 250                 255

Leu Leu Asp Pro Asn Pro Asn Thr Arg Ile Thr Ile Ser Lys Ile Met
                 260                 265                 270

Asp Ser Ser Trp Phe Lys Lys Pro Val Pro Lys Asn Leu Val Gly Lys
             275                 280                 285

Lys Arg Glu Glu Leu Asn Leu Glu Glu Lys Ile Lys His Gln Glu Gln
 290                 295                 300

Glu Val Ser Thr Thr Met Asn Ala Phe His Ile Ile Ser Leu Ser Glu
 305                 310                 315                 320

Gly Phe Asp Leu Ser Pro Leu Phe Glu Glu Lys Lys Arg Glu Glu Lys
                 325                 330                 335

Glu Leu Arg Phe Ala Thr Thr Arg Pro Ala Ser Ser Val Ile Ser Arg
             340                 345                 350

Leu Glu Asp Leu Ala Lys Ala Val Lys Phe Asp Val Lys Lys Ser Glu
 355                 360                 365

Thr Lys Val Arg Leu Gln Gly Gln Glu Asn Gly Arg Lys Gly Lys Leu
 370                 375                 380

Ala Ile Ala Ala Asp Leu Tyr Ala Val Thr Pro Ser Phe Leu Val Val
 385                 390                 395                 400

Glu Val Lys Lys Asp Asn Gly Asp Thr Leu Glu Tyr Asn Gln Phe Cys
                 405                 410                 415

Ser Lys Glu Leu Arg Pro Ala Leu Lys Asp Ile Val Trp Arg Thr Ser
             420                 425                 430

Pro Ala Glu Asn Pro Thr Leu Ala
             435                 440
```

```
<210> SEQ ID NO 37
<211> LENGTH: 793
<212> TYPE: PRT
<213> ORGANISM: Glycine max

<400> SEQUENCE: 37
```

| | | | | | | | | | | | | | | |
|---|---|---|---|---|---|---|---|---|---|---|---|---|---|---|
| Met | Phe | Lys | Phe | Leu | Lys | Glu | Val | Val | Gly | Ser | Gly | Thr | Gly | Val |
| 1 | | | | 5 | | | | | 10 | | | | | 15 |
| Lys | Asp | Leu | Pro | Tyr | Thr | Ile | Ala | Glu | Pro | Tyr | Pro | Ser | Ala | Trp | Gly |
| | | | 20 | | | | | 25 | | | | | 30 | | |
| Ser | Trp | Thr | His | Ser | Arg | Gly | Thr | Ser | Lys | Asp | Asp | Gly | Ser | Pro | Val |
| | | | 35 | | | | | 40 | | | | | 45 | | |
| Ser | Val | Phe | Ser | Leu | Ser | Gly | Ser | Asn | Ala | Gln | Asp | Gly | His | Leu | Ala |
| | 50 | | | | | 55 | | | | | 60 | | | | |
| Ala | Ala | Arg | Asn | Gly | Val | Lys | Arg | Leu | Arg | Thr | Val | Arg | His | Pro | Asn |
| 65 | | | | | 70 | | | | | 75 | | | | | 80 |
| Ile | Leu | Ser | Phe | Leu | His | Ser | Ala | Glu | Ile | Glu | Thr | Tyr | Asp | Ala | Gly |
| | | | | 85 | | | | | 90 | | | | | 95 | |
| Ser | Pro | Lys | Val | Thr | Ile | Tyr | Ile | Val | Thr | Glu | Pro | Val | Met | Pro | Leu |
| | | | 100 | | | | | 105 | | | | | 110 | | |
| Ser | Glu | Lys | Ile | Lys | Glu | Leu | Gly | Leu | Glu | Gly | Thr | Gln | Arg | Asp | Glu |
| | | | 115 | | | | | 120 | | | | | 125 | | |
| Tyr | Tyr | Ala | Leu | Gly | Leu | His | Gln | Ile | Ala | Lys | Ala | Val | Ser | Phe | Leu |
| | 130 | | | | | 135 | | | | | 140 | | | | |
| Asn | Asn | Asp | Cys | Lys | Leu | Val | His | Gly | Asn | Ile | Cys | Met | Ala | Ser | Thr |
| 145 | | | | | 150 | | | | | 155 | | | | | 160 |
| Val | Val | Thr | Pro | Thr | Leu | Asp | Trp | Lys | Leu | His | Ala | Leu | Asp | Val | Leu |
| | | | | 165 | | | | | 170 | | | | | 175 | |
| Ser | Glu | Phe | Asp | Gly | Ser | Ser | Glu | Ala | Ser | Ser | Gly | Gln | Met | Leu | Gln |
| | | | 180 | | | | | 185 | | | | | 190 | | |
| Tyr | Ala | Trp | Leu | Val | Gly | Ser | Gln | Tyr | Lys | Pro | Met | Glu | Leu | Ala | Lys |
| | | | 195 | | | | | 200 | | | | | 205 | | |
| Ser | Asp | Trp | Asp | Ala | Ile | Lys | Lys | Ser | Pro | Pro | Trp | Ala | Ile | Asp | Ser |
| | 210 | | | | | 215 | | | | | 220 | | | | |
| Trp | Gly | Met | Gly | Cys | Leu | Ile | Tyr | Glu | Val | Phe | Ser | Gly | Leu | Arg | Leu |
| 225 | | | | | 230 | | | | | 235 | | | | | 240 |
| Gly | Lys | Thr | Glu | Glu | Leu | Arg | Asn | Ile | Gly | Ser | Ile | Pro | Lys | Ser | Leu |
| | | | | 245 | | | | | 250 | | | | | 255 | |
| Leu | Pro | Asp | Tyr | Gln | Arg | Leu | Leu | Ser | Ser | Met | Pro | Ser | Arg | Arg | Leu |
| | | | 260 | | | | | 265 | | | | | 270 | | |
| Asn | Thr | Ser | Lys | Leu | Ile | Glu | Asn | Ser | Glu | Tyr | Phe | Gln | Asn | Lys | Leu |
| | | | 275 | | | | | 280 | | | | | 285 | | |
| Val | Asp | Thr | Ile | His | Phe | Met | Glu | Ile | Leu | Ser | Leu | Lys | Asp | Ser | Val |
| | 290 | | | | | 295 | | | | | 300 | | | | |
| Glu | Arg | Asp | Thr | Phe | Phe | Arg | Lys | Leu | Pro | Asn | Leu | Ala | Glu | Gln | Leu |
| 305 | | | | | 310 | | | | | 315 | | | | | 320 |
| Pro | Arg | Gln | Ile | Val | Leu | Lys | Lys | Leu | Leu | Pro | Leu | Leu | Ala | Ser | Ala |
| | | | | 325 | | | | | 330 | | | | | 335 | |
| Leu | Glu | Phe | Gly | Ser | Ala | Ala | Ser | Ala | Leu | Thr | Ala | Leu | Leu | Lys |
| | | | 340 | | | | | 345 | | | | | 350 | | |
| Met | Gly | Ser | Trp | Leu | Ser | Ala | Glu | Glu | Phe | Asn | Val | Lys | Val | Leu | Pro |
| | | | 355 | | | | | 360 | | | | | 365 | | |
| Thr | Ile | Val | Lys | Leu | Phe | Ala | Ser | Asn | Asp | Arg | Ala | Ile | Arg | Val | Ala |
| | 370 | | | | | 375 | | | | | 380 | | | | |

```
Leu Leu Gln His Ile Asp Gln Tyr Gly Glu Ser Leu Ser Ala Gln Ala
385                 390                 395                 400

Val Asp Glu Gln Val Tyr Pro His Val Ala Thr Gly Phe Ser Asp Thr
            405                 410                 415

Ser Ala Phe Leu Arg Glu Leu Thr Leu Lys Ser Met Leu Ile Leu Ala
        420                 425                 430

Pro Lys Leu Ser Gln Arg Thr Met Ser Gly Ser Leu Leu Lys Tyr Leu
    435                 440                 445

Ser Lys Leu Gln Val Asp Glu Glu Pro Ala Ile Arg Thr Asn Thr Thr
450                 455                 460

Ile Leu Leu Gly Asn Ile Gly Ser Tyr Leu Asn Glu Gly Thr Arg Lys
465                 470                 475                 480

Arg Val Leu Ile Asn Ala Phe Thr Val Arg Ala Leu Arg Asp Thr Phe
            485                 490                 495

Pro Pro Ala Arg Gly Ala Gly Ile Met Ala Leu Cys Ala Thr Ser Ser
        500                 505                 510

Tyr Tyr Asp Ile Thr Glu Val Ala Thr Arg Ile Leu Pro Asn Val Val
    515                 520                 525

Val Leu Thr Ile Asp Pro Asp Ser Asp Val Arg Thr Lys Ala Phe Gln
530                 535                 540

Ala Val Asp Gln Phe Leu Gln Ile Ala Lys Gln His Tyr Glu Lys Thr
545                 550                 555                 560

Asn Ala Ala Asp Thr Ser Cys Gly Val Gly Ser Ser Val Pro Gly
            565                 570                 575

Asn Ala Ser Leu Leu Gly Trp Ala Met Ser Ser Leu Thr Leu Lys Gly
        580                 585                 590

Lys Pro Ser Asp His Ala Pro Val Ala Ser Ala Ser Thr Ala Ile
    595                 600                 605

Thr Ser Thr Ser Ser Asn Gly Thr Ala Gly Ile Glu Thr Pro Ser Thr
610                 615                 620

Ala Ala Ala His Val Ser Ser Thr Ala Asp Leu Ala Glu His Pro Val
625                 630                 635                 640

Pro Thr Ser Pro Thr Ser Thr Asp Gly Trp Gly Glu Leu Glu Asn Gly
            645                 650                 655

Ile Asp Glu Glu His Gly Ser Asp Arg Asp Gly Trp Asp Asp Leu Glu
        660                 665                 670

Pro Leu Glu Glu Thr Lys Pro Ala Pro Ala Leu Ala Asn Ile Gln Ala
    675                 680                 685

Ala Gln Arg Arg Pro Val Ser Gln Pro Ile Ser His Thr Lys Gln Ala
690                 695                 700

Ser Asn Leu Leu Ser Lys Ser Thr Pro Lys Leu Asn Lys Asp Glu Asp
705                 710                 715                 720

Asp Asp Leu Trp Gly Ser Ile Ala Ala Pro Ala Pro Lys Thr Ala Arg
            725                 730                 735

Pro Leu Asn Leu Lys Ser Ala Gln Thr Asp Asp Asp Pro Trp Ala
        740                 745                 750

Ala Ile Ala Ala Pro Ala Pro Thr Ile Lys Ala Lys Pro Leu Ser Ala
    755                 760                 765

Gly Arg Gly Arg Gly Ala Lys Pro Ala Ala Pro Lys Leu Gly Ala Gln
770                 775                 780

Arg Ile Asn Arg Thr Ser Ser Gly Met
785                 790
```

<210> SEQ ID NO 38
<211> LENGTH: 460
<212> TYPE: PRT
<213> ORGANISM: Glycine max

<400> SEQUENCE: 38

```
Met Glu Gln Lys Gly Ser Val Leu Met Gln Arg Tyr Glu Leu Gly Arg
1               5                   10                  15

Leu Leu Gly Gln Gly Thr Phe Ala Lys Val Tyr His Ala Arg Asn Leu
            20                  25                  30

Ile Thr Gly Met Ser Val Ala Ile Lys Val Val Asp Lys Glu Lys Ile
        35                  40                  45

Leu Lys Val Gly Met Ile Asp Gln Ile Lys Arg Glu Ile Ser Val Met
    50                  55                  60

Arg Leu Ile Arg His Pro His Val Val Glu Leu Tyr Glu Val Met Ala
65                  70                  75                  80

Ser Lys Thr Lys Ile Tyr Phe Val Met Glu His Ala Lys Gly Gly Glu
                85                  90                  95

Leu Phe Asn Lys Val Val Lys Gly Arg Leu Lys Val Asp Val Ala Arg
            100                 105                 110

Lys Tyr Phe Gln Gln Leu Ile Ser Ala Val Asp Tyr Cys His Ser Arg
        115                 120                 125

Gly Val Cys His Arg Asp Leu Lys Pro Glu Asn Leu Leu Leu Asp Glu
    130                 135                 140

Asn Glu Asn Leu Lys Val Ser Asp Phe Gly Leu Ser Ala Leu Ala Glu
145                 150                 155                 160

Ser Lys Cys Gln Asp Gly Leu Leu His Thr Thr Cys Gly Thr Pro Ala
                165                 170                 175

Tyr Val Ala Pro Glu Val Ile Asn Arg Lys Gly Tyr Asp Gly Ile Lys
            180                 185                 190

Ala Asp Ile Trp Ser Cys Gly Val Ile Leu Tyr Val Leu Leu Ala Gly
        195                 200                 205

His Leu Pro Phe Gln Asp Thr Asn Leu Met Glu Met Tyr Arg Lys Ile
    210                 215                 220

Gly Arg Gly Glu Phe Lys Phe Pro Lys Trp Phe Ala Pro Asp Val Arg
225                 230                 235                 240

Arg Phe Leu Ser Arg Ile Leu Asp Pro Asn Pro Lys Ala Arg Ile Ser
                245                 250                 255

Met Ala Lys Ile Met Glu Ser Ser Trp Phe Lys Gly Leu Glu Lys
            260                 265                 270

Pro Ala Ile Thr Val Thr Glu Asn Glu Glu Leu Ala Pro Leu Asp Ala
        275                 280                 285

Asp Gly Ile Phe Glu Ala Cys Glu Asn Asp Gly Pro Ile Ala Glu Pro
    290                 295                 300

Lys Gln Glu Gln Ala Lys Pro Cys Asn Leu Asn Ala Phe Asp Ile Ile
305                 310                 315                 320

Ser Phe Ser Thr Gly Phe Asp Leu Ser Gly Leu Phe Glu Asp Thr Phe
                325                 330                 335

Leu Lys Lys Glu Thr Arg Phe Met Ser Lys Pro Ala Ser Ile Ile
            340                 345                 350

Val Leu Lys Leu Glu Glu Ile Cys Lys Arg Leu Cys Leu Lys Val Lys
        355                 360                 365

Lys Lys Asp Gly Gly Leu Leu Leu Glu Gly Ser Lys Glu Gly Arg
    370                 375                 380
```

```
Lys Gly Thr Leu Gly Val Asp Ala Glu Ile Phe Glu Ile Thr Pro His
385                 390                 395                 400

Phe His Met Val Glu Leu Arg Lys Ser Asn Gly Asp Thr Met Glu Tyr
            405                 410                 415

Gln Lys Leu Phe Lys Gln Asp Ile Arg Pro Ala Leu Lys Asp Ile Val
            420                 425                 430

Trp Thr Trp Gln Gly Glu Lys Pro Gln Gln Glu Gln Glu Gln His Glu
            435                 440                 445

Val Val Gln Glu Glu His Gln Pro Ser His Thr Ala
            450                 455                 460

<210> SEQ ID NO 39
<211> LENGTH: 558
<212> TYPE: PRT
<213> ORGANISM: Glycine max

<400> SEQUENCE: 39

Met Asp Ser Ala Arg Ser Trp Leu Gln Lys Phe Gln Pro Arg Asp Lys
1               5                   10                  15

Thr Arg Ala Ala Gly Lys Lys Glu Glu Asp Gly Asn Gly Gly Asn
            20                  25                  30

Gln Asp Ser Asn Glu Ala Ile Asp Glu Ala Leu Leu Ser Ser Val Thr
            35                  40                  45

Lys Gln Lys Val Ala Ala Lys Gln Tyr Ile Glu Asn His Tyr Lys
50                  55                  60

Glu Gln Met Lys Asn Leu Gln Glu Arg Lys Glu Arg Arg Thr Ile Leu
65                  70                  75                  80

Glu Lys Lys Leu Ala Asp Ala Asp Val Ser Glu Glu Asp Gln Asn Asn
            85                  90                  95

Leu Leu Lys Phe Leu Glu Lys Lys Glu Thr Glu Tyr Met Arg Leu Gln
            100                 105                 110

Arg His Lys Met Gly Val Glu Asp Phe Glu Leu Leu Thr Met Ile Gly
            115                 120                 125

Lys Gly Ala Phe Gly Glu Val Arg Val Cys Arg Glu Lys Thr Ser Gly
            130                 135                 140

His Val Tyr Ala Met Lys Lys Leu Lys Lys Ser Glu Met Leu Arg Arg
145                 150                 155                 160

Gly Gln Val Glu His Val Lys Ala Glu Arg Asn Leu Leu Ala Glu Val
            165                 170                 175

Asp Ser Asn Cys Ile Val Lys Leu Tyr Cys Ser Phe Gln Asp Asp Glu
            180                 185                 190

His Leu Tyr Leu Ile Met Glu Tyr Leu Pro Gly Gly Asp Met Met Thr
            195                 200                 205

Leu Leu Met Arg Lys Asp Ile Leu Thr Glu Asp Glu Ala Arg Phe Tyr
            210                 215                 220

Val Gly Glu Thr Val Leu Ala Ile Glu Ser Ile His Lys His Asn Tyr
225                 230                 235                 240

Ile His Arg Asp Ile Lys Pro Asp Asn Leu Leu Leu Asp Arg Tyr Gly
            245                 250                 255

His Leu Lys Leu Ser Asp Phe Gly Leu Cys Lys Pro Leu Asp Cys Ser
            260                 265                 270

Thr Leu Glu Glu Asn Asp Phe Ser Val Gly Gln Asn Val Asn Gly Ser
            275                 280                 285

Thr Gln Ser Ser Thr Pro Lys Arg Ser Gln Gln Glu Gln Leu Gln His
            290                 295                 300
```

```
Trp Gln Ile Asn Arg Arg Thr Leu Ala Tyr Ser Thr Val Gly Thr Pro
305                 310                 315                 320

Asp Tyr Ile Ala Pro Glu Val Leu Leu Lys Gly Tyr Gly Met Glu
            325                 330                 335

Cys Asp Trp Trp Ser Leu Gly Ala Ile Met Tyr Glu Met Leu Val Gly
                340                 345                 350

Tyr Pro Pro Phe Tyr Ser Asp Asp Pro Met Leu Thr Cys Arg Lys Ile
            355                 360                 365

Val Asn Trp Lys Thr Tyr Leu Lys Phe Pro Glu Glu Ala Arg Leu Ser
370                 375                 380

Pro Glu Ala Lys Asp Leu Ile Ser Lys Leu Leu Cys Asn Val Asn Gln
385                 390                 395                 400

Arg Leu Gly Ser Lys Gly Ala Asp Glu Ile Lys Ala His Pro Phe Phe
                405                 410                 415

Lys Gly Val Glu Trp Asn Lys Leu Tyr Gln Met Glu Ala Ala Phe Ile
            420                 425                 430

Pro Glu Val Asn Asp Glu Leu Asp Thr Gln Asn Phe Glu Lys Phe Asp
            435                 440                 445

Glu Ser Asp Ser Gln Thr Gln Ser Ser Arg Ser Gly Pro Trp Arg
450                 455                 460

Lys Met Leu Ser Ser Lys Lys Asp Leu Asn Phe Val Gly Tyr Thr Tyr
465                 470                 475                 480

Lys Asn Phe Glu Ile Val Asn Asp Tyr Gln Val Pro Gly Met Ala Glu
                485                 490                 495

Leu Lys Lys Lys Gln Ser Lys Pro Lys Arg Pro Thr Ile Lys Ser Leu
                500                 505                 510

Phe Asp Cys Glu Ser Glu Thr Pro Glu Ala Ser Asp Thr Ser Ala Asn
            515                 520                 525

Asp Gln Pro Ala Gln Gly Ser Phe Leu Lys Leu Leu Pro Pro Gln Leu
530                 535                 540

Glu Val Ser Pro His Arg Asp Lys Asn Leu Pro Pro Arg Ser
545                 550                 555

<210> SEQ ID NO 40
<211> LENGTH: 378
<212> TYPE: PRT
<213> ORGANISM: Glycine max

<400> SEQUENCE: 40

Met Lys Ile Pro Cys Phe Ser Cys Phe Ser Pro Ser Thr Thr Glu Lys
1               5                   10                  15

Asn Asn Asn Asn Asp Tyr Pro Asp Glu Glu Ile Asn Asp Gly Ser Phe
                20                  25                  30

Arg Leu Phe Thr His Lys Gln Leu Lys Leu Ala Thr Arg Asn Phe His
            35                  40                  45

Ser Ser Glu Lys Val Gly Glu Gly Gly Phe Gly Ser Val Phe Lys Gly
        50                  55                  60

Lys Leu Val Asp Gly Ser Phe Val Ala Val Lys Val Leu Ser Val Glu
65                  70                  75                  80

Val Glu Ser Met Arg Gly Glu Arg Glu Phe Val Ala Glu Leu Ala Thr
                85                  90                  95

Leu Ala Asn Ile Lys His Gln Asn Leu Val Ser Leu Lys Gly Cys Cys
            100                 105                 110

Val Glu Gly Ala Tyr Arg Tyr Leu Val Tyr Asp Tyr Met Glu Asn Asn
```

```
                115                 120                 125
Ser Leu Tyr Asn Thr Phe Leu Gly Ser Glu Glu Arg Arg Met Arg Phe
    130                 135                 140

Asn Trp Glu Ile Arg Lys Asp Val Ser Ile Gly Val Ala Arg Gly Leu
145                 150                 155                 160

Asp Phe Leu His Glu Glu Leu Lys Pro His Ile Val His Arg Asp Ile
                165                 170                 175

Lys Ala Lys Asn Ile Leu Leu Asp Arg Asn Phe Ile Pro Lys Val Ser
            180                 185                 190

Asp Phe Gly Leu Ala Lys Leu Leu Arg Asp Glu Thr Ser Tyr Ile Ser
        195                 200                 205

Thr Arg Val Ala Gly Thr Leu Gly Tyr Leu Ala Pro Glu Tyr Ala Asn
    210                 215                 220

Ser Gly Gln Val Ser Arg Lys Ser Asp Val Tyr Ser Phe Gly Val Leu
225                 230                 235                 240

Leu Leu Gln Ile Val Ser Gly Leu Ala Val Val Asp Ala Tyr Gln Asp
                245                 250                 255

Ile Glu Arg Phe Ile Val Glu Lys Ala Trp Ala Ala Tyr Gln Ser Asn
            260                 265                 270

Asp Leu Leu Lys Leu Val Asp Pro Met Leu Asn Met Asn Phe Pro Glu
        275                 280                 285

Glu Glu Ala Leu Lys Phe Leu Lys Val Gly Leu Leu Cys Val Gln Glu
    290                 295                 300

Thr Ala Lys Leu Arg Pro Arg Met Ser Glu Val Val Glu Lys Leu Thr
305                 310                 315                 320

Lys Asp Ile Asp Met Arg Asp Val His Ile Ser Lys Pro Gly Phe Val
                325                 330                 335

Ala Asp Leu Arg Asn Ile Arg Ile Lys Gln Gln Asn Leu Asn Ser Ser
            340                 345                 350

Glu Glu Ser Ser Ser Ala Gly Ala Thr Phe Thr Ser Ser Ile Ser Ser
        355                 360                 365

Ser Ala Asn Leu Ala Arg Tyr Leu Leu Asp
    370                 375

<210> SEQ ID NO 41
<211> LENGTH: 648
<212> TYPE: PRT
<213> ORGANISM: Glycine max

<400> SEQUENCE: 41

Met Leu Leu Leu Leu Asn Tyr Leu Phe Leu Phe Asn Phe Ser
1               5                   10                  15

Ile Thr Lys Thr Glu Ala Ile Asp Asn Leu Gln Tyr Leu Asn His Ser
                20                  25                  30

Cys Ser Ser Asn Lys Thr Phe Thr Pro Asn Ser Thr Tyr Gln Ser Asn
            35                  40                  45

Leu Gln Thr Leu Leu Thr Ser Leu Ser Ser His Ala Thr Thr Ala Gln
        50                  55                  60

Phe Phe Asn Thr Thr Gly Gly Asp Ala Ala Gly Glu Asn Ile
65                  70                  75                  80

Tyr Gly Ser Phe Met Cys Arg Gly Asp Val Ser Asn His Thr Cys Gln
                85                  90                  95

Glu Cys Ile Lys Thr Ala Thr Gln Gln Ile Thr Val Arg Cys Leu Asn
            100                 105                 110
```

```
Ser Lys Glu Ala Leu Ile Trp Tyr His Glu Cys Met Val Arg Tyr Ser
            115                 120                 125

Asn Arg Cys Phe Phe Ser Ala Val Glu Glu Trp Pro Arg Phe Asn Phe
        130                 135                 140

Val Asp Phe Asn Val Asn Thr Asn Ser Thr Glu Gly Ile Tyr Gly Tyr
145                 150                 155                 160

Trp Leu Leu Ser Lys Thr Leu Ser Asp Ala Val Gly Glu Ala Val Lys
                165                 170                 175

Ala Gly Thr Lys Lys Phe Ala Thr Lys Asn Ala Thr Val Phe Gly Ser
            180                 185                 190

Gln Arg Val His Thr Leu Val Gln Cys Thr Pro Asp Leu Ser Ser Glu
        195                 200                 205

Asp Cys Ser Lys Cys Leu Gly Asp Ile Met Arg Asp Ile Pro Leu Cys
210                 215                 220

Cys Leu Gly Arg Arg Gly Gly Met Val Leu Phe Pro Ser Cys Thr Leu
225                 230                 235                 240

Met Phe Gly Ile Gly Gln Phe Tyr Arg Asp Phe Pro His Gly Thr Pro
            245                 250                 255

Glu Ser Lys Ser Glu Asn Glu Lys Gly Ser Leu Arg Thr Ile Val Ile
        260                 265                 270

Ile Val Leu Leu Val Val Val Pro Val Met Leu Ser Phe Phe Ser
            275                 280                 285

Tyr His Leu Ile Arg Arg Lys Ala Arg Lys Arg Asn Tyr Lys Ile Leu
        290                 295                 300

Leu Arg Glu Asn Phe Gly Gln Glu Ser Val Thr Ile Glu Gly Leu Gln
305                 310                 315                 320

Phe Asp Leu Asp Ile Ile Ala Ala Ala Thr Asn Asn Phe Ser His Glu
                325                 330                 335

Asn Lys Ile Gly Lys Gly Gly Phe Gly Glu Val Tyr Lys Gly Ile Leu
            340                 345                 350

Pro Asn Gly Arg Arg Ile Ala Val Lys Arg Leu Ser Thr Asn Ser Ser
        355                 360                 365

Gln Gly Ser Val Glu Phe Lys Asn Glu Ile Leu Ser Ile Ala Lys Leu
370                 375                 380

Gln His Arg Asn Leu Val Glu Leu Ile Gly Phe Cys Leu Glu Val Gln
385                 390                 395                 400

Glu Lys Ile Leu Ile Tyr Glu Tyr Met Ser Asn Gly Ser Leu Asp Asn
                405                 410                 415

Phe Leu Phe Asp Pro Gln Gln Lys Lys Leu Ser Trp Ser Gln Arg Tyr
            420                 425                 430

Lys Ile Ile Glu Gly Thr Ala Arg Gly Ile Leu Tyr Leu His Glu His
        435                 440                 445

Ser Arg Leu Lys Val Ile His Arg Asp Leu Lys Pro Ser Asn Ile Leu
450                 455                 460

Leu Asp Glu Asn Met Asn Pro Lys Ile Ser Asp Phe Gly Met Ala Arg
465                 470                 475                 480

Ile Ile Glu Leu Asn Gln Asp Leu Gly Lys Thr Gln Arg Ile Val Gly
                485                 490                 495

Thr Phe Gly Tyr Met Ser Pro Glu Tyr Ala Ile Phe Gly Gln Phe Ser
            500                 505                 510

Glu Lys Ser Asp Val Phe Ser Phe Gly Val Met Ile Ile Glu Ile Ile
        515                 520                 525

Thr Gly Arg Lys Asn Ile Asn Ser His Gln Leu Pro Asp Ile Val Asp
```

```
                530                 535                 540
Ser Leu Met Ser Tyr Val Trp Arg Gln Trp Lys Asp Gln Ala Pro Leu
545                 550                 555                 560

Ser Ile Leu Asp Pro Asn Leu Glu Glu Asn Tyr Ser Gln Phe Glu Val
                565                 570                 575

Ile Lys Cys Ile His Ile Gly Leu Leu Cys Val Gln Glu Asn Lys Asn
                580                 585                 590

Ile Arg Pro Thr Met Thr Lys Val Ile Phe Tyr Leu Asp Gly His Thr
                595                 600                 605

Leu Asp Glu Leu Pro Ser Pro Gln Glu Pro Pro Phe Phe Phe Arg Asp
                610                 615                 620

Ile Lys Asp Lys Lys Ile Pro Met Gln His Phe Ser Val Asn Lys Met
625                 630                 635                 640

Ser Thr Ser Ile Phe Tyr Pro Arg
                645

<210> SEQ ID NO 42
<211> LENGTH: 624
<212> TYPE: PRT
<213> ORGANISM: Glycine max

<400> SEQUENCE: 42

Met Glu Arg Lys Phe Met Ala Leu Gly Phe Ile Trp Trp Val Val Val
1               5                   10                  15

Val His Pro Leu Cys Leu Ile Ser Ala Asn Met Glu Gly Asp Ala Leu
                20                  25                  30

His Ser Leu Arg Thr Asn Leu Gln Asp Pro Asn Asn Val Leu Gln Ser
                35                  40                  45

Trp Asp Pro Thr Leu Val Asn Pro Cys Thr Trp Phe His Val Thr Cys
            50                  55                  60

Asn Asn Asp Asn Ser Val Ile Arg Val Asp Leu Gly Asn Ala Ala Leu
65                  70                  75                  80

Ser Gly Gln Leu Val Pro Gln Leu Gly Gln Leu Lys Asn Leu Gln Tyr
                85                  90                  95

Leu Glu Leu Tyr Ser Asn Asn Ile Thr Gly Pro Ile Pro Ser Asp Leu
                100                 105                 110

Gly Asn Leu Thr Asn Leu Val Ser Leu Asp Leu Tyr Leu Asn His Phe
            115                 120                 125

Thr Gly Pro Ile Pro Asp Ser Leu Gly Lys Leu Ser Lys Leu Arg Phe
        130                 135                 140

Leu Arg Leu Asn Asn Asn Ser Leu Ser Gly Pro Ile Pro Met Ser Leu
145                 150                 155                 160

Thr Asn Ile Thr Ala Leu Gln Val Leu Asp Leu Ser Asn Asn His Leu
                165                 170                 175

Ser Gly Val Val Pro Asp Asn Gly Ser Phe Ser Leu Phe Thr Pro Ile
                180                 185                 190

Ser Phe Ala Asn Asn Met Asp Leu Cys Gly Pro Val Thr Gly His Pro
            195                 200                 205

Cys Pro Gly Ser Pro Pro Phe Ser Pro Pro Pro Phe Val Pro Pro
        210                 215                 220

Pro Pro Ile Ser Ala Pro Gly Gly Asn Gly Ala Thr Gly Ala Ile Ala
225                 230                 235                 240

Gly Gly Val Ala Ala Gly Ala Ala Leu Leu Phe Ala Ala Pro Ala Ile
                245                 250                 255
```

```
Ala Phe Ala Trp Trp Arg Arg Arg Lys Pro Gln Glu Phe Phe Asp
            260                 265                 270

Val Pro Ala Glu Glu Asp Pro Glu Val His Leu Gly Gln Leu Lys Arg
        275                 280                 285

Phe Ser Leu Arg Glu Leu Gln Val Ala Thr Asp Ser Phe Ser Asn Lys
    290                 295                 300

Asn Ile Leu Gly Arg Gly Gly Phe Gly Lys Val Tyr Lys Gly Arg Leu
305                 310                 315                 320

Ala Asp Gly Ser Leu Val Ala Val Lys Arg Leu Lys Glu Glu Arg Thr
                325                 330                 335

Pro Gly Gly Glu Leu Gln Phe Gln Thr Glu Val Glu Met Ile Ser Met
            340                 345                 350

Ala Val His Arg Asn Leu Leu Arg Leu Arg Gly Phe Cys Met Thr Pro
        355                 360                 365

Thr Glu Arg Leu Leu Val Tyr Pro Tyr Met Ala Asn Gly Ser Val Ala
    370                 375                 380

Ser Cys Leu Arg Glu Arg Pro Pro Tyr Gln Glu Pro Leu Asp Trp Pro
385                 390                 395                 400

Thr Arg Lys Arg Val Ala Leu Gly Ser Ala Arg Gly Leu Ser Tyr Leu
                405                 410                 415

His Asp His Cys Asp Pro Lys Ile Ile His Arg Asp Val Lys Ala Ala
            420                 425                 430

Asn Ile Leu Leu Asp Glu Glu Phe Glu Ala Val Val Gly Asp Phe Gly
        435                 440                 445

Leu Ala Lys Leu Met Asp Tyr Lys Asp Thr His Val Thr Thr Ala Val
    450                 455                 460

Arg Gly Thr Ile Gly His Ile Ala Pro Glu Tyr Leu Ser Thr Gly Lys
465                 470                 475                 480

Ser Ser Glu Lys Thr Asp Val Phe Gly Tyr Gly Ile Met Leu Leu Glu
                485                 490                 495

Leu Ile Thr Gly Gln Arg Ala Phe Asp Leu Ala Arg Leu Ala Asn Asp
            500                 505                 510

Asp Asp Val Met Leu Leu Asp Trp Val Lys Gly Leu Leu Lys Glu Lys
        515                 520                 525

Lys Leu Glu Met Leu Val Asp Pro Asp Leu Gln Thr Asn Tyr Ile Glu
    530                 535                 540

Thr Glu Val Glu Gln Leu Ile Gln Val Ala Leu Leu Cys Thr Gln Gly
545                 550                 555                 560

Ser Pro Met Asp Arg Pro Lys Met Ser Glu Val Val Arg Met Leu Glu
                565                 570                 575

Gly Asp Gly Leu Ala Glu Arg Trp Asp Glu Trp Gln Lys Val Glu Val
            580                 585                 590

Leu Arg Gln Glu Val Glu Leu Ala Pro His Pro Asn Ser Asp Trp Ile
    595                 600                 605

Val Asp Ser Thr Glu Asn Leu His Ala Val Glu Leu Ser Gly Pro Arg
610                 615                 620

<210> SEQ ID NO 43
<211> LENGTH: 1109
<212> TYPE: PRT
<213> ORGANISM: Glycine max

<400> SEQUENCE: 43

Met Gln Leu Leu His Ser Asp Glu Pro Ala Pro Glu Arg Gly Asp Ser
1               5                   10                  15
```

```
Pro Glu Lys Pro Asp Asp Pro Asn Ala Asp Thr Asp Ser Leu Asp Pro
            20                  25                  30

Gly Thr Asp Asp Gly Ala Ala Leu Asp Val Thr Gly Lys Ser Val Glu
        35                  40                  45

Phe Pro Ala Ala Glu Asn Ala Gly Asp Ser Ala Glu Ser Leu Tyr Val
    50                  55                  60

Tyr Lys Asn Val Tyr Ser Leu Ile Pro Lys Ser Val Ser Arg Leu Ala
65                  70                  75                  80

Arg Leu Arg Thr Leu Lys Phe Phe Gly Asn Glu Ile Asn Leu Phe Ala
                85                  90                  95

Pro Glu Phe Gly Asn Leu Thr Ala Leu Glu Cys Leu Gln Met Lys Ile
                100                 105                 110

Ser Ser Pro Gly Ile Gly Gly Leu Gln Leu His Thr Leu Lys Gly Leu
            115                 120                 125

Lys Glu Leu Glu Leu Ser Lys Gly Pro Pro Arg Pro Ser Ala Phe Pro
130                 135                 140

Ile Leu Thr Glu Ile Ser Gly Leu Lys Cys Leu Thr Lys Leu Ser Ile
145                 150                 155                 160

Cys His Phe Ser Ile Arg Tyr Leu Pro Pro Glu Ile Gly Cys Leu Lys
                165                 170                 175

Lys Leu Glu Tyr Leu Asp Leu Ser Phe Asn Lys Met Lys Thr Leu Pro
                180                 185                 190

Ala Glu Ile Ser Tyr Leu Lys Gly Leu Ile Ser Met Lys Val Ala Asn
                195                 200                 205

Asn Lys Leu Val Glu Leu Pro Ala Ala Met Ser Ser Leu Ser Arg Leu
        210                 215                 220

Glu Arg Leu Asp Leu Ser Asn Asn Arg Leu Thr Ser Leu Gly Ser Leu
225                 230                 235                 240

Glu Leu Ala Ser Met His Arg Leu Gln Glu Leu Asn Leu Gln Tyr Asn
                245                 250                 255

Lys Leu Leu Gly Ile Phe Gln Ile Pro Ser Trp Ile Cys Cys Asn Met
                260                 265                 270

Asp Gly Asn Asp Lys Ala Arg Cys Lys Asp Asp Cys Ser Ser Ser Val
            275                 280                 285

Glu Met Asp Leu Tyr Glu Ser Asn Phe Gln Glu Asn Asp Glu Thr Leu
            290                 295                 300

Ser Asp Gly Pro His Asn Thr Ser Ser Ser Met Leu Thr Ser Ser Ser
305                 310                 315                 320

Ser Ser Ser Arg Cys Phe Ala Ser Arg Lys Ser Gly Lys Arg Trp Lys
            325                 330                 335

Arg Arg His His Leu Gln Gln Lys Ala Arg Gln Glu Arg Leu Asn Asn
                340                 345                 350

Ser Arg Lys Trp Lys Ala Val Asp His Asp Asp Gln Leu Leu Ser Lys
            355                 360                 365

Lys Ile His Arg Ile Ser Glu Pro Glu Asn His Asp Ser Leu Ala Ser
            370                 375                 380

Glu Ser Cys Ala Glu Ile Val Ser Glu Asn Gly Ser Leu Asp Asp Asn
385                 390                 395                 400

Asn Lys Arg Ile Ser Ser Glu Arg Ala Val Asn Asp Asn Ala Ile Asp
                405                 410                 415

Asn Asp Asn Asn Asp Glu Val Ile Thr Glu Lys Gln Phe Ser Gly Glu
            420                 425                 430
```

-continued

```
Asp Cys Cys Thr Thr Glu Ser Lys Asp Glu Lys Glu Ser Leu Cys
            435                 440                 445

Ser Leu Asp Lys Arg Pro Ser Glu Gln Asp Glu Ala Ser Cys Leu Glu
450                 455                 460

Leu Leu Glu Cys Val Ser Lys Ser Lys Arg His Leu Asp Arg Asp Leu
465                 470                 475                 480

Asp Asn Pro Lys Pro Cys Lys Ser Arg Lys Ser Ile Ser Ser Ser
                485                 490                 495

Leu Leu Ser Cys Lys Tyr Ser Lys Ile Ser Phe Cys Gly Ile Glu Asp
            500                 505                 510

His Leu Ser Asp Gly Phe Tyr Asp Ala Gly Arg Asp Arg Leu Phe Met
            515                 520                 525

Pro Leu Glu Cys Tyr Glu Gln Asn His Cys Leu Ala Ser Arg Glu Val
            530                 535                 540

Ile Leu Leu Asp Arg Lys Ile Asp Glu Glu Leu Asp Ala Val Met Leu
545                 550                 555                 560

Ala Ala Gln Ala Leu Val Tyr Asn Leu Lys Lys Leu Asn Gly Leu Ser
                565                 570                 575

Arg Tyr Gly Asn Gln Asp Gly Val Asp Asn Leu Gln Met Ala Ser Leu
            580                 585                 590

Leu Ala Leu Phe Val Ser Asp His Phe Gly Gly Ser Asp Arg Ser Gly
            595                 600                 605

Ile Val Glu Arg Thr Arg Lys Ser Val Ser Gly Ser Asn Tyr Asn Lys
            610                 615                 620

Pro Phe Val Cys Thr Cys Ser Ala Gly Ser Ser Thr Ser Ile Ser Ser
625                 630                 635                 640

Pro Thr Glu Pro Val Ala Asn Thr Ile Glu Asp Ile Thr Leu Ser Lys
                645                 650                 655

Met Ser Glu Lys Ser Leu Asp Ser Ile Lys Lys Arg Arg Asn Ser Ile
            660                 665                 670

Ile Ile Pro Ile Gly Ser Val Gln Tyr Gly Val Cys Arg His Arg Ala
            675                 680                 685

Leu Leu Phe Lys Tyr Leu Cys Asp His Met Glu Pro Pro Val Pro Cys
            690                 695                 700

Glu Leu Val Arg Gly Tyr Leu Asp Phe Ser Pro His Ala Trp Asn Ile
705                 710                 715                 720

Ile Leu Ile Lys Arg Gly Ala Thr Trp Val Arg Met Leu Ile Asp Ala
                725                 730                 735

Cys Arg Pro Leu Asp Ile Arg Glu Glu Lys Asp Pro Gly Tyr Phe Cys
            740                 745                 750

Arg Tyr Ile Pro Leu Asn Arg Thr Thr Ile Pro Ile Ser Ser Ile Gly
            755                 760                 765

Ser Pro Gly Pro Asp Tyr Ser Phe Pro Ser Leu Thr Thr Cys Asp Glu
            770                 775                 780

Leu Glu Thr Lys Ala Ser Thr Thr Leu Val Lys Cys Lys Phe Gly Ser
785                 790                 795                 800

Val Glu Ala Ala Ala Lys Val Arg Thr Leu Glu Glu Gln Gly Ser Ser
                805                 810                 815

Ala Asp Lys Ile Lys Asn Phe Glu Tyr Asn Cys Leu Gly Glu Ile Arg
            820                 825                 830

Ile Leu Gly Ala Leu Lys His Pro Cys Ile Val Glu Met Tyr Gly His
            835                 840                 845

Gln Ile Ser Cys Gln Trp Ser Val Ser Ala Asp Gly Asn Pro Glu His
```

```
                    850                 855                 860
Arg Val Leu Arg Ser Ala Ile Phe Met Glu Tyr Val Glu Gly Gly Ser
865                 870                 875                 880

Leu Lys Asn Tyr Leu Glu Lys Leu Ser Glu Ala Gly Glu Lys His Val
                885                 890                 895

Pro Val Glu Leu Ala Leu His Ile Ala Lys Asp Val Ser Cys Ala Leu
            900                 905                 910

Ser Glu Leu His Ser Lys His Ile Ile His Arg Asp Ile Lys Ser Glu
        915                 920                 925

Asn Ile Leu Phe Asn Leu Asp Arg Lys Arg Asp Asp Gly Thr Pro Thr
    930                 935                 940

Val Lys Leu Cys Asp Phe Asp Ser Ala Val Pro Leu Arg Ser Thr Leu
945                 950                 955                 960

His Val Cys Cys Ile Ala His Ala Gly Thr Pro Pro Cys Ile Cys
                965                 970                 975

Val Gly Thr Pro Arg Trp Met Ala Pro Glu Val Met Arg Thr Met Tyr
            980                 985                 990

Lys Lys Asn Ser Tyr Gly Leu Glu Ala Asp Ile Trp Ser Phe Gly Cys
        995                 1000                1005

Leu Leu Leu Glu Met Leu Thr Leu Gln Ile Pro Tyr Ser Gly Leu
    1010                1015                1020

Ser Asp Ser His Phe Leu Asp Ser Leu Gln Met Gly Lys Arg Pro
    1025                1030                1035

Gln Leu Thr Asp Glu Leu Arg Val Leu Ser Ser Met Asn Gly Pro
    1040                1045                1050

Thr Met Ile Pro Ser Gly Glu Glu Leu Glu Lys Ser Asp Ala Gly
    1055                1060                1065

Val Asp Met Leu Lys Phe Leu Val Asp Leu Phe His Lys Cys Val
    1070                1075                1080

Glu Glu Asn Pro Ser Lys Arg Pro Thr Ala Glu Glu Ile His Lys
    1085                1090                1095

Met Val Leu Ala His Thr Asp Arg Leu Gln Ile
    1100                1105

<210> SEQ ID NO 44
<211> LENGTH: 696
<212> TYPE: PRT
<213> ORGANISM: Glycine max

<400> SEQUENCE: 44

Met Ala Met Ile Pro Leu Met Met Met Ile Leu Leu Leu Leu Phe Lys
1               5                   10                  15

Phe Pro Ser Val Val Leu Ala Thr Leu Lys Ser Asp Glu Ala Asn Leu
                20                  25                  30

Glu Leu Val Phe Thr Tyr His Lys Cys Asn Glu Glu Leu Gly Asn Phe
            35                  40                  45

Thr Thr Glu Thr Tyr Ser Asn Asn Arg Asn Val Leu Leu Ser Asn Met
        50                  55                  60

Tyr Ser Asp Lys Glu Ile Glu Asn Gly Phe Tyr Asn Ser Ser Tyr Gly
65                  70                  75                  80

Glu Gly Pro Asp Lys Val Tyr Gly Ile Gly Phe Cys Arg Gly Asp Val
                85                  90                  95

Lys Pro Asp Lys Cys Arg Ser Cys Leu Glu Lys Ser Ser Thr Leu Leu
                100                 105                 110
```

```
Thr Asp Arg Cys Pro Val Gln Lys Glu Ala Ile Gly Trp Tyr Asp Leu
        115                 120                 125
Cys Met Leu Arg Tyr Ser Asn Arg Ser Ile Val Glu Gln Pro Val Thr
        130                 135                 140
Asp Thr Asp Asp Ile Ile Lys Cys Ser Asn Thr Asn Ala Thr Asn Lys
145                 150                 155                 160
Asp Arg Phe Asp Lys Glu Leu Asp Asp Leu Val Val Arg Met Arg Ser
                165                 170                 175
Arg Ser Ala Glu Gly Asp Ser Arg Leu Lys Phe Ala Glu Gly Glu Ala
            180                 185                 190
Pro Val Gln Ser Ser Asn Glu Thr Ile His Ala Leu Leu Gln Cys Val
        195                 200                 205
Pro Tyr Leu Ser His Gln Asn Cys Thr Arg Cys Leu Glu Tyr Ala Met
        210                 215                 220
Ser Arg Ile Ser Tyr Trp Cys Asp Gly Lys Thr Gly Gly Trp Tyr Leu
225                 230                 235                 240
Gly Arg Ser Cys Ser Leu Arg Tyr Glu Thr Tyr Leu Phe Phe Glu Leu
                245                 250                 255
Ile Phe His Asp Ala Pro Ala Pro Gln Pro Ser Gln Pro Ala Val Thr
                260                 265                 270
Pro Thr Lys Asp Phe Pro Lys Lys Thr Asn Pro Ser Arg Asn Ile Ile
        275                 280                 285
Val Ile Val Val Pro Val Phe Ala Val Ala Ile Val Val Val Gly Leu
        290                 295                 300
Ile Val Leu Ile Tyr Asn Tyr Phe Gly Ala Arg Arg Pro Arg His Lys
305                 310                 315                 320
Pro Ile Gln Ser Glu Gly Asp Gly Glu Gly Asp Gly Glu Gly Glu Gly
                325                 330                 335
Glu Leu Asp Asn Asp Ile Lys Thr Asp Glu Leu Ala Gln Phe Glu Phe
                340                 345                 350
Ala Thr Ile Lys Phe Ala Thr Asn Asn Phe Ser Asp Ala Asn Lys Leu
        355                 360                 365
Gly Gln Gly Gly Phe Gly Ile Val Tyr Lys Gly Thr Leu Ser Asp Gly
        370                 375                 380
Gln Glu Ile Ala Ile Lys Arg Leu Ser Ile Asn Ser Asn Gln Gly Glu
385                 390                 395                 400
Thr Glu Phe Lys Thr Glu Ile Ser Leu Thr Gly Lys Leu Gln His Arg
                405                 410                 415
Asn Leu Val Arg Leu Leu Gly Phe Cys Phe Ala Lys Arg Glu Arg Leu
                420                 425                 430
Leu Ile Tyr Glu Phe Val Pro Asn Lys Ser Leu Asp Phe Phe Ile Phe
        435                 440                 445
Asp Pro Asn Lys Arg Gly Asn Leu Asn Trp Glu Arg Arg Tyr Asn Ile
        450                 455                 460
Ile Arg Gly Ile Ala Arg Gly Leu Leu Tyr Leu His Glu Asp Ser Arg
465                 470                 475                 480
Leu Gln Val Val His Arg Asp Leu Lys Ile Ser Asn Ile Leu Leu Asp
                485                 490                 495
Glu Glu Leu Asn Pro Lys Ile Ser Asp Phe Gly Met Ala Arg Leu Phe
                500                 505                 510
Glu Ile Asn Gln Thr Glu Ala Asn Thr Asn Thr Val Val Gly Thr Phe
        515                 520                 525
Gly Tyr Met Ala Pro Glu Tyr Ile Lys His Gly Lys Phe Ser Val Lys
```

```
                530                 535                 540
Ser Asp Val Phe Ser Phe Gly Val Met Met Leu Glu Ile Val Cys Gly
545                 550                 555                 560

Gln Arg Asn Ser Lys Ile Arg Gly Asn Glu Glu Asn Ala Glu Asp Leu
            565                 570                 575

Leu Ser Phe Ala Trp Lys Asn Trp Arg Gly Gly Thr Val Ser Asn Ile
            580                 585                 590

Val Asp Thr Thr Leu Lys Asp Tyr Ser Trp Asp Glu Ile Lys Arg Cys
            595                 600                 605

Ile His Ile Gly Leu Leu Cys Val Gln Glu Asp Ile Asn Gly Arg Pro
            610                 615                 620

Thr Met Asn Ser Val Ser Ile Met Leu Asn Ser Ser Phe Ser Leu
625                 630                 635                 640

Ala Glu Pro Ser Glu Pro Ala Phe Leu Met Arg Gly Lys Ser Gln Leu
            645                 650                 655

Pro Met Ile Met Leu Ser Gly Ser Glu Gln Tyr Ser Glu Ala Thr Lys
            660                 665                 670

Ser Ser Asp Ser Gly Ser Gln Phe Ala Gln Gly Ser Ser Asn Lys Ala
            675                 680                 685

Pro Ile Thr Glu Pro Tyr Pro Arg
            690                 695

<210> SEQ ID NO 45
<211> LENGTH: 691
<212> TYPE: PRT
<213> ORGANISM: Glycine max

<400> SEQUENCE: 45

Met Phe Pro Leu Gln Cys Ser Asn His Pro Met Cys Ala Phe Ser Ala
1               5                   10                  15

Val Thr Ala Ile Leu Leu Phe Pro Ala Ala Thr Ser Gln Ala Gln
            20                  25                  30

Ile Leu Lys Lys Glu Thr Tyr Phe Phe Gly Pro Phe Asn Gln Ser Asp
            35                  40                  45

Phe Thr Thr Leu Thr Val Leu Pro Ser Ala Ala Ile Asn Leu Gly Ala
        50                  55                  60

Leu Gln Val Thr Pro Asp Ser Thr Gly Asn Val Ser Leu Ala Asn His
65              70                  75                  80

Ser Gly Arg Ile Phe Phe Asn Asn Pro Phe Thr Leu Trp Asp Asn Asp
            85                  90                  95

Asp Asn Leu Asn Gly Lys Leu Val Ser Phe Asn Thr Ser Phe Leu Ile
            100                 105                 110

Asn Val Phe Arg Pro Gln Asn Asn Pro Pro Gly Glu Gly Ile Thr Phe
            115                 120                 125

Leu Ile Thr Ala Ser Thr Thr Val Pro Asn Asn Ser His Gly Gln Phe
        130                 135                 140

Leu Gly Leu Thr Asn Ala Ala Thr Asp Gly Asn Ala Thr Asn Lys Phe
145                 150                 155                 160

Val Ala Val Glu Leu Asp Thr Val Lys Gln Asp Phe Asp Pro Asp Asp
            165                 170                 175

Asn His Ile Gly Leu Asp Ile Asn Ser Val Arg Ser Asn Val Ser Val
            180                 185                 190

Ser Leu Thr Pro Leu Gly Phe Glu Ile Ala Pro Asn Val Thr Arg Phe
            195                 200                 205
```

```
His Val Leu Trp Val Asp Tyr Asp Gly Asp Arg Lys Glu Ile Asp Val
    210                 215                 220

Tyr Ile Ala Glu Gln Pro Asp Lys Asp Ala Pro Ile Val Ala Lys Pro
225                 230                 235                 240

Ala Lys Pro Val Leu Ser Ser Pro Leu Asp Leu Lys Gln Val Val Asn
                245                 250                 255

Lys Val Ser Tyr Phe Gly Phe Ser Ala Ser Thr Gly Asp Asn Val Glu
            260                 265                 270

Leu Asn Cys Val Leu Arg Trp Asn Ile Thr Ile Glu Val Phe Pro Lys
        275                 280                 285

Lys Asn Gly Ile Gly Lys Ala Leu Lys Ile Gly Leu Ser Val Gly Leu
    290                 295                 300

Thr Met Val Val Leu Ile Val Ala Gly Val Val Gly Trp Val Cys Trp
305                 310                 315                 320

Leu Lys Lys Lys Lys Arg Gly Asn Glu Ser Gln Ile Leu Gly Thr Leu
                325                 330                 335

Lys Ser Leu Pro Gly Thr Pro Arg Glu Phe Arg Tyr Gln Glu Leu Lys
            340                 345                 350

Lys Ala Thr Asn Lys Phe Asp Glu Lys His Lys Leu Gly Gln Gly Gly
        355                 360                 365

Tyr Gly Val Val Tyr Arg Gly Thr Leu Pro Lys Glu Asn Leu Glu Val
    370                 375                 380

Ala Val Lys Met Phe Ser Arg Asp Lys Met Lys Ser Thr Asp Asp Phe
385                 390                 395                 400

Leu Ala Glu Leu Thr Ile Ile Asn Arg Leu Arg His Lys Asn Leu Val
                405                 410                 415

Arg Leu Leu Gly Trp Cys His Arg Asn Gly Val Leu Leu Leu Val Tyr
            420                 425                 430

Asp Tyr Met Pro Asn Gly Ser Leu Asp Asn His Ile Phe Cys Glu Glu
        435                 440                 445

Gly Ser Ser Thr Thr Pro Leu Ser Trp Pro Leu Arg Tyr Lys Ile Ile
    450                 455                 460

Thr Gly Val Ala Ser Ala Leu Asn Tyr Leu His Asn Glu Tyr Asp Gln
465                 470                 475                 480

Lys Val Val His Arg Asp Leu Lys Ala Ser Asn Ile Met Leu Asp Ser
                485                 490                 495

Asp Phe Asn Ala Arg Leu Gly Asp Phe Gly Leu Ala Arg Ala Leu Glu
            500                 505                 510

Asn Asp Lys Thr Ser Tyr Ala Glu Met Glu Gly Val His Gly Thr Met
        515                 520                 525

Gly Tyr Ile Ala Pro Glu Cys Phe His Thr Gly Arg Ala Thr Arg Glu
    530                 535                 540

Ser Asp Val Tyr Gly Phe Gly Ala Val Leu Leu Glu Val Val Cys Gly
545                 550                 555                 560

Gln Arg Pro Trp Thr Lys Asn Glu Gly Tyr Cys Leu Val Asp Trp
                565                 570                 575

Val Trp His Leu His Arg Glu Gln Arg Ile Leu Asp Ala Val Asp Pro
            580                 585                 590

Arg Leu Gly Asn Gly Cys Val Glu Glu Ala Glu Arg Val Leu Lys
        595                 600                 605

Leu Gly Leu Ala Cys Ser His Pro Ile Ala Ser Glu Arg Pro Lys Met
    610                 615                 620

Gln Thr Ile Val Gln Ile Ile Ser Gly Ser Val Asn Val Pro His Val
```

-continued

```
            625                 630                 635                 640
Pro Pro Phe Lys Pro Ala Phe Val Trp Pro Ala Met Asp Leu Ser Ser
                645                 650                 655

Pro Ala Ser Asp Leu Thr Thr Pro Thr Thr Thr Glu Tyr Thr Pro
                660                 665                 670

Met Ser Ser Asp Thr His Ser Met His Val Gln Phe Ser Asp Ser Asn
                675                 680                 685

Ser Leu Ile
        690

<210> SEQ ID NO 46
<211> LENGTH: 1392
<212> TYPE: PRT
<213> ORGANISM: Glycine max

<400> SEQUENCE: 46

Met Ser Arg Gln Thr Thr Ser Ser Ala Phe Thr Lys Ser Lys Thr Leu
1               5                   10                  15

Asp Asn Lys Tyr Met Leu Gly Asp Glu Ile Gly Lys Gly Ala Tyr Gly
                20                  25                  30

Arg Val Tyr Lys Gly Leu Asp Leu Glu Asn Gly Asp Phe Val Ala Ile
            35                  40                  45

Lys Gln Val Ser Leu Glu Asn Ile Ala Gln Glu Asp Leu Asn Ile Ile
        50                  55                  60

Met Gln Glu Ile Asp Leu Leu Lys Asn Leu Asn His Lys Asn Ile Val
65                  70                  75                  80

Lys Tyr Leu Gly Ser Ser Lys Thr Lys Ser His Leu His Ile Val Leu
                85                  90                  95

Glu Tyr Val Glu Asn Gly Ser Leu Ala Asn Ile Ile Lys Pro Asn Lys
                100                 105                 110

Phe Gly Pro Phe Pro Glu Ser Leu Val Ala Val Tyr Ile Ala Gln Val
            115                 120                 125

Leu Glu Gly Leu Val Tyr Leu His Glu Gln Gly Val Ile His Arg Asp
        130                 135                 140

Ile Lys Gly Ala Asn Ile Leu Thr Thr Lys Glu Gly Leu Val Lys Leu
145                 150                 155                 160

Ala Asp Phe Gly Val Ala Thr Lys Leu Thr Glu Ala Asp Val Asn Thr
                165                 170                 175

His Ser Val Val Gly Thr Pro Tyr Trp Met Ala Pro Glu Val Ile Glu
            180                 185                 190

Met Ala Gly Val Cys Ala Ala Ser Asp Ile Trp Ser Val Gly Cys Thr
        195                 200                 205

Val Ile Glu Leu Leu Thr Cys Val Pro Pro Tyr Tyr Asp Leu Gln Pro
    210                 215                 220

Met Pro Ala Leu Phe Arg Ile Val Gln Asp Glu His Pro Pro Ile Pro
225                 230                 235                 240

Asp Ser Leu Ser Pro Asp Ile Thr Asp Phe Leu Leu Gln Cys Phe Lys
                245                 250                 255

Lys Asp Ala Arg Gln Arg Pro Asp Ala Lys Thr Leu Leu Ser His Pro
            260                 265                 270

Trp Ile Gln Asn Cys Arg Arg Val Leu Gln Ser Ser Leu Arg His Ser
        275                 280                 285

Gly Thr Leu Arg Asn Ile Glu Glu Asp Ser Ala Asp Ala Glu Val
    290                 295                 300
```

```
Ser Gly Gly Tyr His Lys Ser Ala Tyr Glu Asn Ser Ser Val Glu Lys
305                 310                 315                 320

Glu Asp Ser Ala Lys Glu His Thr Thr Met Ala Ala Asp Gly Ser Lys
            325                 330                 335

Ala His Glu Asp Asn Ala Ala Asp Ser Asn Phe Ser Asn Glu Gln Thr
        340                 345                 350

Glu Lys Ala Asp Asp Ala Pro Ser Asp Gln Val Leu Thr Leu Ala Ile
    355                 360                 365

His Glu Lys Ser Phe Leu Gln Ala Gly Ser Ser Lys Leu Thr Ser Asn
    370                 375                 380

Arg Glu Val Val Asn Ser Glu Ser Thr Gly Asn His Glu Ile Ser Asn
385                 390                 395                 400

Ala Lys Asp Leu His Glu Val Val Met Asn Gly Glu Gly Gly Ser Pro
                405                 410                 415

Gln Ser Arg Gly Met Ala Ser Lys Val Gly Gly Lys Asp Ser Ser Val
            420                 425                 430

Asn Asn Gly Asn Lys Ser Phe Ala Phe Gly Pro Arg Gly Gln Asp Asn
        435                 440                 445

Gly Pro Leu Lys Lys Ala Met Lys Met Pro Ile Thr Val Glu Gly Asn
450                 455                 460

Glu Leu Ser Arg Phe Ser Asp Pro Pro Gly Asp Ala Tyr Leu Asp Asp
465                 470                 475                 480

Leu Phe His Pro Leu Asp Lys Gln Pro Gly Glu Val Val Ala Glu Ala
                485                 490                 495

Ser Thr Ser Thr Ser Thr Ser His Met Thr Lys Gly Asn Ala Ser Ala
            500                 505                 510

Ile Asp Gly Val Lys Asn Asp Leu Ala Lys Glu Leu Arg Ala Thr Ile
    515                 520                 525

Ala Arg Lys Gln Trp Glu Lys Glu Ser Glu Ile Gly Gln Ala Asn Asn
    530                 535                 540

Gly Gly Asn Leu Leu His Arg Val Met Ile Gly Val Leu Lys Asp Asp
545                 550                 555                 560

Val Ile Asp Ile Asp Gly Leu Val Phe Asp Glu Lys Leu Pro Gly Glu
                565                 570                 575

Asn Leu Phe Pro Leu Gln Ala Val Glu Phe Ser Lys Leu Val Gly Ser
            580                 585                 590

Leu Lys Pro Glu Glu Ser Glu Asp Met Ile Val Ser Ala Cys Gln Lys
        595                 600                 605

Leu Ile Gly Ile Phe His Gln Arg Pro Glu Gln Lys Ile Val Phe Val
    610                 615                 620

Thr Gln His Gly Leu Leu Pro Leu Thr Asp Leu Leu Glu Val Pro Lys
625                 630                 635                 640

Thr Arg Ile Ile Cys Ser Val Leu Gln Leu Ile Asn Gln Ile Val Lys
                645                 650                 655

Asp Asn Thr Asp Phe Gln Glu Asn Ala Cys Leu Val Gly Leu Ile Pro
            660                 665                 670

Ala Val Thr Ser Phe Ala Val Pro Asp Arg Pro Arg Glu Ile Arg Met
        675                 680                 685

Glu Ala Ala Tyr Phe Leu Gln Gln Leu Cys Gln Ser Ser Ser Leu Thr
    690                 695                 700

Leu Gln Met Phe Ile Ala Cys Arg Gly Ile Pro Val Leu Val Gly Phe
705                 710                 715                 720

Leu Glu Ala Asp Tyr Ala Lys Tyr Arg Glu Met Val His Leu Ala Ile
```

```
                    725                 730                 735
Asp Gly Met Trp Gln Val Phe Lys Leu Gln Gln Ser Thr Pro Arg Asn
                740                 745                 750

Asp Phe Cys Arg Ile Ala Ala Lys Asn Gly Ile Leu Leu Arg Leu Ile
                755                 760                 765

Asn Thr Leu Tyr Ser Leu Asn Glu Ser Thr Arg Leu Ala Ser Ser Ser
                770                 775                 780

Ala Gly Gly Phe Ser Val Asp Gly Ser Ala Gln Arg Pro Arg Ser
785                 790                 795                 800

Gly Ile Leu Asp Pro Asn His Pro Tyr Ile Asn Gln Asn Glu Thr Met
                805                 810                 815

Leu Ser Ser Val Asp Gln Gln Asp Pro Pro Lys Val Arg Arg Ala Val
                820                 825                 830

Pro Asp His His Leu Glu Pro Ser Ser Asn Pro Arg Ser Asp
                835                 840                 845

Ala Asn Tyr Pro Val Asp Val Asp Arg Pro Gln Ser Ser Asn Ala Thr
850                 855                 860

Ala Asp Glu Lys Ser Leu Asn Gln Ala Ser Arg Glu Ser Ser Ala Gly
865                 870                 875                 880

Ala Leu Lys Glu Arg Glu Asn Met Asp Arg Trp Lys Thr Asp Pro Ser
                885                 890                 895

Gln Pro Arg Ile Ser Asn Asn Arg Thr Ser Thr Asp Arg Pro Pro Lys
                900                 905                 910

Ser Thr Glu Pro Ser Ser Asn Gly Leu Ser Val Thr Gly Thr Met His
                915                 920                 925

Gln Glu Gln Val Arg Pro Leu Leu Ser Leu Leu Asp Lys Glu Pro Pro
                930                 935                 940

Ser Gly Arg Phe Ser Gly Gln Leu Glu Tyr Met Arg Gln Phe Ser Gly
945                 950                 955                 960

Leu Glu Arg His Glu Ser Val Leu Pro Leu Leu His Ala Thr Glu Lys
                965                 970                 975

Lys Thr Asn Gly Glu Leu Asp Phe Leu Met Ala Glu Phe Ala Asp Val
                980                 985                 990

Ser Gln Arg Gly Arg Glu Asn Gly Asn Leu Asp Ser Ser Ala Arg Val
                995                 1000                1005

Ser His Lys Val Thr Pro Lys Lys Leu Gly Thr Leu Gly Ser Ser
                1010                1015                1020

Glu Gly Ala Ala Ser Thr Ser Gly Ile Ala Ser Gln Thr Ala Ser
                1025                1030                1035

Gly Val Leu Ser Gly Ser Gly Val Leu Asn Ala Arg Pro Gly Ser
                1040                1045                1050

Ala Thr Ser Ser Gly Leu Leu Ser His Met Val Ser Ser Leu Asn
                1055                1060                1065

Ala Glu Val Ala Arg Glu Tyr Leu Glu Lys Val Ala Asp Leu Leu
                1070                1075                1080

Leu Glu Phe Ala Gln Ala Asp Thr Thr Val Lys Ser Tyr Met Cys
                1085                1090                1095

Ser Gln Ser Leu Leu Ser Arg Leu Phe Gln Met Phe Asn Arg Val
                1100                1105                1110

Glu Pro Pro Ile Leu Leu Lys Ile Leu Arg Cys Ile Asn His Leu
                1115                1120                1125

Ser Thr Asp Pro Asn Cys Leu Glu Asn Leu Gln Arg Ala Glu Ala
                1130                1135                1140
```

Ile Lys Tyr Leu Ile Pro Asn Leu Glu Leu Lys Glu Gly Ser Leu
1145                1150                1155

Val Ser Glu Ile His His Glu Val Leu Asn Ala Leu Phe Asn Leu
1160                1165                1170

Cys Lys Ile Asn Lys Arg Arg Gln Glu Gln Ala Ala Glu Asn Gly
1175                1180                1185

Ile Ile Pro His Leu Met Leu Phe Ile Thr Ser Asn Ser Pro Leu
1190                1195                1200

Lys Gln Tyr Ala Leu Pro Leu Leu Cys Asp Met Ala His Ala Ser
1205                1210                1215

Arg Asn Ser Arg Glu Gln Leu Arg Ala His Gly Gly Leu Asp Val
1220                1225                1230

Tyr Leu Asn Leu Leu Glu Asp Glu Leu Trp Ser Val Thr Ala Leu
1235                1240                1245

Asp Ser Ile Ala Val Cys Leu Ala His Asp Asn Asp Asn Arg Lys
1250                1255                1260

Val Glu Gln Ala Leu Leu Lys Lys Asp Ala Val Gln Lys Leu Val
1265                1270                1275

Lys Phe Phe Gln Gly Cys Pro Glu Gln His Phe Val His Ile Leu
1280                1285                1290

Glu Pro Phe Leu Lys Ile Ile Thr Lys Ser Ala Arg Ile Asn Thr
1295                1300                1305

Thr Leu Ala Val Asn Gly Leu Thr Pro Leu Leu Ile Ala Arg Leu
1310                1315                1320

Asp His Gln Asp Ala Ile Ala Arg Leu Asn Leu Leu Arg Leu Ile
1325                1330                1335

Lys Ala Val Tyr Glu His His Pro Gln Pro Lys Lys Leu Ile Val
1340                1345                1350

Glu Asn Asp Leu Pro Glu Lys Leu Gln Asn Leu Ile Gly Glu Arg
1355                1360                1365

Arg Asp Gly Gln Val Leu Val Lys Gln Met Ala Thr Ser Leu Leu
1370                1375                1380

Lys Ala Leu His Ile Asn Thr Val Leu
1385                1390

<210> SEQ ID NO 47
<211> LENGTH: 786
<212> TYPE: PRT
<213> ORGANISM: Glycine max

<400> SEQUENCE: 47

Met Ala Met Asp Glu Tyr Glu Cys His Glu Met Val His Val Ala Val
1               5                   10                  15

Gly Lys Ser Leu Lys Lys Ala Ala Thr Leu Leu Gln Trp Cys Phe Thr
                20                  25                  30

His Phe Ser Lys Pro Gln Ile Phe Leu Leu His Val His Gln Pro Ser
            35                  40                  45

Thr Met Ile Pro Thr Leu Leu Gly Lys Leu Pro Ala Ser Gln Ala Ser
        50                  55                  60

Pro Glu Val Val Ser Ala Tyr Arg Ile Glu Glu Lys Glu Asp Thr Lys
65                  70                  75                  80

Arg Leu Leu Glu Lys Tyr Leu Ser Leu Cys Arg Ala Ala Lys Val Lys
                85                  90                  95

Ala Ser Ser Val Ile Gly Glu Ala Asp Gln Val Gln Lys Gly Ile Val

```
                    100                 105                 110
Asp Leu Val Thr Val His Asn Val Arg Lys Leu Val Ile Gly Ala Ile
            115                 120                 125
Pro Glu Asn Cys Met Lys Ile Lys Arg Asn Ser Ser Lys Ala Asn Tyr
            130                 135             140
Ala Ala Lys Asn Ala Pro Pro Phe Cys Glu Ile Trp Phe Val Tyr Asn
145                 150                 155                 160
Gly Lys His Ile Trp Thr Arg Glu Ala Ser Glu Thr Pro Arg Ser Leu
                165                 170                 175
Ser Ser Arg Ala Gln Pro Glu Thr Thr Thr Ala Glu Ser Leu Ser Cys
            180                 185                 190
Arg Ser Phe His Asp Gly Thr Lys Glu Leu Leu His Ser Glu Cys Leu
            195                 200                 205
Gln Leu Asn Ser Thr Lys Thr Thr Arg Ser Met Val Gln Ser Glu Ile
            210                 215                 220
Ile Glu Ala Glu Ala Thr Phe Ser Ser Lys Ser Ser Ser Cys Asn Ser
225                 230                 235                 240
His Cys Ser Pro Gln His Ser Ala Gly Trp Tyr Leu Asp Thr His Ser
                245                 250                 255
Glu Phe Glu Glu Glu Thr Ile Asp Ser Gln Leu Ile Glu Thr Lys Arg
            260                 265                 270
Glu Ala Lys Ala Ala Thr Asp Lys Ala Leu Ala Glu Leu Leu Lys Ser
            275                 280                 285
Lys Arg Leu Glu Val Lys Ala Ile Glu Ala Ile Ser Lys Val Asn Phe
            290                 295                 300
Phe Glu Ser Ala His Ala His Glu Val Lys Leu Arg Lys Glu Ala Glu
305                 310                 315                 320
Asp Ala Leu Arg Ala Thr Ile Gln Glu Gln Gln Met Phe Leu Asp Glu
                325                 330                 335
Lys Glu Glu Ile Ala Arg Glu Leu Glu Arg Thr Val Arg Ser Ile Ser
            340                 345                 350
Leu Leu Gly Asn Cys Ala His Glu Thr Asn His Lys Arg Asp Glu Ala
            355                 360                 365
Glu Asn Glu Leu Ser Leu Ile Gln Ala Ser Ile Ser Asn Leu Trp His
            370                 375                 380
Glu Lys Gln Gln Ile Arg Gln Gln Lys Met Glu Ala Leu His Trp Leu
385                 390                 395                 400
Glu Arg Trp Lys Ser Cys Gly Gln Val Gly Ala Asp His Cys Asn Gly
                405                 410                 415
Val Ile Gly Phe Ala Glu Glu Phe Pro Glu Leu Ala Glu Phe Ser Leu
            420                 425                 430
Ser Asp Leu Gln Asn Ala Thr Cys Asn Phe Ser Glu Ser Phe Lys Val
            435                 440                 445
Met Glu Gly Gly Tyr Gly Ser Ile Tyr Lys Gly Glu Met Leu Gly Arg
            450                 455                 460
Thr Val Ala Ile Arg Lys Leu His Pro His Asn Met Gln Gly Ser Ser
465                 470                 475                 480
Glu Phe His Gln Glu Ala Gln Ile Leu Gly Ser Leu Gln His Pro His
                485                 490                 495
Leu Val Thr Leu Leu Gly Val Cys Pro Glu Ala Trp Ser Phe Val Tyr
            500                 505                 510
Glu Tyr Leu Pro Ser Gly Ser Leu Gln Asp Tyr Leu Phe Arg Lys Ser
            515                 520                 525
```

```
Ser Phe Leu Pro Leu Thr Arg Asn Ile Arg Ala Gln Trp Ile Ala Glu
    530                 535                 540

Ile Ala Thr Ala Leu Cys Phe Leu His Ser Ser Lys Pro Glu Thr Ile
545                 550                 555                 560

Ile His Gly Gly Leu Thr Leu Glu Thr Val Leu Leu Asp Ser Ala Leu
                565                 570                 575

Ser Cys Lys Ile Cys Glu Phe Gly Phe Ser Arg Leu Val Lys Glu Glu
            580                 585                 590

Ser Val Tyr Leu Pro Asn Phe His Phe Ser Thr Glu Pro Lys Gly Ser
        595                 600                 605

Phe Thr Tyr Thr Asp Pro Glu Phe Gln Arg Thr Gly Val Leu Thr Pro
610                 615                 620

Lys Ser Asp Ile Tyr Ser Phe Gly Ile Ile Leu Gln Leu Leu Thr
625                 630                 635                 640

Gly Arg Thr Pro Val Gly Leu Val Gly Glu Val Arg Arg Ala Val Ser
                645                 650                 655

Cys Gly Lys Leu Tyr Pro Ile Leu Asp Ser Ser Ala Gly Glu Trp Asn
            660                 665                 670

Ser Thr Met Ala Thr Arg Leu Ala Glu Leu Gly Leu Gln Cys Cys Gln
        675                 680                 685

Leu Asn Ser Arg Val Arg Pro Glu Leu Thr Pro Ser Leu Val Arg Glu
690                 695                 700

Leu Lys Gln Leu Leu Val Leu Glu Glu Arg Pro Val Pro Ser Phe Phe
705                 710                 715                 720

Leu Cys Pro Ile Phe Gln Glu Ile Met His Asp Pro Gln Val Ala Ala
                725                 730                 735

Asp Gly Phe Thr Tyr Glu Gly Lys Ala Ile Ser Glu Trp Leu Glu Asn
            740                 745                 750

Gly His Glu Thr Ser Pro Met Thr Asn Leu Lys Leu Thr His Leu Asn
        755                 760                 765

Leu Thr Pro Asn His Ala Leu Arg Leu Ala Ile Gln Gly Trp Leu Cys
770                 775                 780

Lys Ser
785

<210> SEQ ID NO 48
<211> LENGTH: 661
<212> TYPE: PRT
<213> ORGANISM: Glycine max

<400> SEQUENCE: 48

Met Thr Val Glu Lys Arg Ile Val Leu Val Gly Ile Arg Ile Asp Gly
1               5                   10                  15

Tyr Ser Arg Gln Leu Leu Asn Trp Ala Leu Ala Lys Val Ala Glu Pro
            20                  25                  30

Gly Asp Cys Val Ile Ala Val His Val Val Lys Ser Ser Asp Tyr Val
        35                  40                  45

Ser Lys Asn Lys Thr Leu Ile Asp Gly Tyr Leu Glu Val Tyr Glu Gly
    50                  55                  60

Leu Cys Gly Val Lys Val Gly Leu Thr Gly Gln Ile Phe Thr Gly
65              70                  75                  80

Ser Ser Ile Lys Asn Ile Leu Val Arg Glu Ala Lys Lys His Ala Ala
                85                  90                  95

Leu Ala Leu Val Val Gly Gly Arg Ala Ala Thr Ala Lys Tyr Cys Ala
```

```
            100                 105                 110
Lys Arg Leu Gln Pro Thr Thr Asn Val Leu Ala Ile Gln Asp Ser Arg
        115                 120                 125

Ile Val Phe Arg Ser Cys Thr Asn Lys Gln Leu Pro Gly Gly Leu Ile
130                 135                 140

Leu Asp Pro Arg Pro Ser Leu Thr Ile Ile Lys Glu Asn Leu Arg Asp
145                 150                 155                 160

Arg Ala Ile His Ser Ser Ile Cys Asp Ser Ile Val Glu Ile Glu Glu
                165                 170                 175

Ser Thr Arg Lys Asn Ser Leu Glu Ser Lys Glu Glu Ala Phe Asn Gly
                180                 185                 190

Ser Glu Lys Ser Lys Ser Arg Ser Ile Ser Met Phe Ala Gly Asp Ser
        195                 200                 205

Ala Glu Gln Lys Leu Gly Trp Pro Leu Leu Arg Arg Ala Asn Ser Gly
        210                 215                 220

Met Ser Gln Thr Leu His Ala Arg Asp Met Ser Val Val Gln Trp Val
225                 230                 235                 240

Met Thr Leu Pro Asp Arg Ser Pro Asn Lys Gly Ser Ser Ser Ser Ser
                245                 250                 255

Thr Glu Glu Asn Pro Phe Glu Arg Ser Ile Ser Asp Val Glu Tyr Glu
                260                 265                 270

Ser Ser Ser Asn Ser Ser Pro Ser Ser Val Asp Ile Pro Asn Gly Leu
        275                 280                 285

Glu Glu Met Leu Asn Leu Asn Ser Leu Asn Cys Lys Arg Phe Ser Leu
        290                 295                 300

Glu Val Leu Lys Ser Cys Thr Ser Gln Phe Ser Ser Glu Lys Leu Val
305                 310                 315                 320

Gly Lys Gly Gly Ser Asn Arg Val Tyr Lys Gly Val Leu Thr Asp Gly
                325                 330                 335

Lys Ser Ile Ala Val Lys Val Met Gln Ser Ser Lys Glu Ala Trp Lys
                340                 345                 350

Asp Phe Ala Leu Glu Val Glu Ile Ile Ser Ser Leu Glu His Lys Ser
        355                 360                 365

Ile Ala Pro Leu Leu Gly Ile Cys Ile Glu Asn Asn Thr Leu Ile Ser
        370                 375                 380

Val Tyr Asp Tyr Phe Pro Asn Gly Ser Leu Glu Glu Asn Leu His Gly
385                 390                 395                 400

Lys Asn Lys Asp Glu Ser Ile Leu Ser Trp Glu Val Arg Phe Asn Val
                405                 410                 415

Ala Ile Arg Ile Ala Glu Ala Leu Asp Tyr Leu His Arg Glu Ala Leu
                420                 425                 430

Lys Pro Val Ile His Lys Asp Val Lys Ser Ser Asn Ile Leu Leu Ser
                435                 440                 445

Gln Gly Phe Glu Pro Gln Leu Ser Asp Phe Gly Leu Ala Val Trp Gly
        450                 455                 460

Pro Thr Thr Ser Ser Phe Leu Thr Gln Asp Val Val Gly Thr Phe Gly
465                 470                 475                 480

Tyr Leu Ala Pro Glu Tyr Phe Met Tyr Gly Lys Val Ser Asp Lys Ile
                485                 490                 495

Asp Val Tyr Ala Phe Gly Val Val Leu Leu Glu Leu Ile Ser Gly Arg
                500                 505                 510

Glu Pro Ile Asn Ser Ala Ala Cys Lys Gly Gln Glu Ser Leu Val Val
                515                 520                 525
```

```
Trp Ala Lys Pro Ile Ile Glu Ser Gly Asn Val Lys Gly Leu Leu Asp
            530                 535                 540

Pro Asn Leu Glu Gly Lys Phe Asp Glu Ala Gln Leu Gln Arg Met Val
545                 550                 555                 560

Leu Ala Ala Ser Leu Cys Ile Thr Arg Ala Ala Arg Leu Arg Pro Lys
                565                 570                 575

Leu Ser Gln Ile Leu Lys Ile Leu Lys Gly Glu Glu Lys Val Glu Tyr
                580                 585                 590

Phe Leu Asn Ser Gln Gly Asp Asn Gln Glu Asp Ser Glu Asn Gln
                595                 600                 605

Glu Asn Ile Asp Asp Glu Val Tyr Pro Asn Ser Ala Glu Leu His
            610                 615                 620

Leu Ser Leu Ala Leu Leu Gly Val Asp Asp Ser Thr Ser His Ser
625                 630                 635                 640

Ser Thr Asp His Ser Tyr Ser Glu Asp Leu Lys Glu Gln Trp Ser Arg
                645                 650                 655

Ser Ser Ser Phe Asn
            660

<210> SEQ ID NO 49
<211> LENGTH: 419
<212> TYPE: PRT
<213> ORGANISM: Glycine max

<400> SEQUENCE: 49

Met Asp Ser Ala Arg Thr Ala Pro Pro Trp Gln Glu Leu Asp Leu
1               5                   10                  15

Asp Ser Leu Lys Pro Leu Lys Val Leu Gly Lys Gly Gly Met Gly Thr
                20                  25                  30

Val Phe Leu Val Gln Ala Ala Asn Asn Thr Arg Phe Ala Leu Lys Val
                35                  40                  45

Val Asp Lys Thr Cys Val His Ala Lys Leu Asp Ala Glu Arg Arg Ala
            50                  55                  60

Arg Trp Glu Ile Gln Val Leu Ser Thr Leu Ser His Pro Phe Leu Pro
65                  70                  75                  80

Ser Leu Met Gly Thr Phe Glu Ser Pro Gln Phe Leu Ala Trp Ala Leu
                85                  90                  95

Pro Tyr Cys Pro Gly Gly Asp Leu Asn Val Leu Arg Tyr Arg Gln Thr
                100                 105                 110

Asp Arg Ala Phe Ser Pro Ala Val Ile Arg Phe Tyr Val Ala Glu Ile
            115                 120                 125

Leu Cys Ala Leu Asp His Leu His Ser Met Gly Ile Ala Tyr Arg Asp
            130                 135                 140

Leu Lys Pro Glu Asn Val Leu Val Gln Asn Thr Gly His Ile Thr Leu
145                 150                 155                 160

Thr Asp Phe Asp Leu Ser Arg Lys Leu Asn Pro Lys Pro Lys Pro Asn
                165                 170                 175

Pro Gln Val Pro Ser Ile Pro Leu Pro Asn Ser Asn Val Pro Glu Pro
                180                 185                 190

Arg Arg Lys His Arg Arg Asn Phe Ser Arg Trp Ile Ser Leu Phe Pro
            195                 200                 205

Pro Asp Gly Thr His His Asn Asn Asn Lys Asn Gly Leu Lys Lys Ala
            210                 215                 220

Lys Ser Ala Arg Val Ser Pro Val Ser Arg Arg Lys Pro Ser Phe Ser
```

```
            225                 230                 235                 240

Asn Gly Glu Arg Ser Asn Ser Phe Val Gly Thr Glu Tyr Val Ser
                245                 250                 255

Pro Glu Val Val Arg Gly Asp Gly His Glu Phe Ala Val Asp Trp Trp
                260                 265                 270

Ala Leu Gly Ile Leu Ile Tyr Glu Met Leu Tyr Gly Thr Thr Pro Phe
                275                 280                 285

Lys Gly Lys Asn Arg Lys Glu Thr Phe Arg Asn Val Ile Thr Lys Pro
                290                 295                 300

Pro Val Phe Val Gly Lys Arg Thr Ala Leu Thr Asp Leu Ile Glu Lys
305                 310                 315                 320

Leu Leu Glu Lys Asp Pro Thr Lys Arg Leu Gly Tyr Thr Arg Gly Ala
                325                 330                 335

Val Glu Ile Lys Glu His Glu Phe Phe Arg Gly Val Arg Trp Glu Leu
                340                 345                 350

Leu Thr Glu Val Val Arg Pro Pro Phe Ile Pro Thr Arg Asp Asp Gly
                355                 360                 365

Ala Gly Asp Ser Thr Asp Arg Ile Ser Asp Arg Asn Cys Gly Phe Asp
                370                 375                 380

Ile Arg Gly Tyr Phe Leu Asn Leu Lys Ser Ser Pro Ser Leu Pro Gly
385                 390                 395                 400

Ser Pro Leu Pro Ser Pro Ser Cys Arg Phe Lys Lys Asn Val Ser Leu
                405                 410                 415

Thr Glu Phe

<210> SEQ ID NO 50
<211> LENGTH: 463
<212> TYPE: PRT
<213> ORGANISM: Glycine max

<400> SEQUENCE: 50

Met Gly Ile Cys Leu Ser Thr Gln Ile Glu Ala Gly Leu Asn Ser Lys
1               5                   10                  15

His Val Ser Val Asp Ala Lys Asp Leu Ser Ser Pro Ser Ser Lys Ile
                20                  25                  30

Thr Lys Asp Leu Ser Asn Pro Ile Ser Asn Lys Ile Thr Glu Asp Leu
                35                  40                  45

Ser Thr Pro Ile Ser Asn Lys Ile Thr Glu Asp Leu Ser Thr Pro Ile
                50                  55                  60

Ser Asn Lys Ile Thr Glu Asp Leu Ser Thr Pro Ile Ser Asn Lys Ile
65                  70                  75                  80

Thr Glu Asp Leu Ser Thr Pro Ile Ser Lys Val Ser Glu Ile Leu Val
                85                  90                  95

Pro Leu Thr Pro Gln Ile Glu Gly Glu Ile Leu Gln Ser Ser Asn Leu
                100                 105                 110

Lys Asn Phe Ser Leu Thr Glu Leu Thr Ala Ala Thr Arg Asn Phe Arg
                115                 120                 125

Lys Asp Ser Val Leu Gly Gly Glu Gly Asp Phe Gly Ser Val Phe Lys
                130                 135                 140

Gly Trp Ile Asp Asn His Ser Leu Ala Ala Ala Lys Pro Gly Thr Gly
145                 150                 155                 160

Val Val Val Ala Val Lys Arg Leu Ser Leu Asp Ser Phe Gln Gly His
                165                 170                 175

Lys Asp Arg Leu Ala Arg His Gly Met Thr His Glu Ala Ser Leu Glu
```

180                 185                 190
Ala Glu Val Asn Tyr Leu Gly Gln Leu Ser His Pro His Leu Val Lys
            195                 200                 205

Leu Ile Gly Tyr Cys Phe Glu Asp Lys Asp Arg Leu Leu Val Tyr Glu
            210                 215                 220

Phe Met Pro Arg Gly Ser Leu Glu Asn His Leu Phe Met Arg Gly Ser
225                 230                 235                 240

Tyr Phe Gln Pro Leu Ser Trp Gly Leu Arg Leu Lys Val Ala Leu Gly
                245                 250                 255

Ala Ala Lys Gly Leu Ala Phe Leu His Ser Ala Glu Thr Lys Val Ile
            260                 265                 270

Tyr Arg Asp Phe Lys Thr Ser Asn Val Leu Leu Asp Ser Asn Tyr Asn
            275                 280                 285

Ala Lys Leu Ala Asp Leu Gly Leu Ala Lys Asp Gly Pro Thr Arg Glu
            290                 295                 300

Lys Ser His Ala Ser Thr Arg Val Met Gly Thr Tyr Gly Tyr Ala Ala
305                 310                 315                 320

Pro Glu Tyr Leu Ala Thr Gly Asn Leu Ser Ala Lys Ser Asp Val Phe
                325                 330                 335

Ser Phe Gly Val Val Leu Leu Glu Met Leu Ser Gly Arg Arg Ala Val
            340                 345                 350

Asp Lys Asn Arg Pro Ser Gly Gln His Asn Leu Val Glu Trp Ala Lys
            355                 360                 365

Pro Tyr Leu Ser Asn Lys Arg Lys Leu Leu Arg Val Leu Asp Asn Arg
            370                 375                 380

Leu Glu Gly Gln Tyr Glu Leu Asp Glu Ala Cys Lys Val Ala Thr Leu
385                 390                 395                 400

Ser Leu Arg Cys Leu Ala Ile Glu Ser Lys Leu Arg Pro Thr Met Asp
                405                 410                 415

Glu Val Ala Thr Asp Leu Glu Gln Leu Gln Val Pro His Val Lys Gln
            420                 425                 430

Asn Arg Arg Lys Ser Ala Asp His Phe Thr His Gly Arg Ile Ala Thr
            435                 440                 445

Ala Ser Ala Ser Pro Leu Ser Arg Asp Ile Ala Asn Thr His Pro
            450                 455                 460

<210> SEQ ID NO 51
<211> LENGTH: 829
<212> TYPE: PRT
<213> ORGANISM: Glycine max

<400> SEQUENCE: 51

Met Arg Asn Asn Lys Pro Gln Leu Trp Leu Ser Leu Ser Leu Ile Ile
1               5                   10                  15

Thr Cys Phe Ser Phe His Thr Ser Leu Ala Ala Leu Thr Thr Ile Ser
            20                  25                  30

Ala Asn Gln Ser Leu Ser Gly Asp Glu Thr Leu Val Ser Gln His Gly
        35                  40                  45

Asn Phe Glu Leu Gly Phe Phe Asn Thr Gly Asn Asn Ser Asn Lys Phe
    50                  55                  60

Tyr Ile Gly Met Trp Tyr Lys Lys Ile Ser Gln Arg Thr Tyr Val Trp
65                  70                  75                  80

Val Ala Asn Arg Asp Gln Pro Val Ser Asp Lys Asn Ser Ala Lys Leu
                85                  90                  95

```
Thr Ile Leu Glu Gly Asn Leu Val Leu Leu Asp Gln Ser Gln Asn Leu
            100                 105                 110

Val Trp Ser Thr Asn Leu Ser Ser Pro Ser Ser Gly Ser Ala Val Ala
        115                 120                 125

Val Leu Leu Asp Thr Gly Asn Leu Ile Leu Ser Asn Arg Ala Asn Ala
    130                 135                 140

Ser Val Ser Asp Ala Met Trp Gln Ser Phe Asp His Pro Thr Asp Thr
145                 150                 155                 160

Trp Leu Pro Gly Gly Lys Ile Lys Leu Asp Lys Lys Thr Lys Lys Pro
                165                 170                 175

Gln Tyr Leu Thr Ser Trp Lys Asn Arg Glu Asp Pro Ala Pro Gly Leu
            180                 185                 190

Phe Ser Leu Glu Leu Asp Pro Ala Gly Ser Asn Ala Tyr Leu Ile Leu
        195                 200                 205

Trp Asn Lys Ser Glu Gln Tyr Trp Thr Ser Gly Ala Trp Asn Gly Gln
    210                 215                 220

Ile Phe Ser Leu Val Pro Glu Met Arg Leu Asn Tyr Ile Tyr Asn Phe
225                 230                 235                 240

Thr Phe Gln Ser Asn Glu Asn Glu Ser Tyr Phe Thr Tyr Ser Met Tyr
                245                 250                 255

Asn Ser Ser Ile Ile Ser Arg Phe Val Met Asp Gly Ser Gly Gln Ile
            260                 265                 270

Lys Gln Leu Ser Trp Leu Glu Asn Ala Gln Gln Trp Asn Leu Phe Trp
        275                 280                 285

Ser Gln Pro Arg Gln Gln Cys Glu Val Tyr Ala Phe Cys Gly Gly Phe
    290                 295                 300

Gly Ser Cys Thr Glu Asn Ala Met Pro Tyr Cys Asn Cys Leu Asn Gly
305                 310                 315                 320

Tyr Glu Pro Lys Ser Gln Ser Asp Trp Asn Leu Thr Asp Tyr Ser Gly
                325                 330                 335

Gly Cys Val Lys Lys Thr Lys Phe Gln Cys Glu Asn Pro Asn Ser Ser
            340                 345                 350

Asp Lys Glu Lys Asp Arg Phe Leu Pro Ile Leu Asn Met Lys Leu Pro
        355                 360                 365

Asn His Ser Gln Ser Ile Gly Ala Gly Thr Val Gly Glu Cys Glu Ala
    370                 375                 380

Lys Cys Leu Ser Asn Cys Ser Cys Thr Ala Tyr Ala His Asp Asn Ser
385                 390                 395                 400

Gly Cys Ser Ile Trp His Gly Asp Leu Leu Asn Leu Gln Gln Leu Thr
                405                 410                 415

Gln Asp Asp Asn Ser Gly Gln Thr Leu Phe Leu Arg Leu Ala Ala Ser
            420                 425                 430

Glu Phe Asp Asp Ser Asn Ser Asn Lys Gly Thr Val Ile Gly Ala Val
        435                 440                 445

Ala Gly Ala Val Gly Gly Val Val Leu Leu Ile Leu Phe Val Phe
    450                 455                 460

Val Met Leu Arg Arg Arg Lys Arg His Val Gly Thr Arg Thr Ser Val
465                 470                 475                 480

Glu Gly Ser Leu Met Ala Phe Gly Tyr Arg Asp Leu Gln Asn Ala Thr
                485                 490                 495

Lys Asn Phe Ser Glu Lys Leu Gly Gly Gly Phe Gly Ser Val Phe
            500                 505                 510

Lys Gly Thr Leu Pro Asp Ser Ser Val Val Ala Val Lys Lys Leu Glu
```

```
                515                 520                 525
Ser Ile Ser Gln Gly Glu Lys Gln Phe Arg Thr Glu Val Ser Thr Ile
        530                 535                 540

Gly Thr Val Gln His Val Asn Leu Val Arg Leu Arg Gly Phe Cys Ser
545                 550                 555                 560

Glu Gly Thr Lys Lys Leu Leu Val Tyr Asp Tyr Met Pro Asn Gly Ser
                565                 570                 575

Leu Glu Ser Lys Ile Phe His Glu Asp Ser Ser Lys Val Leu Leu Asp
            580                 585                 590

Trp Lys Val Arg Tyr Gln Ile Ala Leu Gly Thr Ala Arg Gly Leu Thr
        595                 600                 605

Tyr Leu His Glu Lys Cys Arg Asp Cys Ile Ile His Cys Asp Val Lys
    610                 615                 620

Pro Glu Asn Ile Leu Leu Asp Ala Asp Phe Ile Pro Lys Val Ala Asp
625                 630                 635                 640

Phe Gly Leu Ala Lys Leu Val Gly Arg Asp Phe Ser Arg Val Leu Thr
                645                 650                 655

Thr Met Arg Gly Thr Arg Gly Tyr Leu Ala Pro Glu Trp Ile Ser Gly
            660                 665                 670

Val Ala Ile Thr Ala Lys Ala Asp Val Tyr Ser Tyr Gly Met Met Leu
        675                 680                 685

Phe Glu Phe Val Ser Gly Arg Arg Asn Ser Glu Ala Ser Glu Asp Gly
    690                 695                 700

Gln Val Arg Phe Phe Pro Thr Ile Ala Ala Asn Met Met His Gln Gly
705                 710                 715                 720

Gly Asn Val Leu Ser Leu Leu Asp Pro Arg Leu Glu Glu Asn Ala Asp
                725                 730                 735

Ile Glu Glu Val Thr Arg Val Ile Lys Val Ala Ser Trp Cys Val Gln
            740                 745                 750

Asp Asp Glu Ser His Arg Pro Ser Met Gly Gln Val Val Gln Ile Leu
        755                 760                 765

Glu Gly Phe Leu Asp Val Thr Leu Pro Pro Ile Pro Arg Thr Leu Gln
    770                 775                 780

Ala Phe Val Asp Asn His Glu Asn Val Val Phe Phe Thr Asp Ser Ser
785                 790                 795                 800

Ser Thr Gln Thr Ser Gln Val Lys Ser Asn Ala Ser Ala Ala Ser Ser
                805                 810                 815

Gln Ala Lys Ser Asn Ile Ser Ser Ser Asn Ser Ser Thr
            820                 825

<210> SEQ ID NO 52
<211> LENGTH: 420
<212> TYPE: PRT
<213> ORGANISM: Glycine max

<400> SEQUENCE: 52

Met Ala Ser Leu Pro Leu Gly His His His His His Lys Pro Ala
1               5                   10                  15

Ala Ala Ala Ile His Pro Ser Gln Pro Pro Gln Ser Gln Pro Gln Pro
            20                  25                  30

Glu Val Pro Arg Arg Ser Ser Asp Met Glu Thr Asp Lys Asp Met Ser
        35                  40                  45

Ala Thr Val Ile Glu Gly Asn Asp Ala Val Thr Gly His Ile Ile Ser
    50                  55                  60
```

Thr Thr Ile Gly Gly Lys Asn Gly Glu Pro Lys Glu Thr Ile Ser Tyr
65                  70                  75                  80

Met Ala Glu Arg Val Val Gly Thr Gly Ser Phe Gly Val Val Phe Gln
                85                  90                  95

Ala Lys Cys Leu Glu Thr Gly Glu Ala Val Ala Ile Lys Lys Val Leu
            100                 105                 110

Gln Asp Arg Arg Tyr Lys Asn Arg Glu Leu Gln Leu Met Arg Leu Met
        115                 120                 125

Asp His Pro Asn Val Ile Ser Leu Lys His Cys Phe Phe Ser Thr Thr
    130                 135                 140

Ser Arg Asp Glu Leu Phe Leu Asn Leu Val Met Glu Tyr Val Pro Glu
145                 150                 155                 160

Ser Met Tyr Arg Val Ile Lys His Tyr Thr Thr Met Asn Gln Arg Met
                165                 170                 175

Pro Leu Ile Tyr Val Lys Leu Tyr Thr Tyr Gln Ile Phe Arg Gly Leu
            180                 185                 190

Ala Tyr Ile His Thr Ala Leu Gly Val Cys His Arg Asp Val Lys Pro
        195                 200                 205

Gln Asn Leu Leu Val His Pro Leu Thr His Gln Val Lys Leu Cys Asp
    210                 215                 220

Phe Gly Ser Ala Lys Val Leu Val Lys Gly Glu Ser Asn Ile Ser Tyr
225                 230                 235                 240

Ile Cys Ser Arg Tyr Tyr Arg Ala Pro Glu Leu Ile Phe Gly Ala Thr
                245                 250                 255

Glu Tyr Thr Ala Ser Ile Asp Ile Trp Ser Ala Gly Cys Val Leu Ala
            260                 265                 270

Glu Leu Leu Leu Gly Gln Pro Leu Phe Pro Gly Glu Asn Gln Val Asp
        275                 280                 285

Gln Leu Val Glu Ile Ile Lys Val Leu Gly Thr Pro Thr Arg Glu Glu
    290                 295                 300

Ile Arg Cys Met Asn Pro Asn Tyr Thr Glu Phe Arg Phe Pro Gln Ile
305                 310                 315                 320

Lys Ala His Pro Trp His Lys Val Phe His Lys Arg Met Pro Pro Glu
                325                 330                 335

Ala Ile Asp Leu Ala Ser Arg Leu Leu Gln Tyr Ser Pro Ser Leu Arg
            340                 345                 350

Cys Thr Ala Leu Glu Ala Cys Ala His Pro Phe Phe Asp Glu Leu Arg
        355                 360                 365

Glu Pro Asn Ala Arg Leu Pro Asn Gly Arg Pro Leu Pro Pro Leu Phe
    370                 375                 380

Asn Phe Lys Gln Glu Leu Ala Gly Ala Ser Pro Glu Leu Ile Asn Arg
385                 390                 395                 400

Leu Ile Pro Glu His Ile Arg Arg Gln Met Gly Leu Ser Phe Pro His
                405                 410                 415

Ser Ala Gly Thr
            420

<210> SEQ ID NO 53
<211> LENGTH: 1044
<212> TYPE: PRT
<213> ORGANISM: Glycine max

<400> SEQUENCE: 53

Met Glu Ser Arg Met Asp His Tyr Glu Ile Met Glu Gln Ile Gly Arg
1               5                   10                  15

```
Gly Ala Phe Gly Ala Ala Ile Leu Val Asn His Lys Ala Glu Lys Lys
            20                  25                  30

Lys Tyr Val Leu Lys Lys Ile Arg Leu Ala Arg Gln Thr Glu Arg Cys
        35                  40                  45

Arg Arg Ser Ala His Gln Glu Met Ala Leu Ile Ala Arg Ile Gln His
50                  55                  60

Pro Tyr Ile Val Gln Phe Lys Glu Ala Trp Val Glu Lys Gly Cys Tyr
65                  70                  75                  80

Val Cys Ile Val Thr Gly Tyr Cys Glu Gly Gly Asp Met Ala Ala Leu
                85                  90                  95

Met Lys Lys Ser Ile Gly Val Tyr Phe Pro Glu Glu Lys Leu Cys Lys
            100                 105                 110

Trp Phe Thr Gln Ile Leu Leu Ala Val Glu Tyr Leu His Ser Asn Phe
        115                 120                 125

Val Leu His Arg Asp Leu Lys Cys Ser Asn Ile Phe Leu Thr Lys Asp
130                 135                 140

Gln Asp Val Arg Leu Gly Asp Phe Gly Leu Ala Lys Thr Leu Lys Ala
145                 150                 155                 160

Asp Asp Leu Ala Ser Ser Val Val Gly Thr Pro Asn Tyr Met Cys Pro
                165                 170                 175

Glu Leu Leu Ala Asp Ile Pro Tyr Gly Phe Lys Ser Asp Ile Trp Ser
            180                 185                 190

Leu Gly Cys Cys Ile Tyr Glu Met Ala Ala His Arg Pro Ala Phe Lys
        195                 200                 205

Ala Phe Asp Met Ala Gly Leu Ile Ser Lys Ile Asn Arg Ser Ser Ile
210                 215                 220

Gly Pro Leu Pro Pro Cys Tyr Ser Pro Ser Leu Lys Thr Leu Ile Lys
225                 230                 235                 240

Gly Met Leu Arg Lys Asn Pro Glu His Arg Pro Thr Ala Ser Glu Ile
                245                 250                 255

Leu Lys His Pro Tyr Leu Leu Pro Tyr Val Asp Gln Tyr Arg Ser Ser
            260                 265                 270

Phe Cys Thr Pro Thr Ala Gly Ser Pro Glu Arg Pro Ile Ser Ala Val
        275                 280                 285

His His Pro Arg Lys Asn Lys Pro Glu Ser Gln Asn Ser Ser Ser Ser
290                 295                 300

Leu Ser Pro Glu Lys Asp Ser Phe Met Ser Ser Glu Lys Asn Thr Ala
305                 310                 315                 320

Asn Glu Val Lys Lys Cys Asp Arg Lys Ile Thr Glu Ile Asp Leu Thr
                325                 330                 335

Ser Ile Glu Asp Asp Ser Ser Glu Gln Leu Leu Pro Glu Glu Glu Gly
            340                 345                 350

Asn Gly Ser Ser Arg Val Asn Ala Lys Thr Asp Glu Lys Glu Leu Thr
        355                 360                 365

Lys Gln Ser Asn Asn Val His His Ser Asn Ala Val Ser Lys Gln Pro
370                 375                 380

Lys Pro Ile Lys Asn Val Val Thr Ala Leu Lys Asp Gly Lys Leu Arg
385                 390                 395                 400

Glu Thr Ser Ser Pro Ile Arg Gly Asn Arg Ile Lys Val Gly Gly Val
                405                 410                 415

Leu Thr His Lys Ile Asn Ser Glu Thr Val Ser Lys Leu Pro Lys Pro
            420                 425                 430
```

```
Asn Phe Gly Ala Tyr Asp Leu Lys Pro Asn Leu Glu Val Pro Thr Thr
            435                 440                 445

Ala Pro Ser Lys Thr Thr Pro Asp Ser Ala Lys Arg Met Gln Gly Leu
450                 455                 460

His Thr Ser Lys His Gln Leu Pro Met Ile Glu Ser Thr Pro Lys Thr
465                 470                 475                 480

Lys Pro Arg His Asn Ala Ile Pro Pro Ser Gly Pro Val Lys Gln Val
                485                 490                 495

Glu Gly Arg Glu Val Pro Ser Lys Pro Arg Gln Lys Thr Arg Pro Ser
            500                 505                 510

Leu Leu Lys Pro Pro Ser Phe Pro Gly His Val Arg Gln Ala Gly Phe
        515                 520                 525

Asp Val Pro Asn Ala Thr Asn Asn Thr Gly Lys Ser Ser Pro Lys Lys
    530                 535                 540

Met Val Trp Glu Pro Lys Met Ser His His Gln Leu Thr Asn Thr His
545                 550                 555                 560

Leu Pro His Val Ser Arg Glu Thr Thr Arg Glu Pro Leu Lys Thr Phe
                565                 570                 575

Glu Thr Ser Ser Lys Gly Met Gln Thr Asp Ser Ser Asn Ser Val Ser
            580                 585                 590

Ser Ser Leu Ser Ile Gln Gly Phe Glu Leu Ser Asp Phe Ala Thr Thr
        595                 600                 605

Phe Ile Asp Leu Ser Glu Pro Thr Leu Pro Asp His Glu Ser Leu Asn
    610                 615                 620

His Thr Glu Asn Val Glu Ser Cys Pro Tyr Ser Ile Ser Cys Ala Ser
625                 630                 635                 640

Tyr Leu His Phe Glu Met Ser Glu Gln Leu Ser Gly Glu Thr Pro Val
                645                 650                 655

Val Thr Pro Cys Phe Gln Asn Ile Thr Ser Asn Glu Lys Val Ser Pro
            660                 665                 670

Ser Leu Thr Leu Asp His Ser Gly Gln Asp Ala Glu Val Met Phe Ala
        675                 680                 685

Ser Asp Asp Ser Phe Ser Ile Asn Gln Arg Thr Ala Ser Ala Gly Ser
    690                 695                 700

Arg Cys Asp Asn Leu Ser Val Asp Pro Ser Ala Glu Ile Thr Gln Glu
705                 710                 715                 720

Ile Lys Asp Pro Gln Asp Ser Lys Glu Met Ser Ser Ala Lys Ser Leu
                725                 730                 735

Gln Gln Ser Leu Leu Ile Ser Gly Glu Lys Ser Val Cys Glu Glu Phe
            740                 745                 750

Gly Pro Ser Ser Lys Gly Ser Asn Arg Leu Asp Lys Val Ser Arg Pro
        755                 760                 765

Lys Leu Met Cys Ile Ser Thr Gly Asp Asp Lys Phe Met Val Arg Glu
    770                 775                 780

Arg Leu Ser Ser Val Asp Glu Thr Ala Pro Ser Ile Ile Ser Thr Lys
785                 790                 795                 800

Ile Ser Ser Gln Lys Val Leu Gln Glu Lys Gly Met Val Leu Gln
                805                 810                 815

Asn Pro Ala Glu Arg Pro Ala Val Gly His Leu Pro Pro Ala Phe
            820                 825                 830

Asp Asp Val Ile His Val Ile Arg His Ser Ser Tyr Arg Val Gly Ser
    835                 840                 845

Glu Gln Pro Gly Lys Glu Ser Val Glu Met Gly Val Gln Asn Val Asp
```

```
                    850                 855                 860
Val Gly Lys Phe Ile Asn Ile Ala Arg Asp Asp Leu Glu Met Arg Asn
865                 870                 875                 880

Val Ser Thr Pro Leu Thr Leu Lys Ser Ser Asn Cys Ser Glu Ala Ile
                    885                 890                 895

Gly Leu Lys Ser Asn Ile Ser Asp Asn Met Glu Ile Arg Asn Leu Ser
                    900                 905                 910

Ser Pro Pro Asn Leu Lys Ser Ser Cys Thr Asp Leu Met Asn Ile
                    915                 920                 925

Lys Ser Ser Phe Ser Asp His Leu Leu Val Arg Lys Gln Asp Val Lys
                    930                 935                 940

Asn Thr Asp Ser Leu Val Ser Lys Ser Asp Ser Ser Glu Tyr Thr Lys
945                 950                 955                 960

His Asn Thr Pro Thr Ala Ala Glu Glu Thr Pro Pro Lys Glu Ile Leu
                    965                 970                 975

Asp Val Lys Ser Ser Arg Gln Arg Ala Glu Ala Leu Glu Gly Leu Leu
                    980                 985                 990

Glu Leu Ser Ala Asp Leu Leu Gln Gln Asn Arg Leu Glu Glu Leu Ala
                    995                 1000                1005

Val Val Leu Lys Pro Phe Gly Lys Asp Lys Val Ser Pro Arg Glu
            1010                1015                1020

Thr Ala Ile Trp Leu Ala Lys Ser Leu Lys Gly Leu Met Ile Glu
            1025                1030                1035

Glu Ser Gly Gly Arg Ser
            1040
```

<210> SEQ ID NO 54
<211> LENGTH: 618
<212> TYPE: PRT
<213> ORGANISM: Glycine max

<400> SEQUENCE: 54

```
Met Thr Thr Phe His Val Val Glu Lys Asp Leu Thr Ser Arg Tyr Ala
1               5                   10                  15

Arg Tyr Asp Glu Leu Leu Gly Lys Gly Ala Phe Lys Thr Val Tyr Lys
                20                  25                  30

Ala Phe Asp Glu Val Asp Gly Ile Glu Val Ala Trp Asn Met Ile Ser
            35                  40                  45

Val Glu Asp Val Val Gln Thr Pro Gln Gln Leu Glu Lys Leu Tyr Ser
50                  55                  60

Glu Ile His Leu Leu Lys Ser Leu Lys His Asp Asn Val Ile Lys Leu
65                  70                  75                  80

Tyr Asn Ser Trp Val Asp Asp Thr Thr Gly Thr Ile Asn Met Ile Thr
                85                  90                  95

Glu Leu Phe Thr Ser Gly Ser Leu Arg Gln Tyr Arg Asn Lys His Lys
            100                 105                 110

Asn Val Asp Met Lys Ala Ile Lys Asn Trp Ala Arg Gln Ile Leu Arg
        115                 120                 125

Gly Leu Cys Phe Leu His Cys His Ser Pro Ile Val His Arg Asp
        130                 135                 140

Leu Lys Cys Asp Asn Ile Phe Val Asn Gly Asn Ser Gly Leu Val Lys
145                 150                 155                 160

Ile Gly Asp Leu Gly Leu Ala Ile Val Met Gln Gln Pro Thr Ala Arg
                165                 170                 175
```

```
Ser Val Ile Gly Thr Pro Glu Phe Met Ala Pro Glu Leu Tyr Glu Glu
                180             185             190

Glu Tyr Asn Glu Leu Val Asp Ile Tyr Ser Phe Gly Met Cys Ile Leu
        195             200             205

Glu Met Val Thr Cys Glu Tyr Pro Tyr Ser Glu Cys Asn Asn Pro Ala
    210             215             220

Gln Ile Tyr Lys Lys Val Thr Ser Gly Ile Lys Pro Ala Ala Leu Ala
225             230             235             240

Lys Val Asn Asp Pro Glu Val Lys Gln Phe Ile Glu Lys Cys Leu Val
                245             250             255

Pro Ala Ser Met Arg Leu Ser Ala Ser Glu Leu Leu Lys Asp Pro Phe
            260             265             270

Leu Ala Thr Glu Asn Thr Lys Glu Ile Asn His Asp Ile Leu Glu Leu
        275             280             285

Pro Asn Pro His Thr Lys Leu Val Asn Pro Thr Cys Glu Pro His
    290             295             300

Pro Met Glu Ile Asp Ser Lys Ser Arg Arg Thr Ser Pro Gly Ser Ser
305             310             315             320

Met Gly Arg Ile Glu Glu Thr Ser Gln Val Ser Phe Asp Leu Val
                325             330             335

Arg Met Thr Glu Asn Asn Lys Phe Met Leu Arg Gly Glu Lys Asn Ala
            340             345             350

Glu Ser Thr Ile Ser Leu Thr Leu Arg Ile Ala Asn Ala Cys Gly Gly
        355             360             365

Ala Arg Asn Ile His Phe Pro Phe Tyr Ile Asn Ser Asp Thr Ala Ile
370             375             380

Ser Ile Ala Glu Glu Met Val Glu His Leu Glu Leu Thr Asn Glu Asp
385             390             395             400

Val Ser Val Ile Ala Glu Leu Ile Asn Asp Met Ile Ala Lys Leu Val
                405             410             415

Pro Asn Leu Lys Pro Leu Ser Glu Lys Leu Ser Ser Gly Thr Asp Gln
            420             425             430

Leu Tyr Arg Pro Ser Ser Glu Val Gln Asn Gly Glu Gln Phe Asn Cys
        435             440             445

His Trp Pro Leu Gln Ser Ser Asp Tyr Asp Met Lys Pro Val Phe Lys
450             455             460

Asp Leu Val His Ser Trp Pro Val Asp Gly Asp Leu Glu Lys Gln
465             470             475             480

Glu Ser Val Met Ser Asp Ile Ser Val Glu Cys Gly Ile Thr Val Ala
                485             490             495

Ser Asp Ser Lys Val Val Glu Pro Asp Ile Phe Ile Phe Asp Glu Phe
            500             505             510

Trp Glu Gly Phe Asp Ala Phe Asn Ser Thr Ser Asp Val Arg Phe Cys
        515             520             525

Gly Gln Glu Asp Gly His Lys Asn Gln Ser Glu Asn Ser Ser Gly Ser
530             535             540

Leu Ile Asn Ser Cys Cys Cys Pro Phe Lys Asn Phe Asp Ile Ser Ser
545             550             555             560

Ile Cys Ser Leu Thr Leu Ala Asp Lys Asp Pro Ser Glu Gly Leu Arg
                565             570             575

Leu Glu Ile Glu Ala Ile Asp Thr Tyr Phe Glu Gln Arg Phe Arg Glu
            580             585             590

Leu Glu Met Met Arg Val Ala Ala Ile Glu Ser Leu Lys Arg Arg His
```

```
                      595                 600                 605
Gly Glu Lys His Thr Cys Asp Val Met His
    610                 615

<210> SEQ ID NO 55
<211> LENGTH: 515
<212> TYPE: PRT
<213> ORGANISM: Glycine max

<400> SEQUENCE: 55

Met Asp Arg Ser Thr Gly Arg Gly Gly Gly Ser Val Asp Met Phe
1               5                   10                  15

Leu Arg Asn Tyr Lys Leu Gly Lys Thr Leu Gly Ile Gly Ser Phe Gly
                20                  25                  30

Lys Val Lys Ile Ala Glu His Val Arg Thr Gly His Lys Val Ala Ile
                35                  40                  45

Lys Ile Leu Asn Arg His Lys Ile Lys Asn Met Glu Met Glu Glu Lys
        50                  55                  60

Val Arg Arg Glu Ile Lys Ile Leu Arg Leu Phe Met His His His Ile
65              70                  75                  80

Ile Arg Leu Tyr Glu Val Val Glu Thr Pro Thr Asp Ile Tyr Val Val
                85                  90                  95

Met Glu Tyr Val Lys Ser Gly Glu Leu Phe Asp Tyr Ile Val Glu Lys
                100                 105                 110

Gly Arg Leu Gln Glu Asp Glu Ala Arg His Phe Phe Gln Gln Ile Ile
            115                 120                 125

Ser Gly Val Glu Tyr Cys His Arg Asn Met Val Val His Arg Asp Leu
130                 135                 140

Lys Pro Glu Asn Leu Leu Leu Asp Ser Lys Phe Asn Ile Lys Ile Ala
145                 150                 155                 160

Asp Phe Gly Leu Ser Asn Ile Met Arg Asp Gly His Phe Leu Lys Thr
                165                 170                 175

Ser Cys Gly Ser Pro Asn Tyr Ala Ala Pro Glu Val Ile Ser Gly Lys
            180                 185                 190

Leu Tyr Ala Gly Pro Glu Val Asp Val Trp Ser Cys Gly Val Ile Leu
        195                 200                 205

Tyr Ala Leu Leu Cys Gly Thr Leu Pro Phe Asp Asp Glu Asn Ile Pro
210                 215                 220

Asn Leu Phe Lys Lys Ile Lys Gly Gly Ile Tyr Thr Leu Pro Ser His
225                 230                 235                 240

Leu Ser Pro Gly Ala Arg Asp Leu Ile Pro Arg Met Leu Val Val Asp
                245                 250                 255

Pro Met Lys Arg Met Thr Ile Pro Glu Ile Arg Gln His Pro Trp Phe
                260                 265                 270

Gln Val His Leu Pro Arg Tyr Leu Ala Val Pro Pro Asp Thr Leu
            275                 280                 285

Gln Gln Ala Lys Lys Ile Asp Glu Glu Ile Leu Gln Glu Val Val Asn
        290                 295                 300

Met Gly Phe Asp Arg Asn Gln Leu Val Glu Ser Leu Ser Asn Arg Ile
305                 310                 315                 320

Gln Asn Glu Gly Thr Val Thr Tyr Tyr Leu Leu Leu Asp Asn Arg Phe
                325                 330                 335

Arg Val Ser Gly Tyr Leu Gly Ala Glu Phe Gln Glu Thr Met Asp
            340                 345                 350
```

-continued

```
Ser Gly Phe Asn Arg Met His Ser Gly Glu Val Ala Ser Pro Val Val
            355                 360                 365

Gly His His Ser Thr Gly Tyr Met Asp Tyr Gln Gly Val Gly Met Arg
    370                 375                 380

Gln Gln Phe Pro Val Glu Arg Lys Trp Ala Leu Gly Leu Gln Ser Arg
385                 390                 395                 400

Ala Gln Pro Arg Glu Ile Met Thr Glu Val Leu Lys Ala Leu Gln Glu
                405                 410                 415

Leu Asn Val Cys Trp Lys Lys Ile Gly His Tyr Asn Met Lys Cys Arg
            420                 425                 430

Trp Val Ala Gly Thr Ala Gly His His Glu Gly Met Ile Asn Asn Ser
        435                 440                 445

Leu His Ser Asn His Tyr Phe Gly Asn Asp Ser Gly Ile Ile Glu Asn
    450                 455                 460

Glu Ala Val Ser Lys Ser Asn Val Val Lys Phe Glu Val Gln Leu Tyr
465                 470                 475                 480

Lys Thr Arg Glu Glu Lys Tyr Leu Leu Asp Leu Gln Arg Val Gln Gly
                485                 490                 495

Pro Gln Phe Leu Phe Leu Asp Leu Cys Ala Ala Phe Leu Ser Gln Leu
            500                 505                 510

Arg Val Leu
        515

<210> SEQ ID NO 56
<211> LENGTH: 382
<212> TYPE: PRT
<213> ORGANISM: Glycine max

<400> SEQUENCE: 56

Met Gly Asn Ala Cys Ala Lys Gly Lys Pro Val Ala His Val Ser Ser
1               5                   10                  15

Ser Asn Phe Ser Gly Ser Lys Lys Pro Ala Ser Lys Pro Lys Gln Tyr
            20                  25                  30

Ser Asn Ser Ser Glu Gln Arg Ser Ala Pro Thr Thr Ser Glu Leu Asn
        35                  40                  45

Val Pro Lys Ser Ile Ser Ser Asn Leu Lys Ser Phe Ser Leu Asn Asp
    50                  55                  60

Leu Lys Glu Ala Thr Lys Asn Phe Arg Arg Glu Asn Leu Ile Gly Glu
65                  70                  75                  80

Gly Gly Phe Gly Arg Val Phe Lys Gly Trp Ile Asp Glu Asn Thr Tyr
                85                  90                  95

Gly Pro Thr Lys Pro Gly Thr Gly Ile Val Val Ala Ile Lys Asn Leu
            100                 105                 110

Lys Pro Glu Ser Phe Gln Gly His Lys Glu Trp Leu Gln Glu Val Asn
        115                 120                 125

Tyr Leu Gly Met Leu Gln His Glu Asn Leu Val Lys Leu Ile Gly Tyr
    130                 135                 140

Cys Leu Glu Gly Lys Asn Arg Leu Leu Val Tyr Glu Phe Met Gln Lys
145                 150                 155                 160

Gly Ser Leu Glu Asn His Leu Phe Arg Lys Gly Val Gln Pro Met Ala
                165                 170                 175

Trp Val Thr Arg Val Asn Ile Ala Ile Gly Val Ala Arg Gly Leu Thr
            180                 185                 190

Phe Leu His Ser Leu Asp Gln Asn Val Ile Phe Arg Asp Leu Lys Ala
        195                 200                 205
```

```
Ser Asn Ile Leu Leu Asp Ser Asp Phe Asn Ala Lys Leu Ser Asp Phe
    210                 215                 220

Gly Leu Ala Arg Asp Gly Pro Thr Gly Asp Asn Thr His Val Ser Thr
225                 230                 235                 240

Arg Val Ile Gly Thr Gln Gly Tyr Ala Ala Pro Glu Tyr Val Ala Thr
                245                 250                 255

Gly His Leu Thr Pro Arg Ser Asp Val Tyr Ser Phe Gly Val Val Leu
                260                 265                 270

Leu Glu Leu Leu Thr Gly Arg Arg Ala Val Glu Asp Asp Gly Pro Gly
            275                 280                 285

Phe Ser Glu Glu Thr Leu Val Asp Trp Ala Lys Pro Phe Leu Asn Asp
290                 295                 300

Asn Arg Arg Val Leu Arg Ile Met Asp Thr Arg Leu Gly Gly Gln Tyr
305                 310                 315                 320

Ser Lys Lys Gly Ala Gln Ala Ala Ala Leu Ala Leu Gln Cys Leu
                325                 330                 335

Asn Thr Asp Pro Lys Phe Arg Pro Pro Met Val Glu Val Leu Ala Ala
                340                 345                 350

Leu Glu Ala Leu Asn Ser Ser Asn Ser Phe Thr Arg Thr Pro Lys His
            355                 360                 365

Glu Ser His Ser Thr Lys Ile Ser Gly Gly Pro Ser Gln Lys
    370                 375                 380

<210> SEQ ID NO 57
<211> LENGTH: 356
<212> TYPE: PRT
<213> ORGANISM: Glycine max

<400> SEQUENCE: 57

Met Lys Lys Gly Asn Leu Gly Leu Gly Leu Lys Leu Ser Val Pro Val
1               5                   10                  15

Ser Asp Gln Ser Asn Phe Ala Arg Phe Leu Thr Glu Ser Gly Thr Phe
            20                  25                  30

Lys Asp Gly Asp Leu Leu Val Asn Arg Asp Gly Val Arg Ile Val Ser
        35                  40                  45

Gln Asn Asp Val Glu Ala Pro Pro Ile Lys Pro Thr Asp Asn Gln
    50                  55                  60

Leu Thr Leu Ala Asp Ile Asp Val Ile Lys Val Val Gly Lys Gly Asn
65                  70                  75                  80

Gly Gly Val Val Gln Leu Val Gln His Lys Trp Thr Ser Gln Phe Phe
                85                  90                  95

Ala Leu Lys Val Ile Gln Met Asn Ile Glu Glu Ser Met Arg Lys Gln
                100                 105                 110

Ile Ala Gln Glu Leu Lys Ile Asn Gln Gln Ala Gln Cys Pro Tyr Val
            115                 120                 125

Val Val Cys Tyr Gln Ser Phe Tyr Glu Asn Gly Val Ile Ser Ile Ile
        130                 135                 140

Leu Glu Tyr Met Asp Gly Gly Ser Leu Ala Asp Leu Leu Lys Lys Val
145                 150                 155                 160

Lys Thr Ile Pro Glu Asp Tyr Leu Ala Ala Ile Cys Lys Gln Val Leu
                165                 170                 175

Lys Gly Leu Val Tyr Leu His His Glu Lys His Ile Ile His Arg Asp
                180                 185                 190

Leu Lys Pro Ser Asn Leu Leu Ile Asn His Ile Gly Glu Val Lys Ile
```

```
                195                 200                 205
Thr Asp Phe Gly Val Ser Ala Ile Met Glu Ser Thr Ser Gly Gln Ala
210                 215                 220

Asn Thr Phe Ile Gly Thr Tyr Asn Tyr Met Ser Pro Glu Arg Ile Asn
225                 230                 235                 240

Gly Ser Gln Arg Gly Tyr Asn Tyr Lys Ser Asp Ile Trp Ser Leu Gly
                245                 250                 255

Leu Ile Leu Leu Glu Cys Ala Leu Gly Arg Phe Pro Tyr Ala Pro Pro
            260                 265                 270

Asp Gln Ser Glu Thr Trp Glu Ser Ile Phe Glu Leu Ile Glu Thr Ile
                275                 280                 285

Val Asp Lys Pro Pro Ile Pro Pro Ser Glu Gln Phe Ser Thr Glu
290                 295                 300

Phe Cys Ser Phe Ile Ser Ala Cys Leu Gln Lys Asp Pro Lys Asp Arg
305                 310                 315                 320

Leu Ser Ala Gln Glu Leu Met Ala His Pro Phe Val Asn Met Tyr Asp
                325                 330                 335

Asp Leu Glu Val Asp Leu Ser Ala Tyr Phe Ser Asn Ala Gly Ser Pro
            340                 345                 350

Leu Ala Thr Leu
            355

<210> SEQ ID NO 58
<211> LENGTH: 451
<212> TYPE: PRT
<213> ORGANISM: Glycine max

<400> SEQUENCE: 58

Met Gly Ser Ser Phe Ser Ser Cys Tyr Glu Gly Glu Ser Val Ser Pro
1               5                   10                  15

Ser Pro Lys Pro Thr Lys Val Val Ala Thr Lys Gly Gly Ser Ser Ser
                20                  25                  30

Asn Arg Val Ser Ile Thr Asp Leu Ser Phe Pro Gly Ser Thr Leu Ser
            35                  40                  45

Glu Asp Leu Ser Val Ser Leu Val Gly Ser Asn Leu His Val Phe Ser
    50                  55                  60

Leu Ser Glu Leu Lys Ile Ile Thr Gln Ser Phe Ser Ser Ser Asn Phe
65                  70                  75                  80

Leu Gly Glu Gly Gly Phe Gly Pro Val His Lys Gly Phe Ile Asp Asp
                85                  90                  95

Lys Leu Arg Pro Gly Leu Glu Ala Gln Pro Val Ala Val Lys Leu Leu
            100                 105                 110

Asp Leu Asp Gly Ser Gln Gly His Lys Glu Trp Leu Thr Glu Val Val
        115                 120                 125

Phe Leu Gly Gln Leu Arg His Pro His Leu Val Lys Leu Ile Gly Tyr
    130                 135                 140

Cys Cys Glu Glu Glu His Arg Leu Leu Val Tyr Glu Tyr Leu Pro Arg
145                 150                 155                 160

Gly Ser Leu Glu Asn Gln Leu Phe Arg Arg Tyr Thr Ala Ser Leu Pro
                165                 170                 175

Trp Ser Thr Arg Met Lys Ile Ala Ala Gly Ala Ala Lys Gly Leu Ala
            180                 185                 190

Phe Leu His Glu Ala Lys Lys Pro Val Ile Tyr Arg Asp Phe Lys Ala
        195                 200                 205
```

Ser Asn Ile Leu Leu Asp Ser Asp Tyr Asn Ala Lys Leu Ser Asp Phe
            210                 215                 220

Gly Leu Ala Lys Asp Gly Pro Glu Gly Asp Thr His Val Ser Thr
225                 230                 235                 240

Arg Val Met Gly Thr Gln Gly Tyr Ala Ala Pro Glu Tyr Ile Met Thr
                245                 250                 255

Gly His Leu Thr Ala Met Ser Asp Val Tyr Ser Phe Gly Val Val Leu
            260                 265                 270

Leu Glu Leu Leu Thr Gly Arg Arg Ser Val Asp Lys Gly Arg Pro Gln
            275                 280                 285

Arg Glu Gln Asn Leu Val Glu Trp Ala Arg Pro Ala Leu Asn Asp Ser
290                 295                 300

Arg Lys Leu Gly Arg Ile Met Asp Pro Arg Leu Glu Gly Gln Tyr Ser
305                 310                 315                 320

Glu Val Gly Ala Arg Lys Ala Ala Leu Ala Tyr Gln Cys Leu Ser
                325                 330                 335

His Arg Pro Arg Ser Arg Pro Leu Met Ser Thr Val Val Asn Val Leu
            340                 345                 350

Glu Pro Leu Gln Asp Phe Asp Asp Val Pro Ile Gly Pro Phe Val Tyr
            355                 360                 365

Thr Val Pro Ala Glu Gln His Asn Glu Val Ala Lys Glu Ser Glu Thr
370                 375                 380

Pro Lys Glu Arg Lys Arg Glu Asn Asp His His His Asn Arg His
385                 390                 395                 400

His His His Arg His Asn Gly His Arg His His Pro Leu Lys Ser
                405                 410                 415

Pro Lys Thr Pro Met Ser Ser Asp Gln Ser Gln Asn Asp Glu His Arg
            420                 425                 430

Asn Gly Arg Arg Ser Gly Ser Asn Ser Pro Asp Thr Ser Asn Ala Ser
            435                 440                 445

Glu Ala Gln
    450

<210> SEQ ID NO 59
<211> LENGTH: 555
<212> TYPE: PRT
<213> ORGANISM: Glycine max

<400> SEQUENCE: 59

Met Asp Ser Ala Arg Ser Trp Leu Gln Lys Phe Gln Pro Arg Asp Lys
1               5                   10                  15

Thr Arg Ala Ala Gly Lys Lys Glu Glu Asp Gly Asn Gly Gly Asn
                20                  25                  30

Gln Asp Ser Asn Glu Pro Val Asp Glu Ala Leu Leu Ser Ser Val Thr
            35                  40                  45

Lys Gln Lys Val Ala Ala Thr Lys Gln Tyr Ile Glu Asn His Tyr Lys
50                  55                  60

Glu Gln Met Lys Asn Leu Gln Glu Arg Lys Glu Arg Arg Thr Ile Leu
65                  70                  75                  80

Glu Lys Lys Leu Ala Asp Ala Asp Val Ser Glu Glu Asp Gln Asn Asn
                85                  90                  95

Leu Leu Lys Phe Leu Glu Lys Lys Glu Thr Glu Tyr Met Arg Leu Gln
            100                 105                 110

Arg His Lys Met Gly Val Asp Asp Phe Glu Leu Leu Thr Met Ile Gly
            115                 120                 125

```
Lys Gly Ala Phe Gly Glu Val Arg Val Cys Arg Glu Lys Thr Ser Asp
130                 135                 140

His Val Tyr Ala Met Lys Leu Lys Lys Ser Glu Met Leu Arg Arg
145                 150                 155                 160

Gly Gln Val Glu His Val Lys Ala Glu Arg Asn Leu Leu Ala Glu Val
                165                 170                 175

Asp Arg Asn Cys Ile Val Lys Leu Tyr Cys Ser Phe Gln Asp Asp Glu
            180                 185                 190

Tyr Leu Tyr Leu Ile Met Glu Tyr Leu Pro Gly Gly Asp Met Met Thr
        195                 200                 205

Leu Leu Met Arg Lys Asp Thr Leu Thr Glu Asp Glu Ala Arg Phe Tyr
210                 215                 220

Val Gly Glu Thr Ile Leu Ala Ile Glu Ser Ile His Lys His Asn Tyr
225                 230                 235                 240

Ile His Arg Asp Ile Lys Pro Asp Asn Leu Leu Asp Arg Tyr Gly
                245                 250                 255

His Leu Lys Leu Ser Asp Phe Gly Leu Cys Lys Pro Leu Asp Cys Ser
            260                 265                 270

Ala Leu Glu Glu Lys Asp Phe Ser Val Gly Gln Asn Val Asn Gly Ser
        275                 280                 285

Thr Gln Ser Ser Thr Pro Lys Arg Ser Gln Gln Glu Gln Leu Gln His
    290                 295                 300

Trp Gln Met Asn Arg Arg Thr Leu Ala Tyr Ser Thr Val Gly Thr Pro
305                 310                 315                 320

Asp Tyr Ile Ala Pro Glu Val Leu Leu Lys Lys Gly Tyr Gly Met Glu
                325                 330                 335

Cys Asp Trp Trp Ser Leu Gly Ala Ile Met Tyr Glu Met Leu Val Gly
            340                 345                 350

Tyr Pro Pro Phe Tyr Ser Asp Asp Pro Met Leu Thr Cys Arg Lys Ile
        355                 360                 365

Val Asn Trp Lys Thr Tyr Leu Lys Phe Pro Glu Glu Ala Arg Leu Ser
370                 375                 380

Pro Glu Ala Lys Asp Leu Ile Ser Lys Leu Leu Cys Asn Val Asn Gln
385                 390                 395                 400

Arg Leu Gly Ser Lys Gly Ala Asp Glu Ile Lys Ala His Pro Phe Phe
                405                 410                 415

Lys Gly Val Glu Trp Asp Lys Leu Tyr Gln Met Glu Ala Ala Phe Ile
            420                 425                 430

Pro Glu Val Asn Asp Glu Leu Asp Thr Gln Asn Phe Glu Lys Phe Asp
        435                 440                 445

Glu Ser Asp Ser Gln Asn Gln Ser Ser Arg Ser Gly Pro Trp Arg
450                 455                 460

Lys Met Leu Ser Ser Lys Asp Leu Asn Phe Val Gly Tyr Thr Tyr Lys
465                 470                 475                 480

Asn Phe Glu Ile Val Asn Asp Tyr Gln Val Pro Gly Ile Ala Glu Leu
                485                 490                 495

Lys Lys Lys Gln Ser Lys Pro Lys Arg Pro Thr Ile Lys Ser Leu Phe
            500                 505                 510

Glu Thr Ser Glu Gly Ser Asp Thr Asp Thr Ser Ala Asn Asp Gln Pro
        515                 520                 525

Ala Gln Gly Ser Phe Leu Lys Leu Leu Pro Pro Gln Leu Glu Val Ser
530                 535                 540
```

```
Pro His Arg Asn Lys Asn Leu Pro Pro Arg Ser
545                 550                 555

<210> SEQ ID NO 60
<211> LENGTH: 688
<212> TYPE: PRT
<213> ORGANISM: Glycine max

<400> SEQUENCE: 60

Met Met Lys His Tyr His Val Leu Tyr Met Phe Leu Phe Phe Leu Pro
1               5                   10                  15

Ile Ser Thr Leu Ser Leu His His Asn Asp Thr His Ala Leu Thr Leu
            20                  25                  30

Phe Arg Arg Gln Ser Asp Leu His Gly Tyr Leu Leu Ser Asn Trp Thr
        35                  40                  45

Gly His Asp Ala Cys Asn Ser Ala Trp Arg Gly Val Leu Cys Ser Pro
    50                  55                  60

Asn Gly Arg Val Thr Ala Leu Ser Leu Pro Ser Leu Asn Leu Arg Gly
65                  70                  75                  80

Pro Leu Asp Pro Leu Thr Pro Leu Thr His Leu Arg Leu Leu Asn Leu
                85                  90                  95

His Asp Asn Arg Leu Asn Gly Thr Val Ser Thr Leu Phe Ser Asn Cys
            100                 105                 110

Thr Asn Leu Gln Leu Leu Tyr Leu Ser Ser Asp Phe Ser Gly Glu
        115                 120                 125

Ile Pro Pro Glu Ile Ser Ser Leu Lys Ser Leu Leu Arg Leu Asp Leu
    130                 135                 140

Ser Asp Asn Asn Leu Arg Gly Lys Val Asp Val Ile Ser Asn Leu Thr
145                 150                 155                 160

Gln Leu Ile Thr Leu Arg Leu Gln Asn Asn Leu Leu Ser Gly Glu Ile
                165                 170                 175

Pro Asp Leu Ser Ser Ser Met Lys Asn Leu Lys Glu Leu Asn Met Thr
            180                 185                 190

Asn Asn Glu Phe Tyr Gly Arg Leu Pro Ser Pro Met Leu Lys Lys Phe
        195                 200                 205

Ser Ser Thr Thr Phe Ser Gly Asn Glu Gly Leu Cys Gly Ala Ser Leu
    210                 215                 220

Phe Pro Gly Cys Ser Phe Thr Thr Pro Pro Asn Asn Asn Asp Ser
225                 230                 235                 240

Asn Asn Asn Asn Asp Asn Asn Ser Asn Glu Lys Glu Pro Ser Gln Thr
                245                 250                 255

Val Ser Ser Asn Pro Ser Ser Phe Pro Glu Thr Ser Ile Ile Ala Arg
            260                 265                 270

Pro Gly Arg Glu Gln Gln Arg Lys Gly Leu Ser Pro Gly Ala Ile Val
        275                 280                 285

Ala Ile Val Ile Ala Asn Cys Val Ala Leu Leu Val Val Ser Phe
    290                 295                 300

Ala Val Ala His Cys Cys Ala Arg Gly Arg Gly Ser Ser Leu Val Gly
305                 310                 315                 320

Ser Gly Glu Ser Tyr Gly Lys Arg Lys Ser Gly Ser Tyr Asn Gly
                325                 330                 335

Ser Asp Glu Lys Lys Val Tyr Gly Gly Gly Ser Asp Gly Thr Ser
            340                 345                 350

Gly Thr Asp Arg Ser Arg Leu Val Phe Phe Asp Arg Arg Ser Glu Phe
        355                 360                 365
```

```
Glu Leu Glu Asp Leu Leu Arg Ala Ser Ala Glu Met Leu Gly Lys Gly
        370                 375                 380

Ser Leu Gly Thr Val Tyr Arg Ala Val Leu Asp Asp Gly Cys Thr Val
385                 390                 395                 400

Ala Val Lys Arg Leu Lys Asp Ala Asn Pro Cys Ala Arg His Glu Phe
                405                 410                 415

Glu Gln Tyr Met Asp Val Ile Gly Lys Leu Lys His Pro Asn Val Val
            420                 425                 430

Arg Leu Lys Ala Tyr Tyr Ala Lys Glu Lys Leu Leu Val Tyr
        435                 440                 445

Asp Tyr Leu Ser Asn Gly Ser Leu His Ala Leu His Gly Asn Arg
450                 455                 460

Gly Pro Gly Arg Ile Pro Leu Asp Trp Thr Thr Arg Ile Ser Leu Val
465                 470                 475                 480

Leu Gly Ala Ala Arg Gly Leu Ala Lys Ile His Ala Glu Tyr Ser Ala
                485                 490                 495

Ala Lys Val Pro His Gly Asn Val Lys Ser Ser Asn Val Leu Leu Asp
                500                 505                 510

Lys Asn Gly Val Ala Cys Ile Ser Asp Phe Gly Leu Ser Leu Leu Leu
                515                 520                 525

Asn Pro Val His Ala Ile Ala Arg Leu Gly Gly Tyr Arg Ala Pro Glu
530                 535                 540

Gln Glu Gln Asn Lys Arg Leu Ser Gln Gln Ala Asp Val Tyr Ser Phe
545                 550                 555                 560

Gly Val Leu Leu Leu Glu Val Leu Thr Gly Arg Ala Pro Ser Ser Gln
                565                 570                 575

Tyr Pro Ser Pro Ala Arg Pro Arg Met Glu Val Glu Pro Glu Gln Ala
                580                 585                 590

Ala Val Asp Leu Pro Lys Trp Val Arg Ser Val Val Arg Glu Glu Trp
                595                 600                 605

Thr Ala Glu Val Phe Asp Gln Glu Leu Leu Arg Tyr Lys Asn Ile Glu
610                 615                 620

Glu Glu Leu Val Ser Met Leu His Val Gly Leu Thr Cys Val Val Ala
625                 630                 635                 640

Gln Pro Glu Lys Arg Pro Thr Met Glu Glu Val Val Lys Met Ile Glu
                645                 650                 655

Glu Ile Arg Val Glu Gln Ser Pro Leu Gly Glu Asp Tyr Asp Val Ser
                660                 665                 670

Cys Asn Ser Leu Ser Pro Ser Ile Pro Thr Thr Glu Asp Gly Leu Ala
                675                 680                 685

<210> SEQ ID NO 61
<211> LENGTH: 1008
<212> TYPE: PRT
<213> ORGANISM: Glycine max

<400> SEQUENCE: 61

Met Thr Asn Pro Lys Asn Gln Thr Thr Leu Ser Ile Ile Ile Val
1               5                   10                  15

Tyr Ile Leu Phe Phe Ser Leu Ala Thr Thr Leu Val Ser Cys Leu Asn
                20                  25                  30

Gln Glu Gly Leu Tyr Leu Tyr Gln Leu Lys Leu Ser Leu Asp Asp Pro
            35                  40                  45

Asp Ser Lys Leu Ser Ser Trp Asn Ser Arg Asp Ala Thr Pro Cys Asn
```

```
            50                  55                  60
Trp Tyr Gly Val Thr Cys Asp Ala Ala Thr Asn Thr Thr Val Thr Glu
 65                  70                  75                  80

Leu Asp Leu Ser Asp Thr Asn Ile Gly Gly Pro Phe Leu Ser Asn Ile
                     85                  90                  95

Leu Cys Arg Leu Pro Asn Leu Val Ser Val Asn Leu Phe Asn Asn Ser
                100                 105                 110

Ile Asn Glu Thr Leu Pro Ser Glu Ile Ser Leu Cys Lys Asn Leu Ile
                    115                 120                 125

His Leu Asp Leu Ser Gln Asn Leu Leu Thr Gly Pro Leu Pro Asn Thr
            130                 135                 140

Leu Pro Gln Leu Leu Asn Leu Arg Tyr Leu Asp Leu Thr Gly Asn Asn
145                 150                 155                 160

Phe Ser Gly Pro Ile Pro Asp Ser Phe Gly Thr Phe Gln Asn Leu Glu
                    165                 170                 175

Val Leu Ser Leu Val Ser Asn Leu Leu Glu Gly Thr Ile Pro Ser Ser
                180                 185                 190

Leu Gly Asn Val Ser Thr Leu Lys Met Leu Asn Leu Ser Tyr Asn Pro
            195                 200                 205

Phe Phe Pro Gly Arg Ile Pro Pro Glu Ile Gly Asn Leu Thr Asn Leu
210                 215                 220

Gln Val Leu Trp Leu Thr Gln Cys Asn Leu Val Gly Val Ile Pro Thr
225                 230                 235                 240

Ser Leu Gly Arg Leu Gly Lys Leu Gln Asp Leu Asp Leu Ala Leu Asn
                    245                 250                 255

Asp Leu Tyr Gly Ser Ile Pro Ser Ser Leu Thr Glu Leu Thr Ser Leu
                260                 265                 270

Arg Gln Ile Glu Leu Tyr Asn Asn Ser Leu Ser Gly Glu Leu Pro Lys
            275                 280                 285

Gly Met Gly Asn Leu Thr Asn Leu Arg Leu Ile Asp Ala Ser Met Asn
            290                 295                 300

His Leu Thr Gly Arg Ile Pro Glu Glu Leu Cys Ser Leu Pro Leu Glu
305                 310                 315                 320

Ser Leu Asn Leu Tyr Glu Asn Arg Phe Glu Gly Leu Pro Ala Ser
                    325                 330                 335

Ile Ala Asp Ser Pro Asn Leu Tyr Glu Leu Arg Leu Phe Gly Asn Arg
                340                 345                 350

Leu Thr Gly Lys Leu Pro Glu Asn Leu Gly Arg Asn Ser Pro Leu Arg
            355                 360                 365

Trp Leu Asp Val Ser Ser Asn Gln Phe Trp Gly Pro Ile Pro Ala Thr
370                 375                 380

Leu Cys Asp Lys Gly Ala Leu Glu Glu Leu Val Ile Tyr Asn Leu
385                 390                 395                 400

Phe Ser Gly Glu Ile Pro Ala Ser Leu Gly Thr Cys Gln Ser Leu Thr
                    405                 410                 415

Arg Val Arg Leu Gly Phe Asn Arg Leu Ser Gly Glu Val Pro Ala Gly
                420                 425                 430

Ile Trp Gly Leu Pro His Val Tyr Leu Leu Glu Leu Val Asp Asn Ser
            435                 440                 445

Phe Ser Gly Ser Ile Ala Arg Thr Ile Gly Ala Ala Asn Leu Ser
450                 455                 460

Leu Leu Ile Leu Ser Lys Asn Asn Phe Thr Gly Thr Ile Pro Asp Glu
465                 470                 475                 480
```

```
Val Gly Trp Leu Glu Asn Leu Val Glu Phe Ser Ala Ser Asp Asn Lys
            485                 490                 495

Phe Thr Gly Ser Leu Pro Asp Ser Ile Val Asn Leu Gly Gln Leu Gly
            500                 505                 510

Ile Leu Asp Phe His Lys Asn Lys Leu Ser Gly Glu Leu Pro Lys Gly
            515                 520                 525

Ile Arg Ser Trp Lys Lys Leu Asn Asp Leu Asn Leu Ala Asn Asn Glu
            530                 535                 540

Ile Gly Gly Arg Ile Pro Asp Glu Ile Gly Gly Leu Ser Val Leu Asn
545                 550                 555                 560

Phe Leu Asp Leu Ser Arg Asn Arg Phe Leu Gly Lys Val Pro His Gly
            565                 570                 575

Leu Gln Asn Leu Lys Leu Asn Gln Leu Asn Leu Ser Tyr Asn Arg Leu
            580                 585                 590

Ser Gly Glu Leu Pro Pro Leu Leu Ala Lys Asp Met Tyr Arg Ser Ser
            595                 600                 605

Phe Leu Gly Asn Pro Gly Leu Cys Gly Asp Leu Lys Gly Leu Cys Asp
            610                 615                 620

Gly Arg Gly Glu Glu Lys Ser Val Gly Tyr Val Trp Leu Leu Arg Thr
625                 630                 635                 640

Ile Phe Val Val Ala Thr Leu Val Phe Leu Val Gly Val Val Trp Phe
            645                 650                 655

Tyr Phe Arg Tyr Lys Asn Phe Gln Asp Ser Lys Arg Ala Ile Asp Lys
            660                 665                 670

Ser Lys Trp Thr Leu Met Ser Phe His Lys Leu Gly Phe Ser Glu Asp
            675                 680                 685

Glu Ile Leu Asn Cys Leu Asp Glu Asp Asn Val Ile Gly Ser Gly Ser
            690                 695                 700

Ser Gly Lys Val Tyr Lys Val Val Leu Ser Ser Gly Glu Val Val Ala
705                 710                 715                 720

Val Lys Lys Ile Trp Gly Val Lys Glu Val Glu Ser Gly Asp
            725                 730                 735

Val Glu Lys Gly Gly Arg Val Gln Asp Asn Ala Phe Asp Ala Glu Val
            740                 745                 750

Glu Thr Leu Gly Lys Ile Arg His Lys Asn Ile Val Lys Leu Trp Cys
            755                 760                 765

Cys Cys Thr Thr Arg Asp Cys Lys Leu Leu Val Tyr Glu Tyr Met Pro
            770                 775                 780

Asn Gly Ser Leu Gly Asp Leu Leu His Ser Ser Lys Gly Gly Leu Leu
785                 790                 795                 800

Asp Trp Pro Thr Arg Tyr Lys Ile Ala Val Asp Ala Ala Glu Gly Leu
            805                 810                 815

Ser Tyr Leu His His Asp Cys Val Pro Ala Ile Val His Arg Asp Val
            820                 825                 830

Lys Ser Asn Asn Ile Leu Leu Asp Val Asp Phe Gly Ala Arg Val Ala
            835                 840                 845

Asp Phe Gly Val Ala Lys Ala Val Glu Thr Thr Pro Lys Gly Ala Lys
            850                 855                 860

Ser Met Ser Val Ile Ala Gly Ser Cys Gly Tyr Ile Ala Pro Glu Tyr
865                 870                 875                 880

Ala Tyr Thr Leu Arg Val Asn Glu Lys Ser Asp Ile Tyr Ser Phe Gly
            885                 890                 895
```

```
Val Val Ile Leu Glu Leu Val Thr Gly Lys Arg Pro Val Asp Pro Glu
                900                 905                 910

Phe Gly Glu Lys Asp Leu Val Lys Trp Val Cys Thr Thr Leu Asp Gln
        915                 920                 925

Lys Gly Val Asp His Leu Ile Asp Pro Arg Leu Asp Thr Cys Phe Lys
        930                 935                 940

Glu Glu Ile Cys Lys Val Phe Asn Ile Gly Leu Met Cys Thr Ser Pro
945                 950                 955                 960

Leu Pro Ile His Arg Pro Ser Met Arg Arg Val Val Lys Met Leu Gln
                965                 970                 975

Glu Val Gly Thr Glu Asn Gln Thr Lys Ser Ala Lys Leu Asp Gly Lys
        980                 985                 990

Leu Ser Pro Tyr Tyr Tyr Asp Asp Ala Ser Asp His Gly Ser Val Val
        995                 1000                1005

<210> SEQ ID NO 62
<211> LENGTH: 512
<212> TYPE: PRT
<213> ORGANISM: Glycine max

<400> SEQUENCE: 62

Met Ala Asp Val Val Ser Lys Ser Pro Thr Pro Thr Ser Asn Leu Ile
1               5                   10                  15

Ser Pro Asn Lys Lys Glu Thr Ser Asn Leu Leu Leu Gly Arg Phe Glu
            20                  25                  30

Ile Gly Lys Leu Leu Gly His Gly Thr Phe Ala Lys Val Tyr Tyr Ala
        35                  40                  45

Arg Asn Ile Lys Thr Gly Glu Gly Val Ala Ile Lys Val Ile Asp Lys
    50                  55                  60

Glu Lys Ile Leu Lys Gly Gly Leu Val Ala His Ile Lys Arg Glu Ile
65                  70                  75                  80

Ser Ile Leu Arg Arg Val Arg His Pro Asn Ile Val Gln Leu Phe Glu
                85                  90                  95

Val Met Ala Thr Lys Ser Lys Ile Tyr Phe Val Met Glu Tyr Val Arg
            100                 105                 110

Gly Gly Glu Leu Phe Asn Lys Val Ala Lys Gly Arg Leu Lys Glu Glu
        115                 120                 125

Val Ala Arg Lys Tyr Phe Gln Gln Leu Ile Ser Ala Val Gly Phe Cys
    130                 135                 140

His Ala Arg Gly Val Tyr His Arg Asp Leu Lys Pro Glu Asn Leu Leu
145                 150                 155                 160

Leu Asp Glu Asn Gly Asn Leu Lys Val Ser Asp Phe Gly Leu Ser Ala
                165                 170                 175

Val Ser Asp Gln Ile Arg Gln Asp Gly Leu Phe His Thr Phe Cys Gly
            180                 185                 190

Thr Pro Ala Tyr Val Ala Pro Glu Val Leu Ala Arg Lys Gly Tyr Asp
        195                 200                 205

Gly Ala Lys Val Asp Leu Trp Ser Cys Gly Val Val Leu Phe Val Leu
    210                 215                 220

Met Ala Gly Tyr Leu Pro Phe His Asp Gln Asn Val Met Ala Met Tyr
225                 230                 235                 240

Lys Lys Ile Tyr Arg Gly Glu Phe Arg Cys Pro Arg Trp Phe Ser Pro
                245                 250                 255

Asp Leu Ser Arg Leu Leu Thr Arg Leu Leu Asp Thr Lys Pro Glu Thr
            260                 265                 270
```

Arg Ile Ala Ile Pro Glu Ile Met Glu Asn Lys Trp Phe Lys Lys Gly
            275                 280                 285

Phe Lys Gln Ile Lys Phe Tyr Val Glu Asp Asp Arg Leu Cys Asn Val
        290                 295                 300

Val Asp Asp Gly Leu Met Asp Asn Asp Asp Thr Ala Ser Ile
305                 310                 315                 320

Val Ser Val Ala Ser Phe Ser Asp Tyr Ser Val Ser Glu Ser Asp Ser
                325                 330                 335

Glu Ile Glu Thr Arg Arg Ile Asn Ala Pro Leu Pro Arg Pro Pro
            340                 345                 350

Ser Leu Asn Ala Phe Asp Ile Ile Ser Phe Ser Pro Gly Phe Asn Leu
                355                 360                 365

Ser Gly Leu Phe Glu Glu Lys Glu Asp Glu Thr Arg Phe Val Thr Ala
            370                 375                 380

Ala Pro Val Asn Arg Ile Ile Ser Lys Leu Glu Glu Ile Ala Gln Leu
385                 390                 395                 400

Val Arg Phe Ser Val Arg Lys Lys Asp Cys Arg Val Ser Leu Glu Gly
                405                 410                 415

Thr Arg Glu Gly Val Arg Gly Pro Leu Thr Ile Ala Ala Glu Ile Phe
            420                 425                 430

Glu Leu Thr Pro Ser Leu Val Val Val Glu Val Lys Lys Lys Gly Gly
                435                 440                 445

Asp Arg Ala Glu Tyr Glu Arg Phe Cys Asn Asp Glu Leu Lys Pro Gly
            450                 455                 460

Leu Gln Asn Leu Met Val Glu Glu Ser Ala Thr Ser Ser Glu Leu Ser
465                 470                 475                 480

Thr Pro Ile Gln Pro Ser Leu Leu Arg Gly Leu Ser Glu Pro Val Pro
                485                 490                 495

Asp Ile Ser Ser Asp Ile Glu Thr Pro Leu Cys Ile Pro Ser Asp Asp
            500                 505                 510

<210> SEQ ID NO 63
<211> LENGTH: 1000
<212> TYPE: PRT
<213> ORGANISM: Glycine max

<400> SEQUENCE: 63

Met Leu Gln Leu Leu Pro Val Phe Leu Leu Leu Leu Glu Gln Ala
1               5                   10                  15

Ser Leu Ile Ser Gly Leu Asn Gln Asp Gly Leu Tyr Leu Tyr Glu Trp
                20                  25                  30

Lys Gln Ser Leu Asp Asp Pro Asp Ser Ser Leu Ser Ser Trp Asn Asn
            35                  40                  45

Arg Asp Ala Thr Pro Cys Asn Trp Ala Gly Val Thr Cys Gly Pro Ser
        50                  55                  60

Asn Thr Thr Val Thr Ala Leu Asp Leu Ser Asn Phe Asn Leu Ser Gly
65                  70                  75                  80

Pro Phe Ser Ala Ser Leu Leu Cys Arg Leu Pro Asn Leu Thr Ser Ile
                85                  90                  95

Ile Leu Phe Asn Asn Ser Ile Asn Gln Thr Leu Pro Leu Gln Ile Ser
                100                 105                 110

Leu Cys Thr Pro Leu Leu His Leu Asp Leu Ser Gln Asn Leu Leu Thr
            115                 120                 125

Gly Phe Leu Pro His Thr Leu Pro Leu Leu Pro Asn Leu Leu His Leu

```
            130                 135                 140
Asp Leu Thr Gly Asn Asn Phe Ser Gly Pro Ile Pro Pro Ser Phe Ala
145                 150                 155                 160

Thr Phe Pro Asn Leu Gln Thr Leu Ser Leu Val Tyr Asn Leu Leu Asp
                165                 170                 175

Asp Val Val Ser Pro Ser Leu Phe Asn Ile Thr Thr Leu Lys Thr Leu
            180                 185                 190

Asn Leu Ser Phe Asn Pro Phe Leu Pro Ser Pro Ile Pro His Ser Leu
        195                 200                 205

Gly Asn Leu Thr Asn Leu Glu Thr Leu Trp Leu Ser Gly Cys Asn Leu
    210                 215                 220

Val Gly Pro Ile Pro Glu Ser Leu Gly Asn Leu Val Asn Leu Arg Val
225                 230                 235                 240

Leu Asp Phe Ser Phe Asn Asn Leu Tyr Gly Pro Ile Pro Ser Ser Leu
                245                 250                 255

Thr Arg Leu Thr Ala Leu Thr Gln Ile Glu Phe Tyr Asn Asn Ser Leu
            260                 265                 270

Ser Ala Glu Phe Pro Lys Gly Met Ser Asn Leu Thr Ser Leu Arg Leu
        275                 280                 285

Ile Asp Val Ser Met Asn His Leu Ser Gly Thr Ile Pro Asp Glu Leu
    290                 295                 300

Cys Arg Leu Pro Leu Glu Ser Leu Asn Leu Tyr Glu Asn Arg Phe Thr
305                 310                 315                 320

Gly Glu Leu Pro Pro Ser Ile Ala Asp Ser Pro Asn Leu Tyr Glu Leu
                325                 330                 335

Arg Leu Phe Gly Asn Lys Leu Ala Gly Lys Leu Pro Glu Asn Leu Gly
            340                 345                 350

Lys Asn Ala Pro Leu Lys Trp Leu Asp Val Ser Thr Asn Arg Phe Ser
        355                 360                 365

Gly Gly Ile Pro Glu Ser Leu Cys Glu His Gly Glu Leu Glu Glu Leu
    370                 375                 380

Leu Met Leu Glu Asn Glu Phe Ser Gly Glu Ile Pro Ala Ser Leu Gly
385                 390                 395                 400

Gly Cys Arg Arg Leu Ser Arg Val Arg Leu Gly Thr Asn Arg Leu Ser
                405                 410                 415

Gly Glu Val Pro Ala Gly Met Trp Gly Leu Pro His Val Tyr Leu Leu
            420                 425                 430

Glu Leu Gly Asn Asn Ser Phe Ser Gly Pro Ile Ala Arg Thr Ile Ala
        435                 440                 445

Gly Ala Arg Asn Leu Ser Leu Leu Ile Leu Ser Lys Asn Asn Phe Ser
    450                 455                 460

Gly Val Ile Pro Asp Glu Ile Gly Trp Leu Glu Asn Leu Gln Glu Phe
465                 470                 475                 480

Ser Gly Ala Asp Asn Asn Phe Asn Gly Ser Leu Pro Gly Ser Ile Val
                485                 490                 495

Asn Leu Gly Gln Leu Gly Thr Leu Asp Leu His Asn Asn Glu Leu Ser
            500                 505                 510

Gly Glu Leu Pro Lys Gly Ile Gln Ser Trp Lys Lys Leu Asn Asp Leu
        515                 520                 525

Asn Leu Ala Asn Asn Glu Ile Gly Gly Lys Ile Pro Asp Glu Ile Gly
    530                 535                 540

Ile Leu Ser Val Leu Asn Phe Leu Asp Leu Ser Asn Asn Glu Ile Ser
545                 550                 555                 560
```

-continued

Gly Asn Val Pro Leu Gly Leu Gln Asn Leu Lys Leu Asn Leu Leu Asn
                565                 570                 575

Leu Ser Tyr Asn Arg Leu Ser Gly Arg Leu Pro Pro Leu Leu Ala Lys
            580                 585                 590

Asp Met Tyr Arg Ala Ser Phe Met Gly Asn Pro Gly Leu Cys Gly Asp
        595                 600                 605

Phe Lys Gly Leu Cys Asp Gly Lys Gly Asp Asp Asn Ser Lys Gly
    610                 615                 620

Phe Val Trp Ile Leu Arg Ala Ile Phe Ile Val Ala Ser Leu Val Phe
625                 630                 635                 640

Val Val Gly Val Val Trp Phe Tyr Phe Arg Tyr Arg Asn Phe Lys Asn
                645                 650                 655

Ala Gly Arg Ser Val Asp Lys Ser Lys Trp Thr Leu Met Ser Phe His
            660                 665                 670

Lys Leu Gly Phe Ser Glu Asp Glu Ile Leu Asn Cys Leu Asp Glu Asp
    675                 680                 685

Asn Val Ile Gly Ser Gly Ser Ser Gly Lys Val Tyr Lys Val Val Leu
    690                 695                 700

Thr Ser Gly Glu Ser Val Ala Val Lys Lys Ile Trp Gly Gly Val Lys
705                 710                 715                 720

Lys Glu Ile Asp Ser Gly Asp Val Glu Lys Gly His Gln Phe Arg Gln
                725                 730                 735

Asp Ser Ser Phe Asp Ala Glu Val Glu Thr Leu Gly Lys Ile Arg His
            740                 745                 750

Lys Asn Ile Val Lys Leu Trp Cys Cys Cys Thr Thr Arg Asp Ser Lys
    755                 760                 765

Leu Leu Val Tyr Glu Tyr Met Pro Asn Gly Ser Leu Gly Asp Leu Leu
    770                 775                 780

His Ser Asn Lys Gly Gly Leu Leu Asp Trp Pro Thr Arg Tyr Lys Ile
785                 790                 795                 800

Ala Val Asp Ala Ala Glu Gly Leu Ser Tyr Leu His His Asp Cys Val
                805                 810                 815

Pro Ser Ile Val His Arg Asp Val Lys Ser Asn Asn Ile Leu Leu Asp
            820                 825                 830

Gly Asp Phe Gly Ala Arg Val Ala Asp Phe Gly Val Ala Lys Val Val
    835                 840                 845

Asp Ala Thr Gly Lys Gly Thr Lys Ser Met Ser Val Ile Ala Gly Ser
    850                 855                 860

Cys Gly Tyr Ile Ala Pro Glu Tyr Ala Tyr Thr Leu Arg Val Asn Glu
865                 870                 875                 880

Lys Ser Asp Ile Tyr Ser Phe Gly Val Val Ile Leu Glu Leu Val Thr
                885                 890                 895

Gly Arg Arg Pro Ile Asp Pro Glu Phe Gly Glu Lys Asp Leu Val Met
            900                 905                 910

Trp Ala Cys Asn Thr Leu Asp Gln Lys Gly Val Asp His Val Ile Asp
    915                 920                 925

Ser Arg Leu Asp Ser Cys Phe Lys Glu Glu Ile Cys Lys Val Leu Asn
    930                 935                 940

Ile Gly Leu Met Cys Thr Ser Pro Leu Pro Ile Asn Arg Pro Ala Met
945                 950                 955                 960

Arg Arg Val Val Lys Met Leu Gln Glu Val Gly Thr Glu Asn Gln Thr
                965                 970                 975

```
Lys Pro Ala Lys Lys Asp Gly Lys Leu Ser Pro Tyr Tyr Asp Asp
            980                 985                 990
Gly Ser Asp His Gly Ser Val Ala
        995                 1000

<210> SEQ ID NO 64
<211> LENGTH: 684
<212> TYPE: PRT
<213> ORGANISM: Glycine max

<400> SEQUENCE: 64

Met Ile Arg His Lys His Thr His His Leu Pro Ser Ile Leu Leu Ser
1               5                   10                  15

Ile Leu Phe Leu Phe Asn Ser Thr Cys Ala Ile Asp Phe Val Phe Asn
            20                  25                  30

Gly Phe Asn Ser Ser Glu Val Leu Leu Phe Gly Asn Ala Thr Val Asp
        35                  40                  45

Ser Arg Ile Leu Thr Leu Thr His Gln Gln Arg Phe Ser Val Gly Arg
50                  55                  60

Ala Leu Tyr Asn Lys Lys Ile Pro Thr Lys Lys Pro Asn Ser Ser Arg
65                  70                  75                  80

Val Tyr Pro Phe Ser Thr Ser Phe Ile Phe Ala Met Ala Pro Phe Glu
                85                  90                  95

Asp Thr Leu Pro Gly His Gly Leu Val Phe Ile Phe Thr Pro Val Thr
            100                 105                 110

Gly Ile Gln Gly Thr Ser Ser Ala Gln His Leu Gly Leu Phe Asn Leu
        115                 120                 125

Thr Asn Asn Gly Asn Ser Ser Asn His Val Phe Gly Val Glu Phe Asp
130                 135                 140

Val Phe Gln Asn Gln Glu Phe Asp Asp Ile Asp Ala Asn His Val Gly
145                 150                 155                 160

Ile Asp Ile Asn Ser Leu Lys Ser Tyr Val Ser His Asp Ala Gly Tyr
                165                 170                 175

Trp Pro Asp Gly Ala Asp Lys Ser Phe Lys Glu Leu Thr Leu Asn Ser
            180                 185                 190

Gly Glu Asn Tyr Gln Val Trp Ile Asp Tyr Glu Asp Ser Trp Ile Asn
        195                 200                 205

Val Thr Met Ala Pro Val Gly Met Lys Arg Pro Ser Arg Pro Leu Leu
210                 215                 220

Asn Val Ser Leu Asn Leu Ser Gln Val Phe Glu Asp Glu Met Phe Val
225                 230                 235                 240

Gly Phe Thr Ser Ala Thr Gly Gln Leu Val Glu Ser His Lys Ile Leu
                245                 250                 255

Gly Trp Ser Phe Ser Asn Glu Lys Phe Ser Leu Ser Asp Glu Leu Ile
            260                 265                 270

Thr Thr Gly Leu Pro Ser Phe Val Leu Pro Lys Asp Ser Ile Phe Lys
        275                 280                 285

Ser Lys Gly Phe Val Ala Gly Phe Thr Val Gly Val Phe Val Ile
290                 295                 300

Cys Leu Leu Val Leu Leu Ala Leu Phe Leu Ile Gln Arg Lys Arg Glu
305                 310                 315                 320

Lys Glu Arg Lys Arg Met Glu Met Glu Asp Trp Glu Leu Glu Tyr Trp
                325                 330                 335

Pro His Arg Met Thr Tyr Glu Glu Ile Glu Ala Ala Thr Lys Gly Phe
            340                 345                 350
```

Ser Glu Glu Asn Val Ile Gly Val Gly Gly Asn Gly Lys Val Tyr Lys
        355                 360                 365

Gly Val Leu Arg Gly Gly Val Glu Val Ala Val Lys Arg Ile Ser His
        370                 375                 380

Glu Asn Asp Gly Leu Arg Glu Phe Leu Ala Glu Val Ser Ser Leu Gly
385                 390                 395                 400

Arg Leu Lys Gln Arg Asn Leu Val Gly Leu Arg Gly Trp Cys Lys Lys
                405                 410                 415

Asp Val Gly Asn Phe Leu Leu Ile Tyr Asp Tyr Met Glu Asn Gly Ser
            420                 425                 430

Leu Asp Lys Arg Val Phe Asp Cys Asp Glu Ser Lys Met Leu Ser Tyr
        435                 440                 445

Glu Asp Arg Ile Arg Ile Leu Lys Asp Val Ala Phe Ala Val Leu Tyr
    450                 455                 460

Leu His Glu Gly Trp Glu Asp Lys Val Val His Arg Asp Ile Lys Ala
465                 470                 475                 480

Ser Asn Val Leu Leu Asp Lys Asp Met Asn Gly Arg Leu Gly Asp Phe
                485                 490                 495

Gly Leu Ala Arg Met His Ser His Gly Gln Val Ala Ser Thr Thr Lys
            500                 505                 510

Leu Val Gly Thr Val Gly Tyr Met Ala Pro Glu Val Phe Lys Thr Gly
        515                 520                 525

Arg Ala Ser Thr Gln Thr Asp Val Tyr Met Phe Gly Ile Leu Ile Leu
    530                 535                 540

Glu Val Leu Cys Gly Arg Arg Pro Leu Glu Glu Gly Lys Pro Pro Leu
545                 550                 555                 560

Val Glu Trp Ile Trp Gln Leu Met Val Gln Gly Gln Val Glu Cys Ala
                565                 570                 575

Leu Asp Glu Arg Leu Arg Ala Lys Gly Glu Phe Asn Val Gln Glu Met
            580                 585                 590

Glu Arg Val Met His Leu Gly Leu Leu Cys Ala Tyr Pro Glu Pro Lys
        595                 600                 605

Thr Arg Pro Thr Met Arg Gln Val Val Asn Val Leu Glu Gly Lys Asn
    610                 615                 620

Glu Val Glu Asp Ser Glu Ile Glu Asn Met Asp Thr Tyr Leu Leu Gln
625                 630                 635                 640

Gln Leu Lys Ser Arg Asp Ile Leu Ser Glu Tyr Ser Gln Tyr Phe Ser
                645                 650                 655

Tyr Thr Ser His Pro Thr Phe Gln Asp Ile Arg Leu Ser Ser Ser Met
            660                 665                 670

Ser Leu Thr Trp Ser Glu Ser Val Val Glu Gly Arg
        675                 680

<210> SEQ ID NO 65
<211> LENGTH: 821
<212> TYPE: PRT
<213> ORGANISM: Glycine max

<400> SEQUENCE: 65

Met Glu Leu Leu Lys Pro Leu His Pro His Ala Pro Ile Leu Arg
1               5                   10                  15

Ile Pro Phe His Ala Val Pro Ser Ser Ser Ser Gln Ser Gln Ser
            20                  25                  30

Gln Val Pro Leu Pro Met Ile Ser Lys Val His Val Ala Val Gly Lys

```
                35                  40                  45
Ser Leu Asp Lys Val Val Pro Leu Leu Arg Trp Thr Leu Asn His Phe
 50                  55                  60

Arg Asn Ala Glu Ile Val Ile Val His Ala Tyr Gln Pro Ser Leu Thr
 65                  70                  75                  80

Ile Pro Thr Leu Leu Gly Lys Leu Pro Ala Ser Gln Ala Ser Pro Ala
                 85                  90                  95

Val Val Ser Ala Phe Arg Lys Val Glu Arg Glu Gln Ile Met Lys Leu
                100                 105                 110

Leu Asp Lys Tyr Leu Ser Ile Cys Arg Ala Ala Arg Val Lys Ala Ala
                115                 120                 125

Ile Ile Val Thr Glu Ala Asp Gln Val Gln Lys Gly Ile Val Asp Leu
                130                 135                 140

Val Ile Lys His Asn Ile Glu Lys Leu Val Ile Gly Ala Val Pro Glu
145                 150                 155                 160

Asn Cys Met Lys Val Lys Arg Asn Ser Ser Lys Ala Asn Tyr Thr Ala
                165                 170                 175

Lys Asn Ala Pro Pro Phe Cys Glu Val Trp Phe Ile Tyr Lys Gly Lys
                180                 185                 190

His Ile Trp Thr Arg Glu Ala Ser Glu Thr Pro Cys Ser Ser Ser Ser
                195                 200                 205

Cys Thr Gln Pro Glu Ile Ala Thr Thr Glu Ser Leu Arg Cys Arg Ser
210                 215                 220

Phe Gln Tyr Gly Lys Asn Glu Leu Phe Asp Ser Glu Tyr Leu Trp Pro
225                 230                 235                 240

Asn Ser Ala Arg Thr Thr Ala Val Ser Gly Ile Arg Ser Trp Val Gln
                245                 250                 255

Gly Glu Ile Ile Glu Thr Glu Ala Thr Phe Ser Ser Lys Ala Ser Ser
                260                 265                 270

Cys Cys Ser His Cys Ser Pro Gln Asn Ser Ser Arg Ala Tyr Phe Asp
                275                 280                 285

Thr Tyr Leu Glu Val Met Glu Glu Arg Ile Asn Lys Gln Leu Ile Glu
                290                 295                 300

Thr Lys Arg Glu Ala Glu Ala Val Thr Asp Glu Ala Phe Thr Glu Leu
305                 310                 315                 320

Leu Lys Cys Glu Lys Leu Glu Val Glu Ala Met Glu Ala Ile Arg Lys
                325                 330                 335

Val Asn Leu Phe Glu Ser Ala His Val Arg Glu Val Lys Leu Arg Lys
                340                 345                 350

Glu Ala Asp Asp Ala Leu Arg Asp Thr Val Gln Glu Gln Gln Lys Leu
                355                 360                 365

Leu Asn Glu Ser Glu Glu Ile Ala Gly Glu Leu Gln Met Thr Met Arg
                370                 375                 380

Asn Ile Ala Leu Leu Asp Ser Arg Ala Gln Glu Ala Asn Arg Arg Arg
385                 390                 395                 400

Asp Glu Ala Ala Asp Glu Leu Ser Leu Ile Gln Glu Ser Ile Ser Thr
                405                 410                 415

Leu Trp Gln Glu Arg Gln Gln Ile Arg Arg Gln Lys Thr Glu Ala Leu
                420                 425                 430

Arg Trp Leu Glu Arg Trp Arg Ser Arg Gly Gln Val Gly Ala Ala His
                435                 440                 445

Cys Asn Gly Val Ile Gly Phe Ala Glu Glu Leu Pro Glu Leu Ala Glu
                450                 455                 460
```

```
Phe Ser Leu Ser Asp Leu Gln Asn Ala Thr Cys Asn Phe Ser Asn Ser
465                 470                 475                 480

Phe Lys Ile Glu Gln Gly Gly Tyr Ser Cys Ile Tyr Lys Gly Glu Met
            485                 490                 495

Leu Gly Arg Thr Val Ala Ile Lys Lys Phe His Gln His Asn Met Gln
        500                 505                 510

Gly Pro Leu Glu Phe Arg Gln Glu Val Gln Val Leu Gly Ser Leu Gln
    515                 520                 525

His Pro His Leu Ile Thr Leu Leu Gly Val Cys Pro Glu Ala Trp Ser
530                 535                 540

Ile Val Tyr Glu Tyr Leu Pro Asn Gly Thr Leu Gln Asp Tyr Leu Phe
545                 550                 555                 560

Arg Lys Ser Asn Asn Ser Pro Leu Thr Trp Asn Thr Arg Ala Arg Met
                565                 570                 575

Ile Ala Glu Ile Ala Ser Ala Leu Cys Phe Leu His Ser Phe Lys Pro
            580                 585                 590

Glu Thr Ile Ile His Gly Asp Leu Lys Pro Glu Thr Val Leu Leu Asp
        595                 600                 605

Ser Ser Leu Gly Cys Lys Met Cys Gly Phe Gly Leu Cys Arg Leu Val
    610                 615                 620

Ser Glu Glu Ser Leu Leu Arg Pro Ser Phe Arg Leu Ser Thr Glu Pro
625                 630                 635                 640

Lys Gly Ala Phe Thr Tyr Thr Asp Pro Glu Phe Gln Arg Thr Gly Ile
                645                 650                 655

Leu Thr Thr Lys Ser Asp Ile Tyr Ser Phe Gly Leu Ile Ile Leu Gln
            660                 665                 670

Leu Leu Thr Gly Arg Thr Pro Val Gly Leu Ala Val Leu Val Arg Asn
        675                 680                 685

Ala Val Ser Cys Gly Lys Leu Ser Ser Ile Leu Asp Ser Ser Ala Gly
    690                 695                 700

Glu Trp Pro Ser Ala Val Ala Met Gln Leu Val Glu Leu Gly Leu Gln
705                 710                 715                 720

Cys Cys Gln Gln Tyr His Arg Asp Arg Pro Glu Leu Thr Pro Thr Leu
                725                 730                 735

Val Arg Glu Leu Glu Gln Leu His Ala Ser Glu Glu Arg Pro Val Pro
            740                 745                 750

Ser Phe Phe Ser Cys Pro Ile Leu Gln Glu Ile Met His Asp Pro Gln
        755                 760                 765

Val Ala Ala Asp Gly Phe Thr Tyr Glu Gly Asp Ala Ile Arg Glu Trp
    770                 775                 780

Leu Glu Asn Gly His Asp Thr Ser Pro Met Thr Asn Leu Lys Leu Ser
785                 790                 795                 800

His Leu Phe Leu Thr Pro Asn Tyr Ala Leu Arg Leu Ala Ile Gln Asp
                805                 810                 815

Trp Leu Cys Lys Ser
            820

<210> SEQ ID NO 66
<211> LENGTH: 1027
<212> TYPE: PRT
<213> ORGANISM: Glycine max

<400> SEQUENCE: 66

Met Glu Thr Ser Leu Asp Tyr Ser Lys Met Leu Phe Leu Leu Leu Leu
```

```
1               5                   10                  15
Gly Ser Thr Ser Leu Ile Phe Leu Ser His Leu Ala Ser Ala Ala Thr
                20                  25                  30
Pro Lys Leu Asn Thr Gln Glu Val Lys Ala Leu Lys Glu Ile Gly Ser
                35                  40                  45
Lys Ile Gly Lys Lys Asp Trp Asn Phe Gly Val Asp Pro Cys Ser Gly
50                              55                  60
Lys Gly Asn Trp Asn Val Pro Asp Ala Arg Lys Ala Phe Val Met Ser
65                  70                  75                  80
Ser Val Ile Cys Asp Cys Ser Phe Asn His Asn Ser Ser Cys His Val
                85                  90                  95
Val Ser Ile Tyr Trp Lys Ala Gln Asn Leu Ser Gly Ser Leu Ser Pro
                100                 105                 110
Glu Phe Ser Lys Leu His Tyr Leu Gln Lys Leu Asp Leu Ser Arg Asn
                115                 120                 125
Ile Ile Thr Gly Ser Ile Pro Pro Gln Trp Gly Thr Met Arg Leu Val
                130                 135                 140
Glu Leu Ser Leu Met Gly Asn Lys Leu Ser Gly Pro Phe Pro Lys Val
145                 150                 155                 160
Leu Thr Asn Ile Thr Thr Leu Arg Asn Leu Ser Ile Glu Gly Asn Gln
                165                 170                 175
Phe Ser Gly His Ile Pro Thr Glu Ile Gly Lys Leu Thr Asn Leu Glu
                180                 185                 190
Lys Leu Val Leu Ser Ser Asn Gly Phe Thr Gly Ala Leu Pro Pro Val
                195                 200                 205
Leu Ser Lys Leu Thr Lys Leu Ile Asp Leu Arg Ile Ser Asp Asn Asn
210                 215                 220
Phe Leu Gly Lys Ile Pro Asp Phe Ile Ser Asn Trp Thr Leu Ile Glu
225                 230                 235                 240
Lys Leu His Met His Gly Cys Ser Leu Glu Gly Pro Ile Pro Ser Ser
                245                 250                 255
Ile Ser Ala Leu Thr Arg Leu Ser Asp Leu Arg Ile Thr Asp Leu Lys
                260                 265                 270
Gly Ser Lys Ser Ser Ala Phe Pro Pro Leu Asn Asn Leu Lys Ser Met
                275                 280                 285
Lys Thr Leu Val Leu Arg Lys Cys Met Ile Lys Gly Glu Ile Pro Glu
                290                 295                 300
Tyr Ile Gly Arg Met Glu Lys Leu Lys Ile Leu Asp Leu Ser Tyr Asn
305                 310                 315                 320
Gly Leu Ser Gly Glu Ile Pro Glu Ser Phe Ala Gln Leu Asp Lys Val
                325                 330                 335
Asp Phe Met Tyr Leu Thr Gly Asn Lys Leu Ser Gly Ile Ile Pro Arg
                340                 345                 350
Trp Val Leu Ala Asn Asn Glu Asn Ile Asp Ile Ser Asp Asn Asn Phe
                355                 360                 365
Ser Trp Asp Ser Ser Ser Pro Thr Glu Cys Gln Arg Gly Ser Val Asn
                370                 375                 380
Leu Val Glu Ser Tyr Ser Ser Val Asn Thr Gln Thr Lys Ile Asn
385                 390                 395                 400
Ser Cys Leu Lys Lys Asn Phe Leu Cys Thr Ala Ser Pro Ser Gln Tyr
                405                 410                 415
Arg Tyr Ser Leu Asn Ile Asn Cys Gly Gly Asn Glu Ala Asn Val Ser
                420                 425                 430
```

```
Gly Asn Ile Tyr Glu Ala Asp Arg Glu Gln Lys Gly Ala Ala Met Leu
        435                 440                 445
Tyr Tyr Thr Ser Gln Asp Trp Ala Leu Ser Ser Thr Gly Asn Phe Met
450                 455                 460
Asp Asn Asp Ile Asp Ser Asp Pro Tyr Ile Val Ala Asn Thr Ser Arg
465                 470                 475                 480
Leu Asn Val Ser Ala Leu Asn Ser Lys Leu Tyr Thr Thr Ala Arg Val
                485                 490                 495
Ser Pro Leu Ala Leu Thr Tyr Tyr Gly Leu Cys Leu Ile Asn Gly Asn
                500                 505                 510
Tyr Thr Val Lys Leu His Phe Ala Glu Ile Ile Phe Ile Asn Asp Arg
            515                 520                 525
Ser Leu Asn Ser Leu Gly Arg Arg Val Phe Asp Val Tyr Ile Gln Gly
            530                 535                 540
Asn Leu Val Leu Lys Asp Phe Asp Ile Arg Arg Glu Ala Gly Gly Thr
545                 550                 555                 560
Gly Lys Ser Ile Glu Lys Thr Phe Asn Ala Ser Val Thr Gln His Thr
                565                 570                 575
Leu Lys Ile His Phe Tyr Trp Ala Gly Lys Gly Thr Thr Gly Ile Pro
                580                 585                 590
Thr Arg Gly Val Tyr Gly Pro Leu Val Ser Ala Ile Ser Val Asn Pro
            595                 600                 605
Asn Phe Lys Pro Pro Ser Gly Glu Gly Lys Arg Thr Tyr Leu Ile Leu
            610                 615                 620
Ala Ile Ile Ile Val Ala Gly Val Leu Val Val Leu Leu Val Leu
625                 630                 635                 640
Val Leu Leu Arg Arg Met Gly Trp Leu Gly Gly Lys Asp Pro Val Tyr
                645                 650                 655
Lys Glu Leu Arg Gly Ile Asp Leu Gln Thr Gly Leu Phe Thr Leu Arg
                660                 665                 670
Gln Ile Lys Ala Ala Thr Lys Asn Phe Asp Ala Leu Asn Lys Ile Gly
            675                 680                 685
Glu Gly Gly Phe Gly Cys Val Tyr Lys Gly Gln Gln Ser Asp Gly Thr
            690                 695                 700
Met Ile Ala Val Lys Gln Leu Ser Ser Lys Ser Lys Gln Gly Asn Arg
705                 710                 715                 720
Glu Phe Val Asn Glu Met Gly Leu Ile Ser Gly Leu Gln His Pro Asn
                725                 730                 735
Leu Val Lys Leu Tyr Gly Cys Cys Val Glu Gly Asn Gln Leu Ile Leu
                740                 745                 750
Ile Tyr Glu Tyr Met Glu Asn Asn Cys Leu Ser Arg Ile Leu Phe Gly
            755                 760                 765
Arg Asp Pro Asn Lys Thr Lys Leu Asp Trp Pro Thr Arg Lys Lys Ile
770                 775                 780
Cys Leu Gly Ile Ala Lys Ala Leu Ala Tyr Leu His Glu Glu Ser Arg
785                 790                 795                 800
Ile Lys Ile Ile His Arg Asp Val Lys Ala Ser Asn Val Leu Leu Asp
                805                 810                 815
Lys Asp Phe Asn Ala Lys Val Ser Asp Phe Gly Leu Ala Lys Leu Ile
                820                 825                 830
Glu Asp Glu Lys Thr His Ile Ser Thr Arg Val Ala Gly Thr Ile Gly
            835                 840                 845
```

```
Tyr Met Ala Pro Glu Tyr Ala Met Arg Gly Tyr Leu Thr Asp Lys Ala
    850                 855                 860

Asp Val Tyr Ser Phe Gly Val Ala Leu Glu Thr Val Ser Gly Lys
865                 870                 875                 880

Ser Asn Thr Asn Phe Arg Pro Asn Glu Asp Phe Val Tyr Leu Leu Asp
                885                 890                 895

Trp Ala Tyr Val Leu Gln Glu Arg Gly Ser Leu Leu Glu Leu Val Asp
                900                 905                 910

Pro Asn Leu Gly Ser Glu Tyr Leu Thr Glu Ala Met Val Val Leu
                915                 920                 925

Asn Val Ala Leu Leu Cys Thr Asn Ala Ser Pro Thr Leu Arg Pro Thr
930                 935                 940

Met Ser Gln Val Val Ser Met Leu Glu Gly Trp Thr Asp Ile Gln Asp
945                 950                 955                 960

Leu Leu Ser Asp Pro Gly Tyr Ser Ala Ile Ser Ser Ser Lys His
                965                 970                 975

Lys Ser Ile Arg Ser His Phe Trp Gln Thr Pro Ser Gly Thr His Ser
                980                 985                 990

Ile Ser Ile Pro Ser Ile Tyr Thr Asp Ser Ser Gly Ser His Val Glu
                995                 1000                1005

Thr Glu Lys Asn Tyr His Pro Val Thr Val Asn Ser Asp Gly Ser
    1010                1015                1020

Asp Lys Ser Asn
    1025

<210> SEQ ID NO 67
<211> LENGTH: 710
<212> TYPE: PRT
<213> ORGANISM: Glycine max

<400> SEQUENCE: 67

Met Ala Val Ser Asn Gly Val Glu Ala Val Leu Glu Phe Leu Arg Lys
1               5                   10                  15

Asn Gly Leu Ser Glu Ala Glu Ser Ala Leu Arg Gln Asp Ile Ile Glu
                20                  25                  30

Asn Asn Asp Leu Gly Asn Phe Asp Tyr Glu Lys Phe Phe Pro Met
            35                  40                  45

Val Pro Pro Pro Pro Val Arg Val Arg Ser Phe Ser Arg Leu Ser
50                  55                  60

Glu Leu Ser Ala Asp Gly Asn Cys Ser Lys Ser Ser Ser Asp Glu Phe
65                  70                  75                  80

Val Ser Ile Gly Ser Pro Thr Ser Arg Val Ser Ser Ser Glu Phe Ile
                85                  90                  95

Asn Pro Tyr Gly Ile Arg Ser Ser Ser Gln Thr Gln Asn Asp Ser Ala
                100                 105                 110

Ser Ser Ser Glu Arg Leu Ser Gln Phe Gly Thr Ala Arg Asp Tyr His
                115                 120                 125

Asp Phe Glu Met Gln Asn Glu Pro Tyr Trp Tyr Asn Glu Lys Asp Asp
                130                 135                 140

Asp Tyr Phe Met Thr Pro Ser Phe Glu Gly Pro Asp Phe Phe Ala Cys
145                 150                 155                 160

Gln Ser Glu Asp Lys Phe Val Met Thr Ala Glu Thr Glu Asn Gln His
                165                 170                 175

Asp Asn Ser Leu Asp Leu Val Tyr Asn Ser Glu Glu Phe Leu Leu Lys
                180                 185                 190
```

-continued

```
Gly Asn Gly Asn Gly Phe Met Asp Lys Ala Cys Leu Tyr Asn His
        195                 200                 205
Ser Ser Val Arg Asp Gly Asn Ala Thr Tyr Ser Lys Glu Tyr Cys His
    210                 215                 220
Val Asp Asn Asn Leu Phe Glu Gly Glu Leu Glu Gly Lys Ala Glu
225                 230                 235                 240
Lys His Thr Val Ala Cys Ser Cys Glu Val Pro Phe Cys Lys Ser Ser
                245                 250                 255
Pro Gly Gly Ser Cys Ser Leu Asp Pro Thr Asn Phe Gly Tyr Pro Asn
            260                 265                 270
Leu Lys Glu Ile His Leu Lys Phe Gly Asp Ile Asn Ser Phe Asp Ser
        275                 280                 285
Thr Ser Glu Leu Thr Val Asn Gln Ser Phe Asp Tyr Tyr Thr Lys Asn
    290                 295                 300
Asp Ser Ser Lys Glu Tyr Asn Gly Pro Tyr Asp Leu Thr Ile Lys Val
305                 310                 315                 320
Asn Gln Lys Asp Leu Pro Asn Gly Leu Asp Thr Tyr Lys Ala Arg Asp
                325                 330                 335
Gly Gly Glu Leu Ala Glu Glu Cys Gln Asp Pro Glu Ile Thr Ala Asp
            340                 345                 350
Gly Glu Asp Thr Thr Asp Asp Glu Leu Leu Lys Tyr Thr Gln Glu Glu
        355                 360                 365
Glu Tyr Glu Val Phe Asp Leu Arg Ile Ile His Arg Lys Asn Arg Thr
    370                 375                 380
Gly Phe Glu Glu Asn Lys Glu Leu Pro Ile Val Leu Asn Thr Val Leu
385                 390                 395                 400
Ala Gly Arg Tyr Tyr Val Thr Glu Tyr Leu Gly Ser Ala Ala Phe Ser
                405                 410                 415
Arg Val Val Gln Ala His Asp Leu Gln Thr Gly Ile Asp Val Cys Leu
            420                 425                 430
Lys Ile Ile Lys Asn Asp Lys Asp Phe Phe Asp Gln Ser Leu Asp Glu
        435                 440                 445
Ile Lys Leu Leu Lys Leu Val Asn Lys His Asp Pro Ala Asp Leu His
    450                 455                 460
His Phe Leu Arg Leu Tyr Asp Tyr Phe Tyr His Gln Glu His Leu Phe
465                 470                 475                 480
Ile Val Thr Glu Leu Leu Gln Ala Asn Leu Tyr Glu Phe Gln Lys Phe
                485                 490                 495
Lys Gln Glu Ser Gly Gly Glu Tyr Phe Thr Leu Asn Arg Leu Gln
            500                 505                 510
Leu Ile Thr Arg Gln Cys Leu Glu Ala Leu Gln Tyr Leu His Ser Leu
        515                 520                 525
Gly Ile Val His Cys Asp Leu Lys Pro Glu Asn Ile Leu Ile Lys Ser
    530                 535                 540
Tyr Arg Arg Cys Glu Ile Lys Val Ile Asp Leu Gly Ser Ser Cys Phe
545                 550                 555                 560
Gln Thr Asp Asn Leu Cys Leu Tyr Val Gln Ser Arg Ser Tyr Arg Ala
                565                 570                 575
Pro Glu Val Met Leu Gly Leu Gln Tyr Asp Glu Lys Ile Asp Ile Trp
            580                 585                 590
Ser Leu Gly Cys Ile Leu Ala Glu Leu Cys Ser Gly Glu Val Leu Phe
        595                 600                 605
```

```
Pro Asn Asp Ala Val Val Met Ile Leu Ala Arg Met Ile Gly Met Phe
    610                 615                 620
Gly Ser Ile Asp Met Glu Met Leu Val Lys Gly Gln Glu Thr His Lys
625                 630                 635                 640
Tyr Phe Thr Lys Glu Tyr Asp Ile Tyr Tyr Val Asn Glu Glu Thr Asp
                645                 650                 655
Gln Leu Glu Tyr Ile Ile Pro Glu Glu Ser Leu Glu Gln His Leu
            660                 665                 670
Gln Val Thr Asp Thr Thr Phe Ile Asp Phe Val Arg Tyr Leu Leu Ser
        675                 680                 685
Ile Asn Pro Lys Arg Arg Pro Thr Ala Arg Gln Ala Leu Arg His Pro
690                 695                 700
Trp Leu Ser Tyr Val Tyr
705                 710

<210> SEQ ID NO 68
<211> LENGTH: 861
<212> TYPE: PRT
<213> ORGANISM: Glycine max

<400> SEQUENCE: 68

Met Gly Met Gly Gly Ile Ala Val Ser Val Val Thr Val Leu Leu Leu
1               5                   10                  15
Met Ile Gly Leu Thr Met Gly Met Ser Leu Ser Ser Arg Thr Glu Trp
            20                  25                  30
Phe Ala Leu Arg Glu Leu Arg Gln Ser Leu Glu Ile Arg Ala Lys Tyr
        35                  40                  45
Trp Pro Ile Lys Ala Glu Pro Cys Gly Asn Trp Thr Gly Val Gln Cys
    50                  55                  60
Arg Asn Gly Arg Val Val Gly Ile Asn Val Ser Gly Leu Arg Arg Thr
65                  70                  75                  80
Arg Trp Gly Arg Leu Asn Pro Ser Phe Glu Val Asp Ser Leu Val Asn
                85                  90                  95
Phe Thr Leu Leu Glu Thr Phe Asn Ala Ser Gly Phe Lys Leu Asn Gly
            100                 105                 110
Ser Ile Pro Glu Trp Leu Gly Glu Arg Leu Gly Val Leu Glu Glu Leu
        115                 120                 125
Asp Leu Ser Leu Cys Ser Ile Lys Gly Ser Ile Pro Asp Ser Ile Gly
    130                 135                 140
Arg Leu Ser Lys Leu Lys Val Leu Leu Leu Ser Gly Asn Phe Leu Thr
145                 150                 155                 160
Gly Arg Met Pro Ser Thr Leu Gly Asn Leu Thr Arg Leu Ser Val Leu
                165                 170                 175
Asp Leu Ser Gly Asn Ser Leu Ser Trp Pro Val Pro Asp Ser Val Ser
            180                 185                 190
Lys Leu Gly Asn Leu Ser Arg Leu Asp Leu Ser Tyr Asn Phe Leu Ser
        195                 200                 205
Gly Ser Val Pro Pro Glu Leu Gly Ala Leu Ser Ser Leu Gln Phe Leu
    210                 215                 220
Asn Leu Ser Gly Asn Ser Phe Thr Gly Ser Val Pro Ser Gln Leu Gly
225                 230                 235                 240
Asn Leu Ser Lys Leu Val Glu Val Asp Leu Ser Met Asn Phe Leu Ser
                245                 250                 255
Arg Ser Leu Ser Gly Gly Leu Phe Ser Ser Val Val Leu Ala Leu Glu
            260                 265                 270
```

```
Val Leu Ile Leu Arg Gly Asn Leu Leu Asp Gly Val Leu Pro Ala Asn
            275                 280                 285

Leu Arg Ser Met Pro Arg Leu His Phe Leu Asp Val Ser Ser Asn Asn
290                 295                 300

Leu Thr Gly Thr Leu Pro Asn Phe Ala Asp Trp Asn Val Ser Ser Ala
305                 310                 315                 320

Gly Val Val Phe Asn Leu Ser Asn Asn Met Phe Tyr Gly Leu Leu Asn
                325                 330                 335

Thr Ser Leu Asp Arg Phe Lys Met Ile Asp Leu Ser Ser Asn Phe Leu
                340                 345                 350

Glu Gly Glu Val Leu Gly Gly Gly Val Ser Asn Val Asp Leu
                355                 360                 365

Asp Arg Asn Cys Leu Gln Arg Ile Pro Asn Gln Arg Asn Leu Glu Asp
            370                 375                 380

Cys Arg Met Phe Tyr Asp Lys Arg Asn Leu Ser Ser Ala Phe Pro Glu
385                 390                 395                 400

Ser Glu Ser Arg Ser Arg Arg Val Ile Phe Met Leu Val Gly Ile
                405                 410                 415

Phe Gly Gly Leu Gly Phe Ile Val Leu Leu Ala Leu Val Leu Met Leu
                420                 425                 430

Val Leu Lys Gln Cys His Asn Arg Lys Ser Leu Glu Val Pro Arg Glu
            435                 440                 445

Thr Lys Asp Gly Gly Ala Val Glu Glu Gly Glu Ser Pro Ile Pro Pro
            450                 455                 460

Lys Asp Ile Asp Phe Val Thr Gly Val Gly Glu Ala Tyr Ser Phe Glu
465                 470                 475                 480

Gln Met Leu Arg Leu Thr Gly Asn Phe Ala Glu Ser Asn Val Ile Lys
                485                 490                 495

His Gly His Ser Gly Asp Leu Phe Leu Gly Val Leu Glu Gly Gly Ala
                500                 505                 510

Thr Val Val Val Lys Lys Val Asp Leu Asn Leu Phe Lys Arg Glu Ser
            515                 520                 525

Tyr Val Val Glu Leu Gly Leu Leu Ser Lys Val Pro His Ala Arg Leu
            530                 535                 540

Val Pro Ile Leu Gly His Cys Leu Asp Asn Glu Asn Glu Lys Cys Ile
545                 550                 555                 560

Val Tyr Lys Tyr Met Pro Asn Arg Asp Leu Ala Thr Ser Leu His Arg
                565                 570                 575

Val Thr Gly Ser Asp Gly Lys Ile Gln Ser Leu Asp Trp Ile Thr Arg
                580                 585                 590

Leu Lys Ile Ala Ile Gly Ala Ala Glu Gly Ile Ala Tyr Leu His Glu
                595                 600                 605

Cys Ser Pro Pro Leu Val His Arg Asp Ile Gln Ala Ser Ser Ile Leu
610                 615                 620

Leu Asp Asp Lys Phe Glu Val Arg Leu Gly Ser Leu Ser Glu Val Thr
625                 630                 635                 640

Ala Gln Gly Asp Leu Gln Gln Gly Val Ile Ser Arg Val Phe Ser Lys
                645                 650                 655

Pro Pro Ser Ser Asn Gln Ala Asp Ser Gly Lys Ser Pro Val Thr Cys
                660                 665                 670

Thr Tyr Asp Val Tyr Cys Phe Gly Lys Ile Leu Leu Glu Leu Ile Thr
                675                 680                 685
```

```
Gly Asn Ile Glu Val Ser Lys Ser Asp Asp Ala Thr Thr Lys Glu Trp
    690                 695                 700

Leu Glu Gln Thr Leu Pro Tyr Ile Thr Ile Tyr Asp Lys Glu Arg Val
705                 710                 715                 720

Thr Lys Ile Ile Asp Pro Ser Leu Ile Val Asp Glu Asp Leu Leu Glu
                725                 730                 735

Glu Val Trp Ala Met Ala Ile Val Ala Asn Ala Cys Leu Lys Pro Lys
                740                 745                 750

Pro Ser Lys Arg Pro Pro Met Arg His Val Leu Lys Ala Leu Glu Asn
            755                 760                 765

Pro Leu Lys Ile Val Arg Glu Glu Asn Thr Ser Ser Ala Arg Leu Arg
770                 775                 780

Thr Asn Ser Ser Arg Lys Ser Trp Ser Thr Ala Phe Phe Gly Ser Trp
785                 790                 795                 800

Arg His Ser Ser Ser Asp Ser Val Val Ala Thr Asn Lys Glu Gly Ser
                805                 810                 815

Asn Asp Thr Lys Lys Ser Gly Lys Val Gly Ser Gln Ser Gly Asn
                820                 825                 830

Asp His Ser Ser Asn Lys Arg Ser Ser Asn Glu Ile Phe Pro Glu
                835                 840                 845

Pro Leu Glu Ile Gln Asp Val Glu Thr Gly Val Thr Arg
850                 855                 860

<210> SEQ ID NO 69
<211> LENGTH: 655
<212> TYPE: PRT
<213> ORGANISM: Glycine max

<400> SEQUENCE: 69

Met Thr Glu Val Thr Leu Asn Ser Ser Val Asn Ile Leu Tyr His Thr
1               5                   10                  15

Ala Lys Lys Ile Ser Met Lys Phe Tyr Ser Leu Gln Ala His Arg Phe
                20                  25                  30

Leu Phe Ile Ile Val Ile Leu Cys Pro Leu Val Ile Ala Asp Leu Ser
            35                  40                  45

Ser Asp Lys Gln Ala Leu Leu Asp Phe Ala Ala Ala Val Pro His Arg
    50                  55                  60

Arg Asn Leu Lys Trp Asn Pro Ala Thr Pro Ile Cys Ser Ser Trp Val
65                  70                  75                  80

Gly Ile Thr Cys Asn Leu Asn Asp Thr Arg Val Val Ser Val Arg Leu
                85                  90                  95

Pro Gly Ile Gly Leu Val Gly Thr Ile Pro Ala Asn Asp Thr Arg Ile
            100                 105                 110

Asp Ser Leu Arg Asn Ile Ser Leu Arg Ala Asn Leu Ser Gly Ser
        115                 120                 125

Leu Pro Ala Asp Ile Thr Ser Leu Pro Ser Leu Gln Tyr Leu Tyr Leu
130                 135                 140

Gln His Asn Asn Leu Ser Gly Asn Ile Pro Thr Ser Leu Ser Thr Arg
145                 150                 155                 160

Leu Asn Val Leu Asp Leu Ser Tyr Asn Ser Phe Thr Gly Ala Ile Pro
                165                 170                 175

Lys Thr Leu Gln Asn Leu Thr Gln Leu Ile Lys Leu Asn Leu Gln Asn
                180                 185                 190

Asn Ser Leu Ser Gly Leu Ile Pro Asn Leu Asn Val Thr Lys Leu Arg
            195                 200                 205
```

```
Arg Leu Asn Leu Ser Tyr Asn His Leu Asn Gly Ser Ile Pro Ala Ala
    210                 215                 220

Leu Gln Ile Phe Pro Asn Ser Ser Phe Glu Gly Asn Ser Leu Cys Gly
225                 230                 235                 240

Leu Pro Leu Lys Ser Cys Pro Val Val Pro Ser Thr Pro Pro Ser
                245                 250                 255

Ser Thr Pro Ala Pro Pro Ser Thr Pro Ala Arg His Ser Ser Lys Ser
            260                 265                 270

Lys Leu Ser Lys Ala Ala Ile Ile Ala Ile Ala Val Gly Gly Gly Val
        275                 280                 285

Leu Leu Leu Leu Val Ala Leu Ile Ile Val Leu Cys Cys Phe Lys Lys
    290                 295                 300

Lys Asp Asp Gly Ser Pro Arg Ala Thr Lys Gly Lys Gly Pro Ser Gly
305                 310                 315                 320

Gly Arg Ser Glu Lys Pro Lys Glu Glu Phe Gly Ser Gly Val Gln Glu
                325                 330                 335

Pro Glu Lys Asn Lys Leu Val Phe Phe Glu Gly Ser Ser Tyr Asn Phe
            340                 345                 350

Asp Leu Glu Asp Leu Leu Arg Ala Ser Ala Glu Val Leu Gly Lys Gly
                355                 360                 365

Ser Tyr Gly Thr Ala Tyr Lys Ala Ile Leu Glu Glu Ser Thr Thr Val
    370                 375                 380

Val Val Lys Arg Leu Lys Glu Ala Val Val Gly Lys Arg Glu Phe Glu
385                 390                 395                 400

Gln Gln Met Glu Ile Val Gly Arg Val Gly His His Pro Asn Val Val
                405                 410                 415

Pro Leu Arg Ala Tyr Tyr Tyr Ser Lys Asp Glu Lys Leu Leu Val Tyr
            420                 425                 430

Asp Tyr Ile Pro Ser Gly Asn Leu Ser Thr Leu Leu His Gly Asn Arg
        435                 440                 445

Ala Ser Gly Arg Thr Pro Leu Asp Trp Asn Ser Arg Ile Lys Ile Ser
    450                 455                 460

Val Gly Ile Ala Arg Gly Ile Ala His Ile His Ser Val Gly Gly Pro
465                 470                 475                 480

Lys Phe Ala His Gly Asn Val Lys Ser Ser Asn Val Leu Leu Asn Gln
                485                 490                 495

Asp Asn Asp Gly Cys Ile Ser Asp Phe Gly Leu Thr Pro Leu Met Asn
            500                 505                 510

Val Pro Ser Thr Pro Ser Arg Ala Ala Gly Tyr Arg Ala Pro Glu Val
        515                 520                 525

Ile Glu Thr Arg Lys His Thr His Lys Ser Asp Val Tyr Ser Phe Gly
    530                 535                 540

Val Leu Leu Leu Glu Met Leu Thr Gly Lys Ala Pro Gln Gln Ser Pro
545                 550                 555                 560

Gly Arg Asp Asp Met Val Asp Leu Pro Arg Trp Val Gln Ser Val Val
                565                 570                 575

Arg Glu Glu Trp Thr Ala Glu Val Phe Asp Val Glu Leu Met Arg Tyr
            580                 585                 590

Gln Asn Ile Glu Glu Glu Met Val Gln Met Leu Gln Ile Ala Met Ala
        595                 600                 605

Cys Val Ala Lys Val Pro Asp Met Arg Pro Ser Met Glu Glu Val Val
    610                 615                 620
```

```
Arg Met Ile Glu Glu Ile Arg Leu Ser Asp Ser Glu Asn Arg Pro Ser
625                 630                 635                 640

Ser Glu Glu Asn Arg Ser Lys Glu Glu Ser Thr Ala Gln Thr Pro
            645                 650                 655

<210> SEQ ID NO 70
<211> LENGTH: 941
<212> TYPE: PRT
<213> ORGANISM: Glycine max

<400> SEQUENCE: 70

Met Lys Ala Leu Ala Leu Leu Ala Ile Ile Val Phe Thr Leu Leu Val
1               5                   10                  15

Arg Ser Gln Glu Glu Asp Tyr Asp Asp Ala Ser Val Met Leu Ala
            20                  25                  30

Leu Lys Asn Ser Leu Asn Pro Pro Gly Trp Ser Asp Pro Asp Pro Cys
                35                  40                  45

Lys Trp Ala Arg Val Leu Cys Ser Asp Asp Lys Arg Val Thr Arg Ile
    50                  55                  60

Gln Ile Gly Arg Leu Asn Leu Gln Gly Thr Leu Pro Thr Thr Leu Gln
65                  70                  75                  80

Lys Leu Thr His Leu Glu His Leu Glu Leu Gln Tyr Asn Asn Ile Ser
                85                  90                  95

Gly Pro Leu Pro Ser Leu Asn Gly Leu Thr Ser Leu Arg Val Phe Leu
            100                 105                 110

Ala Ser Asn Asn Arg Phe Ser Ala Val Pro Ala Asp Phe Phe Ala Gly
                115                 120                 125

Met Ser Gln Leu Gln Ala Val Glu Ile Asp Ser Asn Pro Phe Glu Pro
130                 135                 140

Trp Glu Ile Pro Gln Ser Leu Arg Asn Ala Ser Gly Leu Gln Asn Phe
145                 150                 155                 160

Ser Ala Asn Ser Ala Asn Val Gly Gly Ser Ile Pro Glu Phe Phe Gly
                165                 170                 175

Ser Asp Val Phe Pro Gly Leu Thr Leu Leu His Leu Ala Met Asn Asn
            180                 185                 190

Leu Glu Gly Thr Leu Pro Leu Ser Phe Ser Gly Ser Gln Ile Gln Ser
        195                 200                 205

Leu Trp Leu Asn Gly Gln Lys Ser Val Asn Lys Leu Gly Gly Ser Val
210                 215                 220

Glu Val Leu Gln Asn Met Thr Phe Leu Thr Asp Val Trp Leu Gln Ser
225                 230                 235                 240

Asn Ala Phe Thr Gly Pro Leu Pro Asp Leu Ser Gly Leu Lys Ser Leu
                245                 250                 255

Arg Asp Leu Ser Leu Arg Asp Asn Arg Phe Thr Gly Pro Val Pro Val
            260                 265                 270

Ala Ser Phe Val Gly Leu Lys Thr Leu Lys Val Val Asn Leu Thr Asn
                275                 280                 285

Asn Leu Phe Gln Gly Pro Met Pro Val Phe Gly Asp Gly Val Val Val
            290                 295                 300

Asp Asn Val Lys Asp Ser Asn Ser Phe Cys Leu Pro Ser Pro Gly Asp
305                 310                 315                 320

Cys Asp Pro Arg Val Asp Val Leu Leu Ser Val Val Gly Val Met Gly
                325                 330                 335

Tyr Pro Pro Arg Phe Ala Glu Ser Trp Lys Gly Asn Asp Pro Cys Ala
            340                 345                 350
```

```
Tyr Trp Ile Gly Ile Thr Cys Ser Asn Gly Tyr Ile Thr Val Val Asn
            355                 360                 365

Phe Gln Lys Met Glu Leu Ser Gly Val Ile Ser Pro Glu Phe Ala Lys
            370                 375                 380

Leu Lys Ser Leu Gln Arg Ile Val Leu Ala Asp Asn Asn Leu Thr Gly
385                 390                 395                 400

Ser Ile Pro Glu Glu Leu Ala Thr Leu Pro Ala Leu Thr Gln Leu Asn
                405                 410                 415

Val Ala Asn Asn Gln Leu Tyr Gly Lys Val Pro Ser Phe Arg Lys Asn
            420                 425                 430

Val Val Val Ser Thr Asn Gly Asn Thr Asp Ile Gly Lys Asp Lys Ser
            435                 440                 445

Ser Leu Ser Pro Gln Gly Leu Val Pro Pro Met Ala Pro Asn Ala Lys
            450                 455                 460

Gly Asp Ser Gly Gly Val Ser Gly Ile Gly Gly Lys Lys Ser Ser Ser
465                 470                 475                 480

His Val Gly Val Ile Val Phe Ser Val Ile Gly Ala Val Phe Val Val
                485                 490                 495

Ser Met Ile Gly Phe Leu Val Phe Cys Leu Phe Arg Met Lys Gln Lys
            500                 505                 510

Lys Leu Ser Arg Val Gln Ser Pro Asn Ala Leu Val Ile His Pro Arg
            515                 520                 525

His Ser Gly Ser Asp Asn Glu Ser Val Lys Ile Thr Val Ala Gly Ser
            530                 535                 540

Ser Val Ser Val Gly Ala Ala Ser Glu Thr Arg Thr Val Pro Gly Ser
545                 550                 555                 560

Glu Ala Ser Asp Ile Gln Met Val Glu Ala Gly Asn Met Val Ile Ser
                565                 570                 575

Ile Gln Val Leu Lys Asn Val Thr Asp Asn Phe Ser Glu Lys Asn Val
            580                 585                 590

Leu Gly Gln Gly Gly Phe Gly Thr Val Tyr Arg Gly Glu Leu His Asp
            595                 600                 605

Gly Thr Arg Ile Ala Val Lys Arg Met Glu Cys Gly Ala Ile Ala Gly
            610                 615                 620

Lys Gly Ala Ala Glu Phe Lys Ser Glu Ile Ala Val Leu Thr Lys Val
625                 630                 635                 640

Arg His Arg His Leu Val Ser Leu Leu Gly Tyr Cys Leu Asp Gly Asn
                645                 650                 655

Glu Lys Leu Leu Val Tyr Glu Tyr Met Pro Gln Gly Thr Leu Ser Arg
            660                 665                 670

His Leu Phe Asp Trp Pro Glu Glu Gly Leu Glu Pro Leu Glu Trp Asn
            675                 680                 685

Arg Arg Leu Thr Ile Ala Leu Asp Val Ala Arg Gly Val Glu Tyr Leu
690                 695                 700

His Gly Leu Ala His Gln Ser Phe Ile His Arg Asp Leu Lys Pro Ser
705                 710                 715                 720

Asn Ile Leu Leu Gly Asp Asp Met Arg Ala Lys Val Ala Asp Phe Gly
                725                 730                 735

Leu Val Arg Leu Ala Pro Glu Gly Lys Ala Ser Ile Glu Thr Arg Ile
            740                 745                 750

Ala Gly Thr Phe Gly Tyr Leu Ala Pro Glu Tyr Ala Val Thr Gly Arg
            755                 760                 765
```

```
Val Thr Thr Lys Val Asp Val Phe Ser Phe Gly Val Ile Leu Met Glu
770                 775                 780

Leu Ile Thr Gly Arg Lys Ala Leu Asp Glu Thr Gln Pro Glu Asp Ser
785                 790                 795                 800

Met His Leu Val Thr Trp Phe Arg Arg Met Ser Ile Asn Lys Asp Ser
                805                 810                 815

Phe Arg Lys Ala Ile Asp Ser Thr Ile Glu Leu Asn Glu Glu Thr Leu
            820                 825                 830

Ala Ser Ile His Thr Val Ala Glu Leu Ala Gly His Cys Gly Ala Arg
        835                 840                 845

Glu Pro Tyr Gln Arg Pro Asp Met Gly His Ala Val Asn Val Leu Ser
850                 855                 860

Ser Leu Val Glu Leu Trp Lys Pro Ser Asp Gln Asn Ser Glu Asp Ile
865                 870                 875                 880

Tyr Gly Ile Asp Leu Asp Met Ser Leu Pro Gln Ala Leu Lys Lys Trp
                885                 890                 895

Gln Ala Tyr Glu Gly Arg Ser Gln Met Glu Ser Ser Ala Ser Ser Ser
            900                 905                 910

Leu Leu Pro Ser Leu Asp Asn Thr Gln Thr Ser Ile Pro Thr Arg Pro
        915                 920                 925

Tyr Gly Phe Ala Asp Ser Phe Thr Ser Ala Asp Gly Arg
930                 935                 940

<210> SEQ ID NO 71
<211> LENGTH: 337
<212> TYPE: PRT
<213> ORGANISM: Glycine max

<400> SEQUENCE: 71

Met Glu Lys Thr Gly Val Leu Ser Ala Lys Glu Ala Phe Glu Lys Leu
1               5                   10                  15

Glu Lys Val Gly Glu Gly Thr Tyr Gly Lys Val Tyr Arg Ala Arg Glu
            20                  25                  30

Lys Ala Thr Gly Lys Ile Val Ala Leu Lys Lys Thr Arg Leu His Glu
        35                  40                  45

Asp Glu Glu Gly Val Pro Pro Thr Leu Arg Glu Val Ser Ile Leu
50                  55                  60

Arg Met Leu Ser Arg Asp Pro His Val Val Arg Leu Met Asp Val Lys
65                  70                  75                  80

Gln Gly Gln Asn Lys Glu Gly Lys Thr Val Leu Tyr Leu Val Phe Glu
            85                  90                  95

Tyr Met Asp Thr Asp Leu Lys Lys Phe Ile Arg Ser Phe Arg Gln Ser
            100                 105                 110

Gly Glu Thr Ile Pro Pro His Ile Ile Lys Val Ile Leu Ser Ile Cys
        115                 120                 125

Pro Ser Ile Phe Asn Ile Arg Phe Phe Val His Leu Phe Leu Ser
130                 135                 140

Ile Trp Leu Gln Ser Leu Met Tyr Gln Leu Cys Lys Gly Val Ala Phe
145                 150                 155                 160

Cys His Gly His Gly Ile Leu His Arg Asp Leu Lys Pro His Asn Leu
                165                 170                 175

Leu Met Asp Arg Lys Thr Met Met Leu Lys Ile Ala Asp Leu Gly Leu
            180                 185                 190

Ala Arg Ala Phe Thr Val Pro Ile Lys Lys Tyr Thr His Glu Ile Leu
        195                 200                 205
```

```
Thr Leu Trp Tyr Arg Ala Pro Glu Val Leu Leu Gly Ala Thr His Tyr
    210                 215                 220

Ser Met Ala Val Asp Met Trp Ser Val Gly Cys Ile Phe Ala Glu Leu
225                 230                 235                 240

Val Thr Lys Gln Ala Leu Phe Pro Gly Asp Ser Glu Leu Gln Gln Leu
                245                 250                 255

Leu His Ile Phe Arg Leu Leu Gly Thr Pro Asn Glu Asp Val Trp Pro
                260                 265                 270

Gly Val Ser Lys Leu Met Asn Trp His Glu Tyr Pro Gln Trp Asn Pro
                275                 280                 285

Gln Ser Leu Ser Thr Ala Val Pro Ser Leu Asp Glu Leu Gly Leu Asp
    290                 295                 300

Leu Leu Ser Gln Met Leu Lys Tyr Glu Pro Ser Lys Arg Ile Ser Ala
305                 310                 315                 320

Lys Lys Ala Met Glu His Val Tyr Phe Asp Asp Leu Asp Lys Arg His
                325                 330                 335

Leu

<210> SEQ ID NO 72
<211> LENGTH: 710
<212> TYPE: PRT
<213> ORGANISM: Glycine max

<400> SEQUENCE: 72

Met Ala Arg Ala Arg Phe Pro Leu Ser Ile Leu Leu Ser Leu Val Phe
1               5                   10                  15

Val Ala Leu Pro Leu Ser Leu Ala Asn Thr Asp Pro Ser Asp Val Gln
                20                  25                  30

Ala Leu Glu Val Met Tyr Asn Ala Leu Asn Ser Pro Thr Gln Leu Thr
            35                  40                  45

Gly Trp Lys Ile Gly Gly Gly Asp Pro Cys Gly Glu Ser Trp Lys Gly
        50                  55                  60

Val Thr Cys Glu Gly Ser Ala Val Val Ser Ile Lys Leu Ser Gly Leu
65                  70                  75                  80

Gly Leu Asp Gly Thr Leu Gly Tyr Leu Leu Ser Asp Leu Met Ser Leu
                85                  90                  95

Arg Glu Leu Asp Leu Ser Asp Asn Lys Ile His Asp Thr Ile Pro Tyr
                100                 105                 110

Gln Leu Pro Pro Asn Leu Thr Ser Leu Asn Phe Ala Arg Asn Asn Leu
            115                 120                 125

Ser Gly Asn Leu Pro Tyr Ser Ile Ser Ala Met Val Ser Leu Asn Tyr
        130                 135                 140

Leu Asn Leu Ser Asn Asn Ala Leu Ser Met Thr Val Gly Asp Ile Phe
145                 150                 155                 160

Ala Ser Leu Gln Asp Leu Gly Thr Leu Asp Leu Ser Phe Asn Asn Phe
                165                 170                 175

Ser Gly Asp Leu Pro Pro Ser Phe Val Ala Leu Ala Asn Leu Ser Ser
                180                 185                 190

Leu Phe Leu Gln Lys Asn Gln Leu Thr Gly Ser Leu Gly Val Leu Val
            195                 200                 205

Gly Leu Pro Leu Asp Thr Leu Asn Val Ala Asn Asn Asn Phe Ser Gly
        210                 215                 220

Trp Ile Pro His Glu Leu Ser Ser Ile Arg Asn Phe Ile Tyr Asp Gly
225                 230                 235                 240
```

```
Asn Ser Phe Glu Asn Ser Pro Ala Pro Leu Pro Pro Ala Phe Thr Ser
            245                 250                 255
Pro Pro Pro Asn Gly Pro His Gly Arg His His Ser Gly Ser Gly Ser
            260                 265                 270
His Asn Lys Thr Gln Val Ser Asp Asn Glu Lys Ser Asp Gly His Lys
            275                 280                 285
Gly Leu Thr Val Gly Ala Val Val Gly Ile Val Leu Gly Ser Val Leu
            290                 295                 300
Val Ala Ala Ile Val Leu Leu Ala Leu Val Phe Cys Ile Arg Lys Gln
305                 310                 315                 320
Lys Gly Lys Lys Gly Ala Arg Asn Phe Ser Gly Ser Leu Pro Arg Gly
                325                 330                 335
Val Ile Asn Val Thr Pro Gln Met Gln Glu Gln Arg Val Lys Ser Ala
            340                 345                 350
Ala Val Val Thr Asp Leu Lys Pro Arg Pro Ala Glu Asn Val Thr Val
            355                 360                 365
Glu Arg Val Ala Val Lys Ser Gly Ser Val Lys Gln Met Lys Ser Pro
370                 375                 380
Ile Thr Ser Thr Leu Tyr Thr Val Ala Ser Leu Gln Ser Ala Thr Asn
385                 390                 395                 400
Ser Phe Ser Gln Glu Phe Ile Ile Gly Glu Gly Ser Leu Gly Arg Val
                405                 410                 415
Tyr Lys Ala Asp Phe Pro Asn Gly Lys Val Met Ala Ile Lys Lys Ile
                420                 425                 430
Asp Asn Ser Ala Leu Ser Leu Gln Glu Glu Asp Asn Phe Leu Glu Ala
            435                 440                 445
Val Ser Asn Met Ser Arg Leu Arg His Pro Ser Ile Val Thr Leu Ala
450                 455                 460
Gly Tyr Cys Ala Glu His Gly Gln Arg Leu Leu Val Tyr Glu Tyr Ile
465                 470                 475                 480
Ala Asn Gly Asn Leu His Asp Met Leu His Phe Ala Glu Asp Ser Ser
                485                 490                 495
Lys Ala Leu Ser Trp Asn Ala Arg Val Arg Ile Ala Leu Gly Thr Ala
                500                 505                 510
Arg Ala Leu Glu Tyr Leu His Glu Val Cys Leu Pro Ser Val Val His
            515                 520                 525
Arg Asn Phe Lys Ser Ala Asn Ile Leu Leu Asp Glu Glu Leu Asn Pro
530                 535                 540
His Leu Ser Asp Cys Gly Leu Ala Ala Leu Thr Pro Asn Thr Glu Arg
545                 550                 555                 560
Gln Val Ser Thr Gln Met Val Gly Ser Phe Gly Tyr Ser Ala Pro Glu
                565                 570                 575
Phe Ala Leu Ser Gly Val Tyr Thr Val Lys Ser Asp Val Tyr Ser Phe
                580                 585                 590
Gly Val Val Met Leu Glu Leu Leu Thr Gly Arg Lys Pro Leu Asp Ser
            595                 600                 605
Leu Arg Val Arg Ser Glu Gln Ser Leu Val Arg Trp Ala Thr Pro Gln
610                 615                 620
Leu His Asp Ile Asp Ala Leu Ala Lys Met Val Asp Pro Thr Leu Asn
625                 630                 635                 640
Gly Met Tyr Pro Ala Lys Ser Leu Ser Arg Phe Ala Asp Ile Ile Ala
                645                 650                 655
```

```
Leu Cys Val Gln Pro Glu Pro Glu Phe Arg Pro Pro Met Ser Glu Val
                660                 665                 670

Val Gln Ala Leu Val Arg Leu Val Gln Arg Ala Ser Val Val Lys Arg
        675                 680                 685

Arg Pro Ser Glu Glu Ser Gly Phe Gly His Lys Thr Pro Asp His Glu
    690                 695                 700

Ala Met Asp Met Pro Phe
705             710

<210> SEQ ID NO 73
<211> LENGTH: 960
<212> TYPE: PRT
<213> ORGANISM: Glycine max

<400> SEQUENCE: 73

Met Glu Ile Phe Lys Cys Phe Tyr Ile Lys Asn Leu Ile Leu Val Thr
1               5                   10                  15

Phe Phe Met Val Ser Ser Ala Val Leu Ala Ile Asp Pro Tyr Ser Glu
            20                  25                  30

Ala Leu Leu Ser Leu Lys Ser Glu Leu Val Asp Asp Asn Ser Leu
            35                  40                  45

His Asn Trp Val Val Pro Ser Gly Gly Lys Leu Thr Gly Lys Ser Tyr
    50                  55                  60

Ala Cys Ser Trp Ser Gly Ile Lys Cys Asn Asn Asp Ser Thr Ile Val
65              70                  75                  80

Thr Ser Ile Asp Leu Ser Met Lys Lys Leu Gly Gly Val Val Ser Gly
            85                  90                  95

Lys Gln Phe Ile Ile Phe Thr Asn Leu Thr Ser Leu Asn Leu Ser His
            100                 105                 110

Asn Phe Ser Gly Gln Leu Pro Ala Glu Ile Phe Asn Leu Thr Ser
        115                 120                 125

Leu Thr Ser Leu Asp Ile Ser Arg Asn Asn Phe Ser Gly Pro Phe Pro
    130                 135                 140

Gly Gly Ile Pro Arg Leu Gln Asn Leu Val Val Leu Asp Ala Phe Ser
145                 150                 155                 160

Asn Ser Phe Ser Gly Pro Leu Pro Ala Glu Phe Ser Gln Leu Glu Asn
            165                 170                 175

Leu Lys Val Leu Asn Leu Ala Gly Ser Tyr Phe Arg Gly Ser Ile Pro
            180                 185                 190

Pro Glu Tyr Gly Ser Phe Lys Ser Leu Glu Phe Leu His Leu Ala Gly
        195                 200                 205

Asn Ser Leu Thr Gly Ser Ile Pro Pro Glu Leu Gly His Leu Lys Thr
    210                 215                 220

Val Thr His Met Glu Ile Gly Tyr Asn Glu Tyr Gln Gly Phe Ile Pro
225                 230                 235                 240

Pro Glu Leu Gly Asn Met Ser Gln Leu Gln Tyr Leu Asp Ile Ala Gly
            245                 250                 255

Ala Asn Leu Ser Gly Pro Ile Pro Lys Gln Leu Ser Asn Leu Thr Ser
            260                 265                 270

Leu Gln Ser Ile Phe Leu Phe Arg Asn Gln Leu Thr Gly Ser Ile Pro
        275                 280                 285

Ser Glu Leu Ser Ile Ile Glu Pro Leu Thr Asp Leu Asp Leu Ser Asp
    290                 295                 300

Asn Phe Leu Ile Gly Ser Ile Pro Glu Ser Phe Ser Glu Leu Glu Asn
305                 310                 315                 320
```

```
Leu Arg Leu Leu Ser Val Met Tyr Asn Asp Met Ser Gly Thr Val Pro
            325                 330                 335

Glu Ser Ile Ala Lys Leu Pro Ser Leu Glu Thr Leu Leu Ile Trp Asn
            340                 345                 350

Asn Arg Phe Ser Gly Ser Leu Pro Pro Ser Leu Gly Arg Asn Ser Lys
            355                 360                 365

Leu Lys Trp Val Asp Ala Ser Thr Asn Asp Leu Val Gly Ser Ile Pro
            370                 375                 380

Pro Asp Ile Cys Ala Ser Gly Glu Leu Phe Lys Leu Ile Leu Phe Ser
385                 390                 395                 400

Asn Lys Phe Thr Gly Gly Leu Ser Ile Ser Asn Cys Ser Ser Leu
            405                 410                 415

Val Arg Leu Arg Leu Glu Asp Asn Ser Phe Ser Gly Glu Ile Thr Leu
            420                 425                 430

Lys Phe Ser His Leu Pro Asp Ile Leu Tyr Val Asp Leu Ser Lys Asn
            435                 440                 445

Asn Phe Val Gly Gly Ile Pro Ser Asp Ile Ser Gln Ala Thr Gln Leu
            450                 455                 460

Glu Tyr Phe Asn Val Ser Tyr Asn Pro Gln Leu Gly Gly Ile Ile Pro
465                 470                 475                 480

Ser Gln Thr Trp Ser Leu Pro Gln Leu Gln Asn Phe Ser Ala Ser Ser
            485                 490                 495

Cys Gly Ile Ser Ser Asp Leu Pro Leu Phe Glu Ser Cys Lys Ser Ile
            500                 505                 510

Ser Val Ile Asp Leu Asp Ser Asn Ser Leu Ser Gly Thr Ile Pro Asn
            515                 520                 525

Gly Val Ser Lys Cys Gln Ala Leu Glu Lys Ile Asn Leu Ser Asn Asn
            530                 535                 540

Asn Leu Thr Gly His Ile Pro Asp Glu Leu Ala Ser Ile Pro Val Leu
545                 550                 555                 560

Gly Val Val Asp Leu Ser Asn Asn Lys Phe Asn Gly Pro Ile Pro Ala
            565                 570                 575

Lys Phe Gly Ser Ser Ser Asn Leu Gln Leu Leu Asn Val Ser Phe Asn
            580                 585                 590

Asn Ile Ser Gly Ser Ile Pro Thr Ala Lys Ser Phe Lys Leu Met Gly
            595                 600                 605

Arg Ser Ala Phe Val Gly Asn Ser Glu Leu Cys Gly Ala Pro Leu Gln
            610                 615                 620

Pro Cys Pro Asp Ser Val Gly Ile Leu Gly Ser Lys Gly Thr Trp Lys
625                 630                 635                 640

Val Thr Arg Ile Val Leu Leu Ser Val Gly Leu Leu Ile Val Leu Leu
            645                 650                 655

Gly Leu Val Phe Gly Ile Leu Tyr Leu Arg Arg Gly Ile Lys Ser Gln
            660                 665                 670

Trp Lys Met Ala Ser Phe Ala Gly Leu Pro Gln Phe Thr Ala Asn Asp
            675                 680                 685

Ile Leu Thr Ser Leu Ser Ala Thr Thr Lys Pro Thr Asp Ile Gln Ser
            690                 695                 700

Pro Ser Val Thr Lys Thr Val Leu Pro Thr Gly Ile Thr Val Leu Val
705                 710                 715                 720

Lys Lys Ile Glu Leu Glu Ala Arg Ser Ile Lys Val Val Ser Glu Phe
            725                 730                 735
```

```
Ile Met Arg Leu Gly Asn Ala Arg His Lys Asn Leu Ile Arg Leu Leu
            740                 745                 750

Gly Phe Cys His Asn Gln His Leu Val Tyr Leu Leu Tyr Asp Tyr Leu
        755                 760                 765

Pro Asn Gly Asn Leu Ala Glu Lys Met Glu Met Lys Trp Asp Trp Ala
    770                 775                 780

Ala Lys Phe Arg Thr Val Val Gly Ile Ala Arg Gly Leu Cys Phe Leu
785                 790                 795                 800

His His Glu Cys Tyr Pro Ala Ile Pro His Gly Asp Leu Arg Pro Ser
                805                 810                 815

Asn Ile Val Phe Asp Glu Asn Met Glu Pro His Leu Ala Glu Phe Gly
            820                 825                 830

Phe Lys His Val Ser Arg Trp Ser Lys Gly Ser Ser Pro Thr Thr Thr
        835                 840                 845

Lys Trp Glu Thr Glu Tyr Asn Glu Ala Thr Lys Glu Glu Leu Ser Met
    850                 855                 860

Asp Ile Tyr Lys Phe Gly Glu Met Ile Leu Glu Ile Leu Thr Arg Glu
865                 870                 875                 880

Arg Leu Ala Asn Ser Gly Ala Ser Ile His Ser Lys Pro Trp Glu Val
                885                 890                 895

Leu Leu Arg Glu Ile Tyr Asn Glu Asn Gly Ala Ser Ser Ala Ser Ser
            900                 905                 910

Leu Gln Glu Ile Lys Leu Val Leu Glu Val Ala Met Leu Cys Thr Arg
        915                 920                 925

Ser Arg Ser Ser Asp Arg Pro Ser Met Glu Asp Val Leu Lys Leu Leu
    930                 935                 940

Ser Gly Leu Lys His Leu Glu Asp Gly Arg Thr Ser Lys Glu Gly Gln
945                 950                 955                 960

<210> SEQ ID NO 74
<211> LENGTH: 527
<212> TYPE: PRT
<213> ORGANISM: Glycine max

<400> SEQUENCE: 74

Met Gly Asn Glu Thr Arg Lys Leu Ser Asp Glu Tyr Glu Val Ser Glu
1               5                   10                  15

Val Leu Gly Arg Gly Gly Phe Ser Val Val Arg Lys Gly Thr Lys Lys
            20                  25                  30

Ser Ser Ser Asp Thr Lys Thr His Val Ala Ile Lys Thr Leu Arg Arg
        35                  40                  45

Val Gly Thr Ala Ser Asn Ser Asn Asn Pro Ser Gly Phe Pro Arg Pro
    50                  55                  60

Lys Gly Gly Glu Lys Lys Ser Thr Ala Ala Met Met Gly Phe Pro Thr
65                  70                  75                  80

Trp Arg Gln Val Ser Val Ser Asp Ala Leu Leu Thr Asn Glu Ile Leu
                85                  90                  95

Val Met Arg Arg Ile Val Glu Asn Val Ser Pro His Pro Asn Val Ile
            100                 105                 110

Asp Leu Tyr Asp Val Tyr Glu Asp Ser Asn Gly Val His Leu Val Leu
        115                 120                 125

Glu Leu Cys Ser Gly Gly Glu Leu Phe Asp Arg Ile Val Ala Gln Asp
    130                 135                 140

Arg Tyr Ser Glu Thr Glu Ala Ala Gly Val Val Arg Gln Ile Ala Ser
145                 150                 155                 160
```

Gly Leu Glu Ala Ile His Arg Ala Asn Ile Val His Arg Asp Leu Lys
            165                 170                 175

Pro Glu Asn Cys Leu Phe Leu Asp Val Arg Arg Asp Ser Pro Leu Lys
            180                 185                 190

Ile Met Asp Phe Gly Leu Ser Ser Val Glu Glu Phe Thr Asp Pro Val
            195                 200                 205

Val Gly Leu Phe Gly Ser Ile Asp Tyr Val Ser Pro Glu Ala Leu Ser
210                 215                 220

Gln Gly Lys Ile Thr Thr Lys Ser Asp Met Trp Ser Leu Gly Val Ile
225                 230                 235                 240

Leu Tyr Ile Leu Leu Ser Gly Tyr Pro Pro Phe Ile Ala Gln Asn Asn
            245                 250                 255

Arg Gln Lys Gln Gln Met Ile Met Asn Gly Asn Phe Ser Phe Tyr Glu
            260                 265                 270

Lys Thr Trp Lys Gly Ile Thr Arg Ser Ala Lys Gln Leu Ile Ser Asp
            275                 280                 285

Leu Leu Ile Val Asp Pro Ser Arg Arg Pro Ser Ala Gln Asp Leu Leu
            290                 295                 300

Ser His Pro Trp Val Val Gly Asp Lys Ala Lys Asp Asp Ala Met Asp
305                 310                 315                 320

Pro Glu Ile Val Ser Arg Leu Gln Ser Phe Asn Ala Arg Arg Lys Leu
            325                 330                 335

Arg Ala Val Ala Ile Ala Ser Ile Trp Ser Thr Thr Ile Phe Leu Arg
            340                 345                 350

Thr Lys Lys Leu Lys Ser Leu Val Gly Thr His Asp Leu Thr Glu Glu
            355                 360                 365

Glu Ile Glu Asn Leu Arg Met Ser Phe Lys Lys Ile Cys Val Ser Gly
            370                 375                 380

Asp Asn Ala Thr Leu Ser Glu Phe Glu Glu Val Leu Lys Ala Met Asn
385                 390                 395                 400

Met Pro Ser Leu Ile Pro Leu Ala Pro Arg Ile Phe Asp Leu Phe Asp
            405                 410                 415

Asp Asn Arg Asp Gly Thr Val Asp Met Arg Glu Ile Leu Cys Gly Phe
            420                 425                 430

Ser Ser Phe Lys Asn Ser Lys Gly Asp Asp Ala Leu Arg Leu Cys Phe
            435                 440                 445

Gln Met Tyr Asp Thr Asp Arg Ser Gly Cys Ile Thr Lys Glu Glu Val
            450                 455                 460

Ala Ser Met Leu Arg Ala Leu Pro Glu Asp Cys Leu Pro Thr Asp Ile
465                 470                 475                 480

Thr Glu Pro Gly Lys Leu Asp Glu Ile Phe Asp Leu Met Asp Ala Asn
            485                 490                 495

Ser Asp Gly Lys Val Thr Phe Asp Glu Phe Lys Ala Ala Met Gln Arg
            500                 505                 510

Asp Ser Ser Leu Gln Asp Val Val Leu Ser Ser Leu Arg Pro Gln
            515                 520                 525

<210> SEQ ID NO 75
<211> LENGTH: 614
<212> TYPE: PRT
<213> ORGANISM: Glycine max

<400> SEQUENCE: 75

Met Val Leu His Ser Trp Ile Ser Ser Ser His Ile Leu Val Asn Phe

-continued

```
1               5                   10                  15
Leu Leu Leu Leu Gly Cys Gly Ile Thr Tyr Gly Thr Asp Thr Asp Ile
                20                  25                  30
Phe Cys Leu Lys Ser Ile Lys Glu Ser Leu Glu Asp Pro Tyr Asn Tyr
                35                  40                  45
Leu Lys Phe Ser Trp Asp Phe Asn Asn Lys Thr Glu Gly Tyr Ile Cys
 50                  55                  60
Arg Phe Asn Gly Val Glu Cys Trp His Pro Asp Glu Asn Arg Val Leu
 65                  70                  75                  80
Asn Leu Lys Leu Ser Asn Met Gly Leu Lys Gly Gln Phe Pro Arg Gly
                85                  90                  95
Ile Gln Asn Cys Ser Ser Leu Thr Gly Leu Asp Leu Ser Ile Asn Lys
                100                 105                 110
Leu Ser Gly Thr Ile Pro Gly Asp Ile Ser Thr Leu Ile Pro Phe Ala
                115                 120                 125
Thr Ser Ile Asp Leu Ser Thr Asn Glu Phe Ser Gly Ala Ile Pro Val
                130                 135                 140
Ser Leu Ala Asn Cys Thr Phe Leu Asn Thr Leu Lys Leu Asp Gln Asn
145                 150                 155                 160
Arg Leu Thr Gly Gln Ile Pro Pro Gln Phe Gly Val Leu Ser Arg Ile
                165                 170                 175
Lys Val Phe Ser Val Ser Asn Asn Leu Leu Thr Gly Gln Val Pro Ile
                180                 185                 190
Phe Arg Asp Gly Val Glu Leu His Tyr Ala Asn Asn Gln Gly Leu Cys
                195                 200                 205
Gly Gly Asn Thr Leu Ala Pro Cys Gln Ala Thr Pro Ser Lys Ser Asn
                210                 215                 220
Met Ala Val Ile Ala Gly Ala Ala Ala Gly Val Thr Leu Ala Ala
225                 230                 235                 240
Leu Gly Leu Gly Ile Gly Met Phe Phe Phe Val Arg Arg Val Ser Phe
                245                 250                 255
Lys Lys Lys Glu Glu Asp Pro Glu Gly Asn Lys Trp Ala Arg Ser Leu
                260                 265                 270
Lys Gly Thr Lys Arg Ile Lys Val Ser Met Phe Glu Lys Ser Ile Ser
                275                 280                 285
Lys Met Lys Leu Ser Asp Leu Met Lys Ala Thr Asn Asn Phe Ser Asn
                290                 295                 300
Thr Asn Ile Ile Gly Thr Gly Arg Thr Gly Thr Val Tyr Lys Ala Val
305                 310                 315                 320
Leu Asp Asp Gly Thr Thr Leu Met Val Lys Arg Leu Gln Glu Ser Gln
                325                 330                 335
Tyr Thr Glu Lys Glu Phe Met Ser Glu Met Gly Thr Leu Gly Thr Val
                340                 345                 350
Lys His Arg Asn Leu Val Pro Leu Leu Gly Phe Cys Met Thr Lys Arg
                355                 360                 365
Glu Arg Leu Leu Val Tyr Lys Asn Met Pro Asn Gly Asn Leu His Asp
                370                 375                 380
Gln Leu His Pro Ala Asp Gly Val Ser Thr Leu Asp Trp Thr Thr Arg
385                 390                 395                 400
Leu Lys Ile Ala Ile Gly Ala Ala Lys Gly Leu Ala Trp Leu His His
                405                 410                 415
Ser Cys Asn Pro Arg Ile Ile His Arg Asn Ile Ser Ser Lys Cys Ile
                420                 425                 430
```

-continued

Leu Leu Asp Ala Asp Phe Glu Pro Lys Ile Ser Asp Phe Gly Leu Ala
        435                 440                 445

Arg Leu Met Asn Pro Ile Asp Thr His Leu Ser Thr Phe Val Asn Gly
    450                 455                 460

Glu Phe Gly Asp Leu Gly Tyr Val Ala Pro Glu Tyr Thr Arg Thr Leu
465                 470                 475                 480

Val Ala Thr Pro Lys Gly Asp Ile Tyr Ser Phe Gly Thr Val Leu Leu
                485                 490                 495

Glu Leu Val Thr Gly Glu Arg Pro Thr Asn Val Ser Lys Ala Pro Glu
            500                 505                 510

Thr Phe Lys Gly Asn Leu Val Glu Trp Ile Thr Glu Leu Thr Ser Asn
        515                 520                 525

Ala Lys Leu His Asp Ala Ile Asp Glu Ser Leu Val Arg Lys Asp Val
    530                 535                 540

Asp Ser Glu Leu Phe Gln Phe Leu Lys Val Ala Cys Asn Cys Val Ser
545                 550                 555                 560

Pro Thr Pro Lys Glu Arg Pro Thr Met Phe Glu Val Tyr Gln Leu Leu
                565                 570                 575

Arg Ala Ile Gly Gly Arg Tyr Asn Phe Thr Thr Glu Asp Asp Ile Leu
            580                 585                 590

Val Pro Thr Asp Ile Gly Asn Thr Asp Asn Met Gln Glu Leu Ile Val
        595                 600                 605

Ala Gln Glu Gly Ser Tyr
        610

<210> SEQ ID NO 76
<211> LENGTH: 456
<212> TYPE: PRT
<213> ORGANISM: Glycine max

<400> SEQUENCE: 76

Met Gly Ser Ser Phe Ser Ser Cys Tyr Glu Gly Glu Ser Val Ser Pro
1               5                   10                  15

Ser Pro Lys Pro Thr Lys Val Val Ala Thr Lys Gly Ser Ser Ser
            20                  25                  30

Asn Arg Val Ser Ile Thr Asp Leu Ser Phe Pro Gly Ser Thr Leu Ser
        35                  40                  45

Glu Asp Leu Ser Val Ser Leu Val Gly Ser Asn Leu His Val Phe Ser
    50                  55                  60

Leu Ala Glu Leu Lys Ile Ile Thr Gln Gly Phe Ser Ser Ser Asn Phe
65                  70                  75                  80

Leu Gly Glu Gly Gly Phe Gly Pro Val His Lys Gly Phe Ile Asp Asp
                85                  90                  95

Lys Leu Arg Pro Gly Leu Glu Ala Gln Pro Val Ala Val Lys Leu Leu
            100                 105                 110

Asp Leu Asp Gly Ser Gln Gly His Lys Glu Trp Leu Thr Glu Val Val
        115                 120                 125

Phe Leu Gly Gln Leu Arg His Pro His Leu Val Lys Leu Ile Gly Tyr
    130                 135                 140

Cys Cys Glu Glu Glu His Arg Leu Leu Val Tyr Glu Tyr Leu Pro Arg
145                 150                 155                 160

Gly Ser Leu Glu Asn Gln Leu Phe Arg Arg Tyr Thr Ala Ser Leu Pro
                165                 170                 175

Trp Ser Thr Arg Met Lys Ile Ala Ala Gly Ala Ala Lys Gly Leu Ala

```
            180                 185                 190
Phe Leu His Glu Ala Lys Lys Pro Val Ile Tyr Arg Asp Phe Lys Ala
        195                 200                 205
Ser Asn Ile Leu Leu Asp Ser Asp Tyr Asn Ala Lys Leu Ser Asp Phe
    210                 215                 220
Gly Leu Ala Lys Asp Gly Pro Glu Gly Asp Thr His Val Ser Thr
225                 230                 235                 240
Arg Val Met Gly Thr Gln Gly Tyr Ala Ala Pro Glu Tyr Ile Met Thr
                245                 250                 255
Gly His Leu Thr Ala Met Ser Asp Val Tyr Ser Phe Gly Val Val Leu
            260                 265                 270
Leu Glu Leu Leu Thr Gly Arg Arg Ser Val Asp Lys Gly Arg Pro Gln
        275                 280                 285
Arg Glu Gln Asn Leu Val Glu Trp Ala Arg Ser Ala Leu Asn Asp Ser
    290                 295                 300
Arg Lys Leu Ser Arg Ile Met Asp Pro Arg Leu Glu Gly Gln Tyr Ser
305                 310                 315                 320
Glu Val Gly Ala Arg Lys Ala Ala Leu Ala Tyr Gln Cys Leu Ser
                325                 330                 335
His Arg Pro Arg Ser Arg Pro Leu Met Ser Thr Val Val Asn Val Leu
            340                 345                 350
Glu Pro Leu Gln Asp Phe Asp Asp Val Pro Ile Gly Pro Phe Val Tyr
        355                 360                 365
Thr Val Pro Ala Glu Gln Gln Gln Tyr Asn Glu Val Ala Lys Glu Ser
    370                 375                 380
Glu Thr Pro Lys Glu Arg Lys Arg Glu Asn Gly His His Asn Arg
385                 390                 395                 400
Arg His His His Arg His Asn Gly His Arg His His Pro Leu Lys
                405                 410                 415
Ser Pro Lys Thr Pro Met Pro Ser Asp Gln Ser Gln Asn Asp Glu His
            420                 425                 430
Arg Asn Gly Arg Lys Ser Gly Ser Asn Ser Pro Asp Thr Phe Asn Ala
        435                 440                 445
Ser Glu Ala Gln Arg Ser Met Gly
    450                 455

<210> SEQ ID NO 77
<211> LENGTH: 343
<212> TYPE: PRT
<213> ORGANISM: Glycine max

<400> SEQUENCE: 77

Met Gly Cys Ser Phe Ser Gly Leu Asn Ala Leu Tyr Asp Ser Val Asn
1               5                   10                  15
Gly Gly Gly Asp Val Trp Ile Asn Glu Asn Arg Phe Arg Ile Val Arg
            20                  25                  30
Gln Leu Gly Glu Gly Gly Phe Ala Tyr Val Tyr Leu Val Lys Glu Thr
        35                  40                  45
Pro Asn Asp Ser Ala Val Ala Ala Gly Leu Ser Lys Lys Leu Lys Gly
    50                  55                  60
Ser Ser His Leu Ser Asp Asp Gly Thr Tyr Ala Met Lys Lys Val Leu
65                  70                  75                  80
Ile Gln Asn Asn Glu Gln Leu Glu Leu Val Arg Glu Glu Ile Arg Val
                85                  90                  95
```

```
Ser Ser Leu Phe Asn His Pro Asn Leu Leu Pro Leu Leu Glu His Ala
            100                 105                 110

Ile Ile Ser Val Lys Pro Thr Gln Glu Thr Ser Trp Asn His Glu Ala
        115                 120                 125

Tyr Leu Leu Phe Pro Val His Leu Asp Gly Thr Leu Leu Asp Asn Ala
    130                 135                 140

Lys Ile Met Lys Ala Lys Lys Glu Phe Tyr Ser Thr Ser Asp Val Leu
145                 150                 155                 160

Gln Ile Phe Arg Gln Leu Cys Ala Gly Leu Lys His Met His Ser Phe
                165                 170                 175

Asp Pro Pro His Ala His Asn Asp Val Lys Pro Gly Asn Val Leu Ile
            180                 185                 190

Thr His Arg Lys Gly Gln Pro Pro Leu Ala Ile Leu Met Asp Phe Gly
        195                 200                 205

Ser Ala Arg Pro Ala Arg Lys Gln Ile Gly Ser Arg Ser Glu Ala Leu
    210                 215                 220

Gln Leu Gln Glu Trp Ala Ser Glu His Cys Ser Ala Pro Phe Arg Ala
225                 230                 235                 240

Pro Glu Leu Trp Asp Cys Pro Ser Gln Ala Asp Ile Asp Glu Arg Thr
                245                 250                 255

Asp Ile Trp Ser Leu Gly Cys Thr Leu Tyr Ala Ile Met Tyr Gly Val
            260                 265                 270

Ser Pro Phe Glu Tyr Ala Leu Gly Glu Ser Gly Ser Leu Gln Leu
        275                 280                 285

Ala Ile Val Asn Ala Gln Val Lys Trp Pro Ala Gly Pro Lys Pro Pro
290                 295                 300

Tyr Pro Glu Ala Leu His Gln Phe Val Ser Trp Met Leu Gln Pro Thr
305                 310                 315                 320

Ala Ser Met Arg Pro Arg Ile Asp Asp Ile Ile His Val Asp Lys
                325                 330                 335

Leu Val Ala Lys Phe Ser Gln
            340
```

<210> SEQ ID NO 78
<211> LENGTH: 377
<212> TYPE: PRT
<213> ORGANISM: Glycine max

<400> SEQUENCE: 78

```
Met Lys Cys Phe Phe Phe Lys Glu Lys Cys Lys Ser Ala Pro Glu Leu
1               5                   10                  15

His Lys Lys Lys Thr Pro Ala Val Asn Arg Ala Ala Asn Ser Thr Gly
            20                  25                  30

Ser Val Ser Ser Pro Lys Ser Val Lys Asp Leu Tyr Arg Glu Lys Glu
        35                  40                  45

His Ser Phe Arg Val Phe Thr Leu Gln Glu Leu Arg Asp Ala Thr Asn
    50                  55                  60

Gly Phe Asn Arg Met Leu Lys Leu Gly Glu Gly Gly Phe Gly Ser Val
65                  70                  75                  80

Tyr Lys Gly Ser Ile Thr Gln Pro Asp Gly Gln Gly Asp Pro Ile
            85                  90                  95

Pro Val Ala Ile Lys Arg Leu Asn Thr Arg Gly Phe Gln Gly His Lys
            100                 105                 110

Glu Trp Leu Ala Glu Val Gln Phe Leu Gly Ile Val Asn His Pro Asn
        115                 120                 125
```

-continued

Leu Val Lys Leu Leu Gly Tyr Cys Ser Val Asp Ala Glu Arg Gly Ile
            130                 135                 140

Gln Arg Leu Leu Val Tyr Glu Phe Met Pro Asn Arg Ser Leu Glu Asp
145                 150                 155                 160

His Leu Phe Asn Lys Asn Leu Pro Thr Leu Pro Trp Lys Thr Arg Leu
                165                 170                 175

Glu Ile Met Leu Gly Ala Ala Gln Gly Leu Ala Tyr Leu His Glu Gly
            180                 185                 190

Leu Glu Ile Gln Val Ile Tyr Arg Asp Phe Lys Ser Ser Asn Val Leu
        195                 200                 205

Leu Asp Ala Asp Phe His Pro Lys Leu Ser Asp Phe Gly Leu Ala Arg
210                 215                 220

Glu Gly Pro Gln Gly Asp Gln Thr His Val Ser Thr Ala Val Val Gly
225                 230                 235                 240

Thr Gln Gly Tyr Ala Ala Pro Glu Tyr Ile Glu Thr Gly His Leu Lys
                245                 250                 255

Val Gln Ser Asp Met Trp Ser Phe Gly Val Val Leu Tyr Glu Ile Leu
            260                 265                 270

Thr Gly Arg Arg Ser Leu Glu Arg Asn Arg Pro Thr Ala Glu Gln Lys
        275                 280                 285

Leu Leu Asp Trp Val Lys Gln Tyr Pro Ala Asp Thr Ser Arg Phe Val
290                 295                 300

Ile Ile Met Asp Ala Arg Leu Arg Asn Gln Tyr Ser Leu Pro Ala Ala
305                 310                 315                 320

Arg Lys Ile Ala Lys Leu Ala Asp Ser Cys Leu Lys Lys Asn Pro Glu
                325                 330                 335

Asp Arg Pro Ser Met Ser Gln Ile Val Glu Ser Leu Lys Gln Ala Leu
            340                 345                 350

Gln Tyr Ser Asp Thr Thr Ser Gln Asp Ile Ala Glu Ser Ser Ser Ser
        355                 360                 365

Ser Arg Ser Lys Leu Val Arg Lys Lys
370                 375

<210> SEQ ID NO 79
<211> LENGTH: 674
<212> TYPE: PRT
<213> ORGANISM: Glycine max

<400> SEQUENCE: 79

Met Leu Gly Thr Pro His Thr Leu Ile Leu Leu Phe Leu Phe Leu
1               5                   10                  15

Ile Thr Thr Phe Ser His Ser Leu Val Phe Asn Ile Thr Asn Phe Asp
            20                  25                  30

Asp Pro Ala Ala Ala Thr Ala Ile Ser Tyr Glu Gly Asp Gly Arg Thr
        35                  40                  45

Thr Asn Gly Ser Ile Asp Leu Asn Lys Val Ser Tyr Leu Phe Arg Val
    50                  55                  60

Gly Arg Ala Ile Tyr Ser Lys Pro Leu His Leu Trp Asp Arg Ser Ser
65                  70                  75                  80

Asp Leu Ala Ile Asp Phe Val Thr Arg Phe Thr Phe Ser Ile Glu Lys
                85                  90                  95

Leu Asn Leu Thr Glu Val Ala Tyr Gly Asp Gly Phe Ala Phe Tyr Leu
            100                 105                 110

Ala Pro Leu Gly Tyr Arg Ile Pro Pro Asn Ser Gly Gly Gly Thr Phe

```
            115                 120                 125
Gly Leu Phe Asn Ala Thr Thr Asn Ser Asn Leu Pro Glu Asn His Val
        130                 135                 140
Val Ala Val Glu Phe Asp Thr Phe Ile Gly Ser Thr Asp Pro Pro Thr
145                 150                 155                 160
Lys His Val Gly Val Asp Asp Asn Ser Leu Thr Ser Ala Ala Phe Gly
                165                 170                 175
Asn Phe Asp Ile Asp Asp Asn Leu Gly Lys Lys Cys Tyr Thr Leu Ile
                180                 185                 190
Thr Tyr Ala Ala Ser Thr Gln Thr Leu Phe Val Ser Trp Ser Phe Lys
                195                 200                 205
Ala Lys Pro Ala Ser Thr Asn His Asn Asp Asn Ser Ser Phe Ser
210                 215                 220
Tyr Gln Ile Asp Leu Lys Lys Ile Leu Pro Glu Trp Val Asn Ile Gly
225                 230                 235                 240
Phe Ser Ala Ser Thr Gly Leu Ser Thr Glu Arg Asn Thr Ile Tyr Ser
                245                 250                 255
Trp Glu Phe Ser Ser Ser Leu Asn Gly Ser Pro Ala Asp Phe Glu Asn
                260                 265                 270
Val Lys Leu Lys His Gln Ser Ser Lys Leu Ala Leu Ile Leu Ala Val
                275                 280                 285
Leu Cys Pro Leu Val Leu Leu Phe Val Leu Ala Ser Leu Val Ala Val
290                 295                 300
Phe Leu Ile Arg Lys Lys Arg Ser His Asp Asp Cys Met Leu Tyr
305                 310                 315                 320
Glu Val Gly Asp Asp Glu Leu Gly Pro Thr Ser Val Lys Phe Asp Leu
                325                 330                 335
Asp Lys Gly Thr Ile Pro Arg Arg Phe Glu Tyr Lys Glu Leu Val Asp
                340                 345                 350
Ala Thr Asn Gly Phe Ser Asp Asp Arg Arg Leu Gly Gln Gly Ala Ser
                355                 360                 365
Gly Gln Val Tyr Lys Gly Val Leu Ser Tyr Leu Gly Arg Val Val Ala
                370                 375                 380
Val Lys Arg Ile Phe Ala Asp Phe Glu Asn Ser Glu Arg Val Phe Thr
385                 390                 395                 400
Asn Glu Val Arg Ile Ile Ser Arg Leu Ile His Lys Asn Leu Val Gln
                405                 410                 415
Phe Ile Gly Trp Cys His Glu Glu Gly Glu Phe Leu Leu Val Phe Glu
                420                 425                 430
Tyr Met Pro Asn Gly Ser Leu Asp Ser His Leu Phe Gly Asn Lys Arg
                435                 440                 445
Val Leu Glu Trp His Leu Arg Tyr Lys Ile Val Leu Gly Val Val Asn
                450                 455                 460
Ala Leu His Tyr Leu His Glu Asp Ala Glu Gln Cys Val Leu His Arg
465                 470                 475                 480
Asp Ile Lys Ser Ala Asn Val Leu Leu Asp Thr Glu Phe Asn Thr Lys
                485                 490                 495
Val Gly Asp Phe Gly Met Ala Lys Leu Val Asp Pro Arg Leu Arg Thr
                500                 505                 510
Gln Arg Thr Gly Val Val Gly Thr Tyr Gly Tyr Leu Ala Pro Glu Tyr
                515                 520                 525
Val Asn Val Gly Arg Ala Ser Arg Glu Ser Asp Ile Tyr Ser Phe Gly
                530                 535                 540
```

```
Val Val Ser Leu Glu Met Ala Ser Gly Arg Arg Thr Tyr Gln Asp Gly
545                 550                 555                 560

Glu Phe His Val Ser Leu Met Asn Trp Val Trp Gln Leu Tyr Val Glu
                565                 570                 575

Gly Glu Ile Met Arg Ala Ala Asp Glu Lys Leu Asn Asn Glu Phe Glu
                580                 585                 590

Val Asp Gln Met Arg Ser Leu Leu Val Val Gly Leu Trp Cys Thr Asn
                595                 600                 605

Pro Asn Asp Lys Glu Arg Pro Lys Ala Ala Gln Val Ile Lys Val Leu
                610                 615                 620

Asn Leu Glu Ala Pro Leu Pro Val Leu Pro Leu Asp Met Tyr Glu Arg
625                 630                 635                 640

Ala Pro Pro Met Glu Ile Ile Arg Met Pro His His Pro Ser Gly Lys
                645                 650                 655

Asn His Ser Gly Met Ser Thr Pro Ile Thr Ser Ser Leu Val Ser Val
                660                 665                 670

Gly Arg

<210> SEQ ID NO 80
<211> LENGTH: 712
<212> TYPE: PRT
<213> ORGANISM: Glycine max

<400> SEQUENCE: 80

Met Leu Arg Asp Glu Ser Val Gly Ser Arg Ala Arg His Ser Ala
1               5                   10                  15

Thr Ala Thr Ala Thr Val Ser Asn Lys Val Leu Val Ala Val Lys Ala
                20                  25                  30

Glu Lys Val Ile Ser Asn Thr Ala Leu Ala Trp Ala Leu Thr His Val
                35                  40                  45

Ala His Ser Thr Asp Ser Ile Thr Leu Leu Ala Val Tyr Ser Ser His
                50                  55                  60

Lys Thr Gly Arg Arg Phe Trp Asn Phe Ser Arg Leu Ala Gly Asp Cys
65                  70                  75                  80

Thr Asn Gly Pro Ala Gly Lys Leu Pro Glu Gln Ile Ser Asp Ile Ser
                85                  90                  95

Glu Ser Cys Ala Gln Met Val Leu Gln Leu His Asn Gln Ile Glu Val
                100                 105                 110

Arg Val Lys Ile Lys Val Val Thr Gly Thr Pro Ser Gly Ala Val Ala
                115                 120                 125

Ala Glu Ala Arg Trp Ser Gly Ser His Trp Val Ile Leu Asp Lys Lys
                130                 135                 140

Leu Lys Gln Glu Val Lys His Cys Thr Asp Glu Leu Asn Cys Ser Ile
145                 150                 155                 160

Val Val Met Asn Gly Ser Gln Ala Lys Ile Leu Arg Leu Asn Leu Arg
                165                 170                 175

Ser Ser Asn Glu Leu Gln Thr Pro Phe Phe Ser Ala Asn Ser Ser Pro
                180                 185                 190

Gly Ile Glu Ile Ala Lys Leu Lys Gly Arg Arg Leu Lys His Ser Thr
                195                 200                 205

Pro Val Gly Ser Pro Glu Glu Ala Val Tyr Glu Gln Asn Pro Leu Tyr
                210                 215                 220

Glu Gly Gln Gly Pro Glu Lys Arg Thr Asp Glu Ser Ile Asn Glu Pro
225                 230                 235                 240
```

```
Thr Lys Asp Phe His Val Gln Pro Pro Leu Tyr Phe Asp Leu Glu Arg
            245                 250                 255

Asp Ser Pro Pro Ser Trp Thr Arg Pro Ala Ser Ser Val Ala Ser
            260                 265                 270

Asp Asn Lys Thr Ile Phe Trp Ile Pro Gln Asn His Asn Ile Val Asp
            275                 280                 285

Lys Phe Gln Lys Thr Lys Asn Asn Ser Val Ile Gln Arg Thr Lys Ser
            290                 295                 300

Pro Thr Ser Lys Thr Leu Leu Glu Asn Phe Ile Arg Cys Asp Gln Glu
305                 310                 315                 320

Ile Trp Thr Asn Glu Leu Gly Phe Asp Gln Ala Gln Ser Arg Ser Tyr
            325                 330                 335

Val Pro Asn Leu Gly Ile Arg Asp Asn Asn Ser Val Pro Leu Gly Arg
            340                 345                 350

Thr Thr Ser Ile Pro Pro Leu Cys Ser Gln Cys Lys Asn Lys Ala
            355                 360                 365

Pro Val Phe Gly Lys Pro Pro Lys Arg Phe Ser Tyr Lys Glu Leu Glu
            370                 375                 380

Glu Ala Thr Asp Met Phe Ser Asp Glu Asn Phe Leu Ala Glu Gly Arg
385                 390                 395                 400

Phe Gly Val Val His Gln Gly Ile Leu Lys Asp Gly Gln Val Val Ala
            405                 410                 415

Val Lys Gln Leu Lys Phe Gly Ser Gln Ala Asp Leu Asp Phe Cys
            420                 425                 430

Arg Glu Val Arg Val Leu Ser Cys Ala Gln His Arg Asn Val Val Leu
            435                 440                 445

Leu Ile Gly Phe Cys Ile Glu Ser Asn Leu Arg Ile Leu Val Tyr Glu
            450                 455                 460

Tyr Ile Cys Asn Gly Ser Leu Asp Leu Tyr Leu Tyr Gly Asp Glu Ser
465                 470                 475                 480

Met Pro Leu Asp Trp Asn Ser Arg Leu Lys Ile Ala Ile Gly Thr Ala
            485                 490                 495

Arg Gly Leu Arg Tyr Leu His Glu Asp Cys Arg Val Gly Cys Ile Ala
            500                 505                 510

His Arg Asp Leu Arg Pro Lys Asn Ile Leu Val Thr His Asp Phe Glu
            515                 520                 525

Pro Met Val Ala Asp Phe Gly Leu Ala Arg Trp His Ser Glu Trp Asn
530                 535                 540

Ile Asp Thr Glu Asp Arg Val Ile Gly Thr Ser Gly Tyr Leu Ala Pro
545                 550                 555                 560

Glu Tyr Leu Asp Ala Gly Asn Leu Thr Tyr Lys Val Asp Val Tyr Ala
            565                 570                 575

Phe Gly Ile Val Leu Leu Glu Leu Ile Thr Gly Arg Arg Ile Ser Glu
            580                 585                 590

Leu Glu Gln Phe Asn Gly His Ser Tyr Leu Ser Glu Trp Phe His Pro
            595                 600                 605

Ile Arg Met Leu Glu Pro Gly His Ile Leu Gln Asn Val Arg Ser Leu
            610                 615                 620

Lys Pro Cys Phe Asp Ser Lys Glu Ser Val Glu Phe Asn Leu Gln Leu
625                 630                 635                 640

Gln Ala Met Ala Arg Ala Val Ser Leu Cys Leu Arg Val Asp Pro Asp
            645                 650                 655
```

```
Ala Arg Pro Pro Met Ser Lys Ile Leu Arg Val Leu Glu Gly Gly Asn
            660                 665                 670

Pro Val Arg Pro Met Gly Leu Asp Ile Asn Ser Val Gly Asn Thr Ser
            675                 680                 685

Gly His Leu Ser Gly Leu Lys Ser His Thr Pro Pro Lys Gly Thr Ile
            690                 695                 700

Asn His Ser Arg Arg Leu Ser His
705                 710

<210> SEQ ID NO 81
<211> LENGTH: 854
<212> TYPE: PRT
<213> ORGANISM: Glycine max

<400> SEQUENCE: 81

Met Gly Met Glu Gly Ile Ala Val Ser Val Thr Met Leu Leu Leu
1               5                   10                  15

Met Val Gly Leu Thr Met Gly Met Ser Ser Arg Thr Glu Trp Phe Ala
            20                  25                  30

Leu Arg Glu Leu Arg Gln Ser Leu Glu Ile Arg Ala Lys Tyr Trp Pro
        35                  40                  45

Ile Lys Ala Glu Pro Cys Gly Asn Trp Thr Gly Val Gln Cys Arg Asn
50                  55                  60

Gly Arg Val Val Gly Ile Asn Val Ser Gly Leu Arg Arg Thr Arg Trp
65                  70                  75                  80

Gly Arg Leu Asn Pro Ser Phe Glu Val Gly Ser Leu Val Asn Phe Thr
            85                  90                  95

Leu Leu Glu Thr Phe Asn Ala Ser Gly Phe Lys Leu Asn Gly Ser Ile
            100                 105                 110

Pro Glu Trp Leu Gly Glu Ser Leu Gly Val Leu Glu Val Leu Asp Leu
        115                 120                 125

Ser Phe Cys Ser Ile Lys Gly Ser Ile Pro Asp Ser Ile Gly Trp Leu
130                 135                 140

Ser Lys Leu Lys Val Leu Leu Leu Ser Gly Asn Phe Leu Thr Gly Arg
145                 150                 155                 160

Met Pro Ser Thr Phe Gly Asn Leu Thr Arg Leu Ser Val Leu Asn Leu
            165                 170                 175

Ser Gly Asn Ser Leu Ser Gly Thr Val Pro Asp Ser Val Ser Lys Leu
        180                 185                 190

Gly Asn Leu Ser Arg Leu Asp Leu Ser Tyr Asn Phe Leu Ser Gly Ser
        195                 200                 205

Val Pro Pro Glu Leu Gly Ala Leu Ser Ser Leu Gln Phe Phe Asn Leu
210                 215                 220

Ser Gly Asn Ser Phe Thr Gly Thr Phe Pro Gln Leu Gly Asn Leu
225                 230                 235                 240

Ser Lys Leu Val Asp Val Asp Leu Ser Met Asn Phe Leu Ser Gly Ser
            245                 250                 255

Leu Pro Gly Gly Ser Ser Ser Gly Leu Leu Ala Leu Lys Val Leu
        260                 265                 270

Ile Leu Arg Gly Asn Leu Phe Asp Gly Val Leu Pro Ala Asp Leu Trp
        275                 280                 285

Pro Met Pro Arg Leu His Phe Leu Asp Val Ser Ser Asn Asn Leu Thr
        290                 295                 300

Gly Thr Leu Pro Asn Phe Thr Ser Trp Asn Val Ser Ser Val Gly Phe
305                 310                 315                 320
```

```
Val Phe Asn Leu Ser Asn Asn Leu Phe Tyr Gly Leu Leu Asn Thr Ser
            325                 330                 335

Leu Asp Arg Phe Glu Ile Ile Asp Leu Ser Ser Asn Tyr Leu Glu Gly
            340                 345                 350

Glu Val Pro Gly Gly Val Asn Asn Val Ser Leu Asp Arg Asn Cys
            355                 360                 365

Leu Gln Arg Ile Pro Asn Gln Arg Asp Leu Glu Asp Cys Arg Val Phe
            370                 375                 380

Tyr Asp Asn Arg Ser Leu Pro Phe Gly Phe Leu Lys Ser Gly Ser Arg
385                 390                 395                 400

Ser Arg Val Ile Phe Ile Leu Val Gly Ile Phe Gly Gly Leu Gly Phe
            405                 410                 415

Ile Val Leu Leu Ala Leu Val Leu Met Leu Val Leu Lys Gln Cys His
            420                 425                 430

Asn Arg Arg Ser Leu Gly Val Gln Arg Gly Thr Lys Asp Gly Gly Pro
            435                 440                 445

Val Gln Glu Gly Glu Ser Pro Ile Pro Pro Lys Asp Thr Val Phe Val
            450                 455                 460

Thr Val Gly Asp Ala Phe Ser Phe Glu Gln Met Leu His Leu Thr Ser
465                 470                 475                 480

Asn Phe Ala Glu Ala Asn Val Ile Lys His Gly His Ser Gly Asp Leu
            485                 490                 495

Phe Leu Gly Val Leu Glu Gly Gly Ala Thr Val Val Lys Lys Val
            500                 505                 510

Asp Leu Asn Leu Phe Lys Arg Glu Ser Tyr Val Val Glu Leu Gly Leu
            515                 520                 525

Leu Ser Lys Val Pro His Ala Arg Leu Val Pro Ile Leu Gly His Cys
            530                 535                 540

Leu Asp Asn Glu Asn Glu Lys Phe Ile Val Tyr Lys Tyr Met Pro Asn
545                 550                 555                 560

Arg Asp Leu Ala Thr Ser Leu His Arg Val Thr Gly Ser Asp Gly Lys
            565                 570                 575

Leu Gln Ser Leu Asp Trp Ile Thr Arg Leu Lys Ile Ala Ile Gly Ala
            580                 585                 590

Ala Glu Gly Ile Ala Tyr Leu His Glu Cys Ser Pro Pro Leu Val His
            595                 600                 605

Arg Asp Ile Gln Ala Ser Ser Ile Leu Leu Asp Lys Phe Glu Val
610                 615                 620

Arg Leu Gly Ser Leu Ser Glu Val Thr Ala Gln Gly Asp Leu Gln Gln
625                 630                 635                 640

Gly Val Ile Ser Arg Val Phe Ser Lys Pro Pro Ser Ser Asn Gln Ala
            645                 650                 655

Asp Ser Gly Lys Ser Ser Val Thr Cys Ala Tyr Asp Ile Tyr Cys Phe
            660                 665                 670

Gly Lys Ile Leu Leu Glu Leu Ile Thr Gly Asn Ile Glu Val Ser Lys
            675                 680                 685

Leu Asp Asp Ala Ser Thr Lys Glu Trp Leu Glu Gln Thr Leu Pro Tyr
            690                 695                 700

Ile Thr Ile Tyr Asp Lys Glu Arg Val Thr Lys Ile Ile Asp Pro Ser
705                 710                 715                 720

Leu Ile Val Asp Glu Asp Leu Leu Glu Glu Val Trp Ala Met Ala Ile
            725                 730                 735
```

```
Val Ala Asn Ala Cys Leu Asn Pro Lys Pro Ser Lys Arg Pro Pro Met
                740                 745                 750

Arg His Val Leu Lys Ala Leu Glu Asn Pro Leu Lys Ile Val Arg Glu
        755                 760                 765

Glu Asn Thr Ser Ser Ala Arg Leu Arg Ser Asn Ser Ser Arg Lys Ser
    770                 775                 780

Trp Ser Thr Ala Phe Phe Gly Ser Trp Arg His Ser Ser Ser Asp Ser
785                 790                 795                 800

Val Val Ala Thr Asn Lys Glu Gly Ser Ser Asp Thr Lys Lys Ser Gly
                805                 810                 815

Lys Val Gly Ser Gln Ser Ser Gly Asn Asp His Ser Ser Asn Lys
        820                 825                 830

Arg Ser Ser Asn Glu Ile Phe Pro Glu Pro Leu Glu Ile Leu Asp Val
        835                 840                 845

Glu Thr Gly Val Ala Arg
        850

<210> SEQ ID NO 82
<211> LENGTH: 510
<212> TYPE: PRT
<213> ORGANISM: Glycine max

<400> SEQUENCE: 82

Met Ser Ala Asn Ser Ser Leu His Val Glu Leu Ser Arg Lys Thr Ser
1               5                   10                  15

Phe Leu Gly Leu Arg Leu Trp Val Leu Ile Gly Ile Gly Val Gly Val
                20                  25                  30

Phe Ile Val Val Ile Leu Cys Val Leu Ser Val Trp Val Met Phe Arg
                35                  40                  45

Arg Lys Ser Lys Arg Ser Leu Asp Lys Tyr Ser Leu Ser Gln Ile Pro
        50                  55                  60

His Val Ser Lys Asp Ile Ile Val Asp Met Val Gly Val Gln Ile Ser
65                  70                  75                  80

His Asp Gln Ser Glu Ser Val Ala Ile Pro Val His Asp Lys Pro Ser
                85                  90                  95

Glu Asn Asn Ser Asn Lys Leu Phe Ser His Leu His Lys Ser Lys Ser
                100                 105                 110

Gly Asp Ala Asp Asn Ile Ser Gln Cys Ser Ser Val Tyr His His Glu
        115                 120                 125

Arg Gly Phe Ser Ser Met Ser Gly Glu Glu Gly Ser Ser Gly Thr Val
130                 135                 140

Lys Lys Gln Ser Ala Leu Ser Phe Gly Gly Met Val Thr Ala Ser Pro
145                 150                 155                 160

Leu Val Gly Leu Pro Glu Ile Ser His Leu Gly Trp Gly His Trp Phe
                165                 170                 175

Thr Leu Arg Asp Leu Glu Leu Ala Thr Asn Arg Phe Ser Pro Glu Asn
        180                 185                 190

Val Ile Gly Glu Gly Gly Tyr Gly Val Val Tyr Arg Gly Lys Leu Ile
        195                 200                 205

Asn Gly Ser Glu Val Ala Val Lys Lys Ile Leu Asn Asn Leu Gly Gln
210                 215                 220

Ala Glu Lys Glu Phe Arg Val Glu Val Glu Ala Ile Gly His Val Arg
225                 230                 235                 240

His Lys Asn Leu Val Arg Leu Leu Gly Tyr Cys Val Glu Gly Val His
                245                 250                 255
```

```
Arg Leu Leu Val Tyr Glu Tyr Val Asn Asn Gly Asn Leu Glu Gln Trp
            260                 265                 270

Leu His Gly Ala Met Ser Gln Gln Gly Thr Leu Thr Trp Glu Ala Arg
        275                 280                 285

Met Lys Val Ile Thr Gly Thr Ala Lys Ala Leu Ala Tyr Leu His Glu
    290                 295                 300

Ala Ile Glu Pro Lys Val Val His Arg Asp Ile Lys Ser Ser Asn Ile
305                 310                 315                 320

Leu Ile Asp Thr Glu Phe Asn Ala Lys Val Ser Asp Phe Gly Leu Ala
                325                 330                 335

Lys Leu Leu Asp Ser Gly Glu Ser His Ile Thr Thr Arg Val Met Gly
            340                 345                 350

Thr Phe Gly Tyr Val Ala Pro Glu Tyr Ala Asn Thr Gly Leu Leu Asn
        355                 360                 365

Glu Arg Ser Asp Ile Tyr Ser Phe Gly Val Leu Leu Leu Glu Ala Val
    370                 375                 380

Thr Gly Lys Asp Pro Val Asp Tyr Ser Arg Pro Ala Asn Glu Val Asn
385                 390                 395                 400

Leu Val Glu Trp Leu Lys Met Met Val Gly Thr Arg Ala Glu Glu
                405                 410                 415

Val Val Asp Ser Arg Leu Glu Val Lys Pro Ser Ile Arg Ala Leu Lys
            420                 425                 430

Arg Ala Leu Leu Val Ala Leu Arg Cys Val Asp Pro Glu Ala Glu Lys
        435                 440                 445

Arg Pro Lys Met Ser Gln Val Arg Met Leu Glu Ala Asp Glu Tyr
    450                 455                 460

Pro Phe Arg Glu Asp Arg Arg Asn Arg Lys Ser Arg Thr Ala Ser Met
465                 470                 475                 480

Glu Ile Glu Ser Leu Lys Asp Ile Ser Gly Pro Ser Asp Ala Glu Lys
                485                 490                 495

Leu Lys Gly Ser Glu Gly His Glu Pro Glu Thr Thr Gln Gly
            500                 505                 510

<210> SEQ ID NO 83
<211> LENGTH: 649
<212> TYPE: PRT
<213> ORGANISM: Glycine max

<400> SEQUENCE: 83

Met Glu Lys Thr Ile His Leu Val Tyr Phe Lys Cys Leu Val Phe Leu
1               5                   10                  15

Leu Met Lys Gln Val Ile Val Met Ala Glu Pro Arg Ala Arg Thr Val
            20                  25                  30

Asn Ile Thr Cys Asn Asn Lys Leu Glu His Asn Thr Thr Ile Phe Val
        35                  40                  45

Pro Asn Phe Val Ala Thr Met Glu Lys Ile Ser Glu Gln Met Arg Asn
    50                  55                  60

Thr Gly Tyr Gly Thr Ala Val Val Gly Thr Gly Pro Asp Thr Asn
65                  70                  75                  80

Tyr Gly Leu Ala Gln Cys Tyr Gly Asp Leu Ser Leu Leu Asp Cys Val
                85                  90                  95

Leu Cys Tyr Ala Glu Ala Arg Thr Val Leu Pro Gln Cys Phe Pro Tyr
            100                 105                 110

Asn Gly Gly Arg Ile Tyr Leu Asp Gly Cys Phe Met Arg Ala Glu Asn
```

-continued

```
            115                 120                 125
Tyr Ser Phe Tyr Asp Glu Tyr Ile Gly Pro Gly Asp Lys Ala Val Cys
            130                 135                 140
Gly Asn Thr Thr Arg Lys Ser Thr Ser Phe Gln Ala Ala Lys Lys
145                 150                 155                 160
Ala Val Leu Ser Ala Val Gln Ala Ala Asn Asn Lys Gly Tyr Ala
                    165                 170                 175
Arg Lys Glu Val Phe Val Ala Gly Thr Thr Asn Asp Ala Ala Tyr Val
                180                 185                 190
Leu Ala Asn Cys Trp Arg Ser Leu Asp Thr Arg Ser Cys Arg Ala Cys
            195                 200                 205
Leu Glu Asn Ala Ser Ser Ser Ile Leu Gly Cys Leu Pro Trp Ser Glu
        210                 215                 220
Gly Arg Ala Leu Asn Thr Gly Cys Phe Met Arg Tyr Ser Asp Thr Asp
225                 230                 235                 240
Phe Leu Asn Lys Glu Gln Glu Asn Gly Ser Ser Gly Gly Asn Val Leu
                    245                 250                 255
Val Ile Val Val Ala Val Val Ser Ser Val Ile Val Leu Val Val Gly
                260                 265                 270
Ile Ala Ile Val Val Tyr Ile Arg Lys His Arg Tyr Ile Gln Met Lys
            275                 280                 285
Arg Arg Gly Ser Asn Asp Ala Glu Lys Leu Ala Lys Ser Leu His His
        290                 295                 300
Asn Ser Leu Asn Phe Lys Tyr Ser Thr Leu Glu Lys Ala Thr Asn Ser
305                 310                 315                 320
Phe Asp Glu Ala Asn Lys Leu Gly Gln Gly Phe Gly Thr Val Tyr
                    325                 330                 335
Lys Gly Val Leu Ala Asp Gly Arg Glu Ile Ala Ile Lys Arg Leu Tyr
                340                 345                 350
Phe Asn Asn Arg His Arg Ala Ala Asp Phe Phe Asn Glu Val Asn Ile
            355                 360                 365
Ile Ser Ser Val Glu His Lys Asn Leu Val Arg Leu Leu Gly Cys Ser
        370                 375                 380
Cys Ser Gly Pro Glu Ser Leu Leu Ile Tyr Glu Tyr Leu Pro Asn Arg
385                 390                 395                 400
Ser Leu Asp Arg Phe Ile Phe Asp Lys Asn Lys Gly Arg Glu Leu Asn
                    405                 410                 415
Trp Asp Lys Arg Tyr Asp Ile Ile Ile Gly Thr Ala Glu Gly Leu Val
                420                 425                 430
Tyr Leu His Glu Asn Ser Asn Ile Arg Ile Ile His Arg Asp Ile Lys
            435                 440                 445
Ala Ser Asn Ile Leu Leu Asp Ala Lys Leu Arg Ala Lys Ile Ala Asp
        450                 455                 460
Phe Gly Leu Ala Arg Ser Phe Gln Glu Asp Lys Ser His Ile Ser Thr
465                 470                 475                 480
Ala Ile Ala Gly Thr Leu Gly Tyr Met Ala Pro Glu Tyr Leu Ala His
                    485                 490                 495
Gly Gln Leu Thr Glu Lys Ala Asp Val Tyr Ser Phe Gly Val Leu Leu
                500                 505                 510
Leu Glu Ile Ile Thr Gly Arg Leu Asn Asn Arg Ser Lys Ala Ser Glu
            515                 520                 525
Tyr Ser Asp Ser Leu Val Thr Met Thr Trp Lys His Phe Gln Ser Gly
        530                 535                 540
```

```
Thr Ala Glu Gln Leu Ile Asp Pro Cys Leu Val Val Asp Asn His
545                 550                 555                 560

Arg Ser Asn Phe Lys Asn Glu Ile Leu Arg Val Leu His Ile Gly Leu
                565                 570                 575

Leu Cys Thr Gln Glu Ile Pro Ser Leu Arg Pro Ser Met Ser Lys Ala
            580                 585                 590

Leu Lys Met Leu Thr Lys Lys Glu His Leu Asp Leu Glu Ala Pro
        595                 600                 605

Ser Asn Pro Pro Phe Ile Asp Glu Ser Thr Met Glu Leu His Asp Gln
610                 615                 620

Asn Asp Asp Pro Phe Tyr Pro Leu Asn Ala Glu Asp Ser Leu Ala Thr
625                 630                 635                 640

Met Ser His Ser Ser Phe Tyr Ala Arg
                645

<210> SEQ ID NO 84
<211> LENGTH: 349
<212> TYPE: PRT
<213> ORGANISM: Glycine max

<400> SEQUENCE: 84

Met Leu Phe Asp Arg Leu Ala Phe Cys Cys Ser Lys His Thr Ser Ser
1               5                   10                  15

Ser Gln Arg Lys Tyr Pro Thr Val Ile Glu Glu Leu Cys His Gln Phe
            20                  25                  30

Ser Leu Ala Asn Leu Lys Lys Ser Thr Asn Asn Phe Asp Glu Asn Gly
        35                  40                  45

Val Ile Gly Tyr Gly Arg Phe Gly Lys Val Tyr Lys Gly Cys Leu Gln
    50                  55                  60

His Asn Asp Gly Ser Asp Tyr Ser Val Thr Leu Lys Arg Leu Gly Val
65                  70                  75                  80

Lys Asp Ser Arg Gly Leu Glu Gln Phe Lys Asn Glu Ile Glu Leu Leu
                85                  90                  95

Cys Gln Leu Arg His Pro Asn Cys Val Ser Leu Ile Gly Phe Cys Asn
            100                 105                 110

His Lys Lys Glu Lys Ile Leu Val Tyr Glu Tyr Met Ser Asn Gly Ser
        115                 120                 125

Leu His Gln His Leu Arg Gly Gly Leu Leu Ser Trp Lys Lys Arg Leu
130                 135                 140

Glu Ile Cys Ile Glu Ala Ala His Gly Leu His Tyr Leu His Thr Gly
145                 150                 155                 160

Ala Lys Arg Thr Ile Ile His Arg Asn Ile Asn Pro Ser Asn Ile Leu
                165                 170                 175

Leu Asp Asn Asn Met Lys Ser Lys Leu Thr Asp Phe Arg Leu Ser Ile
            180                 185                 190

Gln Gly Pro Arg Tyr Gly Ser Lys Pro Lys Pro Ile Lys Val Tyr Val
        195                 200                 205

Ile Glu Gly Ser Leu Gly Tyr Met Pro Met Glu Tyr Ile Val Asp Gly
    210                 215                 220

Thr Ile Thr Asp Lys Phe Asp Val Phe Ser Phe Gly Met Val Leu Leu
225                 230                 235                 240

Glu Val Val Cys Gly Arg Asn Cys Leu Ile Ile Pro Thr Glu Thr Glu
                245                 250                 255

Val Leu Glu Lys Pro Val Glu Glu Asn Ile Asp Gln Asn Ile Lys Gly
```

```
                   260                 265                 270
Lys Ile Ala Pro Glu Cys Trp Gln Val Phe Ile Asp Ile Ile Arg
            275                 280                 285

Cys Leu Lys Tyr Glu Pro Asp Glu Arg Pro Thr Met Gly Glu Val Glu
        290                 295                 300

Val Gln Leu Glu His Ala Leu Ser Met Gln Glu Gln Ala Asp Ile Thr
305                 310                 315                 320

Asn Thr Asn Ser Asp Tyr Thr Leu Phe Ser Thr Thr Ile His Leu
                325                 330                 335

Gly Leu Glu Leu Glu Ser Asn Pro Glu Glu Ser Asp Thr
            340                 345

<210> SEQ ID NO 85
<211> LENGTH: 424
<212> TYPE: PRT
<213> ORGANISM: Glycine max

<400> SEQUENCE: 85

Met Val Arg Gln Ala Asp Leu Val Ile Ile Gly Val Ser Val Gly Leu
1               5                   10                  15

Thr Leu Gly Ile Leu Ile Ser Cys Leu Ile Phe Phe Gly Ile Arg Trp
            20                  25                  30

Tyr Lys Lys Arg Ala His Ile Arg Arg Ser Ala Asn Glu Ser Ser Leu
        35                  40                  45

Thr Thr Leu Pro Ile Arg Thr Asn Gly Leu Gly Thr Ser Ser Asp Phe
    50                  55                  60

Ser Ala Ser Leu Asp Ser Ser Ile Ala Ser Trp Ser Glu Asn Leu
65                  70                  75                  80

Lys Arg Asn Ser His Phe Ser Trp Trp Asn His Gln Asn Lys Asp Arg
                85                  90                  95

Phe Ala Ser Ala Ser Gly Ile Leu Lys Tyr Leu Tyr Lys Glu Ile Gln
            100                 105                 110

Lys Ala Thr Gln Asn Phe Thr Thr Thr Leu Gly Gln Gly Ser Phe Gly
        115                 120                 125

Thr Val Tyr Lys Ala Thr Met Pro Thr Gly Glu Val Val Ala Val Lys
    130                 135                 140

Val Leu Ala Pro Asn Ser Lys Gln Gly Glu Lys Glu Phe Gln Thr Glu
145                 150                 155                 160

Val Phe Leu Leu Gly Arg Leu His His Arg Asn Leu Val Asn Leu Val
                165                 170                 175

Gly Tyr Cys Val Asp Lys Gly Gln Arg Ile Leu Val Tyr Gln Tyr Met
            180                 185                 190

Ser Asn Gly Ser Leu Ala Asn Leu Leu Tyr Gly Glu Glu Lys Glu Leu
        195                 200                 205

Ser Trp Asp Gln Arg Leu Gln Ile Ala Leu Asp Ile Ser His Gly Ile
    210                 215                 220

Glu Tyr Leu His Glu Gly Ala Val Pro Pro Val Ile His Arg Asp Leu
225                 230                 235                 240

Lys Ser Ala Asn Ile Leu Leu Asp His Ser Met Arg Ala Lys Val Ala
                245                 250                 255

Asp Phe Gly Leu Ser Lys Glu Glu Ile Phe Asp Asp Arg Asn Ser Gly
            260                 265                 270

Leu Lys Gly Thr Tyr Gly Tyr Met Asp Pro Ala Tyr Ile Ser Thr Ser
        275                 280                 285
```

```
Lys Leu Thr Thr Lys Ser Asp Ile Tyr Ser Phe Gly Ile Ile Val Phe
            290                 295                 300

Glu Leu Ile Thr Ala Ile His Pro His Gln Asn Leu Met Glu Tyr Val
305                 310                 315                 320

Asn Leu Ala Ala Met Asp His Asp Gly Val Asp Glu Ile Leu Asp Lys
                325                 330                 335

Gln Leu Val Gly Lys Cys Asn Leu Glu Glu Val Arg Gln Leu Ala Lys
            340                 345                 350

Ile Gly His Lys Cys Leu His Lys Ser Pro Arg Lys Arg Pro Ser Ile
            355                 360                 365

Gly Glu Val Ser Gln Phe Ile Ser Arg Ile Lys Gln Arg Arg Gln Arg
370                 375                 380

His Leu Thr Glu Asp Asn Leu Ser Phe Ala Ser Asn Asn Phe Ser Arg
385                 390                 395                 400

Ala Val Ser Arg Leu Glu Asp Arg Gln Val Glu Leu Ser Arg Met Pro
                405                 410                 415

Thr Ile Asn Leu Thr Glu Thr Val
            420

<210> SEQ ID NO 86
<211> LENGTH: 648
<212> TYPE: PRT
<213> ORGANISM: Glycine max

<400> SEQUENCE: 86

Met Glu Thr Glu Asn Gly Asp Thr Arg Ser Lys Lys Met Glu Tyr
1               5                   10                  15

Glu Val Ile Glu Gln Ile Gly Arg Gly Ala Phe Gly Ser Ala Phe Leu
            20                  25                  30

Val Leu His Lys Ser Glu Lys Lys Arg Tyr Val Leu Lys Lys Ile Arg
            35                  40                  45

Leu Ala Lys Gln Thr Glu Lys Phe Lys Arg Thr Ala His Gln Glu Met
        50                  55                  60

Asn Leu Ile Ala Lys Leu Asn Asn Pro Tyr Ile Val Asp Tyr Lys Asp
65                  70                  75                  80

Ala Trp Val Glu Lys Glu Asp His Ile Cys Ile Ile Thr Gly Tyr Cys
                85                  90                  95

Glu Gly Gly Asp Met Ala Glu Asn Ile Lys Lys Ala Arg Gly Ser Phe
            100                 105                 110

Phe Pro Glu Glu Lys Val Cys Lys Trp Leu Thr Gln Leu Leu Ile Ala
        115                 120                 125

Val Asp Tyr Leu His Ser Asn Arg Val Ile His Arg Asp Leu Lys Cys
130                 135                 140

Ser Asn Ile Phe Leu Thr Lys Asp Asn Ile Arg Leu Gly Asp Phe
145                 150                 155                 160

Gly Leu Ala Lys Arg Leu Asn Ala Glu Asp Leu Ala Ser Ser Val Val
                165                 170                 175

Gly Thr Pro Asn Tyr Met Cys Pro Glu Leu Leu Ala Asp Ile Pro Tyr
            180                 185                 190

Gly Tyr Lys Ser Asp Met Trp Ser Leu Gly Cys Cys Met Phe Glu Ile
        195                 200                 205

Ala Ala His Gln Pro Ala Phe Arg Ala Pro Asp Met Ala Gly Leu Ile
    210                 215                 220

Asn Lys Ile Asn Arg Ser Ser Ile Ser Pro Leu Pro Ile Val Tyr Ser
225                 230                 235                 240
```

```
Ser Thr Leu Lys Gln Leu Ile Lys Ser Met Leu Arg Lys Asn Pro Glu
            245                 250                 255
His Arg Pro Thr Ala Ala Glu Leu Leu Arg His Pro Leu Leu Gln Pro
        260                 265                 270
Tyr Val Leu Arg Cys His Asn Ala Ser Ser Asn Val Leu Pro Val Tyr
            275                 280                 285
Pro Leu Val Asn Pro Lys Asp Lys Ala Arg Arg Pro Asn Lys Ser Ser
    290                 295                 300
Gly Gly Lys Asp His Lys Asp Lys Glu Ala Gly Leu Val Asn Cys Leu
305                 310                 315                 320
Glu Arg Ile His Pro Ile Glu Gly Asn Ala Asp Ile Gln Ile Ser Asn
            325                 330                 335
Leu Pro Asn Asp Val Val Thr Ile Ser Thr Ser Ala Glu Asp Asn Leu
        340                 345                 350
Glu Thr Arg Met Ala Asn Leu Thr Ser Tyr Ile Val Glu Ser Ser Thr
            355                 360                 365
Ser Ile Ser Gly Ser Lys Asp Gly Ser Thr Thr Ser Glu Ser Thr Ile
    370                 375                 380
Cys Ser Val Cys Lys Glu Asp Phe Lys Ser Arg Pro Ala Arg Glu Met
385                 390                 395                 400
Thr Asn Asn Glu Ile Ser Ser Lys Ser Thr Gln Asp Ser Leu His Glu
            405                 410                 415
Glu Gln Arg Phe Ala Ala Lys His Phe His Lys Leu Glu Asp Asp Asp
            420                 425                 430
Ile Asn Ala Val Thr Ala Glu Val Glu Asp Ala Ser Cys Asn Gly Gly
            435                 440                 445
Leu Asp Asn Ala Glu Ala Gln Arg Glu Asp Ser Asn Leu Glu Asp Ser
    450                 455                 460
Gly Lys Ser Thr Met Ser Ser Glu Gly Ser Ser Thr Asp Lys Asp
465                 470                 475                 480
Lys Ser Ile Asn Glu Glu Arg Ser Ser Leu Ile Val His Pro Ile Arg
            485                 490                 495
Val Glu Asn Asp Thr Glu Ser Gly Asn Arg Leu Lys Lys Ser Glu Asn
            500                 505                 510
Pro Asp Val Tyr Thr Glu Val Pro His Met Asn Cys Leu Met Ser Val
        515                 520                 525
Ser Asn Asp Ala Leu Pro Val Lys Asp Asp Ile Ala Asn Gly His
    530                 535                 540
Ile Leu Cys Ser Thr His Lys Asp Asp Asn Val Val Glu Val Asp Gln
545                 550                 555                 560
Ala Pro Ser Gly Ile Ser Leu Ser Val Ile Thr Glu Val Asp Gly Asp
            565                 570                 575
Glu Thr Ile Lys Thr Pro Leu Asp Ser Pro Cys Gln Gln Arg Ala Asp
            580                 585                 590
Ala Leu Glu Ser Leu Leu Glu Leu Cys Ala Gln Leu Leu Lys Gln Asp
        595                 600                 605
Lys Leu Glu Glu Leu Ala Gly Val Leu Arg Pro Phe Gly Lys Glu Ala
    610                 615                 620
Val Ser Ser Arg Glu Thr Ala Ile Trp Leu Ala Lys Ser Leu Ile Ser
625                 630                 635                 640
Ser Gln Lys Phe Asn Pro Glu Thr
            645
```

<210> SEQ ID NO 87
<211> LENGTH: 467
<212> TYPE: PRT
<213> ORGANISM: Glycine max

<400> SEQUENCE: 87

| | | | | | | | | | | | | | | |
|---|---|---|---|---|---|---|---|---|---|---|---|---|---|---|
| Met | Ser | Val | Met | Met | Asp | His | Val | Ile | Gly | Gly | Lys | Phe | Lys | Leu | Gly |
| 1 | | | | 5 | | | | | 10 | | | | | 15 | |
| Arg | Lys | Ile | Gly | Ser | Gly | Ser | Phe | Gly | Glu | Leu | Tyr | Ile | Ala | Val | Asn |
| | | | 20 | | | | | 25 | | | | | 30 | | |
| Ile | Gln | Thr | Gly | Glu | Glu | Val | Ala | Val | Lys | Leu | Glu | Pro | Val | Lys | Thr |
| | | | | 35 | | | | | 40 | | | | | 45 | |
| Lys | His | Pro | Gln | Leu | Leu | Tyr | Glu | Ser | Lys | Leu | Tyr | Met | Leu | Leu | Gln |
| | 50 | | | | | 55 | | | | | 60 | | | | |
| Gly | Gly | Thr | Gly | Ile | Pro | His | Leu | Lys | Trp | Phe | Gly | Val | Glu | Gly | Asp |
| 65 | | | | | 70 | | | | | 75 | | | | | 80 |
| Tyr | Asn | Val | Met | Ala | Ile | Asp | Leu | Leu | Gly | Pro | Ser | Leu | Glu | Asp | Leu |
| | | | | 85 | | | | | 90 | | | | | 95 | |
| Phe | Asn | Tyr | Cys | Asn | Arg | Lys | Leu | Thr | Leu | Lys | Thr | Val | Leu | Met | Leu |
| | | | 100 | | | | | 105 | | | | | 110 | | |
| Ala | Asp | Gln | Leu | Ile | Asn | Arg | Val | Glu | Tyr | Met | His | Ser | Arg | Gly | Phe |
| | | | | 115 | | | | | 120 | | | | | 125 | |
| Leu | His | Arg | Asp | Ile | Lys | Pro | Asp | Asn | Phe | Leu | Met | Gly | Leu | Gly | Arg |
| | 130 | | | | | 135 | | | | | 140 | | | | |
| Lys | Ala | Asn | Gln | Val | Tyr | Ile | Ile | Asp | Tyr | Gly | Leu | Ala | Lys | Lys | Tyr |
| 145 | | | | | 150 | | | | | 155 | | | | | 160 |
| Arg | Asp | Leu | Gln | Thr | His | Arg | His | Ile | Pro | Tyr | Arg | Glu | Asn | Lys | Asn |
| | | | | 165 | | | | | 170 | | | | | 175 | |
| Leu | Thr | Gly | Thr | Ala | Arg | Tyr | Ala | Ser | Val | Asn | Thr | His | Leu | Gly | Ile |
| | | | 180 | | | | | 185 | | | | | 190 | | |
| Glu | Gln | Ser | Arg | Arg | Asp | Asp | Leu | Glu | Ser | Leu | Gly | Tyr | Val | Leu | Met |
| | | | | 195 | | | | | 200 | | | | | 205 | |
| Tyr | Phe | Leu | Arg | Gly | Ser | Leu | Pro | Trp | Gln | Gly | Leu | Lys | Ala | Gly | Thr |
| | 210 | | | | | 215 | | | | | 220 | | | | |
| Lys | Lys | Gln | Lys | Tyr | Asp | Lys | Ile | Ser | Glu | Lys | Lys | Met | Ser | Thr | Ser |
| 225 | | | | | 230 | | | | | 235 | | | | | 240 |
| Ile | Glu | Val | Leu | Cys | Lys | Ser | Tyr | Pro | Ser | Glu | Phe | Val | Ser | Tyr | Phe |
| | | | | 245 | | | | | 250 | | | | | 255 | |
| Asn | Tyr | Cys | Arg | Thr | Leu | Arg | Phe | Glu | Asp | Lys | Pro | Asp | Tyr | Ser | Tyr |
| | | | 260 | | | | | 265 | | | | | 270 | | |
| Leu | Lys | Arg | Leu | Phe | Arg | Asp | Leu | Phe | Ile | Arg | Glu | Gly | Tyr | Gln | Phe |
| | | | | 275 | | | | | 280 | | | | | 285 | |
| Asp | Tyr | Val | Phe | Asp | Trp | Thr | Ile | Leu | Lys | Tyr | Pro | Gln | Ile | Gly | Gly |
| | 290 | | | | | 295 | | | | | 300 | | | | |
| Ser | Ser | Ser | Arg | Gly | Arg | His | Glu | Ser | Gly | Lys | Ala | Ala | Met | His | Ala |
| 305 | | | | | 310 | | | | | 315 | | | | | 320 |
| Gly | Pro | Ser | Val | Gln | Lys | Pro | Glu | Lys | Val | Ser | Val | Gly | Lys | Glu | Ile |
| | | | | 325 | | | | | 330 | | | | | 335 | |
| Arg | Glu | Lys | Phe | Ser | Gly | Ala | Val | Glu | Ala | Phe | Ser | Arg | Arg | Asn | Pro |
| | | | 340 | | | | | 345 | | | | | 350 | | |
| Thr | Ser | Pro | Ser | Pro | Arg | Gly | Asp | His | Ser | Lys | His | Arg | Ser | Phe | Glu |
| | | | | 355 | | | | | 360 | | | | | 365 | |
| Glu | Val | Ala | Val | His | Lys | Asp | Val | Tyr | Arg | Asp | Gln | Glu | Lys | Gly | Arg |
| | 370 | | | | | 375 | | | | | 380 | | | | |

```
Asn Ser Ser Arg Tyr Gly Ser Ser Arg Arg Pro Ile Ile Ser Ser
385                 390                 395                 400

Ser Thr Arg Pro Ser Ser Gly Asp His Thr Asp Ser Arg Thr Gly
            405                 410                 415

Arg Leu Thr Ser Ser Gly Asn Arg Ser Ser Ala Ser His Arg Asn Ile
        420                 425                 430

Gln Pro Met Tyr Glu Thr Lys Gln Pro Thr Tyr Met Arg Ser Gly Ser
        435                 440                 445

Thr Arg Gly Asn Arg Asp Asp Pro Leu Arg Ser Phe Glu Leu Leu Ser
    450                 455                 460

Ile Arg Lys
465

<210> SEQ ID NO 88
<211> LENGTH: 721
<212> TYPE: PRT
<213> ORGANISM: Glycine max

<400> SEQUENCE: 88

Met Val Glu Phe Gln Arg Leu Leu Val Cys Ile Thr Thr Cys Ile Leu
1               5                   10                  15

Cys Trp Met Pro Asn Gly Ala Thr Ala Ala Thr Asp Pro Asn Asp Ala
            20                  25                  30

Ala Ala Val Arg Phe Leu Phe Gln Asn Met Asn Ser Pro Gln Leu
        35                  40                  45

Gly Trp Pro Pro Asn Gly Asp Asp Pro Cys Gly Gln Ser Trp Lys Gly
    50                  55                  60

Ile Thr Cys Ser Gly Asn Arg Val Thr Glu Ile Lys Leu Ser Asn Leu
65                  70                  75                  80

Gly Leu Thr Gly Ser Leu Pro Tyr Gly Leu Gln Val Leu Thr Ser Leu
                85                  90                  95

Thr Tyr Val Asp Met Ser Ser Asn Ser Leu Gly Gly Ser Ile Pro Tyr
            100                 105                 110

Gln Leu Pro Pro Tyr Leu Gln His Leu Asn Leu Ala Tyr Asn Asn Ile
        115                 120                 125

Thr Gly Thr Val Pro Tyr Ser Ile Ser Asn Leu Thr Ala Leu Thr Asp
    130                 135                 140

Leu Asn Phe Ser His Asn Gln Leu Gln Gln Gly Leu Gly Val Asp Phe
145                 150                 155                 160

Leu Asn Leu Ser Thr Leu Ser Thr Leu Asp Leu Ser Phe Asn Phe Leu
                165                 170                 175

Thr Gly Asp Leu Pro Gln Thr Met Ser Ser Leu Ser Arg Ile Thr Thr
            180                 185                 190

Met Tyr Leu Gln Asn Asn Gln Phe Thr Gly Thr Ile Asp Val Leu Ala
        195                 200                 205

Asn Leu Pro Leu Asp Asn Leu Asn Val Glu Asn Asn Phe Thr Gly
    210                 215                 220

Trp Ile Pro Glu Gln Leu Lys Asn Ile Asn Leu Gln Thr Gly Gly Asn
225                 230                 235                 240

Ala Trp Ser Ser Gly Pro Ala Pro Pro Pro Gly Thr Pro
                245                 250                 255

Ala Pro Lys Ser Asn Gln His His Lys Ser Gly Gly Gly Ser Thr Thr
            260                 265                 270

Pro Ser Asp Thr Ala Thr Gly Ser Ser Ser Ile Asp Glu Gly Lys Lys
```

```
              275                 280                 285
Ser Gly Thr Gly Gly Ala Ile Ala Gly Ile Val Ile Ser Val Ile
290                 295                 300

Val Val Gly Ala Ile Val Ala Phe Phe Leu Val Lys Arg Lys Ser Lys
305                 310                 315                 320

Lys Ser Ser Ser Asp Leu Glu Lys Gln Asp Asn Gln Ser Phe Ala Pro
                325                 330                 335

Leu Pro Ser Asn Glu Val His Glu Lys Ser Met Gln Thr Ser Ser
                340                 345                 350

Val Thr Asp Leu Lys Thr Phe Asp Thr Ser Ala Ser Ile Asn Leu Lys
                355                 360                 365

Pro Pro Pro Ile Asp Arg His Lys Ser Phe Asp Glu Glu Phe Ser
370                 375                 380

Lys Arg Pro Thr Ile Val Lys Lys Thr Val Thr Ala Pro Ala Asn Val
385                 390                 395                 400

Lys Ser Tyr Ser Ile Ala Glu Leu Gln Ile Ala Thr Gly Ser Phe Ser
                405                 410                 415

Val Asp His Leu Val Gly Glu Gly Ser Phe Gly Arg Val Tyr Arg Ala
                420                 425                 430

Gln Phe Asp Asp Gly Gln Val Leu Ala Val Lys Lys Ile Asp Ser Ser
                435                 440                 445

Ile Leu Pro Asn Asp Leu Thr Asp Asp Phe Ile Gln Ile Ile Ser Asn
450                 455                 460

Ile Ser Asn Leu His His Pro Asn Val Thr Glu Leu Val Gly Tyr Cys
465                 470                 475                 480

Ser Glu Tyr Gly Gln His Leu Leu Val Tyr Glu Phe His Lys Asn Gly
                485                 490                 495

Ser Leu His Asp Phe Leu His Leu Ser Asp Glu Tyr Ser Lys Pro Leu
                500                 505                 510

Ile Trp Asn Ser Arg Val Lys Ile Ala Leu Gly Thr Ala Arg Ala Leu
                515                 520                 525

Glu Tyr Leu His Glu Val Ser Ser Pro Ser Val Val His Lys Asn Ile
530                 535                 540

Lys Ser Ala Asn Ile Leu Leu Asp Thr Glu Leu Asn Pro His Leu Ser
545                 550                 555                 560

Asp Ser Gly Leu Ala Ser Tyr Ile Pro Asn Ala Asp Gln Ile Leu Asn
                565                 570                 575

His Asn Val Gly Ser Gly Tyr Asp Ala Pro Glu Val Ala Leu Ser Gly
                580                 585                 590

Gln Tyr Thr Leu Lys Ser Asp Val Tyr Ser Phe Gly Val Val Met Leu
                595                 600                 605

Glu Leu Leu Ser Gly Arg Asn Pro Phe Asp Ser Arg Pro Arg Ser
                610                 615                 620

Glu Gln Ser Leu Val Arg Trp Ala Thr Pro Gln Leu His Asp Ile Asp
625                 630                 635                 640

Ala Leu Ala Lys Met Val Asp Pro Ala Met Lys Gly Leu Tyr Pro Val
                645                 650                 655

Lys Ser Leu Ser Arg Phe Ala Asp Val Ile Ala Leu Cys Val Gln Pro
                660                 665                 670

Glu Pro Glu Phe Arg Pro Pro Met Ser Glu Val Val Gln Ala Leu Val
                675                 680                 685

Arg Leu Val Gln Arg Ala Asn Met Ser Lys Arg Thr Phe Ser Ser Ser
690                 695                 700
```

Asp His Gly Gly Ser Gln Arg Gly Ser Asp Glu Pro Val Leu Arg Asp
705                 710                 715                 720

Ile

<210> SEQ ID NO 89
<211> LENGTH: 688
<212> TYPE: PRT
<213> ORGANISM: Glycine max

<400> SEQUENCE: 89

Met Asn Leu Phe Phe Phe Leu Lys Pro Leu Ser Ser Leu Met Ile Leu
1               5                   10                  15

Ser Tyr Ile Ile Leu Phe Phe Leu Leu Val Arg Asn Thr Ser Cys Asp
            20                  25                  30

Val Asp Pro Asn Tyr Val Ala Cys Pro Lys Thr Cys Ala Asn Asn
        35                  40                  45

Asn Gln Ser Ile Ser Tyr Pro Phe Tyr Ile Glu Glu Thr Gln Glu Pro
        50                  55                  60

Phe Cys Gly Asn Pro Gly Phe Ala Ile Ser Cys Gly Pro Asn Gly Phe
65                  70                  75                  80

Pro Ile Leu Asn Leu Ser Asn Thr His Tyr Ile Ile His Gln Ile Phe
                85                  90                  95

Tyr Glu Asn Gln Thr Leu Arg Val Ser Asn Ala Ala Phe Ser Val Ser
            100                 105                 110

Arg Ser Asn Thr Thr Asn Ser Lys Gly Cys Leu Pro Val Pro Leu Thr
        115                 120                 125

His Asn Leu Thr Leu Pro Ser Thr Pro Glu Phe Asp Ile Ala Pro Asn
130                 135                 140

Gln Ser Asn Met Arg Leu Phe Tyr Gly Cys Glu Ser Leu Leu Pro Trp
145                 150                 155                 160

Pro Glu Glu His Arg Val Gly Cys Pro Asn Glu Thr Ser Ser Val Leu
                165                 170                 175

Ala Phe Tyr Lys Glu Asp Lys Asn Ile Ser Leu Val Ser Lys Asn Cys
            180                 185                 190

Arg Gly Glu Val Val Asp Thr Ile Val Glu Asp Gly Ile Ile Glu Gly
        195                 200                 205

Gly Val Glu Glu Ala Leu Arg Lys Gly Leu Leu Leu Thr Trp Lys Ala
210                 215                 220

Gly Asn Cys Ser Glu Cys His Ser Ser Gly Gly Arg Cys Gly Phe Asp
225                 230                 235                 240

Ser Ile Met Tyr Thr Phe Arg Cys Phe Cys Thr Asp Arg Val His Ser
                245                 250                 255

Ala Lys Cys Asp Pro Asp Asn Gly Pro Val Ile Lys Lys Gly Ser Ser
            260                 265                 270

Leu Lys Leu Val Ile Gly Ile Gly Ile Pro Ser Met Leu Ala Ile Gly
        275                 280                 285

Leu Leu Phe Leu Phe Leu Leu Tyr Lys Arg Lys Tyr Ala Thr Ser Gly
    290                 295                 300

Gly Gln Leu Glu Ser Arg Asp Ser Tyr Ser Asp Ser Ser Ser Asn Pro
305                 310                 315                 320

His Arg Glu Thr Ser Ser Glu Tyr Phe Gly Val Pro Leu Phe Leu Tyr
                325                 330                 335

Glu Gln Leu Lys Glu Ala Thr Asn Asn Phe Asp His Thr Lys Glu Leu
            340                 345                 350

-continued

Gly Asp Gly Gly Phe Gly Thr Val Tyr His Gly Lys Leu Pro Asp Gly
            355                 360                 365

Arg Glu Val Ala Val Lys Arg Leu Tyr Glu His Asn Trp Lys Arg Val
370                 375                 380

Glu Gln Phe Met Asn Glu Val Lys Ile Leu Thr Arg Leu Arg His Lys
385                 390                 395                 400

Tyr Leu Val Ser Leu Tyr Gly Cys Thr Ser Arg His Ser Arg Glu Leu
            405                 410                 415

Leu Leu Val Tyr Glu Tyr Ile Ser Asn Gly Thr Val Ala Cys His Leu
            420                 425                 430

His Gly Glu Leu Ala Lys Pro Gly Ser Leu Pro Trp Ser Ile Arg Met
            435                 440                 445

Lys Ile Ala Ile Glu Thr Ala Ile Ala Leu Thr Tyr Leu His Ala Ser
            450                 455                 460

Asp Ile Ile His Arg Asp Val Lys Thr Asn Asn Ile Leu Leu Asp Asn
465                 470                 475                 480

Asn Phe Cys Val Lys Val Ala Asp Phe Gly Leu Ser Arg Asp Phe Pro
            485                 490                 495

Asn Asn Val Thr His Val Ser Thr Ala Pro Gln Gly Ser Pro Gly Tyr
            500                 505                 510

Leu Asp Pro Glu Tyr Tyr Asn Cys Tyr Gln Leu Thr Ser Lys Ser Asp
            515                 520                 525

Val Tyr Ser Phe Gly Val Val Leu Ile Glu Leu Ile Ser Ser Lys Pro
            530                 535                 540

Ala Val Asp Met Asn Arg Ser Arg Asp Glu Ile Asn Leu Ser Asn Leu
545                 550                 555                 560

Ala Val Arg Lys Ile Gln Glu Ser Ala Ile Ser Glu Leu Val Asp Pro
            565                 570                 575

Ser Leu Gly Phe Asp Ser Asp Asn Gly Ile Lys Gly Met Ile Val Ser
            580                 585                 590

Val Ala Gly Leu Ala Phe Gln Cys Leu Gln Arg Glu Lys Asp Leu Arg
            595                 600                 605

Pro Ser Met Asp Glu Val Leu Asp Glu Leu Arg Arg Ile Glu Ser Gly
            610                 615                 620

Lys Asp Glu Gly Glu Val Gln Asp Glu Gly Asp Val Asn Gly Ala Ala
625                 630                 635                 640

Val Ser His Ser Ser Ala His Ser Pro Pro Ala Ser Pro Glu Trp
            645                 650                 655

Glu Glu Val Arg Leu Leu Arg Asn Ile Lys Pro Thr Ser Pro Asn Thr
            660                 665                 670

Val Thr Asp Lys Trp Glu Ser Lys Cys Thr Thr Pro Asn Ile Ser Gly
            675                 680                 685

<210> SEQ ID NO 90
<211> LENGTH: 675
<212> TYPE: PRT
<213> ORGANISM: Glycine max

<400> SEQUENCE: 90

Met Ala Asp Leu Ser Cys Ile His Leu Phe Phe Leu Cys Cys Leu Phe
1               5                   10                  15

Leu Lys Phe Ile Pro Gln Gly Asn Ala Ser Met Phe His Thr Ala Phe
            20                  25                  30

Cys Asp Asn Lys Glu Gly Asn Tyr Thr Ala Asn Ser Thr Tyr Asn Thr

```
            35                  40                  45
Asn Leu Asn Thr Leu Leu Ser Ser Leu Ser Ser His Thr Glu Ile Asn
        50                  55                  60
Tyr Gly Phe Tyr Asn Phe Ser Tyr Gly Gln Asn Pro Asp Lys Val Asn
 65                  70                  75                  80
Ala Ile Gly Leu Cys Arg Gly Asp Val Glu Pro His Glu Cys Arg Ser
                85                  90                  95
Cys Leu Asn Asp Ser Arg Val Thr Ile Lys Gln Phe Cys Pro Asn Gln
               100                 105                 110
Lys Lys Ala Leu Leu Trp Leu Asn Thr Ser Lys Cys Met Leu Arg Tyr
           115                 120                 125
Ser Pro Arg Ser Ile Phe Gly Ile Met Glu Ile Glu Pro Ser Gln Ser
130                 135                 140
Leu Met Asn Ile Asn Asn Val Thr Glu Pro Asp Lys Phe Ser Gln Ala
145                 150                 155                 160
Leu Ala Asn Leu Met Arg Asn Leu Lys Gly Val Ala Ala Ser Gly Asp
               165                 170                 175
Ser Arg Arg Lys Tyr Ala Thr Asp Asn Val Thr Ala Ser Ser Phe Gln
           180                 185                 190
Thr Ile Tyr Gly Met Ala Glu Cys Thr Pro Asp Leu Ser Glu Lys Asp
       195                 200                 205
Cys Asn Asp Cys Leu Asp Gly Ala Ile Ser Lys Ile Pro Thr Cys Cys
210                 215                 220
Gln Asp Lys Ile Gly Gly Arg Val Leu Arg Pro Ser Cys Asn Ile Arg
225                 230                 235                 240
Phe Glu Ser Ala Ser Phe Tyr Glu Asn Thr Pro Ile Leu Asn Pro Asp
               245                 250                 255
Val Pro Pro Pro Ser Pro Ala Val Ala Ile Pro Ser Ile Asn Ser
           260                 265                 270
Thr Ser Pro Lys Glu Ser Ser Asn Thr Ile Arg Ile Val Ile Ala Ile
       275                 280                 285
Val Val Pro Thr Val Val Val Pro Leu Ile Cys Leu Cys Ile Tyr
290                 295                 300
Ser Arg Arg Ser Lys Ala Arg Lys Ser Ser Leu Val Lys Gln His Glu
305                 310                 315                 320
Asp Asp Asp Glu Ile Glu Ile Ala Gln Ser Leu Gln Phe Asn Phe Asp
               325                 330                 335
Thr Ile Arg Val Ala Thr Glu Asp Phe Ser Asp Ser Asn Lys Leu Gly
           340                 345                 350
Gln Gly Gly Phe Gly Ala Val Tyr Arg Gly Arg Leu Ser Asp Gly Gln
       355                 360                 365
Met Ile Ala Val Lys Arg Leu Ser Arg Glu Ser Ser Gln Gly Asp Thr
370                 375                 380
Glu Phe Lys Asn Glu Val Leu Leu Val Ala Lys Leu Gln His Arg Asn
385                 390                 395                 400
Leu Val Arg Leu Leu Gly Phe Cys Leu Glu Gly Lys Glu Arg Leu Leu
               405                 410                 415
Ile Tyr Glu Tyr Val Pro Asn Lys Ser Leu Asp Tyr Phe Ile Phe Asp
           420                 425                 430
Pro Thr Lys Lys Ala Gln Leu Asn Trp Glu Met Arg Tyr Lys Ile Ile
       435                 440                 445
Thr Gly Val Ala Arg Gly Leu Leu Tyr Leu His Glu Asp Ser His Leu
450                 455                 460
```

```
Arg Ile Ile His Arg Asp Leu Lys Ala Ser Asn Ile Leu Leu Asn Glu
465                 470                 475                 480

Glu Met Asn Pro Lys Ile Ala Asp Phe Gly Met Ala Arg Leu Val Leu
                485                 490                 495

Met Asp Gln Thr Gln Ala Asn Thr Asn Arg Ile Val Gly Thr Tyr Gly
            500                 505                 510

Tyr Met Ala Pro Glu Tyr Ala Met His Gly Gln Phe Ser Met Lys Ser
            515                 520                 525

Asp Val Phe Ser Phe Gly Val Leu Val Leu Glu Ile Ser Gly His
            530                 535                 540

Lys Asn Ser Gly Ile Arg His Gly Glu Asn Val Glu Asp Leu Leu Ser
545                 550                 555                 560

Phe Ala Trp Arg Asn Trp Arg Glu Gly Thr Ala Val Lys Ile Val Asp
                565                 570                 575

Pro Ser Leu Asn Asn Asn Ser Arg Asn Glu Met Leu Arg Cys Ile His
            580                 585                 590

Ile Gly Leu Leu Cys Val Gln Glu Asn Leu Ala Asp Arg Pro Thr Met
            595                 600                 605

Thr Thr Ile Met Leu Met Leu Asn Ser Tyr Ser Leu Ser Leu Pro Ile
610                 615                 620

Pro Ser Lys Pro Ala Phe Tyr Val Ser Ser Arg Thr Gly Ser Ile Ser
625                 630                 635                 640

Ala Thr Gln Ser Trp Gly Tyr Ser Ser Gly Glu Ser Arg Ser Arg Glu
                645                 650                 655

Leu Thr Ile Lys Ser Ala Gln Glu Ala Glu Asn Glu Phe Thr Asp Pro
                660                 665                 670

Tyr Pro Arg
        675

<210> SEQ ID NO 91
<211> LENGTH: 869
<212> TYPE: PRT
<213> ORGANISM: Glycine max

<400> SEQUENCE: 91

Met Asp Thr Thr Ser Thr Gln Ile Ala Ser Gly Thr Ile Leu Phe Leu
1               5                   10                  15

Leu Leu Leu Phe Phe Pro Tyr Leu Ser Ile Ala Asp Val Ile Tyr Ser
                20                  25                  30

Pro Val Glu Leu Phe Ser Ile Asn Cys Gly Ser Ser Ser Asn Leu Ser
            35                  40                  45

Thr Arg Asp Gly Arg Asn Trp Thr Ala Asp Ile Lys Phe Leu Ser Glu
50                  55                  60

Asn Lys Asp Ser Val Ala Ala Pro Ala Leu Thr Pro Ser Thr Leu Glu
65                  70                  75                  80

Gly Pro Tyr Thr Asp Ala Arg Leu Ser His Ser Gln Phe Thr Tyr Ser
                85                  90                  95

Phe Pro Val Ser Thr Gly Pro Lys Phe Leu Arg Leu Phe Phe Tyr Ser
            100                 105                 110

Thr Ser Tyr Gln Asn Phe His Arg Ser Lys Ala Tyr Phe Ser Val Lys
            115                 120                 125

Ala Gly Pro Tyr Thr Leu Leu Gln Asn Phe Asn Ala Ser Leu His Ala
130                 135                 140

Asp Ala Gly Asn Glu Pro Gly Asp Tyr Leu Phe Arg Glu Tyr Cys Ile
```

```
                145                 150                 155                 160
            Asn Leu Lys Asp Gly Asp Arg Leu Asn Ile Thr Phe Ile Ala Ser Lys
                            165                 170                 175

Thr Ser Gln Asn Pro Asp Ser Tyr Ala Phe Ile Asn Gly Ile Glu Ile
                            180                 185                 190

Val Ser Met Pro Pro Phe Leu Tyr Tyr Thr Asn Pro His Asp Val Asp
                            195                 200                 205

Ile Thr Gly Leu Pro His Leu Val Gly Val Asn Thr Asn Leu Phe Pro
                            210                 215                 220

Ile Glu Asn Asn Phe Thr Leu Glu Thr Lys Tyr Arg Leu Arg Val Gly
            225                 230                 235                 240

Asp Gln Glu Ile Pro Ala Ser Gln Asp Thr Gly Met Leu Arg Ser Trp
                            245                 250                 255

Asp Val Asp Ser Lys Tyr Val Thr Thr Gln Ser Val Leu Ser Leu Asp
                            260                 265                 270

Ile Gly Pro Gly Ile Lys Leu Arg Phe Thr Lys Ile Pro Asn Tyr Thr
                            275                 280                 285

Ala Pro Asp Thr Val Tyr Arg Ser Val Arg Asn Met Gly Asn Asn Gly
                            290                 295                 300

Thr Ile Asn Met Gly Phe Asn Leu Thr Trp Gln Leu Pro Ile Asp Ser
            305                 310                 315                 320

Gly Phe Thr Tyr Leu Leu Arg Leu His Phe Cys Gln Leu Asn Pro Glu
                            325                 330                 335

Met Lys Asn Pro Gly Tyr Gln Ser Phe Phe Ile Phe Val Gln Asp Gln
                            340                 345                 350

Leu Val Glu Lys Trp Ala Asp Ile Leu Ser Trp Ser Asp Lys Gln Glu
                            355                 360                 365

Gly Val Pro Val Val Lys Gln Tyr Val Val Phe Ile Pro Gly Asn Gln
                            370                 375                 380

Gln Glu Thr Leu Asn Leu Ser Leu Lys Met His Pro Asn Pro Gln Ser
            385                 390                 395                 400

Leu Ala Lys Asp Ala Gln Ile Asn Ala Ile Glu Leu Phe Lys Ile Asn
                            405                 410                 415

Asn Ser Thr Gly Ser Leu Ala Gly Pro Asn Pro Asp Pro Asp Arg Leu
                            420                 425                 430

Pro Glu Thr Pro Lys Val Pro Leu Gln Arg Pro Asn Asn Lys Ser Ser
                            435                 440                 445

Gly Thr Thr Arg Thr Leu Ala Ala Val Ala Gly Ala Val Ser Ala
                450                 455                 460

Ala Val Leu Leu Ser Phe Ile Val Ala Phe Phe Leu Ile Lys Arg Lys
            465                 470                 475                 480

Lys Lys Met Gly Ser Lys Glu Lys Asp Glu Thr Pro Leu Gly Gly Gly
                            485                 490                 495

Leu Ser Ser Leu Pro Thr Asn Leu Cys Arg His Phe Ser Ile Ala Glu
                            500                 505                 510

Ile Arg Ala Ser Thr Asn Asn Phe Asp Glu His Phe Val Val Gly Met
                            515                 520                 525

Gly Gly Phe Gly Asn Val Tyr Lys Gly Tyr Ile Asp Asp Gly Ser Thr
                            530                 535                 540

Arg Val Ala Ile Lys Arg Leu Lys Pro Asp Ser Arg Gln Gly Ala Gln
            545                 550                 555                 560

Glu Phe Met Asn Glu Ile Glu Met Leu Ser Gln Leu Arg His Leu His
                            565                 570                 575
```

```
Leu Val Ser Leu Val Gly Tyr Cys Tyr Glu Ser Asn Glu Met Ile Leu
            580                 585                 590

Val Tyr Asp Phe Met Asp Arg Gly Thr Leu Arg Glu His Leu Tyr Asp
        595                 600                 605

Thr Asp Asn Pro Ser Leu Ser Trp Lys Gln Arg Leu Gln Ile Cys Val
    610                 615                 620

Gly Ala Ala Arg Gly Leu His Tyr Leu His Thr Gly Ala Lys His Thr
625                 630                 635                 640

Ile Ile His Arg Asp Val Lys Ser Thr Asn Ile Leu Leu Asp Glu Lys
                645                 650                 655

Trp Val Ala Lys Val Ser Asp Phe Gly Leu Ser Arg Ile Gly Pro Ile
            660                 665                 670

Ser Ser Ser Met Thr His Val Ser Thr Gln Val Lys Gly Ser Val Gly
        675                 680                 685

Tyr Ile Asp Pro Glu Tyr Tyr Lys Arg Gln Arg Leu Thr Glu Lys Ser
    690                 695                 700

Asp Val Tyr Ser Phe Gly Val Val Leu Leu Glu Val Leu Ser Gly Arg
705                 710                 715                 720

Gln Pro Leu Leu Arg Trp Glu Glu Lys Gln Arg Ile Ser Leu Val Asn
                725                 730                 735

Trp Ala Lys His Cys Asn Glu Lys Gly Thr Leu Ser Glu Ile Val Asp
            740                 745                 750

Ala Lys Leu Lys Gly Gln Ile Ala Pro Gln Cys Leu Gln Arg Tyr Gly
        755                 760                 765

Glu Val Ala Leu Ser Cys Leu Leu Glu Asp Gly Thr Gln Arg Pro Ser
770                 775                 780

Met Asn Asp Ala Val Arg Met Leu Glu Phe Val Leu His Leu Gln Glu
785                 790                 795                 800

Gly Ala Val Asn Glu Val Thr Glu Ser Glu Asp Thr Glu Asp Val Phe
                805                 810                 815

Ser Ser Ser His Ser Ser Leu Leu Phe Ser Asp Tyr Ser Lys Ser Thr
            820                 825                 830

Ala Leu Ser Met Ala Thr Asn Val Gly Asp Cys Ser Tyr Gly Ser Lys
        835                 840                 845

Asp Ser Glu Glu Arg Ser Ile Pro Asp His Leu Phe Ser Glu Ile Lys
850                 855                 860

Asp Pro Lys Gly Arg
865

<210> SEQ ID NO 92
<211> LENGTH: 674
<212> TYPE: PRT
<213> ORGANISM: Artificial Sequence
<220> FEATURE:
<223> OTHER INFORMATION: Kinase dead varient

<400> SEQUENCE: 92

Met Lys Lys Val Cys His Cys Pro Ile Phe Leu Ala Leu Ala Leu Cys
1               5                   10                  15

Leu Cys Ile Leu Cys Val Ala Ala Glu Ala Ala Gly Gln Asn Asp Thr
            20                  25                  30

Leu Ala Leu Thr Glu Phe Arg Leu Gln Thr Asp Thr His Gly Asn Leu
        35                  40                  45

Leu Thr Asn Trp Thr Gly Ala Asp Ala Cys Ser Ala Ala Trp Arg Gly
    50                  55                  60
```

-continued

```
Val Glu Cys Ser Pro Asn Gly Arg Val Val Gly Leu Thr Leu Pro Ser
 65                  70                  75                  80

Leu Asn Leu Arg Gly Pro Ile Asp Thr Leu Ser Thr Leu Thr Tyr Leu
                 85                  90                  95

Arg Phe Leu Asp Leu His Glu Asn Arg Leu Asn Gly Thr Ile Ser Pro
                100                 105                 110

Leu Leu Asn Cys Thr Ser Leu Glu Leu Leu Tyr Leu Ser Arg Asn Asp
            115                 120                 125

Phe Ser Gly Glu Ile Pro Ala Glu Ile Ser Ser Leu Arg Leu Leu Leu
130                 135                 140

Arg Leu Asp Ile Ser Asp Asn Asn Ile Arg Gly Pro Ile Pro Thr Gln
145                 150                 155                 160

Leu Ala Lys Leu Thr His Leu Leu Thr Leu Arg Leu Gln Asn Asn Ala
                165                 170                 175

Leu Ser Gly His Val Pro Asp Leu Ser Ala Ser Leu Leu Asn Leu Thr
                180                 185                 190

Val Leu Asn Val Thr Asn Asn Glu Leu Arg Gly His Val Pro Asp Ser
            195                 200                 205

Met Leu Thr Lys Phe Gly Asn Val Ser Phe Ser Gly Asn His Ala Leu
            210                 215                 220

Cys Gly Ser Thr Pro Leu Pro Lys Cys Ser Glu Thr Glu Pro Asp Thr
225                 230                 235                 240

Glu Thr Thr Thr Ile Thr Val Pro Ala Lys Pro Ser Ser Phe Pro Gln
                245                 250                 255

Thr Ser Ser Val Thr Val Pro Asp Thr Pro Arg Lys Lys Gly Leu Ser
                260                 265                 270

Ala Gly Val Ile Val Ala Ile Val Val Ala Val Cys Val Ala Val Leu
                275                 280                 285

Val Ala Thr Ser Phe Ala Val Ala His Cys Cys Ala Arg Gly Ser Thr
290                 295                 300

Ser Gly Ser Val Val Gly Ser Glu Thr Ala Lys Arg Lys Ser Gly Ser
305                 310                 315                 320

Ser Ser Gly Ser Glu Lys Lys Val Tyr Gly Asn Gly Asn Leu Asp
                325                 330                 335

Arg Asp Ser Asp Gly Thr Asn Thr Glu Thr Glu Arg Ser Lys Leu Val
                340                 345                 350

Phe Phe Asp Arg Arg Asn Gln Phe Glu Leu Glu Asp Leu Leu Arg Ala
                355                 360                 365

Ser Ala Glu Met Leu Gly Lys Gly Ser Leu Gly Thr Val Tyr Arg Ala
                370                 375                 380

Val Leu Asp Asp Gly Cys Thr Val Ala Val Arg Arg Leu Lys Asp Ala
385                 390                 395                 400

Asn Pro Cys Glu Arg Asn Glu Phe Glu Gln Tyr Met Asp Val Val Gly
                405                 410                 415

Lys Leu Lys His Pro Asn Ile Val Arg Leu Arg Ala Tyr Tyr Tyr Ala
                420                 425                 430

Lys Glu Glu Lys Leu Leu Val Tyr Asp Tyr Leu Pro Asn Gly Ser Leu
                435                 440                 445

His Ala Leu Leu His Gly Asn Arg Gly Pro Gly Arg Ile Pro Leu Asp
                450                 455                 460

Trp Thr Thr Arg Ile Ser Leu Met Leu Gly Ala Ala Arg Gly Leu Ala
465                 470                 475                 480
```

```
Arg Ile His Ala Glu Tyr Asn Ala Ser Lys Ile Pro His Gly Asn Val
                485                 490                 495

Arg Ser Ser Asn Val Leu Leu Asp Lys Asn Gly Val Ala Leu Ile Ser
            500                 505                 510

Asp Phe Gly Leu Ser Leu Leu Leu Asn Pro Val His Ala Ile Ala Arg
        515                 520                 525

Leu Gly Gly Tyr Arg Ala Pro Glu Gln Val Glu Val Lys Arg Leu Ser
    530                 535                 540

Gln Glu Ala Asp Val Tyr Gly Phe Gly Val Leu Leu Glu Val Leu
545                 550                 555                 560

Thr Gly Arg Ala Pro Ser Lys Glu Tyr Thr Ser Pro Ala Arg Glu Ala
                565                 570                 575

Glu Val Asp Leu Pro Lys Trp Val Lys Ser Val Val Lys Glu Glu Trp
            580                 585                 590

Thr Ser Glu Val Phe Asp Gln Glu Leu Leu Arg Tyr Lys Asn Ile Glu
        595                 600                 605

Asp Glu Leu Val Ala Met Leu His Val Gly Leu Ala Cys Val Ala Ala
    610                 615                 620

Gln Ala Glu Lys Arg Pro Cys Met Leu Glu Val Val Lys Met Ile Glu
625                 630                 635                 640

Glu Ile Arg Val Glu Glu Ser Pro Leu Gly Asp Asp Tyr Asp Glu Ala
                645                 650                 655

Arg Ser Arg Thr Ser Leu Ser Pro Ser Leu Ala Thr Thr Glu Asp Asn
            660                 665                 670

Leu Ala

<210> SEQ ID NO 93
<211> LENGTH: 978
<212> TYPE: PRT
<213> ORGANISM: Artificial Sequence
<220> FEATURE:
<223> OTHER INFORMATION: kinase dead varient

<400> SEQUENCE: 93

Met Gln Ala Leu Phe Ser Ser Met Arg Val Phe Leu Arg Leu Val Trp
1               5                   10                  15

Leu Leu Glu Leu Leu Cys Val Ala Val Thr Ala Val Asn Pro Ser Leu
            20                  25                  30

Asn Asp Asp Val Leu Gly Leu Ile Val Phe Lys Ala Asp Ile Arg Asp
        35                  40                  45

Pro Lys Gly Lys Leu Ala Ser Trp Asn Glu Asp Glu Ser Ala Cys
    50                  55                  60

Gly Gly Ser Trp Val Gly Val Lys Cys Asn Pro Arg Ser Asn Arg Val
65                  70                  75                  80

Val Glu Val Asn Leu Asp Gly Phe Ser Leu Ser Gly Arg Ile Gly Arg
                85                  90                  95

Gly Leu Gln Arg Leu Gln Phe Leu Arg Lys Leu Ser Leu Ala Asn Asn
            100                 105                 110

Asn Leu Thr Gly Gly Ile Asn Pro Asn Ile Ala Arg Ile Asp Asn Leu
        115                 120                 125

Arg Val Ile Asp Leu Ser Gly Asn Ser Leu Ser Gly Glu Val Ser Glu
    130                 135                 140

Asp Val Phe Arg Gln Cys Gly Ser Leu Arg Thr Val Ser Leu Ala Arg
145                 150                 155                 160

Asn Arg Phe Ser Gly Ser Ile Pro Ser Thr Leu Gly Ala Cys Ser Ala
```

```
            165                 170                 175
Leu Ala Ala Ile Asp Leu Ser Asn Asn Gln Phe Ser Gly Ser Val Pro
            180                 185                 190

Ser Arg Val Trp Ser Leu Ser Ala Leu Arg Ser Leu Asp Leu Ser Asp
            195                 200                 205

Asn Leu Leu Glu Gly Glu Ile Pro Lys Gly Ile Glu Ala Met Lys Asn
            210                 215                 220

Leu Arg Ser Val Ser Val Ala Arg Asn Arg Leu Thr Gly Asn Val Pro
225                 230                 235                 240

Tyr Gly Phe Gly Ser Cys Leu Leu Arg Ser Ile Asp Leu Gly Asp
                    245                 250                 255

Asn Ser Phe Ser Gly Ser Ile Pro Gly Asp Phe Lys Glu Leu Thr Leu
            260                 265                 270

Cys Gly Tyr Ile Ser Leu Arg Gly Asn Ala Phe Ser Gly Gly Val Pro
            275                 280                 285

Gln Trp Ile Gly Glu Met Arg Gly Leu Glu Thr Leu Asp Leu Ser Asn
            290                 295                 300

Asn Gly Phe Thr Gly Gln Val Pro Ser Ser Ile Gly Asn Leu Gln Ser
305                 310                 315                 320

Leu Lys Met Leu Asn Phe Ser Gly Asn Gly Leu Thr Gly Ser Leu Pro
                    325                 330                 335

Glu Ser Met Ala Asn Cys Thr Lys Leu Leu Val Leu Asp Val Ser Arg
            340                 345                 350

Asn Ser Met Ser Gly Trp Leu Pro Leu Trp Val Phe Lys Ser Asp Leu
            355                 360                 365

Asp Lys Val Leu Val Ser Glu Asn Val Gln Ser Gly Ser Lys Lys Ser
370                 375                 380

Pro Leu Phe Ala Met Ala Glu Leu Ala Val Gln Ser Leu Gln Val Leu
385                 390                 395                 400

Asp Leu Ser His Asn Ala Phe Ser Gly Glu Ile Thr Ser Ala Val Gly
            405                 410                 415

Gly Leu Ser Ser Leu Gln Val Leu Asn Leu Ala Asn Asn Ser Leu Gly
            420                 425                 430

Gly Pro Ile Pro Pro Ala Val Gly Glu Leu Lys Thr Cys Ser Ser Leu
            435                 440                 445

Asp Leu Ser Tyr Asn Lys Leu Asn Gly Ser Ile Pro Trp Glu Ile Gly
            450                 455                 460

Gly Ala Val Ser Leu Lys Glu Leu Val Leu Glu Lys Asn Phe Leu Asn
465                 470                 475                 480

Gly Lys Ile Pro Thr Ser Ile Glu Asn Cys Ser Leu Leu Thr Thr Leu
            485                 490                 495

Ile Leu Ser Gln Asn Lys Leu Ser Gly Pro Ile Pro Ala Ala Val Ala
            500                 505                 510

Lys Leu Thr Asn Leu Gln Thr Val Asp Val Ser Phe Asn Asn Leu Thr
            515                 520                 525

Gly Ala Leu Pro Lys Gln Leu Ala Asn Leu Ala Asn Leu Leu Thr Phe
            530                 535                 540

Asn Leu Ser His Asn Asn Leu Gln Gly Glu Leu Pro Ala Gly Gly Phe
545                 550                 555                 560

Phe Asn Thr Ile Thr Pro Ser Ser Val Ser Gly Asn Pro Ser Leu Cys
                    565                 570                 575

Gly Ala Ala Val Asn Lys Ser Cys Pro Ala Val Leu Pro Lys Pro Ile
            580                 585                 590
```

Val Leu Asn Pro Asn Thr Ser Thr Asp Thr Gly Pro Ser Ser Leu Pro
            595                 600                 605

Pro Asn Leu Gly His Lys Arg Ile Ile Leu Ser Ile Ser Ala Leu Ile
610                 615                 620

Ala Ile Gly Ala Ala Val Ile Val Ile Gly Val Ile Ser Ile Thr
625                 630                 635                 640

Val Leu Asn Leu Arg Val Arg Ser Ser Thr Ser Arg Asp Ala Ala Ala
            645                 650                 655

Leu Thr Phe Ser Ala Gly Asp Glu Phe Ser His Ser Pro Thr Thr Asp
            660                 665                 670

Ala Asn Ser Gly Lys Leu Val Met Phe Ser Gly Glu Pro Asp Phe Ser
            675                 680                 685

Ser Gly Ala His Ala Leu Leu Asn Lys Asp Cys Glu Leu Gly Arg Gly
            690                 695                 700

Gly Phe Gly Ala Val Tyr Gln Thr Val Leu Arg Asp Gly His Ser Val
705                 710                 715                 720

Ala Ile Lys Arg Leu Thr Val Ser Ser Leu Val Lys Ser Gln Glu Asp
            725                 730                 735

Phe Glu Arg Glu Val Lys Lys Leu Gly Lys Ile Arg His Gln Asn Leu
            740                 745                 750

Val Glu Leu Glu Gly Tyr Tyr Trp Thr Pro Ser Leu Gln Leu Leu Ile
            755                 760                 765

Tyr Glu Tyr Leu Ser Gly Gly Ser Leu Tyr Lys His Leu His Glu Gly
            770                 775                 780

Ser Gly Gly Asn Phe Leu Ser Trp Asn Glu Arg Phe Asn Val Ile Leu
785                 790                 795                 800

Gly Thr Ala Lys Ala Leu Ala His Leu His His Ser Asn Ile Ile His
            805                 810                 815

Tyr Asn Ile Arg Ser Thr Asn Val Leu Leu Asp Ser Tyr Gly Glu Pro
            820                 825                 830

Lys Val Gly Asp Phe Gly Leu Ala Arg Leu Leu Pro Met Leu Asp Arg
            835                 840                 845

Tyr Val Leu Ser Ser Lys Ile Gln Ser Ala Leu Gly Tyr Met Ala Pro
            850                 855                 860

Glu Phe Ala Cys Lys Thr Val Lys Ile Thr Glu Lys Cys Asp Val Tyr
865                 870                 875                 880

Gly Phe Gly Val Leu Val Leu Glu Ile Val Thr Gly Lys Arg Pro Val
            885                 890                 895

Glu Tyr Met Glu Asp Asp Val Val Leu Cys Asp Met Val Arg Gly
                900                 905                 910

Ala Leu Glu Glu Gly Arg Val Glu Glu Cys Ile Asp Glu Arg Leu Gln
            915                 920                 925

Gly Lys Phe Pro Ala Glu Glu Ala Ile Pro Val Met Lys Leu Gly Leu
            930                 935                 940

Ile Cys Thr Ser Gln Val Pro Ser Asn Arg Pro Asp Met Gly Glu Val
945                 950                 955                 960

Val Asn Ile Leu Glu Leu Ile Arg Cys Pro Ser Glu Gly Gln Glu Glu
            965                 970                 975

Leu Ala

<210> SEQ ID NO 94
<211> LENGTH: 419
<212> TYPE: PRT

<213> ORGANISM: Artificial Sequence
<220> FEATURE:
<223> OTHER INFORMATION: kinase dead varient

<400> SEQUENCE: 94

```
Met Asp Ser Ala Arg Thr Ala Pro Pro Trp Gln Glu Leu Asp Leu
1               5                   10                  15

Asp Ser Leu Lys Pro Leu Lys Val Leu Gly Lys Gly Met Gly Thr
            20                  25                  30

Val Phe Leu Val Gln Ala Ala Asn Asn Thr Arg Phe Ala Leu Arg Val
        35                  40                  45

Val Asp Lys Thr Cys Val His Ala Lys Leu Asp Ala Glu Arg Arg Ala
    50                  55                  60

Arg Trp Glu Ile Gln Val Leu Ser Thr Leu Ser His Pro Phe Leu Pro
65                  70                  75                  80

Ser Leu Met Gly Thr Phe Glu Ser Pro Gln Phe Leu Ala Trp Ala Leu
                85                  90                  95

Pro Tyr Cys Pro Gly Gly Asp Leu Asn Val Leu Arg Tyr Arg Gln Thr
            100                 105                 110

Asp Arg Ala Phe Ser Pro Ala Val Ile Arg Phe Tyr Val Ala Glu Ile
        115                 120                 125

Leu Cys Ala Leu Asp His Leu His Ser Met Gly Ile Ala Tyr Arg Asp
130                 135                 140

Leu Arg Pro Glu Asn Val Leu Val Gln Asn Thr Gly His Ile Thr Leu
145                 150                 155                 160

Thr Asp Phe Asp Leu Ser Arg Lys Leu Asn Pro Lys Pro Lys Pro Asn
                165                 170                 175

Pro Gln Val Pro Ser Ile Pro Leu Pro Asn Ser Asn Val Pro Glu Pro
            180                 185                 190

Arg Arg Lys His Arg Arg Asn Phe Ser Arg Trp Ile Ser Leu Phe Pro
        195                 200                 205

Pro Asp Gly Thr His His Asn Asn Lys Asn Gly Leu Lys Lys Ala
210                 215                 220

Lys Ser Ala Arg Val Ser Pro Val Ser Arg Arg Lys Pro Ser Phe Ser
225                 230                 235                 240

Asn Gly Glu Arg Ser Asn Ser Phe Val Gly Thr Glu Glu Tyr Val Ser
                245                 250                 255

Pro Glu Val Val Arg Gly Asp Gly His Glu Phe Ala Val Asp Trp Trp
            260                 265                 270

Ala Leu Gly Ile Leu Ile Tyr Glu Met Leu Tyr Gly Thr Thr Pro Phe
        275                 280                 285

Lys Gly Lys Asn Arg Lys Glu Thr Phe Arg Asn Val Ile Thr Lys Pro
290                 295                 300

Pro Val Phe Val Gly Lys Arg Thr Ala Leu Thr Asp Leu Ile Glu Lys
305                 310                 315                 320

Leu Leu Glu Lys Asp Pro Thr Lys Arg Leu Gly Tyr Thr Arg Gly Ala
                325                 330                 335

Val Glu Ile Lys Glu His Glu Phe Phe Arg Gly Val Arg Trp Glu Leu
            340                 345                 350

Leu Thr Glu Val Val Arg Pro Pro Phe Ile Pro Thr Arg Asp Asp Gly
        355                 360                 365

Ala Gly Asp Ser Thr Asp Arg Ile Ser Asp Arg Asn Cys Gly Phe Asp
370                 375                 380

Ile Arg Gly Tyr Phe Leu Asn Leu Lys Ser Ser Pro Ser Leu Pro Gly
```

```
385                 390                 395                 400
Ser Pro Leu Pro Ser Pro Ser Cys Arg Phe Lys Lys Asn Val Ser Leu
                405                 410                 415

Thr Glu Phe

<210> SEQ ID NO 95
<211> LENGTH: 688
<212> TYPE: PRT
<213> ORGANISM: Artificial Sequence
<220> FEATURE:
<223> OTHER INFORMATION: kinase dead varient

<400> SEQUENCE: 95

Met Met Lys His Tyr His Val Leu Tyr Met Phe Leu Phe Phe Leu Pro
1               5                   10                  15

Ile Ser Thr Leu Ser Leu His His Asn Asp Thr His Ala Leu Thr Leu
            20                  25                  30

Phe Arg Arg Gln Ser Asp Leu His Gly Tyr Leu Leu Ser Asn Trp Thr
        35                  40                  45

Gly His Asp Ala Cys Asn Ser Ala Trp Arg Gly Val Leu Cys Ser Pro
    50                  55                  60

Asn Gly Arg Val Thr Ala Leu Ser Leu Pro Ser Leu Asn Leu Arg Gly
65                  70                  75                  80

Pro Leu Asp Pro Leu Thr Pro Leu Thr His Leu Arg Leu Leu Asn Leu
                85                  90                  95

His Asp Asn Arg Leu Asn Gly Thr Val Ser Thr Leu Phe Ser Asn Cys
            100                 105                 110

Thr Asn Leu Gln Leu Leu Tyr Leu Ser Ser Asn Asp Phe Ser Gly Glu
        115                 120                 125

Ile Pro Pro Glu Ile Ser Ser Leu Lys Ser Leu Arg Leu Asp Leu
    130                 135                 140

Ser Asp Asn Asn Leu Arg Gly Lys Val Asp Val Ile Ser Asn Leu Thr
145                 150                 155                 160

Gln Leu Ile Thr Leu Arg Leu Gln Asn Asn Leu Leu Ser Gly Glu Ile
                165                 170                 175

Pro Asp Leu Ser Ser Ser Met Lys Asn Leu Lys Glu Leu Asn Met Thr
            180                 185                 190

Asn Asn Glu Phe Tyr Gly Arg Leu Pro Ser Pro Met Leu Lys Lys Phe
        195                 200                 205

Ser Ser Thr Thr Phe Ser Gly Asn Glu Gly Leu Cys Gly Ala Ser Leu
    210                 215                 220

Phe Pro Gly Cys Ser Phe Thr Thr Pro Asn Asn Asp Ser
225                 230                 235                 240

Asn Asn Asn Asn Asp Asn Asn Ser Asn Glu Lys Glu Pro Ser Gln Thr
                245                 250                 255

Val Ser Ser Asn Pro Ser Ser Phe Pro Glu Thr Ser Ile Ile Ala Arg
            260                 265                 270

Pro Gly Arg Glu Gln Gln Arg Lys Gly Leu Ser Pro Gly Ala Ile Val
        275                 280                 285

Ala Ile Val Ile Ala Asn Cys Val Ala Leu Leu Val Val Ser Phe
    290                 295                 300

Ala Val Ala His Cys Cys Ala Arg Gly Arg Gly Ser Ser Leu Val Gly
305                 310                 315                 320

Ser Gly Glu Ser Tyr Gly Lys Arg Lys Ser Glu Ser Ser Tyr Asn Gly
                325                 330                 335
```

```
Ser Asp Glu Lys Lys Val Tyr Gly Gly Glu Ser Asp Gly Thr Ser
            340                 345                 350

Gly Thr Asp Arg Ser Arg Leu Val Phe Phe Asp Arg Ser Glu Phe
        355                 360                 365

Glu Leu Glu Asp Leu Leu Arg Ala Ser Ala Glu Met Leu Gly Lys Gly
    370                 375                 380

Ser Leu Gly Thr Val Tyr Arg Ala Val Leu Asp Asp Gly Cys Thr Val
385                 390                 395                 400

Ala Val Arg Arg Leu Lys Asp Ala Asn Pro Cys Ala Arg His Glu Phe
                405                 410                 415

Glu Gln Tyr Met Asp Val Ile Gly Lys Leu Lys His Pro Asn Val Val
            420                 425                 430

Arg Leu Lys Ala Tyr Tyr Tyr Ala Lys Glu Lys Leu Leu Val Tyr
        435                 440                 445

Asp Tyr Leu Ser Asn Gly Ser Leu His Ala Leu Leu His Gly Asn Arg
    450                 455                 460

Gly Pro Gly Arg Ile Pro Leu Asp Trp Thr Thr Arg Ile Ser Leu Val
465                 470                 475                 480

Leu Gly Ala Ala Arg Gly Leu Ala Lys Ile His Ala Glu Tyr Ser Ala
                485                 490                 495

Ala Lys Val Pro His Gly Asn Val Arg Ser Ser Asn Val Leu Leu Asp
            500                 505                 510

Lys Asn Gly Val Ala Cys Ile Ser Asp Phe Gly Leu Ser Leu Leu Leu
        515                 520                 525

Asn Pro Val His Ala Ile Ala Arg Leu Gly Gly Tyr Arg Ala Pro Glu
    530                 535                 540

Gln Glu Gln Asn Lys Arg Leu Ser Gln Gln Ala Asp Val Tyr Ser Phe
545                 550                 555                 560

Gly Val Leu Leu Leu Glu Val Leu Thr Gly Arg Ala Pro Ser Ser Gln
                565                 570                 575

Tyr Pro Ser Pro Ala Arg Pro Arg Met Glu Val Glu Pro Glu Gln Ala
            580                 585                 590

Ala Val Asp Leu Pro Lys Trp Val Arg Ser Val Val Arg Glu Glu Trp
        595                 600                 605

Thr Ala Glu Val Phe Asp Gln Glu Leu Leu Arg Tyr Lys Asn Ile Glu
    610                 615                 620

Glu Glu Leu Val Ser Met Leu His Val Gly Leu Thr Cys Val Val Ala
625                 630                 635                 640

Gln Pro Glu Lys Arg Pro Thr Met Glu Glu Val Val Lys Met Ile Glu
                645                 650                 655

Glu Ile Arg Val Glu Gln Ser Pro Leu Gly Asp Tyr Asp Val Ser
            660                 665                 670

Cys Asn Ser Leu Ser Pro Ser Ile Pro Thr Thr Glu Asp Gly Leu Ala
        675                 680                 685

<210> SEQ ID NO 96
<211> LENGTH: 1027
<212> TYPE: PRT
<213> ORGANISM: Artificial Sequence
<220> FEATURE:
<223> OTHER INFORMATION: kinase dead varient

<400> SEQUENCE: 96

Met Glu Thr Ser Leu Asp Tyr Ser Lys Met Leu Phe Leu Leu Leu Leu
1               5                   10                  15
```

Gly Ser Thr Ser Leu Ile Phe Leu Ser His Leu Ala Ser Ala Ala Thr
            20                  25                  30
Pro Lys Leu Asn Thr Gln Glu Val Lys Ala Leu Lys Glu Ile Gly Ser
            35                  40                  45
Lys Ile Gly Lys Lys Asp Trp Asn Phe Gly Val Asp Pro Cys Ser Gly
50                  55                  60
Lys Gly Asn Trp Asn Val Pro Asp Ala Arg Lys Ala Phe Val Met Ser
65                  70                  75                  80
Ser Val Ile Cys Asp Cys Ser Phe Asn His Asn Ser Ser Cys His Val
                85                  90                  95
Val Ser Ile Tyr Trp Lys Ala Gln Asn Leu Ser Gly Ser Leu Ser Pro
            100                 105                 110
Glu Phe Ser Lys Leu His Tyr Leu Gln Lys Leu Asp Leu Ser Arg Asn
            115                 120                 125
Ile Ile Thr Gly Ser Ile Pro Pro Gln Trp Gly Thr Met Arg Leu Val
            130                 135                 140
Glu Leu Ser Leu Met Gly Asn Lys Leu Ser Gly Pro Phe Pro Lys Val
145                 150                 155                 160
Leu Thr Asn Ile Thr Thr Leu Arg Asn Leu Ser Ile Glu Gly Asn Gln
                165                 170                 175
Phe Ser Gly His Ile Pro Thr Glu Ile Gly Lys Leu Thr Asn Leu Glu
            180                 185                 190
Lys Leu Val Leu Ser Ser Asn Gly Phe Thr Gly Ala Leu Pro Pro Val
            195                 200                 205
Leu Ser Lys Leu Thr Lys Leu Ile Asp Leu Arg Ile Ser Asp Asn Asn
210                 215                 220
Phe Leu Gly Lys Ile Pro Asp Phe Ile Ser Asn Trp Thr Leu Ile Glu
225                 230                 235                 240
Lys Leu His Met His Gly Cys Ser Leu Glu Gly Pro Ile Pro Ser Ser
                245                 250                 255
Ile Ser Ala Leu Thr Arg Leu Ser Asp Leu Arg Ile Thr Asp Leu Lys
            260                 265                 270
Gly Ser Lys Ser Ser Ala Phe Pro Pro Leu Asn Asn Leu Lys Ser Met
            275                 280                 285
Lys Thr Leu Val Leu Arg Lys Cys Met Ile Lys Gly Glu Ile Pro Glu
            290                 295                 300
Tyr Ile Gly Arg Met Glu Lys Leu Lys Ile Leu Asp Leu Ser Tyr Asn
305                 310                 315                 320
Gly Leu Ser Gly Glu Ile Pro Glu Ser Phe Ala Gln Leu Asp Lys Val
                325                 330                 335
Asp Phe Met Tyr Leu Thr Gly Asn Lys Leu Ser Gly Ile Ile Pro Arg
            340                 345                 350
Trp Val Leu Ala Asn Asn Glu Asn Ile Asp Ile Ser Asp Asn Asn Phe
            355                 360                 365
Ser Trp Asp Ser Ser Pro Thr Glu Cys Gln Arg Gly Ser Val Asn
            370                 375                 380
Leu Val Glu Ser Tyr Ser Ser Val Asn Thr Gln Thr Lys Ile Asn
385                 390                 395                 400
Ser Cys Leu Lys Lys Asn Phe Leu Cys Thr Ala Ser Pro Ser Gln Tyr
                405                 410                 415
Arg Tyr Ser Leu Asn Ile Asn Cys Gly Gly Asn Glu Ala Asn Val Ser
            420                 425                 430

```
Gly Asn Ile Tyr Glu Ala Asp Arg Glu Gln Lys Gly Ala Ala Met Leu
            435                 440                 445

Tyr Tyr Thr Ser Gln Asp Trp Ala Leu Ser Ser Thr Gly Asn Phe Met
450                 455                 460

Asp Asn Asp Ile Asp Ser Asp Pro Tyr Ile Val Ala Asn Thr Ser Arg
465                 470                 475                 480

Leu Asn Val Ser Ala Leu Asn Ser Lys Leu Tyr Thr Thr Ala Arg Val
                485                 490                 495

Ser Pro Leu Ala Leu Thr Tyr Tyr Gly Leu Cys Leu Ile Asn Gly Asn
            500                 505                 510

Tyr Thr Val Lys Leu His Phe Ala Glu Ile Ile Phe Ile Asn Asp Arg
            515                 520                 525

Ser Leu Asn Ser Leu Gly Arg Arg Val Phe Asp Val Tyr Ile Gln Gly
            530                 535                 540

Asn Leu Val Leu Lys Asp Phe Asp Ile Arg Arg Glu Ala Gly Gly Thr
545                 550                 555                 560

Gly Lys Ser Ile Glu Lys Thr Phe Asn Ala Ser Val Thr Gln His Thr
                565                 570                 575

Leu Lys Ile His Phe Tyr Trp Ala Gly Lys Gly Thr Thr Gly Ile Pro
            580                 585                 590

Thr Arg Gly Val Tyr Gly Pro Leu Val Ser Ala Ile Ser Val Asn Pro
            595                 600                 605

Asn Phe Lys Pro Pro Ser Glu Gly Lys Arg Thr Tyr Leu Ile Leu
            610                 615                 620

Ala Ile Ile Ile Val Ala Gly Val Leu Val Val Leu Leu Val Leu
625                 630                 635                 640

Val Leu Leu Arg Arg Met Gly Trp Leu Gly Gly Lys Asp Pro Val Tyr
                645                 650                 655

Lys Glu Leu Arg Gly Ile Asp Leu Gln Thr Gly Leu Phe Thr Leu Arg
                660                 665                 670

Gln Ile Lys Ala Ala Thr Lys Asn Phe Asp Ala Leu Asn Lys Ile Gly
            675                 680                 685

Glu Gly Gly Phe Gly Cys Val Tyr Lys Gly Gln Gln Ser Asp Gly Thr
            690                 695                 700

Met Ile Ala Val Arg Gln Leu Ser Ser Lys Ser Lys Gln Gly Asn Arg
705                 710                 715                 720

Glu Phe Val Asn Glu Met Gly Leu Ile Ser Gly Leu Gln His Pro Asn
                725                 730                 735

Leu Val Lys Leu Tyr Gly Cys Cys Val Glu Gly Asn Gln Leu Ile Leu
            740                 745                 750

Ile Tyr Glu Tyr Met Glu Asn Asn Cys Leu Ser Arg Ile Leu Phe Gly
            755                 760                 765

Arg Asp Pro Asn Lys Thr Lys Leu Asp Trp Pro Thr Arg Lys Lys Ile
770                 775                 780

Cys Leu Gly Ile Ala Lys Ala Leu Ala Tyr Leu His Glu Glu Ser Arg
785                 790                 795                 800

Ile Lys Ile Ile His Arg Asp Val Arg Ala Ser Asn Val Leu Leu Asp
                805                 810                 815

Lys Asp Phe Asn Ala Lys Val Ser Asp Phe Gly Leu Ala Lys Leu Ile
            820                 825                 830

Glu Asp Glu Lys Thr His Ile Ser Thr Arg Val Ala Gly Thr Ile Gly
            835                 840                 845

Tyr Met Ala Pro Glu Tyr Ala Met Arg Gly Tyr Leu Thr Asp Lys Ala
```

```
                850                 855                 860
Asp Val Tyr Ser Phe Gly Val Ala Leu Glu Thr Val Ser Gly Lys
865                 870                 875                 880

Ser Asn Thr Asn Phe Arg Pro Asn Glu Asp Phe Val Tyr Leu Leu Asp
                885                 890                 895

Trp Ala Tyr Val Leu Gln Glu Arg Gly Ser Leu Leu Glu Leu Val Asp
                900                 905                 910

Pro Asn Leu Gly Ser Glu Tyr Leu Thr Glu Glu Ala Met Val Val Leu
                915                 920                 925

Asn Val Ala Leu Leu Cys Thr Asn Ala Ser Pro Thr Leu Arg Pro Thr
                930                 935                 940

Met Ser Gln Val Val Ser Met Leu Glu Gly Trp Thr Asp Ile Gln Asp
945                 950                 955                 960

Leu Leu Ser Asp Pro Gly Tyr Ser Ala Ile Ser Ser Ser Lys His
                965                 970                 975

Lys Ser Ile Arg Ser His Phe Trp Gln Thr Pro Ser Gly Thr His Ser
                980                 985                 990

Ile Ser Ile Pro Ser Ile Tyr Thr  Asp Ser Ser Gly Ser  His Val Glu
                995                 1000                1005

Thr Glu  Lys Asn Tyr His Pro  Val Thr Val Asn Ser  Asp Gly Ser
    1010                1015                1020

Asp Lys  Ser Asn
    1025

<210> SEQ ID NO 97
<211> LENGTH: 614
<212> TYPE: PRT
<213> ORGANISM: Artificial Sequence
<220> FEATURE:
<223> OTHER INFORMATION: kinase dead varient

<400> SEQUENCE: 97

Met Val Leu His Ser Trp Ile Ser Ser His Ile Leu Val Asn Phe
1               5                   10                  15

Leu Leu Leu Leu Gly Cys Gly Ile Thr Tyr Gly Thr Asp Thr Asp Ile
                20                  25                  30

Phe Cys Leu Lys Ser Ile Lys Glu Ser Leu Glu Asp Pro Tyr Asn Tyr
            35                  40                  45

Leu Lys Phe Ser Trp Asp Phe Asn Asn Lys Thr Glu Gly Tyr Ile Cys
        50                  55                  60

Arg Phe Asn Gly Val Glu Cys Trp His Pro Asp Glu Asn Arg Val Leu
65                  70                  75                  80

Asn Leu Lys Leu Ser Asn Met Gly Leu Lys Gly Gln Phe Pro Arg Gly
                85                  90                  95

Ile Gln Asn Cys Ser Ser Leu Thr Gly Leu Asp Leu Ser Ile Asn Lys
                100                 105                 110

Leu Ser Gly Thr Ile Pro Gly Asp Ile Ser Thr Leu Ile Pro Phe Ala
            115                 120                 125

Thr Ser Ile Asp Leu Ser Thr Asn Glu Phe Ser Gly Ala Ile Pro Val
        130                 135                 140

Ser Leu Ala Asn Cys Thr Phe Leu Asn Thr Leu Lys Leu Asp Gln Asn
145                 150                 155                 160

Arg Leu Thr Gly Gln Ile Pro Pro Gln Phe Gly Val Leu Ser Arg Ile
                165                 170                 175

Lys Val Phe Ser Val Ser Asn Asn Leu Leu Thr Gly Gln Val Pro Ile
```

```
            180                 185                 190
Phe Arg Asp Gly Val Glu Leu His Tyr Ala Asn Asn Gln Gly Leu Cys
            195                 200                 205
Gly Gly Asn Thr Leu Ala Pro Cys Gln Ala Thr Pro Ser Lys Ser Asn
            210                 215                 220
Met Ala Val Ile Ala Gly Ala Ala Gly Val Thr Leu Ala Ala
225                 230                 235                 240
Leu Gly Leu Gly Ile Gly Met Phe Phe Val Arg Arg Val Ser Phe
                    245                 250                 255
Lys Lys Lys Glu Glu Asp Pro Glu Gly Asn Lys Trp Ala Arg Ser Leu
            260                 265                 270
Lys Gly Thr Lys Arg Ile Lys Val Ser Met Phe Glu Lys Ser Ile Ser
            275                 280                 285
Lys Met Lys Leu Ser Asp Leu Met Lys Ala Thr Asn Asn Phe Ser Asn
            290                 295                 300
Thr Asn Ile Ile Gly Thr Gly Arg Thr Gly Thr Val Tyr Lys Ala Val
305                 310                 315                 320
Leu Asp Asp Gly Thr Thr Leu Met Val Arg Arg Leu Gln Glu Ser Gln
                    325                 330                 335
Tyr Thr Glu Lys Glu Phe Met Ser Glu Met Gly Thr Leu Gly Thr Val
            340                 345                 350
Lys His Arg Asn Leu Val Pro Leu Leu Gly Phe Cys Met Thr Lys Arg
            355                 360                 365
Glu Arg Leu Leu Val Tyr Lys Asn Met Pro Asn Gly Asn Leu His Asp
            370                 375                 380
Gln Leu His Pro Ala Asp Gly Val Ser Thr Leu Asp Trp Thr Thr Arg
385                 390                 395                 400
Leu Lys Ile Ala Ile Gly Ala Ala Lys Gly Leu Ala Trp Leu His His
                    405                 410                 415
Ser Cys Asn Pro Arg Ile Ile His Arg Asn Ile Ser Ser Arg Cys Ile
                    420                 425                 430
Leu Leu Asp Ala Asp Phe Glu Pro Lys Ile Ser Asp Phe Gly Leu Ala
            435                 440                 445
Arg Leu Met Asn Pro Ile Asp Thr His Leu Ser Thr Phe Val Asn Gly
            450                 455                 460
Glu Phe Gly Asp Leu Gly Tyr Val Ala Pro Glu Tyr Thr Arg Thr Leu
465                 470                 475                 480
Val Ala Thr Pro Lys Gly Asp Ile Tyr Ser Phe Gly Thr Val Leu Leu
                    485                 490                 495
Glu Leu Val Thr Gly Glu Arg Pro Thr Asn Val Ser Lys Ala Pro Glu
            500                 505                 510
Thr Phe Lys Gly Asn Leu Val Glu Trp Ile Thr Glu Leu Thr Ser Asn
            515                 520                 525
Ala Lys Leu His Asp Ala Ile Asp Glu Ser Leu Val Arg Lys Asp Val
            530                 535                 540
Asp Ser Glu Leu Phe Gln Phe Leu Lys Val Ala Cys Asn Cys Val Ser
545                 550                 555                 560
Pro Thr Pro Lys Glu Arg Pro Thr Met Phe Glu Val Tyr Gln Leu Leu
                    565                 570                 575
Arg Ala Ile Gly Gly Arg Tyr Asn Phe Thr Thr Glu Asp Asp Ile Leu
                    580                 585                 590
Val Pro Thr Asp Ile Gly Asn Thr Asp Asn Met Gln Glu Leu Ile Val
            595                 600                 605
```

Ala Gln Glu Gly Ser Tyr
    610

<210> SEQ ID NO 98
<211> LENGTH: 649
<212> TYPE: PRT
<213> ORGANISM: Artificial Sequence
<220> FEATURE:
<223> OTHER INFORMATION: kinase dead varient

<400> SEQUENCE: 98

Met Glu Lys Thr Ile His Leu Val Tyr Phe Lys Cys Leu Val Phe Leu
1               5                   10                  15

Leu Met Lys Gln Val Ile Val Met Ala Glu Pro Arg Ala Arg Thr Val
            20                  25                  30

Asn Ile Thr Cys Asn Asn Lys Leu Glu His Asn Thr Thr Ile Phe Val
        35                  40                  45

Pro Asn Phe Val Ala Thr Met Glu Lys Ile Ser Glu Gln Met Arg Asn
    50                  55                  60

Thr Gly Tyr Gly Thr Ala Val Val Gly Thr Gly Pro Asp Thr Asn
65                  70                  75                  80

Tyr Gly Leu Ala Gln Cys Tyr Gly Asp Leu Ser Leu Asp Cys Val
                85                  90                  95

Leu Cys Tyr Ala Glu Ala Arg Thr Val Leu Pro Gln Cys Phe Pro Tyr
            100                 105                 110

Asn Gly Gly Arg Ile Tyr Leu Asp Gly Cys Phe Met Arg Ala Glu Asn
        115                 120                 125

Tyr Ser Phe Tyr Asp Glu Tyr Ile Gly Pro Gly Asp Lys Ala Val Cys
    130                 135                 140

Gly Asn Thr Thr Arg Lys Ser Ser Phe Gln Ala Ala Ala Lys Lys
145                 150                 155                 160

Ala Val Leu Ser Ala Val Gln Ala Ala Ala Asn Asn Lys Gly Tyr Ala
                165                 170                 175

Arg Lys Glu Val Phe Val Ala Gly Thr Thr Asn Asp Ala Ala Tyr Val
            180                 185                 190

Leu Ala Asn Cys Trp Arg Ser Leu Asp Thr Arg Ser Cys Arg Ala Cys
        195                 200                 205

Leu Glu Asn Ala Ser Ser Ser Ile Leu Gly Cys Leu Pro Trp Ser Glu
    210                 215                 220

Gly Arg Ala Leu Asn Thr Gly Cys Phe Met Arg Tyr Ser Asp Thr Asp
225                 230                 235                 240

Phe Leu Asn Lys Glu Gln Glu Asn Gly Ser Ser Gly Asn Val Leu
                245                 250                 255

Val Ile Val Val Ala Val Val Ser Val Ile Val Leu Val Gly
            260                 265                 270

Ile Ala Ile Val Val Tyr Ile Arg Lys His Arg Tyr Ile Gln Met Lys
        275                 280                 285

Arg Arg Gly Ser Asn Asp Ala Glu Lys Leu Ala Lys Ser Leu His His
    290                 295                 300

Asn Ser Leu Asn Phe Lys Tyr Ser Thr Leu Glu Lys Ala Thr Asn Ser
305                 310                 315                 320

Phe Asp Glu Ala Asn Lys Leu Gly Gln Gly Gly Phe Gly Thr Val Tyr
                325                 330                 335

Lys Gly Val Leu Ala Asp Gly Arg Glu Ile Ala Ile Arg Arg Leu Tyr
            340                 345                 350

```
Phe Asn Asn Arg His Arg Ala Ala Asp Phe Phe Asn Glu Val Asn Ile
            355                 360                 365

Ile Ser Ser Val Glu His Lys Asn Leu Val Arg Leu Leu Gly Cys Ser
        370                 375                 380

Cys Ser Gly Pro Glu Ser Leu Leu Ile Tyr Glu Tyr Leu Pro Asn Arg
385                 390                 395                 400

Ser Leu Asp Arg Phe Ile Phe Asp Lys Asn Lys Gly Arg Glu Leu Asn
                405                 410                 415

Trp Asp Lys Arg Tyr Asp Ile Ile Gly Thr Ala Glu Gly Leu Val
            420                 425                 430

Tyr Leu His Glu Asn Ser Asn Ile Arg Ile His Arg Asp Ile Arg
            435                 440                 445

Ala Ser Asn Ile Leu Leu Asp Ala Lys Leu Arg Ala Lys Ile Ala Asp
        450                 455                 460

Phe Gly Leu Ala Arg Ser Phe Gln Glu Asp Lys Ser His Ile Ser Thr
465                 470                 475                 480

Ala Ile Ala Gly Thr Leu Gly Tyr Met Ala Pro Glu Tyr Leu Ala His
                485                 490                 495

Gly Gln Leu Thr Glu Lys Ala Asp Val Tyr Ser Phe Gly Val Leu Leu
            500                 505                 510

Leu Glu Ile Ile Thr Gly Arg Leu Asn Asn Arg Ser Lys Ala Ser Glu
        515                 520                 525

Tyr Ser Asp Ser Leu Val Thr Met Thr Trp Lys His Phe Gln Ser Gly
        530                 535                 540

Thr Ala Glu Gln Leu Ile Asp Pro Cys Leu Val Asp Asp Asn His
545                 550                 555                 560

Arg Ser Asn Phe Lys Asn Glu Ile Leu Arg Val Leu His Ile Gly Leu
                565                 570                 575

Leu Cys Thr Gln Glu Ile Pro Ser Leu Arg Pro Ser Met Ser Lys Ala
            580                 585                 590

Leu Lys Met Leu Thr Lys Lys Glu His Leu Asp Leu Glu Ala Pro
            595                 600                 605

Ser Asn Pro Pro Phe Ile Asp Glu Ser Thr Met Glu Leu His Asp Gln
        610                 615                 620

Asn Asp Asp Pro Phe Tyr Pro Leu Asn Ala Glu Asp Ser Leu Ala Thr
625                 630                 635                 640

Met Ser His Ser Ser Phe Tyr Ala Arg
                645

<210> SEQ ID NO 99
<211> LENGTH: 869
<212> TYPE: PRT
<213> ORGANISM: Artificial Sequence
<220> FEATURE:
<223> OTHER INFORMATION: kinase dead varient

<400> SEQUENCE: 99

Met Asp Thr Thr Ser Thr Gln Ile Ala Ser Gly Thr Ile Leu Phe Leu
1               5                   10                  15

Leu Leu Leu Phe Phe Pro Tyr Leu Ser Ile Ala Asp Val Ile Tyr Ser
            20                  25                  30

Pro Val Glu Leu Phe Ser Ile Asn Cys Gly Ser Ser Ser Asn Leu Ser
        35                  40                  45

Thr Arg Asp Gly Arg Asn Trp Thr Ala Asp Ile Lys Phe Leu Ser Glu
    50                  55                  60
```

-continued

```
Asn Lys Asp Ser Val Ala Ala Pro Ala Leu Thr Pro Ser Thr Leu Glu
 65                  70                  75                  80

Gly Pro Tyr Thr Asp Ala Arg Leu Ser His Ser Gln Phe Thr Tyr Ser
                 85                  90                  95

Phe Pro Val Ser Thr Gly Pro Lys Phe Leu Arg Leu Phe Phe Tyr Ser
            100                 105                 110

Thr Ser Tyr Gln Asn Phe His Arg Ser Lys Ala Tyr Phe Ser Val Lys
        115                 120                 125

Ala Gly Pro Tyr Thr Leu Leu Gln Asn Phe Asn Ala Ser Leu His Ala
130                 135                 140

Asp Ala Gly Asn Glu Pro Gly Asp Tyr Leu Phe Arg Glu Tyr Cys Ile
145                 150                 155                 160

Asn Leu Lys Asp Gly Asp Arg Leu Asn Ile Thr Phe Ile Ala Ser Lys
                165                 170                 175

Thr Ser Gln Asn Pro Asp Ser Tyr Ala Phe Ile Asn Gly Ile Glu Ile
            180                 185                 190

Val Ser Met Pro Pro Phe Leu Tyr Tyr Thr Asn Pro His Asp Val Asp
        195                 200                 205

Ile Thr Gly Leu Pro His Leu Val Gly Val Asn Thr Asn Leu Phe Pro
210                 215                 220

Ile Glu Asn Asn Phe Thr Leu Glu Thr Lys Tyr Arg Leu Arg Val Gly
225                 230                 235                 240

Asp Gln Glu Ile Pro Ala Ser Gln Asp Thr Gly Met Leu Arg Ser Trp
                245                 250                 255

Asp Val Asp Ser Lys Tyr Val Thr Thr Gln Ser Val Leu Ser Leu Asp
            260                 265                 270

Ile Gly Pro Gly Ile Lys Leu Arg Phe Thr Lys Ile Pro Asn Tyr Thr
        275                 280                 285

Ala Pro Asp Thr Val Tyr Arg Ser Val Arg Asn Met Gly Asn Asn Gly
290                 295                 300

Thr Ile Asn Met Gly Phe Asn Leu Thr Trp Gln Leu Pro Ile Asp Ser
305                 310                 315                 320

Gly Phe Thr Tyr Leu Leu Arg Leu His Phe Cys Gln Leu Asn Pro Glu
                325                 330                 335

Met Lys Asn Pro Gly Tyr Gln Ser Phe Phe Ile Phe Val Gln Asp Gln
            340                 345                 350

Leu Val Glu Lys Trp Ala Asp Ile Leu Ser Trp Ser Asp Lys Gln Glu
        355                 360                 365

Gly Val Pro Val Val Lys Gln Tyr Val Val Phe Ile Pro Gly Asn Gln
370                 375                 380

Gln Glu Thr Leu Asn Leu Ser Leu Lys Met His Pro Asn Pro Gln Ser
385                 390                 395                 400

Leu Ala Lys Asp Ala Gln Ile Asn Ala Ile Glu Leu Phe Lys Ile Asn
                405                 410                 415

Asn Ser Thr Gly Ser Leu Ala Gly Pro Asn Pro Asp Pro Asp Arg Leu
            420                 425                 430

Pro Glu Thr Pro Lys Val Pro Leu Gln Arg Pro Asn Asn Lys Ser Ser
        435                 440                 445

Gly Thr Thr Arg Thr Leu Ala Ala Val Ala Gly Ala Val Ser Ala
450                 455                 460

Ala Val Leu Leu Ser Phe Ile Val Ala Phe Phe Leu Ile Lys Arg Lys
465                 470                 475                 480
```

```
Lys Lys Met Gly Ser Lys Glu Lys Asp Glu Thr Pro Leu Gly Gly Gly
                485                 490                 495

Leu Ser Ser Leu Pro Thr Asn Leu Cys Arg His Phe Ser Ile Ala Glu
            500                 505                 510

Ile Arg Ala Ser Thr Asn Asn Phe Asp Glu His Phe Val Val Gly Met
            515                 520                 525

Gly Gly Phe Gly Asn Val Tyr Lys Gly Tyr Ile Asp Asp Gly Ser Thr
            530                 535                 540

Arg Val Ala Ile Arg Arg Leu Lys Pro Asp Ser Arg Gln Gly Ala Gln
545                 550                 555                 560

Glu Phe Met Asn Glu Ile Glu Met Leu Ser Gln Leu Arg His Leu His
                565                 570                 575

Leu Val Ser Leu Val Gly Tyr Cys Tyr Glu Ser Asn Glu Met Ile Leu
            580                 585                 590

Val Tyr Asp Phe Met Asp Arg Gly Thr Leu Arg Glu His Leu Tyr Asp
            595                 600                 605

Thr Asp Asn Pro Ser Leu Ser Trp Lys Gln Arg Leu Gln Ile Cys Val
            610                 615                 620

Gly Ala Ala Arg Gly Leu His Tyr Leu His Thr Gly Ala Lys His Thr
625                 630                 635                 640

Ile Ile His Arg Asp Val Arg Ser Thr Asn Ile Leu Leu Asp Glu Lys
                645                 650                 655

Trp Val Ala Lys Val Ser Asp Phe Gly Leu Ser Arg Ile Gly Pro Ile
            660                 665                 670

Ser Ser Ser Met Thr His Val Ser Thr Gln Val Lys Gly Ser Val Gly
            675                 680                 685

Tyr Ile Asp Pro Glu Tyr Tyr Lys Arg Gln Arg Leu Thr Glu Lys Ser
            690                 695                 700

Asp Val Tyr Ser Phe Gly Val Val Leu Leu Glu Val Leu Ser Gly Arg
705                 710                 715                 720

Gln Pro Leu Leu Arg Trp Glu Glu Lys Gln Arg Ile Ser Leu Val Asn
                725                 730                 735

Trp Ala Lys His Cys Asn Glu Lys Gly Thr Leu Ser Glu Ile Val Asp
            740                 745                 750

Ala Lys Leu Lys Gly Gln Ile Ala Pro Gln Cys Leu Gln Arg Tyr Gly
            755                 760                 765

Glu Val Ala Leu Ser Cys Leu Leu Glu Asp Gly Thr Gln Arg Pro Ser
            770                 775                 780

Met Asn Asp Ala Val Arg Met Leu Glu Phe Val Leu His Leu Gln Glu
785                 790                 795                 800

Gly Ala Val Asn Glu Val Thr Glu Ser Glu Thr Glu Asp Val Phe
                805                 810                 815

Ser Ser Ser His Ser Ser Leu Leu Phe Ser Asp Tyr Ser Lys Ser Thr
            820                 825                 830

Ala Leu Ser Met Ala Thr Asn Val Gly Asp Cys Ser Tyr Gly Ser Lys
            835                 840                 845

Asp Ser Glu Glu Arg Ser Ile Pro Asp His Leu Phe Ser Glu Ile Lys
            850                 855                 860

Asp Pro Lys Gly Arg
865

<210> SEQ ID NO 100
<211> LENGTH: 130
<212> TYPE: PRT
```

<213> ORGANISM: Glycine max

<400> SEQUENCE: 100

| Ile | Ile | Gly | Thr | Gly | Arg | Thr | Gly | Thr | Val | Tyr | Lys | Ala | Val | Leu | Asp |
|---|---|---|---|---|---|---|---|---|---|---|---|---|---|---|---|
| 1 | | | | 5 | | | | | 10 | | | | | 15 | |

| Asp | Gly | Thr | Thr | Leu | Met | Val | Lys | Arg | Leu | Gln | Glu | Ser | Gln | Tyr | Thr |
|---|---|---|---|---|---|---|---|---|---|---|---|---|---|---|---|
| | | | 20 | | | | | 25 | | | | | 30 | | |

| Glu | Lys | Glu | Phe | Met | Ser | Glu | Met | Gly | Thr | Leu | Gly | Thr | Val | Lys | His |
|---|---|---|---|---|---|---|---|---|---|---|---|---|---|---|---|
| | | 35 | | | | | 40 | | | | | 45 | | | |

| Arg | Asn | Leu | Val | Pro | Leu | Leu | Gly | Phe | Cys | Met | Thr | Lys | Arg | Glu | Arg |
|---|---|---|---|---|---|---|---|---|---|---|---|---|---|---|---|
| | 50 | | | | | 55 | | | | | 60 | | | | |

| Leu | Leu | Val | Tyr | Lys | Asn | Met | Pro | Asn | Gly | Asn | Leu | His | Asp | Gln | Leu |
|---|---|---|---|---|---|---|---|---|---|---|---|---|---|---|---|
| 65 | | | | | 70 | | | | | 75 | | | | | 80 |

| His | Pro | Ala | Asp | Gly | Val | Ser | Thr | Leu | Asp | Trp | Thr | Thr | Arg | Leu | Lys |
|---|---|---|---|---|---|---|---|---|---|---|---|---|---|---|---|
| | | | | 85 | | | | | 90 | | | | | 95 | |

| Ile | Ala | Ile | Gly | Ala | Ala | Lys | Gly | Leu | Ala | Trp | Leu | His | His | Ser | Cys |
|---|---|---|---|---|---|---|---|---|---|---|---|---|---|---|---|
| | | | 100 | | | | | 105 | | | | | 110 | | |

| Asn | Pro | Arg | Ile | Ile | His | Arg | Asn | Ile | Ser | Ser | Lys | Cys | Ile | Leu | Leu |
|---|---|---|---|---|---|---|---|---|---|---|---|---|---|---|---|
| | | | 115 | | | | | 120 | | | | | 125 | | |

| Asp | Ala |
|---|---|
| | 130 |

<210> SEQ ID NO 101
<211> LENGTH: 126
<212> TYPE: PRT
<213> ORGANISM: Homo sapiens

<400> SEQUENCE: 101

| Lys | Ile | Gly | Glu | Gly | Ser | Tyr | Gly | Val | Val | Phe | Lys | Cys | Arg | Asn | Arg |
|---|---|---|---|---|---|---|---|---|---|---|---|---|---|---|---|
| 1 | | | | 5 | | | | | 10 | | | | | 15 | |

| Asp | Thr | Gly | Gln | Ile | Val | Ala | Ile | Lys | Lys | Phe | Leu | Glu | Ser | Glu | Asp |
|---|---|---|---|---|---|---|---|---|---|---|---|---|---|---|---|
| | | | 20 | | | | | 25 | | | | | 30 | | |

| Asp | Pro | Val | Ile | Lys | Lys | Ile | Ala | Leu | Arg | Glu | Ile | Arg | Met | Leu | Lys |
|---|---|---|---|---|---|---|---|---|---|---|---|---|---|---|---|
| | | | 35 | | | | | 40 | | | | | 45 | | |

| Gln | Leu | Lys | His | Pro | Asn | Leu | Val | Asn | Leu | Leu | Glu | Val | Phe | Arg | Arg |
|---|---|---|---|---|---|---|---|---|---|---|---|---|---|---|---|
| | 50 | | | | | 55 | | | | | 60 | | | | |

| Lys | Arg | Arg | Leu | His | Leu | Val | Phe | Glu | Tyr | Cys | Asp | His | Thr | Val | Leu |
|---|---|---|---|---|---|---|---|---|---|---|---|---|---|---|---|
| 65 | | | | | 70 | | | | | 75 | | | | | 80 |

| His | Glu | Leu | Asp | Arg | Tyr | Gln | Arg | Gly | Val | Pro | Glu | His | Leu | Val | Lys |
|---|---|---|---|---|---|---|---|---|---|---|---|---|---|---|---|
| | | | | 85 | | | | | 90 | | | | | 95 | |

| Ser | Ile | Thr | Trp | Gln | Thr | Leu | Gln | Ala | Val | Asn | Phe | Cys | His | Lys | His |
|---|---|---|---|---|---|---|---|---|---|---|---|---|---|---|---|
| | | | 100 | | | | | 105 | | | | | 110 | | |

| Asn | Cys | Ile | His | Arg | Asp | Val | Lys | Pro | Glu | Asn | Ile | Leu | Ile |
|---|---|---|---|---|---|---|---|---|---|---|---|---|---|
| | | | 115 | | | | | 120 | | | | | 125 |

<210> SEQ ID NO 102
<211> LENGTH: 121
<212> TYPE: PRT
<213> ORGANISM: Gallus gallus

<400> SEQUENCE: 102

| Lys | Leu | Gly | Arg | Gly | Lys | Tyr | Ser | Glu | Val | Phe | Glu | Ala | Ile | Asn | Ile |
|---|---|---|---|---|---|---|---|---|---|---|---|---|---|---|---|
| 1 | | | | 5 | | | | | 10 | | | | | 15 | |

| Thr | Asn | Asn | Glu | Lys | Val | Val | Val | Lys | Ile | Leu | Lys | Pro | Val | Lys | Lys |
|---|---|---|---|---|---|---|---|---|---|---|---|---|---|---|---|
| | | | 20 | | | | | 25 | | | | | 30 | | |

| Lys | Lys | Ile | Lys | Arg | Glu | Ile | Lys | Ile | Leu | Glu | Asn | Leu | Arg | Gly | Gly |
|---|---|---|---|---|---|---|---|---|---|---|---|---|---|---|---|
| | | | 35 | | | | | 40 | | | | | 45 | | |

```
Pro Asn Ile Ile Thr Leu Ala Asp Ile Val Lys Asp Pro Val Ser Arg
    50                  55                  60

Thr Pro Ala Leu Val Phe Glu His Val Asn Asn Thr Asp Phe Lys Gln
65                  70                  75                  80

Leu Tyr Gln Thr Leu Thr Asp Tyr Asp Ile Arg Phe Tyr Met Tyr Glu
                85                  90                  95

Ile Leu Lys Ala Leu Asp Tyr Cys His Ser Met Gly Ile Met His Arg
            100                 105                 110

Asp Val Lys Pro His Asn Val Met Ile
            115                 120

<210> SEQ ID NO 103
<211> LENGTH: 126
<212> TYPE: PRT
<213> ORGANISM: Homo sapiens

<400> SEQUENCE: 103

Lys Ile Gly Glu Gly Ser Tyr Gly Val Val Phe Lys Cys Arg Asn Arg
1               5                   10                  15

Asp Thr Gly Gln Ile Val Ala Ile Lys Lys Phe Leu Glu Ser Glu Asp
                20                  25                  30

Asp Pro Val Ile Lys Lys Ile Ala Leu Arg Glu Ile Arg Met Leu Lys
            35                  40                  45

Gln Leu Lys His Pro Asn Leu Val Asn Leu Leu Glu Val Phe Arg Arg
        50                  55                  60

Lys Arg Arg Leu His Leu Val Phe Glu Tyr Cys Asp His Thr Val Leu
65                  70                  75                  80

His Glu Leu Asp Arg Tyr Gln Arg Gly Val Pro Glu His Leu Val Lys
                85                  90                  95

Ser Ile Thr Trp Gln Thr Leu Gln Ala Val Asn Phe Cys His Lys His
            100                 105                 110

Asn Cys Ile His Arg Asp Val Lys Pro Glu Asn Ile Leu Ile
        115                 120                 125

<210> SEQ ID NO 104
<211> LENGTH: 127
<212> TYPE: PRT
<213> ORGANISM: Saccharomyces cerevisiae

<400> SEQUENCE: 104

Gln Val Gly Glu Gly Thr Tyr Gly Lys Val Tyr Lys Ala Lys Asn Thr
1               5                   10                  15

Asn Thr Glu Lys Leu Val Ala Leu Lys Lys Leu Arg Leu Gln Gly Glu
                20                  25                  30

Arg Glu Gly Phe Pro Ile Thr Ser Ile Arg Glu Ile Lys Leu Leu Gln
            35                  40                  45

Ser Phe Asp His Pro Asn Val Ser Thr Ile Lys Glu Ile Met Val Glu
        50                  55                  60

Ser Gln Lys Thr Val Tyr Met Ile Phe Glu Tyr Ala Asp Asn Asp Leu
65                  70                  75                  80

Ser Gly Leu Leu Leu Asn Lys Glu Val Gln Ile Ser His Ser Gln Cys
                85                  90                  95

Lys His Leu Phe Lys Gln Leu Leu Gly Met Glu Tyr Leu His Asp
            100                 105                 110

Asn Lys Ile Leu His Arg Asp Val Lys Gly Ser Asn Ile Leu Ile
        115                 120                 125
```

```
<210> SEQ ID NO 105
<211> LENGTH: 125
<212> TYPE: PRT
<213> ORGANISM: Rattus norvegicus

<400> SEQUENCE: 105

Gln Leu Gly Asp Gly Thr Tyr Gly Ser Val Leu Met Gly Lys Ser Asn
1               5                   10                  15

Glu Ser Gly Glu Leu Val Ala Ile Lys Arg Met Lys Arg Lys Phe Tyr
            20                  25                  30

Ser Trp Asp Glu Cys Met Asn Leu Arg Glu Val Lys Ser Leu Lys Lys
        35                  40                  45

Leu Asn His Ala Asn Val Ile Lys Leu Lys Glu Val Ile Arg Glu Asn
    50                  55                  60

Asp His Leu Tyr Phe Ile Phe Glu Tyr Met Lys Glu Asn Leu Tyr Gln
65                  70                  75                  80

Leu Met Lys Asp Arg Asn Lys Leu Phe Pro Glu Ser Val Ile Arg Asn
                85                  90                  95

Ile Met Tyr Gln Ile Leu Gln Gly Leu Ala Phe Ile His Lys His Gly
            100                 105                 110

Phe Phe His Arg Asp Met Lys Pro Glu Asn Leu Leu Cys
        115                 120                 125

<210> SEQ ID NO 106
<211> LENGTH: 129
<212> TYPE: PRT
<213> ORGANISM: Rattus norvegicus

<400> SEQUENCE: 106

Val Ile Gly Asn Gly Ser Phe Gly Val Val Tyr Gln Ala Arg Leu Ala
1               5                   10                  15

Glu Thr Arg Glu Leu Val Ala Ile Lys Lys Val Leu Gln Asp Lys Arg
            20                  25                  30

Phe Lys Asn Arg Glu Leu Gln Ile Met Arg Lys Leu Asp His Cys Asn
        35                  40                  45

Ile Val Arg Leu Arg Tyr Phe Phe Tyr Ser Ser Gly Glu Lys Lys Asp
    50                  55                  60

Glu Leu Tyr Leu Asn Leu Val Leu Glu Tyr Val Pro Glu Thr Val Tyr
65                  70                  75                  80

Arg Val Ala Arg His Phe Thr Lys Ala Lys Leu Ile Ile Pro Ile Ile
                85                  90                  95

Tyr Val Lys Val Tyr Met Tyr Gln Leu Phe Arg Ser Leu Ala Tyr Ile
            100                 105                 110

His Ser Gln Gly Val Cys His Arg Asp Ile Lys Pro Gln Asn Leu Leu
        115                 120                 125

Val

<210> SEQ ID NO 107
<211> LENGTH: 125
<212> TYPE: PRT
<213> ORGANISM: Saccharomyces cerevisiae

<400> SEQUENCE: 107

Val Val Gly Gln Gly Ala Phe Ala Thr Val Lys Lys Ala Ile Glu Arg
1               5                   10                  15

Thr Thr Gly Lys Thr Phe Ala Val Lys Ile Ile Ser Lys Arg Lys Val
```

```
                    20                  25                  30

Ile Gly Asn Met Asp Gly Val Thr Arg Glu Leu Glu Val Leu Gln Lys
            35                  40                  45

Leu Asn His Pro Arg Ile Val Arg Leu Lys Gly Phe Tyr Glu Asp Thr
        50                  55                  60

Glu Ser Tyr Tyr Met Val Met Glu Phe Val Ser Gly Gly Asp Leu Met
65                  70                  75                  80

Asp Phe Val Ala Ala His Gly Ala Val Gly Glu Asp Ala Gly Arg Glu
                85                  90                  95

Ile Ser Arg Gln Ile Leu Thr Ala Ile Lys Tyr Ile His Ser Met Gly
            100                 105                 110

Ile Ser His Arg Asp Leu Lys Pro Asp Asn Ile Leu Ile
        115                 120                 125

<210> SEQ ID NO 108
<211> LENGTH: 121
<212> TYPE: PRT
<213> ORGANISM: Mus musculus

<400> SEQUENCE: 108

Thr Ile Gly Val Gly Ser Tyr Ser Val Cys Lys Arg Cys Val His Lys
1               5                   10                  15

Ala Thr Asn Met Glu Tyr Ala Val Lys Val Ile Asp Lys Ser Lys Arg
            20                  25                  30

Asp Pro Ser Glu Glu Ile Glu Ile Leu Leu Arg Tyr Gly Gln His Pro
        35                  40                  45

Asn Ile Ile Thr Leu Lys Asp Val Tyr Asp Asp Gly Lys His Val Tyr
    50                  55                  60

Leu Val Thr Glu Leu Met Arg Gly Gly Glu Leu Leu Asp Lys Ile Leu
65                  70                  75                  80

Arg Gln Lys Phe Phe Ser Glu Arg Glu Ala Ser Phe Val Leu His Thr
                85                  90                  95

Ile Ser Lys Thr Val Glu Tyr Leu His Ser Gln Gly Val Val His Arg
            100                 105                 110

Asp Leu Lys Pro Ser Asn Ile Leu Tyr
        115                 120

<210> SEQ ID NO 109
<211> LENGTH: 253
<212> TYPE: PRT
<213> ORGANISM: Artificial Sequence
<220> FEATURE:
<223> OTHER INFORMATION: alignment of protein kinase domains

<400> SEQUENCE: 109

Leu Lys Pro Leu Lys Val Leu Gly Lys Gly Gly Met Gly Thr Val Phe
1               5                   10                  15

Leu Val Gln Ala Ala Asn Asn Thr Arg Phe Ala Leu Lys Val Val Asp
            20                  25                  30

Lys Thr Cys Val His Ala Lys Leu Asp Ala Glu Arg Arg Ala Arg Trp
        35                  40                  45

Glu Ile Gln Val Leu Ser Thr Leu Ser His Pro Phe Leu Pro Ser Leu
    50                  55                  60

Met Gly Thr Phe Glu Ser Pro Gln Phe Leu Ala Trp Ala Leu Pro Tyr
65                  70                  75                  80

Cys Pro Gly Gly Asp Leu Asn Val Leu Arg Tyr Arg Gln Thr Asp Arg
                85                  90                  95
```

```
Ala Phe Ser Pro Ala Val Ile Arg Phe Tyr Val Ala Glu Ile Leu Cys
                100                 105                 110

Ala Leu Asp His Leu His Ser Met Gly Ile Ala Tyr Arg Asp Leu Lys
            115                 120                 125

Pro Glu Asn Val Leu Val Gln Asn Thr Gly His Ile Thr Leu Thr Asp
    130                 135                 140

Phe Asp Leu Ser Arg Lys Leu Asn Pro Lys Pro Lys Pro Asn Pro Gln
145                 150                 155                 160

Val Pro Ser Ile Pro Leu Pro Asn Ser Asn Val Pro Glu Pro Arg Arg
                165                 170                 175

Lys His Arg Arg Asn Phe Ser Arg Trp Ile Ser Leu Phe Pro Pro Asp
            180                 185                 190

Gly Thr His His Asn Asn Asn Lys Asn Gly Leu Lys Lys Ala Lys Ser
        195                 200                 205

Ala Arg Val Ser Pro Val Ser Arg Arg Lys Pro Ser Phe Ser Asn Gly
    210                 215                 220

Glu Arg Ser Asn Ser Phe Val Gly Thr Glu Glu Tyr Val Ser Pro Glu
225                 230                 235                 240

Val Val Arg Gly Asp Gly His Glu Phe Ala Val Asp Trp
                245                 250

<210> SEQ ID NO 110
<211> LENGTH: 241
<212> TYPE: PRT
<213> ORGANISM: Artificial Sequence
<220> FEATURE:
<223> OTHER INFORMATION: alignment of protein kinase domains

<400> SEQUENCE: 110

Phe Ser Asn Thr Asn Ile Ile Gly Thr Gly Arg Thr Gly Thr Val Tyr
1               5                   10                  15

Lys Ala Val Leu Asp Asp Gly Thr Thr Leu Met Val Lys Arg Leu Gln
                20                  25                  30

Glu Ser Gln Tyr Thr Glu Lys Glu Phe Met Ser Glu Met Gly Thr Leu
            35                  40                  45

Gly Thr Val Lys His Arg Asn Leu Val Pro Leu Leu Gly Phe Cys Met
        50                  55                  60

Thr Lys Arg Glu Arg Leu Leu Val Tyr Lys Asn Met Pro Asn Gly Asn
65                  70                  75                  80

Leu His Asp Gln Leu His Pro Ala Asp Gly Val Ser Thr Leu Asp Trp
                85                  90                  95

Thr Thr Arg Leu Lys Ile Ala Ile Gly Ala Ala Lys Gly Leu Ala Trp
                100                 105                 110

Leu His His Ser Cys Asn Pro Arg Ile Ile His Arg Asn Ile Ser Ser
            115                 120                 125

Lys Cys Ile Leu Leu Asp Ala Asp Phe Glu Pro Lys Ile Ser Asp Phe
        130                 135                 140

Gly Leu Ala Arg Leu Met Asn Pro Ile Asp Thr His Leu Ser Thr Phe
145                 150                 155                 160

Val Asn Gly Glu Phe Gly Asp Leu Gly Tyr Val Ala Pro Glu Tyr Thr
                165                 170                 175

Arg Thr Leu Val Ala Thr Pro Lys Gly Asp Ile Tyr Ser Phe Gly Thr
            180                 185                 190

Val Leu Leu Glu Leu Val Thr Gly Glu Arg Pro Thr Asn Val Ser Lys
        195                 200                 205
```

Ala Pro Glu Thr Phe Lys Gly Asn Leu Val Glu Trp Ile Thr Glu Leu
            210                 215                 220

Thr Ser Asn Ala Lys Leu His Asp Ala Ile Asp Glu Ser Leu Val Arg
225                 230                 235                 240

Lys

<210> SEQ ID NO 111
<211> LENGTH: 239
<212> TYPE: PRT
<213> ORGANISM: Artificial Sequence
<220> FEATURE:
<223> OTHER INFORMATION: alignment of protein kinase domains

<400> SEQUENCE: 111

Phe Asp Glu His Phe Val Gly Met Gly Gly Phe Gly Asn Val Tyr
1               5                   10                  15

Lys Gly Tyr Ile Asp Asp Gly Ser Thr Arg Val Ala Ile Lys Arg Leu
            20                  25                  30

Lys Pro Asp Ser Arg Gln Gly Ala Gln Glu Phe Met Asn Glu Ile Glu
            35                  40                  45

Met Leu Ser Gln Leu Arg His Leu His Leu Val Ser Leu Val Gly Tyr
    50                  55                  60

Cys Tyr Glu Ser Asn Glu Met Ile Leu Val Tyr Asp Phe Met Asp Arg
65                  70                  75                  80

Gly Thr Leu Arg Glu His Leu Tyr Asp Thr Asp Asn Pro Ser Leu Ser
                85                  90                  95

Trp Lys Gln Arg Leu Gln Ile Cys Val Gly Ala Ala Arg Gly Leu His
            100                 105                 110

Tyr Leu His Thr Gly Ala Lys His Thr Ile Ile His Arg Asp Val Lys
        115                 120                 125

Ser Thr Asn Ile Leu Leu Asp Glu Lys Trp Val Ala Lys Val Ser Asp
130                 135                 140

Phe Gly Leu Ser Arg Ile Gly Pro Ile Ser Ser Ser Met Thr His Val
145                 150                 155                 160

Ser Thr Gln Val Lys Gly Ser Val Gly Tyr Ile Asp Pro Glu Tyr Tyr
                165                 170                 175

Lys Arg Gln Arg Leu Thr Glu Lys Ser Asp Val Tyr Ser Phe Gly Val
            180                 185                 190

Val Leu Leu Glu Val Leu Ser Gly Arg Gln Pro Leu Leu Arg Trp Glu
        195                 200                 205

Glu Lys Gln Arg Ile Ser Leu Val Asn Trp Ala Lys His Cys Asn Glu
    210                 215                 220

Lys Gly Thr Leu Ser Glu Ile Val Asp Ala Lys Leu Lys Gly Gln
225                 230                 235

<210> SEQ ID NO 112
<211> LENGTH: 238
<212> TYPE: PRT
<213> ORGANISM: Artificial Sequence
<220> FEATURE:
<223> OTHER INFORMATION: alignment of protein kinase domains

<400> SEQUENCE: 112

Phe Asp Ala Leu Asn Lys Ile Gly Glu Gly Gly Phe Gly Cys Val Tyr
1               5                   10                  15

Lys Gly Gln Gln Ser Asp Gly Thr Met Ile Ala Val Lys Gln Leu Ser
            20                  25                  30

-continued

Ser Lys Ser Lys Gln Gly Asn Arg Glu Phe Val Asn Glu Met Gly Leu
        35                  40                  45

Ile Ser Gly Leu Gln His Pro Asn Leu Val Lys Leu Tyr Gly Cys Cys
 50                  55                  60

Val Glu Gly Asn Gln Leu Ile Leu Ile Tyr Glu Tyr Met Glu Asn Asn
 65                  70                  75                  80

Cys Leu Ser Arg Ile Leu Phe Gly Arg Asp Pro Asn Lys Thr Lys Leu
                 85                  90                  95

Asp Trp Pro Thr Arg Lys Lys Ile Cys Leu Gly Ile Ala Lys Ala Leu
                100                 105                 110

Ala Tyr Leu His Glu Glu Ser Arg Ile Lys Ile Ile His Arg Asp Val
            115                 120                 125

Lys Ala Ser Asn Val Leu Leu Asp Lys Asp Phe Asn Ala Lys Val Ser
        130                 135                 140

Asp Phe Gly Leu Ala Lys Leu Ile Glu Asp Glu Lys Thr His Ile Ser
145                 150                 155                 160

Thr Arg Val Ala Gly Thr Ile Gly Tyr Met Ala Pro Glu Tyr Ala Met
                165                 170                 175

Arg Gly Tyr Leu Thr Asp Lys Ala Asp Val Tyr Ser Phe Gly Val Val
                180                 185                 190

Ala Leu Glu Thr Val Ser Gly Lys Ser Asn Thr Asn Phe Arg Pro Asn
            195                 200                 205

Glu Asp Phe Val Tyr Leu Leu Asp Trp Ala Tyr Val Leu Gln Glu Arg
        210                 215                 220

Gly Ser Leu Leu Glu Leu Val Asp Pro Asn Leu Gly Ser Glu
225                 230                 235

<210> SEQ ID NO 113
<211> LENGTH: 237
<212> TYPE: PRT
<213> ORGANISM: Artificial Sequence
<220> FEATURE:
<223> OTHER INFORMATION: alignment of protein kinase domains

<400> SEQUENCE: 113

Phe Asp Glu Ala Asn Lys Leu Gly Gln Gly Gly Phe Gly Thr Val Tyr
 1               5                  10                  15

Lys Gly Val Leu Ala Asp Gly Arg Glu Ile Ala Ile Lys Arg Leu Tyr
                20                  25                  30

Phe Asn Asn Arg His Arg Ala Ala Asp Phe Phe Asn Glu Val Asn Ile
            35                  40                  45

Ile Ser Ser Val Glu His Lys Asn Leu Val Arg Leu Leu Gly Cys Ser
 50                  55                  60

Cys Ser Gly Pro Glu Ser Leu Leu Ile Tyr Glu Tyr Leu Pro Asn Arg
 65                  70                  75                  80

Ser Leu Asp Arg Phe Ile Phe Asp Lys Asn Lys Gly Arg Glu Leu Asn
                 85                  90                  95

Trp Asp Lys Arg Tyr Asp Ile Ile Gly Thr Ala Glu Gly Leu Val
                100                 105                 110

Tyr Leu His Glu Asn Ser Asn Ile Arg Ile Ile His Arg Asp Ile Lys
            115                 120                 125

Ala Ser Asn Ile Leu Leu Asp Ala Lys Leu Arg Ala Lys Ile Ala Asp
        130                 135                 140

Phe Gly Leu Ala Arg Ser Phe Gln Glu Asp Lys Ser His Ile Ser Thr
145                 150                 155                 160

```
Ala Ile Ala Gly Thr Leu Gly Tyr Met Ala Pro Glu Tyr Leu Ala His
                165                 170                 175

Gly Gln Leu Thr Glu Lys Ala Asp Val Tyr Ser Phe Gly Val Leu Leu
                180                 185                 190

Leu Glu Ile Ile Thr Gly Arg Leu Asn Asn Arg Ser Lys Ala Ser Glu
                195                 200                 205

Tyr Ser Asp Ser Leu Val Thr Met Thr Trp Lys His Phe Gln Ser Gly
                210                 215                 220

Thr Ala Glu Gln Leu Ile Asp Pro Cys Leu Val Val Asp
225                 230                 235

<210> SEQ ID NO 114
<211> LENGTH: 236
<212> TYPE: PRT
<213> ORGANISM: Artificial Sequence
<220> FEATURE:
<223> OTHER INFORMATION: alignment of protein kinase domains

<400> SEQUENCE: 114

Leu Asn Lys Asp Cys Glu Leu Gly Arg Gly Gly Phe Gly Ala Val Tyr
1               5                   10                  15

Gln Thr Val Leu Arg Asp Gly His Ser Val Ala Ile Lys Lys Leu Thr
                20                  25                  30

Val Ser Ser Leu Val Lys Ser Gln Glu Asp Phe Glu Arg Glu Val Lys
                35                  40                  45

Lys Leu Gly Lys Ile Arg His Gln Asn Leu Val Glu Leu Gly Tyr
    50                  55                  60

Tyr Trp Thr Pro Ser Leu Gln Leu Leu Ile Tyr Glu Tyr Leu Ser Gly
65                  70                  75                  80

Gly Ser Leu Tyr Lys His Leu His Glu Gly Ser Gly Asn Phe Leu
                85                  90                  95

Ser Trp Asn Glu Arg Phe Asn Val Ile Leu Gly Thr Ala Lys Ala Leu
                100                 105                 110

Ala His Leu His His Ser Asn Ile Ile His Tyr Asn Ile Lys Ser Thr
                115                 120                 125

Asn Val Leu Leu Asp Ser Tyr Gly Glu Pro Lys Val Gly Asp Phe Gly
                130                 135                 140

Leu Ala Arg Leu Leu Pro Met Leu Asp Arg Tyr Val Leu Ser Ser Lys
145                 150                 155                 160

Ile Gln Ser Ala Leu Gly Tyr Met Ala Pro Glu Phe Ala Cys Lys Thr
                165                 170                 175

Val Lys Ile Thr Glu Lys Cys Asp Val Tyr Gly Phe Gly Val Leu Val
                180                 185                 190

Leu Glu Ile Val Thr Gly Lys Arg Pro Val Glu Tyr Met Glu Asp Asp
                195                 200                 205

Val Val Val Leu Cys Asp Met Val Arg Gly Ala Leu Glu Glu Gly Arg
                210                 215                 220

Val Glu Glu Cys Ile Asp Glu Arg Leu Gln Gly Lys
225                 230                 235

<210> SEQ ID NO 115
<211> LENGTH: 239
<212> TYPE: PRT
<213> ORGANISM: Artificial Sequence
<220> FEATURE:
<223> OTHER INFORMATION: alignment of protein kinase domains
```

<400> SEQUENCE: 115

```
Arg Ala Ser Ala Glu Met Leu Gly Lys Gly Ser Leu Gly Thr Val Tyr
1               5                   10                  15

Arg Ala Val Leu Asp Asp Gly Cys Thr Val Ala Val Lys Arg Leu Lys
            20                  25                  30

Asp Ala Asn Pro Cys Glu Arg Asn Glu Phe Glu Gln Tyr Met Asp Val
        35                  40                  45

Val Gly Lys Leu Lys His Pro Asn Ile Val Arg Leu Arg Ala Tyr Tyr
    50                  55                  60

Tyr Ala Lys Glu Glu Lys Leu Leu Val Tyr Asp Tyr Leu Pro Asn Gly
65                  70                  75                  80

Ser Leu His Ala Leu Leu His Gly Asn Arg Gly Pro Gly Arg Ile Pro
                85                  90                  95

Leu Asp Trp Thr Thr Arg Ile Ser Leu Met Leu Gly Ala Ala Arg Gly
            100                 105                 110

Leu Ala Arg Ile His Ala Glu Tyr Asn Ala Ser Lys Ile Pro His Gly
        115                 120                 125

Asn Val Lys Ser Ser Asn Val Leu Leu Asp Lys Asn Gly Val Ala Leu
    130                 135                 140

Ile Ser Asp Phe Gly Leu Ser Leu Leu Leu Asn Pro Val His Ala Ile
145                 150                 155                 160

Ala Arg Leu Gly Gly Tyr Arg Ala Pro Glu Gln Val Glu Val Lys Arg
                165                 170                 175

Leu Ser Gln Glu Ala Asp Val Tyr Gly Phe Gly Val Leu Leu Leu Glu
            180                 185                 190

Val Leu Thr Gly Arg Ala Pro Ser Lys Glu Tyr Thr Ser Pro Ala Arg
        195                 200                 205

Glu Ala Glu Val Asp Leu Pro Lys Trp Val Lys Ser Val Val Lys Glu
    210                 215                 220

Glu Trp Thr Ser Glu Val Phe Asp Gln Glu Leu Leu Arg Tyr Lys
225                 230                 235
```

<210> SEQ ID NO 116
<211> LENGTH: 247
<212> TYPE: PRT
<213> ORGANISM: Artificial Sequence
<220> FEATURE:
<223> OTHER INFORMATION: alignment of protein kinase domains

<400> SEQUENCE: 116

```
Arg Ala Ser Ala Glu Met Leu Gly Lys Gly Ser Leu Gly Thr Val Tyr
1               5                   10                  15

Arg Ala Val Leu Asp Asp Gly Cys Thr Val Ala Val Lys Arg Leu Lys
            20                  25                  30

Asp Ala Asn Pro Cys Ala Arg His Glu Phe Glu Gln Tyr Met Asp Val
        35                  40                  45

Ile Gly Lys Leu Lys His Pro Asn Val Val Arg Leu Lys Ala Tyr Tyr
    50                  55                  60

Tyr Ala Lys Glu Glu Lys Leu Leu Val Tyr Asp Tyr Leu Ser Asn Gly
65                  70                  75                  80

Ser Leu His Ala Leu Leu His Gly Asn Arg Gly Pro Gly Arg Ile Pro
                85                  90                  95

Leu Asp Trp Thr Thr Arg Ile Ser Leu Val Leu Gly Ala Ala Arg Gly
            100                 105                 110

Leu Ala Lys Ile His Ala Glu Tyr Ser Ala Ala Lys Val Pro His Gly
```

```
                115            120              125
Asn Val Lys Ser Ser Asn Val Leu Leu Asp Lys Asn Gly Val Ala Cys
            130                 135             140

Ile Ser Asp Phe Gly Leu Ser Leu Leu Leu Asn Pro Val His Ala Ile
145                 150                 155                 160

Ala Arg Leu Gly Gly Tyr Arg Ala Pro Glu Gln Glu Gln Asn Lys Arg
                165                 170                 175

Leu Ser Gln Gln Ala Asp Val Tyr Ser Phe Gly Val Leu Leu Leu Glu
            180                 185                 190

Val Leu Thr Gly Arg Ala Pro Ser Ser Gln Tyr Pro Ser Pro Ala Arg
            195                 200                 205

Pro Arg Met Glu Val Glu Pro Glu Gln Ala Ala Val Asp Leu Pro Lys
            210                 215                 220

Trp Val Arg Ser Val Val Arg Glu Glu Trp Thr Ala Glu Val Phe Asp
225                 230                 235                 240

Gln Glu Leu Leu Arg Tyr Lys
                245
```

<210> SEQ ID NO 117
<211> LENGTH: 208
<212> TYPE: PRT
<213> ORGANISM: Glycine max

<400> SEQUENCE: 117

```
Arg Ala Ser Ala Glu Met Leu Gly Lys Gly Ser Leu Gly Thr Val Tyr
1               5                   10                  15

Arg Ala Val Leu Asp Asp Gly Cys Thr Val Ala Val Lys Arg Leu Lys
                20                  25                  30

Asp Ala Asn Pro Cys Glu Arg Asn Glu Phe Glu Gln Tyr Met Asp Val
            35                  40                  45

Val Gly Lys Leu Lys His Pro Asn Ile Val Arg Leu Arg Ala Tyr Tyr
    50                  55                  60

Tyr Ala Lys Glu Glu Lys Leu Leu Val Tyr Asp Tyr Leu Pro Asn Gly
65                  70                  75                  80

Ser Leu His Ala Leu His Gly Asn Arg Gly Pro Gly Arg Ile Pro
                85                  90                  95

Leu Asp Trp Thr Thr Arg Ile Ser Leu Met Leu Gly Ala Ala Arg Gly
                100                 105                 110

Leu Ala Arg Ile His Ala Glu Tyr Asn Ala Ser Lys Ile Pro His Gly
            115                 120                 125

Asn Val Lys Ser Ser Asn Val Leu Leu Asp Lys Asn Gly Val Ala Leu
            130                 135                 140

Ile Ser Asp Phe Gly Leu Ser Leu Leu Leu Asn Pro Val His Ala Ile
145                 150                 155                 160

Ala Arg Leu Gly Gly Tyr Arg Ala Pro Glu Gln Val Glu Val Lys Arg
                165                 170                 175

Leu Ser Gln Glu Ala Asp Val Tyr Gly Phe Gly Val Leu Leu Leu Glu
            180                 185                 190

Val Leu Thr Gly Arg Ala Pro Ser Lys Glu Tyr Thr Ser Pro Ala Arg
            195                 200                 205
```

<210> SEQ ID NO 118
<211> LENGTH: 206
<212> TYPE: PRT
<213> ORGANISM: Glycine max -continued

```
<400> SEQUENCE: 118

Leu Asn Lys Asp Cys Glu Leu Gly Arg Gly Gly Phe Gly Ala Val Tyr
1               5                   10                  15

Gln Thr Val Leu Arg Asp Gly His Ser Val Ala Ile Lys Lys Leu Thr
            20                  25                  30

Val Ser Ser Leu Val Lys Ser Gln Glu Asp Phe Glu Arg Glu Val Lys
        35                  40                  45

Lys Leu Gly Lys Ile Arg His Gln Asn Leu Val Glu Leu Glu Gly Tyr
    50                  55                  60

Tyr Trp Thr Pro Ser Leu Gln Leu Leu Ile Tyr Glu Tyr Leu Ser Gly
65                  70                  75                  80

Gly Ser Leu Tyr Lys His Leu His Glu Gly Ser Gly Gly Asn Phe Leu
                85                  90                  95

Ser Trp Asn Glu Arg Phe Asn Val Ile Leu Gly Thr Ala Lys Ala Leu
            100                 105                 110

Ala His Leu His His Ser Asn Ile Ile His Tyr Asn Ile Lys Ser Thr
        115                 120                 125

Asn Val Leu Leu Asp Ser Tyr Gly Glu Pro Lys Val Gly Asp Phe Gly
    130                 135                 140

Leu Ala Arg Leu Leu Pro Met Leu Asp Arg Tyr Val Leu Ser Ser Lys
145                 150                 155                 160

Ile Gln Ser Ala Leu Gly Tyr Met Ala Pro Glu Phe Ala Cys Lys Thr
                165                 170                 175

Val Lys Ile Thr Glu Lys Cys Asp Val Tyr Gly Phe Gly Val Leu Val
            180                 185                 190

Leu Glu Ile Val Thr Gly Lys Arg Pro Val Glu Tyr Met Glu
        195                 200                 205

<210> SEQ ID NO 119
<211> LENGTH: 232
<212> TYPE: PRT
<213> ORGANISM: Glycine max

<400> SEQUENCE: 119

Leu Lys Pro Leu Lys Val Leu Gly Lys Gly Met Gly Thr Val Phe
1               5                   10                  15

Leu Val Gln Ala Ala Asn Asn Thr Arg Phe Ala Leu Lys Val Val Asp
            20                  25                  30

Lys Thr Cys Val His Ala Lys Leu Asp Ala Glu Arg Arg Ala Arg Trp
        35                  40                  45

Glu Ile Gln Val Leu Ser Thr Leu Ser His Pro Phe Leu Pro Ser Leu
    50                  55                  60

Met Gly Thr Phe Glu Ser Pro Gln Phe Leu Ala Trp Ala Leu Pro Tyr
65                  70                  75                  80

Cys Pro Gly Gly Asp Leu Asn Val Leu Arg Tyr Arg Gln Thr Asp Arg
                85                  90                  95

Ala Phe Ser Pro Ala Val Ile Arg Phe Tyr Val Ala Glu Ile Leu Cys
            100                 105                 110

Ala Leu Asp His Leu His Ser Met Gly Ile Ala Tyr Arg Asp Leu Lys
        115                 120                 125

Pro Glu Asn Val Leu Val Gln Asn Thr Gly His Ile Thr Leu Thr Asp
    130                 135                 140

Phe Asp Leu Ser Arg Lys Leu Asn Pro Lys Pro Lys Pro Asn Pro Gln
145                 150                 155                 160
```

```
Val Pro Ser Ile Pro Leu Pro Asn Ser Asn Val Pro Glu Pro Arg Arg
                165                 170                 175

Lys His Arg Arg Asn Phe Ser Arg Trp Ile Ser Leu Phe Pro Pro Asp
            180                 185                 190

Gly Thr His His Asn Asn Asn Lys Asn Gly Leu Lys Lys Ala Lys Ser
        195                 200                 205

Ala Arg Val Ser Pro Val Ser Arg Arg Lys Pro Ser Phe Ser Asn Gly
    210                 215                 220

Glu Arg Ser Asn Ser Phe Val Gly
225                 230
```

<210> SEQ ID NO 120
<211> LENGTH: 211
<212> TYPE: PRT
<213> ORGANISM: Glycine max

<400> SEQUENCE: 120

```
Arg Ala Ser Ala Glu Met Leu Gly Lys Gly Ser Leu Gly Thr Val Tyr
1               5                   10                  15

Arg Ala Val Leu Asp Asp Gly Cys Thr Val Ala Val Lys Arg Leu Lys
            20                  25                  30

Asp Ala Asn Pro Cys Ala Arg His Glu Phe Glu Gln Tyr Met Asp Val
        35                  40                  45

Ile Gly Lys Leu Lys His Pro Asn Val Val Arg Leu Lys Ala Tyr Tyr
    50                  55                  60

Tyr Ala Lys Glu Glu Lys Leu Leu Val Tyr Asp Tyr Leu Ser Asn Gly
65                  70                  75                  80

Ser Leu His Ala Leu Leu His Gly Asn Arg Gly Pro Gly Arg Ile Pro
                85                  90                  95

Leu Asp Trp Thr Thr Arg Ile Ser Leu Val Leu Gly Ala Ala Arg Gly
            100                 105                 110

Leu Ala Lys Ile His Ala Glu Tyr Ser Ala Ala Lys Val Pro His Gly
        115                 120                 125

Asn Val Lys Ser Ser Asn Val Leu Leu Asp Lys Asn Gly Val Ala Cys
    130                 135                 140

Ile Ser Asp Phe Gly Leu Ser Leu Leu Leu Asn Pro Val His Ala Ile
145                 150                 155                 160

Ala Arg Leu Gly Gly Tyr Arg Ala Pro Glu Gln Glu Gln Asn Lys Arg
                165                 170                 175

Leu Ser Gln Gln Ala Asp Val Tyr Ser Phe Gly Val Leu Leu Leu Glu
            180                 185                 190

Val Leu Thr Gly Arg Ala Pro Ser Ser Gln Tyr Pro Ser Pro Ala Arg
        195                 200                 205

Pro Arg Met
    210
```

<210> SEQ ID NO 121
<211> LENGTH: 208
<212> TYPE: PRT
<213> ORGANISM: Glycine max

<400> SEQUENCE: 121

```
Phe Asp Ala Leu Asn Lys Ile Gly Glu Gly Gly Phe Gly Cys Val Tyr
1               5                   10                  15

Lys Gly Gln Gln Ser Asp Gly Thr Met Ile Ala Val Lys Gln Leu Ser
            20                  25                  30
```

Ser Lys Ser Lys Gln Gly Asn Arg Glu Phe Val Asn Glu Met Gly Leu
        35                  40                  45

Ile Ser Gly Leu Gln His Pro Asn Leu Val Lys Leu Tyr Gly Cys Cys
 50                  55                  60

Val Glu Gly Asn Gln Leu Ile Leu Ile Tyr Glu Tyr Met Glu Asn Asn
 65                  70                  75                  80

Cys Leu Ser Arg Ile Leu Phe Gly Arg Asp Pro Asn Lys Thr Lys Leu
                 85                  90                  95

Asp Trp Pro Thr Arg Lys Lys Ile Cys Leu Gly Ile Ala Lys Ala Leu
                100                 105                 110

Ala Tyr Leu His Glu Glu Ser Arg Ile Lys Ile Ile His Arg Asp Val
                115                 120                 125

Lys Ala Ser Asn Val Leu Leu Asp Lys Asp Phe Asn Ala Lys Val Ser
130                 135                 140

Asp Phe Gly Leu Ala Lys Leu Ile Glu Asp Glu Lys Thr His Ile Ser
145                 150                 155                 160

Thr Arg Val Ala Gly Thr Ile Gly Tyr Met Ala Pro Glu Tyr Ala Met
                165                 170                 175

Arg Gly Tyr Leu Thr Asp Lys Ala Asp Val Tyr Ser Phe Gly Val Val
                180                 185                 190

Ala Leu Glu Thr Val Ser Gly Lys Ser Asn Thr Asn Phe Arg Pro Asn
                195                 200                 205

<210> SEQ ID NO 122
<211> LENGTH: 211
<212> TYPE: PRT
<213> ORGANISM: Glycine max

<400> SEQUENCE: 122

Phe Ser Asn Thr Asn Ile Ile Gly Thr Gly Arg Thr Gly Thr Val Tyr
 1                   5                  10                  15

Lys Ala Val Leu Asp Asp Gly Thr Thr Leu Met Val Lys Arg Leu Gln
                 20                  25                  30

Glu Ser Gln Tyr Thr Glu Lys Glu Phe Met Ser Glu Met Gly Thr Leu
                 35                  40                  45

Gly Thr Val Lys His Arg Asn Leu Val Pro Leu Leu Gly Phe Cys Met
 50                  55                  60

Thr Lys Arg Glu Arg Leu Leu Val Tyr Lys Asn Met Pro Asn Gly Asn
 65                  70                  75                  80

Leu His Asp Gln Leu His Pro Ala Asp Gly Val Ser Thr Leu Asp Trp
                 85                  90                  95

Thr Thr Arg Leu Lys Ile Ala Ile Gly Ala Ala Lys Gly Leu Ala Trp
                100                 105                 110

Leu His His Ser Cys Asn Pro Arg Ile Ile His Arg Asn Ile Ser Ser
                115                 120                 125

Lys Cys Ile Leu Leu Asp Ala Asp Phe Glu Pro Lys Ile Ser Asp Phe
130                 135                 140

Gly Leu Ala Arg Leu Met Asn Pro Ile Asp Thr His Leu Ser Thr Phe
145                 150                 155                 160

Val Asn Gly Glu Phe Gly Asp Leu Gly Tyr Val Ala Pro Glu Tyr Thr
                165                 170                 175

Arg Thr Leu Val Ala Thr Pro Lys Gly Asp Ile Tyr Ser Phe Gly Thr
                180                 185                 190

Val Leu Leu Glu Leu Val Thr Gly Glu Arg Pro Thr Asn Val Ser Lys
                195                 200                 205

Ala Pro Glu
    210

<210> SEQ ID NO 123
<211> LENGTH: 209
<212> TYPE: PRT
<213> ORGANISM: Glycine max

<400> SEQUENCE: 123

Phe Asp Glu Ala Asn Lys Leu Gly Gln Gly Gly Phe Gly Thr Val Tyr
1               5                   10                  15

Lys Gly Val Leu Ala Asp Gly Arg Glu Ile Ala Ile Lys Arg Leu Tyr
            20                  25                  30

Phe Asn Asn Arg His Arg Ala Ala Asp Phe Phe Asn Glu Val Asn Ile
        35                  40                  45

Ile Ser Ser Val Glu His Lys Asn Leu Val Arg Leu Leu Gly Cys Ser
    50                  55                  60

Cys Ser Gly Pro Glu Ser Leu Leu Ile Tyr Glu Tyr Leu Pro Asn Arg
65                  70                  75                  80

Ser Leu Asp Arg Phe Ile Phe Asp Lys Asn Lys Gly Arg Glu Leu Asn
                85                  90                  95

Trp Asp Lys Arg Tyr Asp Ile Ile Gly Thr Ala Glu Gly Leu Val
            100                 105                 110

Tyr Leu His Glu Asn Ser Asn Ile Arg Ile Ile His Arg Asp Ile Lys
        115                 120                 125

Ala Ser Asn Ile Leu Leu Asp Ala Lys Leu Arg Ala Lys Ile Ala Asp
    130                 135                 140

Phe Gly Leu Ala Arg Ser Phe Gln Glu Asp Lys Ser His Ile Ser Thr
145                 150                 155                 160

Ala Ile Ala Gly Thr Leu Gly Tyr Met Ala Pro Glu Tyr Leu Ala His
                165                 170                 175

Gly Gln Leu Thr Glu Lys Ala Asp Val Tyr Ser Phe Gly Val Leu Leu
            180                 185                 190

Leu Glu Ile Ile Thr Gly Arg Leu Asn Asn Arg Ser Lys Ala Ser Glu
        195                 200                 205

Tyr

<210> SEQ ID NO 124
<211> LENGTH: 209
<212> TYPE: PRT
<213> ORGANISM: Glycine max

<400> SEQUENCE: 124

Phe Asp Glu His Phe Val Val Gly Met Gly Gly Phe Gly Asn Val Tyr
1               5                   10                  15

Lys Gly Tyr Ile Asp Asp Gly Ser Thr Arg Val Ala Ile Lys Arg Leu
            20                  25                  30

Lys Pro Asp Ser Arg Gln Gly Ala Gln Glu Phe Met Asn Glu Ile Glu
        35                  40                  45

Met Leu Ser Gln Leu Arg His Leu His Leu Val Ser Leu Val Gly Tyr
    50                  55                  60

Cys Tyr Glu Ser Asn Glu Met Ile Leu Val Tyr Asp Phe Met Asp Arg
65                  70                  75                  80

Gly Thr Leu Arg Glu His Leu Tyr Asp Thr Asp Asn Pro Ser Leu Ser
                85                  90                  95

Trp Lys Gln Arg Leu Gln Ile Cys Val Gly Ala Ala Arg Gly Leu His
                100                 105                 110

Tyr Leu His Thr Gly Ala Lys Thr Ile Ile His Arg Asp Val Lys
        115                 120                 125

Ser Thr Asn Ile Leu Leu Asp Glu Lys Trp Val Ala Lys Val Ser Asp
130                 135                 140

Phe Gly Leu Ser Arg Ile Gly Pro Ile Ser Ser Met Thr His Val
145                 150                 155                 160

Ser Thr Gln Val Lys Gly Ser Val Gly Tyr Ile Asp Pro Glu Tyr Tyr
            165                 170                 175

Lys Arg Gln Arg Leu Thr Glu Lys Ser Asp Val Tyr Ser Phe Gly Val
            180                 185                 190

Val Leu Leu Glu Val Leu Ser Gly Arg Gln Pro Leu Leu Arg Trp Glu
            195                 200                 205

Glu

<210> SEQ ID NO 125
<211> LENGTH: 206
<212> TYPE: PRT
<213> ORGANISM: Zea mays

<400> SEQUENCE: 125

Lys Val Glu Leu Gly Arg Gly Glu Ser Gly Thr Val Tyr Lys Gly Val
1               5                   10                  15

Leu Glu Asp Asp Arg His Val Ala Val Lys Lys Leu Glu Asn Val Arg
            20                  25                  30

Gln Gly Lys Glu Val Phe Gln Ala Glu Leu Ser Val Ile Gly Arg Ile
        35                  40                  45

Asn His Met Asn Leu Val Arg Ile Trp Gly Phe Cys Ser Glu Gly Ser
    50                  55                  60

His Arg Leu Leu Val Ser Glu Tyr Val Glu Asn Gly Ser Leu Ala Asn
65                  70                  75                  80

Ile Leu Phe Ser Glu Gly Asn Ile Leu Leu Asp Trp Glu Gly Arg
            85                  90                  95

Phe Asn Ile Ala Leu Gly Val Ala Lys Gly Leu Ala Tyr Leu His His
            100                 105                 110

Glu Cys Leu Glu Trp Val Ile His Cys Asp Val Lys Pro Glu Asn Ile
        115                 120                 125

Leu Leu Asp Gln Ala Phe Glu Pro Lys Ile Thr Asp Phe Gly Leu Val
    130                 135                 140

Lys Leu Leu Asn Arg Gly Gly Ser Thr Gln Asn Val Ser His Val Arg
145                 150                 155                 160

Gly Thr Leu Gly Tyr Ile Ala Pro Glu Trp Val Ser Ser Leu Pro Ile
            165                 170                 175

Thr Ala Lys Val Asp Val Tyr Ser Tyr Gly Val Val Leu Leu Glu Leu
            180                 185                 190

Leu Thr Gly Thr Arg Val Ser Glu Leu Val Gly Gly Thr Asp
            195                 200                 205

<210> SEQ ID NO 126
<211> LENGTH: 211
<212> TYPE: PRT
<213> ORGANISM: Homo sapiens

<400> SEQUENCE: 126

Glu Glu Ile Ile Gly Ile Gly Gly Phe Gly Lys Val Tyr Arg Ala Phe

```
1               5                   10                  15
Trp Ile Gly Asp Glu Val Ala Val Lys Ala Ala Arg His Asp Pro Asp
            20                  25                  30
Glu Asp Ile Ser Gln Thr Ile Glu Asn Val Arg Gln Glu Ala Lys Leu
            35                  40                  45
Phe Ala Met Leu Lys His Pro Asn Ile Ile Ala Leu Arg Gly Val Cys
        50                  55                  60
Leu Lys Glu Pro Asn Leu Cys Leu Val Met Glu Phe Ala Arg Gly Gly
65                  70                  75                  80
Pro Leu Asn Arg Val Leu Ser Gly Lys Arg Ile Pro Pro Asp Ile Leu
                85                  90                  95
Val Asn Trp Ala Val Gln Ile Ala Arg Gly Met Asn Tyr Leu His Asp
            100                 105                 110
Glu Ala Ile Val Pro Ile Ile His Arg Asp Leu Lys Ser Ser Asn Ile
            115                 120                 125
Leu Ile Leu Gln Lys Val Glu Asn Gly Asp Leu Ser Asn Lys Ile Leu
        130                 135                 140
Lys Ile Thr Asp Phe Gly Leu Ala Arg Glu Trp His Arg Thr Thr Lys
145                 150                 155                 160
Met Ser Ala Ala Gly Thr Tyr Ala Trp Met Ala Pro Glu Val Ile Arg
                165                 170                 175
Ala Ser Met Phe Ser Lys Gly Ser Asp Val Trp Ser Tyr Gly Val Leu
            180                 185                 190
Leu Trp Glu Leu Leu Thr Gly Glu Val Pro Phe Arg Gly Ile Asp Gly
            195                 200                 205
Leu Ala Val
    210

<210> SEQ ID NO 127
<211> LENGTH: 203
<212> TYPE: PRT
<213> ORGANISM: Gallus gallus

<400> SEQUENCE: 127

Val Arg Lys Leu Gly Arg Gly Lys Tyr Ser Glu Val Phe Glu Ala Ile
1               5                   10                  15
Asn Ile Thr Asn Asn Glu Lys Val Val Val Lys Ile Leu Lys Pro Val
            20                  25                  30
Lys Lys Lys Lys Ile Lys Arg Glu Ile Lys Ile Leu Glu Asn Leu Arg
            35                  40                  45
Gly Gly Pro Asn Ile Ile Thr Leu Ala Asp Ile Val Lys Asp Pro Val
        50                  55                  60
Ser Arg Thr Pro Ala Leu Val Phe Glu His Val Asn Asn Thr Asp Phe
65                  70                  75                  80
Lys Gln Leu Tyr Gln Thr Leu Thr Asp Tyr Asp Ile Arg Phe Tyr Met
                85                  90                  95
Tyr Glu Ile Leu Lys Ala Leu Asp Tyr Cys His Ser Met Gly Ile Met
            100                 105                 110
His Arg Asp Val Lys Pro His Asn Val Met Ile Asp His Glu His Arg
            115                 120                 125
Lys Leu Arg Leu Ile Asp Trp Gly Leu Ala Glu Phe Tyr His Pro Gly
        130                 135                 140
Gln Glu Tyr Asn Val Arg Val Ala Ser Arg Tyr Phe Lys Gly Pro Glu
145                 150                 155                 160
```

-continued

```
Leu Leu Val Asp Tyr Gln Met Tyr Asp Tyr Ser Leu Asp Met Trp Ser
            165                 170                 175

Leu Gly Cys Met Leu Ala Ser Met Ile Phe Arg Lys Glu Pro Phe Phe
        180                 185                 190

His Gly His Asp Asn Tyr Asp Gln Leu Val Ile
        195                 200

<210> SEQ ID NO 128
<211> LENGTH: 209
<212> TYPE: PRT
<213> ORGANISM: Rattus norvegicus

<400> SEQUENCE: 128

Ile Lys Val Ile Gly Asn Gly Ser Phe Gly Val Val Tyr Gln Ala Arg
1               5                   10                  15

Leu Ala Glu Thr Arg Glu Leu Val Ala Ile Lys Lys Val Leu Gln Asp
            20                  25                  30

Lys Arg Phe Lys Asn Arg Glu Leu Gln Ile Met Arg Lys Leu Asp His
        35                  40                  45

Cys Asn Ile Val Arg Leu Arg Tyr Phe Phe Tyr Ser Ser Gly Glu Lys
    50                  55                  60

Lys Asp Glu Leu Tyr Leu Asn Leu Val Leu Glu Tyr Val Pro Glu Thr
65                  70                  75                  80

Val Tyr Arg Val Ala Arg His Phe Thr Lys Ala Lys Leu Ile Ile Pro
                85                  90                  95

Ile Ile Tyr Val Lys Val Tyr Met Tyr Gln Leu Phe Arg Ser Leu Ala
            100                 105                 110

Tyr Ile His Ser Gln Gly Val Cys His Arg Asp Ile Lys Pro Gln Asn
        115                 120                 125

Leu Leu Val Asp Pro Asp Thr Ala Val Leu Lys Leu Cys Asp Phe Gly
    130                 135                 140

Ser Ala Lys Gln Leu Val Arg Gly Glu Pro Asn Val Ser Tyr Ile Cys
145                 150                 155                 160

Ser Arg Tyr Tyr Arg Ala Pro Glu Leu Ile Phe Gly Ala Thr Asp Tyr
                165                 170                 175

Thr Ser Ser Ile Asp Val Trp Ser Ala Gly Cys Val Leu Ala Glu Leu
            180                 185                 190

Leu Leu Gly Gln Pro Ile Phe Pro Gly Asp Ser Gly Val Asp Gln Leu
        195                 200                 205

Val

<210> SEQ ID NO 129
<211> LENGTH: 199
<212> TYPE: PRT
<213> ORGANISM: Saccharomyces cerevisiae

<400> SEQUENCE: 129

Lys Gln Val Ile Gly Arg Gly Ser Tyr Gly Val Val Tyr Lys Ala Ile
1               5                   10                  15

Asn Lys His Thr Asp Gln Val Val Ala Ile Lys Glu Val Val Tyr Glu
            20                  25                  30

Asn Asp Glu Glu Leu Asn Asp Ile Met Ala Glu Ile Ser Leu Leu Lys
        35                  40                  45

Asn Leu Asn His Asn Asn Ile Val Lys Tyr His Gly Phe Ile Arg Lys
    50                  55                  60

Ser Tyr Glu Leu Tyr Ile Leu Leu Glu Tyr Cys Ala Asn Gly Ser Leu
```

```
                65                  70                  75                  80

Arg Arg Leu Ile Ser Arg Ser Thr Gly Leu Ser Glu Asn Glu Ser
                85                  90                  95

Lys Thr Tyr Val Thr Gln Thr Leu Leu Gly Leu Lys Tyr Leu His Gly
                    100                 105                 110

Glu Gly Val Ile His Arg Asp Ile Lys Ala Ala Asn Ile Leu Leu Ser
                115                 120                 125

Ala Asp Asn Thr Val Lys Leu Ala Asp Phe Gly Val Ser Thr Ile Val
                130                 135                 140

Asn Ser Ser Ala Leu Thr Leu Ala Gly Thr Leu Asn Trp Met Ala Pro
145                 150                 155                 160

Glu Ile Leu Gly Asn Arg Gly Ala Ser Thr Leu Ser Asp Ile Trp Ser
                165                 170                 175

Leu Gly Ala Thr Val Val Glu Met Leu Thr Lys Asn Pro Pro Tyr His
                180                 185                 190

Asn Leu Thr Asp Ala Asn Ile
                195
```

<210> SEQ ID NO 130
<211> LENGTH: 206
<212> TYPE: PRT
<213> ORGANISM: Bos taurus

<400> SEQUENCE: 130

```
His Arg Ile Ile Gly Arg Gly Gly Phe Gly Glu Val Tyr Gly Cys Arg
1               5                   10                  15

Lys Ala Asp Thr Gly Lys Met Tyr Ala Met Lys Cys Leu Asp Lys Lys
                20                  25                  30

Arg Ile Lys Met Lys Gln Gly Glu Thr Leu Ala Leu Asn Glu Arg Ile
            35                  40                  45

Met Leu Ser Leu Val Ser Thr Gly Asp Cys Pro Phe Ile Val Cys Met
        50                  55                  60

Ser Tyr Ala Phe His Thr Pro Asp Lys Leu Ser Phe Ile Leu Asp Leu
65                  70                  75                  80

Met Asn Gly Gly Asp Leu His Tyr His Leu Ser Gln His Gly Val Phe
                85                  90                  95

Ser Glu Ala Asp Met Arg Phe Tyr Ala Ala Glu Ile Ile Leu Gly Leu
                    100                 105                 110

Glu His Met His Asn Arg Phe Val Val Tyr Arg Asp Leu Lys Pro Ala
                115                 120                 125

Asn Ile Leu Leu Asp Glu His Gly His Val Arg Ile Ser Asp Leu Gly
                130                 135                 140

Leu Ala Cys Asp Phe Ser Lys Lys Lys Pro His Ala Ser Val Gly Thr
145                 150                 155                 160

His Gly Tyr Met Ala Pro Glu Val Leu Gln Lys Gly Val Ala Tyr Asp
                165                 170                 175

Ser Ser Ala Asp Trp Phe Ser Leu Gly Cys Met Leu Phe Lys Leu Leu
                180                 185                 190

Arg Gly His Ser Pro Phe Arg Gln His Lys Thr Lys Asp Lys
                195                 200                 205
```

<210> SEQ ID NO 131
<211> LENGTH: 205
<212> TYPE: PRT
<213> ORGANISM: Drosophila melanogaster

<400> SEQUENCE: 131

```
Val Ser Thr Leu Gly Ile Gly Phe Gly Arg Val Glu Leu Val Lys
1               5                   10                  15

Ala His His Gln Asp Arg Val Asp Ile Phe Ala Leu Lys Cys Leu Lys
            20                  25                  30

Lys Arg His Ile Val Asp Thr Lys Gln Glu Glu His Ile Phe Ser Glu
        35                  40                  45

Arg His Ile Met Leu Ser Ser Arg Ser Pro Phe Ile Cys Arg Leu Tyr
    50                  55                  60

Arg Thr Phe Arg Asp Glu Lys Tyr Val Tyr Met Leu Leu Glu Ala Cys
65                  70                  75                  80

Met Gly Gly Glu Ile Trp Thr Met Leu Arg Asp Arg Gly Ser Phe Glu
                85                  90                  95

Asp Asn Ala Ala Gln Phe Ile Ile Gly Cys Val Leu Gln Ala Phe Glu
            100                 105                 110

Tyr Leu His Ala Arg Gly Ile Ile Tyr Arg Asp Leu Lys Pro Glu Asn
        115                 120                 125

Leu Met Leu Asp Glu Arg Gly Tyr Val Lys Ile Val Asp Phe Gly Phe
    130                 135                 140

Ala Lys Gln Ile Gly Thr Ser Ser Lys Thr Trp Thr Phe Cys Gly Thr
145                 150                 155                 160

Pro Glu Tyr Val Ala Pro Glu Ile Ile Leu Asn Lys Gly His Asp Arg
                165                 170                 175

Ala Val Asp Tyr Trp Ala Leu Gly Ile Leu Ile His Glu Leu Leu Asn
            180                 185                 190

Gly Thr Pro Pro Phe Ser Ala Pro Asp Pro Met Gln Thr
        195                 200                 205
```

<210> SEQ ID NO 132
<211> LENGTH: 202
<212> TYPE: PRT
<213> ORGANISM: Mus musculus

<400> SEQUENCE: 132

```
Lys Glu Thr Ile Gly Val Gly Ser Tyr Ser Val Cys Lys Arg Cys Val
1               5                   10                  15

His Lys Ala Thr Asn Met Glu Tyr Ala Val Lys Val Ile Asp Lys Ser
            20                  25                  30

Lys Arg Asp Pro Ser Glu Glu Ile Glu Ile Leu Leu Arg Tyr Gly Gln
        35                  40                  45

His Pro Asn Ile Ile Thr Leu Lys Asp Val Tyr Asp Asp Gly Lys His
    50                  55                  60

Val Tyr Leu Val Thr Glu Leu Met Arg Gly Gly Glu Leu Leu Asp Lys
65                  70                  75                  80

Ile Leu Arg Gln Lys Phe Phe Ser Glu Arg Glu Ala Ser Phe Val Leu
                85                  90                  95

His Thr Ile Ser Lys Thr Val Glu Tyr Leu His Ser Gln Gly Val Val
            100                 105                 110

His Arg Asp Leu Lys Pro Ser Asn Ile Leu Tyr Val Asp Glu Ser Gly
        115                 120                 125

Asn Pro Glu Cys Leu Arg Ile Cys Asp Phe Gly Phe Ala Lys Gln Leu
    130                 135                 140

Arg Ala Glu Asn Gly Leu Leu Met Thr Pro Cys Tyr Thr Ala Asn Phe
145                 150                 155                 160
```

```
Val Ala Pro Glu Val Leu Lys Arg Gln Gly Tyr Asp Glu Gly Cys Asp
                165                 170                 175

Ile Trp Ser Leu Gly Ile Leu Leu Tyr Thr Met Leu Ala Gly Tyr Thr
            180                 185                 190

Pro Phe Ala Asn Gly Pro Ser Asp Thr Pro
        195                 200

<210> SEQ ID NO 133
<211> LENGTH: 198
<212> TYPE: PRT
<213> ORGANISM: Plasmodium falciparum

<400> SEQUENCE: 133

Asn Lys Lys Ile Gly Lys Gly Ser Phe Ser Thr Ala Tyr Ile Gly Thr
1               5                   10                  15

Asn Ile Leu Tyr Gly Asn Arg Val Val Lys Glu Val Asp Lys Ser
                20                  25                  30

Lys Val Lys Glu Ser Asn Val Tyr Thr Glu Ile Glu Val Leu Arg Lys
            35                  40                  45

Val Met His Lys Tyr Ile Ile Lys Leu Ile Ser Ala Tyr Glu Gln Glu
        50                  55                  60

Gly Phe Val Tyr Leu Val Leu Glu Tyr Leu Lys Gly Gly Glu Leu Phe
65                  70                  75                  80

Glu Tyr Leu Asn Asn Asn Gly Pro Tyr Thr Glu Gln Val Ala Lys Lys
                85                  90                  95

Ala Met Lys Arg Val Leu Ile Ala Leu Glu Ala Leu His Ser Asn Gly
            100                 105                 110

Val Val His Arg Asp Leu Lys Met Glu Asn Leu Met Leu Glu Asn Pro
        115                 120                 125

Asn Asp Pro Ser Ser Leu Lys Ile Ile Asp Phe Gly Leu Ala Ser Phe
                130                 135                 140

Leu Asn Ser Pro Ser Met Asn Met Arg Cys Gly Ser Pro Gly Tyr Val
145                 150                 155                 160

Ala Pro Glu Ile Leu Lys Cys Ala Ser Tyr Gly Thr Lys Val Asp Ile
                165                 170                 175

Phe Ser Leu Gly Val Ile Leu Phe Asn Ile Leu Cys Gly Tyr Pro Pro
            180                 185                 190

Phe Arg Gly Asn Asn Val
        195
```

KINASE-DEAD MUTATION: A NEW APPROACH TO ENHANCE SOYBEAN RESISTANCE TO SOYBEAN CYST NEMATODE

CROSS-REFERENCE TO RELATED APPLICATION

This application claims the benefit of U.S. Provisional Application Ser. No. 63/009,120, filed Apr. 13, 2020, the disclosure of which is hereby incorporated by reference in its entirety, including all figures, tables and amino acid or nucleic acid sequences.

This invention was made with government support under awarded by USDA-National Institute of Food and Agriculture—Agriculture and Food Research Initiative (Grant No. 2018-67013-27822). The government has certain rights in the invention.

The Sequence Listing for this application is labeled "Seq-List.txt" which was created on Apr. 9, 2021 and is 589 KB. The entire content of the sequence listing is incorporated herein by reference in its entirety.

BACKGROUND OF THE INVENTION

The United States ranks first in the world in soybean production, accounting for over 50% of the world's soybean production. In addition, strong global demand for soybeans is expected to continue to meet needs for vegetable oil and meal/protein for various industrial applications and animal feed. Therefore, increased soybean yield is needed to ensure adequate supplies. However, soybean yield is always threatened by pathogen infection, especially by the soybean cyst nematode (SCN, *Heterodera glycines*), the most damaging soybean pathogen; annual losses in the US from SCN range from 93 to 123 million bushels. Protecting soybean from SCN is a critical crop security issue. While the current best management strategy to control nematode infection in soybean fields is the use of nematode resistant cultivars coupled with effective cultural practices, SCN has the ability to adapt to these strategies and readily overcomes resistance, threatening control measures and producer profitability. Therefore, discovery of new sources of genetic resistance for engineering broad and durable resistance against SCN is of great importance for soybean producers and to the economy of the United States.

Protein kinases phosphorylate proteins for functional changes and are involved in nearly all cellular processes, thereby regulating almost all aspects of plant growth and development, and responses to biotic and abiotic stresses (Champion et al., 2004; Colcombet and Hirt, 2008). Protein kinase genes exist by the hundreds in all plant species in which they have been surveyed, and comprise more than 3% of the annotated proteins in plants (Lehti-Shiu et al., 2009; Lehti-Shiu and Shiu, 2012). The protein kinase repertoire or kinome has significantly more members in plants than other eukaryotes, including animals. Recent gene duplication events and high retention rate of duplicates in plants is likely the reason for increasing kinome growth, and has functional significance (Hanada et al., 2008; Lehti-Shiu and Shiu, 2012; Liu et al., 2015).

In this application we developed and validated a new approach for identifying bona fide target genes for SCN resistance. This novel approach relies on: (1) identifying highly interconnected kinase hub genes to prioritize SCN resistance gene candidates for further functional validation using (2) the novel kinase-dead mutation approach.

BRIEF SUMMARY OF THE INVENTION

The instant invention pertains to the function of kinases in establishing kinase signaling cascades during SCN infection of soybeans. Kinase hub genes were identified based on gene co-expression networks and the kinase hub genes were analyzed to obtain insights into the roles of the genes during SCN infection. Mutating only one or two encoding sequences of amino acids of the kinases expressed by the kinase hub genes creates SCN-resistant soybeans. The mutations can completely abolish or significantly reduce (significantly inhibit) the activity of these enzymes but do not interfere with substrate recognition i.e., these kinases can be modified to create "kinase-dead mutants" that have no enzymatic activity or significantly reduced enzymatic activity but function antagonistically to the wild-type kinase (have dominant-negative effects). Identifying kinase hub genes and the consequence of kinase-dead mutations can identify means to inhibit SCN infection induced kinase signaling cascades. Additionally, a method of the subject invention provides a method for the analysis of co-expression networks to identify means for stress tolerance and disease resistance in plants.

BRIEF DESCRIPTION OF THE DRAWINGS

(FIG. 2A) Venn diagram demonstrating the number of unique and common kinase hub genes in control and stress networks. (FIG. 2B) Example of a protein kinase-hub gene (Glyma.06G145500) showing limited and high co-expression events in control and stress co-expression networks, respectively. (FIG. 2C) Bar graph showing the number of kinase-hub genes that are specific to control and stress networks. (FIG. 2D) Venn diagram demonstrating the number of kinase-hub genes that are differentially expressed in the feeding site of SCN (syncytium).

FIG. 4: Example of multiple sequence alignment of protein kinase domains of a syncytium-kinase hub gene (Glyma.04G222800) and other species showing the conserved lysine residues (K) in the ATP binding pocket and the substrate binding pocket (SEQ ID NOs: 100-108, respectively).

(FIG. 5A) Nematode susceptibility assay of transgenic hairy root plants overexpressing wild-type variants of three kinase hub genes (Glyma.04G222800, Glyma.13G150000 and Glyma.18G141500) showing increased susceptibility compared to the transgenic hairy root plants expressing the empty vector (control). (FIG. 5B) Nematode susceptibility assay of transgenic hairy root plants overexpressing kinase-dead variants of 8 kinase hub genes (Glyma.03G189800, Glyma.16G079200, Glyma.14G026300, Glyma.04G222800, Glyma.18G141500, Glyma.18G269900, Glyma.12G056000, and Glyma.13G150000) showing significantly reduced susceptibility compared to the transgenic hairy root plants expressing the empty vector (control). Asterisks indicate statistically significant differences from control plants (P<0.05) as determined by ANOVA.

FIGS. 6A-6B: Multiple sequence alignment of protein kinase domains of 8 syncytium-kinase hub genes. (FIG. 6A) Multiple sequence alignment of soybean kinase protein sequences showing 24 conserved amino acids including 2 lysine residues (K) in the ATP binding pocket and the substrate binding pocket (SEQ ID NOs: 109-116, respectively). (FIG. 6B) Multiple sequence alignment of kinase protein sequences of soybean (SEQ ID NOs: 117-124, respectively) and other species (P17801 (*Zea mays* (Maize)), SEQ ID NO: 125, P80192 (*Homo sapiens*), SEQ ID NO: 126, P21868 (*Gallus gallus*), SEQ ID NO: 127, P18265 (*Rattus norvegicus*), SEQ ID NO: 128, P27636 (*Saccharomyces cerevisiae* S288C), SEQ ID NO: 129, P21146 (*Bos Taurus*), SEQ ID NO: 130, Q03042 (*Drosophila melanogaster*), SEQ ID NO: 131, P18653 (*Mus musculus*), SEQ ID NO: 132, Q8I534 (*Plasmodium falciparum* (isolate 3D %), SEQ ID NO: 133), showing 14 conserved amino acids including 2 lysine residues (K) in the ATP binding pocket and the substrate binding pocket. Invariant and highly conserved amino acids are shown in red lettering.

BRIEF DESCRIPTION OF THE SEQUENCES

Figure 1B:
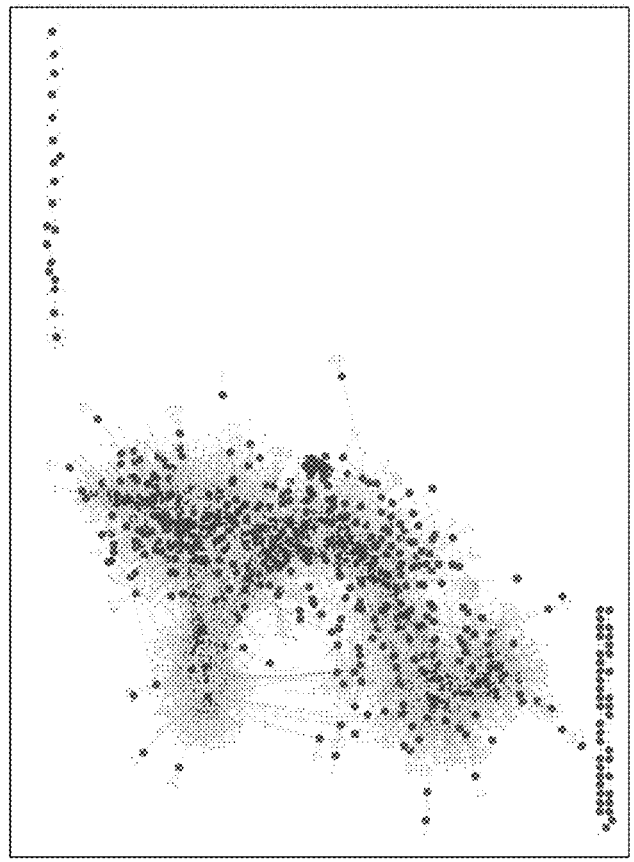
FIGS. 1A-1B: Gene co-expression networks of soybean genes under control and stress conditions. Two independent co-expression networks were generated using control (FIG. 1A) and stress (FIG. 1B) gene expression data. Nodes indicate gene and edges indicate co-expression events between co-expressed genes. Nodes in red represent protein kinases.

SEQ ID NOs: 1 to 91 provide candidate amino acid sequences that confer SCN resistance when overexpressed, inactivated, or overexpressed and inactivated.

SEQ ID NOs: 92 to 99 provide amino acid sequences of kinase-dead mutants that confer SCN resistance.

DETAILED DISCLOSURE OF THE INVENTION

The present invention relates to novel and useful methods for introducing, in a reliable and predictable manner, SCN resistance into non-resistant soybeans. The method involves identifying highly connected kinase hub genes that change expression in the SCN feeding site. The identified kinase hub genes identified to be associated with the SCN resistance can be mutated to generate kinase-dead mutants, which have significantly reduced or no enzymatic activity but have a dominant-negative effect in sequestering substrates (for example ATP), causing a loss-of-function phenotype.

Kinases have highly conserved domains, allowing for the identification of amino acids essential for the function of the enzymes. Thus, one aspect of the invention provides kinase-dead mutants that comprise one or more amino acid mutation at conserved (invariant) or highly conserved amino acid positions. For example, single, double, or triple amino acid alterations (mutations) can inhibit enzymatic activity (for example, a lysine residue in the ATP binding pocket and a lysine residue in the substrate binding pocket of the kinase can be mutated to any other amino acid, for example an arginine or a conserved aspartic acid residue in the catalytic domain of the kinase can be mutated with any other amino acid), but the kinase-dead mutants maintain the ability to recognize/bind substrates or bind to other proteins. Altering the expression levels of kinase-dead mutants and/or wild-type kinases can enhance resistance to SCN. Because these modifications are genetic changes in the plant, offspring can inherit tolerance to SCN.

Kinase hub genes encode kinase enzymes that are involved in nearly all aspects of plant growth and development and stress tolerance. Many kinases have compensatory signaling and redundant functions. So, novel targeting approaches to select critical kinases within the kinome are imperative to efficiently disrupt signaling cascades driven by aberrant kinase activity induced by plant pathogens or other stresses. In certain embodiments of the subject invention, the method of identifying kinase genes involved in common signal transduction pathways, preferably in cells that are undergoing stress or pathogen infection, can be used to identify kinases involved in the stress event or pathogen infection (for example, SCN pathogenesis) and provide targets that can be mutated to provide resistance to the stress or pathogen infection, for example, kinase-dead mutants.

In this disclosure, the term "isolated nucleic acid" molecule means a nucleic acid molecule that is separated from other nucleic acid molecules that are usually associated with the isolated nucleic acid molecule. Thus, an "isolated nucleic acid molecule" includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamide) containing restriction-digested genomic DNA, is not an "isolated nucleic acid".

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide", "peptide", and "protein" are used interchangeably herein to refer to a polymer of amino acids. The terms apply to amino acid polymers in which one or more amino acid residues are artificial chemical mimetic of a corresponding naturally occurring amino acids, as well as to naturally occurring amino acid polymers and non-naturally occurring amino acid polymers. As used herein, the terms encompass amino acid chains of any length, including full-length proteins, wherein the amino acid residues are linked by covalent peptide bonds.

As used in herein, the terms "identical" or percent "identity", in the context of describing two or more polynucleotide or amino acid sequences, refer to two or more sequences or subsequences that are the same or have a specified percentage of amino acid residues or nucleotides that are the same (for example, a variant protein used in the method of this invention has at least 80% sequence identity, preferably 85%, 90%, 91%, 92%, 93, 94%, 95%, 96%, 97%, 98%, 99%, or 100% identity, to a reference sequence), when compared and aligned for maximum correspondence over a comparison window, or designated region as measured using one of the following sequence comparison algorithms or by manual alignment and visual inspection. Such sequences are then said to be "substantially identical". With regard to polynucleotide sequences, this definition also refers to the complement of a test sequence. The comparison window, in certain embodiments, refers to the full length sequence of a given polypeptide, for example a specific kinase, or, in other embodiments, specific domain within the kinase sequence (e.g., the catalytic domain, ATP binding pocket or the substrate binding pocket of a kinase).

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depends in part on how the value is measured, i.e., the limitations of the measurement system. In the context of compositions containing amounts of ingredients where the terms "about" is used, these compositions contain the stated amount of the ingredient with a variation (error range) of 0-10% around the value (X±10%). In other contexts the term "about" is provides a variation (error range) of 0-10% around a given value (X±10%). As is apparent, this variation represents a range that is up to 10% above or below a given value, for example, X±1%, X±2%, X±3%, X±4%, X±5%, X±6%, X±7%, X±8%, X±9%, or X±10%.

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

An endogenous nucleic acid is a nucleic acid that is naturally present in a cell. For example, a nucleic acid present in the genomic DNA of a cell is an endogenous nucleic acid.

An exogenous nucleic acid is any nucleic acid that is not naturally present in a cell. For example, a nucleic acid vector introduced into a cell constitutes an exogenous nucleic acid. Other examples of an exogenous nucleic acid include the vectors comprising a heterologous promoter linked to an endogenous nucleic acid, e.g., a nucleic acid encoding a kinase.

The subject invention provides for the use of "homologous nucleic acid sequences" or "homologs of nucleic acid sequences". Homologs of nucleic acid sequences will be understood to mean any nucleotide sequence obtained by mutagenesis according to techniques well known to persons skilled in the art, and exhibiting modifications in relation to the parent sequences. For example, mutations in the regulatory and/or promoter sequences for the expression of a polypeptide that result in a modification of the level of expression of a polypeptide according to the invention provide for a "homolog of a nucleotide sequence". Likewise, substitutions, deletions, or additions of nucleic acid to the polynucleotides of the invention provide for "homologs" of nucleotide sequences. In various embodiments, "homologs" of nucleic acid sequences have substantially the same biological activity as the corresponding reference gene, i.e., a gene homologous to a native gene would encode for a protein having the same biological activity as the corresponding protein encoded by the naturally occurring gene. Typically, a homolog of a gene shares a sequence identity with the gene of at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. These percentages are purely statistical and differences between two nucleic acid sequences can be distributed randomly and over the entire sequence length.

Likewise, the subject invention also provides for the use of kinase homologs. A kinase homolog has substantially the same biological activity as the reference kinase, i.e., the kinase homolog would have substantially the same biological activity as the reference kinase. Typically, a homolog of a reference kinase shares a sequence identity with the reference protein of at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. These percentages are purely statistical and differences between two nucleic acid sequences can be distributed randomly and over the entire sequence length.

Likewise, the subject invention also provides for "kinase-dead mutants". Kinase-dead mutants are understood to mean any kinases obtained by mutagenesis according to techniques well known to persons skilled in the art, and exhibiting modifications in relation to the parent kinase. Such modifications in a protein sequence include substitutions, deletions, or additions of amino acids. In various embodiments, the kinase-dead mutant has one or more biological activity that is substantially different from one or more biological activity of the native protein kinase (for example, the kinase-dead mutant is unable to transfer a phosphate group to a substrate). In one embodiment, a kinase-dead mutant can comprise one or more mutation in the ATP binding pocket and/or the substrate binding pocket such that the functions of these domains differs from the native protein (for example, binding substrate in a manner that differs from the native protein). Alternatively, the catalytic domain can be mutated such that the kinase is unable to transfer a phosphate group to a substrate while the ATP binding pocket and/or the substrate binding pocket are not mutated. In one embodiment, the kinase-dead mutant can comprise mutations in all three domains.

With respect to kinase-dead mutants, one or more amino acid mutations are introduced into what are identified as highly conserved and/or invariant amino acids. In the context of this invention, a highly conserved and/or invariant amino acid is one that is conserved in all kinases. Highly conserved amino acids are those in which less than 20% of the amino acids differ from a reference (consensus) sequence at a given amino acid position (see, for example, FIGS. 6A and 6B).

Kinase-dead mutants exhibit no enzymatic activity or significantly reduced enzymatic activity. In the context of this application, "significantly reduced enzymatic activity" refers to a reduction in the enzymatic activity of the kinase-dead mutant as compared to the reference kinase (the non-mutated kinase from which the kinase-dead mutant was made). "Significantly reduced enzymatic activity" refers to a reduction of substrate phosphorylation in an amount of at least (or at least about) 80%. Thus, a kinase-dead mutant has between about 80% and about 99.99% less enzymatic activity as compared to the non-mutated parent kinase of the same sequence. In some embodiments, the kinase-dead mutant exhibits no enzymatic activity.

In certain embodiments, genetic modifications are made to plants or plant cells that "significantly reduces or abolishes the expression of a gene", for example a gene encoding a kinase. This phrase refers to a reduction of gene expression in an amount of at least (or at least about) 30% as compared to a non-genetically modified plant from which the genetically modified plant was derived (e.g., a soybean plant). Thus, plants that are genetically modified to exhibit significantly reduced or abolished expression of a gene (for example, significantly reduce or abolish the expression of an active protein from the gene) exhibit a reduction in gene expression or expression of active protein that can range from about 30% to about 99.99% or are devoid of expression (expression is abolished) of the gene or an active protein encoded by the gene.

As used herein, "kinome" is the protein kinase repertoire in an organism.

As used herein, "co-expressed" or "co-expression" is when the expression patterns of two or more genes are correlated across multiple tissues and/or stress conditions.

As used herein "hub genes" are genes that are highly connected regulatory genes.

The soybean has 2,166 putative genes that encode protein kinases. These protein kinases encompass a vast, interconnected network; however, the role of this network in nematode infection resistance remains mostly unknown.

Analysis of the gene expression landscape networks mediated by stress and control conditions can be a powerful approach to determine changes in network structures and topology. The samples used to determine the expression can be found in various plant tissues such as, for example, cotyledon, embryo, seed, whole seedling, root, lateral root, root hair, root tip, nodule, leaf, flower, and pod. The stress conditions can be abiotic stressors such as, for example, elevated or decreased $CO_2$ concentrations relative to normal conditions, cold, heat, drought, increased ozone concentration, elevated and decreased salt concentrations, elevated or decreased pH, iron deprivation, nitrogen deprivation, phosphorous deprivation, and potassium deprivation or biotic stressors such as, for example, *Aphis glycines, Macrophomina phaseolina, Fusarium oxysporum, Heterodera glycine,*

*Phytophthora sojae, Sclerotinia sclerotiorum*, soybean mosaic virus, and other plants that are considered weeds, which compete with the soybean plant for sunlight, water, and/or nutrients.

To determine the construction of the gene expression networks, the pairwise gene expression correlation between individual soybean genes was identified using Pearson correlation coefficient (PCC) from RNA-seq datasets. The PCC value can be 0.70, with a false discovery rate of less than 0.05. The co-expression network generated using control gene expression data comprised of 61,162 edges and 8,685 nodes. Of these 8,685 nodes 806 are putative protein kinases. Similarly, the co-expression network generated using stress gene expression data comprised of 70,037 edges and 9,600 nodes. Of these 9,600 nodes 887 are kinases. This disclosure indicates that protein kinases constitute a significant part of gene co-expression nodes.

A hub gene is a gene that is co-expressed with at least twenty-five genes. To determine which genes are hub genes, control and stress gene expression data is evaluated to determine if the twenty-five gene threshold is met. In certain embodiments, the prevalence of kinase hub genes was determined. Using the twenty-five gene threshold, 392 kinase hub genes were identified in the control condition network and 464 kinase hub genes were identified in the stress condition network. 271 kinase hub genes were found to be common to both gene co-expression networks, 121 kinase hub genes were specific to the control network, and 193 kinase hub genes were specific to the stress gene co-expression network. Some of the protein kinase hub gene that were common between stressed and controlled condition networks showed altered topology as they were more densely interconnected with other genes under one condition compared to another condition.

The protein kinase hub genes can be further classified based on the relative expression difference in the stress condition network or the control condition network. The genes are assigned to the stress condition network if the number of co-expressed genes were at least two-fold higher and have at least 25 more co-expression events than the control condition network. The genes are assigned to the control condition network if the number of co-expressed genes were at least two-fold higher and have at least 25 more co-expression events than the stress condition network. In certain embodiments, 145 kinase hub genes that were highly interconnected in control condition network compared to the stress condition network were identified and 247 kinase hub genes that were highly interconnected in stress condition network compared to the control condition network were identified, for a total of 392 highly interconnected kinase hub genes.

To identify hub genes that change the topology of signaling pathways in stressed or pathogen infected tissues, the expression patterns were determined in stressed or pathogen infected tissues, preferably in the feeding site of SCN, compared to non-stressed or pathogen infected tissues. This comparison can provide one or more genes that are central to modulating signaling network structure and function in site(s) of stress or pathogen infections. In certain embodiments, the gene list of highly interconnected kinase hubs indicated above (392 genes) was compared with the reference list of syncytial differentially expressed genes (6,903 genes), and 91 protein kinases were identified as "syncytium highly connected hubs," central to modulating signaling network structure and function in the nematode feeding site. Out of these 91 kinase hub genes, 40 kinase hub genes were highly interconnected in the control condition network and 51 kinase hub genes were highly interconnected in the stress condition network.

The disclosure provides that the amino acid sequences listed in Table 1 (SEQ ID NOs: 1 to 91) provide resistance or susceptibility to a stressor or pathogen in a plant cell or a plant, particularly, a soybean plant cell or a soybean plant. For example, overexpressing in a plant cell or a plant, particularly, a soybean plant cell or a soybean plant, one or more genes that encode an amino acid sequence selected from SEQ ID NOs: 1 to 91 or homologs thereof and/or one or more "kinase-dead" mutant renders the plant cell or the plant resistant to SCN. Also, inactivating in a plant cell or a plant, particularly, a soybean plant cell or a soybean plant, one or more genes that encode an amino acid sequence selected from SEQ ID NOs: 1 to 91 or homologs thereof renders the plant cell or the plant, particularly resistant to SCN.

In certain embodiments a kinase can be inactivated by mutation of one or more amino acids to form a kinase-dead mutant. For example, one or two amino acids can be mutated to form a kinase-dead mutant. Other embodiments provide for the mutation of at least 1, 2, 3, 4, 5, 6, 7, 8, 9, 10, 11, 12, 13, 14, 15, 20, 24, 30 or greater invariant and/or highly conserved amino acids in the ATP binding pocket and/or the substrate binding pocket of the kinase to form a kinase-dead mutant. In preferred embodiments, the mutation of an amino acid residue can result in a substitution. In certain embodiments, the conserved amino acid residue is a lysine that substituted with a different amino acid residue such as, for example, alanine, arginine, asparagine, aspartate, cysteine, glutamate, histidine, isoleucine, leucine, lysine, methionine, phenylalanine, proline, serine, threonine, tryptophan, tyrosine, or valine. The lysine can be substituted with another charged amino acid such as, for example, glutamic acid, aspartic acid, or, preferably, arginine. In preferred embodiments, the kinase-dead mutant has properties such that enzymatic activity is affected (the enzymatic activity is significantly reduced) but there is no effect on substrate recognition or binding to other proteins.

In certain embodiments, the kinase-dead mutant can interrupt the signaling networks and alter expression of downstream genes that mediate stress and/or pathogen infection, particularly SCN infection by mutating genes that encode highly interconnected kinase hub genes in the syncytium. Kinases and downstream genes can be involved in essential signaling processes needed for SCN or other pathogens to infect any soybean cultivar. In certain embodiments, resistance generated through this novel approach can be effective against all SCN HG types and other plant pathogens. Additionally, the resistance can be durable through the evolution of new SCN HG types.

TABLE 1

SEQ ID NOs: 1 to 91 providing candidate amino acid sequences that confer SCN resistance when overexpressed, inactivated, or overexpressed and inactivated.

| SEQ ID NO: | Glyma ID NO. |
|---|---|
| 1 | Glyma.01G098400 |
| 2 | Glyma.01G132300 |
| 3 | Glyma.01G155600 |
| 4 | Glyma.02G036500 |
| 5 | Glyma.02G100000 |
| 6 | Glyma.02G127800 |
| 7 | Glyma.02G134600 |
| 8 | Glyma.02G202900 |

TABLE 1-continued

SEQ ID NOs: 1 to 91 providing candidate amino acid sequences that confer SCN resistance when over to a gene or from a heterologous gene. Further, it is recognized that some promoters can contain one or more native, enhancers or enhancer-like elements. An example of one such enhancer is the 35S enhancer, which can be a single enhancer, or duplicated. See for example, McPherson et al, U.S. Pat. No. 5,322,938, which is hereby incorporated by reference in its entirety.

The promoter for driving expression of the genes of interest may be selected based on a number of criteria including, but not limited to, what the desired use is for the operably linked polynucleotide, what location in the plant is expression of the gene of interest desired, and at what level is expression of gene of interest desired or whether it needs to be controlled in another spatial or temporal manner. In one aspect, a promoter that directs expression to particular tissue may be desirable. When referring to a promoter that directs expression to a particular tissue is meant to include promoters referred to as tissue specific or tissue preferred. Included within the scope of the invention are promoters that express highly in the plant tissue, express more in the plant tissue than in other plant tissue, or express exclusively in the plant tissue. For example, "seed-specific" promoters may be employed to drive expression. Specific-seed promoters include those promoters active during seed development, promoters active during seed germination, and/or that are expressed only in the seed. Seed-specific promoters, such as annexin, P34, beta-phaseolin, alpha subunit of beta-conglycinin, oleosin, zein, napin promoters have been identified in many plant species such as maize, wheat, rice and barley. See U.S. Pat. Nos. 7,157,629, 7,129,089, and 7,109,392. Such seed-preferred promoters further include, but are not limited to, Cim1 (cytokinin-induced message); cZ19B1 (maize 19 kDa zein); and milps (myo-inositol-1-phosphate synthase); (see WO 00/11177, herein incorporated by reference). The 27 kDa gamma-zein promoter is a preferred endosperm-specific promoter. The maize globulin-1 and oleosin promoters are preferred embryo-specific promoters. For dicots, seed-specific promoters include, but are not limited to, bean beta phaseolin, napin, beta-conglycinin, soybean lectin, cruciferin, and the like. For monocots, seed-specific promoters include, but are not limited to, promoters of the 15 kDa beta-zein, 22 kDa alpha-zein, 27 kDa gamma-zein, waxy, shrunken 1, shrunken 2, globulin 1, an LtpI, an Ltp2, and oleosin genes. See also WO 00/12733, where seed-preferred promoters from end1 and end2 genes are disclosed; herein incorporated by reference. Each of these aforementioned references is hereby incorporated by reference in its entirety, particularly as it relates to the promoters disclosed within the reference.

In preferred embodiments, a promoter used in the present invention is a promoter for soybean ubiquitin promoters, for example, the promoters for soybean ubiquitin B (UBB)/ ubiquitin C (UBC) gene. Certain examples of soybean ubiquitin promoters that could be used in the present invention are described in United States patent application publication numbers 20140053296 and 20100186119. Each of these publications is incorporated by reference in its entirety, particularly, the sequence listing.

The promoters useful in the present invention can also include constitutive, inducible or tissue-specific (preferred) promoters that are operably linked to a gene encoding a protein comprising of any one of SEQ ID NOs: 1 to 91 or homologs thereof and are heterologous to the nucleic acid sequences to which they are operably linked. In other words, the promoters are not those found operably linked to a gene encoding SEQ ID NOs: 1 to 91 or homologs thereof in their native context within a plant, such as a soybean plant. However, genes encoding kinase-dead mutants of SEQ ID NOs: 1 to 91 or homologs thereof can be operably linked to a promoter present in the native context of SEQ ID NOs: 1 to 91 or homologs thereof. In preferred embodiments, gene comprises a nucleic acid sequence that encodes SEQ ID NOs: 92-99 can be operably linked to a promoter present in the native context of SEQ ID Nos: 92-99. Constitutive promoters, generally, are active in most or all tissues of a plant; inducible promoters, which generally are inactive or exhibit a low basal level of expression, and can be induced to a relatively high activity upon contact of cells with an appropriate inducing agent; tissue-specific (or tissue-preferred) promoters, which generally are expressed in only one or a few particular cell types (e.g., root cells); and developmental- or stage-specific promoters, which are active only during a defined period during the growth or development of a plant. Often promoters can be modified, if necessary, to vary the expression level. Certain embodiments comprise promoters exogenous to the species being manipulated (e.g. a soybean plant).

Non-limiting examples of root-specific promoters (a subset of tissue-specific promoters) include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CRIBIO promoter (WO06055487, published May 26, 2006), the CRWAQ81 (WO05035770, published Apr. 21, 2005) and the maize ZRP2.47 promoter (NCBI accession number: U38790; GI No. 1063664). Each of these aforementioned references is hereby incorporated by reference in its entirety, particularly as it relates to the promoters disclosed within the reference.

Exemplary constitutive promoters include the 35S cauliflower mosaic virus (CaMV) promoter (Odell et al. (1985) Nature 313:810-812), the maize ubiquitin promoter (Christensen et al. (1989) Plant Mol. Biol. 12:619-632 and Christensen et al. (1992) Plant Mol. Biol. 18:675-689); the core promoter of the Rsyn7 promoter and other constitutive promoters disclosed in WO 99/43838 and U.S. Pat. No. 6,072,050; rice actin (McElroy et al. (1990) Plant Cell 2:163-171); pEMU (Last et al. (1991) Theor. Appl. Genet. 81:581-588); MAS (Velten et al. (1984) EMBO J. 3:2723-2730); ALS promoter (U.S. Pat. No. 5,659,026); rice actin promoter (U.S. Pat. No. 5,641,876; WO 00/70067), maize histone promoter (Brignon et al., Plant Mol Bio 22(6):1007-1015 (1993); Rasco-Gaunt et al., Plant Cell Rep. 21(6):569-576 (2003)) and the like. Other constitutive promoters include, for example, those described in U.S. Pat. Nos. 5,608,144 and 6,177,611, and PCT publication WO 03/102198. Each of these aforementioned references is hereby incorporated by reference in its entirety, particularly as it relates to the promoters disclosed within the reference.

An inducible promoter/regulatory element is one that is capable of directly or indirectly activating transcription of a gene encoding one or more of SEQ ID NOs: 1 to 91 in response to an inducer. The inducer can be a chemical agent such as a protein, metabolite, growth regulator, herbicide or phenolic compound; or a physiological stress, such as that imposed directly by heat, cold, salt, or toxic elements, or indirectly through the action of a pathogen or disease agent such as a virus; or other biological or physical agent or environmental condition. A plant cell containing an inducible promoter/regulatory element may be exposed to an inducer by externally applying the inducer to the cell or plant such as by spraying, watering, heating or similar methods. An inducing agent useful for inducing expression from an inducible promoter is selected based on the particular inducible regulatory element. In response to exposure to an inducing agent, transcription from the inducible regulatory element generally is initiated de novo or is increased above a basal or constitutive level of expression.

Any inducible promoter/regulatory element can be used in the instant invention (See Ward et al., Plant Mol. Biol. 22: 361-366, 1993). Non-limiting examples of such promoters/regulatory elements include: a metallothionein regulatory element, a copper-inducible regulatory element, or a tetracycline-inducible regulatory element, the transcription from which can be effected in response to divalent metal ions, copper or tetracycline, respectively (Furst et al., Cell 55:705-717, 1988; Mett et al., Proc. Natl. Acad. Sci., USA 90:4567-4571, 1993; Gatz et al., Plant J. 2:397-404, 1992; Roder et al., Mol. Gen. Genet. 243:32-38, 1994). Inducible promoters/regulatory elements also include an ecdysone regulatory element or a glucocorticoid regulatory element, the transcription from which can be effected in response to ecdysone or other steroid (Christopherson et al., Proc. Natl. Acad. Sci., USA 89:6314-6318, 1992; Schena et al., Proc. Natl. Acad. Sci., USA 88:10421-10425, 1991; U.S. Pat. No. 6,504,082); a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; and the light-inducible promoter derived from the pea rbcS gene or peapsaDb gene (Yamamoto et al. (1997) Plant J. 12(2):255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6): 1129-1138), a plant hormone inducible regulatory element (Yamaguchi-Shinozaki et al., Plant Mol. Biol. 15:905, 1990; Kares et al., Plant Mol. Biol. 15:225, 1990), and the like. An inducible promoter/regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991). Stress inducible promoters include salt/water stress-inducible promoters such as P5CS (Zang et al. (1997) Plant Sciences 129:81-89); cold-inducible promoters, such as, cor15a (Hajela et al. (1990) Plant Physiol. 93:1246-1252), cor15b (Wlihelm et al. (1993) Plant Mol Biol 23:1073-1077), wsc120 (Ouellet et al. (1998) FEBS Lett. 423-324-328), ci7 (Kirch et al. (1997) Plant Mol Biol. 33:897-909), ci21A (Schneider et al. (1997) Plant Physiol. 113:335-45); drought-inducible promoters, such as, Trg-31 (Chaudhary et al (1996) Plant Mol. Biol. 30:1247-57), rd29 (Kasuga et al. (1999) Nature Biotechnology 18:287-291); osmotic inducible promoters, such as Rab17 (Vilardell et al. (1991) Plant Mol. Biol. 17:985-93) and osmotin (Raghothama et al. (1993) Plant Mol Biol 23:1117-28); and heat inducible promoters, such as heat shock proteins (Barros et al. (1992) Plant Mol. 19:665-75; Marrs et al. (1993) Dev. Genet. 14:27-41), smHSP (Waters et al. (1996) J. Experimental Botany 47:325-338), and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al. (1993) Mol. Gen. Genetics 236:331-340). Certain promoters are inducible by wounding, including the Agrobacterium pmas promoter (Guevara-Garcia et al. (1993) Plant J. 4(3):495-505) and the Agrobacterium ORF13 promoter (Hansen et al., (1997) Mol. Gen. Genet. 254(3):337-343). Each of these aforementioned references is hereby incorporated by reference in its entirety, particularly as it relates to the promoters disclosed within the reference.

Overexpression of a gene comprising a nucleic acid sequence encoding any one of SEQ ID NOs: 1 to 91 or homologs thereof and/or kinase-dead mutants of SEQ ID NOs: 1 to 91 or homologs thereof can also be achieved by one or one or more mutations in the endogenous promoter of the gene, wherein the one or more mutations increase the expression of the gene. In preferred embodiments, the kinase-dead mutant of SEQ ID NOs: 1 to 91 is selected from SEQ ID NOs: 92-99. For a particular gene, a skilled artisan can identify one or more mutations that would increase the expression of the gene and such embodiments are within the purview of the invention. In certain preferred embodiments, the overexpression is of a gene encoding an inactive protein.

Certain preferred embodiments of the invention provide a method of producing a plant cell or a plant that is resistant to SCN, the method comprising overexpressing in the plant cell or the plant a gene comprising a nucleic acid sequence encoding a kinase protein, particularly a kinase selected from SEQ ID NOs: 1 to 91 or homologs thereof and/or one or more kinase-dead mutant of SEQ ID NOs: 1 to 91 or homologs thereof. In preferred embodiments, the nucleic acid sequence encodes a kinase-dead mutant selected from SEQ ID NOs: 92 to 99. The overexpressed gene encoding the kinase or the kinase-dead protein can comprise a nucleic acid sequence encoding Glyma.03G189800 (SEQ ID NO: 15), Glyma.16G079200 (SEQ ID NO: 75), Glyma.14G026300 (SEQ ID NO: 66), Glyma.04G222800 (SEQ ID NO: 17), Glyma.18G141500 (SEQ ID NO: 83), Glyma.18G269900 (SEQ ID NO: 91), Glyma.12G056000 (SEQ ID NO: 49), Glyma.13G150000 (SEQ ID NO: 60), or a homolog thereof. The overexpressed gene encoding the kinase-dead protein is selected from SEQ ID NOs: 92 to 99.

TABLE 2

SEQ ID NOs: 92 to 99 provide amino acid sequences of kinase-dead mutants of Glyma.03G189800 (SEQ ID NO: 15), Glyma.16G079200 (SEQ ID NO: 75), Glyma.14G026300 (SEQ ID NO: 66), Glyma.04G222800 (SEQ ID NO: 17), Glyma.18G141500 (SEQ ID NO: 83), Glyma.18G269900 (SEQ ID NO: 91), Glyma.12G056000 (SEQ ID NO: 49), Glyma.13G150000 (SEQ ID NO: 60) that confer SCN resistance.

| SEQ ID NO: | Kinase-dead mutant of: |
|---|---|
| 92 | Glyma.03G189800 (SEQ ID NO: 15) |
| 93 | Glyma.04G222800 (SEQ ID NO: 17) |
| 94 | Glyma.12G056000 (SEQ ID NO: 49) |
| 95 | Glyma.13G150000 (SEQ ID NO: 60) |
| 96 | Glyma.14G026300 (SEQ ID NO: 66) |
| 97 | Glyma.16G079200 (SEQ ID NO: 75) |
| 98 | Glyma.18G141500 (SEQ ID NO: 83) |
| 99 | Glyma.18G269900 (SEQ ID NO: 91) |

Additional embodiments of the invention also provide a plant cell comprising an overexpressed gene comprising a nucleic acid sequence encoding any one of SEQ ID NOs: 1 to 91 or homologs thereof. The plant cell or the plant can be a soybean plant cell or soybean plant.

Further embodiments of the invention provide a method of producing an SCN resistant plant cell or a plant comprising inactivating in the plant one or more genes comprising a nucleic acid sequence encoding any one of SEQ ID NOs: 1 to 91 or homologs thereof and/or expressing one or more kinase-dead mutant of SEQ ID NOs: 1 to 91 or homologs thereof. In preferred embodiments, the nucleic acid sequence encodes a kinase-dead mutant selected from SEQ ID NOs: 92 to 99. In preferred embodiments, the plant cell or a plant is a soybean plant cell or soybean plant.

Typically, inactivating a gene in a plant cell or a plant comprises introducing into the gene one or more mutations that inhibit, significantly reduce or abolish the expression of an active protein from the gene. Mutations in a gene that inhibit, significantly reduce or abolish the expression of a protein from the gene can be achieved either by deleting the entire coding region of the gene or a portion of the coding region of the gene, by introducing a frame shift mutation within the coding region of the gene, by introducing a missense mutation, insertion of sequences that disrupt the activity of the protein encoded by the gene, by introducing a stop codon or any combination of the aforementioned gene mutations. Inactivating a gene can also be performed by using molecular markers or other traditional breeding methods to integrate activated or inhibited genes in any soybean germplasm. Further, inactivating one or more genes can be performed by introducing and/or expressing the one or more genes under soybean endogenous promoters and/or any exogenous promoters.

In preferred embodiments, inactivating a gene in a plant cell or a plant comprises introducing into the gene one or more mutations that alters at least one, two, three, four, five, or more amino acid residues of the encoded protein. The introduced changes, preferably, either increase the expression or do not alter the expression of the gene. In preferred embodiments, the one or more mutations inactivate the enzymatic activity of the protein but do not alter substrate recognition or protein binding. An alternation of the amino acid sequence can comprise the deletion of amino acid, addition of an amino acid, or a change of an amino acid residue. Mutations of the nucleotide sequence can be achieved either by deleting the entire coding region of the gene or a portion of the coding region of the gene, by introducing a frame shift mutation within the coding region of the gene, by introducing a missense mutation, insertion of sequences that disrupt the activity of the protein encoded by the gene, by introducing a stop codon or any combination of the aforementioned gene mutations. Inactivating a gene can also be performed by using molecular markers or other traditional breeding methods to integrate activated or inhibited genes in any soybean germplasm. Further, inactivating one or more genes can be performed by introducing and/or expressing the one or more genes under soybean endogenous promoters and/or any exogenous promoters. The result of the alteration of at least one, two, three, four, five, or more amino acid resides can inactivate the enzymatic function of the protein but the protein can still bind or recognize substrates or other proteins.

Methods of inactivating a gene of interest in a plant cell or a plant to inhibit, significantly reduce, or abolish the expression of an active protein or retain expression but inactivate protein enzymatic function are well known to a person of ordinary skill in the art and such embodiments are within the purview of the invention. Certain such embodiments are identified below.

Sanagala et al. (2017), Journal of Genetic Engineering and Biotechnology; 15(2):317-321, describe several methods of inactivating a gene, for example, by implementing homologous recombination, zinc finger nucleases, Transcription activator-like effector nucleases (TALENs), and the clustered regularly interspaced short palindromic repeats/CRISPR-associated (CRISPR/Cas) system. The Sanagala et al. reference is incorporated herein by reference in its entirety.

In preferred embodiments, inactivating a gene of interest is performed using the CRISPR/Cas system. An example of such system to inactivate genes in a plant cell or a plant is provided by Ordon et al. (2017), The Plant Journal; 89:155-168. The Ordon et al. reference is incorporated herein by reference in its entirety.

Typically, a CRISPR/Cas system mediated inactivation of a gene involves the use of a guide RNA targeted to a gene of interest. A DNA oligomer targeted to a gene of interest can be transcribed into single guide RNA (sgRNA). sgRNA guides the Cas9 DNA endonuclease to the gene of interest by sgRNA hybridization to the target site. The endonuclease Cas9 makes a double strand break 3 bp upstream of Palindromic Adjacent Motif (PAM). The DNA breakage engages the repair mechanism, such as homologous recombination (HR) or the non-homologous end joining (NHEJ) mechanism. The NHEJ mechanism is a major double strand break repair pathway in plants and is known to be error prone. NHEJ DNA repair process introduces errors in the DNA repair, which causes irreversible mutations at the gene of interest. The chances of errors in DNA repair can be increased by providing multiple sgRNA. Based on the sequence of a gene comprising a nucleic acid sequence encoding any one of SEQ ID NOs: 1 to 91 or homologs thereof, a person of ordinary skill in the art can design and perform an inactivation of the gene using the CRISPR/Cas system and such embodiments are within the purview of the invention.

Methods of inactivating a gene of interest in a plant cell or a plant to inhibit, significantly reduce, or abolish the expression of an active protein or retain expression but inactivate protein enzymatic function also include introduction into the plant cell or the plant one or more inhibitory oligonucleotides, such as small interfering RNA (siRNA) or short hairpin RNAs (shRNA). Methods of producing and introducing inhibitory RNA are also well known to a person of ordinary skill in the art and such embodiments are within the purview of the invention.

Certain preferred embodiments of the invention provide a method of producing a plant cell or a plant that is resistant to SCN, the method comprising inactivating in the plant cell or the plant a gene encoding a kinase protein. The inactivated gene can comprise a nucleic acid sequence encoding Glyma.03G189800 (SEQ ID NO: 15), Glyma.16G079200 (SEQ ID NO: 75), Glyma.14G026300 (SEQ ID NO: 66), Glyma.04G222800 (SEQ ID NO: 17), Glyma.18G141500 (SEQ ID NO: 83), Glyma.18G269900 (SEQ ID NO: 91), Glyma.12G056000 (SEQ ID NO: 49), Glyma.13G150000 (SEQ ID NO: 60), or a homolog thereof. In certain embodiments the inactivated gene, can be overexpressed in the plant cell or the plant, which can comprise a nucleic acid sequence encoding of Glyma.03G189800 (SEQ ID NO: 15), Glyma.16G079200 (SEQ ID NO: 75), Glyma.14G026300 (SEQ ID NO: 66), Glyma.04G222800 (SEQ ID NO: 17), Glyma.18G141500 (SEQ ID NO: 83), Glyma.18G269900 (SEQ ID NO: 91), Glyma.12G056000 (SEQ ID NO: 49), Glyma.13G150000 (SEQ ID NO: 60), or a homolog thereof. Furthermore, one or more kinase-dead mutant Glyma.03G189800 (SEQ ID NO: 15), Glyma.16G079200 (SEQ ID NO: 75), Glyma.14G026300 (SEQ ID NO: 66), Glyma.04G222800 (SEQ ID NO: 17), Glyma.18G141500 (SEQ ID NO: 83), Glyma.18G269900 (SEQ ID NO: 91), Glyma.12G056000 (SEQ ID NO: 49), Glyma.13G150000 (SEQ ID NO: 60) can be expressed in a plant to confer SCN resistance. In preferred embodiments, the nucleic acid sequence encodes a kinase-dead mutant selected from SEQ ID NOs: 92 to 99.

Additional embodiments of the invention also provide a plant or a plant cell comprising an inactivated gene comprising a nucleic acid sequence encoding SEQ ID NOs: 1 to 91 or homologs thereof. The plant cell or the plant can be a soybean plant cell or soybean plant.

In the methods of producing a plant cell described herein the plant cell can be in a plant part, for example, a seed, endosperm, ovule or pollen. The plant can be a soybean plant.

Further embodiments of the invention provide methods for identifying a gene that induces SCN resistance when overexpressed, inactivated, or overexpressed and inactivated in a plant cell or a plant, the method comprising the steps of: (a) overexpressing a kinase or kinase-dead (inactivated) hub gene in a plant cell or a plant, compared to the expression in a plant cell or a plant known to be susceptible to SCN, or inactivating a kinase hub gene in a plant cell or a plant known to be resistant to SCN, (b) testing the SCN resistance in the plant cell or the plant comprising the overexpressed, inactivated, or the overexpressed and inactivated gene, and (c) identifying the gene that induces resistance in the plant cell or the plant when overexpressed, inactivated, or both overexpressed and inactivated in the plant cell or the plant when overexpressed or inactivated. In preferred embodiments, an overexpressed and/or inactivated gene comprises a nucleic acid sequence encoding any one of SEQ ID NOs: 1-91 or homologs thereof. In some embodiments, one or more genes comprising nucleic acid sequences encoding SEQ ID NOs: 1-91 or homologs thereof are overexpressed or one or more genes comprising nucleic acid sequences encoding SEQ ID NOs: 1-91 or homologs thereof are inactivated. In certain embodiments, one or more genes comprising nucleic acid sequences encoding SEQ ID NOs: 1-91 or homologs thereof are overexpressed and one or more genes comprising nucleic acid sequences encoding SEQ ID NOs: 1-91 or homologs thereof are inactivated. Yet other embodiments provide for the expression or overexpression of kinase-dead mutants of SEQ ID NOs: 1 to 91 or homologs thereof in a plant. In preferred embodiments, one or more kinase-dead mutant selected from SEQ ID NOs: 92 to 99 is expressed or overexpressed in a plant cell. The plant cell or the plant can be a soybean plant cell or a soybean plant.

The details discussed above for overexpressing and inactivating genes in a plant cell or a plant are also applicable to the methods of identifying a gene that induces SCN resistance in a plant cell or a plant when overexpressed or inactivated and such embodiments are within the purview of the invention.

As discussed above, comparing the kinomes of the parental soybean lines that are susceptible to SCN with mutant soybean lines comprising kinase-dead proteins that are resistant to SCN resulted in the identification of heritable genes related to SCN parasitism of soybean. Thus, the disclosure provides genes involved in the biochemical basis of kinase function in SCN resistance. Such comparisons can also be used to identify genes involved in conferring traits other than SCN resistance.

A method of identifying one or more kinase genes that confer a trait to a plant when expressed, inactivated, or overexpressed and inactivated, the method comprising the steps of:

a) providing a kinase gene;
b) analyzing the mRNA expression profiles of the kinase gene during controlled conditions and under stressed conditions (for example, a biotic or abiotic stress);
c) comparing the mRNA expression profiles of the kinase gene during the stress conditions to the kinase gene during controlled conditions to identify the kinase gene that are highly interconnected in control condition network compared to the stress condition network;
d) identifying the kinase hub genes based on co-expression with at least twenty-five genes specific to the stress network and specific to the controlled network;
e) comparing the interconnected kinase hub genes identified in step d) with differentially expressed genes in a plant cell;
f) identifying the protein kinase hub genes that are differentially expressed in the plant cell to identify highly connected hub kinase genes;
g) creating kinase-dead variants of the highly connected hub kinase genes;
h) expressing or overexpressing a kinase-dead variants of the identified highly connected hub kinase genes and/or inactivating highly connected hub kinase genes in the plant cell; and
i) identifying one or more genes that confer a trait to the plant when the kinase-dead variant is expressed or overexpressed and/or the highly connected hub-kinase gene is inactivated. In various embodiments, the method can further comprise the generation of a plant expressing or overexpressing the kinase-dead variant and/or inactivating the highly connected hub-kinase gene in a plant and conferring a desired trait (for example, resistance to a biotic and/or abiotic stress as disclosed herein) to the plant when the kinase-dead variant is expressed or overexpressed and/or the highly connected hub-kinase gene is inactivated.

As used herein, the phrase "a gene confers a trait" or grammatical variations thereof indicates that a plant containing the gene exhibits the trait and an otherwise genetically identical plant lacking the gene does not exhibit the trait. Thus, in two otherwise genetically identical plants, the presence of a trait in the plant containing the gene encoding the kinase-dead variant and the absence of the trait in the plant not containing the gene is attributed to the presence or the absence of the gene.

In preferred embodiments of the invention, the plant is a soybean plant and the trait is resistance to SCN. In certain embodiments, the plant cell is a syncytial cell. In certain embodiments, the kinase-dead variant is created by mutating the nucleotides encoding one or two amino acids of the kinase.

Exemplary embodiments of such methods are described in Examples 1 to 5 below. A skilled artisan can implement such methods to identify genes that confer a trait of interest in a plant and such embodiments are within the purview of the invention.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Genome-Wide Identification and Functional Classification of Soybean Protein Kinases With the availability of the soybean whole-genome sequences along with the annotation of the encoded proteins (Schmutz et al., 2010), we identified and functionally classified the entire soybean protein kinase repertoire or kinome, which includes 2,166 putative protein kinase genes, representing 4.67% of all soybean protein-coding genes. The soybean kinome was classified into 19 groups, 81 families and 122 subfamilies (Liu et al., 2015). Gene structure, subcellular localization prediction and gene expression patterns pointed to extensive functional divergence of protein kinase subfamilies.

Figure 1A:
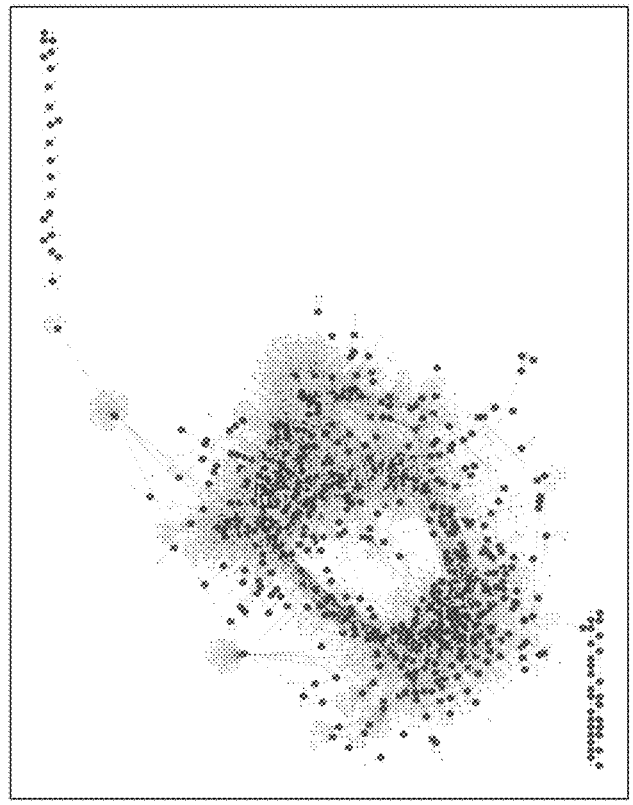

Example 2—Generation of Global Gene Co-Expression Networks and Identification of Highly Connected Kinase-Hub Genes Differential networking of gene expression has emerged as a powerful approach to detect changes in network structures and topology to identify differentially connected hubs among two networks (de la Fuente, 2010; Palumbo et al., 2014). We generated two independent coexpression networks of soybean genes using control and stress response gene expression data from publicly available RNA-seq datasets (FIGS. 1A and B). The coexpression networks were generated from 394 samples collected under normal conditions, and 281 samples collected under various stress conditions. These samples were from different tissues such as cotyledon, embryo, seed, whole seedling, root, lateral root, root hair, root tip, nodule, leaf, flower and pod. The RNA-seq samples collected under stressed conditions included samples that were treated with various abiotic stresses ($CO_2$, cold, drought, heat, ozone, salt, pH, iron deprivation, nitrogen deprivation, phosphorous deprivation and potassium deprivation), or biotic stresses (*Aphis glycines, Macrophomina phaseolina, Fusarium oxysporum, Heterodera glycine, Phytophthora sojae, Sclerotinia sclerotiorum*, soybean mosaic virus, and weed). Construction of the networks were performed by determining all pairwise gene expression correlations between individual soybean genes using Pearson correlation coefficient (PCC) value of 0.70 and a false discovery rate less than 0.05. The co-expression network generated using control gene expression data comprised of 61,162 edges and 8,685 nodes (FIG. 1A). Of these 8,685 nodes 806 are putative protein kinases (Red dots in FIG. 1A). Similarly, the co-expression network generated using stress gene expression data comprised of 70,037 edges and 9,600 nodes (FIG. 1B). Of these 9,600 nodes 887 are kinases (Red dots in FIG. 1B). These results indicate that protein kinases constitute a significant part of gene co-expression nodes.

Figure 2A:
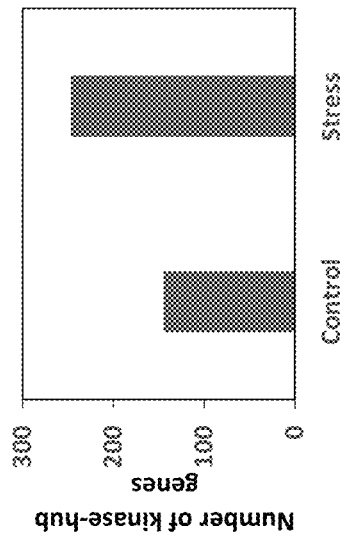
FIGS. 2A-2D: Identification of kinase hub genes that are differentially expressed in SCN-induced syncytium.
Figure 2C:
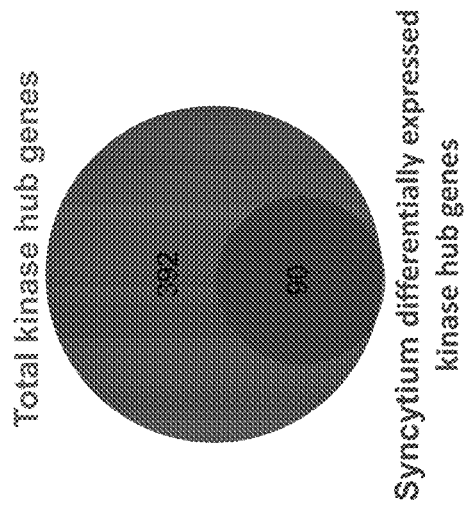
Figure 2B:
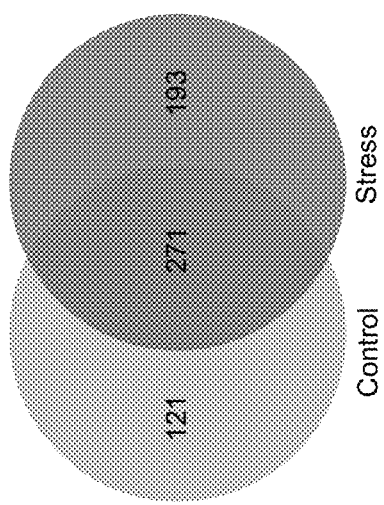

We identified all the kinase hub genes in the gene co-expression network generated using control and stress gene expression data. A protein kinase was considered a hub only if it is co-expressed with at least twenty-five genes. Using this parameter, we identified 392 kinase hub genes in control condition network and 464 kinase hub genes in stress condition network (FIG. 2A). We found that 271 kinase hub genes are common to both gene co-expression networks, 121 kinase hub genes were specific to the control network, and 193 kinase hub genes were specific to the stress gene co-expression network (FIG. 3A). Some of the protein kinase hub gene that were common between stressed and controlled condition networks showed altered topology as they were more densely interconnected with other genes under one condition compared to another condition. For example, a protein kinase Glyma.06G145500 co-expresses with 26 genes under controlled conditions, while the same protein kinase co-expresses with 309 genes under stressed condition (FIG. 2B). Therefore, we assigned these protein kinase hub genes to be specific to stressed conditions if the number of co-expressed genes were at least two-fold higher and has at least 25 more co-expression events than control condition network and vice versa. Using this criterion, we identified 145 kinase hub genes that were highly interconnected in control condition network compared to the stress condition network and 247 kinase hub genes that were highly interconnected in stress condition network compared to the control condition network (FIG. 2C). In total, we identified 392 protein kinase hub genes that are specific to control or stress condition network. Since these protein kinase hub genes show altered topology under control and stress conditions, we hypothesize that these kinase hub genes play key role in plant responses to various biotic or abiotic stresses.

Figure 2D:
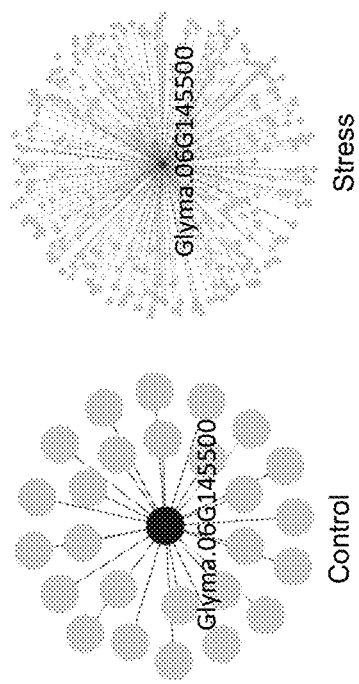

Example 3—Identification of Highly Connected Kinase Hubs that Change the Expression in the SCN Feeding Site Highly connected hub genes have been shown to play key roles in the biology of lower organisms (yeast, fly and worm) and higher organisms (mice and humans) (Vidal et al., 2011). Identifying hub genes that change the topology of signaling pathways in the feeding site of SCN is expected to lead to identifying crucial targets for genetic manipulation. We reasoned that highly connected kinase hubs with key role in mediating plant susceptibility to SCN should exhibit differential expression in the syncytium relative to non-syncytial cells. Therefore, we compared the gene list of highly interconnected kinase hubs indicated above (392 genes) with our reference list of syncytial differentially expressed genes (6,903 genes), and identified 91 protein kinases as "syncytium highly connected hubs," central to modulating signaling network structure and function in the nematode feeding site (FIG. 2D; Table 1). Out of these 91 kinase hub genes, 40 kinase hub genes were highly interconnected in control condition network and 51 kinase hub genes were highly interconnected in stress condition network. Subcellular localization prediction of these kinases provided suggestions for extracellular, cytoplasmic or nuclear localizations, suggesting a role of these hubs in signals perception and transmission to the nucleus to control gene expression of downstream targets.

Example 4—Kinase-Dead Mutation: A New Approach for Functional Studies of Kinases The robust conservation of kinase domains among kinome members has allowed the identification of critical amino acids required for the activity of these enzymes. The provided multiple sequence alignments of the protein kinase domains of 8 syncytium-kinase hub genes showing the conserved amino acids including 2 lysine residues (K) in the ATP binding pocket and the substrate binding pocket (FIGS. 6A and 6B) demonstrate sites that can be mutated to inactivate the kinase. In various embodiments, the underlined lysine residues in the sequences identified in the section entitled "Sequences found in Table 2" are substituted with arginine residues in kinase-dead mutants represented by the exemplary amino acid sequences of SEQ ID NOs: 92 to 99.

Figure 3:
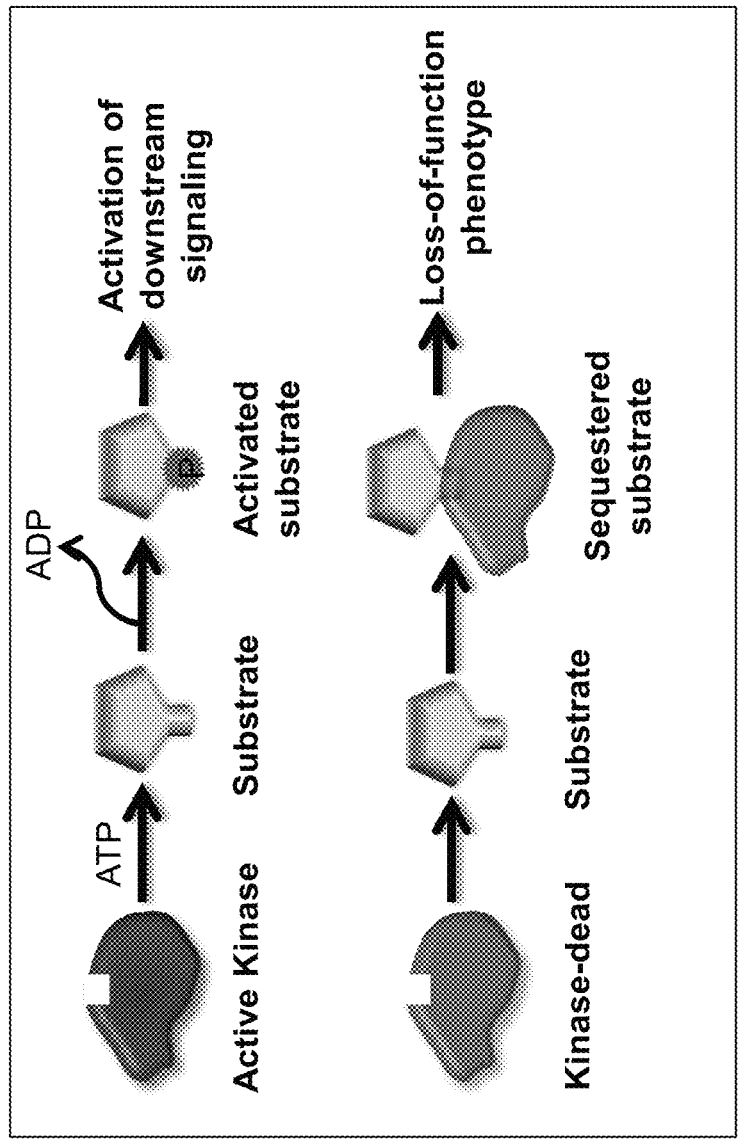
FIG. 3: Schematic illustration of kinase-dead mutation mediating a loss-of-function effects. The chemical activity of an active kinase enzyme involves transforming a phosphate group from a nucleotide triphosphate (ATP) to the target protein, a process known as phosphorylation that results in a functional changes of the target protein (substrate). In contrast, an inactive kinase (kinase-dead) binds to its substrate but without phosphorylation, thereby sequestering the activity of the substrate, causing a loss-of-function phenotype.

Mutations in only one or two amino acids can completely abolish or significantly reduce the activity of these enzymes but do not interfere with substrate recognition or binding to other proteins. As a result, protein kinases can be modified to generate kinase-dead mutants, which have no enzymatic activity but have dominant-negative effects in sequestering the activity of the substrates/interactors, causing loss-of-function phenotype (FIG. 3). In this function, kinase-dead mutations of syncytium highly interconnected kinase hub genes will interrupt the signaling networks and alter expression of downstream genes that mediate SCN susceptibility, resulting in plant resistance to SCN. Because these kinases and downstream genes would be involved in essential signaling processes needed for SCN to infect any soybean cultivar, resistance generated through this novel approach is expected to be effective against all SCN HG types and new HG types are unlikely to evolve (the resistance will be durable). Therefore, kinase-dead mutations can be established as highly effective approach to examine the contribution of hub kinases, identified above, to soybean responses to SCN.

Figure 5B:
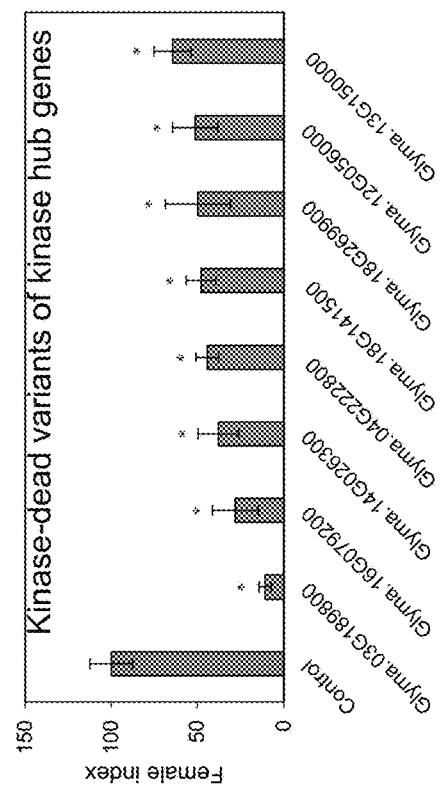
FIGS. 5A-5B: Overexpression of kinase-dead variants of syncytium kinase hub genes significantly increased soybean resistance to SCN.
Figure 5A:
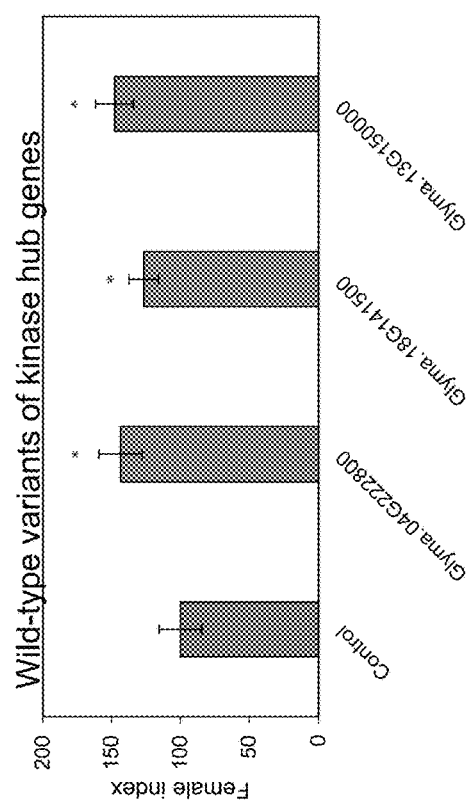

Example 5—Overexpression of Kinase-Dead Variants of Syncytium Hub-Kinase Genes Significantly Enhanced Soybean Resistance to SCN We performed a proof-of-concept study to assess the impact of manipulating kinase hub genes on SCN parasitism of soybean plants. If syncytium hub-kinase genes have functions in mediating soybean susceptibility to SCN, one can reasonably postulate that ectopic expression of inactive variants in soybean will function antagonistically to the wild-type variants, resulting in increased soybean resistance to SCN. To this end, we overexpressed the wild-type coding sequences and kinase-dead variants of 8 syncytium highly connected kinase hub genes using soybean hairy root system and challenged the transgenic roots with SCN. The kinase-inactive variants were generated by mutating the two conserved lysine residues in the ATP binding pocket and the substrate binding pocket to arginine (FIG. 4). These lysines interact directly with ATP and mutation of these residues lead to a classical "kinase-dead" mutant. Because the main function of protein kinases is the phosphorylation of specific substrates, kinase-dead mutations confer loss-of-function phenotypes. Several transgenic hairy root plants overexpressing these 8 kinase-dead variants under the control of a soybean ubiquitin promoter were generated in the SCN susceptible cv 'Williams 82'. The transgenic roots were identified and selected using the green fluorescent protein (GFP). Transgenic plants expressing the empty vector containing only the GFP marker gene were used as control. Both transgenic and control plants were inoculated with 3000 eggs of SCN (HG type 0 or race 3) in three biologically independent experiments each with at least 5 plants. Five weeks after inoculation the number of cysts per plant were counted and used to calculate female index. The female index was calculated by dividing the average number of cysts on the transgenic hairy root lines by the average cysts on the control plants (empty vector) multiplied by 100. We found that growth, development and morphology of the transgenic hairy roots overexpressing wild-type or kinase-dead genes were indistinguishable from those overexpressing the empty vector. We found that transgenic soybean plants overexpressing the wild-type variant of various kinase hub genes (Glyma.04G222800, Glyma.13G150000 and Glyma.18G141500) showed significantly higher number of cysts per root system compared to the transgenic hairy root plants expressing the empty vector (FIG. 5A). However, when we overexpressed 8 kinase hub genes in inactive (kinase-dead) form (Glyma.03G189800, Glyma.16G079200, Glyma.14G026300, Glyma.04G222800, Glyma.18G141500, Glyma.18G269900, Glyma.12G056000, and Glyma.13G150000) the transgenic hairy roots showed significant reduction in SCN susceptibility, ranging between 35 and 90% (FIG. 5B) compared with the control plants. The amino acid sequences of the kinase-dead mutants are provided in Table 2. These results confirm: (1) kinase hubs are master regulators of soybean susceptibility to SCN; and (2) the structure-function of the kinase-dead mutation in enhancing soybean resistance to SCN.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

```
Sequences found in Table 1
>Glyma.01G098400
                                                          SEQ ID NO: 1
MGACWSSRIKAVSPSNTGFTSRSVSRDGHDIQSSSRNSSASIPMTPRSEGEILQFSNLKSYSYNELKMATKNFCP
DSVLGEGGPGSVFKGWIDEHSLAVTRPGTGMVIAVKKLNQDSFQGHKEWLAEINYLGQLQNPNLVKLIGYCLEDQ
HRLLVYEYMPKGSVENHLFRRGSHFQQLSWTLRLKISLGAARGLAFLHSTETKVIYRDFKTSNILLDTNYNAKLS
DFGLARDGPTGDKSHVSTRVMGTHGYAAPEYLATGHLTAKSDVYSFGVVLLEMLSGRRAIDKNRPSGEQCLVEWA
KPYLSNKRRVFRVMDSRLEGQYSLTQAQRAATLAFQCLSVEPKYRPNMDEVVKALEQLRESNDKVKNGDHKKCRV
SGSGLGHPNGLPASTSKGSIDAAKKFNYPRPSASLLYS*

>Glyma.01G132300
                                                          SEQ ID NO: 2
MSYRERNKGKGEEKEYENSTTRGLDSKSVSHNNGSIEEELLTIDENLLIDPKLLFIGSKIGEGAHGRVYEGRYRD
QIVAIKVLHRGGTLEERVALENRFAREVNMMSRVHHENLVKFIGACKDPLMVIVTEMLPGLSLRKYLTTIRPKQL
DPYVAIKFALDIARAMDWLHANGIIHRDLKPDNLLLTENQKSVKLADFGLAREESVTEMMTAETGTYRWMAPELY
STVTLCQGEKKHYNNKVDVYSFGIVLWELLTNRMPFEGMSNLQAAYAAAFKQERPNLPDDISPDLAFIIQSCWVE
DPNMRPSFSQIIRLLNEFHFTLQQPSPSMPLEPENEPEAITSNGTITDFSTRNKVKFSFIRHLFSSKRTKS*
```

-continued

>Glyma.01G155600

SEQ ID NO: 3

MFPLQCSNHPMCAFSAAVITILLLFPAATSQAQILKKETYFFGPFNQSYFTTFAVLPSAAINLGALQVTPDSTGN
VSLANQSGRIFFSTPFTLWDDENLNGKLVSFNTSFLINVFRPQNNPPGEGIAFLIAPSSSTVPNNSHGQFLGLTN
AATDGNATNKFIAVELDTVKQDFDPDDNHIGLDINSVRSNVSVSLTPLGFEIAPNVTRFHVLWVDYDGDRKEIDV
YIAEQPDKDVPIVAKPAKPVLSSPLDLKQVLNKVSYFGFSASTGDNVELNCVLRWNITIEVFPKKNGNGKAYKIG
LSVGLTLLVLIVAGVVGFRVYWIRKKKRENESQILGTLKSLPGTPREFRYQELKKATNNFDDKHKLGQGGYGVVY
RGTLLPKENLQVAVKMFSRDKMKSTDDFLAELTIINRLRHKNLVFLGYCVHGNGVLLLVYDYMPNGSLDNHIFCE
EGSSTTPLSWPLRYKIITGVASALNYLHNEYDQKVVHRDLKASNIMLDSNFNARLGDFGLARALENDKTSYAEME
GVHGTMGYIAPECFHTGRATRESDVYGFGAVLLEVVCGQRPWTKNEGYECLVDWVWHLHREQRILDAVNPRLGND
CVVEEAERVLKLGLACSHPIASERPKMQTIVQILSGSVHVPHLPPFKPAFVWPAMDLSSLASDLTTQTTTTEYTP
MSSDTHSMHVQFSDSSSLV*

>Glyma.02G036500

SEQ ID NO: 4

MEHSSSLVFWLLGLLLLLLMEISSAALSPSGINYEVVALMAIKNDLIDPHNVLENWDINSVDPCSWRMITCSPDG
SVSALGLPSQNLSGTLSPGIGNLTNLQSVLLQNNAISGRIPAAIGSLEKLQTLDLSNNTFSGEIPSSLGGLKNLN
YLRLNNNSLTGSCPQSLSNIEGLTLVDLSYNNLSGSLPRISARTLKIVGNSLICGPKANNCSTILPEPLSFPPDA
LRGQSDSGKKSHHVALAFGASFGAAFVLVIIVGFLVWWRYRRNQQIFFDVNEHYDPEVRLGHLKRFSFKELRAAT
DHENSKNILGRGGEGIVYKACLNDGSVVAVKRLKDYNAAGGEIQFQTEVETISLAVHRNLLRLSGFCSTQHERLL
VYPYMSNGSVASRLKDHIHGRPALDWTRRKRIALGTARGLVYLHEQCDPKIIHRDVKAANILLDEDFEAVVGDFG
LAKLLDHRDSHVTTAVRGTVGHIAPEYLSTGQSSEKTDVFGFGILLLELITGHKALDFGRAANQKGVMLDWVKKL
HQDGRLSQMVDKDLKGNFDLIELEEMVQVALLCTQFNPSHRPKMSEVLKMLEGDGLAERWEASQRIETPRFRSCE
PQRYSDLIEESSLVVEAMELSGPR*

>Glyma.02G100000

SEQ ID NO: 5

MATIGIGVGVTKLQQPHRPKSKSLFLGQRLRISPFWGEPQCSERRLFGVSNPPRVVQVFALGGGEWLDTVHNLFV
GVGVGLPCSVMQCGDVIYRSTLPKSNGLTLTVPGVILALGTLSYLWATPGVAPGFFDMFVLAFVERLFRPTYKKD
DFVLGKKLGEGSFGVVYRVSLANKPSSKEGDLVLKKATEYGAVEIWMNERVRRACASSCADFVYGFLESSSKKAA
EYWLIWRFEGDATLADLMQSRDFPYNVETLILGEVQDLPKGLERENRIIQTIMRQILFALDGLHSTGIVHRDIKP
QNVIFSEESRTFKIIDLGAATDLRVGINYIPKEFLLDPRYAAPEQYIMSTQTPSAPSVPVATALSPVLWQLNLPD
RFDIYSAGLIFLQMAFPSLRSDNSLIQFNRQLKRCDYDLVAWRKTAEARSELRKGFELLDLDGGIGWELLKSMVR
YKARQRLSAKAALAHPYFVREGLLALSFMQTLRLQLLRATQQDYSEAARWIIQLMAKSGTQKDGGFTEAQLQELR
EIEPKKKASAPRNALASALKLQRKIIRTIRTLNESMDELTRRRKSFWWSRWIPREE*

>Glyma.02G127800

SEQ ID NO: 6

MERSGDVALFCLALFFLWTSVAALLSPKGVNYEVQALMSIKNSLVDPHSVLNNWDTDAVDPCNWAMVICSSDHFV
IALGIPSQSISGTLSPIGNLTNLQTVLLQDNNITGPIPFEIGRLQKLQTLDLSDNFFTGQLPDTLSYMKGLHYL
RLNNNSLTGPIPSSLANMTQLAFLDISYNNLSEPVPRINAKTFNIIGNPQICATGVEKNCFRTTSIPSAPNNSQD
SQSTKRPKSHKFALAFASSLSCICLLILGLGFLIWWRQRYNKQIFFDVNEQHREEVCLGNLKKFHFRELQLATNN
FSSKNLIGKGGFGNVYKGYVQDGTVIAVKRLKDGNAIGGEIQFQTEVEMISLAVHRNLLRLYGFCMTATERLLVY
PYMSNGSVASRLKAKPALDWATRKRIALGAGRGLLYLHEQCDPKIIHRDVKAANILLDDYCEAVVGDFGLAKLLD
HRDSHVTTAVRGTVGHIAPEYLSTGQSSEKTDVFGFGILLLELISGQRALEFGKAANQKGAMLDWVKKIHQEKKI
DLLVDKDLKNNYDRIELDEIVQVALLCTQYLPSHRPKMSEVVRMLEGDGLAEKWEASQSAESTRSRGNELSSSER
YSDLTDDSSLLAQAMELSGPR*

>Glyma.02G134600

SEQ ID NO: 7

MGVCTSKPQKPNPYALREAEAEADPSQNPKTTLSPAGADTPRRKDDVSTGKRSPFFPFYSPSPARFLKKSPAPAG
GSRSASSTPRRFFRRPFPPPPSPAKHIRAVLARRQGKKASATAAIPEEGEEGAADLDKRFGFSKEFTSRLEVGEEV
GRGHFGYTCSARFKKGELKGQQVAVKVIPKAKMTTAIAIEDVRREVKILRALNGHNNLIQFYDAFEDQDNVYIVM
ELCEGGELLDMILSRGGKYSEDDAKAVMVQILNVVAFCHLQGVLKPENFLYAKKDESSELKAIDFGLSDFV
RPDERLNDIVGSAYYVAPEVLHRSYGTEADVWSIGVIAYILLCGSRPFWARTESGIFRAVLKADPSFDETPWPSL
SLEAKDFVKRILNKDPRKRISAAQALSHPWIRNCNNVKVPLDILIFKLMKTYMRSSSLRKAALRALSKTLTADEL
YYLRGQFALLEPSKNGSISLENVNKALMKYATDAMKESRIPDFLSSLNSLQYRRMDFEEFCAAALSVHQLEALDR
WEQHARCAYELFDKDGNRAIVIEELASELGLGPSIPVHVVLHDWIRHTDGKLSFLGFVKLLHGVSSRSLAKVQ*

>Glyma.02G202900

SEQ ID NO: 8

MSEKEKGNNSEGQSTLLHGKYELGRVLGHGTFAKVYHARNLNTGQHVAMKVVGKEKVIKVGMMEQVKREISVMKM
VKHQNIVELHEVMASKSKIYIAMELVRGGELFNKVSKGRLKEDVARLYFQQLISAVDFCHSRGVYHRDLKPENLL
LDEHGNLKVSDFGLTAFSEHLKEDGLLHTTCGTPAYVSPEVIAKKGYDGAKADIWSCGVILYVLLAGFLPFQDDN
LVAMYKKIYRGDFKCPPWFSLDARKLVTKLLDPNPNTRISISKVMESSWFKKPVPRKLAAEKVDLEEEKIESQLE
TINAFHIISLSEGFNLSPLFEDKRREEMRFATAGTPSTVISRLEEVAKAGKFDVRSSETKVRLQGQERGRKGKLA
IAADIYAVIPSFMVVEVKKDNGDTLEYNQFCSKQLRPALKDIFWNSSQNSAPASA*

>Glyma.02G208500

SEQ ID NO: 9

MERYEILKDIGSGNFAVAKLVRDNYTNELFAVKFIERGQKIDEHVQREIMNHRSLKHPNIIRFKEVLLTPTHLAI
VMEYASGGELFERICNAGRFSEDEARFFFQQLISGVSYCHSMQICHRDLKLENTLLDGSTAPRVKICDFGYSKSS
VLHSQPKSTVGTPAYIAPEVLTRKEYDGKIADVWSCGVTLYVMLVGAYPFEDPADPRNFKKTIGKILSVQYSVPD
YVRVSMECRHLLSQIFVASPEKRITIPEIKNHPWFLRNLPMELTEGGSWQMNDVNNPSQNVEEVLSIIQEARKSL
NVPKVGGLLTGGSMDLDDFDADEDLEDLETSGEFVCPI*

>Glyma.02G246000

SEQ ID NO: 10

MMSLCSSKGTCSGDTNAHVSSSTVGNYSSDKKRHNNKFITFLRKTMWEYALACVGVVPCGGNNDLNGQRKTTLEH
NKAWLLADSGAELASADPRSVHSSFRFSFCSQVEVESFNMSYSASAAAAATFLMVNLDYESQVRELKWRRIQSLE

-continued

KSLSPVANTLIRFSYDEILSATRNFSKERVLGRGALSCVFRGRVGIWRTAVAIKRLDKEDKECAKAFCRELMIAS
SLNDTNVVPLVGFCIDSEEGLFLVYKYVSGGSLEHHLHGRKKGVKGSSPLPWSVRYEVAIGIAEAVAYLHNGTER
CVVHRDIKPSNILLSSKKIPKLCDFGLASWTSAPSVPFLCKTVKGTFGYLAPEYFEHGKVSDKTDVYALGVVLLE
LLTGRNPIEAKRPPGEENLVVWAKPLLRKGKGAIEELLDPQVKYNSSYTDQMVRMIDAASVCVTSEESRRPSIGE
IVAILKGEVEHVLSRRRKSGYFGNGYMIDNYPKLQETNNEMKSHLALAMLGVPECEDDDFVYCR*

>Glyma.02G286000
SEQ ID NO: 11
MILIDLLQPIMSSNSSLNMELSKKTSFLGLKRWVLIGIGVGAFIVLILCILSIWAMFRRKCRRSLDKYSVSQIPN
VSKDIDVDKVGVQSSHVQPENVVIPVHDKASDKNSDNVSVHLGKSKSGDPDNISQCSSIYHHERGESSMSAEEGS
SGNVKKQSTLSHGGLATASPLVGLPEFSHLGWGHWFTLRDLEMATNRFSSENIIGEGGYGIVYRGRLINGTEVAV
KKLLNNLGQAEKEFRVEVEAIGHVRHKHLVRLLGYCVEGVHRLLVYEYVNNGNLEQWLHGNMHQYGTLTWEARMK
VILGTAKALAYLHEAIEPKVIHRDIKSSNILIDDEFNAKVSDEGLAKLLDSGESHITTRVMGTEGYVAPEYANSG
LLNEKSDIYSFGVLLLEAVTGRDPVDYARPANEVNLVEWLKTMVGTRRAEEVVDSSLEVKPPLRALKRTLLVALR
CIDPDADKRPKMSQVVRMLEADEYPEREDRRKRKSGTASMEIETVKDISGPSDAEKMVISESHVEEG*

>Glyma.03G020700
SEQ ID NO: 12
MPSRPPPLSPPATAAASHRREIILCGAIGGALFLTALIISVMIFIYRKLSYSRTAPFEHNQRRFSYTVLRRATNS
FSPSTKLGHGGFGSVHKATLPSGQTVALKVMDSPGSLQGEREFHNELTLCSNLKSPFVISLLGFSSDRRGKKLVL
VYELMPNRSLQDALLDRRCPELMSWGKRFDVAVSVARGLEYLHHVCDPPVIHGDIKPSNVLLDRDFRAKIGDFGL
ARVKNVEDLGMVDENEKKKDEEFSVLEGESVVDVDRSPESCPVRAAEYSDASPVGGDKLSVVSDGGGCFESVDSG
SVSVNKKKCGGGGGGGGSGRDWWWRQESGGGGESGREGVEQKKKRKSKGSRGSIDWWLDGLSAKIGGFSGDVPKS
GGISSTPSMRGTVCYIAPEYGGGGQLSEKCDVYSFGVLLLVLVAGRRPLQVTASPISEFERANLISWARQLAHNG
RLLDLVDTSIHSLDKEQALLCITIALLCLQRSPGKRPSIKEVVGMLSGEAEPPHLPFEFSPSPPSNFPFKTRKKA
R*

>Glyma.03G088800
SEQ ID NO: 13
MSDSDTRQNDITKPLDLENLRVVSAVGRGAKGVVFLARTGDRSSEECVALKVIPKALILQKAKLINDVEYTRVSF
EEQVLRRFDHLLLPRLRGVFETEKVVGFGIDYCHGGTLHSLRKKQTEKMFSDDTIRFYAVELVLALEYLHNLGIV
YRDLKPENVMIQDNGHIMLVDFDLSKKLNPKSPHSLSQNSSPSPNSKTKQTRKQRLMRFYSFCNSGILPCDSDSE
PPLSSVNSVRHTESDLVEKSNSFVGTEEYVAPEIVSGKGHGFSVDWWSYGVVLYEMLYGTTPPFKGSNRKETFYRI
LMKEPELTGEKTALRDLIGKLLEKNPDRRIQVNEIKGHNFFKGVKWDTVLHIARPPYIPENEVENKVGFSKSDVE
VFVDNVFFPTGDDGGEKTKTLLDNNNNNNNNNNNNNNNKVWIDELSHVPIGKKNDDFLIF*

>Glyma.03G156800
SEQ ID NO: 14
MEQYEILEQIGKGAFGSALLVRHKHEKKKYVLKKIRLARQTDRTRRSAHQEMELISKVRNPFIVEYKDSWVEKGC
FVCIIIGYCEGGDMAEAIKKANGINFPEEKLCKWLVQLLMALDYLHGNHILRDVKCSNIFLIKDQDIRLGDFGL
AKMLSSDDLASSVVGTPSYMCPELLADIPYGSKSDIWSLGCCIYEMAAYKPAFKAFDIQSLLIKINKCIVSPMPT
MYSAAFRGLVKSMLRKNPELRPTAAELLNHPHLQPYIHKIQLKLNSPRRSTFPFQWPESNYVRRTRFVDPESVYT
LSDLDKCLSFSNDMALNPSVSGTEQVSQCSTQRAHGLSTCSKEKIYELSVGCVREKYKTDKSKASKFSTVERTPR
SRAVTVSATTKRHTIATSKTTHSGPKRDSLPASHAPSRKFSTPPRTRARATPNLYTNVLGSLDSLDVSINAPRID
KIVEFPMAFCEDPFSPIRGPSSTSARCSSSSAGSTADCSITKDKCTIQEDKVTLPTSITDACPAPKETKCSYEHV
KDCVSSHSSTDLDQRRFDTSSYQQRAEALEGLLEFSARLLQQQRFDELGVLLKPFGLEKVSPRETAIWLTKSFKQ
TAV*

>Glyma.03G189800
SEQ ID NO: 15
MKKVCHCPIFLALALCLCILCVAAEAAGQNDTLALTEFRLQTDTHGNLLTNWTGADACSAAWRGVECSPNGRVVG
LTLPSLNLRGPIDTLSTLTYLRFLDLHENRLNGTISPLLNCTSLELLYLSRNDFSGEIPAEISSLRLLLRLDISD
NNIRGPIPTQLAKLTHLLTLRLQNNALSGHVPDLSASLLNLTVLNVTNNELRGHVPDSMLTKFGNVSFSGNHALC
GSTPLPKCSETEPDTETTTITVPAKPSSFPQTSSVTVPDTPRKKGLSAGVIVAIVVAVCVAVLVATSFAVAHCCA
RGSTSGSVVGSETAKRKSGSSSGSEKKVYGNGNLDRDSDGTNTETERSKLVFFDRRNQFELEDLLRASAEMLGK
GSLGTVYRAVLDDGCTVAVKRLKDANPCERNEFEQYMDVVGKLKHPNIVRLRAYYYAKEEKLLVYDYLPNGSLHA
LLHGNRGPGRIPLDWTTRISLMLGAARGLARIHAEYNASKIPHGNVKSSNVLLDKNGVALISDFGLSLLLNPVHA
IARLGGYRAPEQVEVKRLSQEADVYGFGVLLLEVLTGRAPSKEYTSPAREAEVDLPKWVKSVVKEEWTSEVFDQE
LLRYKNIEDELVAMLHVGLACVAAQAEKRPCMLEVVKMIEEIRVEESPLGDDYDEARSRTSLSPSLATTEDNLA*

>Glyma.04G085200
SEQ ID NO: 16
MAKGSYSISSKARSMKFIFLFMFMLNFILSDGDQHEVQLLLSFKASLHDPLHFLSNWVSFTSSATICKWHGINCD
NNANSSHVNAVVLSGKNITGEVSSSIFQLPYLTNLDLSNNQLVGEITFTHSHNSLSQTRYLNLSNNNLTGSLPQP
LFSVLFSNLETLDLSNNMFSGNIPDQIGLLSSLRYLDLGGNVLVGKIPNSITNMTALEYLTLASNQLVDKIPEEI
GAMKSLKWIYLGYNNLSGEIPSSIGELLSLNHLDLVYNNLTGLIPHSLGHLTELQYLFLYQNKLSGPIPGSIFEL
KKMISLDLSDNSLSGEISERVVKLQSLEILHLFSNKFTGKIPKGVASLPRLQVLQLWSNGLTGEIPEELGKHSNL
TVLDLSTNNLSGKIPDSICYSGSLFKLLFSNSFEGEIPKSLTSFSGNLPSELSTLPRVYFL
DISGNQLSGRIDDRKWDMPSLQMLSLANNNFSGEIPNSFGTQNLEDLDLSYNHFSGSIPLGFRSLPELVELMLSN
NKLFGNIPEEICSCKKLVSLDLSQNQLSGEIPVKLSEMPVLGLLDLSQNQFSGQIPQNLGSVESLVQVNISHNHF
HGSLPSTGAFLAINASAVIGNNLCDRDGDASSGLPPCKNNNQNPTWLFIMLCFLLALVAFAAASFLVLYVRKRKN
FSEVRRVENEDGTWEVKFFYSKAARLINVDDVLKTVKEGKVVSKGTNWVWYEGKCMENDMQFVVKEISDLNSLPL
SMWEETVKIRKVRHPNIINLIATCRCGKRGYLVYEHEEGEKLSEIVNSLSWQRRCKIAVGVAKALKFLHSQASSM
LLVGEVSPEIVWVDAKGVPRLKVTPPLMPCLDVKGFVSSPYVAQEVIERKNVTEKSEIYGFGVMLVELLTGRSAM
DIEAGNGMHKTIVEWARYCYSDCHLDTWIDPVMKGGDALRYQNDIVEMMNLALHCTATDPTARPCARDVLKALET
VHRTTFC*

>Glyma.04G222800
SEQ ID NO: 17
MQALFSSMRVFLRLVWLLELLCVAVTAVNPSLNDDVLGLIVFKADIRDPKGKLASWNEDDESACGGSWVGVKCNP
RSNRVVEVNLDGFSLSGRIGRGLQRLQFLRKLSLANNNLTGGINPNIARIDNLRVIDLSGNSLSGEVSEDVFRQC -continued GSLRTVSLARNRFSGSIPSTLGACSALAAIDLSNNQFSGSVPSRVWSLSALRSLDLSDNLLEGEIPKGIEAMKNL
RSVSVARNRLTGNVPYGFGSCLLLRSIDLGDNSFSGSIPGDFKELTLCGYISLRGNAFSGGVPQWIGEMRGLETL
DLSNNGFTGQVPSSIGNLQSLKMLNFSGNGLTGSLPESMANCTKLLVLDVSRNSMSGWLPLWVFKSDLDKVLVSE
NVQSGSKKSPLFAMAELAVQSLQVLDLSHNAFSGEITSAVGGLSSLQVLNLANNSLGGPIPPAVGELKTCSSLDL
SYNKLNGSIPWEIGGAVSLKELVLEKNFLNGKIPTSIENCSLLTTLILSQNKLSGPIPAAVAKLTNLQTVDVSFN
NLTGALPKQLANLANLLTFNLSHNNLQGELPAGGFFNTITPSSVSGNPSLCGAAVNKSCPAVLPKPIVLNPNTST
DTGPSSLPPNLGHKRIILSISALIAIGAAAVIVIGVISITVLNLRVRSSTSRDAAALTFSAGDEFSHSPTTDANS
GKLVMFSGEPDFSSGAHALLNKDCELGRGGFGAVYQTVLRDGHSVAIKKLTVSSLVKSQEDFEREVKKLGKIRHQ
NLVELEGYYWTPSLQLLIYEYLSGGSLYKHLHEGSGGNFLSWNERFNVILGTAKALAHLHHSNIIHYNIKSTNVL
LDSYGEPKVGDFGLARLLPMLDRYVLSSKIQSALGYMAPEFACKTVKITEKCDVYGFGVLVLEIVTGKRPVEYME
DDVVVLCDMVRGALEEGRVEECIDERLQGKFPAEEAIPVMKLGLICTSQVPSNRPDMGEVVNILELIRCPSEGQE
ELA*

>Glyma.05G006700
SEQ ID NO: 18

MEHVLEKRFPLNAEDYTLYEEVGEGVSASVYRALCVPLNEIVAIKVLDLEKCNNDLDGIRREVQTMNLIDYPNVL
RAHCSFTAGHNLWVVMPYMAGGSCLHIMKSNYPEGFEEPVIATLLHEVLKALVYLHAHGHIHRDVKAGNILLDSN
GAVKLADFGVSACMFDTGDRQRSRNTFVGTPCWMAPEVMQQLHGYDFKADIWSFGITALELAHGHAPFSKYPPMK
VLLMTLQNAPPGLDYERDKKFSKAFKELVATCLVKDPKKRPSSEKLLKHHFFKQARASKYLARTILEGLAPLGDR
FRMLKAKEADLLVQNKALYEDKDQLSQKEYIRGISAWNFNLEDLKSQAALIQDDDIPNAEEPQRDKKQKDRLDNF
KVSAERLSAGAANHSDDAPTQDKEDLHLLFQDGFNNLQDLEGSLVSFPTKPLQALKGCFDMCEDDINNSSPRDLD
HDGRIDNESSRPSTSLQQNTTSQQKKFPSGSLLPDNFLFPKMVVTDGDRDLYLQTKYSSERNHSGPLQYRQKRDTN
NLPLVDDTSDGAFFRRRGRFTLTDLSPMGPSNSTSGPVVSPTSPPNQNFMSTAILPSLQCILQHNGLQREEIIKL
IKYAEQSSGKNTESVEAGTGDMLQAPPATTRERELHFQVIQLQQSIGSLVEELQRQKMKNVQLEKQLNSMANRVE
K*

>Glyma.05G213200
SEQ ID NO: 19

MGNCSSGAGAPTTYSDDHPHHNGITVLPPNSNPSPQLPKPPPTSSSSSLGRVLGRPMEDVRSIYIFGRELGRGQ
FGVTYLVTHKATKEQFACKSIATRKLVNRDDIDDIRREVQTMIVELKGAYEDRHSVNLVMELCAGGE
LFDRIITKGHYSERAAANSCRQIVTVVHNCHSMGVMHRDLKPENFLLLNKNDDSPLKATDFGLSVFFKPGDVFRD
LVGSAYYVAPEVLRRSYGPEADIWSAGVILYILLSGVPPFWAENEQGIFDAILRGHIDFASDPWPSISSSAKDLV
KKMLRADPKERLSAVEVLNHPWMRVDGDAPDKPLDIAVLTRMKQFRAMNKLKKVALKVIAENLSEEEIIGLKEMF
KSMDTDNSGTITFEELKAGLPKLGTKLSESEVRQLMEAADVDGNGTIDYIEFITATMMHMNRMEREDHLYKAFEYF
DNDKSGYITMEELESALKKYNMGDEKTIKEIIAEVDTDNDGRINYDEFVAMMRKGNPDITHITQRRRK*

>Glyma.05G220600
SEQ ID NO: 20

MGICFSIEDQNHLSISDSNAKPKPAVGHESGAPLASMNIKDLREGAGYSNVDIFTYEELRLATKHFRPDFILGEG
GFGVVYKGVIDHSVRSGYKSTEVAIKELNREGFQGDREWLAEVNYLGQFSHPNLVKLIGYCCEDDHRLLVYEYMA
SGSLEKHLFRRVGSTLTWSKRMKIALHAARGLAFLHGAERPIIYRDFKTSNILLDADFNAKLSDFGLAKDGPMGD
QTHVSTRVMGTYGYAAPEYVMTGHLTARSDVYGFGVVLLEMLIGRRALDKSRPSREHNLVEWARPLLNHNKKLLK
ILDPKLEGQYSSKTALKVAHLAYQCLSQNPKGRPLMSQVVEILENFQSKGENEEDQMLQTGDISITLYEVPKGSN
GTPT*

>Glyma.05G229800
SEQ ID NO: 21

MEMDPPPKSWSIHTRSEIIAKYEVMERVGSGAYADVYRGRRLSDGLTVALKEIHDYQSAFREIDALQLLEGSPNV
VVLHEYFWREDEDAVLVLEFLRTDLATVIADTAKANQPLPAGELKCWMIQILSGLDACHRHMVLHRDLKPSNLLI
SEHGLLKIADFGQARILMEPGIDASNNHEEYSRVLDDIDNKDTITSTHDGNATCNTSDVDREEEELGCFTSCVGT
RWFRAPELLYGSRNYGLEVDLWSLGCIFAELLTLQPLFPGTADIDQLSRIIGVLGNLDENAWAACSKLPDYGIIS
FSKVENPAGLEACLPNRSPDEVALVKKLVCYDPAKRATAMELLHDKYFSDEPLPVLVSELRVPLTRKEQDGDSPG
GWGDINDMDSDSDSQFDEFGPLNITRTGTGFSIQFP*

>Glyma.06G017500
SEQ ID NO: 22

MSCFSCFVSRGKDVRRVEIDNGSRSATSSSEGKGKKSVSNKGTSTAAASFGFRELAEATRGFKEVNLLGEGGFGR
VYKGRLSTGEYVAVKQLIHDGRQGFHEFVTEVLMLSLLHDSNLVKLIGYCTDGDQRLLVYEYMPMGSLEDHLFDP
HPDKEPLSWSTRMKIAVGAARGLEYLHCKADPPVIYRDLKSANILLDNEFNPKLSDFGLAKLGPVGDNTHVSTRV
MGTYGYCAPEYAMSGKLTLKSDIYSFGVLLLELITGRRAIDTNRRPGEQNLVSWRQFFSDRKKFVQMIDPLLQE
NFPLRCLNQAMAITAMCIQEQPKFRPLIGDIVVALEYLASHSNP*

>Glyma.07G004700
SEQ ID NO: 23

MSAPAEAPSFTASPPSETTPSPNSTALSPPPPSTINATVSPPPPEAASPPTSTVNSGLSTGTVSGTVIGAVLGSV
GMLIIGGIFFCFYRNWKRKKNHSQPPQPKADIAGGTLQNWQDSVPPTTDGKVGFSPKPPPGGLVNQQQSSAALLT
LVVVNSSNTSSSLGSEKAKSYISPSPGTSLALSQSTFTYDELSMAIDGFSRSNLLGQGGFGYVHKGVLPNGKIVAV
KQLKSESRQGEREFHAEVDVISRVHHRHLVSLVGYCVSDSQMLVKYEYVENDTLEFHLHGKDRLPMDWSTRMKIA
IGSAKGLAYLHEDCNPKIIHRDIKASNILLDESFEAKVADFGLAKFSSDTDTHVSTRVMGTFGYMAPEYAASGKL
TEKSDVFSFGVLLELITGRKPVDKTQTFIDDSMVEWARPLLSQALENGNLNGLVDPRLQTNYNLDEMIRMTTCA
ATCVRYSARLRPRMSQVVRALEGNISLEDLNDGIAPGHSRVFGSFESSSYDSVQYREDLKNFKKLALESQEQGIS
EYSGPSSEYGRHPSVSTSSDQQNTQEMEMGNKKGSNHDSGIQVLD*

>Glyma.07G011300
SEQ ID NO: 24

MSREQQKRGKQEKGSDGAEKVIVAVKASKEIPKTALVWSLSHVVQPGDCITLLVVVPSQSSGRRLWGFPRFAGDC
ASGIKKYPPGTISEQKSDLTDSCSQMILQLHNVYDPNKINVRIKIVSGSPCGAVAAEAKKTQANWVVLDKQLKHE
EKRCMEELQCNIVVMKRSQPKVLRLNLIGPQKKDVEEAGPSPSEQDDMPENRTKIKLDSLNSIKGPTVTPTSSPE
LGTPFTATEAGTSSVSSSDPGTSPFFISEMNGEFKKEETIKESQELVDTNSDTESESLSTSSASMRYQPWITELL
LHQQSSQRNEERSDISHGIPQASTTRAFLEKYSRLDRGAGFEISTYRNDMDFSGNLREAIALSGNAPPGPPPLCS
ICQHKAPVFGKPPRWFTYSELELATGGFSQANFLAEGGFGSVHRGVLPEGQVIAVKQHKLASSQGDLEFCSEVEV

-continued

LSCAQHRNVVMLIGFCIEDKRRLLVYEYICNGSLDSHLYGRQRDTLEWSARQKIAVGAARGLRYLHEECRVGCII
HRDMRPNNILITHDFEPLVGDFGLARWQPDGTGVETRVIGTFGYLAPEYAQSGQITEKADVYSFGVVLVELVTG
RKAVDLTRPKGQQCLTEWARPLLEEYAIEELIDPRLGKHYSEHEVYCMLHAASLCIQRDPQCRPRMSQVLRILEG
DMVMDSNYISTPGYDAGNRSGRLWSEPLQRQQHYSGPLLEESLESFSGKLSLDKYKPSYWGDRDKARRASCEDDI
*

>Glyma.07G023500

SEQ ID NO: 25

MDPQNQHPPNPRSIIFNKYEMGRVLGQGNFAKVYHARNLNTNESVAIKVIKKEKLKKERLVKQIKREVSVMRLVR
HPHIVELKEVMATKGKIFLVMEYVKGGELFAKVNKGKLTEDLARKYFQQLISAVDFCHSRGVTHRDLKPENLLLD
QNEDLKVSDFGLSTLPEQRRADGMLVTPCGTPAYVAPEVLKKKGYDGSKADLWSCGVILFALLCGYLPFQGENVM
RIYRKAFRAEYEFPEWISPQAKNLISNLLVADPGKRYSIPDIMRDPWFQVGFMRPIAFSIKESYVEDNIDFDDVE
NNQEEEVTMRKPARPFYNAFEIISSLSHGFDLRSLFETRKRSPSMFICKFSASAVLAKVEAVAKKLNFRVTGKKE
FVVRMQGTEEGRKGKLAMTVEVFEVAPEVAVAEFTKSAGDTLEYVKFCEEQVRPSLKDIVWSWQGD*

>Glyma.07G260200

SEQ ID NO: 26

MGCHGSKEKKSNTSYGSAATGSGSGSGSGGGYNTVQPSPPTTDQVQASAQTPENRKASPTVQKKADTSIVGKPFD
DIKKYYSIGKELGRGQFGITYLCTENSSGGIYACKSILKRKLVSKADREDMKREIQIMQHLSGQPNIVEFKGAFE
DRFSVHLVMELCSGGELFDRIIAQGHYSERAAASLCRSIVNVVHICHFMGVMHRDLKPENFLLSTKDDHATLKAT
DFGLSVFIEQGKVYHDMVGSAYYVAPEVLRRSYGKEIDIWSAGIILYILLSGVPPFWAETEKGIFNAILEGEIDF
VSEPWPSISDSAKDLVRKMLTQDPKKRITSAQVLEHPWMREGGDASDKPIDSAVLSRMKQFRAMNKLKKLALKVI
AENLSEEEIKGLKAMFANMDTDSSGTITYEELKTGLARIGSRLSEAEVKQLMDAADVDGNGSIDYLEFISATMHR
HRLERDEHLYKAFQYFDKDNSGYITRDELETAMTQHGMGDEATIKEIISEVDTDNDGRINYEEFCAMMRSGMPHQ
GQLL*

>Glyma.08G002900

SEQ ID NO: 27

MGDGSGNRWSRAEWVQQYDLLGKIGEGTYGLVFLARTKGTPSKSIAIKKFKQSKDGDGVSPTAIREIMLLREITH
ENVVKLVNVHINHADMSLYLAFDYAEHDLYEIIRHHRDKLNHSINQYTVKSLLWQLLNGLSYLHSNWMIHRDLKP
SNILVMGEGEEHGVVKIADFGLARIYQAPLKPLSDNGVVVTIWYRAPELLLGAKHYTSAVDMWAVGCIFAELLTL
KPLFQGAEVKATSNPFQLDQLDKIFKVLGHPTLEKWPSLASLPHWQQDVQHIQGHKYDNAGLYNVVHLSPKSPAY
DLLSKMLEYDPRKRLTAAQALEHEYFKIEPLPGRNALVPCQLGEKIVNYPTRPVDTTTDLEGTTNLPPSQTVNAV
SGSMPGPHGSNRSVPRPVNVVGMQRMPPQAMAAYNLSSQAAMGDGMNPGGISKQRGVPQAHQPQQLRRKEQMGMP
GYPAQQKSRRI*

>Glyma.08G124800

SEQ ID NO: 28

MGNCWCRWESSEYRVSSNVKSEQNQGTKQRHDDSKLPSNPEEVEDLRRDSAANPLIAFTYDELKIITANFRQDRV
LGGGGFGRVYKGFISEELREGLPTLAVAVKVHDGDNSHQGHREWLAEVIFLGQLSHPNLVKLIGYCCEDEHRVLI
YEYMSRGSVEHNLFSKILLPLPWSIRMKIAFGAAKGLAFLHEAEKPVIYRDEKTSNILLDQEYNSKLSDEGLAKD
GPVGDKSHVSTRVMGTYGYAAPEYIMTGHLTPRSDVYSFGVVLLELLTGRKSLDKLRPAREQNLAEWALPLLKEK
KKFLNIIDPRLGDGDYPIKAVHKAAMLAYHCLNRNPKARPLMRDIVDSLEPLQAHTEVPIGKTLTIISEVPESGLK
MKDDAI*

>Glyma.08G176200

SEQ ID NO: 29

MASTLLPFLFLSMVLLPFQTIAQTKSNIAIGESHTAGASTSPWLVSSPSGDFAFGFLPLEDTPDHFMLCIWYAKI
QDKTIVWFANRDQPAPKGSKVVLTADDGLVLITAPNGHMLWKTGGLTLRVSSGVLNDTGNFVLQDGHSKTVWESF
KDYRDTLLPYQTMEKGHKLSSKLGRNYFNKGRFVLFFQNDGSLVMHSINMPSGYANENYYQSGTIESNTNTSTSA
GTQLVEDGTGDMYVLRKNNEKYNLSKGGSRASSTTQFYYLRATLDFDGVFTLYQHPKGSSGSGGWSQVWSHPDNI
CKDYVASAGSGVCGYNSICSLRDDKRPNCRCPKWYSLVDPNDPNGSCKPDFVQACAVDKLSNRQDLYDFEVLIDT
DWPQSDYVLQRPFNEEQCRQSCMEDCMCSVAIFRLGDSCWKKKLPLSNGRVDATLNGAKAFMKVRKDNSSLIVPP
IIVNKNNKNTSILVGSVLLGSSAFLNLILVGAICLSTSYVFRYKKKLRSIGRSDTIVETNLRRFTYEELKKATND
FDKVLGKGAFGIVYEGVINMCSDTRVAVKRLNTFLMEDVHKEFKNELNAIGLTHHKNLVRLLGFCETEEKRLLVY
EYMSNGTLASLLFNIVEKPSWKLRLQIAIGIARGLLYLHEECSTQIIHCDIKPQNILLDDYYNARISDFGLAKLL
NMNQSRTNTAIRGTKGYVALEWFKNMPITAKVDVYSYGVLLLEIVSCRKSVEFEAEDEEKAILAEWAYDCYIEGT
LHALVEGDKEALDDMKTFEKLVMIALWCVQEDPSLRPTMRNVTQMLEGVVEVKMPPCPSQFSVQYS*

>Glyma.08G201600

SEQ ID NO: 30

MPVLRSGARKGRAAPKQQQQKQQQSPVVEGEAIATRIRRRRAAAAAAAAVPESNNNNNNTNNQQQQVEQVAVVNE
NVAVAAREEDNRVAEEEGVVRGGGAEREEVAEKKMGGCDSGGRSNGKANAAGEDDANTPQVPQKIQVGNSPSYKV
EKKLGKGGFGQVYVGRRTGGNLNERTGPGAVEVALKLEHRTSKGCTYGPPYEWQVYNTLGGSHGVPQVHYKGRQG
DYYVMVMDMLGPSLWDVWNNSHHMTTEMVACIAIEAISILEKMHSRGYVHGDVKPENFLLGAPGTPDEKKLFLV
DLGLATKWRDSTTGSHVEYDQRPDVFRGTVRYASVHAHLGRTASRRDDLESLAYTLIFLLRGRLPWQGFQGENKG
FLVCKKKMGTSPETLCCFSPLPFKQFVEHVVNLKFDEEPNYAKYISLFDGVVGPNPDIRPINTEGAQKLIGHKRG
RLVMEEEDDEQPKKKIRIGLPASQWISVNARRPMKQRYHYNVSDTRLSQNLIEKGNEDGLYISSVASCQNLWALI
MDAGTGFTAQVYELSPFFLHKEWIMEHWEKNYYISAIAGAVNGSSLVVMSKGTQYLQQSYKVSDSFPPFKWINKKW
REGFYVTAMATSGSRWGVVMSRGAGFSDQVVELDFLYPSEGIHKRWDCGYRITATAATWDQAAFVLSVPRRKPLD
ETQETLRTSAFPSTHVKEKWAKNLYIASICYGRTVS*

>Glyma.08G231100

SEQ ID NO: 31

MLILVLGLASATFLVFVAVYLFYSKRRVSKYNESKDIESSEHKEDEEMAQKEDLMIFQGGEDLTICDILDAPGEV
IGKSNYGTLYKALLQRSNKVSLLRFLRPVCTARGEELDEMIHFLGRIRHPNLVPLLGFYTGPRGEKLLVHPFYRH
GSLTQFIRDGNGECYKWSNICRISIGIAKGLEHLHTSQEKPIIHGNLKSKNILLDRSYQPYISDSGLHLLLNPTA
GQEMLESSAAQGYKAPELIKMKDASEESDIYSLGVILLELLSGKEPINEHPTPDEDFYLPNFMRNAVLGHRIADL
YHPAILLRNSRDDSIPVTEECILKVFQLAMACCSPSPSVRPNIKQVLKKLEEIMF*

\>Glyma.08G235900

SEQ ID NO: 32

MARCILSHVLAFALVAGLCVFSCLVNVAQAQSANATTDPSEARALNSIFSKWDILANPTQWNISSELCSGRAIDA
TTTIDDTTFNPFIKCDCSYDSRTTCRITALKVYAMSIVGTIPEELWTLTYLTNLNLGQNYLTGSLPPNIGNLTRM
QYLSIGINNFSGELPKELGNLTELRSLAFGSNKFRGSLPSELGKLTNLEQIYFDSSGISGPIPSTFANLKNLLHV
GASDTELTGKIPDFIGNWSKLQTLRFQGNSFNGSIPSSFSNLSSLTELRISGLSNGSSSLEFLRNMKSLTILELR
NNNISGSISSTIGELHNLNQLDLSFNNITGQNLGSIFNLSSLTYLFLGNNKENGTLPMQKSSSLVNIDLSYNDLS
GSLPSWVNEPNLQLNLVANNLDVSNASGLPIGLNCLQKNFPCNQGIGPRYSDFAIKCGGNQIRSADGIVYEMDNQT
LGPATYFVTDANRWAISNVGLFTGSSNPVYKSFVSNQFTGTVNSELFQTARLSASSLRYYGLGLENGFYNITLQF
AETAILDSTRSWESLGRRVFDIYIQGTRVLKDFDIQKEAGGISYKAIQRQFRFEVTENYLEIHLFWAGKGTCCIP
TQGTYGPLIQAIHAIPDFIPTVSNKPPSSNNNNIGLILGIVLGVGVVSVLSIFAIFCIIRRRRRDDEKELLGID
TKPYTFSYSELKNAINDFNLENKLGEGGFGPVYKGTLNDGRVIAVKQLSVGSHQGKSQFITEIATISAVQHRNLV
KLYGCCIEGSKRLLVYEYLENKSLDQALFGKCLTLNWSTRYDICLGVARGLTYLHEESRLRIVHRDVKASNILLD
YELIPKISDFGLAKLYDDKKTHISTGVAGTIGYLAPEYAMRGHLTEKADVFSFGVVALELVSGRPNSDSSLEGEK
VYLLEWAWQLHEKNCIIDLVDDRLSEFNEEEVKRVVGIALLCTQTSPTLRPSMSRVVAMLSGDIEVSTVTSKPGY
LSDWKFEDVSSFMTGIEIKGSDTNYQNSSGSTSMMGGVDYYSPRDVSKPILKETLWEGR\*

\>Glyma.09G030000

SEQ ID NO: 33

MDQYEKVEKIGEGTYGVVYKARDRATNETIALKKIRLEQEDEGVPSTAIREISLLKEMQHRNIVRLQDVVHSEKR
LYLVFEYLDLDLKKHMDSSPEFVKDPRQVKMFLYQILCGIAYCHSHRVLHRDLKPQNLLIDRRTNSLKLADFGLA
RAFGIPVRTFTHEVVTLWYRAPEILLGSRHYSTPVDVWSVGCIFAEMVNRRPLFPGDSEIDELFKIFRILGTPNE
DTWPGVTSLPDFKSTFPKWPSKDLANVVPNLDAAGLNLLSSMLCLDPSKRITARSAVEHEYEKDIKFVP\*

\>Glyma.09G063200

SEQ ID NO: 34

MGVVLALILQLVKLCIIGFVVEFQGSEGSVISPSPAFLPVIHPSGEAPAPIHHGLSWESSPPKSPSDPNEFGISP
SNEIIPVDPSPSEPPGTLHPREPWRTIAPIPPEVPNGSFLPPPVTTLPPPTSAPTPQKVKGFEPSISPSPSTSTI
ASSPPAPYNAAHAPSTSEGSVPPSIQPSPPQSKTTPAIRPPVSTPIAPAPIAITSGNLPKTSPVSQPIEHGSLPP
KIDERNKSHKPEPALPALVPIPSTILPKISPVSQPTENGSLPHREGANNGHISEPISPAPTVFSFPEHSPESQPT
EHGSLPPTVPRRNINTGRTLEPVSQAPVATAPAILPKNSSVSQPTHHGNSPPDVQNRTANNGHSHTPAPEMPPSV
TPPRPFPVDPPLVHPVIPAAPPPKSPAPGGEPVSAPVYKTPKPPSAIVHFHAQAPVVSPVSTPSRSFNWTKGGEP
VSAPPYKTPKPLPVIVHSPAQAPSSAHKARQFHHAPEPPISSPESPFNKDHPPASSPSTTFYKHHHTRNTVTSPA
PASSHSISPSTSKHQDGSNPPLPLTSRQRHHAPPPMNTGSSVSPSGLPIQSPVSQVSPAPSPLFKISPHSTKIP
LPPPKVSPSRPSSKTPKKPVRPRFQALPPPPPNEDCISLVCSDPYTSTPPGAPCKCVWPMKVGLRLSVSLYTFFP
LVSEFASEIATGVFMKQSQVRIMGADAANQQPDKTIVFVDLVPLGEEFDNTTAFLTSERFWHKQVVIKTSYFGDY
DVLYVTYPGLPPSPPLPPSSISIIDGGPYSGGGNNGRTIKPLGVDISKRQHKGGLSKGIIAIIALSVFLVVVLCF
AAALALFKYRDHVSQPPSTPRVLPPLTKAPGAAGSVVGGGLASASTSFRSNIAAYTGSAKTFSMNDIEKATDNFH
ASRVLGEGGFGLVYSGTLEDGTKVAVKVLKREDHHGDREFLSEVEMLSRLHHRNLVKLIGICAEVSFRCLVYELI
PNGSVESHLHGVDKENSPLDWSARLKIALGSARGLAYLHEDSSPHVIHRDFKSSNILLENDFTPKVSDFGLARTA
ADEGNRHISTRVMGTFGYVAPEYAMTGHLLVKSDVYSYGVVLLELLTGRKPVDMSRPPGQENLVAWARPLLSSEE
GLEAMIDPSLGHDVPSDSVAKVAAIASMCVQPEVSDRPFMGEVVQALKLVCNECDEAREAGSSSSSVDLSHSRQP
SDNLQGQFSATNYDSGIDIENGLLASELFSSSARYGRRVSGSFRRHSYSGPLNTGRSKRLWQIIRKLSGGSISEH
GTMFKL\*

\>Glyma.09G089700

SEQ ID NO: 35

MTSRSGQGSSGGGSSRTRVGKYELGRTLGEGNFAKVKFARHVETRENVAIKILDKEKLLKHKMIAQIKREISTMK
LIRHPNVIRMYEVMASKTKIYIVLEFVTGGELFDKIARSGRLKEDEARKYFQQLICAVDYCHSRGVEHRDLKPEN
LLLDANGVLKVSDFGLSALPQQVREDGLLHTTCGTPNYVAPEVINNKGYDGAKADLWSCGVILFVLMAGYLPFEE
TNLSALYKKIFKAEFTCPPWFSSSAKKLINKILDPNPATRITFAEVIENDWFKKGYKPPVFEQANVSLDDLDSIF
SDSTDSQNLVVERREEGPMAPVAPVTMNAFELISKSQGLNLSSLFEKQMGLVKRETRFTSKCSADEIISKIEKAA
GPLGFDVKKNNCKLKIQGEKTGRKGHLSVATEILEVAPSLYMVELRKSEGDTLEFHKFYKNLATGLKDIVWKAEP
IDEEKDGANPSK\*

\>Glyma.09G098000

SEQ ID NO: 36

MMGEKSNSNSGDAINSTLLHGKYELGRLLGHGSFAKVYHARHLNTGKSVAMKVVGKEKVVKVGMMEQIKREISAM
NMVKHPNIVQLHEVMASKSKIYIAMELVRGGELFNKIARGRLREETARLYFQQLISAVDFCHSRGVFHRDLKPEN
LLLDDDGNLKVTDFGLSTFSEHLRHDGLLHTTCGTPAYVAPEVIGKRGYDGAKADIWSCGVILYVLLAGFLPFQD
ENLVALYKKIYRGDFKCPPWFSSEARRLITKLLDPNPNTRITISKIMDSSWFKKPVPKNLVGKKREELNLEEKIK
HQEQEVSTTMNAFHIISLSEGFDLSPLFEEKKREEKELRFATTRPASSVISRLEDLAKAVKFDVKKSETKVRLQG
QENGRKGKLAIAADLYAVTPSFLVVEVKKDNGDTLEYNQFCSKELRPALKDIVWRTSPAENPTLA\*

\>Glyma.09G252000

SEQ ID NO: 37

MFKFLKEVVGGSGTGVKDLPYTIAEPYPSAWGSWTHSRGTSKDDGSPVSVFSLSGSNAQDGHLAAARNGVKRLRT
VRHPNILSFLHSAEIETYDAGSPKVTIYIVTEPVMPLSEKIKELGLEGTQRDEYYALGLHQIAKAVSFLNNDCKL
VHGNICMASTVVTPTLDWKLHALDVLSEFDGSSEASSGQMLQYAWLVGSQYKPMELAKSDWDAIKKSPPWAIDSW
GMGCLIYEVFSGLRLGKTEELRNIGSIPKSLLPDYQRLLSSMPSRRLNTSKLIENSEYFQNKLVDTIHFMEILSL
KDSVERDTFFRKLPNLAEQLPRQIVLKKLLPLLASALEFGSAAASALTALLKMGSWLSAEEFNVKVLPTIVKLFA
SNDRAIRVALLQHIDQYGESLSAQAVDEQVYPHVATGFSDTSAFLRELTLKSMLILAPKLSQRTMSGSLLKYLSK
LQVDEEPAIRTNTTILLGNIGSYLNEGTRKRVLINAFTVRALRDTFPPARGAGIMALCATSSYYDITEVATRILP
NVVVLTIDPDSDVRTKAFQAVDQFLQIAKQHYEKTNAADTSCGVGSSSVPGNASLLGWAMSSLTLKGKPSDHAPV
ASASSTAITSTSSNGTAGIETPSTAAAHVSSTADLAEHPVPTSPTSTDGWGELENGIDEEHGSDRDGWDDLEPLE
ETKPAPALANIQAAQRRPVSQPISHTKQASNLLSKSTPKLNKDEDDDLWGSIAAPAPKTARPLNLKSAQTDDDDP
WAAIAAPAPTIKAKPLSAGRGRGAKPAAPKLGAQRINRTSSGM\*

-continued

>Glyma.09G277000

SEQ ID NO: 38

MEQKGSVLMQRYELGRLLGQGTFAKVYHARNLITGMSVAIKVVDKEKILKVGMIDQIKREISVMRLIRHPHVVEL
YEVMASKTKIYFVMEHAKGGELFNKVVKGRLKVDVARKYFQQLISAVDYCHSRGVCHRDLKPENLLLDENENLKV
SDFGLSALAESKCQDGLLHTTCGTPAYVAPEVINRKGYDGIKADIWSCGVILYVLLAGHLPFQDTNLMEMYRKIG
RGEFKFPKWFAPDVRRFLSRILDPNPKARISMAKIMESSWFKKGLEKPAITVTENEELAPLDADGIFEACENDGP
IAEPKQEQAKPCNLNAFDIISFSTGFDLSGLFEDTFLKKETRFMSKKPASIIVLKLEEICKRLCLKVKKKDGGLL
KLEGSKEGRKGTLGVDAEIFEITPHFHMVELRKSNGDTMEYQKLFKQDIRPALKDIVWTWQGEKPQQEQEQHEVV
QEEHQPSHTA*

>Glyma.10G038400

SEQ ID NO: 39

MDSARSWLQKFQPRDKTRAAGKKKEEDGNGGNQDSNEAIDEALLSSVTKQKVAAAKQYIENHYKEQMKNLQERKE
RRTILEKKLADADVSEEDQNNLLKFLEKKETEYMRLQRHKMGVEDFELLTMIGKGAFGEVRVCREKTSGHVYAMK
KLKKSEMLRRGQVEHVKAERNLLAEVDSNCIVKLYCSFQDDEHLYLIMEYLPGGDMMTLLMRKDILTEDEARFYV
GETVLAIESIHKHNYIHRDIKPDNLLLDRYGHLKLSDFGLCKPLDCSTLEENDFSVGQNVNGSTQSSTPKRSQQE
QLQHWQINRRTLAYSTVGTPDYIAPEVLLKKGYGMECDWWSLGAIMYEMLVGYPPFYSDDPMLTCRKIVNWKTYL
KFPEEARLSPEAKDLISKLLCNVNQRLGSKGADEIKAHPFFKGVEWNKLYQMEAAFIPEVNDELDTQNFEKFDES
DSQTQSSSRSGPWRKMLSSKKDLNFVGYTYKNFEIVNDYQVPGMAELKKKQSKPKRPTIKSLFDCESETPEASDT
SANDQPAQGSFLKLLPPQLEVSPHRDKNLPPRS*

>Glyma.10G052500

SEQ ID NO: 40

MKIPCFSCFSPSTTEKNNNNDYPDEEINDGSFRLFTHKQLKLATRNFHSSEKVGEGGFGSVFKGKLVDGSFVAVK
VLSVEVESMRGEREFVAELATLANIKHQNLVSLKGCCVEGAYRYLVYDYMENNSLYNTFLGSEERRMRFNWEIRK
DVSIGVARGLDFLHEELKPHIVHRDIKAKNILLDRNFIPKVSDFGLAKLLRDETSYISTRVAGTLGYLAPEYANS
GQVSRKSDVYSFGVLLLQIVSGLAVVDAYQDIERFIVEKAWAAYQSNDLLKLVDPMLNMNFPEEEALKFLKVGLL
CVQETAKLRPRMSEVVEKLTKDIDMRDVHISKPGFVADLRNIRIKQQNLNSSEESSSAGATFTSSISSSANLARY
LLD*

>Glyma.10G109200

SEQ ID NO: 41

MLLLLLNYLFFLFNFSITKTEAIDNLQYLNHSCSSNKTFTPNSTYQSNLQTLLTSLSSHATTAQFFNTTTGGGDA
AGENIYGSFMCRGDVSNHTCQECIKTATQQITVRCLNSKEALIWYHECMVRYSNRCFFSAVEEWPRFNFVDFNVN
TNSTEGIYGYWLLSKTLSDAVGEAVKAGTKKFATKNATVFGSQRVHTLVQCTPDLSSEDCSKCLGDIMRDIPLCC
LGRRGGMVLFPSCTLMEGIGQFYRDFPHGTPESKSENEKGSLRTIVIIVLLVVVVPVMLSFFSYHLIRRKARKRN
YKILLRENFGQESVTIEGLQFDLDIIAAATNNFSHENKIGKGGFGEVYKGILPNGRRIAVKRLSTNSSQGSVEFK
NEILSIAKLQHRNLVELIGFCLEVQEKILIYEYMSNGSLDNFLFDPQQKKLSWSQRYKIIEGTARGILYLHEHSR
LKVIHRDLKPSNILLDENMNPKISDFGMARIIELNQDLGKTQRIVGTFGYMSPEYAIFGQFSEKSDVFSFGVMII
EIITGRKNINSHQLPDIVDSLMSYVWRQWKDQAPLSILDPNLEENYSQFEVIKCIHIGLLCVQENKNIRPTMTKV
IFYLDGHTLDELPSPQEPPFFFRDIKDKKIPMQHFSVNKMSTSIFYPR*

>Glyma.10G218800

SEQ ID NO: 42

MERKFMALGFIWWVVVVHPLCLISANMEGDALHSLRTNLQDPNNVLQSWDPTLVNPCTWFHVTCNNDNSVIRVDL
GNAALSGQLVPQLGQLKNLQYLELYSNNITGPIPSDLGNLTNLVSLDLYLNHFTGPIPDSLGKLSKLRFLRLNNN
SLSGPIPMSLTNITALQVLDLSNNHLSGVVPDNGSFSLFTPISFANNMDLCGPVTGHPCPGSPPFSPPPPFVPPP
PISAPGGNGATGAIAGGVAAGAALLFAAPAIAFAWWRRRKPQEFFFDVPAEEDPEVHLGQLKRFSLRELQVATDS
FSNKNILGRGGFGKVYKGRLADGSLVAVKRLKEERTPGGELQFQTEVEMISMAVHRNLLRLRGFCMTPTERLLVY
PYMANGSVASCLRERPPYQEPLDWPTRKRVALGSARGLSVLDHCDPKIIHRDVKAANILLDEEFEAVVGDPGLA
KLMDYKDTHVTTAVRGTIGHIAPEYLSTGKSSEKTDVFGYGIMLLELITGQRAFDLARLANDDDVMLLDWVKGLL
KEKKLEMLVDPDLQTNYIETEVEQLIQVALLCTQGSPMDRPKMSEVVRMLEGDGLAERWDEWQKVEVLRQEVELA
PHPNSDWIVDSTENLHAVELSGPR*

>Glyma.10G243000

SEQ ID NO: 43

MQLLHSDEPAPERGDSPEKPDDPNADTDSLDPGTDDGAALDVTGKSVEFPAAENAGDSAESLYVYKNVYSLIPKS
VSRLARLRTLKFFGNEINLFAPEFGNLTALECLQMKISSPGIGLQHLTLKGLKEELSKGPPRPSAFPILTEIS
GLKCLTKLSICHFSIRYLPPEIGCLKKLEYLDLSFNKMKTLPAEISYLKGLISMKVANNKLVELPAAMSSLSRLE
RLDLSNNRLTSLGSLELASMHRLQELNLQYNKLLGIFQIPSWICCNMDGNDKARCKDDCSSSVEMDLYESNFQEN
DETLSDGPHNTSSSMLTSSSSSRCFASRKSGKRWKRRHHLQQKARQERLNNSRKWKAVDHDDQLLSKKIHRISE
PENHDSLASESCAEIVSENGSLDDNNKRISSERAVNDNAIDNDNNDEVITEKQFSGEDCCTTESKDEKEESLCSL
DKRPSEQDEASCLELLECVSKSKRHLDRDLDNPKPCKSRKSISSSSLLSCKYSKISFCGIEDHLSDGFYDAGRDR
LFMPLECYEQNHCLASREVILLDRKIDEELDAVMLAAQALVYNLKKLNGLSRYGNQDGVDNLQMASLLALFVSDH
FGGSDRSGIVERTRKSVSGSNYNKPFVCTCSAGSSTSISSPTEPVANTIEDITLSKMSEKSLDSIKKRRNSIIIP
IGSVQYGVCRHRALLFKYLCDHMEPPVPCELVRGYLDFSPHAWNIILIKRGATWVRMLIDACRPLDIREEKDPEY
FCRYIPLNRTTIPISSIGSPGPDYSFPSLTTCDELETKASTTLVKCKFGSVEAAAKVRTLEEQGSSADKIKNFEY
NCLGEIRILGALKHPCIVEMYGHQISCQWSVSADGNPEHRVLRSAIFMEYVEGGSLKNYLEKLSEAGEKHVPVEL
ALHIAKDVSCALSELHSKHIIHRDIKSENILFNLDRKRDDGTPTVKLCDFDSAVPLRSTLHVCCIAHAGTPPPCI
CVGTPRWMAPEVMRTMYKKNSYGLEADIWSFGCLLLEMLTLQIPYSGLSDSHFLDSLQMGKRPQLTDERLVLSSM
NGPTMIPSGEELEKSDAGVDMLKFVLDLFHKCVEENPSKRPTAEEIHKMVLAHTDRLQI*

>Glyma.10G253200

SEQ ID NO: 44

MAMIPLMMMILLLLFKPPSVVLATLKSDEANLELVFTYHKCNEELGNFTTETYSNNRVNLLSNMYSDKEIENGFY
NSSYGEGPDKVYGIGFCRGDVKPDKCRSCLEKSSTLLTDRCPVQKEAIGWYDLCMLRYSNRSIVEQPVTDTDDII
KCSNTNATNKDRFDKELDDLVVRMRSRSAEGDSRLKFAEGEAPVQSSNETIHALLQCVPYLSHQNCTRCLEYAMS
RISYWCDGKTGGWYLGRSCSLRYETYLFFELIFHDAPAPQPSQPAVTPTKDFPKKTNPSRNIIVIVVPVFAVAIV
VVGLIVLIYNYFGARRPRHKPIQSEGDGEGDGEGEGELDNDIKTDELAQFEFATIKFATNNFSDANKLGQGGFGI
VYKGTLSDGQEIAIKRLSINSNQGETEFKTEISLTGKLQHRNLVRLLGFCFAKRERLLIYEFVPNKSLDFFIFDP

-continued

NKRGNLNWERRYNIIRGIARGLLYLHEDSRLQVVHRDLKISNILLDEELNPKISDFGMARLFEINQTEANTNTVV
GTFGYMAPEYIKHGKFSVKSDVFSFGVMMLEIVCGQRNSKIRGNEENAEDLLSFAWKNWRGGTVSNIVDTTLKDY
SWDEIKRCIHIGLLCVQEDINGRPTMNSVSIMLNSSSFSLAEPSEPAFLMRGKSQLPMIMLSGSEQYSEATKSSD
SGSQFAQGSSNKAPITEPYPR*

>Glyma.11G089100

SEQ ID NO: 45

MFPLQCSNHPMCAFSAVTAILLLFPAATSQAQILKKETYFFGPFNQSDFTTLTVLPSAAINLGALQVTPDSTGNV
SLANHSGRIFFNNPFTLWDNDDNLNGKLVSFNTSFLINVFRPQNNPPGEGITFLITASTTVPNNSHGQFLGLTNA
ATDGNATNKFVAVELDTVKQDFDPDDNHIGLDINSVRSNVSVSLTPLGFEIAPNVTRFHVLWVDYDGDRKEIDVY
IAEQPDKDAPIVAKPAKPVLSSPLDLKQVVNKVSYFGFSASTGDNVELNCVLRWNITIEVFPKKNGIGKALKIGL
SVGLTMVVLIVAGVVGWVCWLKKKRGNESQILGTLKSLPGTPREFRYQELKKATNKFDEKHKLGQQGYGVVYRG
TLPKENLEVAVKMFSRDKMKSTDDFLAELTIINRLRHKNLVRLLGWCHRNGVLLLVYDYMPNGSLDNHIFCEEGS
STTPLSWPLRYKIITGVASALNYLHNEYDQKVVHRDLKASNIMLDSDFNARLGDFGLARALENDKTSYAEMEGVH
GTMGYIAPECFHTGRATRESDVYGFGAVLLEVVCGQRPWTKNEGYECLVDWVWHLHREQRILDAVDPRLGNGCVV
EEAERVLKLGLACSHPIASERPKMQTIVQIISGSVNVPHVPPFKPAFVWPAMDLSSPASDLTTPTTTTEYTPMSS
DTHSMHVQFSDSNSLI*

>Glyma.11G101700

SEQ ID NO: 46

MSRQTTSSAFTKSKTLDNKYMLGDEIGKGAYGRVYKGLDLENGDFVAIKQVSLENIAQEDLNIIMQEIDLLKNLN
HKNIVKYLGSSKTKSHLHIVLEYVENGSLANIIKPNKFGPFPESLVAVYIAQVLEGLVYLHEQGVIHRDIKGANI
LITKEGLVKLADFGVATKLTEADVNTHSVVGTPYWMAPEVIEMAGVCAASDIWSVGCTVIELLTCVPPYYDLQPM
PALFRIVQDEHPPIPDSLSPDITDFLLQCFKKDARQRPDAKTLLSHPWIQNCRRVLQSSLRHSGTLRNIEEDDSA
DAEVSGGYHKSAYENSSVEKEDSAKEHTTMAADGSKAHEDNAADSNFSNEQTEKADDAPSDQVLTLAIHEKSFLQ
AGSSKLTSNREVVNSESTGNHEISNAKDLHEVVMNGEGGSPQSRGMASKVGGKDSSVNNGNKSFAFGPRGQDNGP
LKKAMKMPITVEGNELSRFSDPPGDAYLDDLFHPLDKQPGEVVAEASTSTSTSHMTKGNASAIDGVKNDLAKELR
ATIARKQWEKESEIGQANNGGNLLHRVMIGVLKDDVIDIDGLVFDEKLPGENLFPLQAVEFSKLVGSLKPEESED
MIVSACQKLIGIFHQRPEQKIVFVTQHGLLPLTDLLEVPKTRIICSVLQLINQIVKDNTDFQENACLVGLIPAVT
SPAVPDRPREIRMEAAYFLQQLCQSSSLTLQMFIACRGIPVLVGFLEADYAKYREMVHLAIDGMWQVFKLQQSTP
RNDFCRIAAKNGILLRLINTLYSLNESTRLASSSAGGGFSVDGSAQRPRSGILDPNHPYINQNETMLSSVDQQDP
PKVRRAVPDHHLEPSSSNPRRSDANYPVDVDRPQSSNATADEKSLNQASRESSAGALKERENMDRWKTDPSQPRI
SNNRTSTDRPPKSTEPSSNGLSVTGTMHQEQVRPLLSLLDKEPPSGRFSGQLEYMRQFSGLERHESVLPLLHATE
KKTNGELDFLMAEFADVSQRGRENGNLSDSSARVSHKVTPKKLGTLGSSEGAASTSGIASQTASGVLSGSGVLNAR
PGSATSSGLLSHMVSSLNAEVAREYLEKVADLLLEFAQADTTVKSYMCSQSLLSRLFQMFNRVEPPILLKILRCI
NHLSTDPNCLENLQRAEAIKYLIPNLELKEGSLVSEIHHEVLNALFNLCKINKRRQEQAAENGIIPHLMLFITSN
SPLKQYALPLLCDMAHASRNSREQLRAHGGLDVYLNLLEDELWSVTALDSIAVCLAHDNDNRKVEQALLKKDAVQ
KLVKFFQGCPEQHFVHILEPFLKIITKSARINTTLAVNGLTPLLIARLDHQDAIARLNLLRLIKAVYEHHPQPKK
LIVENDLPEKLQNLIGERRDGQVLVKQMATSLLKALHINTVL*

>Glyma.11G139700

SEQ ID NO: 47

MAMDEYECHEMVHVAVGKSLKKAATLLQWCFTHFSKPQIFLLHVHQPSTMIPTLLGKLPASQASPEVVSAYRIEE
KEDTKRLLEKYLSLCRAAKVKASSVIGEADQVQKGIVDLVTVHNVRKLVIGAIPENCMKIKRNSSKANYAAKNAP
PPFCEIWFVYNGKHIWTREASETPRSLSSRAQPETTTAESLSCRSFHDGTKELLHSECLQLNSTKTTRSMVQSEII
EAEATFSSKSSSCNSHCSPQHSAGWYLDTHSEFEEETIDSQLIETKREAKAATDKALAELLKSKRLEVKAIEAIS
KVNFFESAHAHEVKLRKEAEDALRATIQEQQMFLDEKEEIARELERTVRSISLLGNCAHETNHKRDEAENELSLI
QASISNLWHEKQQIRQQKMEALHWLERWKSCGQVGADHCNGVIGFAEEFPELAEFSLSDLQNATCNFSESFKVME
GGYGSIYKGEMLGRTVAIRKLHPHNMQGSSEFHQEAQILGSLQHPHLVTLLGVCPEAWSFVYEYLPSGSLQDYLF
RKSSFLPLTRNIRAQWIAEIATALCFLHSSKPETIIHGGLTLETVLLDSALSCKICEFGFSRLVKEESVYLPNFH
FSTEPKGSFTYTDPEFQRTGVLTPKSDIYSFGIIILQLLTGRTPVGLVGEVRRAVSCGKLYPILDSSAGEWNSTM
ATRLAELGLQCCQLNSRVRPELTPSLVRELKQLLVLEERPVPSFFLCPIFQEIMHDPQVAADGFTYEGKAISEWL
ENGHETSPMTNLKLTHLNLTPNHALRLAIQGWLCKS*

>Glyma.12G032900

SEQ ID NO: 48

MTVEKRIVLVGIRIDGYSRQLLNWALAKVAEPGDCVIAVHVVKSSDYVSKNKTLIDGYLEVYEGLCGVKKVGLTG
QIFTGSSIKNILVREAKKHAALALVVGGRAATAKYCAKRLQPTTNVLAIQDSRIVFRSCTNKQLPGGLILDPRPS
LTIIKENLRDRAIHSSICDSIVEIEESTRKNSLESKEEAFNGSEKSKSRSISMFAGDSAEQKLGWPLLRRANSGM
SQTLHARDMSVVQWVMTLPDRSPNKGSSSSSTEENPFERSISDVEYESSSNSSPSSVDIPNGLEEMLNLNSLNCK
RFSLEVLKSCTSQFSSEKLVGKGGSNRVYKGVLTDGKSIAVKVMQSSKEAWKDFALEVEIISSLEHKSIAPLLGI
CIENNTLISVYDYFPNGSLEENLHGKNKDESILSWEVRFNVAIRIAEALDYLHREALKPVIHKDVKSSNILLSQG
FEPQLSDFGLAVWGPTTSSFLTQDVVGTFGYLAPEYFMYGKVSDKIDVYAFGVVLLELISGREPINSAACKGQES
LVVWAKPIIESGNVKGLLDPNLEGKFDEAQLQRMVLAASLCITRAARLRPKLSQILKILKGEEKVEYFLNSQGDN
DQEDSENQENIDDEVYPNSSAELHLSLALLGVDDDSTSHSSTDHSYSEDLKEQWSRSSSFN*

>Glyma.12G056000

SEQ ID NO: 49

MDSARTAPPPWQELDLDSLKPLKVLGKGGMGTVFLVQAANNTRFALKVVDKTCVHAKLDAERRARWEIQVLSTLS
HPFLPSLMGTFESPQFLAWALPYCPGGDLNVLRYRQTDRAFSPAVIRFYVAEILCALDHLHSMGIAYRDLKPENV
LVQNTGHITLTDFDLSRKLNPKPKPNPQVPSIPLPNSNVPEPRRKHRRNFSRWISLFPPDGTHHNNNKNGLKKAK
SARVSPVSRRKPSFSNGERSNSFVGTEEYVSPEVVRGDGHEFAVDWWALGILIYEMLYGTTPFKGKNRKETFRNV
ITKPPVFVGKRTALTDLIEKLLEKDPTKRLGYTRGAVEIKEHEFFRGVRWELLTEVVRPPFIPTRDDGAGDSTDR
ISDRNCGFDIRGYFLNLKSSPSLPGSPLPSPSCRFKKNVSLTEF*

>Glyma.12G062900

SEQ ID NO: 50

MGICLSTQIEAGLNSKHVSVDAKDLSSPSSKITKDLSNPISNKITEDLSTPISNKITEDLSTPISNKITEDLSTP
ISNKITEDLSTPISKVSEILVPLTPQIEGEILQSSNLKNFSLTELTAATRNFRKDSVLGGEGDFGSVFKGWIDNH
SLAAAKPGTGVVAVKRLSLDSFQGHKDRLARHGMTHEASLEAEVNYLGQLSHPHLVKLIGYCFEDKDRLLVYEF
MPRGSLENHLFMRGSYFQPLSWGLRLKVALGAAKGLAFLHSAETKVIYRDFKTSNVLLDSNYNAKLADLGLAKDG

-continued

PTREKSHASTRVMGTYGYAAPEYLATGNLSAKSDVFSFGVVLLEMLSGRRAVDKNRPSGQHNLVEWAKPYLSNKR
KLLRVLDNRLEGQYELDEACKVATLSLRCLAIESKLRPTMDEVATDLEQLQVPHVKQNRRKSADHFTHGRIATAS
ASPLSRDIANTHP*

>Glyma.12G104100

SEQ ID NO: 51

MRNNKPQLWLSLSLIITCFSFHTSLAALTTISANQSLSGDETLVSQHGNFELGFFNTGNNSNKFYIGMWYKKISQ
RTYVWVANRDQPVSDKNSAKLTILEGNLVLLDQSQNLVWSTNLSSPSSGSAVAVLLDTGNLILSNRANASVSDAM
WQSFDHPTDTWLPGGKIKLDKKTKKPQYLTSWKNREDPAPGLFSLELDPAGSNAYLILWNKSEQYWTSGAWNGQI
FSLVPEMRLNYIYNFTFQSNENESYFTYSMYNSSIISRFVMDGSGQIKQLSWLENAQQWNLFWSQPRQQCEVYAF
CGGFGSCTENAMPYCNCLNGYEPKSQSDWNLTDYSGGCVKKTKFQCENPNSSDKEKDRFLPILNMKLPNHSQSIG
AGTVGECEAKCLSNCSCTAYAHDNSGCSIWHGDLLNLQQLTQDDNSGQTLFLRLAASEFDDSNSNKGTVIGAVAG
AVGGVVVLLILFVFVMLRRRKRHVGTRTSVEGSLMAFGYRDLQNATKNFSEKLGGGGFGSVFKGTLPDSSVVAVK
KLESISQGEKQFRTEVSTIGTVQHVNLVRLRGFCSEGTKKLLVYDYMPNGSLESKIFHEDSSKVLLDWKVRYQIA
LGTARGLTYLHEKCRDCIIHCDVKPENILLDADFIPKVADFGLAKLVGRDFSRVLTTMRGTRGYLAPEWISGVAI
TAKADVYSYGMMLFEFVSGRRNSEASEDGQVRFFPTIAANMMHQGGNVLSLLDPRLEENADIEEVTRVIKVASWC
VQDDESHRPSMGQVVQILEGFLDVTLPPIPRTLQAFVDNHENVVFFTDSSSTQTSQVKSNASAASSQAKSNISSS
NSST*

>Glyma.12G129600

SEQ ID NO: 52

MASLPLGHHHHHHKPAAAAIHPSQPPQSQPQPEVPRRSSDMETDKDMSATVIEGNDAVTGHIISTTIGGKNGEPK
ETISYMAERVVGTGSFGVVFQAKCLETGEAVAIKKVLQDRRYKNRELQLMRLMDHPNVISLKHCFFSTTSRDELF
LNLVMEYVPESMYRVIKHYTTMNQRMPLIYVKLYTYQIERGLAYIHTALGVCHRDVKPQNLLVHPLTHQVKLCDF
GSAKVLVKGESNISYICSRYYRAPELIFGATEYTASIDIWSAGCVLAELLLGQPLFPGENQVDQLVEIIKVLGTP
TREEIRCMNPNYTEFRFPQIKAHPWHKVFHKRMPPEAIDLASRLLQYSPSLRCTALEACAHPFFDELREPNARLP
NGRPLPPLFNFKQELAGASPELINRLIPEHIRRQMGLSFPHSAGT*

>Glyma.12G187700

SEQ ID NO: 53

MESRMDHYEIMEQIGRGAFGAAILVNHKAEKKKYVLKKIRLARQTERCRRSAHQEMALIARIQHPYIVQFKEAWV
EKGCYVCIVTGYCEGGDMAALMKKSIGVYFPEEKLCKWFTQILLAVEYLHSNFVLHRDLKCSNIFLTKDQDVRLG
DFGLAKTLKADDLASSVVGTPNYMCPELLADIPYGFKSDIWSLGCCIYEMAAHRPAFKAFDMAGLISKINRSSIG
PLPPCYSPSLKTLIKGMLRKNPEHRPTASEILKHPYLLPVYDQYRSSFCTPTAGSPERPISAVHHPRKNKPESQN
SSSSLSPEKDSFMSSEKNTANEVKKCDRKITEIDLTSIEDDSSEQLLPEEEGNGSSRVNAKTDEKELTKQSNNVH
HSNAVSKQPKPIKNVVTALKDGKLRETSSPIRGNRIKVGGVLTHKINSETVSKLPKPNFGAYDLKPNLEVPTTAP
SKTTPDSAKRMQGLHTSKHQLPMIESTPKTKPRHNAIPPSGPVKQVEGREVPSKPRQKTRPSLLKPPSFPGHVRQ
AGFDVPNATNNTGKSSPKKMVWEPKMSHHQLTNTHLPHVSRETTREPLKTFETSSKGMQTDSSNSVSSSLSIQGF
ELSDFATTFIDLSEPTLPDHESLNHTENVESCPYSISCASYLHFEMSEQLSGETPVVTPCFQNITSNEKVSPSLT
LDHSGQDAEVMFASDDSFSINQRTASAGSRCDNLSVDPSAEITQEIKDPQDSKEMSSAKSLQQSLLISGEKSVCE
EFGPSSKGSNRLDKVSRPKLMCISTGDDKFMVRERLSSVDETAPSIISTKISSQKVLQEEKGMVLQNPAPERPAV
GHLPPAFDDVIHVIRHSSYRVGSEQPGKESVEMGVQNVDVGKFINIARDDLEMRNVSTPLTLKSSNCSEAIGLKS
NISDNMEIRNLSSPPNLKSSSCTDLMNIKSSFSDHLLVRKQDVKNTDSLVSKSDSSEYTKHNTPTAAEETPPKEI
LDVKSSRQRAEALEGLLELSADLLQQNRLEELAVVLKPFGKDKVSPRETAIWLAKSLKGLMIEESGGRS*

>Glyma.13G002100

SEQ ID NO: 54

MTTFHVVEKDLTSRYARYDELLGKGAFKTVYKAFDEVDGIEVAWNMISVEDVVQTPQQLEKLYSEIHLLKSLKHD
NVIKLYNSWVDDTTGTINMITELFTSGSLRQYRNKHKNVDMKAIKNWARQILRGLCFLHCHSPPIVHRDLKCDNI
FVNGNSGLVKIGDLGLAIVMQQPTARSVIGTPEFMAPELYEEEYNELVDIYSEGMCILEMVTCEYPYSECNNPAQ
IYKKVTSGIKPAALAKVNDPEVKQFIEKCLVPASMRLSASELLKDPFLATENTKEINHDILELPNPHTKLVNPPT
CEPHPMEIDSKSRRTSPGSSMGRIEETSQVSFFDLVRMTENNKFMLRGEKNAESTISLTLRIANACGGARNIHFP
FYINSDTAISIAEEMVEHLELTNEDVSVIAELINDMIAKLVPNLKPLSEKLSSGTDQLYRPSSEVQNGEQFNCHW
PLQSSDYDMKPVFKDLVHSWPVDGDDLEKQESVMSDISVECGITVASDSKVVEPDIFIFDEFWEGFDAFNSTSDV
RFCGQEDGHKNQSENSSGSLINSCCCPFKNFDISSICSLTLADKDPSEGLRLEIEAIDTYFEQRFRELEMMRVAA
IESLKRRHGEKHTCDVMH*

>Glyma.13G060400

SEQ ID NO: 55

MDRSTGRGGGGSVDMFLRNYKLGKTLGIGSFGKVKIAEHVRTGHKVAIKILNRHKIKNMEMEEKVRREIKILRLF
MHHHIIRLYEVVETPTDIYVVMEYVKSGELFDYIVEKGRLQEDEARHFFQQIISGVEYCHRNMVVHRDLKPENLL
LDSKFNIKIADFGLSNIMRDGHFLKTSCGSPNYAAPEVISGKLYAGPEVDVWSCGVILYALLCGTLPFDDENIPN
LFKKIKGGIYTLPSHLSPGARDLIPRMLVVDPMKRMTIPEIRQHPWPQVHLPRYLAVPPPDTLQQAKKIDEEILQ
EVVNMGFDRNQLVESLSNRIQNEGTVTYYLLLDNRFRVSSGYLGAEFQETMDSGFNRMHSGEVASPVVGHHSTGY
MDYQGVGMRQQFPVERKWALGLQSRAQPREIMTEVLKALQELNVCWKKIGHYNMKCRWVAGTAGHHEGMINNSLH
SNHYFGNDSGIIENEAVSKSNVVKFEVQLYKTREEKYLLDLQRVQGPQFLFLDLCAAFLSQLRVL*

>Glyma.13G073900

SEQ ID NO: 56

MGNACAKGKPVAHVSSSNFSGSKKPASKPKQYSNSSEQRSAPTTSELNVPKSISSNLKSFSLNDLKEATKNFRRE
NLIGEGGFGRVFKGWIDENTYGPTKPGTGIVVAIKNLKPESFQGHKEWLQEVNYLGMLQHENLVKLIGYCLEGKN
RLLVYEFMQKGSLENHLFRKGVQPMAWVTRVNIAIGVARGLTFLHSLDQNVIFRDLKASNILLDSDFNAKLSDFG
LARDGPTGDNTHVSTRVIGTQGYAAPEYVATGHLTPRSDVYSFGVVLLELLTGRRAVEDDGPGFSEETLVDWAKP
FLNDNRRVLRIMDTRLGGQYSKKGAQAAAALALQCLNTDPKFRPPMVEVLAALEALNSSNSFTRTPKHESHSTKI
SGGPSQK*

>Glyma.13G106900

SEQ ID NO: 57

MKKGNLGLGLKLSVPVSDQSNFARFLTESGTFKDGDLLVNRDGVRIVSQNDVEAPPPIKPTDNQLTLADIDVIKV
VGKGNGGVVQLVQHKWTSQFFALKVIQMNIEESMRKQIAQELKINQQAQCPYVVVCYQSFYENGVISIILEYMDG
GSLADLLKKVKTIPEDYLAAICKQVLKGLVYLHHEKHIIHRDLKPSNLLINHIGEVKITDFGVSAIMESTSGQAN

-continued

TFIGTYNYMSPERINGSQRGYNYKSDIWSLGLILLECALGRFPYAPPDQSETWESIFELIETIVDKPPPIPPSEQ
FSTEFCSFISACLQKDPKDRLSAQELMAHPFVNMYDDLEVDLSAYESNAGSPLATL*

>Glyma.13G110700

SEQ ID NO: 58

MGSSFSSCYEGESVSPSPKPTKVVATKGGSSSNRVSITDLSFPGSTLSEDLSVSLVGSNLHVFSLSELKIITQSF
SSSNFLGEGGFGPVHKGFIDDKLRPGLEAQPVAVKLLDLDGSQGHKEWLTEVVFLGQLRHPHLVKLIGYCCEEEH
RLLVVEYLPRGSLENQLFRRYTASLPWSTRMKIAAGAAKGLAFLHEAKKPVIYRDFKASNILLDSDYNAKLSDFG
LAKDGPEGDDTHVSTRVMGTQGYAAPEYIMTGHLTAMSDVYSFGVVLLELLTGRRSVDKGRPQREQNLVEWARPA
LNDSRKLGRIMDPRLEGQYSEVGARKAAALAYQCLSHRPRSRPLMSTVVNVLEPLQDFDDVPIGPFVYTVPAEQH
NEVAKESETPKERKRENDHHHHNRHHHHHRHNGHRHHPLKSPKTPMSSDQSQNDEHRNGRRSGSNSPDTSNASEA
Q*

>Glyma.13G124800

SEQ ID NO: 59

MDSARSWLQKFQPRDKTRAAGKKKEEDGNGGNQDSNEPVDEALLSSVTKQKVAATKQYIENHYKEQMKNLQERKE
RRTILEKKLADADVSEEDQNNLLKFLEKKETEYMRLQRHKMGVDDFELLTMIGKGAFGEVRVCREKTSDHVYAMK
KLKKSEMLRRGQVEHVKAERNLLAEVDRNCIVKLYCSFQDDEYLYLIMEYLPGGDMMTLLMRKDTLTEDEARFYV
GETILAIESIHKHNYIHRDIKPDNLLLDRYGHLKLSDFGLCKPLDCSALEEKDFSVGQNVNGSTQSSTPKRSQQE
QLQHWQMNRRTLAYSTVGTPDYIAPEVLLKKGYGMECDWWSLGAIMYEMLVGYPPFYSDDPMLTCRKIVNWKTYL
KFPEEARLSPEAKDLISKLLCNVNQRLGSKGADEIKAHPFFKGVEWDKLYQMEAAFIPEVNDELDTQNFEKEDES
DSQNQSSSRSGPWRKMLSSKDLNFVGYTYKNFEIVNDYQVPGIAELKKKQSKPKRPTIKSLFETSEGSDTDTSAN
DQPAQGSFLKLLPPQLEVSPHRNKNLPPRS*

>Glyma.13G150000

SEQ ID NO: 60

MMKHYHVLYMFLFFLPISTLSLHHNDTHALTLFRRQSDLHGYLLSNWTGHDACNSAWRGVLCSPNGRVTALSLPS
LNLRGPLDPLTPLTHLRLLNLHDNRLNGTVSTLFSNCTNLQLLYLSSNDFSGEIPPEISSLKSLLRLDLSDNNLR
GKVDVISNLTQLITLRLQNNLLSGEIPDLSSSMKNLKELNMTNNEFYGRLPSPMLKKFSSTTFSGNEGLCGASLF
PGCSFTTTPPNNNDSNNNNDNNSNEKEPSQTVSSNPSSFPETSIIARPGRKGQRKGLSPGAIVAIVIANCVALLV
VVSFAVAHCCARGRGSSLVGSGESYGKRKSESSYNGSDEKKVYGGGESDGTSGTDRSRLVFFDRRSEFELEDLLR
ASAEMLGKGSLGTVYRAVLDDGCTVAVKRLKDANPCARHEFEQYMDVIGKLKHPNVVRLKAYYYAKEEKLLVYDY
LSNGSLHALLHGNRGPGRIPLDWTTRISLVLGAARGLAKIHAEYSAAKVPHGNVKSSNVLLDKNGVACISDFGLS
LLLNPVHAIARLGGYRAPEQEQNKRLSQQADVYSFGVLLLEVLTGRAPSSQYPSPARPRMEVEPEQAAVDLPKWV
RSVVREEWTAEVFDQELLRYKNIEEELVSMLHVGLTCVVAQPEKRPTMEEVVKMIEEIRVEQSPLGEDYDVSCNS
LSPSIPTTEDGLA*

>Glyma.13G174900

SEQ ID NO: 61

MTNPKNQTTLSIIIIVYILFFSLATTLVSCLNQEGLYLYQLKLSLDDPDSKLSSWNSRDATPCNWYGVTCDAATN
TTVTELDLSDTNIGGPFLSNILCRLPNLVSVNLFNNSINETLPSEISLCKNLIHDLSQNLLTGPLPNTLPQLLN
LRYLDLTGNNFSGPIPDSFGTFQNLEVLSLVSNLLEGTIPSSLGNVSTLKMLNLSYNPFFPGRIPPEIGNLTNLQ
VLWLTQCNLVGVIPTSLGRLGKLQDLDLALNDLYGSIPSSLTELTSLRQIELYNNSLSGELPKGMGNLTNLRLID
ASMNHLTGRIPEELCSLPLESLNLYENRFEGELPASIADSPNLYELRLFGNRLTGKLPENLGRNSPLRWLDVSSN
QFWGPIPATLCDKGALEELLVIYNLFSGEIPASLGTCQSLTRVRLGFNRLSGEVPAGIWGLPHVYLLELVDNSFS
GSIARTIAGAANLSLLILSKNNFTGTIPDEVGWLENLVEFSASDNKFTGSLPDSIVNLGQLGILDFHKNKLSGEL
PKGIRSWKKLNDLNLANNEIGGRIPDEIGGLSVLNFLDLSRNRFLGKVPHGLQNLKLNQLNLSYNRLSGELPPLL
AKDMYRSSFLGNPGLCGDLKGLCDGRGEEKSVGYVWLLRTIFVVATLVFLVGVVWFYFRYKNFQDSKRAIDKSKW
TLMSFHKLGFSEDEILNCLDEDNVIGSGSSGKVYKVVLSSGEVVAVKKIWGGVKKEVESGDVEKGGRVQDNAFDA
EVETLGKIRHKNIVKLWCCCTTRDCKLLVYEYMPNGSLGDLLHSSKGGLLDWPTRYKIAVDAAEGLSYLHHDCVP
AIVHRDVKSNNILLDVDFGARVADFGVAKAVETTPKGAKSMSVIAGSCGYIAPEYAYTLRVNEKSDIYSFGVVIL
ELVIGKRPVDPEFGEKDLVKWVCTTLDQKGVDHLIDPRLDTCFKEEICKVFNIGLMCTSPLPIHRPSMRRVVKML
QEVGTENQTKSAKKDGKLSPYYYDDASDHGSVV*

>Glyma.13G228400

SEQ ID NO: 62

MADVVSKSPTPTSNLISPNKKETSNLLLGRFEIGKLLGHGTFAKVYYARNIKTGEGVAIKVIDKEKILKGGLVAH
IKREISILRRVRHPNIVQLFEVMATKSKIYFVMEYVRGGELFNKVAKGRLKEEVARKYFQQLISAVGFCHARGVY
HRDLKPENLLLDENGNLKVSDFGLSAVSDQIRQDGLFHTFCGTPAYVAPEVLARKGYDGAKVDLWSCGVVLFVLM
AGYLPFHDQNVMAMYKKIYRGEFRCPRWFSPDLSRLLTRLLDTKPETRIAIPEIMENKWFKKGFKQIKFYVEDDR
LCNVVDDDGLMDNDDDTASIVSVASFSDYSVSESDSEIETRRRINAPLPRPPSLNAFDIISFSPGFNLSGLFEEK
EDETRFVTAAPVNRIISKLEEIAQLVRFSVRKKDCRVSLEGTREGVRGPLTIAAEIFELTPSLVVVEVKKKGGDR
AEYERFCNDELKPGLQNLMVEESATSSELSTPIQPSLLRGLSEPVPDISSDIETPLCIPSDD*

>Glyma.13G235000

SEQ ID NO: 63

MLQLLPVFLLLLLEQASLISGLNQDGLYLYEWKQSLDDPDSSLSSWNNRDATPCNWAGVTCGPSNTTVTALDLSN
FNLSGPFSASLLCRLPNLTSIILFNNSINQTLPLQISLCTPLLHLDLSQNLLTGFLPHTLPLLHLDLTGNN
FSGPIPPSFATFPNLQTLSLVYNLLDDVVSPSLFNITTLKTLNLSFNPFLPSPIPHSLGNLTNLETLWLSGCNLV
GPIPESLGNLVNLRVLDFSFNNLYGPIPSSLTRLTALTQIEFYNNSLSAEFPKGMSNLTSLRLIDVSMNHLSGTI
PDELCRLPLESLNLYENRFTGELPPSIADSPNLYELRLFGNKLAGKLPENLGKNAPLKWLDVSTNRFSGGIPESL
CEHGELEELLMLENEFSGEIPASLGGCRRLSRVRLGTNRLSGVPAMGWLPHVYLLELGNNSFSGPIARTIAGA
RNLSLLILSKNNFSGVIPDEIGWLENLQEFSGADNNFNGSLPGSIVNLGQLGTLDLHNNELSGELPKGIQSWKKL
NDLNLANNEIGGKIPDEIGILSVLNFLDLSNNEISGNVPLGLQNLKLNLLNLSYNRLSGRLPPLLAKDMYRASFM
GNPGLCGDFKGLCDGKGDDNSKGFVWILRAIFIVASLVFVVGVVWFYFRYRNFKNAGRSVDKSKWTLMSFHKLG
FSEDEILNCLDEDNVIGSGSSGKVYKVVLTSGESVAVKKIWGGVKKEIDSGDVEKGHQFRQDSSFDAEVETLGKI
RHKNIVKLWCCCTTRDSKLLVYEYMPNGSLGDLLHSNKGGLLDWPTRYKIAVDAAEGLSYLHHDCVPSIVHRDVK
SNNILLDGDFGARVADFGVAKVVDATGKGTKSMSVIAGSCGYIAPEYAYTLRVNEKSDIYSFGVILELVTGRRP
IDPEFGEKDLVMWACNTLDQKGVDHVIDSRLDSCFKEEICKVLNIGLMCTSPLPINRPAMRRVVKMLQEVGTENQ
TKPAKKDGKLSPYYYDDGSDHGSVA*

-continued

>Glyma.13G238700

SEQ ID NO: 64

MIRHKHTHHLPSILLSILFLFNSTCAIDFVFNGFNSSEVLLFGNATVDSRILTLTHQQRFSVGRALYNKKIPTKK
PNSSRVYPFSTSFIFAMAPFEDTLPGHGLVFIFTPVTGIQGTSSAQHLGLENLTNNGNSSNHVFGVEFDVFQNQE
FDDIDANHVGIDINSLKSYVSHDAGYWPDGADKSFKELTLNSGENYQVWIDYEDSWINVTMAPVGMKRPSRPLLN
VSLNLSQVFEDEMFVGFTSATGQLVESHKILGWSFSNEKFSLSDELITTGLPSFVLPKDSIFKSKGFVAGFTVGV
FFVICLLVLLALFLIQRKREKERKRMEMEDWELEYWPHRMTYEEIEAATKGFSEENVIGVGGNGKVYKGVLRGGV
EVAVKRISHENDGLREFLAEVSSLGRLKQRNLVGLRGWCKKDVGNFLLIYDYMENGSLDKRVFDCDESKMLSYED
RIRILKDVAFAVLYLHEGWEDKVVHRDIKASNVLLDKDMNGRLGDFGLARMHSHGQVASTTKLVGTVGMAPEVF
KTGRASTQTDVYMFGILILEVLCGRRPLEEGKPPLVEWIWQLMVQGQVECALDERLRAKGEFNVQEMERVMHLGL
LCAYPEPKTRPTMRQVVNVLEGKNEVEDSEIENMDTYLLQQLKSRDILSEYSQYFSYTSHPTFQDIRLSSSMSLT
WSESVVEGR*

>Glyma.13G335700

SEQ ID NO: 65

MELLKPLHPHHAPILRIPFHAVPSSSSSQSQSQVPLPMISKVHVAVGKSLDKVVPLLRWTLNHFRNAEIVIVHAY
QPSLTIPTLLGKLPASQASPAVVSAFRKVEREQIMKLLDKYLSICRAARVKAAIIVTEADQVQKGIVDLVIKHNI
EKLVIGAVPENCMKVKRNSSKANYTAKNAPPFCEVWFIYKGKHIWTREASETPCSSSSCTQPEIATTESLRCRSF
QYGKNELFDSEYLWPNSARTTAVSGIRSWVQGEIIETEATFSSKASSCCSHCSPQNSSRAYFDTYLEVMEERINK
QLIETKREAEAVTDEAFTELLKCEKLEVEAMEAIRKVNLFESAHVREVKLRKEADDALRDTVQEQQKLLNESEEI
AGELQMTMRNIALLDSRAQEANRRRDEAADELSLIQESISTLWQERQQIRRQKTEALRWLERWRSRGQVGAAHCN
GVIGFAEELPELAEFSLSDLQNATCNFSNSFKIEQGGYSCILGMLGRTVAIKKFHQHNMQGPLEFRQEVQVLG
SLQHPHLITLLGVCPEAWSIVYEYLPNGTLQDYLFRKSNNSPLTWNTRARMIAEIASALCFLHSFKPETIIHGDL
KPETVLLDSSLGCKMCGFGLCRLVSEEESLLRPSFRLSTEPKGAFTYTDPEFQRTGILTTKSDIYSFGLIILQLLT
GRTPVGLAVLVRNAVSCGKLSSILDSSAGEWPSAVAMQLVELGLQCCQQYHRDRPELTPTLVRELEQLHASEERP
VPSFFSCPILQEIMHDPQVAADGFTYEGDAIREWLENGHDTSPMTNLKLSHLFLTPNYALRLAIQDWLCKS*

>Glyma.14G026300

SEQ ID NO: 66

METSLDYSKMLFLLLLGSTSLIFLSHLASAATPKLNTQEVKALKEIGSKIGKKDWNFGVDPCSGKGNWNVPDARK
AFVMSSVICDCSFNHNSSCHVVSIYWKAQNLSGSLSPEFSKLHYLQKLDLSRNIITGSIPPQWGTMRLVELSLMG
NKLSGPFPKVLTNITTLRNLSIEGNQFSGHIPTEIGKLTNLEKLVLSSNGFTGALPPVLSKLTKLIDLRISDNNF
LGKIPDFISNWTLIEKLHMHGCSLEGPIPSSISALTRLSDLRITDLKGSKSSAFPPLNNLKSMKTLVLRKCMIKG
EIPEYIGRMEKLKILDLSYNGLSGEIPESFAQLDKVDEMYLTGNKLSGIIPRWVLANNENIDISDNNFSWDSSSP
TECQRGSVNLVESYSSSVNTQTKINSCLKKNFLCTASPSQYRYSLNINCGGNEANVSGNIYEADREQKGAAMLYY
TSQDWALSSTGNFMDNDIDSDPYIVANTSRLNVSALNSKLYTTARVSPLALTYYGLCLINGNYTVKLHFAEIIFI
NDRSLNSLGRRVFDVYIQGNLVLKDFDIRREAGGTGKSIEKTFNASVTQHTLKIHFYWAGKGTTGIPTRGVYGPL
VSAISVNPNFKPPSGEGKRTYLILAIIIVAGVLVVVLLVLVLLRRMGWLGGKDPVYKELRGIDLQTGLFTLRQIK
AATKNFDALNKIGEGGFGCVYKGQQSDGTMIAVKQLSSKSKQGNREFVNEMGLISGLQHPNLVKLYGCCVEGNQL
ILIYEYMENNCLSRILFGRDPNKTKLDWPTRKKICLGIAKALAYLHEESRIKIIHRDVKASNVLLDKDFNAKVSD
FGLAKLIEDEKTHISTRVAGTIGYMAPEYAMRGYLTDKADVYSFGVVALETVSGKSNTNFRPNEDFVYLLDWAYV
LQERGSLLELVDPNLGSEYLTEEAMVVLNVALLCTNASPTLRPTMSQVVSMLEGWTDIQDLLSDPGYSAISSSSK
HKSIRSHFWQTPSGTHSISIPSIYTDSSGSHVETEKNYHPVTVNSDGSDKSN*

>Glyma.14G058900

SEQ ID NO: 67

MAVSNGVEAVLEFLRKNGLSEAESALRQDIIENNDLGNFDYEKFFFPMVPPPPPVRVRSFSRLSELSADGNCSKS
SSDEFVSIGSPISRVSSSEFINPYGIRSSSQTQNDSASSSERLSQFGTARDYHDFEMQNEPYWYNEKDDDYFMTP
SFEGPDFFACQSEDKFVMTAETENQHDNSLDLVYNSEEFLLKGNGNGGEMDKACLYNHSSVRDGNATYSKEYCHV
DNNNLFEGELEGKAEKHTVACSCEVPFCKSSPGGSCSLDPTNFGYPNLKEIHLKFGDINSFDSTSELTVNQSFDY
YTKNDSSKEYNGPYDLTIKVNQKDLPNGLDTYKARDGGELAEECQDPEITADGEHTTDDELLKYTQEEEYEVEDL
RIIHRKNRTGFEENKELPIVLNTVLAGRYYVTEYLGSAAFSRVVQAHDLQTGIDVCLKIIKNDKDFFDQSLDEIK
LLKLVNKHDPADLHHFLRLYDYFYHQEHLFIVTELLQANLYEFQKFKQESGGEEYFTLNRLQLITRQCLEALQYL
HSLGIVHCDLKPENILIKSYRRCEIKVIDLGSSCFQTDNLCLYVQSRSYRAPEVMLGLQYDEKIDIWSLGCILAE
LCSGEVLFPNDAVVMILARMIGMFGSIDMEMLVKGQETHKYFTKEYDIYYVNEETDQLEYIIPEESSLEQHLQVT
DTTFIDFVRYLLSINPKRRPTARQALRHPWLSYVY*

>Glyma.14G074700

SEQ ID NO: 68

MGMGGIAVSVVTVLLLMIGLTMGMSLSSRTEWFALRELRQSLEIRAKYWPIKAEPCGNWTGVQCRNGRVVGINVS
GLRRTRWGRLNPSFEVDSLVNFTLLETFNASGFKLNGSIPEWLGERLGVLEELDLSLCSIKGSIPDSIGRLSKLK
VLLLSGNFLTGRMPSTLGNLTRLSVLDLSGNSLSWPVPDSVSKLGNLSRLDLSYNFLSGSVPPELGALSSLQFLN
LSGNSFTGSVPSQLGNLSKLVEVDLSMNFLSRSLSGGLFSSVVLALEVLILRGNLLDGVLPANLRSMPRLHFLDV
SSNNLTGTLPNFADWNVSSAGVVFNLSNNMFYGLLNTSLDRFKMIDLSSNFLEGEVLGGGGGVSNLDDLDRNCLQR
IPNQRNLEDCRMFYDKRNLSSAFPESESRSRRRVIFMLVGIFGGLGFIVLLAVLMLVLKQCHNRKSLEVPRETK
DGGAVEEGESPIPPKDIDFVTGVGEAYSFEQMLRLTGNFAESNVIKHGHSGDLFLGVLEGGATVVVKKVDLNLFK
RESYVVELGLLSKVPHARLVPILGHCLDNENEKCIVYKMPNRDLATSLHRVTGSDGKIQSLDWITRLKIAIGAA
EGIAYLHECSPPLVHRDIQASSILLDDKFEVRLGSLSEVTAQGDLQQGVISRVFSKPPSSNQADSGKSPVTCTYD
VYCFGKILLELITGNIEVSKSDDATTKEWLEQTLPYITIYDKERVTKIIDPSLIVDEDLLEEVWAMAIVANACLK
PKPSKRPPMRHVLKALENPLKIVREENTSSARLRTNSSRKSWSTAFFGSWRHSSSDSVVATNKEGSNDTKKSGKV
GSQSSGNDHSSSNKRSSNEIFPEPLEIQDVETGVTR*

>Glyma.14G206000

SEQ ID NO: 69

MTEVTLNSSVNILYHTAKKISMKFYSLQAHRFLFIIVILCPLVIADLSSDKQALLDFAAAVPHRRNLKWNPATPI
CSSWVGITCNLNDIRVVSVRLPGIGLVGTIPANDTRIDSLRNISLRANLLSGSLPADITSLPSLQYLYLQHNNLS
GNIPTSLSTRLNVLDLSYNSFTGAIPKTLQNLTQLIKLNLNQNNSLSGLIPNLNVTKLRRLNLSYNHLNGSIPAAL
QIFPNSSFEGNSLCGLPLKSCPVVPSTPPPSSTPAPPSTPARHSSKSKLSKAAIIAIAVGGGVLLLLVALIIVLC
CFKKKDDGSPRATKGKGPSGGRSEKPKEEFGSGVQEPEKNKLVFFEGSSYNFDLEDLLRASAEVLGKGSYGTAYK
AILEESTTVVVKRLKEAVVGKREFQQMEIVGRVGHHPNVVPLRAYYYSKDEKLLVYDYIPSGNLSTLLHGNRAS
GRTPLDWNSRIKISVGIARGIAHIHSVGGPKFAHGNVKSSNVLLNQDNDGCISDFGLTPLMNVPSTPSRAAGYRA

-continued

PEVIETRKHTHKSDVYSFGVLLLEMLTGKAPQQSPGRDDMVDLPRWVQSVVREEWTAEVFDVELMRYQNIEEEMV
QMLQIAMACVAKVPDMRPSMEEVVRMIEEIRLSDSENRPSSEENRSKEESTAQTP*

>Glyma.14G212100

SEQ ID NO: 70

MKALALLAIIVFTLLVRSQEEEDYDDASVMLALKNSLNPPGWSDPDPCKWARVLCSDDKRVTRIQIGRLNLQGTL
PTTLQKLTHLEHLELQYNNISGPLPSLNGLTSLRVFLASNNRFSAVPADFFAGMSQLQAVEIDSNPFEPWEIPQS
LRNASGLQNFSANSANVGGSIPEFFGSDVFPGLTLLHLAMNNLEGTLPLSFSGSQIQSLWLNGQKSVNKLGGSVE
VLQNMTFLTDVWLQSNAFTGPLPDLSGLKSLRDLSLRDNRFTGPVPVASFVGLKTLKVVNLTNNLFQGPMPVFGD
GVVVDNVKDSNSFCLPSPGDCDPRVDVLLSVVGVMGYPPRFAESWKGNDPCAYWIGITCSNGYITVVNFQKMELS
GVISPEFAKLKSLQRIVLADNNLTGSIPEELATLPALTQLNVANNQLYGKVPSFRKNVVVSTNGNTDIGKDKSSL
SPQGLVPPMAPNAKGDSGGVSGIGGKKSSSHVGVIVFSVIGAVFVVSMIGFLVFCLFRMKQKKLSRVQSPNALVI
HPRHSGSDNESVKITVAGSSVSVGAASETRTVPGSEASDIQMVEAGNMVISIQVLKNVTDNFSEKNVLGQGGFGT
VYRGELHDGTRIAVKRMECGAIAGKGAAEFKSEIAVLTKVRHRHLVSLLGYCLDGNEKLLVYEYMPQGTLSRHLF
DWPEEGLEPLEWNRRLTIALDVARGVEYLHGLAHQSFIHRDLKPSNILLGDDMRAKVADFGLVRLAPEGKASIET
RIAGTFGYLAPEYAVTGRVTTKVDVFSFGVILMELITGRKALDETQPEDSMHLVTWFRRMSINKDSFRKAIDSTI
ELNEETLASIHTVAELAGHCGAREPYQRPDMGHAVNVLSSLVELWKPSDQNSEDIYGIDLDMSLPQALKKWQAYE
GRSQMESSASSSLLPSLDNTQTSIPTRPYGFADSFTSADGR*

>Glyma.14G224000

SEQ ID NO: 71

MEKTGVLSAKEAFEKLEKVGEGTYGKVYRAREKAIGKIVALKKTRLHEDEEGVPPTTLREVSILRMLSRDPHVVR
LMDVKQGQNKEGKTVLYLVFEYMDTDLKKFIRSFRQSGETIPPHIIKVILSICPSIFNIRFFFVHLFLSIWLQSL
MYQLCKGVAFCHGHGILHRDLKPHNLLMDRKTMMLKIADLGLARAFTVPIKKYTHEILTLWYRAPEVLLGATHYS
MAVDMWSVGCIFAELVTKQALFPGDSELQQLLHIFRLLGTPNEDVWPGVSKLMNWHEYPQWNPQSLSTAVPSLDE
LGLDLLSQMLKYEPSKRISAKKAMEHVYFDDLDKRHL*

>Glyma.15G111600

SEQ ID NO: 72

MARARFPLSILLSLVFVALPLSLANTDPSDVQALEVMYNALNSPTQLTGWKIGGGDPCGESWKGVTCEGSAVVSI
KLSGLGLDGTLGYLLSDLMSLRELDLSDNKIHDTIPYQLPPNLTSLNFARNNLSGNLPYSISAMVSLNYLNLSNN
ALSMTVGDIFASLQDLGTLDLSFNNFSGDLPPSFVALANLSSLFLQKNQLTGSLGVLVLGPLDTLNVANNNFSGW
IPHELSSIRNFIYDGNSFENSPAPLPPAFTSPPPNGPHGRHHSGSGSHNKTQVSDNEKSDGHKGLTVGAVVGIVL
GSVLVAAIVLLALVFCIRKQKGKKGARNFSGSLPRGVINVTPQMQEQRVKSAAVVTDLKPRPAENVTVERVAVKS
GSVKQMKSPITSTLYTVASLQSATNSFSQEFIIGEGSLGRVYKADFPNGKVMAIKKIDNSALSLQEEDNFLEAVS
NMSRLRHPSIVTLAGYCAEHGQRLLVYEYIANGNLHDMLHFAEDSSKALSWNARVRIALGTARALEYLHEVCLPS
VVHRNFKSANILLDEELNPHLSDCGLAALTPNTERQVSTQMVGSFGYSAPEFALSGVYTVKSDVYSFGVVMLELL
TGRKPLDSLRVRSEQSLVRWATPQLHDIDALAKMVDPTLNGMYPAKSLSRFADIIALCVQPEPEFRPPMSEVVQA
LVRLVQRASVVKRRPSEESGFGHKTPDHEAMDMPF*

>Glyma.15G203600

SEQ ID NO: 73

MEIFKCFYIKNLILVTFFMVSSAVLAIDPYSEALLSLKSELVDDDNSLHNWVVPSGGKLTGKSYACSWSGIKCNN
DSTIVTSIDLSMKKLGGVVSGKQFIIFTNLTSLNLSHNFFSGQLPAEIFNLTSLTSLDISRNNFSGPFPGGIPRL
QNLVVLDAFSNSFSGPLPAEFSQLENLKVLNLAGSYFRGSIPPEYGSFKSLEFLHLAGNSLTGSIPPELGHLKTV
THMEIGYNEYQGFIPPELGNMSQLQYLDIAGANLSGPIPKQLSNLTSLQSIFLFRNQLTGSIPSELSIIEPLTDL
DLSDNFLIGSIPESFSELENLRLLSVMYNDMSGTVPESIAKLPSLETLLIWNNRFSGSLPPSLGRNSKLKWVDAS
TNDLVGSIPPDICASGELFKLILFSNKFTGGLSSISNCSSLVRLRLEDNSFSGEITLKFSHLPDILYVDLSKNNF
VGGIPSDISQATQLEYFNVSYNPQLGGIIPSQTWSLPQLQNFSASSCGISSDLPLFESCKSISVIDLDSNSLSGT
IPNGVSKCQALEKINLSNNNLTGHIPDELASIPVLGVVDLSNNKFNGPIPAKFGSSSNLQLLNVSFNNISGSIPT
AKSFKLMGRSAFVGNSELCGAPLQPCPDSVGILGSKGTWKVTRIVLLSVGLLIVLGLVFGILYLRRGIKSQWKM
ASFAGLPQFTANDILTSLSATTKPTDIQSPSVTKTVLPTGITVLVKKIELEARSIKVVSEFIMRLGNARHKNLIR
LLGFCHNQHLVYLLYDYLPNGNLAEKMEMKWDWAAKFRTVVGIARGLCFLHHECYPAIPHGDLRPSNIVFDENME
PHLAEFGFKHVSRWSKGSSPTTTKWETEYNEATKEELSMDIYKFGEMILEILTRERLANSGASIHSKPWEVLLRE
IYNENGASSASSLQEIKLVLEVAMLCTRSRSSDRPSMEDVLKLLSGLKHLEDGRTSKEGQ*

>Glyma.15G222300

SEQ ID NO: 74

MGNETRKLSDEYEVSEVLGRGGFSVVRKGTKKSSSDTKTHVAIKTLRRVGTASNSNNPSGFPRPKGGEKKSTAAM
MGFPTWRQVSVSDALLTNEILVMRRIVENVSPHPNVIDLYDVYEDSNGVHLVLELCSGGELFDRIVAQDRYSETE
AAGVVRQIASGLEAIHRANIVHRDLKPENCLFLDVRRDSPLKIMDFGLSSVEEFTDPVVGLFGSIDYVSPEALSQ
GKITTKSDMWSLGVILYILLSGYPPFIAQNNRQKQQMIMNGNFSFYEKTWKGITRSAKQLISDLLIVDPSRRPSA
QDLLSHPWVVGDKAKDDAMDPEIVSRLQSFNARRKLRAVAIASIWSTTIFLRTKKLKSLVGTHDLTEEEIENLRM
SFKKICVSGDNATLSEFEEVLKAMNMPSLIPLAPRIFDLFDDNRDGTVDMREILCGFSSFKNSKGDDALRLCFQM
YDTDRSGCITKEEVASMLRALPEDCLPTDITEPGKLDEIFDLMDANSDGKVTFDEFKAAMQRDSSLQDVVLSSLR
PQ*

>Glyma.16G079200

SEQ ID NO: 75

MVLHSWISSSHILVNFLLLLGCGITYGTDTDIFCLKSIKESLEDPYNYLKFSWDFNNKTEGYICRFNGVECWHPD
ENRVLNLKLSNMGLKGQFPRGIQNCSSLTGLDLSINKLSGTIPGDISTLIPFATSIDLSTNEFSGAIPVSLANCT
FLNTLKLDQNRLTGQIPPQFGVLSRIKVFSVSNNLLTGQVPIFRDGVELHYANNQGLCGGNTLAPCQATPSKSNM
AVIAGAAAGGVTLAALGLGIGMFFFVRRVSFKKKEEDPEGNKWARSLKGTKRIKVSMFEKSISKMKLSDLMKATN
NFSNTNIIGTGRTGTVYKAVLDDGTTLMVKRLQESQYTEKEFMSEMGTLGTVKHRNLVPLLGFCMTKRERLLVYK
NMPNGNLHDQLHPADGVSTLDWTTRLKIAIGAAKGLAWLHHSCNPRIIHRNISSKCILLDADFEPKISDFGLARL
MNPIDTHLSTFVNGEFGDLGYVAPEYTRTLVATPKGDIYSEGTVLLELVTGERPTNVSKAPETFKGNLVEWITEL
TSNAKLHDAIDESLVRKDVDSELFQFLKVACNCVSPTPKERPTMFEVYQLLRAIGGRYNFTTEDDILVPTDIGNT
DNMQELIVAQEGSY*

-continued

>Glyma.17G048900

SEQ ID NO: 76

MGSSFSSCYEGESVSPSPKPTKVVATKGGSSSNRVSITDLSFPGSTLSEDLSVSLVGSNLHVFSLAELKIITQGF
SSSNFLGEGGFGPVHKGFIDDKLRPGLEAQPVAVKLLDLDGSQGHKEWLTEVVFLGQLRHPHLVKLIGYCCEEEH
RLLVYEYLPRGSLENQLFRRYTASLPWSTRMKIAAGAAKGLAFLHEAKKPVIYRDFKASNILLDSDYNAKLSDFG
LAKDGPEGDDTHVSTRVMGTQGYAAPEYIMTGHLTAMSDVYSFGVVLLELLTGRRSVDKGRPQREQNLVEWARSA
LNDSRKLSRIMDPRLEGQYSEVGARKAAALAYQCLSHRPRSRPLMSTVVNVLEPLQDFDDVPIGPFVYTVPAEQQ
QYNEVAKESETPKERKRENGHHHNRRHHHHRHNGHRHHPLKSPKTPMPSDQSQNDEHRNGRKSGSNSPDTFNASE
AQRSMG*

>Glyma.17G083100

SEQ ID NO: 77

MGCSFSGLNALYDSVNGGGDVWINENRFRIVRQLGEGGFAYVYLVKETPNDSAVAAGLSKKLKGSSHLSDDGTYA
MKKVLIQNNEQLELVREEIRVSSLFNHPNLLPLLEHAIISVKPTQETSWNHEAYLLFPVHLDGTLLDNAKIMKAK
KEFYSTSDVLQIFRQLCAGLKHMHSFDPPHAHNDVKPGNVLITHRKGQPPLAILMDFGSARPARKQIGSRSEALQ
LQEWASEHCSAPFRAPELWDCPSQADIDERTDIWSLGCTLYAIMYGVSPFEYALGESGGSLQLAIVNAQVKWPAG
PKPPYPEALHQFVSWMLQPTASMRPRIDDIIIHVDKLVAKESQ*

>Glyma.17G149900

SEQ ID NO: 78

MKCEFFKEKCKSAPELHKKKTPAVNRAANSTGSVSSPKSVKDLYREKEHSFRVFTLQELRDATNGFNRMLKLGEG
GFGSVYKGSITQPDGQGGDPIPVAIKRLNTRGFQGHKEWLAEVQFLGIVNHPNLVKLLGYCSVDAERGIQRLLVY
EFMPNRSLEDHLFNKNLPTLPWKTRLEIMLGAAQGLAYLHEGLEIQVYIRDFKSSNVLLDADFHPKLSDFGLARE
GPQGDQTHVSTAVVGIQGYAAPEYIETGHLKVQSDMWSFGVVLYEILTGRRSLERNRPTAEQKLLDWVKQYPADT
SRFVIIMDARLRNQYSLPAARKIAKLADSCLKKNPEDRPSMSQIVESLKQALQYSDTTSQDIAESSSSSRSKLVR
KK*

>Glyma.17G218500

SEQ ID NO: 79

MLGTPHTLILLLFLFLITTFSHSLVFNITNFDDPAAATAISYEGDGRTTNGSIDLNKVSYLFRVGRAIYSKPLHL
WDRSSDLAIDFVTRFTFSIEKLNLTEVAYGDGFAFYLAPLGYRIPPNSGGGTFGLFNATTNSNLPENHVVAVEFD
TFIGSTDPPTKHVGVDDNSLTSAAFGNFDIDDNLGKKCYTLITYAASTQTLFVSWSFKAKPASTNHNDNSSSFSY
QIDLKKILPEWVNIGFSASTGLSTERNTIYSWEFSSSLNGSPADFENVKLKHQSSKLALILAVLCPLVLLFVLAS
LVAVFLIRKKRRSHDDCMLYEVGDDELGPTSVKFDLDKGTIPRRFEYKELVDATNGFSDDRRLGQGASGQVYKGV
LSYLGRVVAVKRIFADFENSERVFTNEVRIISRLIHKNLVQFIGWCHEEGEFLLVFEYMPNGSLDSHLFGNKRVL
EWHLRYKIVLGVVNALHYLHEDAEQCVLHRDIKSANVLLDTEFNTKVGDFGMAKLVDPRLRTQRTGVVGTYGYLA
PEYVNVGRASRESDIYSFGVVSLEMASGRRTYQDGEFHVSLMNWVVWQLYVEGEIMRAADEKLNNEFEVDQMRSLL
VVGLWCTNPNDKERPKAAQVIKVLNLEAPLPVLPLDMYERAPPMEIIRMPHHPSGKNHSGMSTPITSSLVSVGR*

>Glyma.17G246300

SEQ ID NO: 80

MLRDESVGSRSARHSATATATVSNKVLVAVKAEKVISNTALAWALTHVAHSTDSITLLAVYSSHKTGRRFWNFSR
LAGDCTNGPAGKLPEQISDISESCAQMVLQLHNQIEVRVKIKVVTGTPSGAVAAEARWSGSHWVILDKKLKQEVK
HCTDELNCSIVVMNGSQAKILRLNLRSSNELQTPFFSANSSPGIEIAKLKGRRLKHSTPVGSPEEAVYEQNPLYE
GQGPEKRTDESINEPTKDFHVQPPLYFDLERDSPPPSWTRPASSVASDNKTIFWIPQNHNIVDKFQKTKNNSVIQ
RTKSPTSKTLLENFIRCDQEIWTNELGFDQAQSRSYVPNLGIRDNNSVPLGRTTSIPPPLCSQCKNKAPVFGKPP
KRFSYKELEEATDMFSDENFLAEGRFGVVHQGILKDGQVVAVKQLKFGGSQADLDFCREVRVLSCAQHRNVVLLI
GFCIESNLRILVYEYICNGSLDLYLYGDESMPLDWNSRLKIAIGTARGLRYLHEDCRVGCIAHRDLRPKNILVTH
DFEPMVADFGLARWHSEWNIDTEDRVIGTSGYLAPEYLDAGNLTYKVDVYAFGIVLLELITGRRISELEQFNGHS
YLSEWFHPIRMLEPGHILQNVRSLKPCFDSKESVEFNLQLQAMARAVSLCLRVDPDARPPMSKILRVLEGGNPVR
PMGLDINSVGNTSGHLSGLKSHTPPKGTINHSRRLSH*

>Glyma.17G250800

SEQ ID NO: 81

MGMEGIAVSVVTMLLLMVGLTMGMSSRTEWFALRELRQSLEIRAKYWPIKAEPCGNWTGVQCRNGRVVGINVSGL
RRTRWGRLNPSFEVGSLVNFTLLETFNASGFKLNGSIPEWLGESLGVLEVLDLSFCSIKGSIPDSIGWLSKLKVL
LLSGNFLTGRMPSTFGNLTRLSVLNLSGNSLSGTVPDSVSKLGNLSRLDLSYNFLSGSVPPELGALSSLQFFNLS
GNSFTGTFPSQLGNLSKLVDVDLSMNFLSGSLPGGSSSSGLLALKVLILRGNLFDGVLPADLWPMPRLHFLDVSS
NNLTGTLPNFTSWNVSSVGFVFNLSNNLFYGLLNTSLDRFEIIDLSSNYLEGEVPGGGVNNVSLDRNCLQRIPNQ
RDLEDCRVFYDNRSLPFGFLKSGSRSRVIFILVGIFGGLGFIVLLALVLMLVLKQCHNRRSLGVQRGTKDGGPVQ
EGESPIPPKDTVFVTVGDAFSFEQMLHLTSNFAEANVIKHGHSGDLFLGVLEGGATVVVKKVDLNLFKRESYVVE
LGLLSKVPHARLVPILGHCLDNENEKFIVYKYMPNRDLATSLHRVTGSDGKLQSLDWITRLKIAIGAAEGIAYLH
ECSPPLVHRDIQASSILLDDKFEVRLGSLSEVTAQGDLQQGVISRVFSKPPSSNQADSGKSSVTCAYDIYCFGKI
LLELELITGNIEVSKLDDASTKEWLEQTLPYITIYDKERVTKIIDPSLIVDEDLLEEVWAMAIVANACLNPKPSKRP
PMRHVLKALENPLKIVREENTSSARLRSNSSRKSWSTAFFGSWRHSSSDSVVATNKEGSSDTKKSGKVGSQSSGN
DHSSSNKRSSNEIFPEPLEILDVETGVAR*

>Glyma.18G107600

SEQ ID NO: 82

MSANSSLHVELSRKTSFLGLRLWVLIGIGVGVFIVVILCVLSVWVMFRRKSKRSLDKYSLSQIPHVSKDIIVDMV
GVQISHDQSESVAIPVHDKPSENNSNKLFSHLHKSKSGDADNISQCCSSVYHHERGFSSMSGEEGSSGTVKKQSAL
SFGGMVTASPLVGLPEISHLGWGHWFTLRDLELATNRFSPENVIGEGGYGVVYRGKLINGSEVAVKKILNNLGQA
EKEFRVEVEAIGHVRHKNLVRLLGYCVEGVHRLLVYEYVNNGNLEQWLHGAMSQQGTLTWEARMKVITGTAKALA
YLHEAIEPKVVHRDIKSSNILIDTEFNAKVSDFGLAKLLDSGESHITTRVMGTFGYVAPEYANTGLLNERSDIYS
FGVLLLEAVTGKDPVDYSRPANEVNLVEWLKKMMVGTRRAEEVVDSRLEVKPSIRALKRALLVALRCVDPEAEKRP
KMSQVVRMLEADEYPEREDRRNRKSRTASMEIESLKDISGPSDAEKLKGSEGHEPETTQG*

-continued

>Glyma.18G141500

SEQ ID NO: 83

MEKTIHLVYFKCLVFLLMKQVIVMAEPRARTVNITCNNKLEHNTTIFVPNFVATMEKISEQMRNTGYGTAVVGTG
GPDTNYGLAQCYGDLSLLDCVLCYAEARTVLPQCFPYNGGRIYLDGCFMRAENYSFYDEYIGPGDKAVCGNTTRK
STSFQAAAKKAVLSAVQAAANNKGYARKEVEVAGTTNDAAYVLANCWRSLDTRSCRACLENASSSILGCLPWSEG
RALNTGCFMRYSDTDFLNKEQENGSSGGNVLVIVVAVVSSIVLVVGIAIVVYIRKHRYIQMKRRGSNDAEKLAK
SLHHNSLNFKYSTLEKATNSFDEANKLGQGGFGTVYKGVLADGREIAIKRLYFNNRHRAADFFNEVNIISSVEHK
NLVRLLGCSCSGPESLLIYEYLPNRSLDRFIFDKNKGRELNWDKRYDIIIGTAEGLVYLHENSNIRIIHRDIKAS
NILLDAKLRAKIADFGLARSFQEDKSHISTAIAGTLGYMAPEYLAHGQLTEKADVYSFGVLLLEIITGRLNNRSK
ASEYSDSLVTMTWKHFQSGTAEQLIDPCLVVDDNHRSNFKNEILRVLHIGLLCTQEIPSLRPSMSKALKMLTKKE
EHLDLEAPSNPPFIDESTMELHDQNDDPFYPLNAEDSLATMSHSSFYAR*

>Glyma.18G273100

SEQ ID NO: 84

MLFDRLAFCCSKHTSSSQRKYPTVIEELCHQFSLANLKKSTNNFDENGVIGYGRFGKVYKGCLQHNDGSDYSVTL
KRLGVKDSRGLEQFKNEIELLCQLRHPNCVSLIGFCNHKKEKILVYEYMSNGSLHQHLRGGLLSWKKRLEICIEA
AHGLHYLHTGAKRTIIHRNINPSNILLDNNMKSKLTDFRLSIQGPRYGSKPKPIKVYVIEGSLGYMPMEYIVDGT
ITDKFDVFSFGMVLLEVVCGRNCLIIPTETEVLEKPVEENIDQNIKGKIAPECWQVFIDIIIRCLKYEPDERPTM
GEVEVQLEHALSMQEQADITNTNSDYTLFSTTTIHLGLELESNPEESDT*

>Glyma.19G036600

SEQ ID NO: 85

MVRQADLVIIGVSVGLTLGILISCLIFFGIRWYKKRAHIRRSANESSLTTLPIRTNGLGTSSDFSASLDSSIASS
WSENLKRNSHFSWWNHQNKDRFASASGILKYLYKEIQKATQNFTTTLGQGSFGTVYKATMPTGEVVAVKVLAPNS
KQGEKEFQTEVFLLGRLHHRNLVNLVGYCVDKGQRILVYQYMSNGSLANLLYGEEKELSWDQRLQIALDISHGIE
YLHEGAVPPVIHRDLKSANILLDHSMRAKVADFGLSKEEIFDDRNSGLKGTYGYMDPAYISTSKLTTKSDIYSFG
IIVFELITAIHPHQNLMEYVNLAAMDHDGVDEILDKQLVGKCNLEEVRQLAKIGHKCLHKSPRKRPSIGEVSQFI
SRIKQRRQRHLTEDNLSFASNNFSRAVSRLEDRQVELSRMPTINLTETV*

>Glyma.19G143000

SEQ ID NO: 86

METENGDTRSKKMEEYEVIEQIGRGAFGSAFLVLHKSEKKRYVLKKIRLAKQTEKFKRTAHQEMNLIAKLNNPYI
VDYKDAWVEKEDHICIITGYCEGGDMAENIKKARGSFFPEEKVCKWLTQLLIAVDYLHSNRVIHRDLKCSNIFLT
KDNNIRLGDFGLAKRLNAEDLASSVVGTPNYMCPELLADIPYGYKSDMWSLGCCMFEIAAHQPAFRAPDMAGLIN
KINRSSISPLPIVYSSTLKQLIKSMLRKNPEHRPTAAELLRHPLLQPYVLRCHNASSNVLPVYPLVNPKDKARRP
NKSSGGKDHKDKEAGLVNCLERIHPIEGNADIQISNLPNDVVTISTSAEDNLETRMANLTSYIVESSTSISGSKD
GSTTSESTICSVCKEDFKSRPAREMTNNEISSKSTQDSLHEEQRFAAKHFHKLEDDDINAVTAEVEDASCNGGLD
NAEAQREDSNLEDSGKSTMSSEGSSSTDKDKSINEERSSLIVHPIRVENDTESGNRLKKSENPDVYTEVPHMNCL
MSVSNDALPVKDDDIANGHILCSTHKDDNVVEVDQAPSGISLSVITEVDGDETIKTPLDSPCQQRADALESLLEL
CAQLLKQDKLEELAGVLRPFGKEAVSSRETAIWLAKSLISSQKFNPET*

>Glyma.19G166100

SEQ ID NO: 87

MSVMMDHVIGGKFKLGRKIGSGSFGELYIAVNIQTGEEVAVKLEPVKTKHPQLLYESKLYMLLQGGTGIPHLKWF
GVEGDYNVMAIDLLGPSLEDLFNYCNRKLTLKTVLMLADQLINRVEYMHSRGFLHRDIKPDNFLMGLGRKANQVY
IIDYGLAKKYRDLQTHRHIPYRENKNLTGTARYASVNTHLGIEQSRRDDLESLGYVLMYFLRGSLPWQGLKAGTK
KQKYDKISEKKMSTSIEVLCKSYPSEFVSYFNYCRTLRFEDKPDYSYLKRLFRDLFIREGYQFDYVFDWTILKYP
QIGGSSSRGRHESGKAAMHAGPSVQKPEKVSVGKEIREKFSGAVEAFSRRNPTSPSPRGDHSKHRSFEEVAVHKD
VYRDQEKGRNSSRYGSSSRRPIISSSTRPSSSGDHTDSRTGRLTSSGNRSSASHRNIQPMYETKQPTYMRSGSTR
GNRDDPLRSFELLSIRK*

>Glyma.19G261700

SEQ ID NO: 88

MVEFQRLLVCITTCILCWMPNGATAATDPNDAAAVRFLFQNMNSPPQLGWPPNGDDPCGQSWKGITCSGNRVTEI
KLSNLGLTGSLPYGLQVLTSLTYVDMSSNSLGGSIPYQLPPYLQHLNLAYNNITGTVPYSISNLTALTDLNFSHN
QLQQGLGVDFLNLSTLSTLDLSFNFLTGDLPQTMSSLSRITTMYLQNNQFTGTIDVLANLPLDNLNVENNNFTGW
IPEQLKNINLQTGGNAWSSGPAPPPPPGTPPAPKSNQHHKSGGGSTTPSDTATGSSSIDEGKKSGTGGGAIAGIV
ISVIVVGAIVAFFLVKRKSKKSSSDLEKQDNQSFAPLPSNEVHEEKSMQTSSVTDLKTFDTSASINLKPPPIDRH
KSFDDEEFSKRPTIVKKTVTAPANVKSYSIAELQIATGSFSVDHLVGEGSFGRVYRAQFDDGQVLAVKKIDSSIL
PNDLTDDFIQIISNISNLHHPNVTELVGYCSEYGQHLLVYEFHKNGSLHDFLHLSDEYSKPLIWNSRVKIALGTA
RALEYLHEVSSPSVVHKNIKSANILLDTELNPHLSDSGLASYIPNADQILNHNVGSGYDAPEVALSGQYTLKSDV
YSFGVVMLELLSGRNPFDSSRPRSEQSLVRWATPQLHDIDALAKMVDPAMKGLYPVKSLSRFADVIALCVQPEPE
FRPPMSEVVQALVRLVQRANMSKRTFSSSDHGGSQRGSDEPVLRDI*

>Glyma.20G120200

SEQ ID NO: 89

MNLFFFLKPLSSLMILSYIILFFLLVRNTSCDVDPNYVACPPKTCANNNQSISYPFYIEETQEPFCGNPGFAISC
GPNGFPILNLSNTHYIIHQIFYENQTLRVSNAAFSVSRSNTTNSKGCLPVPLTHNLTLPSTPEFDIAPNQSNMRL
FYGCESLLPWPEEHRVGCPNETSSVLAFYKEDKNISLVSKNCRGEVVDTIVEDGIIEGGVEEALRKGLLLTWKAG
NCSECHSSGGRCGFDSIMYTFRCFCTDRVHSAKCDPDNGPVIKKGSSLKLVIGIGIPSMLAIGLLFLFLLYKRKY
ATSGGQLESRDSYSDSSSNPHRETSSEYFGVPLFLYEQLKEATNNFDHTKELGDGGFGTVYHGKLPDGREVAVKR
LYEHNWKRVEQFMNEVKILTRLRHKYLVSLYGCTSRHSRELLLVYEYISNGTVACHLHGELAKPGSLPWSIRMKI
AIETAIALTYLHASDIIHRDVKTNNILLDNNFCVKVADFGLSRDFPNNVTHVSTAPQGSPGYLDPEYYNCYQLTS
KSDVYSFGVVLIELISSKPAVDMNRSRDEINLSNLAVRKIQESAISELVDPSLGFDSNGIKGMIVSVAGLAFQC
LQREKDLRPSMDEVLDELRRIESGKDEGEVQDEGDVNGAAVSHSSAHSPPPASPEWEEVRLLRNIKPTSPNTVTD
KWESKCTTPNISG*

-continued

>Glyma.20G137700

SEQ ID NO: 90

MADLSCIHLFFLCCLFLKFIPQGNASMFHTAFCDNKEGNYTANSTYNTNLNTLLSSLSSHTEINYGFYNFSYGQN
PDKVNAIGLCRGDVEPHECRSCLNDSRVTIKQFCPNQKKALLWLNTSKCMLRYSPRSIFGIMEIEPSQSLMNIIN
VTEPDKFSQALANLMRNLKGVAASGDSRRKYATDNVTASSFQTIYGMAECTPDLSEKDCNDCLDGAISKIPTCCQ
DKIGGRVLRPSCNIRFESASFYENTPILNPDVPPPSPAVAIPPSINSTSPKESSNTIRIVIAIVVPTVVVVPLIC
LCIYSRRSKARKSSLVKQHEDDDEIEIAQSLQFNFDTIRVATEDFSDSNKLQGGGFGAVYRGRLSDGQMIAVKRL
SRESSQGDTEFKNEVLLVAKLQHRNLVRLLGFCLEGKERLLIYEYVPNKSLDYFIFDPTKKAQLNWEMRYKIITG
VARGLLYLHEDSHLRIIHRDLKASNILLNEEMNPKIADFGMARLVLMDQTQANTNRIVGTYGYMAPEYAMHGQFS
MKSDVFSFGVLVLEIISGHKNSGIRHGENVEDLLSFAWRNWREGTAVKIVDPSLNNNSRNEMLRCIHIGLLCVQE
NLADRPTMTTIMLMLNSYSLSLPIPSKPAFYVSSRTGSISATQSWGYSSGESRSRELTIKSAQEAENEFTDPYPR*

>Glyma.18G269900

SEQ ID NO: 91

MDTTSTQIASGTILFLLLLFFPYLSIADVIYSPVELFSINCGSSSNLSTRDGRNWTADIKFLSENKDSVAAPALT
PSTLEGPYTDARLSHSQFTYSFPVSTGPKFLRLFFYSTSYQNFHRSKAYFSVKAGPYTLLQNFNASLHADAGNEP
GDYLFREYCINLKDGDRLNITFIASKTSQNPDSYAFINGIEIVSMPPFLYYTNPHDVDITGLPHLVGVNTNLFPI
ENNFTLETKYRLRVGDQEIPASQDTGMLRSWDVDSKYVTTQSVLSLDIGPGIKLRFTKIPNYTAPDTVYRSVRNM
GNNGTINMGFNLTWQLPIDSGFTYLLRLHFCQLNPEMKNPGYQSFFIFVQDQLVEKWADILSWSDKQEGVPVVKQ
YVVFIPGNQQETLNLSLKMHPNPQSLAKDAQINAIELFKINNSTGSLAGPNPDPDRLPETPKVPLQRPNNKSSGT
TRTLAAAVAGAVSAAVLLSFIVAFFLIKRKKMGSKEKDETPLGGGLSSLPTNLCRHFSIAEIRASTNNFDEHFV
VGMGGFGNVYKGYIDDGSTRVAIKRLKPDSRQGAQEFMNEIEMLSQLRHLHLVSLVGYCYESNEMILVYDFMDRG
TLREHLYDTDNPSLSWKQRLQICVGAARGLHYLHTGAKHTIIHRDVKSTNILLDEKWVAKVSDFGLSRIGPISSS
MTHVSTQVKGSVGYIDPEYYKRQRLTEKSDVYSFGVVLLEVLSGRQPLLRWEEKQRISLVNWAKHCNEKGTLSEI
VDAKLKGQIAPQCLQRYGEVALSCLLEDGTQRPSMNDAVRMLEFVLHLQEGAVNEVTESEDTEDVFSSSHSSLLF
SDYSKSTALSMATNVGDCSYGSKDSEERSIPDHLFSEIKDPKGR*

Sequences found in Table 2
>Glyma.03G189800 (wild type)

SEQ ID NO: 15

MKKVCHCPIFLALALCLCILCVAAEAAGQNDTLALTEFRLQTDTHGNLLTNWTGADACSAAWRGVECS
PNGRVVGLTLPSLNLRGPIDTLSTLTYLRFLDLHENRLNGTISPLLNCTSLELLYLSRNDFSGEIPAE
ISSLRLLLRLDISDNNIRGPIPTQLAKLTHLLTLRLQNNALSGHVPDLSASLLNLTVLNVTNNELRGH
VPDSMLTKFGNVSFSGNHALCGSTPLPKCSETEPDTETTTITVPAKPSSFPQTSSVTVPDTPRKKGLS
AGVIVAIVVAVCVAVLVATSFAVAHCCARGSTSGSVVGSETAKRKSGSSSGSEKKVYGNGGNLDRDSD
GTNTETERSKLVFFDRRNQFELEDLLRASAEMLGKGSLGTVYRAVLDDGCTVAVKRLKDANPCERNEF
EQYMDVVGKLKHPNIVRLRAYYYAKEEKLLVYDYLPNGSLHALLHGNRGPGRIPLDWTTRISLMLGAA
RGLARIHAEYNASKIPHGNVKSSNVLLDKNGVALISDFGLSLLLNPVHAIARLGGYRAPEQVEVKRLS
QEADVYGEGVLLLEVLIGRAPSKEYTSPAREAEVDLPKWVKSVVKEEWTSEVEDQELLRYKNIEDELV
AMLHVGLACVAAQAEKRPCMLEVVKMIEEIRVEESPLGDDYDEARSRTSLSPSLATTEDNLA

>Glyma.04G222800 (wild type)

SEQ ID NO: 17

MQALFSSMRVFLRLVWLLELLCVAVTAVNPSLNDDVLGLIVFKADIRDPKGKLASWNEDDESACGGSW
VGVKCNPRSNRVVEVNLDGFSLSGRIGRGLQRLQFLRKLSLANNNLTGGINPNIARIDNLRVIDLSGN
SLSGEVSEDVFRQCGSLRTVSLARNRFSGSIPSTLGACSALAAIDLSNNQFSGSVPSRVWSLSALRSL
DLSDNLLEGEIPKGIEAMKNLRSVSVARNRLTGNVPYGFGSCLLLRSIDLGDNSFSGSIPGDFKELTL
CGYISLRGNAFSGGVPQWIGEMRGLETLDLSNNGFTGQVPSSIGNLQSLKMLNFSGNGLTGSLPESMA
NCTKLLVLDVSRNSMSGWLPLWVFKSDLDKVLVSENVQSGSKKSPLFAMAELAVQSLQVLDLSHNAFS
GEITSAVGGLSSLQVLNLANNSLGGPIPPAVGELKTCSSLDLSYNKLNGSIPWEIGGAVSLKELVLEK
NFLNGKIPTSIENCSLLTTLILSQNKLSGPIPAAVAKLTNLQTVDVSFNNLIGALPKQLANLANLLTF
NLSHNNLQGELPAGGFFNTITPSSVSGNPSLCGAAVNKSCPAVLPKPIVLNPNTSTDTGPSLPPNLG
HKRIILSISALIAIGAAAVIVIGVISITVLNLRVRSSTSRDAAALTFSAGDEFSHSPTTDANSGKLVM
FSGEPDFSSGAHALLNKDCELGRGGFGAVYQTVLRDGHSVAIKKLTVSSLVKSQEDFEREVKKLGKIR
HQNLVELEGYYWTPSLQLLIYEYLSGGSLYKHLHEGSGGNFLSWNERFNVILGTAKALAHLHHSNIIH
YNIKSTNVLLDSYGEPKVGDFGLARLLPMLDRYVLSSKIQSALGYMAPEFACKTVKITEKCDVYGFGV
LVLEIVTGKRPVEYMEDDVVVLCDMVRGALEEGRVEECIDERLQGKFPAEEAIPVMKLGLICTSQVPS
NRPDMGEVVNILELIRCPSEGQEELA

>Glyma.12G056000 (wild type)

SEQ ID NO: 49

MDSARTAPPPWQELDLDSLKPLKVLGKGGMGTVFLVQAANNTRFALKVVDKTCVHAKLDAERRARWEI
QVLSTLSHPFLPSLMGTFESPQFLAWALPYCPGGDLNVLRYRQTDRAFSPAVIRFYVAEILCALDHLH
SMGIAYRDLKPENVLVQNTGHITLTDFDLSRKLNPKPKPNPQVPSIPLPNSNVPEPRRKHRRNFSRWI
SLFPPDGTHHNNNKNGLKKAKSARVSPVSRRKPSFSNGERSNSFVGTEEYVSPEVVRGDGHEFAVDWW
ALGILIYEMLYGTTPFKGKNRKETFRNVITKPPVFVGKRTALTDLIEKLLEKDPTKRLGYTRGAVEIK
EHEFFRGVRWELLTEVVRPPFIPTRDDGAGDSTDRISDRNCGFDIRGYFLNLKSSPSLPGSPLPSPSC
RFKKNVSLTEF

>Glyma.13G150000 (wild type)

SEQ ID NO: 60

MMKHYHVLYMFLFFLPISTLSLHHNDTHALTLFRRQSDLHGYLLSNWTGHDACNSAWRGVLCSPNGRV
TALSLPSLNLRGPLDPLTPLTHLRLLNLHDNRLNGTVSTLFSNCTNLQLLYLSSNDFSGEIPPEISSL
KSLLRLDLSDNNLRGKVDVISNLTQLITLRLQNNLLSGEIPDLSSSMKNLKELNMTNNEFYGRLPSPM
LKKFSSTTFSGNEGLCGASLFPGCSFTTTPPNNNDSNNNNDNNSNEKEPSQTVSSNPSSFPETSIIAR
PGREQQRKGLSPGAIVAIVIANCVALLVVVSFAVAHCCARGRGSSLVGSGESYGKRKSESSYNGSDEK
KVYGGGESDGTSGTDRSRLVFFDRRSEFELEDLLRASAEMLGKGSLGTVYRAVLDDGCTVAVKRLKDA
NPCARHEFEQYMDVIGKLKHPNVVRLKAYYYAKEEKLLVYDYLSNGSLHALLHGNRGPGRIPLDWTTR

-continued

ISLVLGAARGLAKIHAEYSAAKVPHGNVKSSNVLLDKNGVACISDFGLSLLLNPVHAIARLGGYRAPE
QEQNKRLSQQADVYSFGVLLLEVLIGRAPSSQYPSPARPRMEVEPEQAAVDLPKWVRSVVREEWTAEV
FDQELLRYKNIEEELVSMLHVGLTCVVAQPEKRPTMEEVVKMIEEIRVEQSPLGEDYDVSCNSLSPSI
PTTEDGLA

>Glyma.14G026300 (wild type)
SEQ ID NO: 66

METSLDYSKMLFLLLLGSTSLIFLSHLASAATPKLNTQEVKALKEIGSKIGKKDWNFGVDPCSGKGNW
NVPDARKAFVMSSVICDCSFNHNSSCHVVSIYWKAQNLSGSLSPEFSKLHYLQKLDLSRNIITGSIPP
QWGTMRLVELSLMGNKLSGPFPKVLTNITTLRNLSIEGNQFSGHIPTEIGKLTNLEKLVLSSNGFTGA
LPPVLSKLTKLIDLRISDNNFLGKIPDFISNWTLIEKLHMHGCSLEGPIPSSISALTRLSDLRITDLK
GSKSSAFPPLNNLKSMKTLVLRKCMIKGEIPEYIGRMEKLKILDLSYNGLSGEIPESFAQLDKVDFMY
LTGNKLSGIIPRWVLANNENIDISDNNFSWDSSSPTECQRGSVNLVESYSSSVNTQTKINSCLKKNFL
CTASPSQYRYSLNINCGGNEANVSGNIYEADREQKGAAMLYYTSQDWALSSTGNFMDNDIDSDPYIVA
NTSRLNVSALNSKLYTTARVSPLALTYYGLCLINGNYTVKLHFAEIIFINDRSLNSLGRRVFDVYIQG
NLVLKDFDIRREAGGTGKSIEKTFNASVTQHTLKIHFYWAGKGTTGIPTRGVYGPLVSAISVNPNFKP
PSGEGKRTYLILAIIIVAGVLVVVLLVLLRRMGWLGGKDPVYKELRGIDLQTGLFTLRQIKAATKN
FDALNKIGEGGFGCVYKGQQSDGTMIAVKQLSSKSKQGNREFVNEMGLISGLQHPNLVKLYGCCVEGN
QLILIYEYMENNCLSRILFGRDPNKTKLDWPTRKKICLGIAKALAYLHEESRIKIIHRDVKASNVLLD
KDFNAKVSDFGLAKLIEDEKTHISTRVAGTIGYMAPEYAMRGYLTDKADVYSFGVVALETVSGKSNTN
FRPNEDFVYLLDWAYVLQERGSLLELVDPNLGSEYLTEEAMVVLNVALLCTNASPTLRPTMSQVVSML
EGWTDIQDLLSDPGYSAISSSSKHKSIRSHFWQTPSGTHSISIPSIYTDSSGSHVETEKNYHPVTVNS
DGSDKSN

>Glyma.16G079200 (wild type)
SEQ ID NO: 75

MVLHSWISSSHILVNFLLLLGCGITYGTDTDIFCLKSIKESLEDPYNYLKFSWDFNNKTEGYICRFNG
VECWHPDENRVLNLKLSNMGLKGQFPRGIQNCSSLTGLDLSINKLSGTIPGDISTLIPFATSIDLSTN
EFSGAIPVSLANCTFLNTLKLDQNRLTGQIPPQFGVLSRIKVFSVSNNLLTGQVPIFRDGVELHYANN
QGLCGGNTLAPCQATPSKSNMAVIAGAAAGGVTLAALGLGIGMFFFVRRVSFKKKEEDPEGNKWARSL
KGTKRIKVSMFEKSISKMKLSDLMKATNNFSNTNIIGTRGTRVYKAVLDDGTTLMVKRLQEGSQYTEK
EFMSEMGTLGTVKHRNLVPLLGFCMTKRERLLVYKNMPNGNLHDQLHPADGVSTLDWTTRLKIAIGAA
KGLAWLHHSCNPRIIHRNISSKCILLDADFEPKISDFGLARLMNPIDTHLSTFVNGEFGDLGYVAPEY
TRTLVATPKGDIYSFGTVLLELVTGERPTNVSKAPETFKGNLVEWITELTSNAKLHDAIDESLVRKDV
DSELFQFLKVACNCVSPTPKERPTMFEVYQLLRAIGGRYNFTTEDDILVPTDIGNTDNMQELIVAQEG
SY

>Glyma.18G141500 (wild type)
SEQ ID NO: 83

MEKTIHLVYFKCLVFLLMKQVIVMAEPRARTVNITCNNKLEHNTTIFVPNEVATMEKISEQMRNTGYG
TAVVGTGGPDTNYGLAQCYGDLDSLLDCVLCYAEARTVLPQCFPYNGGRIYLDGCFMRAENYSFYDEYI
GPGDKAVCGNTTRKSTSFQAAAKKAVLSAVQAAANNKGYARKEVEVAGTTNDAAYVLANCWRSLDTRS
CRACLENASSSILGCLPWSEGRALNTGCFMRYSDTDFLNKEQENGSSGGNVLVIVVAVVSSVIVLVVG
IAIVVYIRKHRYIQMKRRGSNDAEKLAKSLHHNSLNFKYSTLEKATNSFDEANKLGQGGFGTVYKGVL
ADGREIAIKRLYFNNRHRAADFFNEVNIISSVEHKNLVRLLGCSCSGPESLLIYEYLPNRSLDRFIFD
KNKGRELNWDKRYDIIIGTAEGLVYLHENSNIRIIHRDIKASNILLDAKLRAKIADEGLARSFQEDKS
HISTAIAGTLGYMAPEYLAHGQLTEKADVYSFGVLLLEIITGRLNNRSKASEYSDSLVTMTWKHFQSG
TAEQLIDPCLVVDDNHRSNFKNEILRVLHIGLLCTQEIPSLRPSMSKALKMLTKKEEHLDLEAPSNPP
FIDESTMELHDQNDDPFYPLNAEDSLATMSHSSFYAR

>Glyma.18G269900 (wild type)
SEQ ID NO: 91

MDTTSTQIASGTILFLLLLFFPYLSIADVIYSPVELFSINCGSSSNLSTRDGRNWTADIKFLSENKDS
VAAPALTPSTLEGPYTDARLSHSQFTYSFPVSTGPKFLRLFFYSTSYQNFHRSKAYFSVKAGPYTLLQ
NFNASLHADAGNEPGDYLFREYCINLKDGDRLNITFIASKTSQNPDSYAFINGIEIVSMPPFLYYTNP
HDVDITGLPHLVGVNTNLFPIENNFTLETKYRLRVGDQEIPASQDTGMLRSWDVDSKYVTTQSVLSLD
IGPGIKLRFTKIPNYTAPDTVYRSVRNMGNNGTINMGFNLTWQLPIDSGFTYLLRLHFCQLNPEMKNP
GYQSFFIFVQDQLVEKWADILSWSDKQEGVPVVKQYVVFIPGNQQETLNLSLKMHPNPQSLAKDAQIN
AIELFKINNSTGSLAGPNPDPDRLPETPKVPLQRPNNKSSGTTRTLAAAVAGAVSAAVLLSFIVAFFL
IKRKKKMGSKEKDETPLGGGLSSLPTNLCRHFSIAEIRASTNNFDEHFVVGMGGFGNVYKGYIDDGST
RVAIKRLKPDSRQGAQEFMNEIEMLSQLRHLHLVSLVGYCYESNEMILVYDFMDRGTLREHLYDTDNP
SLSWKQRLQICVGAARGLHYLHTGAKHTIIHRDVKSTNILLDEKWVAKVSDFGLSRIGPISSSMTHVS
TQVKGSVGYIDPEYYKRQRLTEKSDVYSFGVVLLEVLSGRQPLLRWEEKQRISLVNWAKHCNEKGTLS
EIVDAKLKGQIAPQCLQRYGEVALSCLLEDGTQRPSMNDAVRMLEFVLHLQEGAVNEVTESEDTEDVF
SSSHSSLLFSDYSKSTALSMATNVGDCSYGSKDSEERSIPDHLFSEIKDPKGR

>Glyma.03G189800 (kinase-dead)
SEQ ID NO: 92

MKKVCHCPIFLALALCLCILCVAAEAAGQNDTLALTEFRLQTDTHGNLLTNWTGADACSAAWRGVECS
PNGRVVGLTLPSLNLRGPIDTLSTLTYLRFLDLHENRLNGTISPLLNCTSLELLYLSRNDFSGEIPAE
ISSLRLLLRLDISDNNIRGPIPTQLAKLTHLLTLRLQNNALSGHVPDLSASLLNLTVLNVTNNELRGH
VPDSMLTKFGNVSFSGNHALCGSTPLPKCSETEPDTETTTITVPAKPSSFPQTSSVTVPDTPRKKGLS
AGVIVAIVVAVCAVLVATSFAVAHCCARGSTSGSVVGSETAKRKSGSSSGSEKKVYGNGGNLDRDSD
GTNTETERSKLVFFDRRNQFELEDLLRASAEMLGKGSLGTVYRAVLDDGCTVAVRRLKDANPCERNEF
EQYMDVVGKLKHPNIVRLRAYYYAKEEKLLVYDYLPNGSLHALLHGNRGPGRIPLDWTTRISLMLGAA
RGLARIHAEYNASKIPHGNVRSSNVLLDKNGVALISDFGLSLLLNPVHAIRLGGYRAPEQVEVKRLS
QEADVYGFGVLLLEVLTGRAPSKEYTSPAREAEVDLPKWVKSVVKEEWTSEVFDQELLRYKNIEDELV
AMLHVGLACVAAQAEKRPCMLEVVKMIEEIRVEESPLGDDYDEARSRTLSPSLATTEDNLA

-continued

>Glyma.04G222800 (kinase-dead)
SEQ ID NO: 93

MQALFSSMRVFLRLVWLLELLCVAVTAVNPSLNDDVLGLIVFKADIRDPKGKLASWNEDDESACGGSW
VGVKCNPRSNRVVEVNLDGFSLSGRIGRGLQRLQFLRKLSLANNNLTDGINPNIARIDNLRVIDLSGN
SLSGEVSEDVFRQCGSLRTVSLARNRFSGSIPSTLGACSALAAIDLSNNQFSGSVPSRVWSLSALRSL
DLSDNLLEGEIPKGIEAMKNLRSVSVARNRLTGNVPYGFGSCLLLRSIDLGDNSFSGSIPGDFKELTL
CGYISLRGNAFSGGVPQWIGEMRGLETLDLSNNGFTGQVPSSIGNLQSLKMLNFSGNGLTGSLPESMA
NCTKLLVLDVSRNSMSGWLPLWVFKSDLDKVLVSENVQSGSKKSPLFAMAELAVQSLQVLDLSHNAFS
GEITSAVGGLSSLQVLNLANNSLGGPIPPAVGELKTCSSLDLSYNKLNGSIPWEIGGAVSLKELVLEK
NFLNGKIPTSIENCSLLTTLILSQNKLSGPIPAAVAKLTNLQTVDVSFNNLTGALPKQLANLANLLTF
NLSHNNLQGELPAGGFFNTITPSSVSGNPSLCGAAVNKSCPAVLPKPIVLNPNTSTDTGPSSLPPNLG
HKRIILSISALIAIGAAAVIVIGVISITVLNLRVRSSTSRDAAALTFSAGDEFSHSPTTDANSGKLVM
FSGEPDFSSGAHALLNKDCELGRGGFGAVYQTVLRDGHSVAIKRLTVSSLVKSQEDFEREVKKLGKIR
HQNLVELEGYYWTPSLQLLIYEYLSGGSLYKHLHEGSGGNFLSWNERFNVILGTAKALAHLHHSNIIH
YNIRSTNVLLDSYGEPKVGDFGLARLLPMLDRYVLSSKIQSALGYMAPEFACKTVKITEKCDVYGFGV
LVLEIVTGKRPVEYMEDDVVVLCDMVRGALEEGRVEECIDERLQGKFPAEEAIPVMKLGLICTSQVPS
NRPDMGEVVNILELIRCPSEGQEELA

>Glyma.12G056000 (kinase-dead)
SEQ ID NO: 94

MDSARTAPPPWQELDLDSLKPLKVLGKGGMGTVFLVQAANNTRFALRVVDKTCVHAKLDAERRARWEI
QVLSTLSHPFLPSLMGTFESPQFLAWALPYCPGGDLNVLRYRQTDRAFSPAVIRFYVAEILCALDHLH
SMGIAYRDLRPENVLVQNTGHITLTDFDLSRKLNPKPKPNPQVPSIPLPNSNVPEPRRKHRRNFSRWI
SLFPPDGTHHNNNKNGLKKAKSARVSPVSRRKPSFSNGERSNSFVGTEEYVSPEVVRGDGHEFAVDWW
ALGILIYEMLYGTTPPFKGKNRKETFRNVITKPPVFVGKRTALTDLIEKLLEKDPTKRLGYTRGAVEIK
EHEFFRGVRWELLTEVVRPPFIPTRDDGAGDSTDRISDRNCGFDIRGYFLNLKSSPSLPGSPLPSPSC
RFKKNVSLTEF

>Glyma.13G150000 (kinase-dead)
SEQ ID NO: 95

MMKHYHVLYMFLFFLPISTLSLHHNDTHALTLFRRQSDLHGYLLSNWTGHDACNSAWRGVLCSPNGRV
TALSLPSLNLRGPLDPLTPLTHLRLLNLHDNRLNGTVSTLFSNCTNLQLLYLSSNDFSGEIPPEISSL
KSLLRLDLSDNNLRGKVDVISNLTQLITLRLQNNLLSGEIDLSSSMKNLKELNMTNNEFYGRLPSPM
LKKFSSTTFSGNEGLCGASLFPGCSFTTTPPNNNDSNNNNDNNSNEKEPSQTVSSNPSSFPETSIIAR
PGREQQRKGLSPGAIVAIVIANCVALLVVSFAVAHCCARGRGSSLVGSGESYGKRKSESSYNGSDEK
KVYGGGESDGTSGTDRSRLVFFDRRSEFELEDLLRASAEMLGKGSLGTVYRAVLDDGCTVAVRRLKDA
NPCARHEFEQYMDVIGKLKHPNVVRLKAYYYAKEEKLLVYDYLSNGSLHALLHGNRGPGRIPLDWTTR
ISLVLGAARGLAKIHAEYSAAKVPHGNVRSSNVLLDKNGVACIGDFGLSLLLNPVHAIARLGGYRAPE
QEQNKRLSQQADVYSFGVLLLEVLTGRAPSSQYPSPARPRMEVEPEQAAVDLPKWVRSVVREEWTAEV
FDQELLRYKNIEEELVSMLHVGLTCVVAQPEKRPTMEEVVKMIEEIRVEQSPLGEDYDVSCNSLSPSI
PTTEDGLA

>Glyma.14G026300 (kinase-dead)
SEQ ID NO: 96

METSLDYSKMLFLLLLGSTSLIFLSHLASAATPKLNTQEVKALKEIGSKIGKKDWNFGVDPCSGKGNW
NVPDARKAFVMSSVICDCSFNHNSCHVVSIYWKAQNLSGSLSPEFSKLHYLQKLDLSRNIITGSIPP
QWGTMRLVELSLMGNKLSGPFPKVLTNITTLRNLSIEGNQFSGHIPTEIGKLTNLEKLVLSSNGFTGA
LPPVLSKLTKLIDLRISDNNFLGKIPDFISNWTLIEKLHMHGCSLEGPIPSSISALTRLSDLRITDLK
GSKSSAFPPLNNLKSMKTLVLRKCMIKGEIPEYIGRMEKLKILDLSYNGLSGEIPESFAQLDKVDFMY
LTGNKLSGIIPRWVLANNENIDISDNNFSWDSSSPTECQRGSVNLVESYSSSVNTQTKINSCLKKNFL
CTASPSQYRYSLNINCGGNEANVSGNIYEADREQKGAAMLYYTSQDWALSSTGNFMDNDIDSDPYIVA
NTSRLNVSALNSKLYTTARVSPLALTYYGLCLINGNYTVKLHFAETIFINDRSLNSLGRRVFDVYIQG
NLVLKDFDIRREAGGTGKSIEKTFNASVTQHTLKIHFYWAGKGTTGIPTRGVYGPLVSAISVNPNFKP
PSGEGKRTYLILAIIIVAGVLVVVLLVLVLLLRRMGWLGGKDPVYKELRGIDLQTGLFTLRQIKAATKN
FDALNKIGEGGFGCVYKGQQSDGTMIAVRQLSSKSKQGNREFVNEMGLISGLQHPNLVKLYGCCVEGN
QLILIYEYMENNCLSRILFGRDPNKTKLDWPTRKKICLGIAKALAYLHEESRIKIIHRDVRASNVLLD
KDFNAKVSDFGLAKLIEDEKTHISTRVAGTIGYMAPEYAMRGYLTDKADVYSFGVVALETVSGKSNTN
FRPNEDFVYLLDWAYVLQERGSLLELVDPNLGSEYLTEEAMVVLNVALLCTNASPTLRPTMSQVVSML
EGWTDIQDLLSDPGYSAISSSSKHKSIRSHFWQTPSGTHSISIPSIYTDSSGSHVETEKNYHPVTVNS
DGSDKSN

>Glyma.16G079200 (kinase-dead)
SEQ ID NO: 97

MVLHSWISSSHILVNFLLLLGCGITYGTDTDIFCLKSIKESLEDPYNYLKFSWDFNNKTEGYICRFNG
VECWHPDENRVLNLKLSNMGLKGQFPRGIQNCSSLTGLDLSINKLSGTIPGDISTLIPFATSIDLSTN
EFSGAIPVSLANCTFLNTLKLDQNRLTGQIPPQFGVLSRIKVFSVSNNLLTGQVPIFRDGVELHYANN
QGLCGGNTLAPCQATPSKSNMAVIAGAAAGGVTLAALGLGIGMFFFVRRVSFKKKEEDPEGNKWARSL
KGTKRIKVSMFEKSISKMKLSDLMKATNNFSNTNIIGTGRTGTVVYKAVLDDGTTLMVRRLQESQYTEK
EFMSEMGTLGTVKHRNLVPLLGFCMTKRERLLVYKNMPNGNLHDQLHPADGVSTLDWTTRLKIAIGAA
KGLAWLHHSCNPRIIHRNISSRCILLDADFEPKISDFGLARLMNPIDTHLSTFVNGEFGDLGYVAPEY
TRTLVATPKGDIYSFGTVLLELVTGERPTNVSKAPETFKGNLVEWITELTSNAKLHDAIDESLVRKDV
DSELFQFLKVACNCVSPTPKERPTMFEVYQLLRAIGGRYNFTTEDDILVPTDIGNTDNMQELIVAQEG
SY

>Glyma.18G141500 (kinase-dead)
SEQ ID NO: 98

MEKTIHLVYFKCLVFLLMKQVIVMAEPRARTVNITCNNKLEHNTTIFVFNFVATMEKISEQMRNTGYG
TAVVGTGGPDTNYGLAQCYGDLSLLDCVLCYAEARTVLPQCFPYNGGRIYLDGCFMRAENYSFYDEYI
GPGDKAVCGNTTRKSTSFQAAAKKAVLSAVQAAANNKGYARKEVFVAGTTNDAAYVLANCWRSLDTRS
CRACLENASSSILGCLPWSEGRALNTGCFMRYSDTDFLNKEQENGSSGGNVLVIVVAVVSSVIVLVVG

```
                                              -continued
IAIVVYIRKHRYIQMKRRGSNDAEKLAKSLHHNSLNFKYSTLEKATNSFDEANKLGQGGFGTVYKGVL
ADGREIAIRRLYFNNRHRAADFFNEVNIISSVEHKNLVRLLGCSCSGPESLLIYEYLPNRSLDRFIFD
KNKGRELNWDKRYDIIIGTAEGLVYLHENSNIRIIHRDIRASNILLDAKLRAKIADFGLARSFQEDKS
HISTAIAGTLGYMAPEYLAHGQLTEKADVYSFGVLLLEIITGRLNNRSKASEYSDSLVTMTWKHFQSG
TAEQLIDPCLVVDDNHRSNFKNEILRVLHIGLLCTQEIPSLRPSMSKALKMLTKKEEHLDLEAPSNPP
FIDESTMELHDQNDDPFYPLNAEDSLATMSHSSFYAR >Glyma.18G269900 (kinase-dead)
                                                          SEQ ID NO: 99
MDTTSTQIASGTILFLLLLFFPYLSIADVIYSPVELFSINCGSSSNLSTRDGRNWTADIKFLSENKDS
VAAPALTPSTLEGPYTDARLSHSQFTYSFPVSTGPKFLRLFFYSTSYQNFHRSKAYFSVKAGPYTLLQ
NFNASLHADAGNEPGDYLFREYCINLKDGDRLNITFIASKTSQNPDSYAFINGIEIVSMPPFLYYTNP
HDVDITGLPHLVGVNTNLFPIENNFTLETKYRLRVGDQEIPASQDTGMLRSWDVDSKYVTTQSVLSLD
IGPGIKLRFTKIPNYTAPDTVYRSVRNMGNNGTINMGFNLTWQLPIDSGFTYLLRLHFCQLNPEMKNP
GYQSFFIFVQDQLVEKWADILSWSDKQEGVPVVKQYVVFIPGNQQETLNLSLKMHPNPQSLAKDAQIN
AIELFKINNSTGSLAGPNPDPDRLPETPKVPLQRPNNKSSGTTRTLAAAVAGAVSAAVLLSFIVAFFL
IKRKKKMGSKEKDETPLGGGLSSLPTNLCRHFSIAEIRASTNNFDEHFVVGMGGFGNVYKGYIDDGST
RVAIRRLKPDSRQGAQEFMNEIEMLSQLRHLHLVSLVGYCYESNEMILVYDFMDRGTLREHLYDTDNP
SLSWKQRLQICVGAARGLHYLHTGAKHTIIHRDVRSTNILLDEKWVAKVSDFGLSRIGPISSSMTHVS
TQVKGSVGYIDPEYYKRQRLTEKSDVYSFGVVLLEVLSGRQPLLRWEEKQRISLVNWAKHCNEKGTLS
EIVDAKLKGQIAPQCLQRYGEVALSCLLEDGTQRPSMNDAVRMLEFVLHLQEGAVNEVTESEDTEDVF
SSSHSSLLFSDYSKSTALSMATNVGDCSYGSKDSEERSIPDHLFSEIKDPKGR
```

REFERENCES

1. Block A, Li G, Fu Z Q, Alfano J R (2008) Phytopathogen type III effector weaponry and their plant targets. Current Opin Plant Biology 11: 396-403.
2. Champion A, Kreis M, Mockaitis K, Picaud A, Henry Y (2004) *Arabidopsis* kinome: after the casting. Funct Integr Genomic 4: 163-187.
3. Colcombet J, Hirt H (2008) *Arabidopsis* MAPKs: a complex signalling network involved in multiple biological processes. Biochem J 413: 217-226.
4. de la Fuente A (2010) From 'differential expression' to 'differential networking'-identification of dysfunctional regulatory networks in diseases. Trends Genet 26: 326-333.
5. Dou D, Zhou J M (2012) Phytopathogen effectors subverting host immunity: different foes, similar battleground. Cell Host Microbe 12: 484-495.
6. Gao L L, Xue H W (2012) Global analysis of expression profiles of rice receptor-like kinase genes. Mol Plant 5: 143-153.
7. Gish L A, Clark S E (2011) The RLK/Pelle family of kinases. Plant J 66: 117-127.
8. Hanada K, Zou C, Lehti-Shiu M D, Shinozaki K, Shiu S-H (2008) Importance of lineage-specific expansion of plant tandem duplicates in the adaptive response to environmental stimuli. Plant Physiol 148: 993-1003.
9. Hanks S K, Hunter T (1995) Protein kinases 6. The eukaryotic protein kinase superfamily: kinase (catalytic) domain structure and classification. FASEB J 9: 576-596.
10. Hewezi T (2015) Cellular signaling pathways and post-translational modifications mediated by nematode effector proteins. Plant Physiol 169: 1018-1026.
11. Hewezi T, Baum T J (2013) Manipulation of plant cells by cyst and root-knot nematode effectors. Mol Plant Microbe In 26: 9-16.
12. Hewezi T, Juvale P S, Piya S, Maier T R, Rambani A, Rice J H, Mitchum M G, Davis E L, Hussey R S, Baum T J (2015) The cyst nematode effector protein 10A07 targets and recruits host posttranslational machinery to mediate its nuclear trafficking and to promote parasitism in *Arabidopsis*. Plant Cell 27: 891-907.
13. Hogenhout S A, Van der Hoorn R A, Terauchi R, Kamoun S (2009) Emerging concepts in effector biology of plant-associated organisms. Mol Plant Microbe In 22: 115-122.
14. Kandoth P K, Ithal N, Recknor J, Maier T, Nettleton D, Baum T J, Mitchum M G (2011) The soybean Rhg1 locus for resistance to the soybean cyst nematode *Heterodera glycines* regulates the expression of a large number of stress- and defense-related genes in degenerating feeding cells. Plant Physiol 155: 1960-1975.
15. Klink V P, Hosseini P, Matsye P, Alkharouf N W, Matthews B F (2009) A gene expression analysis of syncytia laser microdissected from the roots of the *Glycine max* (soybean) genotype PI 548402 (Peking) undergoing a resistant reaction after infection by *Heterodera glycines* (soybean cyst nematode). Plant Mol Biol 71: 525-567.
16. Klink V P, Hosseini P, Matsye P D, Alkharouf N W, Matthews B F (2010) Syncytium gene expression in *Glycine max*([PI 88788]) roots undergoing a resistant reaction to the parasitic nematode *Heterodera glycines*. Plant Physiol Biochem 48: 176-193.
17. Klink V P, Overall C C, Alkharouf N W, MacDonald M H, Matthews B F (2007) Laser capture microdissection (LCM) and comparative microarray expression analysis of syncytial cells isolated from incompatible and compatible soybean (*Glycine max*) roots infected by the soybean cyst nematode (*Heterodera glycines*). Planta 226: 1389-1409.
18. Lehti-Shiu M D, Shiu S H (2012) Diversity, classification and function of the plant protein kinase superfamily. Philos Trans R Soc Lond B Biol Sci 367: 2619-2639.
19. Lehti-Shiu M D, Zou C, Hanada K, Shiu S H (2009) Evolutionary history and stress regulation of plant receptor-like kinase/pelle genes. Plant Physiol 150: 12-26.
20. Liu J Y, Chen N N, Grant J N, Cheng Z M, Stewart C N, Hewezi T (2015) Soybean kinome: functional classification and gene expression patterns. J Exp Bot 66: 1919-1934.
21. Mendy B, Wang'ombe MW, Radakovic Z S, Holbein J, Ilyas M, Chopra D, Holton N, Zipfel C, Grundler F M, Siddique S (2017) *Arabidopsis* leucine-rich repeat receptor-like kinase NILR1 is required for induction of innate immunity to parasitic nematodes. PLoS Patho 13.
22. Morillo S A, Tax F E (2006) Functional analysis of receptor-like kinases in monocots and dicots. Curr Opin Plant Biol 9: 460-469.
23. Palumbo M C, Zenoni S, Fasoli M, Massonnet M, Farina L, Castiglione F, Pezzotti M, Paci P (2014) Integrated network analysis identifies fight-club nodes as a class of hubs encompassing key putative switch genes that induce major transcriptome reprogramming during grapevine development. Plant Cell 26: 4617-4635.
24. Rodriguez M C, Petersen M, Mundy J (2010) Mitogen-activated protein kinase signaling in plants. Annu Rev Plant Biol 61: 621-649.
25. Schmutz J, Cannon S B, Schuster J, Ma J X, Mitros T, Nelson W, Hyten D L, Song Q J, Thelen J J, Cheng J L, Xu D, Hellsten U, May G D, Yu Y, Sakurai T, Umezawa T, Bhattacharyya M K, Sandhu D, Valliyodan B, Lindquist E, Peto M, Grant D, Shu S Q, Goodstein D, Barry K, Futrell-Griggs M, Abernathy B, Du J C, Tian Z X, Zhu L C, Gill N, Joshi T, Libault M, Sethuraman A, Zhang X C, Shinozaki K, Nguyen H T, Wing R A, Cregan P, Specht J, Grimwood J, Rokhsar D, Stacey G, Shoemaker R C, Jackson S A (2010) Genome sequence of the palaeopolyploid soybean. Nature 463: 178-183.
26. Shiu S H, Bleecker A B (2003) Expansion of the receptor-like kinase/Pelle gene family and receptor-like proteins in *Arabidopsis*. Plant Physiol 132: 530-543.
27. Shiu S H, Karlowski W M, Pan R S, Tzeng Y H, Mayer K F X, Li W H (2004) Comparative analysis of the receptor-like kinase family in *Arabidopsis* and rice. Plant Cell 16: 1220-1234.
28. Stuart J M, Segal E, Koller D, Kim S K (2003) A gene-coexpression network for global discovery of conserved genetic modules. Science 302: 249-255.
29. Tena G, Boudsocq M, Sheen J (2011) Protein kinase signaling networks in plant innate immunity. Curr Opin Plant Biol 14: 519-529.
30. Vidal M, Cusick M E, Barabasi A L (2011) Interactome networks and human disease. Cell 144: 986-998.
31. Vij S, Giri J, Dansana P K, Kapoor S, Tyagi A K (2008) The receptor-like cytoplasmic kinase (OsRLCK) gene family in rice: Organization, phylogenetic relationship, and expression during development and stress. Mol Plant 1: 732-750.
32. Vuong T D, Jiao Y, Shannon J G, Nguyen H T. 2013. Nematode resistance in soybean. In: Varshney R, Tuberosa R, eds. Translational genomics for crop breeding: Biotic stress. Wiley-Blackwell, 95-124.
33. Wei K F, Wang Y M, Xie D X (2014) Identification and expression profile analysis of the protein kinase gene superfamily in maize development. Mol Breeding 33: 155-172.
34. Wolfe C J, Kohane I S, Butte A J (2005) Systematic survey reveals general applicability of "guilt-by-association" within gene coexpression networks. BMC Bioinformatics 6: 227.

We claim:

1. An isolated nucleic acid sequence encoding a kinase dead mutant protein comprising SEQ ID NO: 93.

2. A vector comprising the nucleic acid of claim 1.

3. A plant cell or plant comprising the nucleic acid of claim 1 or a vector comprising said nucleic acid.

4. The plant cell or plant of claim 3, said plant cell or plant being a soybean plant cell or soybean plant.

5. The plant cell of claim 3, wherein the plant cell is in a plant part.

6. The plant cell of claim 5, wherein the plant part is a seed, endosperm, ovule or pollen.

7. The plant cell of claim 3, wherein the plant is a soybean plant or other cyst nematode-host plant.

* * * * *

UNITED STATES PATENT AND TRADEMARK OFFICE
CERTIFICATE OF CORRECTION

| | | |
|---|---|---|
| PATENT NO. | : 12,018,270 B2 | Page 1 of 1 |
| APPLICATION NO. | : 17/227472 | |
| DATED | : June 25, 2024 | |
| INVENTOR(S) | : Tarek Abdelfattah Hewezi and Sarbottam Piya | |

It is certified that error appears in the above-identified patent and that said Letters Patent is hereby corrected as shown below:

In the Specification

Column 3,
Line 31, "(isolate 3D %)" should read --*isolate 3D7*--.

Column 25,
Line 18, "DHEN" should read --DHFN--.
Line 18, "GGEGI" should read --GGFGI--.
Line 33, "VICS" should read --VTCS--.
Line 55, "VIP" should read --VTP--.

Column 27,
Line 13, "YPER" should read --YPFR--.

Signed and Sealed this
Twenty-first Day of October, 2025

John A. Squires
*Director of the United States Patent and Trademark Office*